United States Patent
Hoekstra et al.

(10) Patent No.: US 9,663,488 B2
(45) Date of Patent: May 30, 2017

(54) METALLOENZYME INHIBITOR COMPOUNDS

(71) Applicant: Viamet Pharmaceuticals, Inc., Durham, NC (US)

(72) Inventors: William J. Hoekstra, Durham, NC (US); Christopher M. Yates, Raleigh, NC (US); Stephen W. Rafferty, Lake Worth, FL (US)

(73) Assignee: Viamet Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 14/763,468

(22) PCT Filed: Jan. 27, 2014

(86) PCT No.: PCT/US2014/013204
§ 371 (c)(1),
(2) Date: Jul. 24, 2015

(87) PCT Pub. No.: WO2014/117090
PCT Pub. Date: Jul. 31, 2014

(65) Prior Publication Data
US 2015/0353546 A1  Dec. 10, 2015

Related U.S. Application Data

(60) Provisional application No. 61/757,594, filed on Jan. 28, 2013.

(51) Int. Cl.
| | |
|---|---|
| C07D 401/04 | (2006.01) |
| A61K 31/4375 | (2006.01) |
| A61K 31/4709 | (2006.01) |
| A61K 31/47 | (2006.01) |
| A61K 31/5377 | (2006.01) |
| A61K 31/4545 | (2006.01) |
| A61K 31/444 | (2006.01) |
| A61K 31/496 | (2006.01) |
| A61K 31/541 | (2006.01) |
| C07D 471/04 | (2006.01) |
| A61K 45/06 | (2006.01) |
| C07D 215/14 | (2006.01) |
| C07D 215/52 | (2006.01) |

(52) U.S. Cl.
CPC ........ *C07D 401/04* (2013.01); *A61K 31/4375* (2013.01); *A61K 31/444* (2013.01); *A61K 31/4545* (2013.01); *A61K 31/47* (2013.01); *A61K 31/4709* (2013.01); *A61K 31/496* (2013.01); *A61K 31/5377* (2013.01); *A61K 31/541* (2013.01); *A61K 45/06* (2013.01); *C07D 215/14* (2013.01); *C07D 215/52* (2013.01); *C07D 471/04* (2013.01)

(58) Field of Classification Search
CPC .. C07D 401/04; C07D 471/04; C07D 215/14; C07D 215/52; A61K 45/06; A61K 31/4709; A61K 31/4375; A61K 31/4545; A61K 31/5377; A61K 31/47; A61K 31/444; A61K 31/496; A61K 31/541
See application file for complete search history.

(56) References Cited

U.S. PATENT DOCUMENTS

| | | | |
|---|---|---|---|
| 9,403,758 B2 * | 8/2016 | Patterson | C07D 213/79 |
| 2004/0110802 A1 * | 6/2004 | Thorarensen | C07D 209/42 514/355 |
| 2011/0015158 A1 | 1/2011 | Schotzinger et al. | |

FOREIGN PATENT DOCUMENTS

| | | | |
|---|---|---|---|
| CN | 101084895 | * | 12/2007 |
| EP | 14742899 | | 6/2016 |
| WO | 2007100775 | * | 9/2007 |
| WO | WO 2008/105515 A1 | | 9/2008 |
| WO | WO-2011082245 A2 | | 7/2011 |
| WO | WO-2012082746 A2 | | 6/2012 |
| WO | WO-2012177638 A1 | | 12/2012 |

OTHER PUBLICATIONS

Partial Supplementary European Search Report mailed Jun. 28, 2016 in connection with EP 14742899.9.
Zemtsova, et al., Search for New Drugs: Synthesis and antiviral activity of 4-quinolinecarboxylic acid hydrazides, Pharm Chem J. Oct. 2008; 42(10): 571-73. doi:10.1007/s11094-009-0187-1. Translated from Khmiko-Farmatsevticheskii Zhurnal. Oct. 23, 2008;42(10):21.
International Search Report and Written Opinion dated Jun. 30, 2014 for PCT/US2014/013204.

\* cited by examiner

*Primary Examiner* — D M Seaman
(74) *Attorney, Agent, or Firm* — Wolf, Greenfield & Sacks, P.C.

(57) ABSTRACT

The instant invention describes compounds having metalloenzyme modulating activity, and methods of treating diseases, disorders or symptoms thereof mediated by such metalloenzymes.

22 Claims, No Drawings

METALLOENZYME INHIBITOR COMPOUNDS

CROSS-REFERENCE TO RELATED APPLICATIONS

This application is the national phase under 35 U.S.C. §371 of PCT International Application No. PCT/US2014/013204, filed Jan. 27, 2014, which claims the benefit of U.S. Provisional Application No. 61/757,594, filed Jan. 28, 2013, the contents of which are incorporated herein by reference in their entirety.

BACKGROUND

Living organisms have developed tightly regulated processes that specifically imports metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the matrix metalloproteinase (MMP) inhibitor marimastat contains a hydroxamic acid group that binds to the zinc present in the active site of the target isoforms of the enzyme MMP and thereby inactivates the enzyme. Another example includes hydroxamic acid group that has been incorporated into most published inhibitors of histone deacetylases. A third example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. It is believed that off-target inhibition is caused primarily by the indiscriminate binding of the currently utilized hydroxamic acid to zinc in the active site of MMP enzyme isoforms. An example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

A compound of formula (V), or salt, solvate, hydrate or prodrug thereof, wherein:

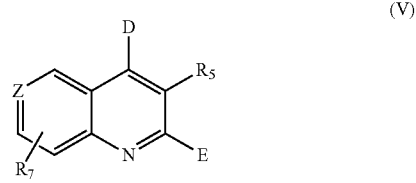

D is

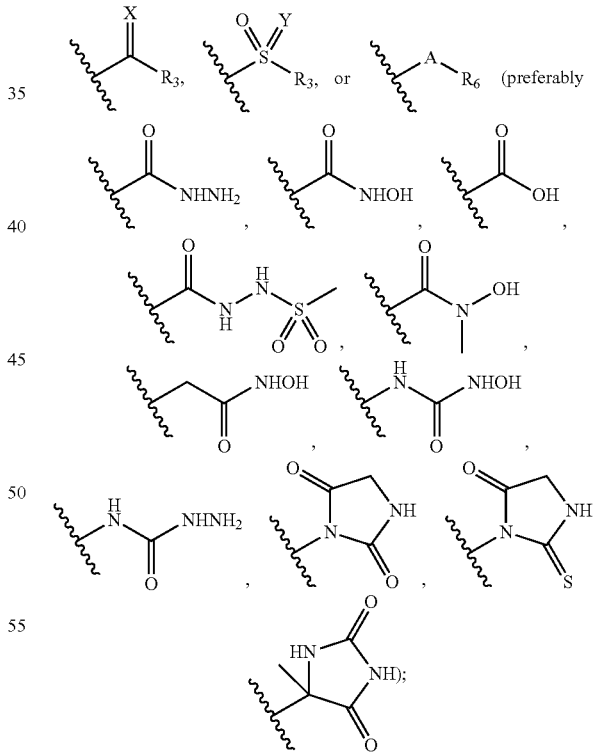

E is optionally substituted aryl or optionally substituted heteroaryl (preferably pyridyl, pyrazinyl, furanyl, or thienyl);

X is O; S; $NR_4$; or H and $R_4$;

$R_3$ is $CH(R_4)NHR_4$, $CH(R_4)NHSO_2R_4$, $CH(R_4)SH$, $CH(R_4)OH$, $CH(R_4)CO_2R_4$, $CH(R_4)CONHR_4$; $CH(R_4)$

CONHOH; CH(R$_4$)CONHNHR$_4$; C(=O)R$_4$, CO$_2$R$_4$, C(=O)NHR$_4$, C(=O)NHNHR$_4$, C(=S)NHR$_4$, C(=S)NHNHR$_4$, C≡N, C(=NH)NH$_2$, NHC(=NH)NH$_2$, N(R$_4$)OH, N(OH)C(=O)R$_4$, NHR$_4$, NHNHR$_4$, NHC(=O)R$_4$, N(R$_4$)NHC(=O)R$_4$, NHC(=O)NHR$_4$, NHC(=S)NHR$_4$, NHSO$_2$R$_4$, NHSO$_2$NHR$_4$; NHNHSO$_2$R$_4$, NO$_2$, SO$_2$NHR$_4$ (only in the case of formula I), SO$_2$NHOH (only in the case of formula I), SO$_3$H (only in the case of formula I), OR$_4$, OSO$_2$R$_4$, OSO$_2$NHR$_4$, SR$_4$, B(OR$_4$)$_2$, CH$_2$B(OR$_4$)$_2$, P(=O)OH, P(=O)$_2$OH, Se(=O)OH, Se(=O)$_2$OH, a heterocycle that is preferably a 5-membered ring with up to 1-4 heteroatoms, or a 5-membered heterocycle that is connected through a CH$_2$;

Y is O or null;

Z is CR$_{16}$ or N;

each R$_4$ is independently a) H; b) optionally substituted alkyl; c) fluoroalkyl; d) optionally substituted aryl; e) optionally substituted heteroaryl; or f) optionally substituted heterocycloalkyl;

each R$_5$ is independently H, alkyl, fluoroalkyl, halogen, alkoxy, fluoroalkoxy, substituted amino, aryl, or heteroaryl;

A is O, S, CH$_2$ or N(R$_4$);

A may also be the following when R$_6$ is null: an optionally substituted heterocycle that is preferably a 5-membered ring with up to 1-4 heteroatoms, B(OR$_4$)$_2$, P(=O)OH, P(=O)$_2$OH, Se(=O)OH, Se(=O)$_2$OH;

R$_6$ is null, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NR$_4$OH, C(=O)NHNHR$_4$, C(=S)NHR$_4$, C(=S)NR$_4$OH, C(=S)NHNHR$_4$, C≡N, C(=NH)NH$_2$, SO$_2$NHNR$_4$ (with the proviso that A cannot be S), SO$_2$NHR$_4$ (with the proviso that A cannot be S), SO$_2$NHOH (with the proviso that A cannot be S); a heterocycle that is preferably a 5-membered ring with up to 1-4 heteroatoms, or a (preferably 5-membered) heterocycle that is connected through a CH$_2$; and each R$_7$ is independently H, alkyl, alkoxy, hydroxy, NHR$_4$, C(=O)R$_4$, NHC(=O)R$_4$, N(alkyl)C(=O)R$_4$, NHSO$_2$R$_4$, N(alkyl)SO$_2$R$_4$, C(=O)NR$_{27}$R$_4$, SO$_2$NR$_{27}$R$_4$, C(=O)NR$_{27}$NHR$_4$, C(=O)NR$_{27}$OR$_4$, halogen, optionally substituted aryl, optionally substituted heteroaryl, or optionally substituted heterocycloalkyl, or optionally substituted heterocycloalkylcarbonyl;

each R$_{16}$ is independently hydrogen, alkyl, alkoxy, hydroxy, NHR$_4$, NHC(=O)R$_4$, halogen, optionally substituted aryl, optionally substituted heteroaryl, or optionally substituted heterocycloalkyl; and each R$_{27}$ is independently a) H; b) alkyl optionally substituted with 1, 2, or 3 independent hydroxy, halogen, amino, alkylthio, or optionally substituted aryl; c) fluoroalkyl; d) optionally substituted aryl; or e) optionally substituted heteroaryl.

A compound of formula (I), (II), (III), or salt, solvate, hydrate or prodrug thereof, wherein:

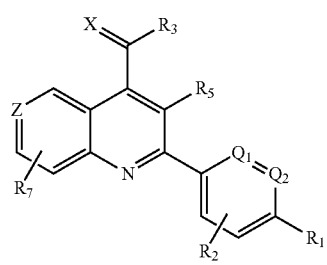
(I)

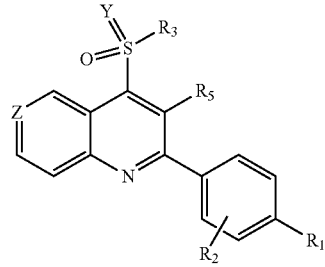
(II)

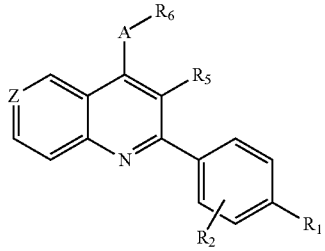
(III)

X is O; S; NR$_4$; or H and R$_4$;

each R$_1$ is independently selected from:
a)

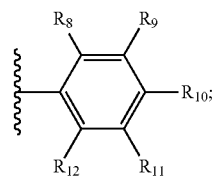

b) optionally substituted heteroaryl; c) C≡C—R$_{13}$; d) C(=O)NR$_4$R$_7$; e) N(R$_7$)C(=O)R$_4$; f) SO$_2$NR$_4$R$_7$; g) N(R$_7$)SO$_2$R$_4$; h) hydrogen; i) hydroxy; j) optionally substituted alkoxy; k) SO$_2$NHR$_4$; l) optionally substituted alkenyl; or m) optionally substituted arylalkyl;

each R$_8$, R$_9$, R$_{10}$, R$_{11}$, and R$_{12}$ is independently selected from:
a) H; b) hydroxyalkylamino; c) optionally substituted alkoxy; d) halogen; e) SO$_2$NHR$_{18}$; f) NHSO$_2$R$_4$; g) NHC(=O)R$_4$; h) C(=O)NHR$_4$; i) optionally substituted heterocycloalkyl; j) optionally substituted heteroaryl; k) cyano; l) hydroxy; m) SO$_2$R$_4$; n) optionally substituted heterocycloalkylcarbonyl; o) optionally substituted heterocycloalkylsulfonyl; p)

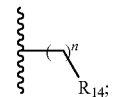

q) mercapto; r) thioalkoxy; s) alkylamino; t) optionally substituted alkyl; or u) dialkylamino;

R$_2$ is H, alkyl, fluoroalkyl, alkoxy, fluoroalkoxy, halogen, aryl, or heteroaryl;

each R$_3$ is independently CH(R$_4$)NHR$_4$, CH(R$_4$)NHSO$_2$R$_4$, CH(R$_4$)SH, CH(R$_4$)OH, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NHNHR$_4$, C(=S)NHR$_4$, C(=S)NHNHR$_4$, C≡N, C(=NH)NH$_2$, NHC(=NH)NH$_2$, N(R$_4$)OH, N(OH)C(=O)R$_4$, NHR$_4$, NHNHR$_4$, NHC(=O)R$_4$, N(R$_4$)NHC(=O)R$_4$, NHC(=O)NHR$_4$, NHC(=S)NHR$_4$, NHSO$_2$R$_4$, NHSO$_2$NHR$_4$; NHNHSO$_2$R$_4$, NO$_2$, SO$_2$NHR$_4$ (only in the case of formula I), SO$_2$NHOH (only in the case of formula I), SO$_3$H (only in the case of formula I), OR$_4$, OSO$_2$R$_4$, OSO$_2$NHR$_4$, SR$_4$, B(OR$_4$)$_2$, CH$_2$B(OR$_4$)$_2$, P(=O)OH, P(=O)$_2$OH, Se(=O)OH, Se(=O)$_2$OH, a heterocycle that is preferably a 5-membered ring with up to 1-4 heteroatoms, or a 5-membered heterocycle that is connected through a CH$_2$;

Y is O or null;

each Z is independently CR$_{16}$ or N;

each R$_4$ is independently a) H; b) optionally substituted alkyl; c) fluoroalkyl; d) optionally substituted aryl; or e) optionally substituted heteroaryl;

each R$_5$ is independently H, alkyl, fluoroalkyl, halogen, alkoxy, fluoroalkoxy, substituted amino, aryl, or heteroaryl;

A is O, S, CH$_2$ or N(R$_4$);

A may also be the following when R$_6$ is null: an optionally substituted heterocycle that is preferably a 5-membered ring with up to 1-4 heteroatoms, B(OR$_4$)$_2$, P(=O)OH, P(=O)$_2$OH, Se(=O)OH, Se(=O)$_2$OH;

R$_6$ is null, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NR$_4$OH, C(=O)NHNHR$_4$, C(=S)NHR$_4$, C(=S)NR$_4$OH, C(=S)NHNHR$_4$, C(=NH)NH$_2$, SO$_2$NHNR$_4$ (with the proviso that A cannot be S), SO$_2$NHR$_4$ (with the proviso that A cannot be S), SO$_2$NHOH (with the proviso that A cannot be S); a heterocycle that is preferably a 5-membered ring with up to 1-4 heteroatoms, or a (preferably 5-membered) heterocycle that is connected through a CH$_2$; and each R$_7$ is independently H, alkyl, alkoxy, hydroxy, NHR$_4$, NHC(=O)R$_4$, halogen, optionally substituted aryl, optionally substituted heteroaryl, or optionally substituted heterocycloalkyl, each R$_{13}$ is independently selected from:
a)

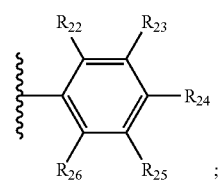

b) optionally substituted heterocycloalkyl; or c) optionally substituted heteroaryl;

each R$_{14}$ is independently selected from heterocycloalkylcarbonyl, heterocycloalkylsulfonyl, or heterocycloalkyl, each optionally substituted;

each R$_{15}$ is independently H; alkyl; fluoroalkyl; aryl; or heteroaryl;

each R$_{16}$ is independently hydrogen, alkyl, alkoxy, hydroxy, NHR$_4$, NHC(=O)R$_4$, halogen, optionally substituted aryl, optionally substituted heteroaryl, or optionally substituted heterocycloalkyl;

each R$_{17}$ is independently a) H; b) optionally substituted alkyl; c) fluoroalkyl; d) aryl; or e) heteroaryl;

each R$_{18}$ is independently a) H; b) optionally substituted alkyl; c) fluoroalkyl; d) aryl; or e) heteroaryl;

each R$_{19}$ is independently a) H; b) optionally substituted alkyl; c) fluoroalkyl; d) aryl; or e) heteroaryl;

each R$_{20}$ is independently a) H; b) optionally substituted alkyl; c) fluoroalkyl; d) aryl; or e) heteroaryl;

each R$_{21}$ is independently a) H; b) optionally substituted alkyl; c) fluoroalkyl; d) aryl; or e) heteroaryl;

each R$_{22}$, R$_{23}$, R$_{24}$, R$_{25}$, and R$_{26}$ is independently selected from:
i) hydrogen; ii) NHC(=O)R$_4$; iii) NHSO$_2$R$_4$; iv) optionally substituted heterocycloalkylcarbonyl; v) optionally substituted heterocycloalkylsulfonyl; vi) halogen; vii) optionally substituted alkyl; viii) hydroxyalkylamino; ix) C(=O)NR$_{15}$R$_{20}$; x) alkoxy; xi) haloalkoxy; xii) haloalkyl; xiii) hydroxy; xiv) SO$_2$NHR$_{21}$; or xv) optionally substituted heterocycloalkyl;

each n is independently 0, 1, 2, 3, or 4; and

Q$_1$ and Q$_2$ are each independently CH or N.

Another aspect is a compound of any of the formulae herein, wherein R$_1$ is

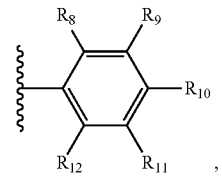

and each R$_8$, R$_9$, R$_{10}$, R$_{11}$, and R$_{12}$ is independently selected from:
a) H; b) hydroxyalkylamino; c) optionally substituted alkoxy; d) halogen; e) SO$_2$NHR$_{18}$; f) NHSO$_2$R$_4$; g) NHC(=O)R$_4$; h) C(=O)NHR$_4$; i) optionally substituted heterocycloalkyl; j) optionally substituted heteroaryl; k) cyano; l) hydroxy; m) SO$_2$R$_4$; n) optionally substituted heterocycloalkylcarbonyl; o) optionally substituted heterocycloalkylsulfonyl; p)

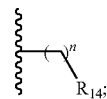

q) mercapto; r) thioalkoxy; s) alkylamino; or t) dialkylamino.

Another aspect is a compound of any of the formulae herein, wherein R$_1$ is heteroaryl optionally substituted with alkoxy wherein alkoxy is optionally substituted with 1, 2, or 3 hydroxy.

Another aspect is a compound of any of the formulae herein, wherein R$_1$ is C≡C—C≡C—R$_{13}$, and R$_{13}$ is selected from a)

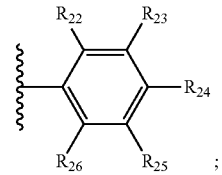

b) optionally substituted heterocycloalkyl; c) optionally substituted heteroaryl; or d) optionally substituted cycloalkyl; and each R$_{22}$, R$_{23}$, R$_{24}$, R$_{25}$, and R$_{26}$ is independently selected from i) hydrogen; ii) NHC(=O)R$_4$; iii) NHSO$_2$R$_4$; iv) optionally substituted heterocycloalkylcarbonyl; v) optionally substituted heterocycloalkylsulfonyl; vi) halogen; vii) optionally substituted alkyl; viii) hydroxyalkylamino;

ix) C(=O)NR$_{15}$R$_{20}$; x) optionally substituted alkoxy; xi) haloalkoxy; xii) haloalkyl; xiii) hydroxy; xiv) SO$_2$NR$_4$R$_{21}$; or xv) optionally substituted heterocycloalkyl.

Another aspect is a compound of any of the formulae herein, wherein R$_1$ is selected from a)

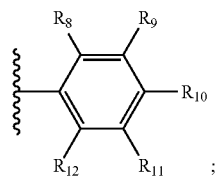

b) heteroaryl optionally substituted with alkoxy wherein alkoxy is optionally substituted with 1, 2, or 3 hydroxy; c) C≡C—R$_{13}$; d) C(=O)NR$_4$R$_7$; e) N(R$_7$)C(=O)R$_4$; f) SO$_2$NR$_4$R$_7$; g) N(R$_7$)SO$_2$R$_4$; h) hydrogen; i) hydroxy; j) optionally substituted alkoxy; k) SO$_2$NHR$_4$; l) optionally substituted alkenyl; or m) optionally substituted arylalkyl; and the remaining variables are as defined above.

Another aspect is a compound of any of the formulae herein, wherein R$_1$ is C≡C—R$_{13}$, and R$_{13}$ is independently selected from a)

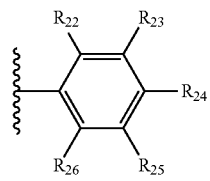

b) optionally substituted heterocycloalkyl; or c) optionally substituted heteroaryl; and each R$_{22}$, R$_{23}$, R$_{24}$, R$_{25}$, and R$_{26}$ is independently selected from i) hydrogen; ii) NHC(=O)R$_4$; iii) NHSO$_2$R$_4$; iv) optionally substituted heterocycloalkylcarbonyl; v) optionally substituted heterocycloalkylsulfonyl; vi) halogen; vii) optionally substituted alkyl; viii) hydroxyalkylamino; ix) C(=O)NR$_{15}$R$_{20}$; x) alkoxy; xi) haloalkoxy; xii) haloalkyl; xiii) hydroxy; xiv) SO$_2$NHR$_{21}$; or xv) optionally substituted heterocycloalkyl.

Another aspect is a compound of any of the formulae herein, wherein R$_1$ is C≡C—R$_{13}$, R$_{13}$ is independently selected from a)

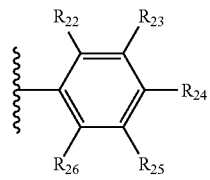

b) optionally substituted heterocycloalkyl; c) optionally substituted heteroaryl; or d) optionally substituted cycloalkyl; and each R$_{22}$, R$_{23}$, R$_{24}$, R$_{25}$, and R$_{26}$ is independently selected from
i) hydrogen; ii) NHC(=O)R$_4$; iii) NHSO$_2$R$_4$; iv) heterocycloalkylcarbonyl optionally substituted with 1, 2, or 3 independent alkyl, CH$_2$C(=O)OR$_{19}$, CH$_2$C(=O)NR$_4$R$_7$, OR$_4$, CH$_2$SO$_2$NR$_4$R$_7$, C(=O)OR$_{19}$, C(=O)NR$_4$R$_7$, or SO$_2$NR$_4$R$_7$; v) heterocycloalkylsulfonyl optionally substituted with 1, 2, or 3 independent C(=O)OR$_4$, C(=O)NR$_4$R$_7$, or SO$_2$NR$_4$R$_7$, or alkyl; vi) halogen; vii) alkyl optionally substituted with heterocycloalkyl wherein heterocycloalkyl is optionally substituted with 1, 2, or 3 independent C(=O)OR$_4$, C(=O)NR$_4$R$_7$, or SO$_2$NR$_4$R$_7$; viii) hydroxyalkylamino; ix) C(=O)NR$_{15}$R$_{20}$; x) alkoxy optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; xi) haloalkoxy; xii) haloalkyl; xiii) hydroxy; xiv) SO$_2$NR$_4$R$_{21}$; or xv) heterocycloalkyl optionally substituted with 1, 2, or 3 independent C(=O)OR$_4$, C(=O)NR$_4$R$_7$, or SO$_2$NR$_4$R$_7$, or CH$_2$C(=O)OR$_4$.

Another aspect is a compound of any of the formulae herein, wherein R$_{13}$ is independently selected from:
a)

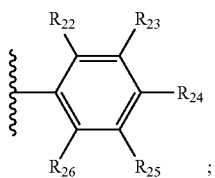

b) heterocycloalkyl optionally substituted with 1, 2, or 3 independent alkyl wherein alkyl is optionally substituted with independent:
  i) OR$_4$;
  ii) NHC(=O)R$_4$;
  iii) C(=O)OR$_4$;
  iv) C(=O)NHR$_4$; or
c) heteroaryl optionally substituted with 1, 2, or 3 independent heterocycloalkylcarbonyl or alkylaminocarbonyl, each optionally substituted with 1, 2, or 3 independent C(=O)OR$_4$, C(=O)NR$_4$R$_7$, or SO$_2$NR$_4$R$_7$.

Another aspect is a compound of any of the formulae herein, wherein R$_{13}$ is independently selected from 1) heteroaryl optionally substituted with 1, 2, or 3 independent a) NR$_{27}$SO$_2$R$_4$ or b) NR$_{27}$C(=O)R$_4$; or 2) cycloalkyl optionally substituted with 1, 2, or 3 independent C(=O)OR$_4$, C(=O)NR$_4$R$_7$, or SO$_2$NR$_4$R$_7$.

Another aspect is a compound of any of the formulae herein, wherein each R$_8$, R$_9$, R$_{10}$, R$_{11}$, and R$_{12}$ is independently selected from:
a) H; b) hydroxyalkylamino; c) optionally substituted alkoxy; d) halogen; e) SO$_2$NHR$_{18}$; f) NHSO$_2$R$_4$; g) NHC(=O)R$_4$; h) C(=O)NHR$_4$; i) optionally substituted heterocycloalkyl; j) optionally substituted heteroaryl; k) cyano; l) hydroxy; m) SO$_2$R$_4$; n) optionally substituted heterocycloalkylcarbonyl; o) optionally substituted heterocycloalkylsulfonyl; p)

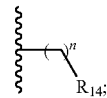

q) mercapto; r) thioalkoxy; s) alkylamino; or t) dialkylamino.

Another aspect is a compound of any of the formulae herein, wherein each R$_8$, R$_9$, R$_{10}$, R$_{11}$, and R$_{12}$ is independently selected from:
a) H; b) hydroxyalkylamino; c) alkoxy optionally substituted with 1, 2, or 3 independent heterocycloalkoxy, heterocycloalkylcarbonyl, hydroxy, amino, NHSO$_2$R$_4$, NHC(=O)R$_4$, C(=O)OR$_4$, C(=O)NHNHR$_4$, or C(=O)NR$_4$OH; d) halogen; e) SO$_2$NHR$_{18}$; f) NHSO$_2$R$_4$; g) NHC(=O)R$_4$; h) C(=O)NHR$_4$; i) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; j) heteroaryl containing 5 to 6 ring atoms optionally substituted with 1, 2, or 3 independent:

(1) C(=O)OR$_{17}$;

(2) heterocycloalkylcarbonyl optionally substituted with 1, 2, or 3 independent C(=O)OR$_{17}$, C(=O)NR$_4$R$_7$, or SO$_2$NR$_4$R$_7$;

(3) alkyl optionally substituted with 1, 2, or 3 independent OC(=O)NHR$_4$, NHC(=O)NHR$_4$, NHSO$_2$R$_4$, hydroxy, or C(=O)NHR$_4$; or (4) C(=O)NHR$_4$;

k) cyano; l) hydroxy; m) SO$_2$R$_4$; n) heterocycloalkylcarbonyl optionally substituted with 1, 2, or 3 independent C(=O)OR$_4$, C(=O)NR$_4$R$_7$, or SO$_2$NR$_4$R$_7$; o) heterocycloalkylsulfonyl optionally substituted with 1, 2, or, 3 independent C(=O)OR$_4$, C(=O)NR$_4$R$_7$, or SO$_2$NR$_4$R$_7$; p)

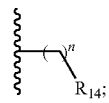

q) mercapto; r) thioalkoxy; s) alkylamino; t) alkyl optionally substituted with 1, 2, or 3 independent heterocycloalkylcarbonyl, heterocycloalkyl, or heterocycloalkylsulfonyl, each optionally substituted with independent C(=O)OR$_4$, C(=O)NR$_4$R$_7$, or SO$_2$NR$_4$R$_7$; u) dialkylamino; or v) —O—(CH$_2$)$_n$—C(=O)-heterocycloalkyl optionally substituted with 1, 2, or 3 independent C(=O)OR$_4$, C(=O)NR$_4$R$_7$, or SO$_2$NR$_4$R$_7$.

Another aspect is a compound of any of the formulae herein, wherein each R$_{22}$, R$_{23}$, R$_{24}$, R$_{25}$, and R$_{26}$ is independently selected from:

i) hydrogen; ii) NHC(=O)R$_4$; iii) NHSO$_2$R$_4$; iv) heterocycloalkylcarbonyl optionally substituted with 1, 2, or 3 independent alkyl, CH$_2$C(=O)OR$_{19}$, CH$_2$C(=O)NR$_4$R$_7$, CH$_2$SO$_2$NR$_4$R$_7$, C(=O)OR$_{19}$, C(=O)NR$_4$R$_7$, or SO$_2$NR$_4$R$_7$; v) heterocycloalkylsulfonyl optionally substituted with 1, 2, or 3 independent C(=O)OR$_4$, C(=O)NR$_4$R$_7$, or SO$_2$NR$_4$R$_7$, or alkyl; vi) halogen; vii) alkyl optionally substituted with heterocycloalkyl wherein heterocycloalkyl is optionally substituted with 1, 2, or 3 independent C(=O)OR$_4$, C(=O)NR$_4$R$_7$, or SO$_2$NR$_4$R$_7$; viii) hydroxyalkylamino; ix) C(=O)NR$_{15}$R$_{20}$; x) alkoxy; xi) haloalkoxy; xii) haloalkyl; xiii) hydroxy; xiv) SO$_2$NHR$_{21}$; or xv) heterocycloalkyl optionally substituted with 1, 2, or 3 independent C(=O)OR$_4$, C(=O)NR$_4$R$_7$, or SO$_2$NR$_4$R$_7$, or CH$_2$C(=O)OR$_4$.

Another aspect is a compound of any of the formulae herein, wherein each R$_{22}$, R$_{23}$, R$_{24}$, R$_{25}$, and R$_{26}$ is independently alkoxy optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl.

Another aspect is a compound of any of the formulae herein, wherein:

X is O; S; NR$_4$; or H and R$_4$;

R$_1$ is selected from:

a)

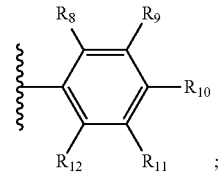

b) heteroaryl optionally substituted with alkoxy wherein alkoxy is optionally substituted with 1, 2, or 3 OR$_4$; c) C≡C—R$_{13}$; d) C(=O)NR$_4$R$_7$; e) N(R$_7$)C(=O)R$_4$; f) SO$_2$NR$_4$R$_7$; g) N(R$_7$)SO$_2$R$_4$; h) hydrogen; i) hydroxy; j) optionally substituted alkoxy; k) SO$_2$NHR$_4$; l) optionally substituted alkenyl; or m) optionally substituted arylalkyl;

each R$_8$, R$_9$, R$_{10}$, R$_{11}$, and R$_{12}$ is independently selected from:

a) H; b) hydroxyalkylamino; c) alkoxy optionally substituted with 1, 2, or 3 independent heterocycloalkoxy, heterocycloalkylcarbonyl, hydroxy, amino, NHSO$_2$R$_4$, NHC(=O)R$_4$, C(=O)OR$_4$, C(=O)NHNHR$_4$, or C(=O)R$_4$OH; d) halogen; e) SO$_2$NHR$_{18}$; f) NHSO$_2$R$_4$; g) NHC(=O)R$_4$; h) C(=O)NHR$_4$; i) heterocycloalkyl containing 5 to 6 ring atoms, optionally substituted with 1, 2, or 3 C(=O)OR$_4$, C(=O)NR$_4$R$_7$, or SO$_2$NR$_4$R$_7$; j) heteroaryl containing 5 to 6 ring atoms optionally substituted with 1, 2, or 3 independent:

(1) C(=O)OR$_{17}$ or SO$_2$NR$_4$R$_7$;

(2) heterocycloalkylcarbonyl optionally substituted with 1, 2, or 3 C(=O)OR$_{17}$;

(3) alkyl optionally substituted with 1, 2, or 3 independent OC(=O)NHR$_4$, NHC(=O)NHR$_4$, NHSO$_2$R$_4$, hydroxy, or C(=O)NHR$_4$; or (4) C(=O)NHR$_4$;

k) cyano; l) hydroxy; m) SO$_2$R$_4$; n) heterocycloalkylcarbonyl optionally substituted with 1, 2, or 3 independent C(=O)OR$_4$, C(=O)NR$_4$R$_7$, or SO$_2$NR$_4$R$_7$; o) heterocycloalkylsulfonyl optionally substituted with 1, 2, or, 3 independent C(=O)OR$_4$, C(=O)NR$_4$R$_7$, or SO$_2$NR$_4$R$_7$; p)

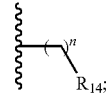

q) mercapto; r) thioalkoxy; s) alkylamino; t) alkyl optionally substituted with 1, 2, or 3 independent heterocycloalkylcarbonyl, heterocycloalkyl, or heterocycloalkylsulfonyl, each optionally substituted with independent C(=O)OR$_4$, C(=O)NR$_4$R$_7$, or SO$_2$NR$_4$R$_7$; u) dialkylamino; or v) —O—(CH$_2$)$_n$—C(=O)-heterocycloalkyl optionally substituted with 1, 2, or 3 independent C(=O)OR$_4$, C(=O)NR$_4$R$_7$, or SO$_2$NR$_4$R$_7$;

R$_2$ is H, alkyl, fluoroalkyl, alkoxy, fluoroalkoxy, halogen, aryl, or heteroaryl;

R$_3$ is CH(R$_4$)NHR$_4$, CH(R$_4$)NHSO$_2$R$_4$, CH(R$_4$)SH, CH(R$_4$)OH, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$,

C(=O)NHR$_4$, C(=O)NHNHR$_4$, C(=S)NHR$_4$, C(=S)NHNHR$_4$, C≡N, C(=NH)NH$_2$, NHC(=NH)NH$_2$, N(R$_4$)OH, N(OH)C(=O)R$_4$, NHR$_4$, NHNHR$_4$, NHC(=O)R$_4$, N(R$_4$)NHC(=O)R$_4$, NHC(=O)NHR$_4$, NHC(=S)NHR$_4$, NHSO$_2$R$_4$, NHSO$_2$NHR$_4$; NHNHSO$_2$R$_4$, NO$_2$, SO$_2$NHR$_4$ (only in the case of formula I), SO$_2$NHOH (only in the case of formula I), SO$_3$H (only in the case of formula I), OR$_4$, OSO$_2$R$_4$, OSO$_2$NHR$_4$, SR$_4$, B(OR$_4$)$_2$, CH$_2$B(OR$_4$)$_2$, P(=O)OH, P(=O)$_2$OH, Se(=O)OH, Se(=O)$_2$OH, a heterocycle that is preferably a 5-membered ring with up to 1-4 heteroatoms, or a 5-membered heterocycle that is connected through a CH$_2$;

Y is O or null;

Z is CR$_{16}$ or N;

each R$_4$ is independently a) H; b) alkyl optionally substituted with 1, 2, or 3 independent hydroxy, halogen, C(=O)OR$_{27}$, amino, alkylthio, or optionally substituted aryl; c) fluoroalkyl; d) optionally substituted aryl; or e) optionally substituted heteroaryl;

each R$_5$ is independently H, alkyl, fluoroalkyl, halogen, alkoxy, fluoroalkoxy, substituted amino, aryl, or heteroaryl;

A is O, S, CH$_2$ or N(R$_4$);

A may also be the following when R$_6$ is null: an optionally substituted heterocycle that is preferably a 5-membered ring with 1-4 heteroatoms, B(OR$_4$)$_2$, P(=O)OH, P(=O)$_2$OH, Se(=O)OH, Se(=O)$_2$OH;

R$_6$ is null, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NR$_4$OH, C(=O)NHNHR$_4$, C(=S)NHR$_4$, C(=S)NR$_4$OH, C(=S)NHNHR$_4$, C(=NH)NH$_2$, SO$_2$NHNR$_4$ (with the proviso that A cannot be S), SO$_2$NHR$_4$ (with the proviso that A cannot be S), SO$_2$NHOH (with the proviso that A cannot be S); a heterocycle that is preferably a 5-membered ring with up to 1-4 heteroatoms, or a (preferably 5-membered) heterocycle that is connected through a CH$_2$; and each R$_7$ is independently H, alkyl, alkoxy, hydroxy, NHR$_4$, NHC(=O)R$_4$, halogen, optionally substituted aryl, optionally substituted heteroaryl, heterocycloalkyl optionally substituted with 1, 2, or 3 independent C(=O)OR$_4$, or NHSO$_2$R$_4$, each R$_{13}$ is independently selected from:
a)

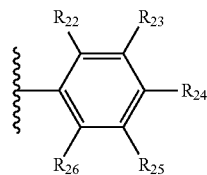

b) heterocycloalkyl optionally substituted with 1, 2, or 3 independent alkyl wherein alkyl is optionally substituted with independent:
i) OR$_4$;
ii) NHC(=O)R$_4$;
iii) C(=O)OR$_4$; or
iv) C(=O)NHR$_4$; or
c) heteroaryl optionally substituted with 1, 2, or 3 independent heterocycloalkylcarbonyl or alkylaminocarbonyl, each optionally substituted with 1, 2, or 3 independent C(=O)OR$_4$, C(=O)NR$_4$R$_7$, or SO$_2$NR$_4$R$_7$;

each R$_{14}$ is independently selected from heterocycloalkylcarbonyl, heterocycloalkylsulfonyl, or heterocycloalkyl, each optionally substituted with 1, 2, or 3 independent C(=O)OR$_4$, C(=O)NR$_4$R$_7$, or SO$_2$NR$_4$R$_7$;

each R$_{15}$ is independently H; alkyl; fluoroalkyl; aryl; or heteroaryl;

each R$_{16}$ is independently hydrogen, alkyl, alkoxy, hydroxy, NHR$_4$, NHC(=O)R$_4$, halogen, optionally substituted aryl, optionally substituted heteroaryl, heterocycloalkyl optionally substituted with 1, 2, or 3 independent C(=O)OR$_4$, C(=O)NR$_4$R$_7$, or SO$_2$NR$_4$R$_7$, or NHSO$_2$R$_4$, each R$_{17}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{18}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$amino, alkylthio, or optionally substituted aryl; c) fluoroalkyl; d) aryl; or e) heteroaryl;

each R$_{19}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{20}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{21}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{22}$, R$_{23}$, R$_{24}$, R$_{25}$, and R$_{26}$ is independently selected from
i) hydrogen; ii) NHC(=O)R$_4$; iii) NHSO$_2$R$_4$; iv) heterocycloalkylcarbonyl optionally substituted with 1, 2, or 3 independent alkyl, CH$_2$C(=O)OR$_{19}$, CH$_2$C(=O)NR$_4$R$_7$, CH$_2$SO$_2$NR$_4$R$_7$, C(=O)OR$_{19}$, C(=O)NR$_4$R$_7$, or SO$_2$NR$_4$R$_7$; v) heterocycloalkylsulfonyl optionally substituted with 1, 2, or 3 independent C(=O)OR$_4$, C(=O)NR$_4$R$_7$, SO$_2$NR$_4$R$_7$, or alkyl; vi) halogen; vii) alkyl optionally substituted with heterocycloalkyl wherein heterocycloalkyl is optionally substituted with 1, 2, or 3 independent C(=O)OR$_4$, C(=O)NR$_4$R$_7$, or SO$_2$NR$_4$R$_7$; viii) hydroxyalkylamino; ix) C(=O)NR$_{15}$R$_{20}$; x) alkoxy; xi) haloalkoxy; xii) haloalkyl; xiii) hydroxy; xiv) SO$_2$NHR$_{21}$; or xv) heterocycloalkyl optionally substituted with 1, 2, or 3 independent C(=O)OR$_4$, C(=O)NR$_4$R$_7$, SO$_2$NR$_4$R$_7$ or CH$_2$C(=O)OR$_4$;

each R$_{27}$ is independently a) H; b) alkyl optionally substituted with 1, 2, or 3 independent hydroxy, halogen, amino, alkylthio, or optionally substituted aryl; c) fluoroalkyl; d) optionally substituted aryl; or e) optionally substituted heteroaryl;

each n is independently 0, 1, 2, 3, or 4; and

Q$_1$ and Q$_2$ are each independently CH or N.

A compound of formula (I), (II), (III), (IV), or salt thereof, wherein:

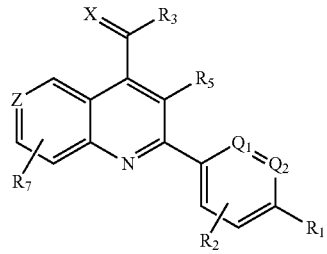

(I)

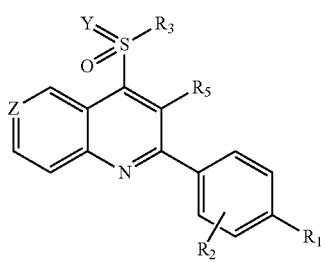

(II)

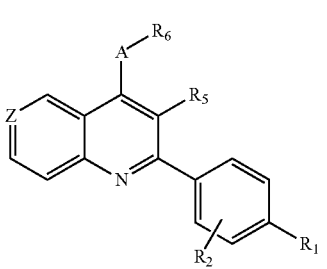

(III)

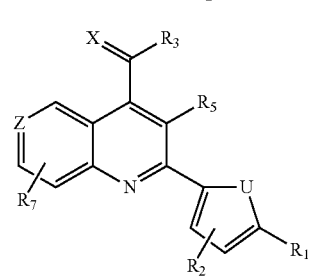

(IV)

U is O or S;
each X is independently O; S; NR$_4$; or H and R$_4$;
each R$_1$ is independently selected from:
a)

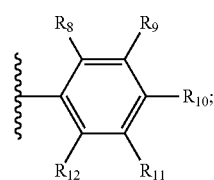

b) heteroaryl optionally substituted with alkoxy wherein alkoxy is optionally substituted with 1, 2, or 3 OR$_4$; c) C≡C—R$_{13}$; d) C(=O)NR$_4$R$_7$; e) N(R$_7$)C(=O)R$_4$; f) SO$_2$NR$_4$R$_7$; g) N(R$_7$)SO$_2$R$_4$; h) hydrogen; i) hydroxy; j) optionally substituted alkoxy; k) SO$_2$NHR$_4$; l) optionally substituted alkenyl; m) optionally substituted arylalkyl; or n) C≡C—C≡C—R$_{13}$;

each R$_8$, R$_9$, R$_{10}$, R$_{11}$, and R$_{12}$ is independently selected from:
a) H; b) hydroxyalkylamino; c) alkoxy optionally substituted with 1, 2, or 3 independent heterocycloalkoxy, heterocycloalkylcarbonyl, hydroxy, amino, NHSO$_2$R$_4$, NHC(=O)R$_4$, C(=O)OR$_4$, C(=O)NHNHR$_4$, or C(=O)NR$_4$OH; d) halogen; e) SO$_2$NHR$_{18}$; f) NHSO$_2$R$_4$; g) NHC(=O)R$_4$; h) C(=O)NHR$_4$; i) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; j) heteroaryl containing 5 to 6 ring atoms optionally substituted with 1, 2, or 3 independent:
  (1) C(=O)OR$_{17}$;
  (2) heterocycloalkylcarbonyl optionally substituted with 1, 2, or 3 independent C(=O)OR$_{17}$, C(=O)NR$_4$R$_7$, or SO$_2$NR$_4$R$_7$;
  (3) alkyl optionally substituted with 1, 2, or 3 independent OC(=O)NHR$_4$, NHC(=O)NHR$_4$, NHSO$_2$R$_4$, hydroxy, or C(=O)NHR$_4$; or
  (4) C(=O)NHR$_4$;
k) cyano; l) hydroxy; m) SO$_2$R$_4$; n) heterocycloalkylcarbonyl optionally substituted with 1, 2, or 3 independent C(=O)OR$_4$, C(=O)NR$_4$R$_7$, or SO$_2$NR$_4$R$_7$; o) heterocycloalkylsulfonyl optionally substituted with 1, 2, or, 3 independent C(=O)OR$_4$, C(=O)NR$_4$R$_7$, or SO$_2$NR$_4$R$_7$; p))

q) mercapto; r) thioalkoxy; s) alkylamino; t) alkyl optionally substituted with 1, 2, or 3 independent heterocycloalkylcarbonyl, heterocycloalkyl, or heterocycloalkylsulfonyl, each optionally substituted with independent C(=O)OR$_4$, C(=O)NR$_4$R$_7$, or SO$_2$NR$_4$R$_7$; u) dialkylamino; or v) —O—(CH$_2$)$_n$—C(=O)-heterocycloalkyl optionally substituted with 1, 2, or 3 independent C(=O)OR$_4$, C(=O)NR$_4$R$_7$, or SO$_2$NR$_4$R$_7$;

each R$_2$ is independently H, alkyl, fluoroalkyl, alkoxy, fluoroalkoxy, halogen, aryl, or heteroaryl;
each R$_3$ is independently CH(R$_4$)NHR$_4$, CH(R$_4$)NHSO$_2$R$_4$, CH(R$_4$)SH, CH(R$_4$)OH, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NHNHR$_4$, C(=S)NHR$_4$, C(=S)NHNHR$_4$, C≡N, C(=NH)NH$_2$, NHC(=NH)NH$_2$, N(R$_4$)OH, N(OH)C(=O)R$_4$, NHR$_4$, NHNHR$_4$, NHC(=O)R$_4$, N(R$_4$)NHC(=O)R$_4$, NHC(=O)NHR$_4$, NHC(=S)NHR$_4$, NHSO$_2$R$_4$, NHSO$_2$NHR$_4$; NHNHSO$_2$R$_4$, NO$_2$, SO$_2$NHR$_4$ (only in the case of formula I), SO$_2$NHOH (only in the case of formula I), SO$_3$H (only in the case of formula I), OR$_4$, OSO$_2$R$_4$, OSO$_2$NHR$_4$, SR$_4$, B(OR$_4$)$_2$, CH$_2$B(OR$_4$)$_2$, P(=O)OH, P(=O)$_2$OH, Se(=O)OH, Se(=O)$_2$OH, a heterocycle that is preferably a 5-membered ring with up to 1-4 heteroatoms, or a 5-membered heterocycle that is connected through a CH$_2$;
Y is O or null;
Z is CR$_{16}$ or N;
each R$_4$ is independently a) H; b) alkyl optionally substituted with 1, 2, or 3 independent hydroxy, halogen, C(=O)OR$_{27}$, amino, alkylthio, or optionally substituted aryl; c) fluoroalkyl; d) optionally substituted aryl; e) optionally substituted heteroaryl; or f) heterocycloalkyl optionally substituted with 1, 2, or 3 independent C(=O)OR$_{27}$, C(=O)NR$_{27}$R$_{27}$, or SO$_2$NR$_{27}$R$_{27}$;

each $R_5$ is independently H, alkyl, fluoroalkyl, halogen, alkoxy, fluoroalkoxy, substituted amino, aryl, or heteroaryl;

A is O, S, $CH_2$ or $N(R_4)$;

A may also be the following when $R_6$ is null: an optionally substituted heterocycle that is preferably a 5-membered ring with 1-4 heteroatoms, $B(OR_4)_2$, $P(=O)OH$, $P(=O)_2OH$, $Se(=O)OH$, $Se(=O)_2OH$;

$R_6$ is null, $CH(R_4)CO_2R_4$, $CH(R_4)CONHR_4$; $CH(R_4)$ CONHOH; $CH(R_4)CONHNHR_4$; $C(=O)R_4$, $CO_2R_4$, $C(=O)NHR_4$, $C(=O)NR_4OH$, $C(=O)NHNHR_4$, $C(=S)$ $NHR_4$, $C(=S)NR_4OH$, $C(=S)NHNHR_4$, $C\equiv N$, $C(=NH)$ $NH_2$, $SO_2NHNR_4$ (with the proviso that A cannot be S), $SO_2NHR_4$ (with the proviso that A cannot be S), $SO_2NHOH$ (with the proviso that A cannot be S); a heterocycle that is preferably a 5-membered ring with up to 1-4 heteroatoms, or a (preferably 5-membered) heterocycle that is connected through a $CH_2$; and each $R_7$ is independently H; alkyl; alkoxy; hydroxy; $C(=O)OR_4$; $NHSO_2R_4$; $N(alkyl)SO_2R_4$; $NHR_4$; NHC $(=O)R_4$; $N(alkyl)C(=O)R_4$; $C(=O)NR_{27}OR_4$, $SO_2NR_{27}R_4$, $C(=O)NR_{27}NHR_4$; $C(=O)NR_{27}OR_4$; halogen; optionally substituted aryl; optionally substituted heteroaryl; heterocycloalkyl optionally substituted with 1, 2, or 3 independent $OR_4$, $C(=O)OR_4$, or $NHSO_2R_4$; or heterocycloalkylcarbonyl optionally substituted with 1, 2, or 3 independent $OR_4$, $C(=O)OR_4$, or $NHSO_2R_4$;

each $R_{13}$ is independently selected from:
a)

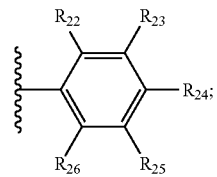

b) heterocycloalkyl optionally substituted with 1, 2, or 3 independent alkyl wherein alkyl is optionally substituted with independent:
 i) $OR_4$;
 ii) $NHC(=O)R_4$;
 iii) $C(=O)OR_4$; or
 iv) $C(=O)NHR_4$;

c) heteroaryl optionally substituted with 1, 2, or 3 independent 1) heterocycloalkylcarbonyl, 2) $NR_{27}SO_2R_4$, 3) alkylaminocarbonyl, each optionally substituted with 1, 2, or 3 independent $C(=O)OR_4$, $C(=O)$ $NR_4R_7$, or $SO_2NR_4R_7$, 4) (heterocycloalkyl)alkyl, or 5) $NR_{27}C(=O)R_4$; or d) cycloalkyl optionally substituted with 1, 2, or 3 independent $C(=O)OR_4$, $C(=O)NR_4R_7$, or $SO_2NR_4R_7$;

each $R_{14}$ is independently selected from heterocycloalkylcarbonyl, heterocycloalkylsulfonyl, or heterocycloalkyl, each optionally substituted with 1, 2, or 3 independent $C(=O)OR_4$, $C(=O)NR_4R_7$, or $SO_2NR_4R_7$;

each $R_{15}$ is independently H; alkyl; fluoroalkyl; aryl; arylalkyl; or heteroaryl;

each $R_{16}$ is independently hydrogen; alkyl; alkoxy; hydroxy; $NHR_4$; $NHC(=O)R_4$; halogen; optionally substituted aryl; optionally substituted heteroaryl; heterocycloalkyl optionally substituted with 1, 2, or 3 independent $C(=O)OR_4$, $C(=O)NR_4R_7$, or $SO_2NR_4R_7$; or $NHSO_2R_4$;

each $R_{17}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{18}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{19}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{20}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, optionally substituted heteroaryl, or optionally substituted aryl; c) fluoroalkyl; d) aryl optionally substituted with 1, 2, or 3 independent $C(=O)OR_4$ or $OR_4$; or e) heteroaryl;

each $R_{21}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{22}$, $R_{23}$, $R_{24}$, $R_{25}$, and $R_{26}$ is independently selected from i) hydrogen; ii) $NHC(=O)R_4$; iii) $NHSO_2R_4$; iv) heterocycloalkylcarbonyl optionally substituted with 1, 2, or 3 independent alkyl, $CH_2C(=O)OR_{19}$, $CH_2C(=O)$ $NR_4R_7$, $OR_4$, $CH_2SO_2NR_4R_7$, $C(=O)OR_{19}$, $C(=O)$ $NR_4R_7$, or $SO_2NR_4R_7$; v) heterocycloalkylsulfonyl optionally substituted with 1, 2, or 3 independent $C(=O)OR_4$, $C(=O)NR_4R_7$, or $SO_2NR_4R_7$, or alkyl; vi) halogen; vii) alkyl optionally substituted with heterocycloalkyl wherein heterocycloalkyl is optionally substituted with 1, 2, or 3 independent $C(=O)OR_4$, $C(=O)NR_4R_7$, or $SO_2NR_4R_7$; viii) hydroxyalkylamino; ix) $C(=O)NR_{15}R_{20}$; x) alkoxy optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; xi) haloalkoxy; xii) haloalkyl; xiii) hydroxy; xiv) $SO_2NR_4R_{21}$; or xv) heterocycloalkyl optionally substituted with 1, 2, or 3 independent $C(=O)OR_4$, $C(=O)NR_4R_7$, or $SO_2NR_4R_7$, or $CH_2C(=O)OR_4$;

each $R_{27}$ is independently a) H; b) alkyl optionally substituted with 1, 2, or 3 independent hydroxy, halogen, amino, alkylthio, or optionally substituted aryl; c) fluoroalkyl; d) optionally substituted aryl; or e) optionally substituted heteroaryl;

each n is independently 0, 1, 2, 3, or 4; and $Q_1$ and $Q_2$ are each independently CH or N.

Another aspect is a compound of any of the formulae herein, wherein $R_1$ is

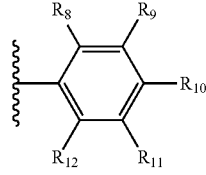

and each $R_8$, $R_9$, $R_{10}$, $R_{11}$, and $R_{12}$ is independently selected from:

a) hydrogen; b) hydroxyalkylamino; c) alkoxy optionally substituted with 1, 2, or 3 independent hydroxy, C(=O)OR$_4$, C(=O)NHNHR$_4$, or C(=O)NR$_4$OH; d) halogen; e) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; f) heteroaryl optionally substituted with 1, 2, or 3 independent:

i) C(=O)OR$_{17}$; or
  ii) heterocycloalkylcarbonyl optionally substituted with 1, 2, or 3 independent C(=O)OR$_{17}$, C(=O)NR$_4$R$_7$, or SO$_2$NR$_4$R$_7$;

g) alkyl optionally substituted with 1, 2, or 3 heterocycloalkylcarbonyl substituted with independent C(=O)OR$_4$, C(=O)NR$_4$R$_7$, or SO$_2$NR$_4$R$_7$; h) heterocycloalkylcarbonyl optionally substituted with 1, 2, or 3 independent C(=O)OR$_4$, C(=O)NR$_4$R$_7$, or SO$_2$NR$_4$R$_7$; or i) heterocycloalkylsulfonyl optionally substituted with 1, 2, or 3 independent C(=O)OR$_4$, C(=O)NR$_4$R$_7$, or SO$_2$NR$_4$R$_7$.

Another aspect is a compound of any of the formulae herein, wherein R$_1$ is

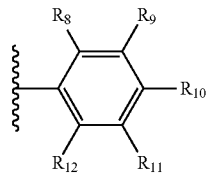

and each R$_8$, R$_9$, R$_{10}$, R$_{11}$, and R$_{12}$ is independently selected from heteroaryl optionally substituted with 1, 2, or 3 independent alkyl wherein said alkyl is optionally substituted with 1, 2, or 3 independent OC(=O)NHR$_4$, NHC(=O)NHR$_4$, NHSO$_2$R$_4$, hydroxy, or C(=O)NHR$_4$.

Another aspect is a compound of any of the formulae herein, wherein each R$_8$, R$_9$, R$_{10}$, R$_{11}$, and R$_{12}$ is independently selected from halogen, hydrogen,

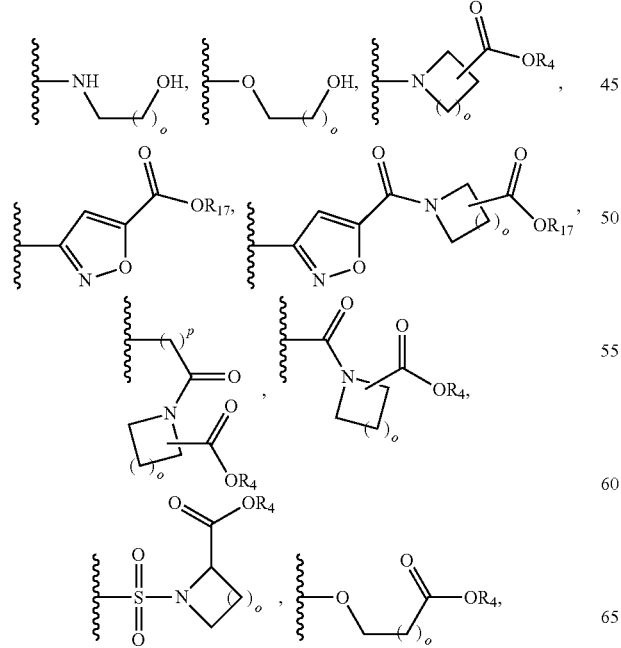

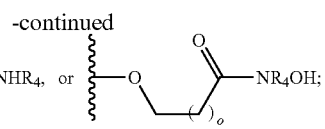

each o is independently 1, 2, 3, or 4; and
each p is independently 1, 2, 3, or 4.

Another aspect is a compound of any of the formulae herein, wherein each R$_8$, R$_9$, R$_{10}$, R$_{11}$, and R$_{12}$ is independently selected from

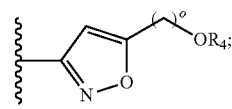

and each o is independently 1, 2, 3, or 4.

Another aspect is a compound of any of the formulae herein, wherein each R$_8$, R$_9$, R$_{10}$, R$_{11}$, and R$_{12}$ is independently selected from hydrogen,

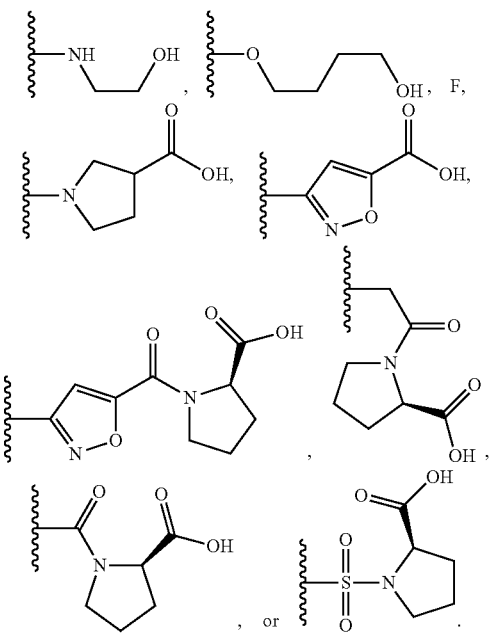

Another aspect is a compound of any of the formulae herein, wherein each R$_8$, R$_9$, R$_{10}$, R$_{11}$, and R$_{12}$ is independently selected from

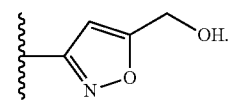

Another aspect is a compound of any of the formulae herein, wherein X is O.

Another aspect is a compound of any of the formulae herein, wherein R$_3$ is selected from NHNHR$_4$, NHNHSO$_2$R$_4$, C(=O)NR$_4$OH, or C(=O)OR$_4$.

Another aspect is a compound of any of the formulae herein, wherein $R_3$ is $NHNH_2$.

Another aspect is a compound of any of the formulae herein, wherein $R_3$ is $NHNH_2$, $R_1$ is

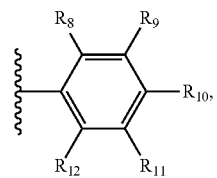

$R_{10}$ is selected from

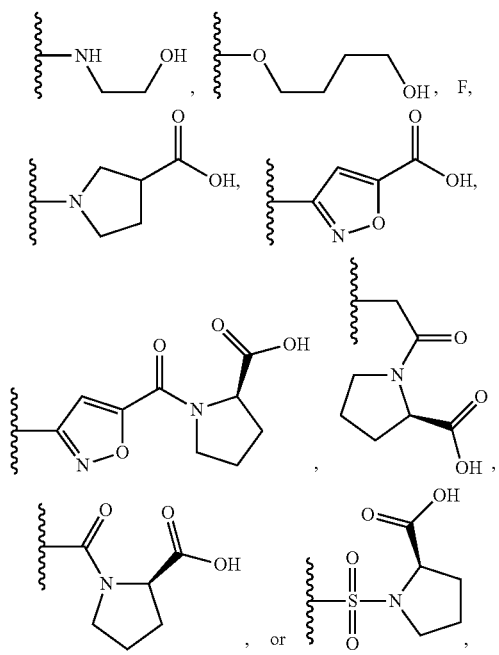

and $R_8$, $R_9$, $R_{11}$, and $R_{12}$ are each H.

Another aspect is a compound of any of the formulae herein, wherein $R_3$ is $NHNH_2$, $R_1$ is

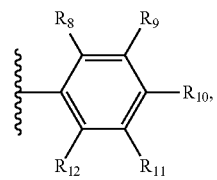

$R_{10}$ is selected from

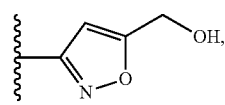 [SMILES: *c1cc(CO)on1]

and $R_8$, $R_9$, $R_{11}$, and $R_{12}$ are each H.

Another aspect is a compound of any of the formulae herein, wherein $R_1$ is $C\equiv C-R_{13}$ and $R_{13}$ is selected from:

a)

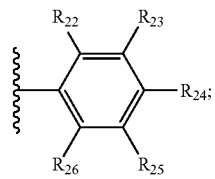

b) heterocycloalkyl optionally substituted with 1, 2, or 3 independent alkyl wherein alkyl is optionally substituted with independent:
  i) $OR_4$;
  ii) $NHC(=O)R_4$;
  iii) $C(=O)OR_4$; or
  iv) $C(=O)NHR_4$; or
c) heteroaryl optionally substituted with 1, 2, or 3 heterocycloalkylcarbonyl wherein heterocycloalkylcarbonyl is optionally substituted with 1, 2, or 3 independent $C(=O)OR_4$, $C(=O)NR_4R_7$, or $SO_2NR_4R_7$.

Another aspect is a compound of any of the formulae herein, wherein $R_1$ is $C\equiv C-R_{13}$ and $R_{13}$ is selected from:
a) heteroaryl optionally substituted with 1, 2, or 3 independent 1) heterocycloalkylcarbonyl, 2) $NR_{27}SO_2R_4$, 3) alkylaminocarbonyl, each optionally substituted with 1, 2, or 3 independent $C(=O)OR_4$, $C(=O)NR_4R_7$, or $SO_2NR_4R_7$, 4) (heterocycloalkyl)alkyl, or 5) $NR_{27}COR_4$; or b) cycloalkyl optionally substituted with 1, 2, or 3 independent $C(=O)OR_4$, $C(=O)NR_4R_7$, or $SO_2NR_4R_7$.

Another aspect is a compound of any of the formulae herein, wherein $R_1$ is $C\equiv C-R_{13}$, $R_{13}$ is

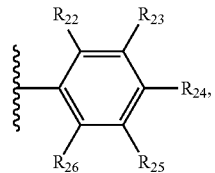

and each $R_{22}$, $R_{23}$, $R_{24}$, $R_{25}$, and $R_{26}$ is independently selected from halogen, hydrogen,

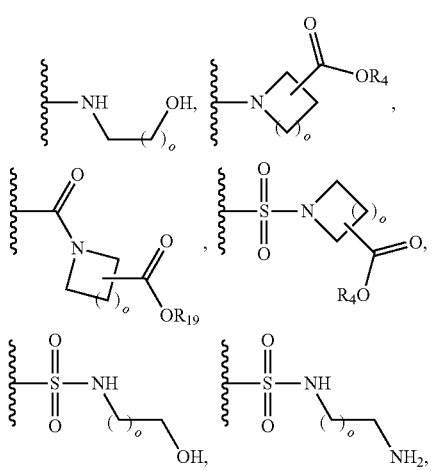

-continued

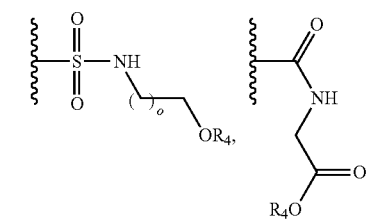

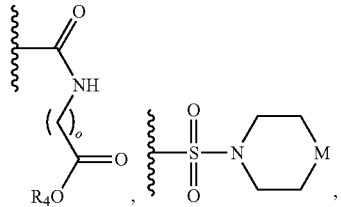

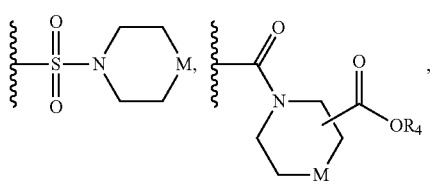

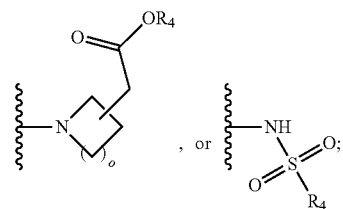

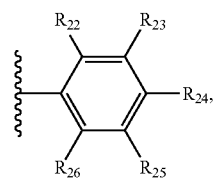, or 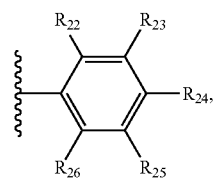

each M is independently O, CH$_2$, or S; and
each o is independently 1, 2, 3, or 4.

Another aspect is a compound of any of the formulae herein, wherein R$_1$ is C≡C—R$_{13}$, R$_{13}$ is

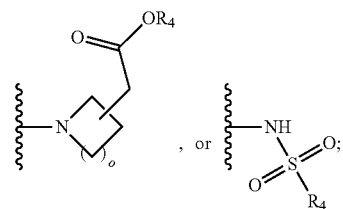

and each R$_{22}$, R$_{23}$, R$_{24}$, R$_{25}$, and R$_{26}$ is independently selected from halogen, hydrogen,

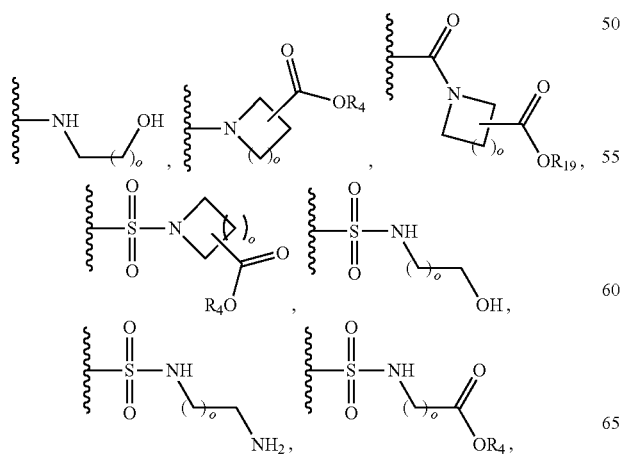

-continued

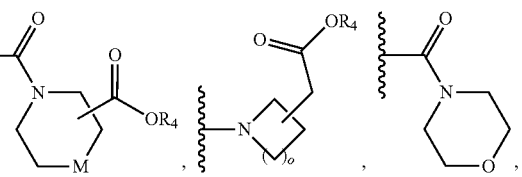

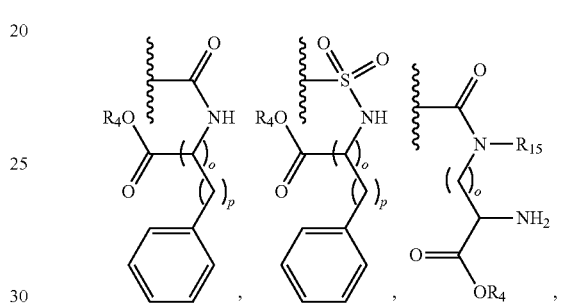

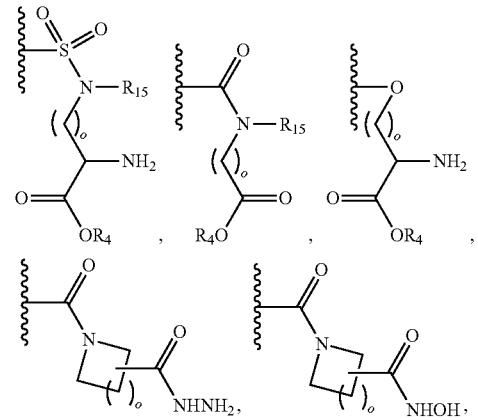

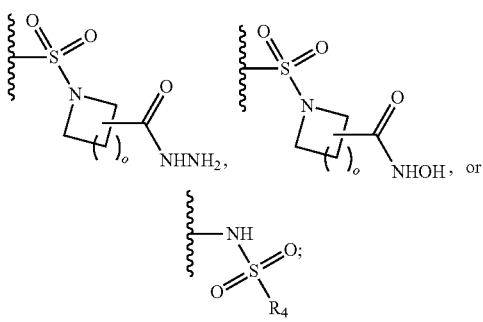

each M is independently O, CH$_2$, or S;
each o is independently 1, 2, 3, or 4; and
each p is 1, 2, 3, or 4.

Another aspect is a compound of any of the formulae herein, wherein each R$_{22}$, R$_{23}$, R$_{24}$, R$_{25}$, and R$_{26}$ is independently selected from hydrogen,

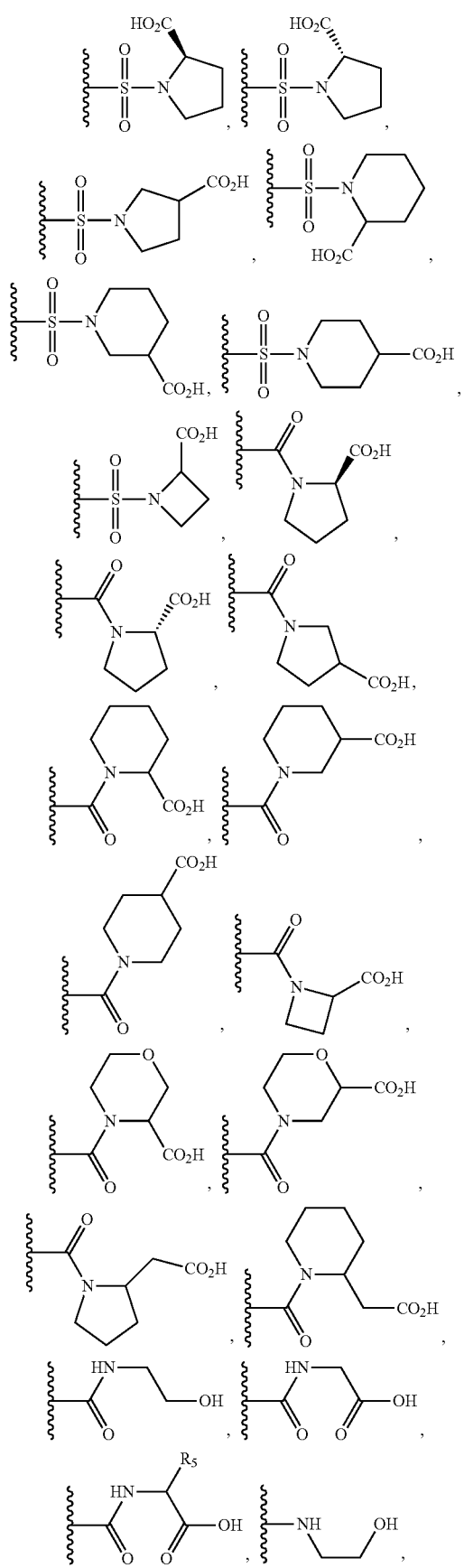
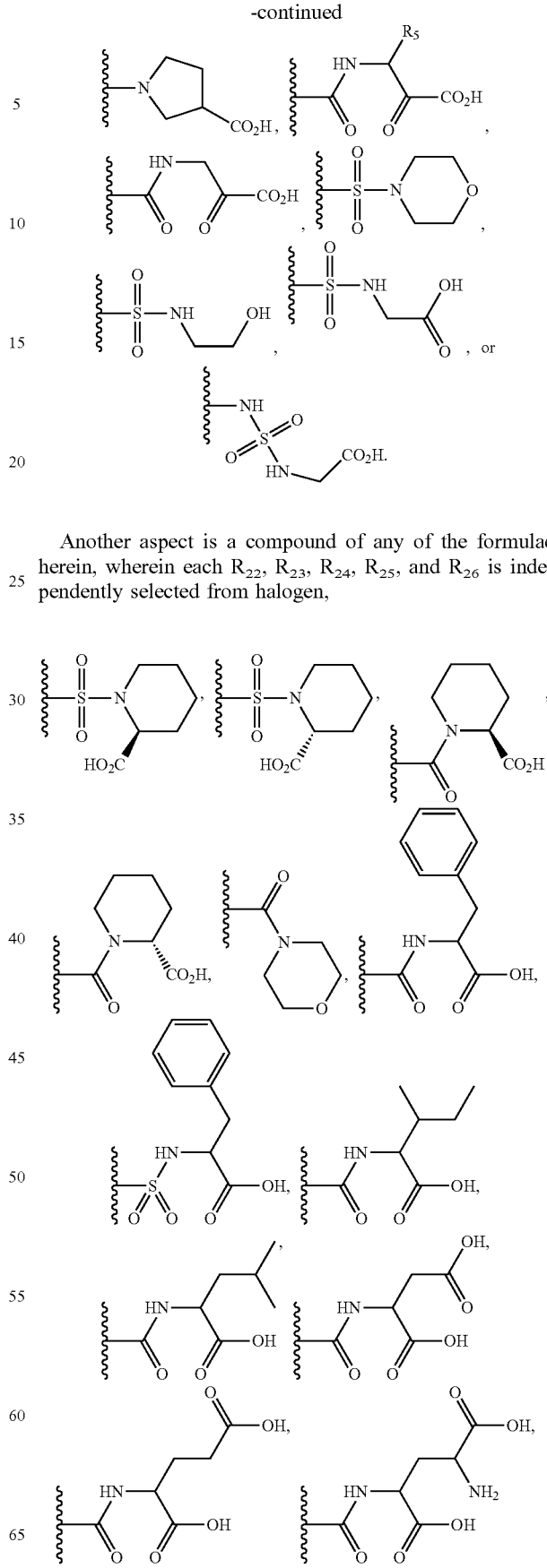
Another aspect is a compound of any of the formulae herein, wherein each $R_{22}$, $R_{23}$, $R_{24}$, $R_{25}$, and $R_{26}$ is independently selected from halogen,

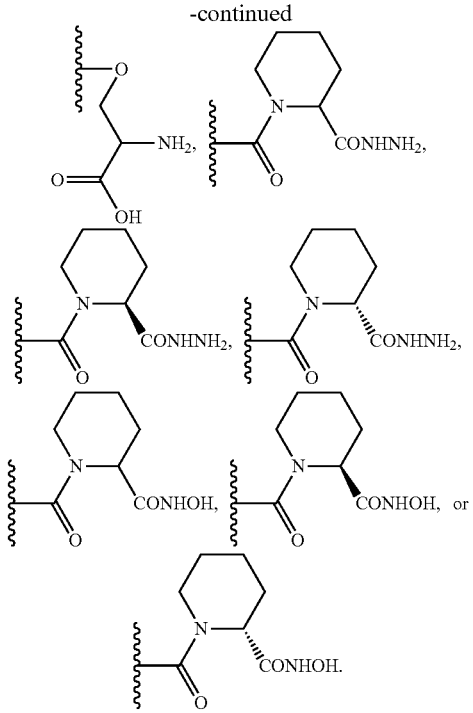
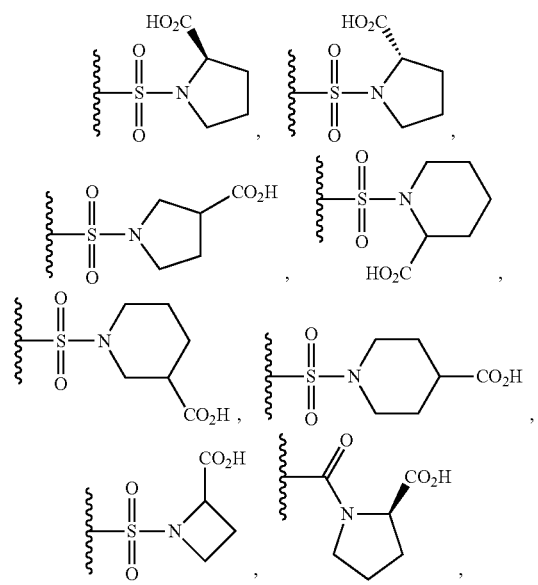
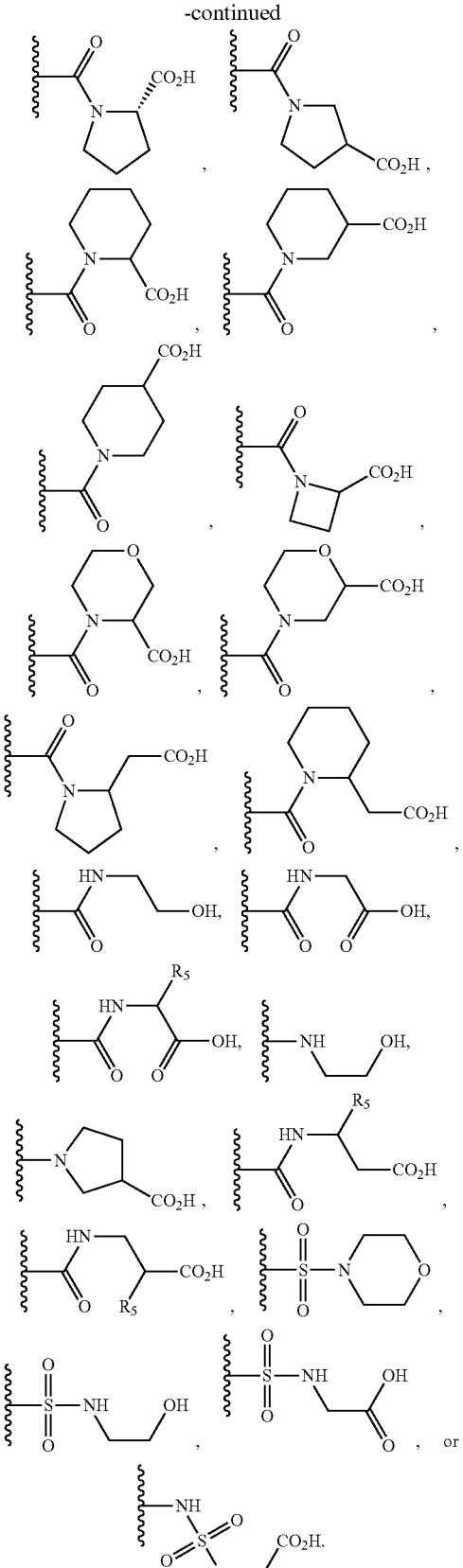
Another aspect is a compound of any of the formulae herein, wherein $R_1$ is $C{\equiv}C{-}R_{13}$, $R_{13}$ is
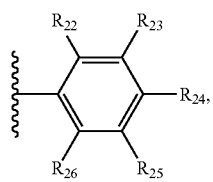
and each $R_{22}$, $R_{23}$, $R_{24}$, $R_{25}$, and $R_{26}$ is independently selected from hydrogen,
Another aspect is a compound of any of the formulae herein, wherein $R_1$ is $C{\equiv}C{-}R_{13}$, $R_{13}$ is

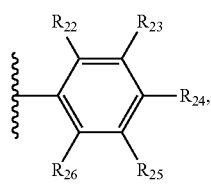
and each $R_{22}$, $R_{23}$, $R_{24}$, $R_{25}$, and $R_{26}$ is independently selected from halogen,
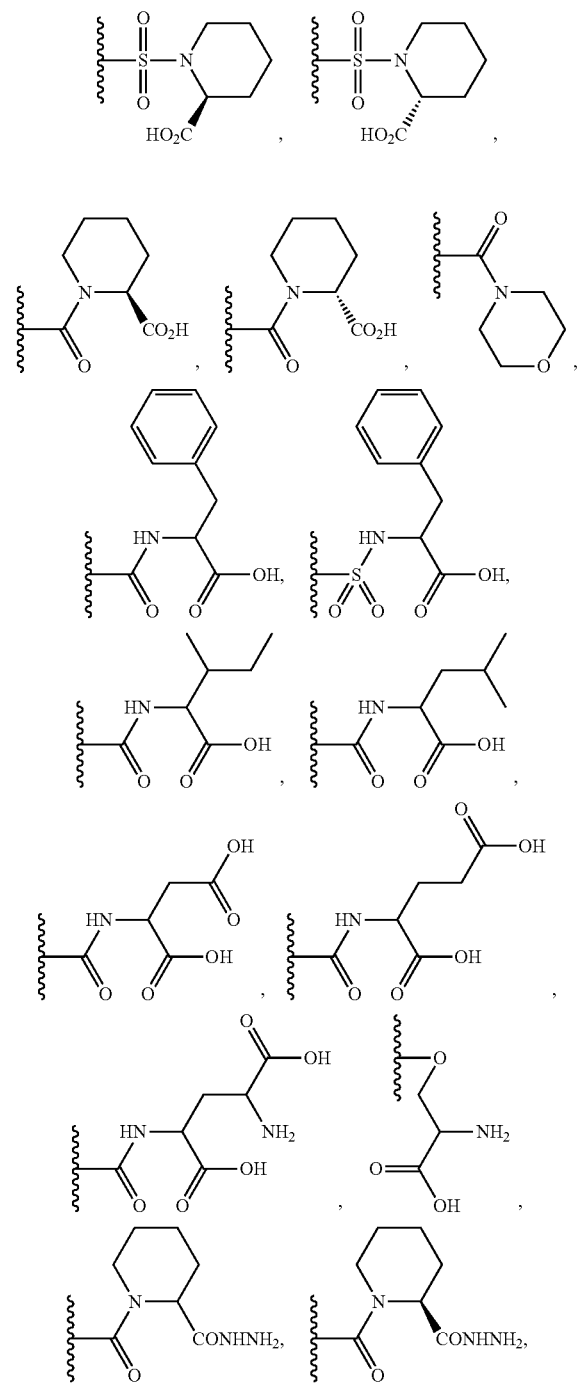
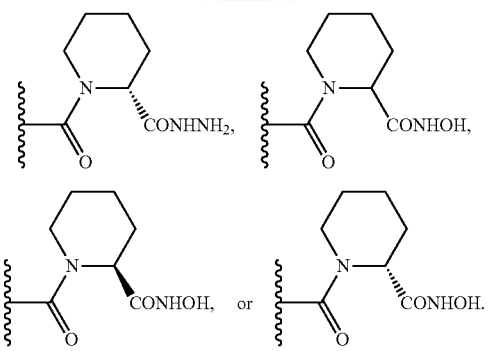
Another aspect is a compound of any of the formulae herein, wherein $R_3$ is $NHNH_2$, $R_1$ is $C{\equiv}C{-}R_{13}$, $R_{13}$ is
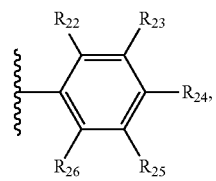
$R_{24}$ is independently selected from hydrogen,
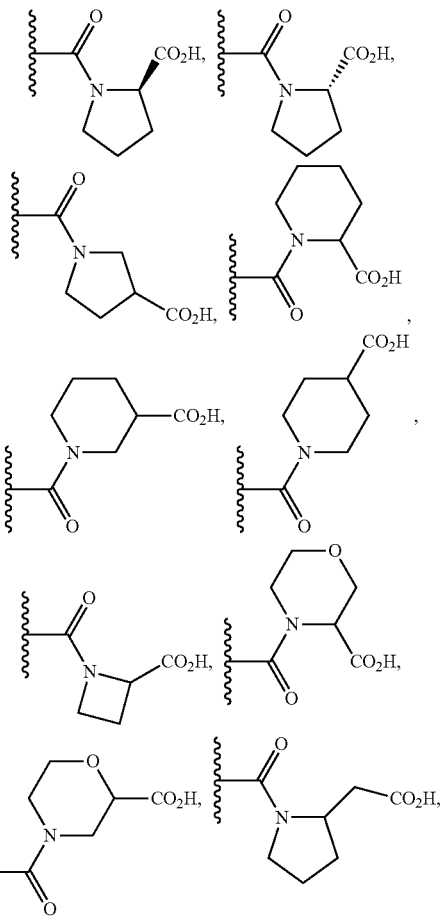

-continued

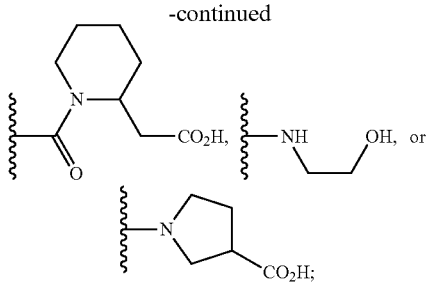

and

R$_{22}$, R$_{23}$, R$_{25}$, and R$_{26}$ are each independently hydrogen or halogen.

Another aspect is a compound of any of the formulae herein, wherein R$_3$ is NHNH$_2$, R$_1$ is C≡C—R$_{13}$, R$_{13}$ is

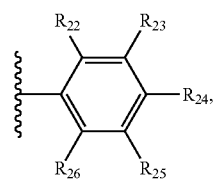

R$_{24}$ is independently selected from

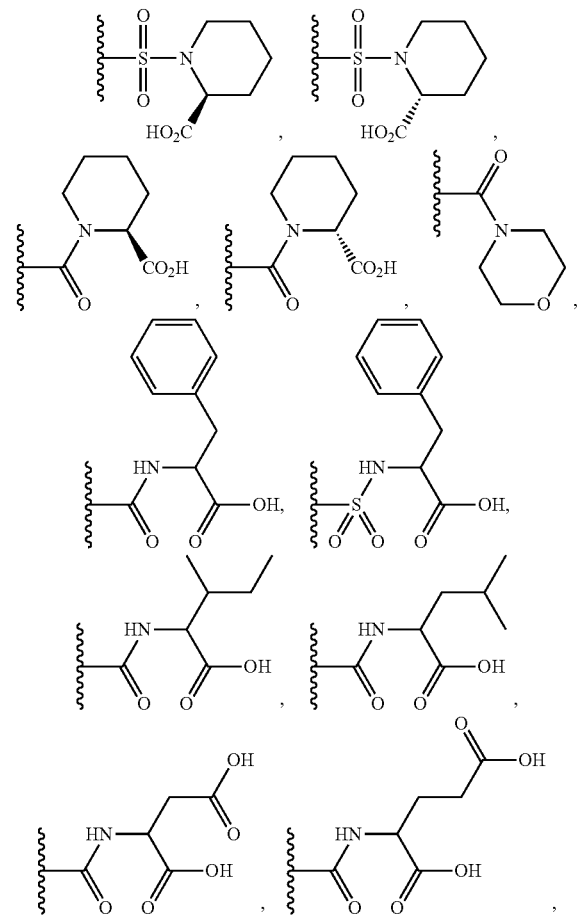

-continued

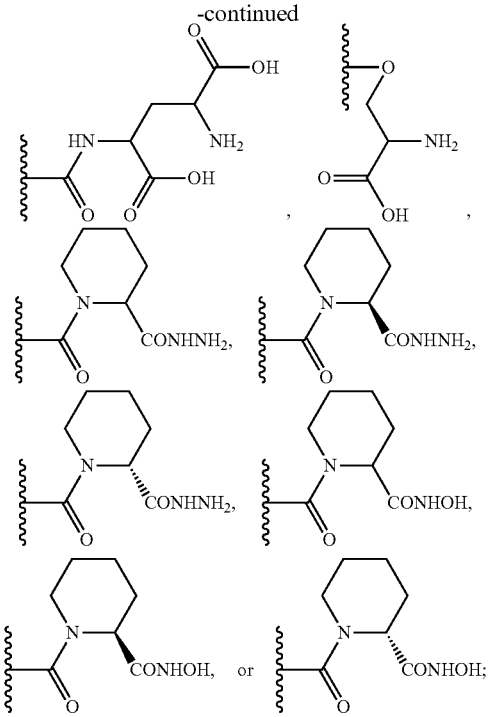

and

R$_{22}$, R$_{23}$, R$_{25}$, and R$_{26}$ are each independently hydrogen or halogen.

Another aspect is a compound of any of the formulae herein, wherein A is NR$_4$ and R$_6$ is C(=O)NR$_4$OH.

Another aspect is a compound of any of the formulae herein, wherein A is an optionally substituted heterocycle that is preferably a 5-membered ring with up to 1-4 heteroatoms and R$_6$ is null.

Another aspect is a compound of any of the formulae herein, wherein A is 5-methylimidazolidinyl-2,4-dione, 2-thioxoimidazolidin-4-one, or imidazolidine-2,4-dione.

Another aspect is a compound of any of the formulae herein, wherein A is 2-thioxoimidazolidin-4-one.

Another aspect is a compound of any of the formulae herein, wherein A is 2-thioxoimidazolidin-4-one, R$_1$ is

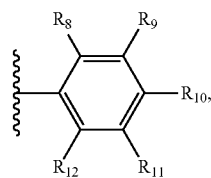

R$_{10}$ is selected from

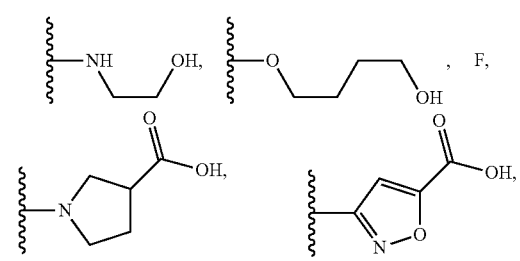

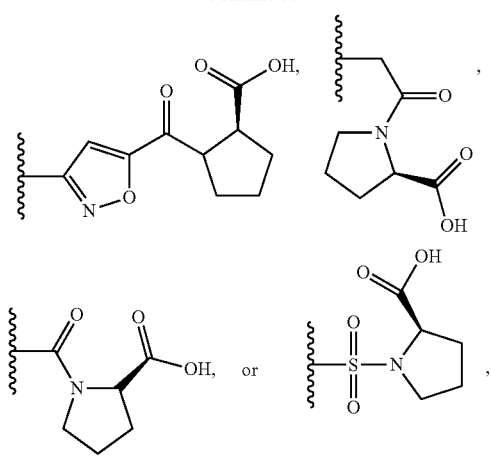

and R$_8$, R$_9$, R$_{11}$, and R$_{12}$ are each H.

Another aspect is a compound of any of the formulae herein, wherein A is 2-thioxoimidazolidin-4-one, R$_1$ is C≡C—R$_{13}$, R$_{13}$ is

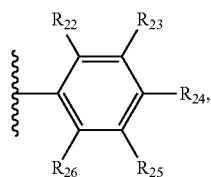

R$_{24}$ is independently selected from hydrogen,

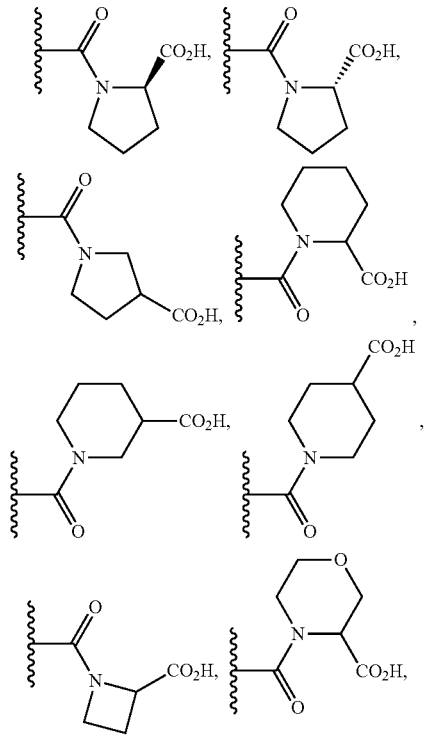

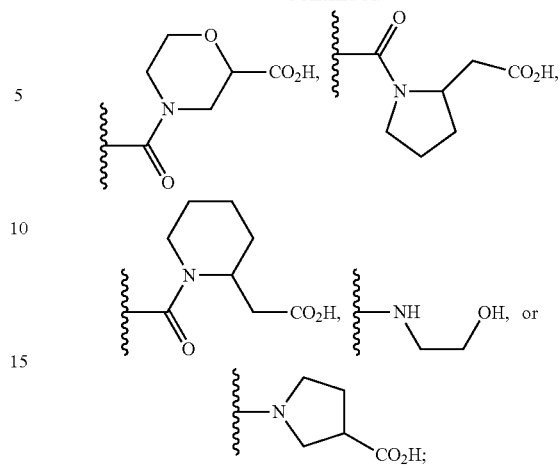

and

R$_{22}$, R$_{23}$, R$_{25}$, and R$_{26}$ are each independently hydrogen or halogen.

Another aspect is a compound of any of the formulae herein, wherein each R$_7$ is independently C(=O)OR$_4$; NHSO$_2$R$_4$; N(alkyl)SO$_2$R$_4$; NHC(=O)R$_4$; N(alkyl)C(=O)R$_4$; C(=O)NR$_{27}$R$_4$; SO$_2$NR$_{27}$R$_4$; C(=O)NR$_{27}$NHR$_4$; C(=O)NR$_{27}$OR$_4$; or heterocycloalkylcarbonyl optionally substituted with 1, 2, or 3 independent OR$_4$, C(=O)OR$_4$, or NHSO$_2$R$_4$.

Another aspect is a compound of any of the formulae herein, wherein each R$_7$ is independently

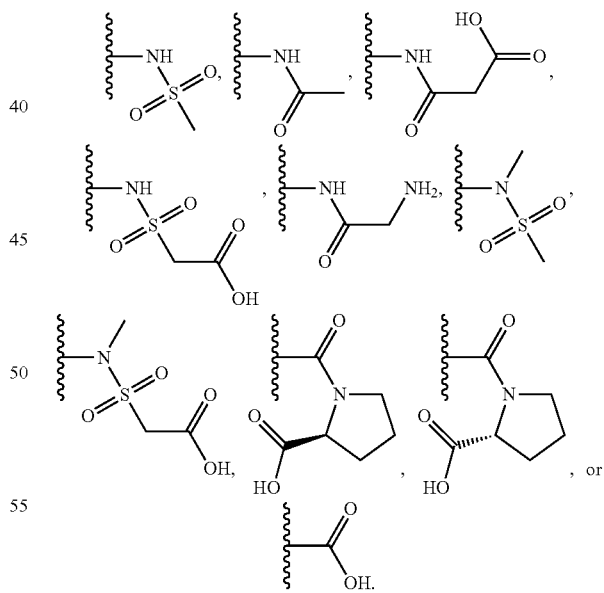

Another aspect is a compound of any of the formulae herein, wherein each R$_7$ is independently C(=O)OR$_4$, NHSO$_2$R$_4$, N(alkyl)SO$_2$R$_4$, NHC(=O)R$_4$, N(alkyl)C(=O)R$_4$, C(=O)NR$_{27}$R$_4$, SO$_2$NR$_{27}$R$_4$, C(=O)NR$_{27}$NHR$_4$, C(=O)NR$_{27}$OR$_4$, or heterocycloalkylcarbonyl optionally substituted with 1, 2, or 3 independent OR$_4$, C(=O)OR$_4$, or NHSO$_2$R$_4$; R$_1$ is

33

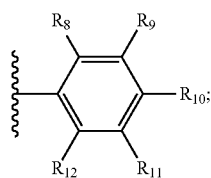

and each $R_8$, $R_9$, $R_{10}$, $R_{11}$, and $R_{12}$ is independently selected from:

a) hydrogen; b) hydroxyalkylamino; c) alkoxy optionally substituted with 1, 2, or 3 independent hydroxy, C(=O)OR$_4$, C(=O)NHNHR$_4$, or C(=O)NR$_4$OH; d) halogen; e) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; f) heteroaryl optionally substituted with 1, 2, or 3 independent:
  i) C(=O)OR$_{17}$; or
  ii) heterocycloalkylcarbonyl optionally substituted with 1, 2, or 3 independent C(=O)OR$_{17}$, C(=O)NR$_4$R$_7$, or SO$_2$NR$_4$R$_7$; or
  iii) alkyl optionally substituted with 1, 2, or 3 independent OC(=O)NHR$_4$, NHC(=O)NHR$_4$, NHSO$_2$R$_4$, hydroxy, or C(=O)NHR$_4$;
g) alkyl optionally substituted with 1, 2, or 3 heterocycloalkylcarbonyl substituted with C(=O)OR$_4$, C(=O)NR$_4$R$_7$, or SO$_2$NR$_4$R$_7$; h) heterocycloalkylcarbonyl optionally substituted with 1, 2, or 3 independent C(=O)OR$_4$, C(=O)NR$_4$R$_7$, or SO$_2$NR$_4$R$_7$; or i) heterocycloalkylsulfonyl optionally substituted with 1, 2, or 3 independent C(=O)OR$_4$, C(=O)NR$_4$R$_7$, or SO$_2$NR$_4$R$_7$.

Another aspect is a compound of any of the formulae herein, wherein $R_1$ is

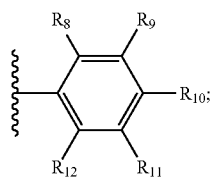

each $R_7$ is independently

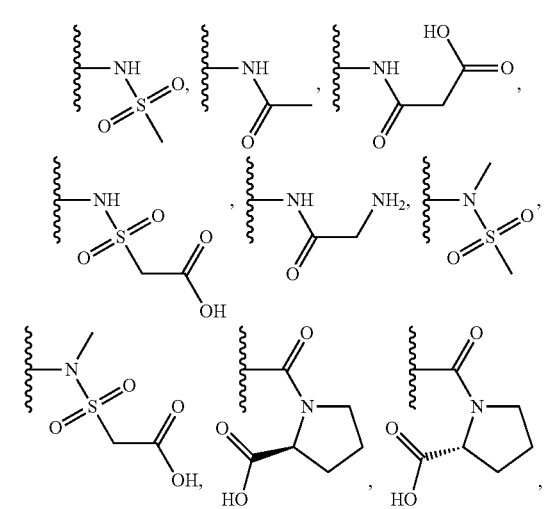

34

-continued

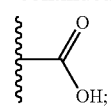

and each $R_8$, $R_9$, $R_{10}$, $R_{11}$, and $R_{12}$ is independently selected from hydrogen,

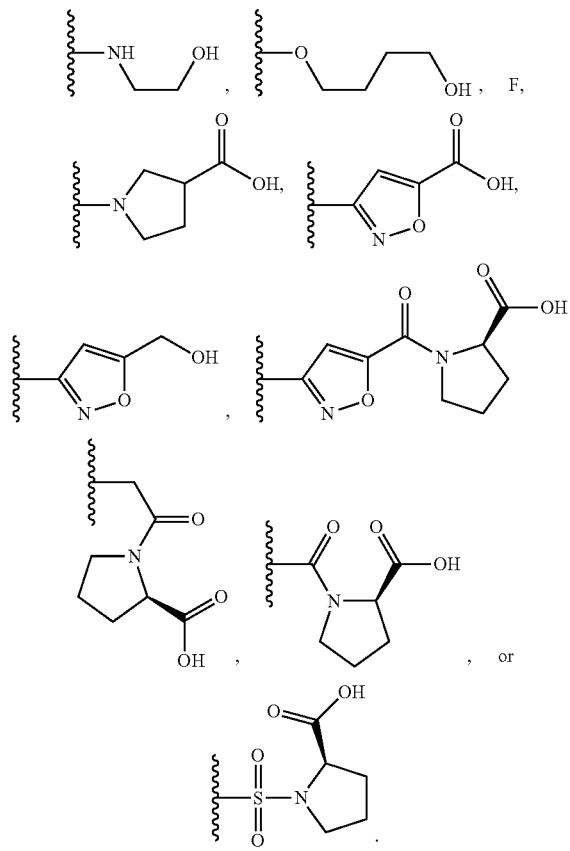

Another aspect is a compound of any of the formulae herein, wherein $R_1$ is

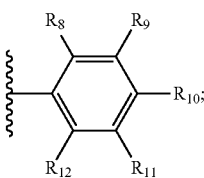

$R_{10}$ is selected from

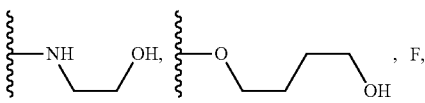

-continued

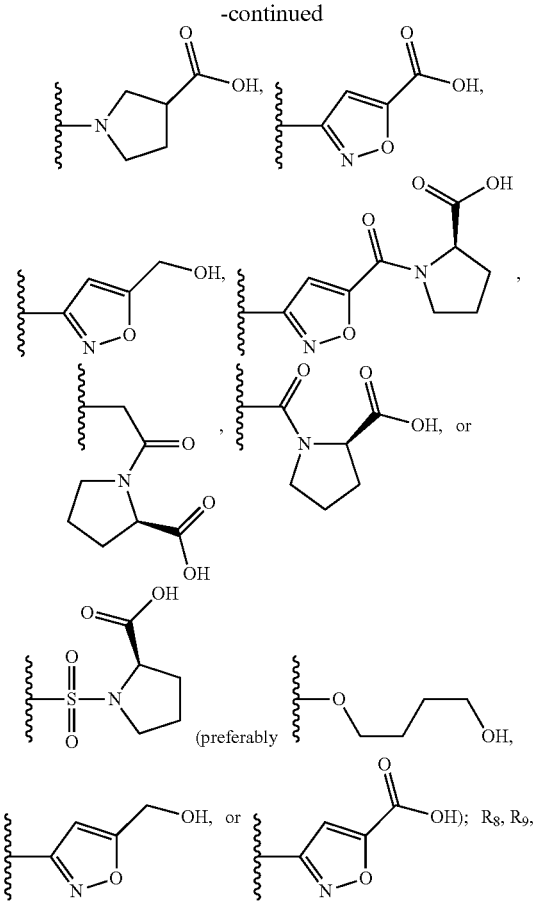

$R_{11}$, and $R_{12}$ are each H; and each $R_7$ is independently

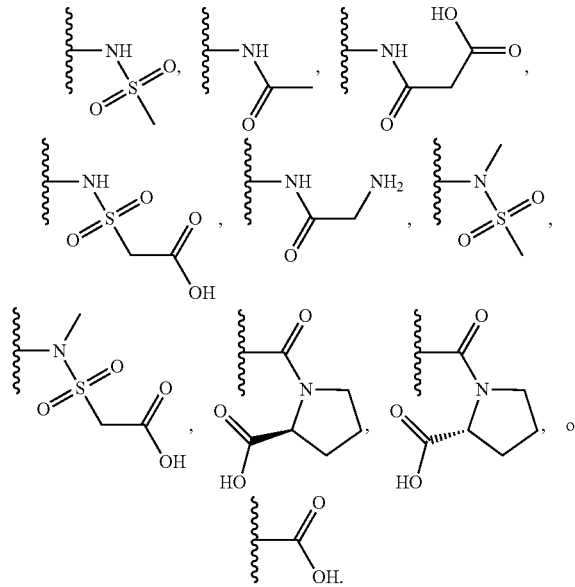

Another aspect is a compound of any of the formulae herein, wherein each $R_7$ is independently $C(=O)OR_4$, $NHSO_2R_4$, $N(alkyl)SO_2R_4$, $NHC(=O)R_4$, $N(alkyl)C(=O)R_4$, $C(=O)NR_{27}R_4$, $SO_2NR_{27}R_4$, $C(=O)NR_{27}NHR_4$, $C(=O)NR_{27}OR_4$, or heterocycloalkylcarbonyl optionally substituted with 1, 2, or 3 independent $OR_4$, $C(=O)OR_4$, or $NHSO_2R_4$; $R_1$ is $C\equiv C-R_{13}$; and $R_{13}$ is independently selected from:

a)

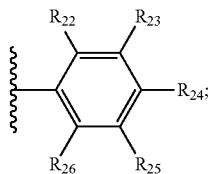

b) heterocycloalkyl optionally substituted with 1, 2, or 3 independent alkyl wherein alkyl is optionally substituted with independent:
  i) $OR_4$;
  ii) $NHC(=O)R_4$;
  iii) $C(=O)OR_4$; or
  iv) $C(=O)NHR_4$;
c) heteroaryl optionally substituted with 1, 2, or 3 independent 1) heterocycloalkylcarbonyl, 2) $NR_{27}SO_2R_4$, 3) alkylaminocarbonyl, each optionally substituted with 1, 2, or 3 independent $C(=O)OR_4$, $C(=O)NR_4R_7$, or $SO_2NR_4R_7$, 4) (heterocycloalkyl)alkyl, or 5) $NR_{27}C(=O)R_4$; or
d) cycloalkyl optionally substituted with 1, 2, or 3 independent $C(=O)OR_4$, $C(=O)NR_4R_7$, or $SO_2NR_4R_7$.

Another aspect is a compound of any of the formulae herein, wherein $R_1$ is $C\equiv C-R_{13}$; each $R_7$ is independently

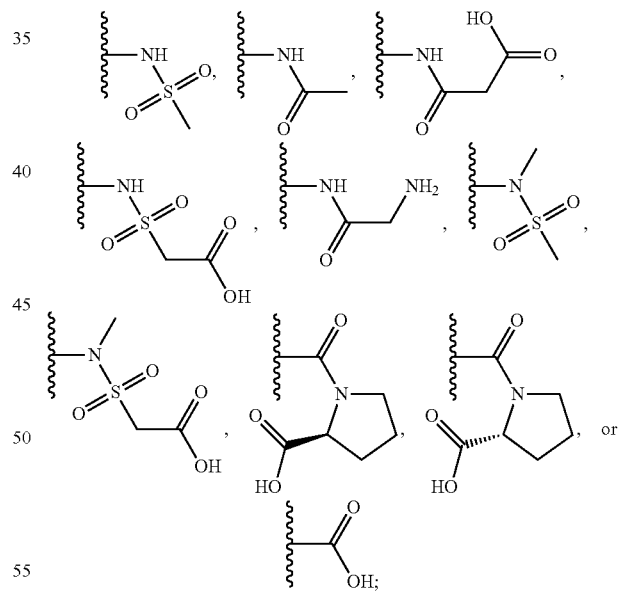

and each $R_{22}$, $R_{23}$, $R_{24}$, $R_{25}$, and $R_{26}$ is independently selected from hydrogen,

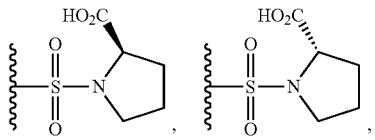

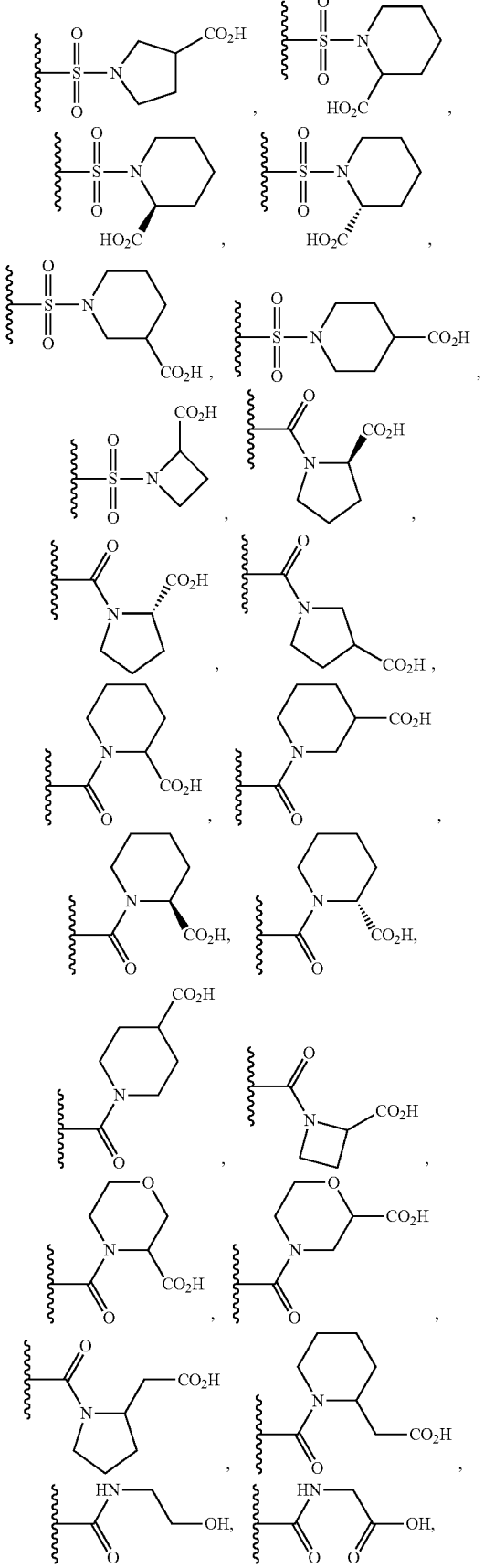
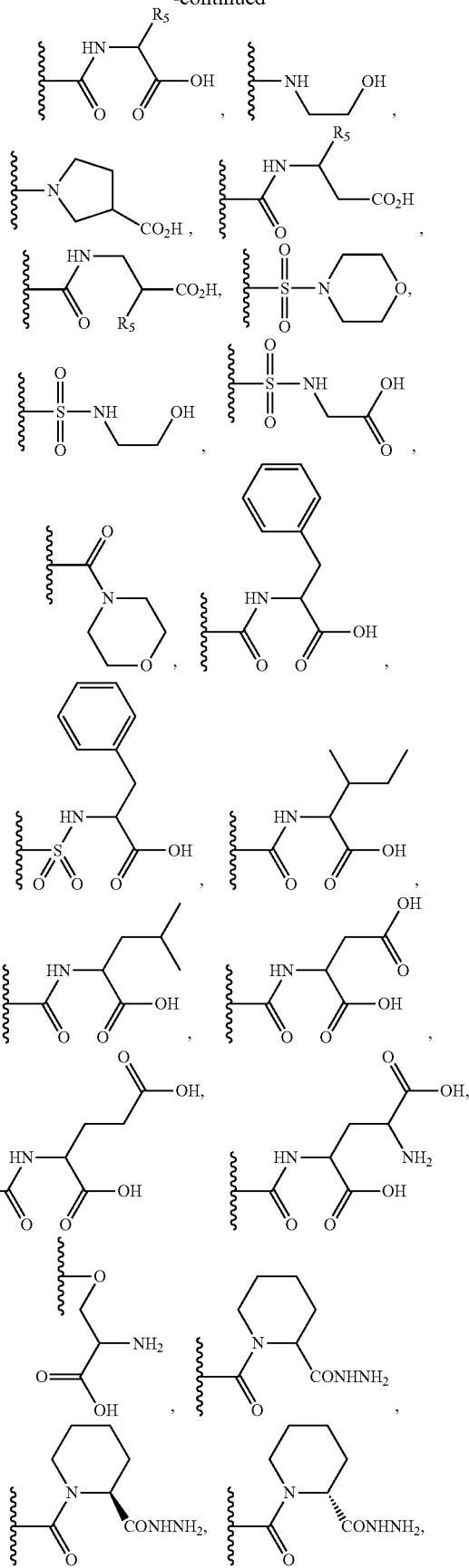

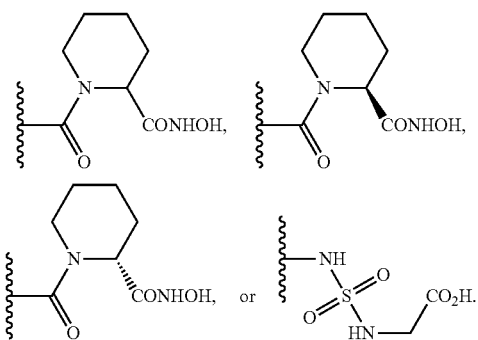

Another aspect is a compound of any of the formulae herein, wherein each $R_7$ is independently

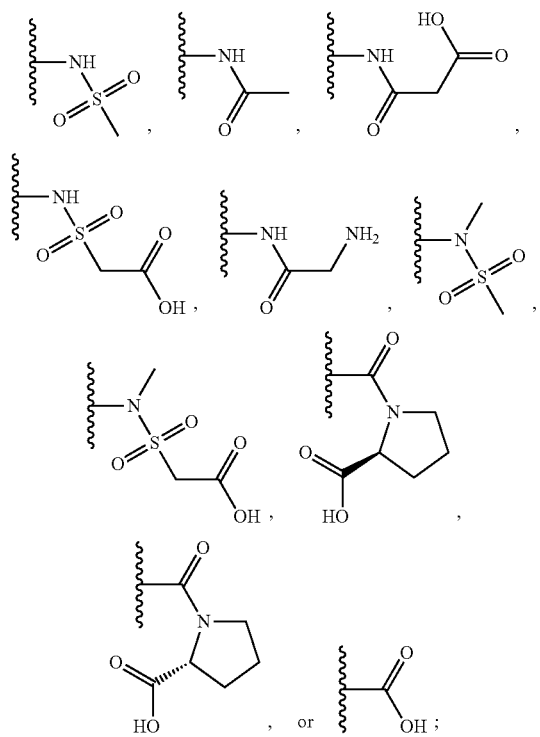

$R_3$ is $NHNH_2$, $R_1$ is $C{\equiv}C-R_{13}$; $R_{24}$ is independently selected from hydrogen,

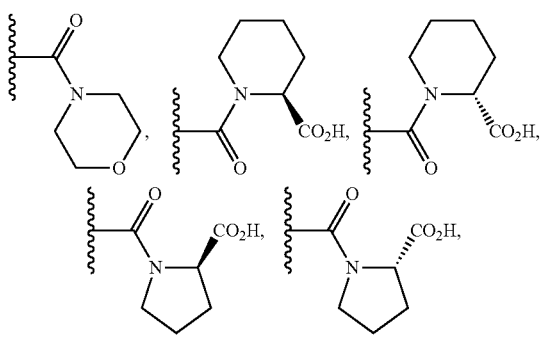

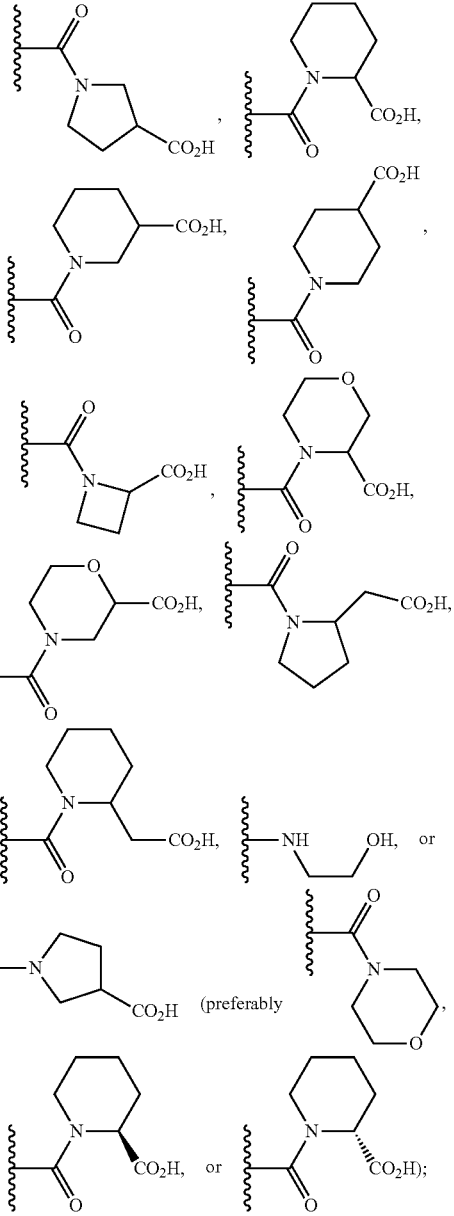

and $R_{22}$, $R_{23}$, $R_{25}$, and $R_{26}$ are each independently hydrogen or halogen.

Another aspect is a compound of any of the formulae herein, wherein:

each $R_1$ is independently 4-(hydroxyethylamino)phenyl, 4-(2-(isopropylcarbonylamino)ethoxy)phenyl, 4-(2-(methanesulfonylamino)ethoxy)phenyl, 4-(5-(hydroxymethyl)isoxazol-3-yl)phenyl, 4-(4-(2-tetrahydropyranyl)oxy)butyloxy)phenyl, 4-(4-hydroxybutyloxy)phenyl, 4-(3-aminopropyloxy)phenyl, 4-(3-(methanesulfonylamino)propyloxy)phenyl, 4-(3-(acetamido)propyloxy)phenyl, 4-fluorophenyl, 4-(methylaminosulfonyl)phenyl, 4-(acetylamino)phenyl, 4-(methylaminocarbonyl)phenyl, 4-(1-(3-carboxypyrrolidinyl)phenyl, 4-(1-(morpholino)ethanonyl)phenyl, 4-(morpholinocarbonyl)methoxyphenyl, 4-(morpholinosulfonyl)methylphenyl, 4-(5-carboxyisoxazol-3-yl)phenyl, 4-(5-(2-carboxy-1-pyrrolidinylcarbonyl)isoxazol-3-yl)phenyl, 4-(5-(((methylaminocarbonyl)oxymethyl)isoxazol-3-yl)phenyl, 4-(5-((methylaminocarbonyl)aminomethyl)isoxazol-3-yl)phenyl, 4-(5-(acetyl aminomethyl)isoxazol-3-yl)phenyl, 4-(5-((acetyl aminomethyl)isoxazol-3-yl)phenyl, 4-(5-((methylsulfonyl)aminomethyl)isoxazol-3-yl)phenyl, 4-cyanophenyl, 3-pyridyl, 4-pyridyl, 3-pyrazolyl, 4-pyrazolyl, 2-oxazolyl, 5-oxazolyl, phenyl, 4-(morpholinomethyl)phenyl, 2-hydroxyphenyl, 2-thiazolyl, 4-(methylsulfonyl)phenyl, 4-(2-hydroxyethylaminosulfonyl)phenyl, 4-(3-hydroxypropylaminosulfonyl)phenyl, 4-(3-carboxypropyloxy)phenyl, 4-(3-(hydrazinocarbonyl)propyloxy)phenyl, 4-(3-(hydroxylaminocarbonyl)propyloxy)phenyl, 4-(3-(ethyloxycarbonyl)propyloxy)phenyl, 4-(aminoethyloxy)phenyl, 4-(acetylaminoethyloxy)phenyl, 4-(1-(2-carboxypyrrolidinyl))phenyl, 4-(1-(3-carboxypiperidinyl))phenyl, 4-(1-(4-carboxypiperidinyl))phenyl, 4-(propionylaminopropyloxy)phenyl, 4-(isobutyrylaminopropyloxy)phenyl, 4-(trifluoromethylcarbonylaminopropyloxy)phenyl, 4-(ethylsulfonylaminopropyloxy)phenyl, 4-(isopropylsulfonylaminopropyloxy)phenyl, 4-(trifluoromethylsulfonylaminopropyloxy)phenyl, 4-(propionylaminoethyloxy)phenyl, 4-(trifluoromethylcarbonylaminoethyloxy)phenyl, 4-(ethylsulfonylaminoethyloxy)phenyl, 4-(isopropylsulfonylaminoethyloxy)phenyl, 4-(trifluoromethylsulfonylaminoethyloxy)phenyl, 3,4-dihydroxyphenyl, 4-(1-(2-carboxypyrrolidinylcarbonyl)methyl)phenyl, 4-(1-(2-carboxypyrrolidinylcarbonyl)methyloxy)phenyl, 4-(1-(2-carboxypyrrolidinylsulfonyl)methyl)phenyl, 4-(morpholinocarbonyl)phenyl, 4-(1-(2-carboxypyrrolidinylcarbonyl))phenyl, 4-(1-(3-carboxypiperidinylcarbonyl))phenyl, 4-(5-(morpholinocarbonyl)isoxazol-3-yl)phenyl, 4-(morpholinosulfonyl)phenyl, 4-(1-(2-carboxypyrrolidinylsulfonyl))phenyl, 4-(1-(3-carboxypiperidinylsulfonyl))phenyl, 4-(5-(methylaminocarbonyl)isoxazol-3-yl)phenyl, 4-(5-(3-carboxypiperidinyl)isoxazol-3-yl)phenyl, 4-(5-(2-carboxypiperidinyl)isoxazol-3-yl)phenyl, 4-(acetylamino)phenylethynyl, 4-(methylsulfonylamino)phenylethynyl, 4-(morpholinocarbonyl)phenylethynyl, 4-(2-carboxypyrrolidinylsulfonyl)phenylethynyl, (1-(hydroxyethyl)pyridon-4-yl)ethynyl, (1-acetylaminoethyl)pyridon-4-yl)ethynyl, (2-fluoro-4-(2-carboxypiperidinyl)carbonylphenyl)ethynyl, (3-fluoro-4-(2-carboxypiperidinyl)carbonylphenyl)ethynyl, 4-(morpholinomethyl)phenylethynyl, 4-(hydroxyethylamino)phenylethynyl, 3-(pyridyl)ethynyl, 4-(methylaminocarbonyl)phenylethynyl, 4-(methylaminosulfonyl)phenylethynyl, 4-(2-carboxypyrrolidinylcarbonyl)phenylethynyl, 4-(3-carboxypiperidinylcarbonyl)phenylethynyl, 4-(3-carboxypyrrolidinylcarbonyl)phenylethynyl, 4-(4-carboxypiperidinylcarbonyl)phenylethynyl, 4-(N-methylpiperazinocarbonyl)phenylethynyl, 4-(hydroxyethylaminocarbonyl)phenylethynyl, 4-((carboxymethyl)aminocarbonyl)phenylethynyl, 4-(2-carboxypyrrolidinylsulfonyl)phenylethynyl, 4-(3-carboxypiperidinylsulfonyl)phenylethynyl, 4-(3-carboxypyrrolidinylsulfonyl)phenylethynyl, 4-(4-carboxypiperidinylsulfonyl)phenylethynyl, 4-(morpholinosulfonyl)phenylethynyl, 4-(N-methylpiperazinylsulfonyl)phenylethynyl, 4-(hydroxyethylaminosulfonyl)phenylethynyl, 4-(hydroxypropylaminosulfonyl)phenylethynyl, 4-((carboxymethyl)aminosulfonyl)phenylethynyl, 4-(aminoethylaminocarbonyl)phenylethynyl, 4-((aminoethyl)aminocarbonyl)phenylethynyl, 4-((aminoethyl)aminosulfonyl)phenylethynyl, 4-(2-carboxyazetidinylcarbonyl)phenylethynyl, 4-(2-carboxypiperidinylcarbonyl)phenylethynyl, 4-(2-carboxyazetidinylsulfonyl)phenylethynyl, 4-(2-carboxypiperidinylsulfonyl)phenylethynyl, 4-(3-carboxy-morpholinocarbonyl)phenylethynyl, 4-(2-carboxy-morpholinocarbonyl)phenylethynyl, (1-(carboxymethyl)pyridon-4-yl)ethynyl, (1-((methylaminocarbonyl)methyl)pyridon-4-yl)ethynyl, 5-(3-carboxypiperidinylcarbonyl)thienylethynyl, 5-(2-carboxypiperidinylcarbonyl)thienylethynyl, 5-(3-carboxypiperidinylcarbonyl)furanylethynyl, 5-(2-carboxypiperidinylcarbonyl)furanylethynyl, 2-(2-carboxypiperidinylcarbonyl)pyridin-5-ylethynyl, 4-(((1-carboxyethyl)aminocarbonyl)phenylethynyl, 4-(((1-carboxy-2-methyl)propyl)aminocarbonyl)phenylethynyl, 4-(((1-carboxy-2-methyl)butyl)aminocarbonyl)phenylethynyl, 4-(((1-carboxy-3-methyl)butyl)aminocarbonyl)phenylethynyl, 4-(((1,3-di-carboxy)propyl)aminocarbonyl)phenylethynyl, 4-(((1,2-di-carboxy)ethyl)aminocarbonyl)phenylethynyl, 4-(((1-carboxy-2-hydroxy)ethyl)aminocarbonyl)phenylethynyl, 4-(((1-carboxy-2-hydroxy)propyl)aminocarbonyl)phenylethynyl, 4-(((1-carboxy-3-methylthio)propyl)aminocarbonyl)phenylethynyl, 4-(((1-carboxy-2-phenyl)ethyl)aminocarbonyl)phenylethynyl, 4-(((1-carboxy-2-(4-hydroxyphenyl)ethyl)aminocarbonyl)phenylethynyl, 4-(3-carboxy-thiomorpholino)phenylethynyl, 4-((((1-carboxy-1,1-dimethyl)methyl))aminocarbonyl)phenylethynyl, 4-(ethylsulfonylamino)phenylethynyl, 4-(isopropylsulfonylamino)phenylethynyl, 4-(trifluoromethylsulfonylamino)phenylethynyl, 4-(carboxymethylsulfonylamino)phenylethynyl, 4-(carboxymethylsulfonylamino)phenylethynyl, 4-(2-(2-carboxymethyl)pyrrolidinylcarbonyl)phenylethynyl, 4-((2-carboxymethyl)pyrrolidin-1-ylcarbonyl)phenylethynyl, 4-((2-carboxymethyl)piperidin-1-ylcarbonyl)phenylethynyl, 4-((N-methyl-N-carboxymethylamino)carbonyl)phenylethynyl, 4-((N-methyl-N-(1-carboxyethyl))aminocarbonyl)phenylethynyl, 4-((N-(2-carboxyethyl))aminocarbonyl)phenylethynyl, 4-((N-methyl-N-(2-carboxyethyl))aminocarbonyl)phenylethynyl, 4-((N-(2-carboxypropyl))aminocarbonyl)phenylethynyl, 4-((N-(2-carboxy-1-methylethyl))aminocarbonyl)phenylethynyl, 4-((N-methyl-N-(2-carboxypropyl))aminocarbonyl)phenylethynyl, 4-((N-methyl-N-(2-carboxy-1-methyl-ethyl))aminocarbonyl)phenylethynyl, 4-(((2-carboxy-2-phenyl)ethyl)aminocarbonyl)phenylethynyl, 4-(((2-carboxy-1-phenyl)ethyl)aminocarbonyl)phenylethynyl, 4-(N-(3-carboxy-4-hydroxyphenyl)aminocarbonyl)phenylethynyl, 4-(N-(3-carboxyphenyl)aminocarbonyl)phenylethynyl, 4-(N-((1,1-dicarboxy)methyl)aminocarbonyl)phenylethynyl, 2-chloro-4-((2-carboxypiperidin-1-yl)carbonyl)phenylethynyl, 4-(2-carboxyanilinocarbonyl)phenylethynyl, 2-methoxy-4-((2-carboxypiperidin-1-yl)carbonyl)phenylethynyl, 2-hydroxy-4-((2-carboxypiperidin-1-yl)carbonyl)phenylethynyl, 2-(trifluoromethyl)-4-((2-carboxypiperidin-1-yl)carbonyl)phenylethynyl, 4-((3-carboxy-4-hydroxypiperidin-1-yl)carbonyl)phenylethynyl, 2-fluoro-4-(((R)-2-carboxypiperidin-1-yl)carbonyl)phenylethynyl, 2-fluoro-4-(((S)-2-carboxypiperidin-1-yl)carbonyl)phenylethynyl, 2,5-difluoro-4-((-2-carboxypiperidin-1-yl)carbonyl)phenylethynyl, 4-(5-oxazolidin-2-onyl)phenylethynyl, 2-chloro-4-((2-carboxypiperidin-1-yl)carbonyl)phenylethynyl, 4-(N—(N-methyl-phenylalanine)carbonyl)phenylethynyl, 2-fluoro-4-(N—(N-methyl-phenylalanine)carbonyl)phenylethynyl, 4-(((3-hydroxy-4-carboxy)phenyl)aminocarbonyl)phenylethynyl, 4-(((N-methyl-1-carboxy-2-methyl)butylamino)carbonyl)phenylethynyl, 2,3-difluoro-4-((-2-carboxypiperidin-1-yl)carbonyl)phenylethynyl, 4-(((N-methyl-1-carboxy-3-methyl)butylamino)carbonyl)phenylethynyl, 2-fluoro-4-(((1-carboxy-2-methyl)butylamino)carbonyl)phenylethynyl, 4-(((N-methyl-1-carboxy-2-methyl)propylamino)carbonyl)phenylethynyl, 4-(((N-methyl-1,3-dicarboxy)propylamino)carbonyl)phenylethynyl, 2-fluoro-4-(((N-methyl-1-carboxy-2-methyl)butylamino)carbonyl)phenylethynyl, 4-(((N-methyl-1,2-dicarboxy)ethylamino)carbonyl)phenylethynyl, 3-methoxy-4-((2-carboxypiperidin-1-yl)carbonyl)phenylethynyl, 3-chloro-4-((2-carboxypiperidin-1-yl)carbonyl)phenylethynyl, 3-(trifluoromethyl)-4-((2-carboxypiperidin-1-yl)carbonyl)phenylethynyl, 3-hydroxy-4-((2-carboxypiperidin-1-yl)carbonyl)phenylethynyl, 5-((2-carboxypiperidin-1-yl)carbonyl)pyrid-2-ylethynyl, 2-chloro-4-(N—(N-methyl-phenylalanine)carbonyl)phenylethynyl, 4-(N-(phenylalanine) sulfonyl)phenylethynyl, 4-(N—(N-methyl-phenylalanine) sulfonyl)phenylethynyl, 2,6-difluoro-4-((2-carboxypiperidin-1-yl)carbonyl)phenylethynyl, 2-chloro-4-(((1-carboxy-2-methyl)butylamino)carbonyl)phenylethynyl, 4-(N—N-ethyl-1-carboxymethylamine)carbonyl)phenylethynyl, 4-(N—N-propyl-1-carboxymethylamine)carbonyl)phenylethynyl, 4-(((N-methyl-1-carboxy-2-methyl)butylamino)sulfonyl)phenylethynyl, 4-(((1-carboxy-2-methyl)butylamino)sulfonyl)phenylethynyl, 4-((carboxymethyl)benylaminocarbonyl)phenylethynyl, 2-(trifluoromethylsulfonylamino)pyrid-5-ylethynyl, 4-(N—(N-isopropyl-1-carboxymethylamine)carbonyl)phenylethynyl, 4-(N—(N-isobutyl-1-carboxymethylamine)carbonyl)phenylethynyl, 2-fluoro-4-(((1-carboxy-2-methyl)butylamino)sulfonyl)phenylethynyl, 4-(N—N-benzyl-phenylalanine)carbonyl)phenylethynyl, 2-fluoro-4-(((N-methyl-1-carboxy-2-methyl)butylamino)sulfonyl)phenylethynyl, (R)-2-fluoro-4-((2-carboxypiperidin-1-yl)sulfonyl)phenylethynyl, (S)-2-fluoro-4-((2-carboxypiperidin-1-yl)sulfonyl)phenylethynyl, 2-fluoro-4-(N-(phenylalanine)sulfonyl)phenylethynyl, 2-fluoro-4-(N—(N-methyl-phenylalanine)sulfonyl)phenylethynyl, 4-(N—(N-ethyl-phenylalanine)carbonyl)phenylethynyl, 4-(N—(N-isopropyl-phenylalanine)carbonyl)phenylethynyl, (R)-2-(2-(carboxypyrrolidinyl)methyl)pyrid-5-ylethynyl, 4-(N—(N-isobutyl-phenylalanine)carbonyl)phenylethynyl, (R)-2-chloro-4-((2-carboxypiperidin-1-yl)sulfonyl)phenylethynyl, (S)-2-chloro-4-((2-carboxypiperidin-1-yl)sulfonyl)phenylethynyl, 2-chloro-4-(((2-amino-2-carboxy)ethylamino)carbonyl)phenylethynyl, 4-(N—N-propyl-phenylalanine) carbonyl)phenylethynyl, 2-fluoro-4-((3-carboxy-piperidinyl)carbonyl)phenylethynyl, (R)-2-fluoro-4-((2-carboxy-pyrrolidinyl)carbonyl)phenylethynyl, 2-chloro-4-((3-carboxy-piperidinyl)carbonyl)phenylethynyl, (R)-2-chloro-4-((2-carboxy-pyrrolidinyl)carbonyl)phenylethynyl, 2-fluoro-4-((3-carboxy-piperidinyl)sulfonyl)phenylethynyl, (R)-2- fluoro-4-((2-carboxy-pyrrolidinyl)sulfonyl)phenylethynyl, 2-chloro-4-((N-isobutyl-N-(carboxymethyl)amino)carbonyl)phenylethynyl, 2-fluoro-4-((N-isobutyl-N- (carboxymethyl)amino)carbonyl)phenylethynyl, 2-chloro-4-((N-isobutyl-N -(carboxymethyl)amino)sulfonyl)phenylethynyl,2-fluoro-4-((N-isobutyl-N-(carboxymethyl)amino)sulfonyl)phenylethynyl, 2-chloro-4-((3-carboxy-piperidinyl)sulfonyl)phenylethynyl, (R)-2- chloro-4-((2-carboxy-pyrrolidinyl)sulfonyl)phenylethynyl, 4-(2-amino-2-carboxyethyloxy) phenylethynyl, 4-((N-isobutyl -N-(1-methyl-carboxymethyl)amino)carbonyl)phenylethynyl, 2-fluoro-4-((N-isobutyl -N-(1-methyl-carboxymethyl) amino)carbonyl)phenylethynyl, 2-chloro-4-((N-methyl-N-(2-amino-2-carboxyethyl)amino)carbonyl)phenylethynyl, 2-chloro-4-((N-isobutyl-N-(1-methyl -carboxymethyl) amino)carbonyl)phenylethynyl, 4-((N-isobutyl-N-(1-hydroxymethyl-carboxymethyl)amino)carbonyl)phenylethynyl, (S)-2-chloro-4-((2-(hydrazinocarbonyl)piperidin-1-yl)carbonyl)phenylethynyl, (S)-2-chloro-4-((2-(N-hydroxylaminocarbonyl) piperidin-1-yl)carbonyl)phenylethynyl, 4-((1-carboxy-1-(imidazol-4-ylmethyl))methylaminocarbonyl)phenylethynyl, 4-((N-isobutyl-N-(1-(4-hydroxybenzyl) -carboxymethyl)amino)carbonyl)phenylethynyl, 4-((1-methoxycarbonyl-1-(imidazol-4-ylmethyl))methylaminocarbonyl)phenylethynyl, 2-fluoro-4-((N-isobutyl-N-(1-hydroxymethyl -carboxymethyl)amino)carbonyl)phenylethynyl, 2-chloro-4-((1-carboxy-1-(imidazol-4-ylmethyl))methylaminocarbonyl) phenylethynyl, 2-fluoro-4-((1-carboxy-1-(imidazol-4-ylmethyl))methylaminocarbonyl)phenylethynyl, 2-chloro-4-((1-methoxycarbonyl-1-(imidazol-4-ylmethyl))methylaminocarbonyl)phenylethynyl, 2-fluoro-4-((1-methoxycarbonyl-1-(imidazol-4-ylmethyl))methylaminocarbonyl)phenylethynyl, 4-((1-aminomethyl-1-carboxy)methylaminocarbonyl)phenylethynyl, 2-chloro-4-((1-aminomethyl-1-carboxy)methylaminocarbonyl) phenylethynyl, 2-fluoro-4-((1-aminomethyl-1-carboxy) methylaminocarbonyl)phenylethynyl, 4-((N-isobutyl-1-aminomethyl-1-carboxy)methylaminocarbonyl) phenylethynyl, 4-(((1-aminomethyl-1-carboxy)methyl)isobutylaminocarbonyl)phenylethynyl, 2-chloro-4-(((1-aminomethyl-1-carboxy)methyl)isobutylaminocarbonyl) phenylethynyl, 2-fluoro-4-(((1-aminomethyl-1-carboxy)methyl)isobutylaminocarbonyl)phenylethynyl, 4-(2-tetrahydroimidazo[1,5-a]pyridine-1,3(2H,5H)-dionyl) phenylethynyl, 4-((N-methyl-1-aminomethyl-1-carboxy)methylaminocarbonyl)phenylethynyl, 4-(((1-aminomethyl-1-carboxy)methyl)(methylamino)carbonyl)phenylethynyl, 2-fluoro-4-(((1-aminomethyl-1-carboxy)methyl)(methylamino)carbonyl)phenylethynyl, 1-(2-carboxycyclopropyl)-buta-1,3-diynyl, 1-(2-((2-carboxypiperidinyl)carbonyl)cyclopropyl)-buta-1,3-diynyl, or 4-((2-carboxypiperidinylcarbonyl)amino)phenylethynyl. Another aspect is a compound of any of the formulae herein, wherein:

each $R_{10}$ is independently hydroxyethylamino, 2((isopropylcarbonyl)amino)ethyloxy, 2-((methanesulfonyl)amino)ethyloxy, 5-(hydroxymethyl)isoxazol-3-yl, (2-(tetrahydropyranyl)oxy)butyloxy, 4-hydroxybutyloxy, 3-aminopropyloxy, 3-((methanesulfonyl)amino)propyloxy, 3-((acetyl)amino)propyloxy, fluoro, N-methylaminosulfonyl, (methanesulfonyl)amino, (acetyl)amino, (methylamino)carbonyl, 3-carboxypyrrolidinyl, (morpholinocarbonyl)methyl, (morpholinocarbonyl)methyloxy, (morpholinosulfonyl) methyl, 5-carboxyisoxazol-3-yl, 5-((2-carboxypyrrolidinyl)carbonyl)isoxazol-3-yl, 5-(((N-methylaminocarbonyl)oxy)methyl)isoxazol-3-yl, 5-(((N-methylaminocarbonyl)amino)methyl)isoxazol-3-yl, 5- (((acetyl)amino)methyl)isoxazol-3-yl, 5-(((methanesulfonyl)amino)methyl)isoxazol-3-yl, cyano, hydrogen, morpholinomethyl, methanesulfonyl, (2-hydroxyethylamino)sulfonyl, (3-hydroxypropylamino) sulfonyl, 3-(carboxy)propyloxy, 3-(hydrazinocarbonyl)propyloxy, 3-(hydroxylaminocarbonyl)propyloxy, 3-(ethyloxycarbonyl)propyloxy, 2-aminoethyloxy, 2-((acetyl)amino) ethyloxy, 2-carboxypyrrolidinyl, 3-carboxypiperidinyl, 4-carboxypiperidinyl, 3-(propionylamino)propyloxy, 3-(isobutyrylamino)propyloxy, 3-(((trifluoromethyl)carbonyl)amino)propyloxy, 3-(ethylsulfonylamino)propyloxy, 3-(isopropylsulfonylamino)propyloxy, 3-(((trifluoromethyl)sulfonyl)amino)propyloxy, 2-(propionylamino)ethyloxy, 2-(((trifluoromethyl)carbonyl)amino)ethyloxy, 2-(ethylsulfonylamino)ethyloxy, 2-(isopropylsulfonylamino)ethyloxy, 2-(((trifluoromethyl)sulfonyl)amino)ethyloxy, hydroxy, ((2-carboxypyrrolidinyl)carbonyl)methyl, ((2-carboxypyrrolidinyl)carbonyl)methyloxy, ((2-carboxypyrrolidinyl)sulfonyl) methyl, morpholinocarbonyl, (2-carboxypyrrolidinyl)

carbonyl, (3-carboxypiperidinyl)carbonyl, 5-(morpholinocarbonyl)isoxazol-3-yl, morpholinosulfonyl, (2-carboxypyrrolidinyl)sulfonyl, (3-carboxypiperidinyl)sulfonyl, 5-(methylaminocarbonyl)isoxazol-3-yl, 5-((3-carboxypiperidinyl)carbonyl) isoxazol-3-yl, 5-((2-carboxypiperidinyl)carbonyl) isoxazol-3-yl, 5-(morpholinocarbonyl) isoxazol-3-yl, 5-(methanesulfonylaminomethyl)isoxazol-3-yl.

Another aspect is a compound of any of the formulae herein, wherein:
each $R_{24}$ is independently acetylamino, methanesulfonylamino, morpholinocarbonyl, (2-carboxypyrrolidinyl)sulfonyl, (2-carboxypiperidinyl)carbonyl, morpholinomethyl, hydroxyethylamino, methylaminocarbonyl, methylaminosulfonyl, (2-carboxypyrrolidinyl)carbonyl, (3-carboxypiperidinyl)carbonyl, (3-carboxypyrrolidinyl)carbonyl, (4-carboxypiperidinyl)carbonyl, (N-methylpiperazinyl)carbonyl, (hydroxyethylamino)carbonyl, (carboxymethylamino)carbonyl, (3-carboxypiperidinyl)sulfonyl, (3-carboxypyrrolidinyl)sulfonyl, (4-carboxypiperidinyl)sulfonyl, morpholinosulfonyl, (N-methylpiperazinyl)sulfonyl, (hydroxyethylamino)sulfonyl, (3-hydroxypropylamino)sulfonyl, (carboxymethylamino)sulfonyl, (aminoethylamino)carbonyl, (aminoethylamino)sulfonyl, (2-carboxyazetidinyl)carbonyl, (2-carboxypiperidinyl)sulfonyl, (2-carboxyazetidinyl)sulfonyl, (2-carboxymorpholinyl)carbonyl, (3-carboxymorpholinyl)carbonyl, (1-carboxyethyl)aminocarbonyl, (1-carboxy-2-methylpropyl)aminocarbonyl, (1-carboxy-2-methylbutyl)aminocarbonyl, (1-carboxy-3-methylbutyl)aminocarbonyl, (1,2-dicarboxyethyl)aminocarbonyl, (1,3-dicarboxypropyl)aminocarbonyl, (1-carboxy-2-hydroxy-ethyl)aminocarbonyl, (1-carboxy-2-hydroxypropyl)aminocarbonyl, (1-carboxy-3-(methylthio)propyl)aminocarbonyl, (1-carboxy-2-phenyl-ethyl)aminocarbonyl, (1-carboxy-2-(4-hydroxyphenyl)-ethyl)aminocarbonyl, (3-carboxy-thiomorpholino)carbonyl, (1-carboxy-1,1-dimethyl)methylaminocarbonyl, ethanesulfonylamino, isopropylsulfonylamino, trifluoromethylsulfonylamino, (carboxymethyl)sulfonylamino, 2-(carboxymethyl)pyrrolidinylcarbonyl, 2-(carboxymethyl)piperidinylcarbonyl, (N-methyl-N-(carboxymethyl)amino)carbonyl, (N-methyl-N-(1-carboxyethyl)amino)carbonyl, (N-(2-carboxyethyl)amino)carbonyl, (N-methyl-N-(2-carboxyethyl)amino)carbonyl, (N-(2-carboxypropyl)amino)carbonyl, (N-(2-carboxy-1-methylethyl)amino)carbonyl, (N-methyl-N-(2-carboxypropyl)amino)carbonyl, (N-methyl-N-(2-carboxy-1-methylethyl)amino)carbonyl, (2-carboxy-2-phenyl-ethyl)aminocarbonyl, (2-carboxy-1-phenyl-ethyl)aminocarbonyl, (3-carboxy-4-hydroxyphenyl)aminocarbonyl, (3-carboxyphenyl)aminocarbonyl, (((1,1-dicarboxy)methyl)amino)carbonyl, (2-carboxyanilino)carbonyl, 3-carboxy-4-hydroxy-piperidinylcarbonyl, (1-carboxy-1-benzyl)methylaminocarbonyl, (1-carboxy-1-benzyl)methyl(methylamino)carbonyl, 3-hydroxy-4-carboxy-anilinocarbonyl, (1-carboxy-2-methyl)butyl(methylamino)carbonyl, (1-carboxy-2-methyl)butylaminocarbonyl, (1-carboxy-3-methyl)butyl(methylamino)carbonyl, (1-carboxy-2-methyl)propyl(methylamino)carbonyl, (1,3-dicarboxy)propyl(methylamino)carbonyl, (1,2dicarboxy)ethyl(methylamino)carbonyl, (1-carboxy-1-benzyl)methylaminosulfonyl, (1-carboxy-1-benzyl)methyl(methylamino)sulfonyl, carboxymethyl(ethylamino)carbonyl, carboxymethyl(propylamino)carbonyl, (1-carboxy-2-methyl)butyl(methylamino)sulfonyl, (1-carboxy-2-methyl)butylaminosulfonyl, carboxymethyl(benzylamino)carbonyl, carboxymethyl(isopropylamino)carbonyl, carboxymethyl(isobutylamino)carbonyl, (1-carboxy-1-benzyl)methyl(benzylamino)carbonyl, (1-carboxy-1-benzyl)methyl(ethylamino)carbonyl, (1-carboxy-1-benzyl)methyl(isopropylamino)carbonyl, (1-carboxy-1-benzyl)methyl(isobutylamino)carbonyl, (1-carboxy-1-benzyl)methyl(propylamino)carbonyl, carboxymethyl(isobutylamino)sulfonyl, 2-amino-2-carboxy-ethyloxy, 1-carboxyethyl(isobutylamino)carbonyl, 2-carboxy-2-aminoethyl(methylamino)carbonyl, 2-carboxy-2-aminoethyl(isobutylamino)carbonyl, (1-carboxy-1-hydroxymethyl)methyl(isobutylamino)carbonyl, 2-(hydrazinocarbonyl)piperidinylcarbonyl, 2-(hydroxylaminocarbonyl)piperidinylcarbonyl, 1-carboxy-1-(imidazol-4-ylmethyl)methylaminocarbonyl, 1-carboxy-1-(4-hydroxyphenylmethyl)methyl(isobutylamino)carbonyl, 1-methoxycarbonyl-1-(imidazol-4-ylmethyl)methylaminocarbonyl, 1-carboxy-1-(aminomethyl)methylaminocarbonyl, 1-carboxy-1-(aminomethyl)methyl(isobutylamino)carbonyl, 2-tetrahydroimidazo[1,5-a]pyridine-1,3(2H,5H)-dionyl, 1-carboxy-1-(aminomethyl)methyl(methylamino)carbonyl, 2-carboxypiperidinylcarbonylamino.

Another aspect is a compound of any of the formulae herein, wherein:
each heteroaryl may be optionally substituted with hydroxybutyloxy, hydroxyalkyl, carboxy, carboxyheterocycloalkylcarbonyl, (alkylaminocarbonyl)oxyalkyl, (alkylaminocarbonyl)aminoalkyl, (alkylcarbonyl)aminoalkyl, (alkylsulfonyl)aminoalkyl, heterocycloalkylcarbonyl, alkylaminocarbonyl, or 2-carboxypiperidinylcarbonyl, trifluoromethylsulfonylamino.

Another aspect is a compound of any of the formulae herein, wherein:
each alkoxy may be optionally substituted with alkylcarbonylamino, alkylsulfonylamino, heterocycloalkyloxy, hydroxy, amino, heterocycloalkylcarbonyl, carboxy, hydrazinocarbonyl, hydroxylaminocarbonyl, alkoxycarbonyl, haloalkylcarbonylamino, haloalkylsulfonylamino, or carboxyheterocycloalkylcarbonyl.

Another aspect is a compound of any of the formulae herein, wherein:
each heterocycloalkyl may be optionally substituted with carboxy, (alkylaminocarbonyl)alkyl, carboxyalkyl, ((alkylaminocarbonyl)amino)alkyl, hydroxyalkyl, hydroxy, hydrazinocarbonyl, hydroxylaminocarbonyl.

Another aspect is a compound of any of the formulae herein, wherein:
each alkyl may be optionally substituted with hydroxy, halo, heterocycloalkylcarbonyl, heterocycloalkylsulfonyl, heterocycloalkyl, carboxyheterocycloalkylcarbonyl, carboxyheterocycloalkylsulfonyl, alkylcarbonylamino, carboxy, alkylaminocarbonyl, alkylthio, aryl, hydroxyaryl, alkylsulfonylamino, carboxyheterocycloalkyl, amino, heteroaryl, alkoxycarbonyl.

In one aspect, the compound of any of the formulae herein (e.g., formulae I-V) is that wherein the compound inhibits (or is identified to inhibit) UDP-3-O—[R-3-hydroxymyristoyl]-GlcNAc deacetylase (LpxC).

In one aspect, the compound of any of the formulae herein (e.g., formulae I-V) is that wherein the compound is identified as having an activity range against a target enzyme and an activity range against an off-target enzyme (e.g., LpxC IC50<1.0 μM and IC50>3.0 μM for CYP3A4; LpxC IC50<0.5 μM and IC50>1.0 μM for CYP3A4; LpxC IC50<0.24 μM and IC50>3.5 μM for CYP3A4; LpxC IC50<XX μM and IC50>YY μM for CYP3A4, in each instance XX is an independent number; in each instance YY is an independent number; in certain aspects XX is a number less than YY). In certain aspects, for example, XX is 2-fold, 5-fold, 10-fold, 50-fold, 100-fold, or 1000-fold less than YY.

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or back-bonding interactions. The compounds can also attain affinity through weaker interactions with the metal such as van der Waals interactions, pi cation interactions, pi-anion interactions, dipole-dipole interactions, ion-dipole interactions. In one aspect, the compound is identified as having a bonding interaction with the metal.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of Formulae (I-V) (and pharmaceutically acceptable salts, solvates, or hydrates thereof):

5-(2-(4'-((2-hydroxyethyl)amino)-[1,1'-biphenyl]-4-yl)-1, 6-naphthyridin-4-yl)-5-methylimidazolidine-2,4-dione (1);

1-hydroxy-3-(2-(4'-((2-hydroxyethyl)amino)-[1,1'-biphenyl]-4-yl)-1,6-naphthyridin-4-yl)urea (2);

2-(4'-((2-hydroxyethyl)amino)-[1,1'-biphenyl]-4-yl)-1,6-naphthyridine-4-carboxylic acid (3);

2-(4'-((2-hydroxyethyl)amino)-[1,1'-biphenyl]-4-yl)-1,6-naphthyridine-4-carbohydrazide (4);

N-(2-((4'-(4-(hydrazinecarbonyl)-1,6-naphthyridin-2-yl)-[1,1'-biphenyl]-4-yl)oxy)ethyl)isobutyramide (5);

N-(2-((4'-(4-(hydrazinecarbonyl)-1,6-naphthyridin-2-yl)-[1,1'-biphenyl]-4-yl)oxy)ethyl)methanesulfonamide (6);

2-(4'-(5-(hydroxymethyl)isoxazol-3-yl)-[1,1'-biphenyl]-4-yl)-1,6-naphthyridine-4-carbohydrazide (7);

3-(2-(4'-(4-((tetrahydro-2H-pyran-2-yl)oxy)butoxy)-[1,1'-biphenyl]-4-yl)-1,6-naphthyridin-4-yl)imidazolidine-2,4-dione (8);

3-(2-(4'-(4-hydroxybutoxy)-[1,1'-biphenyl]-4-yl)-1,6-naphthyridin-4-yl)imidazolidine-2,4-dione (9);

3-(2-(4'-(4-((tetrahydro-2H-pyran-2-yl)oxy)butoxy)-[1,1'-biphenyl]-4-yl)-1,6-naphthyridin-4-yl)-2-thioxoimidazolidin-4-one (10);

3-(2-(4'-(4-hydroxybutoxy)-[1,1'-biphenyl]-4-yl)-1,6-naphthyridin-4-yl)-2-thioxoimidazolidin-4-one (11);

3-(2-(4'-(4-hydroxybutoxy)-[1,1'-biphenyl]-4-yl)quinolin-4-yl)imidazolidine-2,4-dione (12);

2-(4'-(3-aminopropoxy)-[1,1'-biphenyl]-4-yl)-1,6-naphthyridine-4-carbohydrazide (13);

N-(3-((4'-(4-(hydrazinecarbonyl)-1,6-naphthyridin-2-yl)-[1,1'-biphenyl]-4-yl)oxy)propyl)methanesulfonamide (14);

N-(3-((4'-(4-(hydrazinecarbonyl)-1,6-naphthyridin-2-yl)-[1,1'-biphenyl]-4-yl)oxy)propyl)acetamide (15);

N-(4-(hydrazinecarbonyl)-2-(4'-(4-hydroxybutoxy)-[1,1'-biphenyl]-4-yl)quinolin-7-yl)methanesulfonamide (16);

N'-(2-(4'((2-hydroxyethyl)amino)-[1,1'-biphenyl]-4-yl)-1,6-naphthyridine-4-carbonyl)methanesulfonohydrazide (17);

N-hydroxy-2-(2-(4'-((2-hydroxyethyl)amino)-[1,1'-biphenyl]-4-yl)quinolin-4-yl)acetamide (18);

1-(2-(4'-fluoro-[1,1'-biphenyl]-4-yl)-1,6-naphthyridin-4-yl)imidazolidin-2-one (19);

1-(2-(4'-fluoro-[1,1'-biphenyl]-4-yl)-1,6-naphthyridin-4-yl)imidazolidine-2,4-dione (20);

5-(2-(4'-fluoro-[1,1'-biphenyl]-4-yl)-1,6-naphthyridin-4-yl)-1,3,4-oxadiazol-2-amine (21);

4'-(4-(hydrazinecarbonyl)-1,6-naphthyridin-2-yl)-N-methyl-[1,1'-biphenyl]-4-sulfonamide (22);

N-(4'-(4-(hydrazinecarbonyl)-1,6-naphthyridin-2-yl)-[1,1'-biphenyl]-4-yl)methanesulfonamide (23);

N-(4'-(4-(hydrazinecarbonyl)-1,6-naphthyridin-2-yl)-[1,1'-biphenyl]-4-yl)acetamide (24);

4'-(4-(hydrazinecarbonyl)-1,6-naphthyridin-2-yl)-N-methyl-[1,1'-biphenyl]-4-carboxamide (25);

1-(4'-(4-(hydrazinecarbonyl)-1,6-naphthyridin-2-yl)-[1,1'-biphenyl]-4-yl)pyrrolidine-3-carboxylic acid (26);

2-(4'-(2-morpholino-2-oxoethyl)-[1,1'-biphenyl]-4-yl)-1,6-naphthyridine-4-carbohydrazide (27);

2-(4'-(2-morpholino-2-oxoethoxy)-[1,1'-biphenyl]-4-yl)-1,6-naphthyridine-4-carbohydrazide (28);

2-(4'-((morpholinosulfonyl)methyl)-[1,1'-biphenyl]-4-yl)-1,6-naphthyridine-4-carbohydrazide (29);

3-(4'-(4-(hydrazinecarbonyl)-1,6-naphthyridin-2-yl)-[1,1'-biphenyl]-4-yl)isoxazole-5-carboxylic acid (30);

(R)-1-(3-(4'-(4-(hydrazinecarbonyl)-1,6-naphthyridin-2-yl)-[1,1'-biphenyl]-4-yl)isoxazole-5-carbonyl)pyrrolidine-2-carboxylic acid (31);

(3-(4'-(4-(hydrazinecarbonyl)-1,6-naphthyridin-2-yl)-[1,1'-biphenyl]-4-yl)isoxazol-5-yl)methyl methylcarbamate (32);

1-((3-(4'-(4-(hydrazinecarbonyl)-1,6-naphthyridin-2-yl)-[1,1'-biphenyl]-4-yl)isoxazol-5-yl)methyl)-3-methylurea (33);

N-((3-(4'-(4-(hydrazinecarbonyl)-1,6-naphthyridin-2-yl)-[1,1'-biphenyl]-4-yl)isoxazol-5-yl)methyl)acetamide (34);

N-((3-(4'-(4-(hydrazinecarbonyl)-1,6-naphthyridin-2-yl)-[1,1'-biphenyl]-4-yl)isoxazol-5-yl)methyl)methanesulfonamide (35);

(R)-1-(3-(4'-(4-(hydroxy(methyl)carbamoyl)-1,6-naphthyridin-2-yl)-[1,1'-biphenyl]-4-yl)isoxazole-5-carbonyl)pyrrolidine-2-carboxylic acid (36);

N-(4-(hydrazinecarbonyl)-2-(4'-(4-hydroxybutoxy)-[1,1'-biphenyl]-4-yl)quinolin-6-yl)methanesulfonamide (37);

2-(4'-cyano-[1,1'-biphenyl]-4-yl)quinoline-4-carbohydrazide (38);

2-(4'-((2-hydroxyethyl)amino)-[1,1'-biphenyl]-4-yl)-3-methyl-1,6-naphthyridine-4-carbohydrazide (39);

N'-(2-(4'-((2-hydroxyethyl)amino)-[1,1'-biphenyl]-4-yl)-3-methyl-1,6-naphthyridine-4-carbonyl)methanesulfonohydrazide (40);

N-(2-(4'((2-hydroxyethyl)amino)-[1,1'-biphenyl]-4-yl)-1,6-naphthyridin-4-yl)hydrazinecarboxamide (41);

2-(4'-((2-hydroxyethyl)amino)-[1,1'-biphenyl]-4-yl)quinoline-4-carboxylic acid (42);

2-(4'-((2-hydroxyethyl)amino)-[1,1'-biphenyl]-4-yl)quinoline-4-carbohydrazide (43);

2-(4'-((2-hydroxyethyl)amino)-[1,1'-biphenyl]-4-yl)-3-methoxy-1,6-naphthyridine-4-carbohydrazide (44);

2-(4'-((2-hydroxyethyl)amino)-[1,1'-biphenyl]-4-yl)-3-methoxy-1,6-naphthyridine-4-carboxylic acid (45);

2-(4'-((2-hydroxyethyl)amino)-[1,1'-biphenyl]-4-yl)-3-methyl-1,6-naphthyridine-4-carboxylic acid (46);

2-(4'-cyano-[1,1'-biphenyl]-4-yl)quinoline-4-carboxylic acid (47);

2-(2-(4'-((2-hydroxyethyl)amino)-[1,1'-biphenyl]-4-yl)quinolin-4-yl)acetohydrazide (48);

N-hydroxy-2-(4'((2-hydroxyethyl)amino)-[1,1'-biphenyl]-4-yl)-N-methyl-1,6-naphthyridine-4-carboxamide (49);

2-(4'-fluoro-[1,1'-biphenyl]-4-yl)-4-(hydrazinecarbonyl)-1,6-naphthyridine 6-oxide (50);

4-(hydrazinecarbonyl)-2-(4'((2-hydroxyethyl)amino)-[1,1'-biphenyl]-4-yl)-1,6-naphthyridine 6-oxide (51);

3-(2-(4'-((2-hydroxyethyl)amino)-[1,1'-biphenyl]-4-yl)quinolin-4-yl)imidazolidine-2,4-dione (52);

2-(4'-(4-hydroxybutoxy)-[1,1'-biphenyl]-4-yl)-1,6-naphthyridine-4-carbohydrazide (53);

2-(4'-cyano-[1,1'-biphenyl]-4-yl)-1,6-naphthyridine-4-carbohydrazide (54);

2-(5-(4-((2-hydroxyethyl)amino)phenyl)pyridin-2-yl)-1,6-naphthyridine-4-carbohydrazide (55);

2-(6-(4-((2-hydroxyethyl)amino)phenyl)pyridin-3-yl)-1,6-naphthyridine-4-carbohydrazide (56);

2-(4-(pyridin-3-yl)phenyl)-1,6-naphthyridine-4-carbohydrazide (57);

2-(4-(pyridin-2-yl)phenyl)-1,6-naphthyridine-4-carbohydrazide (58);

2-(4-(pyridin-4-yl)phenyl)-1,6-naphthyridine-4-carbohydrazide (59);

2-(4-(1H-pyrazol-3-yl)phenyl)-1,6-naphthyridine-4-carbohydrazide (60);

2-(4-(1H-pyrazol-4-yl)phenyl)-1,6-naphthyridine-4-carbohydrazide (61);

2-(4-(oxazol-2-yl)phenyl)-1,6-naphthyridine-4-carbohydrazide (62);

2-(4-(oxazol-5-yl)phenyl)-1,6-naphthyridine-4-carbohydrazide (63);

2-([1,1'-biphenyl]-4-yl)-1,6-naphthyridine-4-carbohydrazide (64);

2-(4'-fluoro-[1,1'-biphenyl]-4-yl)-1,6-naphthyridine-4-carbohydrazide (65);

2-(4'-(morpholinomethyl)-[1,1'-biphenyl]-4-yl)-1,6-naphthyridine-4-carbohydrazide (66);

2-(4-(5-(4-hydroxybutoxyl)pyridin-2-yl)phenyl)-1,6-naphthyridine-4-carbohydrazide (67);

2-(2'-hydroxy-[1,1'-biphenyl]-4-yl)-1,6-naphthyridine-4-carbohydrazide (68);

2-(4-(thiazol-2-yl)phenyl)-1,6-naphthyridine-4-carbohydrazide (69);

3-(2-(4'-fluoro-[1,1'-biphenyl]-4-yl)-1,6-naphthyridin-4-yl)imidazolidine-2,4-dione (70);

3-(2-(4'-fluoro-[1,1'-biphenyl]-4-yl)-1,6-naphthyridin-4-yl)-2-thioxoimidazolidin-4-one (71);

2-(4'-(methylsulfonyl)-[1,1'-biphenyl]-4-yl)-1,6-naphthyridine-4-carbohydrazide (72);

4'-(4-(hydrazinecarbonyl)-1,6-naphthyridin-2-yl)-N-(2-hydroxyethyl)-[1,1'-biphenyl]-4-sulfonamide (73);

4'-(4-(hydrazinecarbonyl)-1,6-naphthyridin-2-yl)-N-(3-hydroxypropyl)-[1,1'-biphenyl]-4-sulfonamide (74);

3-(2-(4-(5-(4-hydroxybutoxyl)pyridin-2-yl)phenyl)-1,6-naphthyridin-4-yl)-2-thioxoimidazolidin-4-one (75);

4-((4'-(4-(hydrazinecarbonyl)-1,6-naphthyridin-2-yl)-[1,1'-biphenyl]-4-yl)oxy)butanoic acid (76);

2-(4'-(4-hydrazinyl-4-oxobutoxy)-[1,1'-biphenyl]-4-yl)-1,6-naphthyridine-4-carbohydrazide (77);

4-((4'-(4-(hydrazinecarbonyl)-1,6-naphthyridin-2-yl)-[1,1'-biphenyl]-4-yl)oxy)-N-hydroxybutanamide (78);

4-((4'-(4-(2,5-dioxoimidazolidin-1-yl)-1,6-naphthyridin-2-yl)-[1,1'-biphenyl]-4-yl)oxy)-N-hydroxybutanamide (79);

4-((4'-(4-(2,5-dioxoimidazolidin-1-yl)-1,6-naphthyridin-2-yl)-[1,1'-biphenyl]-4-yl)oxy)butanoic acid (80);

ethyl 4-((4'-(4-(2,5-dioxoimidazolidin-1-yl)-1,6-naphthyridin-2-yl)-[1,1'-biphenyl]-4-yl)oxy)butanoate (81);

N-hydroxy-4-((4'-(4-(5-oxo-2-thioxoimidazolidin-1-yl)-1,6-naphthyridin-2-yl)-[1,1'-biphenyl]-4-yl)oxy)butanamide (82);

4-((4'-(4-(5-oxo-2-thioxoimidazolidin-1-yl)-1,6-naphthyridin-2-yl)-[1,1'-biphenyl]-4-yl)oxy)butanoic acid (83);

ethyl 4-((4'-(4-(5-oxo-2-thioxoimidazolidin-1-yl)-1,6-naphthyridin-2-yl)-[1,1'-biphenyl]-4-yl)oxy)butanoate (84);

2-(4'-(2-aminoethoxy)-[1,1'-biphenyl]-4-yl)-1,6-naphthyridine-4-carbohydrazide (85);

N-(2-((4'-(4-(hydrazinecarbonyl)-1,6-naphthyridin-2-yl)-[1,1'-biphenyl]-4-yl)oxy)ethyl)acetamide (86);

(R)-1-(4'-(4-(hydrazinecarbonyl)-1,6-naphthyridin-2-yl)-[1,1'-biphenyl]-4-yl)pyrrolidine-2-carboxylic acid (87);

(S)-1-(4'-(4-(hydrazinecarbonyl)-1,6-naphthyridin-2-yl)-[1,1'-biphenyl]-4-yl)pyrrolidine-2-carboxylic acid (88);

1-(4'-(4-(hydrazinecarbonyl)-1,6-naphthyridin-2-yl)-[1,1'-biphenyl]-4-yl)piperidine-3-carboxylic acid (89);

1-(4'-(4-(hydrazinecarbonyl)-1,6-naphthyridin-2-yl)-[1,1'-biphenyl]-4-yl)piperidine-4-carboxylic acid (90);

N-(3-((4'-(4-(hydrazinecarbonyl)-1,6-naphthyridin-2-yl)-[1,1'-biphenyl]-4-yl)oxy)propyl)propionamide (91);

N-(3-((4'-(4-(hydrazinecarbonyl)-1,6-naphthyridin-2-yl)-[1,1'-biphenyl]-4-yl)oxy)propyl)isobutyramide (92);

2,2,2-trifluoro-N-(3-((4'-(4-(hydrazinecarbonyl)-1,6-naphthyridin-2-yl)-[1,1'-biphenyl]-4-yl)oxy)propyl)acetamide (93);

N-(3-((4'-(4-(hydrazinecarbonyl)-1,6-naphthyridin-2-yl)-[1,1'-biphenyl]-4-yl)oxy)propyl)ethanesulfonamide (94);

N-(3-((4'-(4-(hydrazinecarbonyl)-1,6-naphthyridin-2-yl)-[1,1'-biphenyl]-4-yl)oxy)propyl)propane-2-sulfonamide (95);

1,1,1-trifluoro-N-(3-((4'-(4-(hydrazinecarbonyl)-1,6-naphthyridin-2-yl)-[1,1'-biphenyl]-4-yl)oxy)propyl)methanesulfonamide (96);

N-(2-((4'-(4-(hydrazinecarbonyl)-1,6-naphthyridin-2-yl)-[1,1'-biphenyl]-4-yl)oxy)ethyl)propionamide (97);

2,2,2-trifluoro-N-(2-((4'-(4-(hydrazinecarbonyl)-1,6-naphthyridin-2-yl)-[1,1'-biphenyl]-4-yl)oxy)ethyl)acetamide (98);

N-(2-((4'-(4-(hydrazinecarbonyl)-1,6-naphthyridin-2-yl)-[1,1'-biphenyl]-4-yl)oxy)ethyl)ethanesulfonamide (99);

N-(2-((4'-(4-(hydrazinecarbonyl)-1,6-naphthyridin-2-yl)-[1,1'-biphenyl]-4-yl)oxy)ethyl)propane-2-sulfonamide (100);

1,1,1-trifluoro-N-(2-((4'-(4-(hydrazinecarbonyl)-1,6-naphthyridin-2-yl)-[1,1'-biphenyl]-4-yl)oxy)ethylmethanesulfonamide (101);

2-(3',4'-dihydroxy-[1,1'-biphenyl]-4-yl)-1,6-naphthyridine-4-carbohydrazide (102);

(R)-1-(2-(4'-(4-(hydrazinecarbonyl)-1,6-naphthyridin-2-yl)-[1,1'-biphenyl]-4-yl)acetyl)pyrrolidine-2-carboxylic acid (103);

(R)-1-(2-((4'-(4-(hydrazinecarbonyl)-1,6-naphthyridin-2-yl)-[1,1'-biphenyl]-4-yl)oxy)acetyl)pyrrolidine-2-carboxylic acid (104);

(R)-1-(((4'-(4-(hydrazinecarbonyl)-1,6-naphthyridin-2-yl)-[1,1'-biphenyl]-4-ylmethyl)sulfonyl)pyrrolidine-2-carboxylic acid (105);

2-(4'-(morpholine-4-carbonyl)-[1,1'-biphenyl]-4-yl)-1,6-naphthyridine-4-carbohydrazide (106);

(R)-1-(4'-(4-(hydrazinecarbonyl)-1,6-naphthyridin-2-yl)-[1,1'-biphenyl]-4-carbonyl)pyrrolidine-2-carboxylic acid (107);

1-(4'-(4-(hydrazinecarbonyl)-1,6-naphthyridin-2-yl)-[1,1'-biphenyl]-4-carbonyl)piperidine-3-carboxylic acid (108);

2-(4'-(5-(morpholine-4-carbonyl)isoxazol-3-yl)-[1,1'-biphenyl]-4-yl)-1,6-naphthyridine-4-carbohydrazide (109);

2-(4'-(morpholinosulfonyl)-[1,1'-biphenyl]-4-yl)-1,6-naphthyridine-4-carbohydrazide (110);

(R)-1-((4'-(4-(hydrazinecarbonyl)-1,6-naphthyridin-2-yl)-[1,1'-biphenyl]-4-yl)sulfonyl)pyrrolidine-2-carboxylic acid (111);

1-((4'-(4-(hydrazinecarbonyl)-1,6-naphthyridin-2-yl)-[1,1'-biphenyl]-4-yl)sulfonyl)piperidine-3-carboxylic acid (112);

3-(4'-(4-(hydrazinecarbonyl)-1,6-naphthyridin-2-yl)-[1,1'-biphenyl]-4-yl)-N-methylisoxazole-5-carboxamide (113);

1-(3-(4'-(4-(hydrazinecarbonyl)-1,6-naphthyridin-2-yl)-[1,1'-biphenyl]-4-yl)isoxazole-5-carbonyl)piperidine-3-carboxylic acid (114);

1-(3-(4'-(4-(hydrazinecarbonyl)-1,6-naphthyridin-2-yl)-[1,1'-biphenyl]-4-yl)isoxazole-5-carbonyl)piperidine-2-carboxylic acid (115);

N-(4-((4-(4-(hydrazinecarbonyl)-1,6-naphthyridin-2-yl)phenyl)ethynyl)phenyl)acetamide (116);

N-(4-((4-(4-(hydrazinecarbonyl)-1,6-naphthyridin-2-yl)phenyl)ethynyl)phenyl)methanesulfonamide (117);

2-(4-((4-(morpholine-4-carbonyl)phenyl)ethynyl)phenyl)-1,6-naphthyridine-4-carbohydrazide (118);

(R)-1-((4-((4-(4-(hydrazinecarbonyl)-1,6-naphthyridin-2-yl)phenyl)ethynyl)phenyl)sulfonyl)pyrrolidine-2-carboxylic acid (119);

2-(4-((1-(2-hydroxyethyl)-2-oxo-1,2-dihydropyridin-4-yl)ethynyl)phenyl)-1,6-naphthyridine-4-carbohydrazide (120);

N-(2-(4-((4-(4-(hydrazinecarbonyl)-1,6-naphthyridin-2-yl)phenyl)ethynyl)-2-oxopyridin-1(2H)-yl)ethyl)acetamide (121);

1-(3-fluoro-4-((4-(4-(hydrazinecarbonyl)-1,6-naphthyridin-2-yl)phenyl)ethynyl)benzoyl)piperidine-2-carboxylic acid (122);

1-(4-((2-fluoro-4-(4-(hydrazinecarbonyl)-1,6-naphthyridin-2-yl)phenyl)ethynyl)benzoyl)piperidine-2-carboxylic acid (123);

2-(4-((4-(morpholinomethyl)phenyl)ethynyl)phenyl)-1,6-naphthyridine-4-carbohydrazide (124);

2-(4-((4-((2-hydroxyethyl)amino)phenyl)ethynyl)phenyl)-1,6-naphthyridine-4-carbohydrazide (125);

2-(4-(pyridin-3-ylethynyl)phenyl)-1,6-naphthyridine-4-carbohydrazide (126);

3-(2-(4-((4-(morpholinomethyl)phenyl)ethynyl)phenyl)-1,6-naphthyridin-4-yl)-2-thioxoimidazolidin-4-one (127);

4-((4-(4-(hydrazinecarbonyl)-1,6-naphthyridin-2-yl)phenyl)ethynyl)-N-methylbenzamide (128);

4-((4-(4-(hydrazinecarbonyl)-1,6-naphthyridin-2-yl)phenyl)ethynyl)-N-methylbenzenesulfonamide (129);

(S)-1-(4-((4-(4-(hydrazinecarbonyl)-1,6-naphthyridin-2-yl)phenyl)ethynyl)benzoyl)pyrrolidine-2-carboxylic acid (130);

(R)-1-(4-((4-(4-(hydrazinecarbonyl)-1,6-naphthyridin-2-yl)phenyl)ethynyl)benzoyl)pyrrolidine-2-carboxylic acid (131);

1-(4-((4-(4-(hydrazinecarbonyl)-1,6-naphthyridin-2-yl)phenyl)ethynyl)benzoyl)piperidine-3-carboxylic acid (132);

(−)-1-(4-((4-(4-(hydrazinecarbonyl)-1,6-naphthyridin-2-yl)phenyl)ethynyl)benzoyl)piperidine-3-carboxylic acid (133);

(+)-1-(4-((4-(4-(hydrazinecarbonyl)-1,6-naphthyridin-2-yl)phenyl)ethynyl)benzoyl)piperidine-3-carboxylic acid (134);

1-(4-((4-(4-(hydrazinecarbonyl)-1,6-naphthyridin-2-yl)phenyl)ethynyl)benzoyl)pyrrolidine-3-carboxylic acid (135);

1-(4-((4-(4-(hydrazinecarbonyl)-1,6-naphthyridin-2-yl)phenyl)ethynyl)benzoyl)piperidine-4-carboxylic acid (136);

2-(4-((4-(4-methylpiperazine-1-carbonyl)phenyl)ethynyl)phenyl)-1,6-naphthyridine-4-carbohydrazide (137);

4-((4-(4-(hydrazinecarbonyl)-1,6-naphthyridin-2-yl)phenyl)ethynyl)-N-(2-hydroxyethyl)benzamide (138);

4-((4-(4-(hydrazinecarbonyl)-1,6-naphthyridin-2-yl)phenyl)ethynyl)-N-(3-hydroxypropyl)benzamide (139);

2-(4-((4-(4-(hydrazinecarbonyl)-1,6-naphthyridin-2-yl)phenyl)ethynyl)benzamido)acetic acid (140);

(S)-1-((4-((4-(4-(hydrazinecarbonyl)-1,6-naphthyridin-2-yl)phenyl)ethynyl)phenyl)sulfonyl)pyrrolidine-2-carboxylic acid (141);

1-((4-((4-(4-(hydrazinecarbonyl)-1,6-naphthyridin-2-yl)phenyl)ethynyl)phenyl)sulfonyl)piperidine-3-carboxylic acid (142);

1-((4-((4-(4-(hydrazinecarbonyl)-1,6-naphthyridin-2-yl)phenyl)ethynyl)phenyl)sulfonyl)pyrrolidine-3-carboxylic acid (143);

1-((4-((4-(4-(hydrazinecarbonyl)-1,6-naphthyridin-2-yl)phenyl)ethynyl)phenyl)sulfonyl)piperidine-4-carboxylic acid (144);

2-(4-((4-(morpholinosulfonyl)phenyl)ethynyl)phenyl)-1,6-naphthyridine-4-carbohydrazide (145);

2-(4-((4-((4-methylpiperazin-1-yl)sulfonyl)phenyl)ethynyl)phenyl)-1,6-naphthyridine-4-carbohydrazide (146);

4-((4-(4-(hydrazinecarbonyl)-1,6-naphthyridin-2-yl)phenyl)ethynyl)-N-(2-hydroxyethyl)benzenesulfonamide (147);

4-((4-(4-(hydrazinecarbonyl)-1,6-naphthyridin-2-yl)phenyl)ethynyl)-N-(3-hydroxypropyl)benzenesulfonamide (148);

2-(4-((4-(4-(hydrazinecarbonyl)-1,6-naphthyridin-2-yl)phenyl)ethynyl)phenylsulfonamido)acetic acid (149);

N-(2-aminoethyl)-4-((4-(4-(hydrazinecarbonyl)-1,6-naphthyridin-2-yl)phenyl)ethynyl)benzamide (150);

N-(2-aminoethyl)-4-((4-(4-(hydrazinecarbonyl)-1,6-naphthyridin-2-yl)phenyl)ethynyl)benzenesulfonamide (151);

(R)-1-((4-((4-(4-(5-oxo-2-thioxoimidazolidin-1-yl)-1,6-naphthyridin-2-yl)phenyl)ethynyl)phenyl)sulfonyl)pyrrolidine-2-carboxylic acid (152);

(R)-1-((4-((4-(4-(2,5-dioxoimidazolidin-1-yl)-1,6-naphthyridin-2-yl)phenyl)ethynyl)phenyl)sulfonyl)pyrrolidine-2-carboxylic acid (153);

1-(4-((4-(4-(hydrazinecarbonyl)-1,6-naphthyridin-2-yl)phenyl)ethynyl)benzoyl)azetidine-2-carboxylic acid (154);

1-(4-((4-(4-(hydrazinecarbonyl)-1,6-naphthyridin-2-yl)phenyl)ethynyl)benzoyl)piperidine-2-carboxylic acid (155);

(−)-1-(4-((4-(4-(hydrazinecarbonyl)-1,6-naphthyridin-2-yl)phenyl)ethynyl)benzoyl)piperidine-2-carboxylic acid (156);

(+)-1-(4-((4-(4-(hydrazinecarbonyl)-1,6-naphthyridin-2-yl)phenyl)ethynyl)benzoyl)piperidine-2-carboxylic acid (157);

1-((4-((4-(4-(hydrazinecarbonyl)-1,6-naphthyridin-2-yl)phenyl)ethynyl)phenyl)sulfonyl)azetidine-2-carboxylic acid (158);

1-((4-((4-(4-(hydrazinecarbonyl)-1,6-naphthyridin-2-yl)phenyl)ethynyl)phenyl)sulfonyl)piperidine-2-carboxylic acid (159);

4-(4-((4-(4-(hydrazinecarbonyl)-1,6-naphthyridin-2-yl)phenyl)ethynyl)benzoyl)morpholine-3-carboxylic acid (160);

4-(4-((4-(4-(hydrazinecarbonyl)-1,6-naphthyridin-2-yl)phenyl)ethynyl)benzoyl)morpholine-2-carboxylic acid (161);

2-(4-((4-(4-(hydrazinecarbonyl)-1,6-naphthyridin-2-yl)phenyl)ethynyl)-2-oxopyridin-1(2H)-yl)acetic acid (162);

2-(4-((4-(4-(hydrazinecarbonyl)-1,6-naphthyridin-2-yl)phenyl)ethynyl)-2-oxopyridin-1(2H)-yl)-N-methylacetamide (163);

1-(5-((4-(4-(hydrazinecarbonyl)-1,6-naphthyridin-2-yl)phenyl)ethynyl)thiophene-2-carbonyl)piperidine-3-carboxylic acid (164);

1-(5-((4-(4-(hydrazinecarbonyl)-1,6-naphthyridin-2-yl)phenyl)ethynyl)thiophene-2-carbonyl)piperidine-2-carboxylic acid (165);

1-(5-((4-(4-(hydrazinecarbonyl)-1,6-naphthyridin-2-yl)phenyl)ethynyl)furan-2-carbonyl)piperidine-2-carboxylic acid (166);

1-(5-((4-(4-(hydrazinecarbonyl)-1,6-naphthyridin-2-yl)phenyl)ethynyl)furan-2-carbonyl)piperidine-3-carboxylic acid (167);

1-(5-((4-(4-(hydrazinecarbonyl)-1,6-naphthyridin-2-yl)phenyl)ethynyl)picolinoyl)piperidine-2-carboxylic acid (168);

1-(2-fluoro-4-((4-(4-(hydrazinecarbonyl)-1,6-naphthyridin-2-yl)phenyl)ethynyl)benzoyl)piperidine-2-carboxylic acid (169);

2-(4-((4-(4-(hydrazinecarbonyl)-1,6-naphthyridin-2-yl)phenyl)ethynyl)benzamido)propanoic acid (170);

2-(4-((4-(4-(hydrazinecarbonyl)-1,6-naphthyridin-2-yl)phenyl)ethynyl)benzamido)-3-methylbutanoic acid (171);

2-(4-((4-(4-(hydrazinecarbonyl)-1,6-naphthyridin-2-yl)phenyl)ethynyl)benzamido)-3-methylpentanoic acid (172);

2-(4-((4-(4-(hydrazinecarbonyl)-1,6-naphthyridin-2-yl)phenyl)ethynyl)benzamido)-4-methylpentanoic acid (173);

2-(4-((4-(4-(hydrazinecarbonyl)-1,6-naphthyridin-2-yl)phenyl)ethynyl)benzamido)succinic acid (174);

2-(4-((4-(4-(hydrazinecarbonyl)-1,6-naphthyridin-2-yl)phenyl)ethynyl)benzamido)pentanedioic acid (175);

2-(4-((4-(4-(hydrazinecarbonyl)-1,6-naphthyridin-2-yl)phenyl)ethynyl)benzamido)-3-hydroxypropanoic acid (176);

2-(4-((4-(4-(hydrazinecarbonyl)-1,6-naphthyridin-2-yl)phenyl)ethynyl)benzamido)-3-hydroxybutanoic acid (177);

2-(4-((4-(4-(hydrazinecarbonyl)-1,6-naphthyridin-2-yl)phenyl)ethynyl)benzamido)-4-(methylthio)butanoic acid (178);

2-(4-((4-(4-(hydrazinecarbonyl)-1,6-naphthyridin-2-yl)phenyl)ethynyl)benzamido)-3-phenylpropanoic acid (179);

2-(4-((4-(4-(hydrazinecarbonyl)-1,6-naphthyridin-2-yl)phenyl)ethynyl)benzamido)-3-(4-hydroxyphenyl)propanoic acid (180);

4-(4-((4-(4-(hydrazinecarbonyl)-1,6-naphthyridin-2-yl)phenyl)ethynyl)benzoyl)thiomorpholine-3-carboxylic acid (181);

2-(4-((4-(4-(hydrazinecarbonyl)-1,6-naphthyridin-2-yl)phenyl)ethynyl)benzamido)-2-methylpropanoic acid (182);

N-(4-((4-(4-(hydrazinecarbonyl)-1,6-naphthyridin-2-yl)phenyl)ethynyl)phenyl)ethanesulfonamide (183);

N-(4-((4-(4-(hydrazinecarbonyl)-1,6-naphthyridin-2-yl)phenyl)ethynyl)phenyl)propane-2-sulfonamide (184);

1,1,1-trifluoro-N-(4-((4-(4-(hydrazinecarbonyl)-1,6-naphthyridin-2-yl)phenyl)ethynyl)phenyl)methanesulfonamide (185);

2-(N-(4-((4-(4-(hydrazinecarbonyl)-1,6-naphthyridin-2-yl)phenyl)ethynyl)phenyl)sulfamoyl)acetic acid (186);

2-(1-(4-((4-(4-(hydrazinecarbonyl)-1,6-naphthyridin-2-yl)phenyl)ethynyl)benzoyl)pyrrolidin-2-yl)acetic acid (187);

2-(1-(4-((4-(4-(hydrazinecarbonyl)-1,6-naphthyridin-2-yl)phenyl)ethynyl)benzoyl)piperidin-2-yl)acetic acid (188);

2-(4-((4-(4-(hydrazinecarbonyl)-1,6-naphthyridin-2-yl)phenyl)ethynyl)-N-methylbenzamido)acetic acid (189);

2-(4-((4-(4-(hydrazinecarbonyl)-1,6-naphthyridin-2-yl)phenyl)ethynyl)-N-methylbenzamido)propanoic acid (190);

3-(4-((4-(4-(hydrazinecarbonyl)-1,6-naphthyridin-2-yl)phenyl)ethynyl)benzamido)propanoic acid (191);

3-(4-((4-(4-(hydrazinecarbonyl)-1,6-naphthyridin-2-yl)phenyl)ethynyl)-N-methylbenzamido)propanoic acid (192);

3-(4-((4-(4-(hydrazinecarbonyl)-1,6-naphthyridin-2-yl)phenyl)ethynyl)benzamido)-2-methylpropanoic acid (193);

3-(4-((4-(4-(hydrazinecarbonyl)-1,6-naphthyridin-2-yl)phenyl)ethynyl)benzamido)butanoic acid (194);

3-(4-((4-(4-(hydrazinecarbonyl)-1,6-naphthyridin-2-yl)phenyl)ethynyl)-N-methylbenzamido)-2-methylpropanoic acid (195);

3-(4-((4-(4-(hydrazinecarbonyl)-1,6-naphthyridin-2-yl)phenyl)ethynyl)-N-methylbenzamido)butanoic acid (196);

3-(4-((4-(4-(hydrazinecarbonyl)-1,6-naphthyridin-2-yl)phenyl)ethynyl)benzamido)-2-phenylpropanoic acid (197);

3-(4-((4-(4-(hydrazinecarbonyl)-1,6-naphthyridin-2-yl)phenyl)ethynyl)benzamido)-3-phenylpropanoic acid (198);

5-(4-((4-(4-(hydrazinecarbonyl)-1,6-naphthyridin-2-yl)phenyl)ethynyl)benzamido)-2-hydroxybenzoic acid (199);

3-(4-((4-(4-(hydrazinecarbonyl)-1,6-naphthyridin-2-yl)phenyl)ethynyl)benzamido)benzoic acid (200);

2-(4-((4-(4-(hydrazinecarbonyl)-1,6-naphthyridin-2-yl)phenyl)ethynyl)benzamido)malonic acid (201); or (S)-1-(3-chloro-4-((4-(4-(hydrazinecarbonyl)-1,6-naphthyridin-2-yl)phenyl)ethynyl)benzoyl)piperidine-2-carboxylic acid (202);

2-[4-(2-{4-[4-(hydrazinecarbonyl)-1,6-naphthyridin-2-yl]phenyl}ethynyl)benzamido]benzoic acid (203);

1-[4-(2-{4-[4-(hydrazinecarbonyl)-1,6-naphthyridin-2-yl]phenyl}ethynyl)-3-methoxybenzoyl]piperidine-2-carboxylic acid (204);

1-[4-(2-{4-[4-(hydrazinecarbonyl)-1,6-naphthyridin-2-yl]phenyl}ethynyl)-3-hydroxybenzoyl]piperidine-2-carboxylic acid (205);

1-[4-(2-{4-[4-(hydrazinecarbonyl)-1,6-naphthyridin-2-yl]phenyl}ethynyl)-3-(trifluoromethyl)benzoyl]piperidine-2-carboxylic acid (206);

1-[4-(2-{4-[4-(hydrazinecarbonyl)-1,6-naphthyridin-2-yl]phenyl}ethynyl)benzoyl]-4-hydroxypiperidine-3-carboxylic acid (207);

(2R)-1-[3-fluoro-4-(2-{4-[4-(hydrazinecarbonyl)-1,6-naphthyridin-2-yl]phenyl}ethynyl)benzoyl]piperidine-2-carboxylic acid (208);

(2S)-1-[3-fluoro-4-(2-{4-[4-(hydrazinecarbonyl)-1,6-naphthyridin-2-yl]phenyl}ethynyl)benzoyl]piperidine-2-carboxylic acid (209);

1-[2,5-difluoro-4-(2-{4-[4-(hydrazinecarbonyl)-1,6-naphthyridin-2-yl]phenyl}ethynyl)benzoyl]piperidine-2-carboxylic acid (210);

2-(4-{2-[4-(2-oxo-1,3-oxazolidin-5-yl)phenyl]ethynyl}phenyl)-1,6-naphthyridine-4-carbohydrazide (211);

1-[3-chloro-4-(2-{4-[4-(hydrazinecarbonyl)-1,6-naphthyridin-2-yl]phenyl}ethynyl)benzoyl]piperidine-2-carboxylic acid (212);

2-{1-[4-(2-{4-[4-(hydrazinecarbonyl)-1,6-naphthyridin-2-yl]phenyl}ethynyl)phenyl]-N-methylformamido}-3-phenylpropanoic acid (213);

2-{[3-fluoro-4-(2-{4-[4-(hydrazinecarbonyl)-1,6-naphthyridin-2-yl]phenyl}ethynyl)phenyl]formamido}-3-phenylpropanoic acid (214);

4-[4-(2-{4-[4-(hydrazinecarbonyl)-1,6-naphthyridin-2-yl]phenyl}ethynyl)benzamido]-2-hydroxybenzoic acid (215);

2-{1-[3-fluoro-4-(2-{4-[4-(hydrazinecarbonyl)-1,6-naphthyridin-2-yl]phenyl}ethynyl)phenyl]-N-methylformamido}-3-phenylpropanoic acid (216);

2-{1-[4-(2-{4-[4-(hydrazinecarbonyl)-1,6-naphthyridin-2-yl]phenyl}ethynyl)phenyl]-N-methylformamido}-3-methylpentanoic acid (217);

1-[2,3-difluoro-4-(2-{4-[4-(hydrazinecarbonyl)-1,6-naphthyridin-2-yl]phenyl}ethynyl)benzoyl]piperidine-2-carboxylic acid (218);

2-{1-[4-(2-{4-[4-(hydrazinecarbonyl)-1,6-naphthyridin-2-yl]phenyl}ethynyl)phenyl]-N-methylformamido}-4-methylpentanoic acid (219);

2-{[3-fluoro-4-(2-{4-[4-(hydrazinecarbonyl)-1,6-naphthyridin-2-yl]phenyl}ethynyl)phenyl]formamido}-3-methylpentanoic acid (220);

2-{1-[4-(2-{4-[4-(hydrazinecarbonyl)-1,6-naphthyridin-2-yl]phenyl}ethynyl)phenyl]-N-methylformamido}-3-methylbutanoic acid (221);

2-{1-[4-(2-{4-[4-(hydrazinecarbonyl)-1,6-naphthyridin-2-yl]phenyl}ethynyl)phenyl]-N-methylformamido}pentanedioic acid (222);

N-hydroxy-N-methyl-2-(4-{4-[5-(morpholine-4-carbonyl)-1,2-oxazol-3-yl]phenyl}phenyl)-1,6-naphthyridine-4-carboxamide (223);

2-{1-[3-fluoro-4-(2-{4-[4-(hydrazinecarbonyl)-1,6-naphthyridin-2-yl]phenyl}ethynyl)phenyl]-N-methylformamido}-3-methylpentanoic acid (224);

2-{1-[4-(2-{4-[4-(hydrazinecarbonyl)-1,6-naphthyridin-2-yl]phenyl}ethynyl)phenyl]-N-methylformamido}butanedioic acid (225);

1-[4-(2-{4-[4-(hydrazinecarbonyl)-1,6-naphthyridin-2-yl]phenyl}ethynyl)-2-methoxybenzoyl]piperidine-2-carboxylic acid (226);

1-[2-chloro-4-(2-{4-[4-(hydrazinecarbonyl)-1,6-naphthyridin-2-yl]phenyl}ethynyl)benzoyl]piperidine-2-carboxylic acid (227);

1-[4-(2-{4-[4-(hydrazinecarbonyl)-1,6-naphthyridin-2-yl]phenyl}ethynyl)-2-(trifluoromethyl)benzoyl]piperidine-2-carboxylic acid (228);

1-[4-(2-{4-[4-(hydrazinecarbonyl)-1,6-naphthyridin-2-yl]phenyl}ethynyl)-2-hydroxybenzoyl]piperidine-2-carboxylic acid (229);

1-[6-(2-{4-[4-(hydrazinecarbonyl)-1,6-naphthyridin-2-yl]phenyl}ethynyl)pyridine-3-carbonyl]piperidine-2-carboxylic acid (230);

N-hydroxy-2-(4-{4-[5-(methanesulfonamidomethyl)-1,2-oxazol-3-yl]phenyl}phenyl)-N-methyl-1,6-naphthyridine-4-carboxamide (231);

2-{[3-chloro-4-(2-{4-[4-(hydrazinecarbonyl)-1,6-naphthyridin-2-yl]phenyl}ethynyl)phenyl]formamido}-3-phenylpropanoic acid (232);

2-[4-(2-{4-[4-(hydrazinecarbonyl)-1,6-naphthyridin-2-yl]phenyl}ethynyl)benzenesulfonamido]-3-phenylpropanoic acid (233);

2-[N-methyl4-(2-{4-[4-(hydrazinecarbonyl)-1,6-naphthyridin-2-yl]phenyl}ethynyl)benzenesulfonamido]-3-phenylpropanoic acid (234);

1-[3,5-difluoro-4-(2-{4-[4-(hydrazinecarbonyl)-1,6-naphthyridin-2-yl]phenyl}ethynyl)benzoyl]piperidine-2-carboxylic acid (235);

2-{[3-chloro-4-(2-{4-[4-(hydrazinecarbonyl)-1,6-naphthyridin-2-yl]phenyl}ethynyl)phenyl]formamido}-3-methylpentanoic acid (236);

2-{N-ethyl-1-[4-(2-{4-[4-(hydrazinecarbonyl)-1,6-naphthyridin-2-yl]phenyl}ethynyl)phenyl]formamido}acetic acid (237);

2-{1-[4-(2-{4-[4-(hydrazinecarbonyl)-1,6-naphthyridin-2-yl]phenyl}ethynyl)phenyl]-N-propylformamido}acetic acid (238);

2-[4-(2-{4-[4-(hydrazinecarbonyl)-1,6-naphthyridin-2-yl]phenyl}ethynyl)benzenesulfonamido]-3-methylpentanoic acid (239);

3-methyl-2-[N-methyl4-(2-{4-[4-(hydrazinecarbonyl)-1,6-naphthyridin-2-yl]phenyl}ethynyl)benzenesulfonamido]pentanoic acid (240);

2-{N-benzyl-1-[4-(2-{4-[4-(hydrazinecarbonyl)-1,6-naphthyridin-2-yl]phenyl}ethynyl)phenyl]formamido}acetic acid (241);

N-hydroxy-N-methyl-2-{4-[2-(6-trifluoromethanesulfonamidopyridin-3-yl)ethynyl]phenyl}-1,6-naphthyridine-4-carboxamide (242);

2-{1-[4-(2-{4-[4-(hydrazinecarbonyl)-1,6-naphthyridin-2-yl]phenyl}ethynyl)phenyl]-Nropan-2-yl)formamido}acetic acid (243);

2-{1-[4-(2-{4-[4-(hydrazinecarbonyl)-1,6-naphthyridin-2-yl]phenyl}ethynyl)phenyl]-N-(2-methylpropyl)formamido}acetic acid (244);

N-hydroxy-N-methyl-2-{4-[2-(4-trifluoromethanesulfonamidophenyl)ethynyl]phenyl}-1,6-naphthyridine-4-carboxamide (245);

2-[3-fluoro-4-(2-{4-[4-(hydrazinecarbonyl)-1,6-naphthyridin-2-yl]phenyl}ethynyl)benzenesulfonamido]-3-methylpentanoic acid (246);

2-{N-benzyl-1-[4-(2-{4-[4-(hydrazinecarbonyl)-1,6-naphthyridin-2-yl]phenyl}ethynyl)phenyl]formamido}-3-phenylpropanoic acid (247);

3-methyl-2-[N-methyl3-fluoro-4-(2-{4-[4-(hydrazinecarbonyl)-1,6-naphthyridin-2-yl]phenyl}ethynyl)benzenesulfonamido]pentanoic acid (248);

(2R)-1-[3-fluoro-4-(2-{4-[4-(hydrazinecarbonyl)-1,6-naphthyridin-2-yl]phenyl}ethynyl)benzenesulfonyl]piperidine-2-carboxylic acid (249);

(2S)-1-[3-fluoro-4-(2-{4-[4-(hydrazinecarbonyl)-1,6-naphthyridin-2-yl]phenyl}ethynyl)benzenesulfonyl]piperidine-2-carboxylic acid (250);

2-[3-fluoro-4-(2-{4-[4-(hydrazinecarbonyl)-1,6-naphthyridin-2-yl]phenyl}ethynyl)benzenesulfonamido]-3-phenylpropanoic acid (251);

2-[N-methyl3-fluoro-4-(2-{4-[4-(hydrazinecarbonyl)-1,6-naphthyridin-2-yl]phenyl}ethynyl)benzenesulfonamido]-3-phenylpropanoic acid (252);

1-[4-(2-{5-[4-(hydrazinecarbonyl)-1,6-naphthyridin-2-yl]pyridin-2-yl}ethynyl)benzoyl]piperidine-2-carboxylic acid (253);

1-[3-fluoro-4-(2-{2-fluoro-4-[4-(hydrazinecarbonyl)-1,6-naphthyridin-2-yl]phenyl}ethynyl)benzoyl]piperidine-2-carboxylic acid (254);

2-{N-ethyl-1-[4-(2-{4-[4-(hydrazinecarbonyl)-1,6-naphthyridin-2-yl]phenyl}ethynyl)phenyl]formamido}-3-phenylpropanoic acid (255);

2-{1-[4-(2-{4-[4-(hydrazinecarbonyl)-1,6-naphthyridin-2-yl]phenyl}ethynyl)phenyl]-Nropan-2-yl)formamido}-3-phenylpropanoic acid (256);

1-{3-fluoro-4-[2-(4-{4-[hydroxy(methyl)carbamoyl]-1,6-naphthyridin-2-yl}phenyl)ethynyl]benzoyl}piperidine-2-carboxylic acid (257);

(2R)-1-{[5-(2-{4-[4-(hydrazinecarbonyl)-1,6-naphthyridin-2-yl]phenyl}ethynyl)pyridin-2-yl]methyl}pyrrolidine-2-carboxylic acid (258);

2-{1-[4-(2-{4-[4-(hydrazinecarbonyl)-1,6-naphthyridin-2-yl]phenyl}ethynyl)phenyl]-N-(2-methylpropyl)formamido}-3-phenylpropanoic acid (259);

(2R)-1-[3-chloro-4-(2-{4-[4-(hydrazinecarbonyl)-1,6-naphthyridin-2-yl]phenyl}ethynyl)benzenesulfonyl]piperidine-2-carboxylic acid (260);

(2S)-1-[3-chloro-4-(2-{4-[4-(hydrazinecarbonyl)-1,6-naphthyridin-2-yl]phenyl}ethynyl)benzenesulfonyl]piperidine-2-carboxylic acid (261);

2-amino-3-{[3-chloro-4-(2-{4-[4-(hydrazinecarbonyl)-1,6-naphthyridin-2-yl]phenyl}ethynyl)phenyl]formamido}propanoic acid (262);

2-{1-[4-(2-{4-[4-(hydrazinecarbonyl)-1,6-naphthyridin-2-yl]phenyl}ethynyl)phenyl]-N-propylformamido}-3-phenylpropanoic acid (263);

1-[4-(2-{2-chloro-4-[4-(hydrazinecarbonyl)-1,6-naphthyridin-2-yl]phenyl}ethynyl)benzoyl]piperidine-2-carboxylic acid (264);

1-[3-fluoro-4-(2-{4-[4-(hydrazinecarbonyl)-1,6-naphthyridin-2-yl]phenyl}ethynyl)benzoyl]piperidine-3-carboxylic acid (265);

(2R)-1-[3-fluoro-4-(2-{4-[4-(hydrazinecarbonyl)-1,6-naphthyridin-2-yl]phenyl}ethynyl)benzoyl]pyrrolidine-2-carboxylic acid (266);

1-[3-chloro-4-(2-{4-[4-(hydrazinecarbonyl)-1,6-naphthyridin-2-yl]phenyl}ethynyl)benzoyl]piperidine-3-carboxylic acid (267);

(2R)-1-[3-chloro-4-(2-{4-[4-(hydrazinecarbonyl)-1,6-naphthyridin-2-yl]phenyl}ethynyl)benzoyl]pyrrolidine-2-carboxylic acid (268);

1-[3-fluoro-4-(2-{4-[4-(hydrazinecarbonyl)-1,6-naphthyridin-2-yl]phenyl}ethynyl)benzenesulfonyl]piperidine-3-carboxylic acid (269);

(2R)-1-[3-fluoro-4-(2-{4-[4-(hydrazinecarbonyl)-1,6-naphthyridin-2-yl]phenyl}ethynyl)benzenesulfonyl]pyrrolidine-2-carboxylic acid (270);

2-{1-[3-chloro-4-(2-{4-[4-(hydrazinecarbonyl)-1,6-naphthyridin-2-yl]phenyl}ethynyl)phenyl]-N-(2-methylpropyl)formamido}acetic acid (271);

2-{1-[3-fluoro-4-(2-{4-[4-(hydrazinecarbonyl)-1,6-naphthyridin-2-yl]phenyl}ethynyl)phenyl]-N-(2-methylpropyl)formamido}acetic acid (272);

2-[N-(2-methylpropyl)3-chloro-4-(2-{4-[4-(hydrazinecarbonyl)-1,6-naphthyridin-2-yl]phenyl}ethynyl)benzenesulfonamido]acetic acid (273);

2-[N-(2-methylpropyl)3-fluoro-4-(2-{4-[4-(hydrazinecarbonyl)-1,6-naphthyridin-2-yl]phenyl}ethynyl)benzenesulfonamido]acetic acid (274);

1-[3-chloro-4-(2-{4-[4-(hydrazinecarbonyl)-1,6-naphthyridin-2-yl]phenyl}ethynyl)benzenesulfonyl]piperidine-3-carboxylic acid (275);

(2R)-1-[3-chloro-4-(2-{4-[4-(hydrazinecarbonyl)-1,6-naphthyridin-2-yl]phenyl}ethynyl)benzenesulfonyl]pyrrolidine-2-carboxylic acid (276);

2-amino-3-[4-(2-{4-[4-(hydrazinecarbonyl)-1,6-naphthyridin-2-yl]phenyl}ethynyl)phenoxy]propanoic acid (277);

1-[4-(2-{4-[4-(hydrazinecarbonyl)-1,6-naphthyridin-2-yl]-2-methoxyphenyl}ethynyl)benzoyl]piperidine-2-carboxylic acid (278);

2-{1-[4-(2-{4-[4-(hydrazinecarbonyl)-1,6-naphthyridin-2-yl]phenyl}ethynyl)phenyl]-N-(2-methylpropyl)formamido}propanoic acid (279);

1-[4-(2-{4-[4-(hydrazinecarbonyl)-1,6-naphthyridin-2-yl]-2-hydroxyphenyl}ethynyl)benzoyl]piperidine-2-carboxylic acid (280);

2-[4-(2-{4-[(2S)-2-carboxypiperidine-1-carbonyl]-2-chlorophenyl}ethynyl)phenyl]-1,6-naphthyridine-4-carboxylic acid (281);

2-{1-[3-fluoro-4-(2-{4-[4-(hydrazinecarbonyl)-1,6-naphthyridin-2-yl]phenyl}ethynyl)phenyl]-N-(2-methylpropyl)formamido}propanoic acid (282);

2-amino-3-{1-[3-chloro-4-(2-{4-[4-(hydrazinecarbonyl)-1,6-naphthyridin-2-yl]phenyl}ethynyl)phenyl]-N-methylformamido}propanoic acid (283);

2-{1-[3-chloro-4-(2-{4-[4-(hydrazinecarbonyl)-1,6-naphthyridin-2-yl]phenyl}ethynyl)phenyl]-N-(2-methylpropyl)formamido}propanoic acid (284);

2-{1-[4-(2-{4-[4-(hydrazinecarbonyl)-1,6-naphthyridin-2-yl]phenyl}ethynyl)phenyl]-N-(2-methylpropyl)formamido}-3-hydroxypropanoic acid (285);

2-[4-(2-{2-chloro-4-[(2S)-2-(hydrazinecarbonyl)piperidine-1-carbonyl]phenyl}ethynyl)phenyl]-1,6-naphthyridine-4-carbohydrazide (286);

2-[4-(2-{2-chloro-4-[(2S)-2-(hydrazinecarbonyl)piperidine-1-carbonyl]phenyl}ethynyl)phenyl]-1,6-naphthyridine-4-carboxylic acid (287);

(2S)-1-[3-chloro-4-(2-{4-[4-(hydrazinecarbonyl)-1,6-naphthyridin-2-yl]phenyl}ethynyl)benzoyl]-N-hydroxypiperidine-2-carboxamide (288);

2-{[4-(2-{4-[4-(hydrazinecarbonyl)-1,6-naphthyridin-2-yl]phenyl}ethynyl)phenyl]formamido}-3-(1H-imidazol-4-yl)propanoic acid (289);

2-{1-[4-(2-{4-[4-(hydrazinecarbonyl)-1,6-naphthyridin-2-yl]phenyl}ethynyl)phenyl]-N-(2-methylpropyl)formamido}-3-(4-hydroxyphenyl)propanoic acid (290);

methyl 2-{[4-(2-{4-[4-(hydrazinecarbonyl)-1,6-naphthyridin-2-yl]phenyl}ethynyl)phenyl]formamido}-3-(1H-imidazol-4-yl)propanoate (291);

2-{1-[3-fluoro-4-(2-{4-[4-(hydrazinecarbonyl)-1,6-naphthyridin-2-yl]phenyl}ethynyl)phenyl]-N-(2-methylpropyl)formamido}-3-hydroxypropanoic acid (292);

2-{1-[3-fluoro-4-(2-{4-[4-(hydrazinecarbonyl)-1,6-naphthyridin-2-yl]phenyl}ethynyl)phenyl]-N-(2-methylpropyl)formamido}-3-hydroxypropanoic acid (293);

2-{1-[3-fluoro-4-(2-{4-[4-(hydrazinecarbonyl)-1,6-naphthyridin-2-yl]phenyl}ethynyl)phenyl]-N-(2-methylpropyl)formamido}-3-hydroxypropanoic acid (294);

methyl 2-{[3-chloro-4-(2-{4-[4-(hydrazinecarbonyl)-1,6-naphthyridin-2-yl]phenyl}ethynyl)phenyl]formamido}-3-(1H-imidazol-4-yl)propanoate (295);

methyl 2-{[3-fluoro-4-(2-{4-[4-(hydrazinecarbonyl)-1,6-naphthyridin-2-yl]phenyl}ethynyl)phenyl]formamido}-3-(1H-imidazol-4-yl)propanoate (296);

3-amino-2-{[4-(2-{4-[4-(hydrazinecarbonyl)-1,6-naphthyridin-2-yl]phenyl}ethynyl)phenyl]formamido}propanoic acid (297);

3-amino-2-{[3-chloro-4-(2-{4-[4-(hydrazinecarbonyl)-1,6-naphthyridin-2-yl]phenyl}ethynyl)phenyl]formamido}propanoic acid (298);

3-amino-2-{[3-fluoro-4-(2-{4-[4-(hydrazinecarbonyl)-1,6-naphthyridin-2-yl]phenyl}ethynyl)phenyl]formamido}propanoic acid (299);

(2S)-1-[3-chloro-4-(2-{4-[7-chloro-4-(hydrazinecarbonyl)-1,6-naphthyridin-2-yl]phenyl}ethynyl)benzoyl]piperidine-2-carboxylic acid (300);

3-amino-2-{1-[4-(2-{4-[4-(hydrazinecarbonyl)-1,6-naphthyridin-2-yl]phenyl}ethynyl)phenyl]-N-(2-methylpropyl)formamido}propanoic acid (301);

3-amino-2-{1-[3-chloro-4-(2-{4-[4-(hydrazinecarbonyl)-1,6-naphthyridin-2-yl]phenyl}ethynyl)phenyl]-N-(2-methylpropyl)formamido}propanoic acid (302);

3-amino-2-{1-[3-fluoro-4-(2-{4-[4-(hydrazinecarbonyl)-1,6-naphthyridin-2-yl]phenyl}ethynyl)phenyl]-N-(2-methylpropyl)formamido}propanoic acid (303);

2-{4-[2-(4-{1,3-dioxo-octahydroimidazolidino[1,5-a]pyridin-2-yl}phenyl)ethynyl]phenyl}-1,6-naphthyridine-4-carbohydrazide (304);

3-amino-2-{1-[4-(2-{4-[4-(hydrazinecarbonyl)-1,6-naphthyridin-2-yl]phenyl}ethynyl)phenyl]-N-methylformamido}propanoic acid (305);

(2S)-1-[4-(2-{4-[7-amino-4-(hydrazinecarbonyl)-1,6-naphthyridin-2-yl]phenyl}ethynyl)-3-chlorobenzoyl]piperidine-2-carboxylic acid (306);

3-amino-2-{1-[3-fluoro-4-(2-{4-[4-(hydrazinecarbonyl)-1,6-naphthyridin-2-yl]phenyl}ethynyl)phenyl]-N-methylformamido}propanoic acid (307);

1-[4-(2-{5-[4-(hydrazinecarbonyl)-1,6-naphthyridin-2-yl]thiophen-2-yl}ethynyl)benzoyl]piperidine-2-carboxylic acid (308);

(2S)-1-[3-chloro-4-(2-{4-[4-(hydrazinecarbonyl)-7-methanesulfonamido-1,6-naphthyridin-2-yl]phenyl}ethynyl)benzoyl]piperidine-2-carboxylic acid (309);

(2S)-1-[3-chloro-4-(2-{4-[4-(hydrazinecarbonyl)-7-methoxy-1,6-naphthyridin-2-yl]phenyl}ethynyl)benzoyl]piperidine-2-carboxylic acid (310);

2-(4-{4-[4-(hydrazinecarbonyl)-1,6-naphthyridin-2-yl]phenyl}buta-1,3-diyn-1-yl)cyclopropane-1-carboxylic acid (311);

(2S)-1-[3-chloro-4-(2-{4-[7-acetamido-4-(hydrazinecarbonyl)-1,6-naphthyridin-2-yl]phenyl}ethynyl)benzoyl]piperidine-2-carboxylic acid (312);

(2S)-1-[3-chloro-4-(2-{4-[4-(hydrazinecarbonyl)-7-(morpholin-4-yl)-1,6-naphthyridin-2-yl]phenyl}ethynyl)benzoyl]piperidine-2-carboxylic acid (313);

1-[2-(4-{4-[4-(hydrazinecarbonyl)-1,6-naphthyridin-2-yl]phenyl}buta-1,3-diyn-1-yl)cyclopropanecarbonyl]piperidine-2-carboxylic acid (314);

(2S)-1-[4-(2-{4-[7-(2-carboxyacetamido)-4-(hydrazinecarbonyl)-1,6-naphthyridin-2-yl]phenyl}ethynyl)-3-chlorobenzoyl]piperidine-2-carboxylic acid (315);

(2S)-1-[4-(2-{4-[7-carboxymethanesulfonamido-4-(hydrazinecarbonyl)-1,6-naphthyridin-2-yl]phenyl}ethynyl)-3-chlorobenzoyl]piperidine-2-carboxylic acid (316);

1-{[4-(2-{4-[4-(hydrazinecarbonyl)-1,6-naphthyridin-2-yl]phenyl}ethynyl)phenyl]carbamoyl}piperidine-2-carboxylic acid (317);

(2S)-1-[3-chloro-4-(2-{4-[4-(hydrazinecarbonyl)-7-(3-methoxypyrrolidin-1-yl)-1,6-naphthyridin-2-yl]phenyl}ethynyl)benzoyl]piperidine-2-carboxylic acid (318);

4-(hydrazinecarbonyl)-2-{4-[4-(4-hydroxybutoxy)phenyl]phenyl}-1,6-naphthyridine-7-carboxylic acid (319);

N-[2-(4-{2-[2-chloro-4-(morpholine-4-carbonyl)phenyl]ethynyl}phenyl)-4-(hydrazinecarbonyl)-1,6-naphthyridin-7-yl]methanesulfonamide (320);

(2S)-1-[4-(2-{4-[7-(2-aminoacetamido)-4-(hydrazinecarbonyl)-1,6-naphthyridin-2-yl]phenyl}ethynyl)-3-chlorobenzoyl]piperidine-2-carboxylic acid (321);

2-{[2-(4-{2-[2-chloro-4-(morpholine-4-carbonyl)phenyl]ethynyl}phenyl)-4-(hydrazinecarbonyl)-1,6-naphthyridin-7-yl]sulfamoyl}acetic acid (322);

(2R)-1-[4-(hydrazinecarbonyl)-2-{4-[4-(4-hydroxybutoxyl)phenyl]phenyl}-1,6-naphthyridine-7-carbonyl]pyrrolidine-2-carboxylic acid (323);

(2S)-1-[4-(hydrazinecarbonyl)-2-{4-[4-(4-hydroxybutoxyl)phenyl]phenyl}-1,6-naphthyridine-7-carbonyl]pyrrolidine-2-carboxylic acid (324);

N-[4-(hydrazinecarbonyl)-2-{4-[4-(4-hydroxybutoxy)phenyl]phenyl}-1,6-naphthyridin-7-yl]methanesulfonamide (325);

2-{[4-(hydrazinecarbonyl)-2-{4-[4-(4-hydroxybutoxy)phenyl]phenyl}-1,6-naphthyridin-7-yl]sulfamoyl}acetic acid (326);

N-[4-(hydrazinecarbonyl)-2-(4-{4-[5-(hydroxymethyl)-1,2-oxazol-3-yl]phenyl}phenyl)-1,6-naphthyridin-7-yl]methanesulfonamide (327);

2-{[4-(hydrazinecarbonyl)-2-(4-{4-[5-(hydroxymethyl)-1,2-oxazol-3-yl]phenyl}phenyl)-1,6-naphthyridin-7-yl]sulfamoyl}acetic acid (328);

N-[2-(4-{2-[2-chloro-4-(morpholine-4-carbonyl)phenyl]ethynyl}phenyl)-4-(hydrazinecarbonyl)-1,6-naphthyridin-7-yl]-N-methylmethanesulfonamide (329); or 2-{[2-(4-{2-[2-chloro-4-(morpholine-4-carbonyl)phenyl]ethynyl}phenyl)-4-(hydrazinecarbonyl)-1,6-naphthyridin-7-yl](methyl)sulfamoyl}acetic acid (330).

In another aspect, the invention provides a pharmaceutical composition comprising a compound of any of the formulae herein (e.g., formulae I-V) and a pharmaceutically acceptable carrier.

In other aspects, the invention provides a method of modulating metalloenzyme activity in a subject, comprising contacting the subject with a compound of any of the formulae herein (e.g., formulae I-V), in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of any of the formulae herein (e.g., formulae I-V).

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any of the formulae herein (e.g., formulae I-V), such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formulae I-V), such that metalloenzyme activity in said subject is modulated (e.g., down regulated, inhibited).

The methods herein include those wherein the disease or disorder is mediated by any of 1-deoxy-d-xylulose-5-phosphate reductoisomerase (DXR), 17-alpha hydroxylase (CYP17), aldosterone synthase (CYP11B2), aminopeptidase p, anthrax lethal factor, arginase, beta-lactamase, cytochrome P450 2A6, d-ala d-ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesterase VII, relaxase, retinoic acid hydroxylase (CYP26), TNF-alpha converting enzyme (TACE), UDP-(3-O—(R-3-hydroxymyristoyl))-N-acetylglucosamine deacetylase (LpxC), vascular adhesion protein-1 (VAP-1), or vitamin D hydroxylase (CYP24).

The methods herein include those wherein the disease or disorder is mediated by any of 4-hydroxyphenyl pyruvate dioxygenase, 5-lipoxygenase, adenosine deaminase, alcohol dehydrogenase, aminopeptidase n, angiotensin converting enzyme, aromatase (CYP19), calcineurin, carbamoyl phosphate synthetase, carbonic anhydrase family, catechol o-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesterase IV, phosphodiesterase V, pyruvate ferredoxin oxidoreductase, renal peptidase, ribonucleoside diphosphate reductase, thromboxane synthase (CYP5a), thyroid peroxidase, tyrosinase, urease, or xanthine oxidase.

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is prostate cancer, breast cancer, inflammatory bowel disease, psoriasis, systemic bacterial infection, skin structure bacterial infection, and specifically gram-negative bacterial infection.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Another aspect of the invention is a composition comprising a compound of a formulae herein (e.g., formulae (I-V)) and an agriculturally acceptable carrier.

Another aspect of the invention is a method of treating or preventing a metalloenzyme-mediated disease or disorder in or on a plant comprising contacting a compound herein with the plant.

Another aspect of the invention is a method of inhibiting metalloenzyme activity in or on a plant comprising contacting a compound herein with the plant.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl group.

As used herein, the term "halogen", "hal" or "halo" means —F, —Cl, —Br or —I.

The term "haloalkyl" refers to an -alkyl group that is substituted by one or more halo substituents. Examples of haloalkyl groups include trifluoromethyl, and 2,2,2-trifluoroethyl.

The term "haloalkoxy" refers to an —O-alkyl radical that is substituted by one or more halo substituents. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an alkyl-S-aryl substituent.

The term "arylalkylaminocarbonyl" refers to a —C(O)-amino-alkyl-aryl substituent.

The term "arylalkylsulfonyl" refers to an —S(O)2-alkyl-aryl substituent.

The term "arylalkylsulfinyl" refers to an —S(O)-alkyl-aryl substituent.

The term "aryloxyalkyl" refers to an alkyl-O-aryl substituent.

The term "alkylaryl" refers to an aryl-alkyl substituent.

The term "arylalkyl" refers to an alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroaryloxy" refers to an —O-heteroaryl substituent.

The term "heteroarylalkoxy" refers to an —O-alkyl-heteroaryl substituent.

The term "heteroaryloxyalkyl" refers to an alkyl-O-heteroaryl substituent.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl", "heterocyclyl", or "heterocycle" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "heterocycloalkylcarbonyl" refers to a —C(=O)-heterocycloalkyl substituent.

The term "carboxyheterocycloalkylcarbonyl" refers to a —C(=O)-heterocycloalkyl-CO$_2$H substituent.

The term "heterocycloalkylsulfonyl" refers to a —SO$_2$-heterocycloalkyl substituent.

The term "carboxyheterocycloalkylsulfonyl" refers to a —SO$_2$-heterocycloalkyl-CO$_2$H substituent.

The term "heterocycloalkoxy" refers to an —O-heterocycloalkyl group, which heterocycloalkyl moiety may be optionally substituted with 1-3 substituents.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction)

and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me) C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, hydroxyalkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carboxamido, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

List of Abbreviations

In order that the invention may be more readily understood, certain abbreviations are first defined here for convenience.

TIMP: Tissue Inhibitor of Metalloproteases
MMP: Matrix Metalloproteinase
LpxC: UDP-3-O—[R-3-hydroxymyristoyl]-GlcNAc deacetylase
CYP: Cytochrome P450
DXR: 1-Deoxy-d-xylulose-5-phosphate reductoisomerase
CYP17: 17-Alpha hydroxylase
CYP11B2: Aldosterone synthase
HPV/HSV E1 helicase: Human papillomavirus/Herpes simplex virus E1 helicase
CYP2D6: Retinoic acid hydroxylase
TNF-alpha: Tumor necrosis factor alpha
TACE: TNF-alpha converting enzyme
VAP-1: Vascular adhesion protein-1
CYP24: Vitamin D hydroxylase
CYP19: Aromatase
CYP51: Lanosterol demethylase
CYP5a: Thromboxane synthase
CNS: Central nervous system
DMSO: Dimethylsulfoxide
MIC: Minimum inhibitory concentration
MFC: Minimum fungicidal concentration
TEA or NEt$_3$: Triethylamine
RT: Room temperature
TLC: Thin-layer chromatography
PivCl: Pivaloyl chloride
(COOEt)$_2$: Diethyl oxalate
n-BuLi: n-Butyllithium
DIPEA: Diisopropylethylamine
EDCI: 1-Ethyl-3-(3-dimethylaminopropyl)carbodiimide
HOBt: Hydroxybenzotriazole
DMF: N,N-Dimethylformamide
MeLi: Methyllithium
THF: Tetrahydrofuran
TBS: t-Butyldimethylsilyl
Pd(PPh$_3$)$_4$: Tetrakistriphosphino palladium(0)
EtOH: Ethanol or Ethyl alcohol
MeOH: Methanol or Methyl alcohol
DCM: Dichloromethane EtOAc: Ethyl acetate
NMR: Nuclear magnetic resonance
MS: Mass spectroscopy
ESI: Electrospray injection
IPA: Isopropanol or Isopropyl alcohol
HPLC: High-performance liquid chromatography
KOAc: Potassium acetate
Pd(dppf)$_2$Cl$_2$: [1,1'-Bis(diphenylphosphino)ferrocene]dichloro palladium(II)
t-BuOH: t-Butanol or t-Butyl alcohol
DPPA: Diphenylphosphoryl azide
TFA: Trifluoroacetic acid
NH$_2$—OTHP: O-(Tetrahydro-2H-pyran-2-yl)hydroxylamine
Et$_2$O: Diethylether
(Boc)2O: Di-tert-butyl dicarbonate
LC-MS: Liquid chromatography-mass spectroscopy
MsCl: Methanesulfonylchloride
HNNHBoc: N-(tert-Butoxycarbonyl)hydrazine
NCS: N-chlorosuccinimide
AcOH: Acetic acid
HATU: 1-[Bis(dimethylamino)methylene]-1H-1,2,3-triazolo[4,5-b]pyridinium 3-oxid hexafluorophosphate
CDI: N,N-Carbonyldiimidazole
Fmoc: Fluorenylmethoxycarbonyl
p-TSA: p-Toluenesulfonic acid
TCDI: Thiocarbonyldiimidazole
DMAP: 4-Dimethylaminopyridine
Pd$_2$(dba)$_3$: Tris(dibenzylideneacetone)dipalladium(0)
NMU: N-Methyl-N-nitrosourea
BINAP: (2,2'-Bis(diphenylphosphino)-1,1'-binaphthyl
NaOt-Bu: Sodium tert-butoxide
TMS-Br: Bromotrimethylsilane
HMDS: Hexamethyldisilazane
Boc: t-Butyloxycarbonyl
mCPBA: m-Chloroperbenzoic acid
TMS: Trimethylsilyl
Ac$_2$O: Acetic anhydride
NaB(OAc)$_3$H: Sodium triacetoxyborohydride
PMB-Cl: p-Methoxybenzylchloride
R$_t$: Retention time
ACN: Acetonitrile
MW: Microwave
Tritylchloride: Chlorotriphenylmethane
DEAD: Diethylazodicarboxylate
dppf: 1,1'-Bis(diphenylphosphino)ferrocene
Pd$_2$(dba)$_3$CHCl$_3$: Tris(dibenzylideneacetone)dipalladium (0)-chloroform adduct
TPP: Triphenylphosphine
Pd(OAc)$_2$: Palladium(II) acetate
HBTU: N,N,N',N'-Tetramethyl-O-(1H-benzotriazol-1-yl)uranium hexafluorophosphate Methods of Treatment In one aspect, the invention provides a method of modulating the metalloenzyme activity of a cell in a subject, comprising contacting the subject with a compound of any of the formulae herein (e.g., formulae I-V), in an amount and under conditions sufficient to modulate metalloenzyme activity.

In one embodiment, the modulation is inhibition.

In another aspect, the invention provides a method of treating a subject suffering from or susceptible to a metalloenzyme-mediated disorder or disease, comprising administering to the subject an effective amount of a compound or pharmaceutical composition of any of the formulae herein (e.g., formulae I-V).

In other aspects, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formulae I-V), such that said subject is treated for said disorder.

In certain embodiments, the invention provides a method of treating a disease, disorder or symptom thereof, wherein the disorder is cancer, cardiovascular disease, inflammatory disease or infectious disease. In other embodiments the disease, disorder or symptom thereof is metabolic disease, ophthalmologic disease, central nervous system (CNS) disease, urologic disease, or gastrointestinal disease. In certain embodiments the disease is prostate cancer, breast cancer, inflammatory bowel disease, psoriasis, systemic fungal infection, skin structure fungal infection, mucosal fungal infection, and onychomycosis.

In certain embodiments, the subject is a mammal, preferably a primate or human.

In another embodiment, the invention provides a method as described above, wherein the effective amount of the compound of any of the formulae herein (e.g., formulae I-V) is as described above.

In another embodiment, the invention provides a method as described above, wherein the compound of any of the formulae herein (e.g., formulae I-V) is administered intravenously, intramuscularly, subcutaneously, intracerebroventricularly, orally or topically.

In another embodiment, the invention provides a method as described herein wherein the compound of any of the formulae herein (e.g., formulae I-V) demonstrates selectivity for an activity range against a target enzyme and an activity range against an off-target enzyme (e.g., LpxC IC50<1.0 µM and IC50>3.0 µM for CYP3A4; LpxC IC50<0.5 µM and IC50>1.0 µM for CYP3A4; LpxC IC50<0.24 µM and IC50>3.5 µM for CYP3A4; LpxC IC50<XX µM and IC50>YY µM for CYP3A4, in each instance XX is an independent number; in each instance YY is an independent number; in certain aspects XX is a number less than YY). In certain aspects, for example, XX is 2-fold, 5-fold, 10-fold, 50-fold, 100-fold, or 1000-fold less than YY.

In other embodiments, the invention provides a method as described above, wherein the compound of any of the formulae herein (e.g., formulae I-V) is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

Another object of the present invention is the use of a compound as described herein (e.g., of any of the formulae herein) in the manufacture of a medicament for use in the treatment of a metalloenzyme-mediated disorder or disease. Another object of the present invention is the use of a compound as described herein (e.g., of any of the formulae herein) for use in the treatment of a metalloenzyme-mediated disorder or disease. Another object of the present invention is the use of a compound as described herein (e.g., of any of the formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising the compound of any of the formulae herein (e.g., formulae I-V) and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of any of the formulae herein (e.g., formulae I-V), in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder.

For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Agricultural Applications

The compounds and compositions herein can be used in methods of modulating metalloenzyme activity in a microorganism on a plant comprising contacting a compound herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

One aspect is a method of treating or preventing a fungal disease or disorder in or on a plant comprising contacting a compound of any of the formulae herein with the plant. Another aspect is a method of treating or preventing fungi growth in or on a plant comprising contacting a compound of any of the formulae herein with the plant. Another aspect is a method of inhibiting microorganisms in or on a plant comprising contacting a compound of any of the formulae herein with the plant.

The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound of any of the formulae herein (e.g., formulae I-V); such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

In embodiments, the invention provides for the intermediate compounds of the formulae delineated herein and methods of converting such compounds to compounds of the formulae herein (e.g., in Scheme 1, E to 1; F to H; H to 1) comprising reacting a compound herein with one or more reagents in one or more chemical transformations (including those provided herein) to thereby provide the compound of any of the formulae herein or an intermediate compound thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula (e.g., in Scheme 1, in Scheme 1, E to 1; F to H; H to 1). The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Synthesis of Inhibitors

Scheme 1

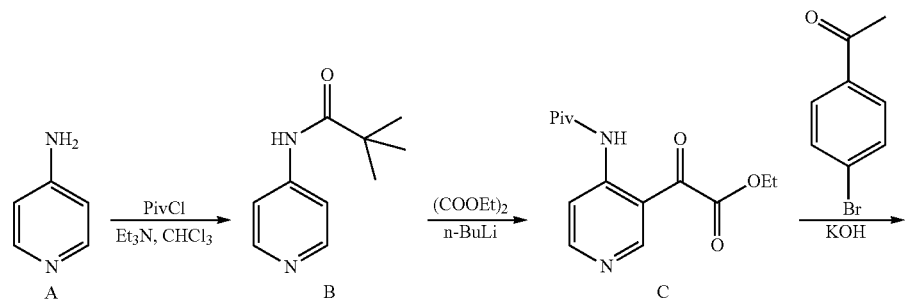

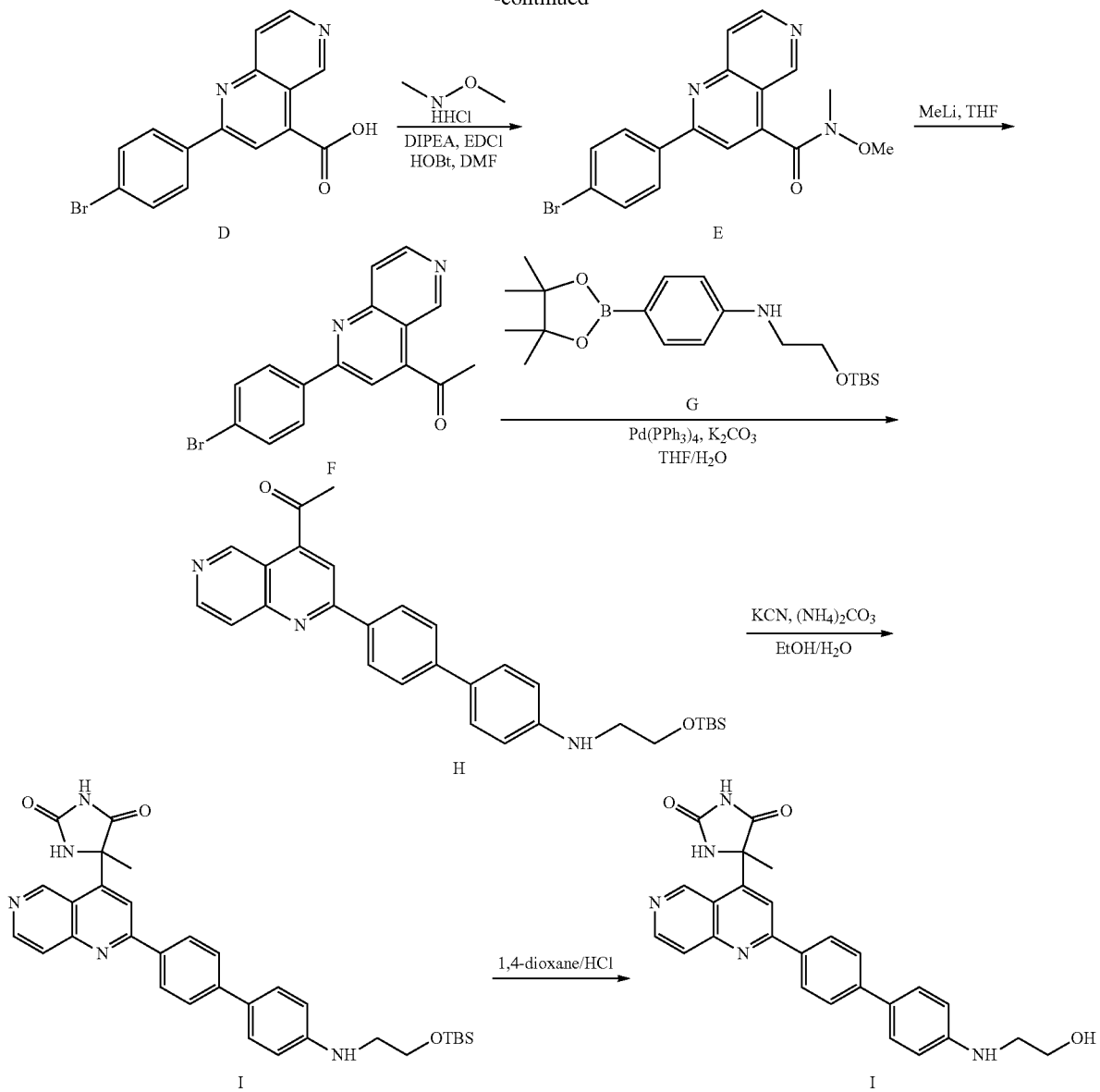

Example 1

5-(2-(4'-((2-hydroxyethyl)amino)-[1,1'-biphenyl]-4-yl)-1,6-naphthyridin-4-yl)-5-methylimidazolidine-2,4-dione hydrochloride (1)

To a stirred solution of 4-amino pyridine (A; 5 g, 53.12 mmol) in CHCl₃ (200 mL) were added triethylamine (TEA or Et₃N) (11.5 mL, 106.2 mmol) followed by pivaloyl chloride (7.15 mL, 69 mmol) dropwise at 0° C. over a period of 10 minutes (min) The reaction mixture was warmed to RT and stirred for 1.5 hours (h). The progress of the reaction was monitored by thin layer chromatography (TLC). The reaction mixture was washed with saturated sodium bicarbonate (NaHCO₃) solution, dried over anhydrous Na₂SO₄ and concentrated under reduced pressure. The obtained crude material was purified by silica gel column chromatography eluting with 10% methanol (MeOH)/dichloromethane (CH₂Cl₂) to afford B (7 g, 73.9%) as an off-white solid. ¹H NMR (200 MHz, DMSO-d₆): δ 9.54 (bs, NH), 8.40 (d, J=5.8 Hz, 2H), 7.67 (d, J=6.4 Hz, 2H), 1.23 (s, 9H). MS (ESI): m/z 179 [M⁺+1].

To a stirred solution of B (3 g, 16.83 mmol) in dry THF (30 mL) was added n-BuLi (21.5 mL, 50.5 mmol, 2.3M in hexane) dropwise at −78° C. under an inert atmosphere. After being stirred for 30 min at 0° C., a solution of diethyl oxalate (5.6 mL, 42 mmol) in dry tetrahydrofuran (THF) (5.6 mL) was added to reaction mixture at −78° C. The resulting reaction mixture was warmed to room temperature (RT) and the stirring was continued for another 2 h. The reaction mixture was diluted with cold water (100 mL) and extracted with diethyl ether (2×20 mL). The combined organic phases were dried over anhydrous sodium sulfate (Na₂SO₄), filtered and concentrated in vacuo. The crude material was purified by silica gel column chromatography eluting with 30% ethyl aceate (EtOAc)/hexane to afford C (1.2 g, 25.6%) as a thick syrup. ¹H NMR (500 MHz, CDCl₃): δ 11.47 (bs, NH), 8.92 (s, 1H), 8.74 (d, J=5.5 Hz, 1H), 8.66 (d, J=5.5 Hz, 1H), 4.51 (q, J=7.5 Hz, 2H), 1.45 (t, J=7.5 Hz, 3H), 1.36 (s, 9H). To a stirred solution of C (14 g, 50.35 mmol) in EtOH:H$_2$O (200 mL, 1:15) was added potassium hydroxide (KOH; 11.3 g, 0.2 mol). The reaction mixture was heated at reflux for 2 h. 4-Bromo propiophenone (20 g, 0.1 mol) was added to the reaction mixture and stirred for another 16 h. After consumption of the starting material by TLC, ethanol was distilled off. The residue was diluted with water (100 mL) and extracted with CH$_2$Cl$_2$ (2×100 mL) to remove excess 4-bromo-propiophenone. The aqueous layer was acidified to pH~2 using acetic acid. The precipitated solid was filtered and dried in vacuo to afford acid D (13 g, 78.7%) as an off-white solid. $^1$H NMR (500 MHz, DMSO-d$_6$): δ 14.3 (bs, 1H), 10.01 (s, 1H), 8.83 (d, J=5.5 Hz, 1H), 8.58 (s, 1H), 8.31 (d, J=8.5 Hz, 2H), 8.04 (d, J=5.5 Hz, 1H), 7.81 (d, J=8.5 Hz, 2H), 2.33 (s, 3H).

To a stirred solution of acid D (2 g, 6.11 mmol) in DMF (20 mL) were added diisopropylethylamine (DIPEA; 2.3 g, 18.3 mmol) followed by 1-ethyl-3-(3-dimethylaminopropyl) carbodiimide (EDCI) (1.75 g, 9.16 mmol) at 0° C. The reaction was stirred for 15 min Hydroxybenzotriazole (HOBt; 1.4 g, 9.16 mmol) was added to the reaction mixture at 0° C. After being stirred for 15 min, N,O-dimethylhydroxylamine hydrochloride (1.19 g, 12.2 mmol) was added to the reaction mixture at 0° C. and stirring was continued for another 16 h at RT. After consumption of the starting material by TLC, the reaction was quenched with cold water (20 mL) and extracted with ethyl acetate (2×20 mL). The combined organic extracts were dried over anhydrous Na$_2$SO$_4$ and concentrated under reduced pressure. The crude material was purified by silica gel column chromatography eluting with 8% MeOH/CH$_2$Cl$_2$. The obtained material was triturated with isopropanol (IPA):pentane (10 mL, 2:8) and dried in vacuo to afford E (1.6 g, 70.4%) as an off-white solid. $^1$H NMR (200 MHz, CDCl$_3$): δ 9.29 (s, 1H), 8.80 (d, J=6.0 Hz, 1H), 8.11 (d, J=6.8 Hz, 2H), 8.00 (d, J=6.0 Hz, 1H), 7.97 (s, 1H), 7.69 (d, J=6.8 Hz, 2H), 3.53-3.44 (m, 6H). MS (ESI): 374 [M$^+$+2].

To a stirred solution of E (1.75 g, 4.7 mmol) in dry THF (50 mL) was added methyllithium (7.11 mL, 11.75 mmol, 1.6M in THF) at −78° C. and stirred for 2 h. The progress of the reaction was monitored by TLC. The reaction mixture was quenched with an aqueous ammonium chloride (NH$_4$Cl) solution (20 mL) and extracted with ethyl acetate (3×20 mL). The combined organic layers were washed with water, brine, dried over anhydrous Na$_2$SO$_4$ and concentrated under reduced pressure. The crude compound was purified by column chromatography eluting with 40% EtOAc/hexane to afford ketone F (1.04 g, 67.9%) as a pale orange liquid. $^1$H NMR (500 MHz, CDCl$_3$): δ 9.83 (s, 1H), 8.83 (d, J=6.0 Hz, 1H), 8.12-8.09 (m, 3H), 8.00 (d, J=6.0 Hz, 1H), 7.72 (d, J=8.5 Hz, 2H), 2.85 (s, 3H). MS (ESI): 327 [M$^+$], 329 [M$^+$+2].

To a stirred solution of ketone F (0.2 g, 0.61 mmol) and N-(2-((tert-butyldimethylsilyl)oxy)ethyl)-4-(4,4,5,5-tetramethyl-1,3,2-dioxaborolan-2-yl)aniline (G; 0.34 g, 0.91 mmol; synthesis described below) in THF:H$_2$O (25 mL, 4:1) was added potassium carbonate (K$_2$CO$_3$; 0.25 g, 1.83 mmol) at RT under inert atmosphere. After purging with nitrogen over a period of 30 min, tetrakis(triphenylphosphine)palladium(0) (Pd(PPh$_3$)$_4$; 0.07 g, 0.06 mmol) was added to reaction mixture and then stirred for 12 h at 80° C. The reaction mixture was diluted with ethyl acetate (20 mL). The organic layer was washed with water, brine, dried over anhydrous Na$_2$SO$_4$ and concentrated in vacuo. The crude material was purified by silica gel column chromatography eluting with 40% EtOAc/hexane to afford H (0.2 g, 66%) as a yellow solid. $^1$H NMR (500 MHz, DMSO-d$_6$): δ 9.63 (s, 1H), 8.78 (d, J=6.0 Hz, 1H), 8.66 (s, 1H), 8.44 (d, J=8.5 Hz, 2H), 8.01 (d, J=6.0 Hz, 1H), 7.82 (d, J=8.5 Hz, 2H), 7.59 (d, J=9.0 Hz, 2H), 6.72 (d, J=6.0 Hz, 2H), 5.88 (t, J=6.0 Hz, 1H, NH), 3.74 (t, J=5.5 Hz, 2H), 3.23 (q, J=5.5 Hz, 2H), 2.91 (s, 3H), 0.88 (s, 9H), 0.05 (s, 6H). MS (ESI): 498 [M$^+$+1].

To a stirred solution of H (0.2 g, 0.4 mmol) in EtOH:H$_2$O (14 mL, 1:1) was added potassium cyanide (KCN; 52.4 mg, 0.8 mmol) followed by ammonium carbonate (0.25 g, 1.6 mmol) at RT. The reaction mixture was heated in a sealed tube at 80° C. for 48 h. The volatiles were evaporated under reduced pressure and the residue was washed with 20% MeOH/CH$_2$Cl$_2$ (15 mL). The organic layer was dried over anhydrous Na$_2$SO$_4$ and concentrated in vacuo. The crude material was purified by silica gel column chromatography eluting with 8% MeOH/CH$_2$Cl$_2$ to afford compound I (16 mg, 7%) as a yellow solid. $^1$H NMR (500 MHz, DMSO-d$_6$): δ 11.32 (s, 1H, NH), 9.65 (s, 1H, NH), 8.97 (s, 1H), 8.76 (d, J=6.0 Hz, 1H), 8.34 (d, J=9.0 Hz, 2H), 8.28 (s, 1H), 8.01 (d, J=6.0 Hz, 1H), 7.81 (d, J=8.0 Hz, 2H), 7.57 (d, J=9.0 Hz, 2H), 6.72 (d, J=8.5 Hz, 2H), 5.87 (bt, NH), 3.74 (t, J=5.5 Hz, 2H), 3.23 (q, J=6.0 Hz, 2H), 2.07 (s, 3H), 0.88 (s, 9H), 0.05 (s, 6H). MS (ESI): 568 [M$^+$+1].

A mixture of compound I (16 mg, 0.028 mmol) in 1,4-dioxane/HCl (5 mL) at 0° C. was warmed to RT and stirred for 1 h. After consumption of the starting material by TLC, the volatiles were evaporated under reduced pressure. The residue was co-distilled with diisopropyl ether (2×2 mL), filtered, washed with n-pentane (2×2 mL) and dried in vacuo to afford 1 (9.9 mg as an HCl salt, 70.8%) as a brown syrup. $^1$H NMR (500 MHz, DMSO-d$_6$): δ 11.34 (s, 1H, NH), 9.88 (s, 1H, NH), 9.06 (s, 1H), 8.82 (d, J=6.5 Hz, 1H), 8.40-8.38 (m, 3H), 8.21 (d, J=5.5 Hz, 1H), 7.86 (d, J=8.0 Hz, 2H), 7.63 (d, J=8.5 Hz, 2H), 6.82 (d, J=8.0 Hz, 2H), 3.51-3.46 (m, 2H), 3.21 (t, J=6.0 Hz, 2H), 2.07 (s, 3H). MS (ESI): 454.6 [M$^+$+1]. HPLC: 83.6%.

Synthesis of intermediate G [N-(2-((tert-butyldimethylsilyl)oxy)ethyl)-4-(4,4,5,5-tetramethyl-1,3,2-dioxaborolan-2-yl)aniline]

To a stirred solution of 4-iodoaniline (10 g, 45.6 mmol) in CH$_2$Cl$_2$ (500 mL) was added pyridine (7.3 mL, 91.2 mmol) at RT. After the reaction mixture was cooled to 0° C., 2-chloroethyl chloroformate (5.2 mL, 50.1 mmol) was added dropwise to the reaction mixture and stirred for 2 h at RT. The reaction mixture was diluted with CH$_2$Cl$_2$ (100 mL) and was washed with water (50 mL), a saturated aqueous CuSO$_4$ solution (2×30 mL), dried over anhydrous Na$_2$SO$_4$ and concentrated under reduced pressure. The obtained crude material was purified by silica gel column chromatography eluting with 8% EtOAc/hexane to afford 2-chloroethyl(4-iodophenyl) carbamate (12.8 g, 86.4%) as a white solid. $^1$H NMR (200 MHz, CDCl$_3$): δ 7.63-7.57 (m, 2H), 7.16 (d, J=8.8 Hz, 2H), 6.66 (bs, NH), 4.42 (t, J=5.4 Hz, 2H), 3.73 (t, J=5.6 Hz, 2H). MS (ESI): m/z 236 [M$^+$+1].

To a stirred solution of 2-chloroethyl(4-iodophenyl)carbamate (0.1 g, 0.307 mmol) in ethanol (4 mL) was added KOH pellets (85.7 mg, 1.53 mmol) at RT. The reaction mixture was gradually heated to reflux for 12 h. After consumption of the starting material (by TLC), the volatiles were removed under reduced pressure. The obtained residue was diluted with water and extracted with EtOAc (2×20 mL). The combined organic layers were dried over anhydrous Na$_2$SO$_4$ and concentrated under reduced pressure. The obtained crude material was purified by silica gel column chromatography eluting with 40% EtOAc/hexane to afford 2-((4-iodophenyl)amino) ethanol (40 mg, 49%) as an off-white solid. $^1$H NMR (200 MHz, CDCl$_3$): δ 7.31 (d, J=8.6 Hz, 2H), 6.43 (d, J=8.6 Hz, 2H), 5.77 (bt, NH), 4.68 (t, J=5.4 Hz, 1H, OH), 3.53 (q, J=5.6 Hz, 2H), 3.06 (q, J=5.6 Hz, 2H). MS (ESI): m/z 263.9 [M$^+$+1].

To a stirred solution of 2-((4-iodophenyl)amino)ethanol (24 g, 91.2 mmol) in DMSO (400 mL) was added bis(pinacolato)diboron (25.6 g, 0.1 mol) followed by potassium acetate (KOAc; 26.8 g, 0.27 mol) at RT under argon atmosphere. After purging with argon over a period of 1 h, [1,1'-bis(diphenylphosphino)ferrocene]dichloropalladium (II) (Pd(dppf)$_2$Cl$_2$; 6.8 g, 9.12 mmol) was added to reaction mixture under argon atmosphere. The resulting mixture was stirred at 100° C. for 14 h. Progress of the reaction was monitored by TLC. The reaction mixture was cooled to RT and filtered through a pad of Celite. The filtrate was concentrated under reduced pressure. The obtained residue was diluted with water (100 mL) and extracted with EtOAc (2×250 mL). The organic layer was washed with water, brine, dried over anhydrous Na$_2$SO$_4$ and concentrated under reduced pressure. The crude compound was purified by silica gel column chromatography eluting with 40% EtOAc/hexane to afford 2-((4-(4,4,5,5-Tetramethyl-1,3,2-dioxaborolan-2-yl)phenyl)amino)ethanol (12 g, 50%) as a sticky solid. $^1$H NMR (200 MHz, CDCl$_3$): δ 7.68-7.60 (m, 2H), 6.68-6.59 (m, 2H), 3.82 (t, J=5.0 Hz, 2H), 3.32 (q, J=5.4 Hz, 2H), 2.28-2.22 (m, 1H), 1.31-1.29 (m, 12H). MS (ESI): m/z 264 [M$^+$+1].

To a stirred solution of 2-(4-(4,4,5,5-tetramethyl-1,3,2-dioxaborolan-2-yl)phenyl)amino)ethanol (2 g, 7.6 mmol) in CH$_2$Cl$_2$ (50 mL) was added imidazole (1.03 g, 15.2 mmol) followed by tert-butylchlorodimethylsilane (1.72 g, 11.4 mmol) at 0° C. and stirred for 2 h. Progress of the reaction was monitored by TLC. The reaction mixture was diluted with water (20 mL) and extracted in CH$_2$Cl$_2$ (2×20 mL). The combined organic layer was dried over anhydrous Na$_2$SO$_4$ and concentrated under reduced pressure. The crude compound was purified by silica gel column chromatography eluting with 8% EtOAc/hexane to afford TBS-boronate G (0.9 g, 32%) as a brown solid. $^1$H NMR (500 MHz, CDCl$_3$): δ 7.63 (d, J=8.5 Hz, 2H), 6.59 (d, J=8.41 Hz, 2H), 4.23 (bs, 1H), 3.80 (t, J=5.5 Hz, 2H), 3.24-3.23 (m, 2H), 1.31 (s, 12H), 0.90 (s, 9H), 0.06 (s, 6H). MS (ESI): m/z 378 [M$^+$+1].

Scheme 2

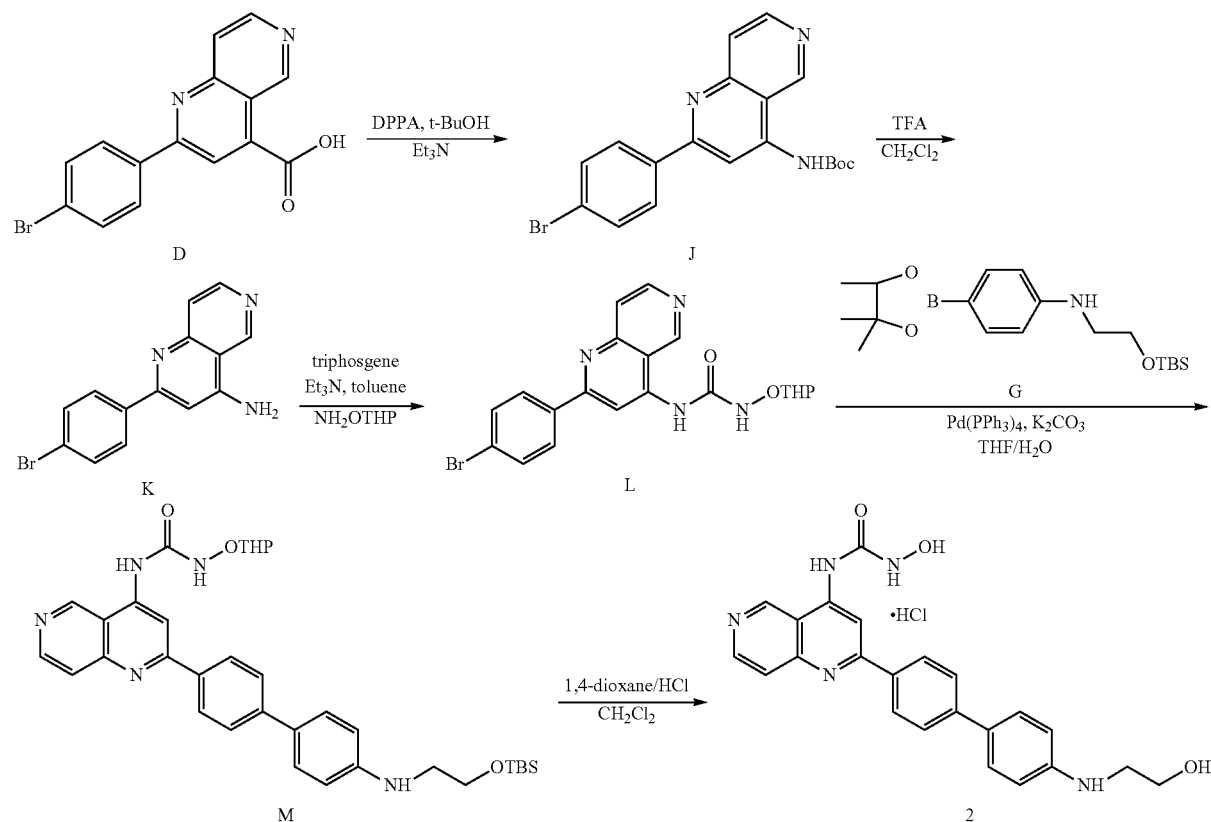

Example 2

1-Hydroxy-3-(2-(4'-(2-hydroxyethylamino)biphenyl-4-yl)-1,6-naphthyridin-4-yl)urea (2)

To a stirred solution of 2-(4-bromophenyl)-1,6-naphthyridine-4-carboxylic acid (D; 3 g, 9.1 mmol) in t-BuOH (50 mL) was added Et$_3$N (2.5 mL, 18.2 mmol) followed by diphenylphosphoryl azide (DPPA; 4.2 mL, 18.2 mmol) at RT. The reaction mixture was heated to reflux for 18 h. The progress of the reaction was monitored by TLC. The volatiles were removed under reduced pressure. The obtained crude material was purified by silica gel column chromatography eluting with 8% MeOH/CH$_2$Cl$_2$ to afford J (2.1 g, 58%) as a brown solid. $^1$H NMR (500 MHz, DMSO-d$_6$): δ 10.32 (s, 1H), 9.73 (s, 1H), 8.69 (d, J=5.5 Hz, 1H), 8.63 (s, 1H), 8.11 (d, J=8.5 Hz, 2H), 7.84 (d, J=5.5 Hz, 1H), 7.78 (d, J=8.5 Hz, 2H), 1.58 (s, 9H). MS (ESI): 400 [M+], 402 [M++2].

To a stirred solution of J (2 g, 5.01 mmol) in CH$_2$Cl$_2$ (50 mL) was added trifluoroacetic acid (TFA; 15 mL, 5.01 mmol) at 0° C. The reaction mixture was warmed to RT and stirred for 12 h. After consumption of the starting material by TLC, the volatiles were evaporated under reduced pressure. To the obtained residue diluted with CH$_2$Cl$_2$ (50 mL), was added Et$_3$N (5 mL) at RT and stirred for another 15 min. The reaction mixture was diluted with CH$_2$Cl$_2$ (50 mL) and washed with H$_2$O (2×50 mL). The organic layer was dried over anhydrous Na$_2$SO$_4$ and concentrated under vacuum to afford K (0.9 g, 60%) as a yellow solid. $^1$H NMR (500 MHz, DMSO-d$_6$): δ 9.54 (s, 1H), 8.56 (d, J=5.5 Hz, 1H), 8.04 (d, J=8.0 Hz, 2H), 7.73 (d, J=9.0 Hz, 2H), 7.64 (d, J=6.0 Hz, 1H), 7.46 (s, 2H), 7.17 (s, 1H). MS (ESI): 301.7 [M++2].

To a stirred solution of K (0.4 g, 1.33 mmol) in toluene (25 mL) was added Et$_3$N (0.6 mL, 4.01 mmol) followed by triphosgene (0.59 g, 2.00 mmol) at 0° C. The reaction mixture was heated at 100° C. for 4 h. After consumption of the starting material by TLC, the reaction mixture was cooled to 0° C. and NH$_2$—OTHP (0.47 g, 4.01 mmol) was added to the reaction mixture and stirring was continued for another 14 h at RT. The precipitated solid was filtered off and the filtrate was concentrated under reduced pressure. The obtained crude material was purified by silica gel column chromatography eluting with 3% MeOH/CH$_2$Cl$_2$ to afford L (20 mg, 3.38%) as an off white solid. $^1$H NMR (500 MHz, DMSO-d$_6$): δ 10.14 (s, 1H, NH), 9.62 (s, 1H), 9.50 (s, 1H), 8.75 (s, 1H), 8.73 (d, J=6.0 Hz, 1H), 8.13 (d, J=8.5 Hz, 2H), 7.88 (d, J=6.0 Hz, 1H), 7.79 (d, J=8.5 Hz, 2H), 4.96 (s, 1H), 4.01-3.97 (m, 1H), 3.62-3.60 (m, 1H), 1.79-1.74 (m, 3H), 1.57-1.56 (m, 3H). MS (ESI): 443 [M+], 445 [M++2].

To a stirred solution of L (0.12 g, 0.27 mmol) in THF:H$_2$O (11 mL, 10:1) was added N-(2-(tert-butyldimethylsilyloxy) ethyl)-4-(4,4,5-trimethyl-1,3,2-dioxaborolan-2-yl) aniline (G; 51 mg, 0.40 mmol) followed by potassium carbonate (K$_2$CO$_3$; 37 mg, 0.81 mmol) at RT under argon atmosphere. After purging with argon over a period of 1 h, Pd(PPh$_3$)$_4$ (10 mg, 0.027 mmol) was added to the reaction mixture and then continued purging with argon for another 15 min. The resulting reaction mixture was heated at 70° C. for 2 h. After consumption of the starting material by TLC, the reaction mixture was filtered through a pad of Celite. The filtrate was dried over anhydrous Na$_2$SO$_4$ and concentrated under reduced pressure. The crude material was purified by silica gel column chromatography eluting with 3% MeOH/CH$_2$Cl$_2$ to afford M (10 mg, 18%) as a yellow solid. $^1$H NMR (500 MHz, DMSO-d$_6$): δ 10.12 (s, 1H), 9.57 (s, 1H), 9.47 (s, 1H), 8.78 (s, 1H), 8.71 (d, J=6.0 Hz, 1H), 8.20 (d, J=8.5 Hz, 2H), 7.87 (d, J=5.5 Hz, 1H), 7.78 (d, J=8.5 Hz, 2H), 7.55 (d, J=6.5 Hz, 2H), 6.72 (d, J=8.5 Hz, 2H), 5.84 (t, J=6.0 Hz, 1H, NH), 4.97 (s, 1H), 4.00-3.99 (m, 1H), 3.74 (t, J=6.0 Hz, 2H), 3.63-3.61 (m, 1H), 3.24-3.20 (m, 2H), 1.80-1.78 (m, 3H), 1.57 (bs, 3H), 0.88 (s, 9H), 0.05 (s, 6H). MS (ESI): 614 [M++1].

To a mixture of M (40 mg, 0.096 mmol) in CH$_2$Cl$_2$ (10 mL) was added 1,4-dioxane/HCl (0.1 mL) at 0° C. The reaction was warmed to RT and stirred for 4 h. After consumption of the starting material by TLC, the volatiles were evaporated under reduced pressure. The obtained crude was washed with CH$_2$Cl$_2$, ether and n-pentane to afford 2 (16.4 mg, 60.74%) as a green solid. $^1$H NMR (500 MHz, DMSO-d$_6$): δ 10.56 (bs, NH), 10.10 (bs, 2H), 8.96 (s, 1H), 8.83 (d, J=6.5 Hz, 1H), 8.27-8.24 (m, 3H), 7.89 (d, J=8.5 Hz, 2H), 7.67 (d, J=6.8 Hz, 2H), 6.91 (bs, 2H), 3.61 (t, J=5.5 Hz, 2H), 3.22 (d, J=5.5 Hz, 2H). MS (ESI): 416 [M++1]. HPLC: 93.73%.

Scheme 3

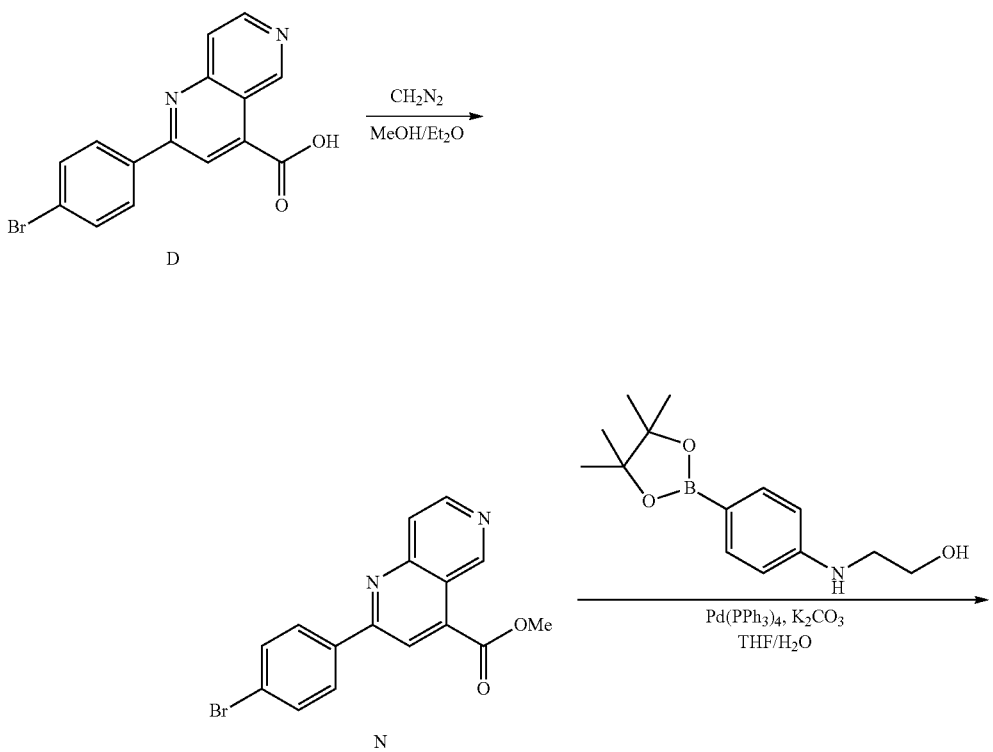

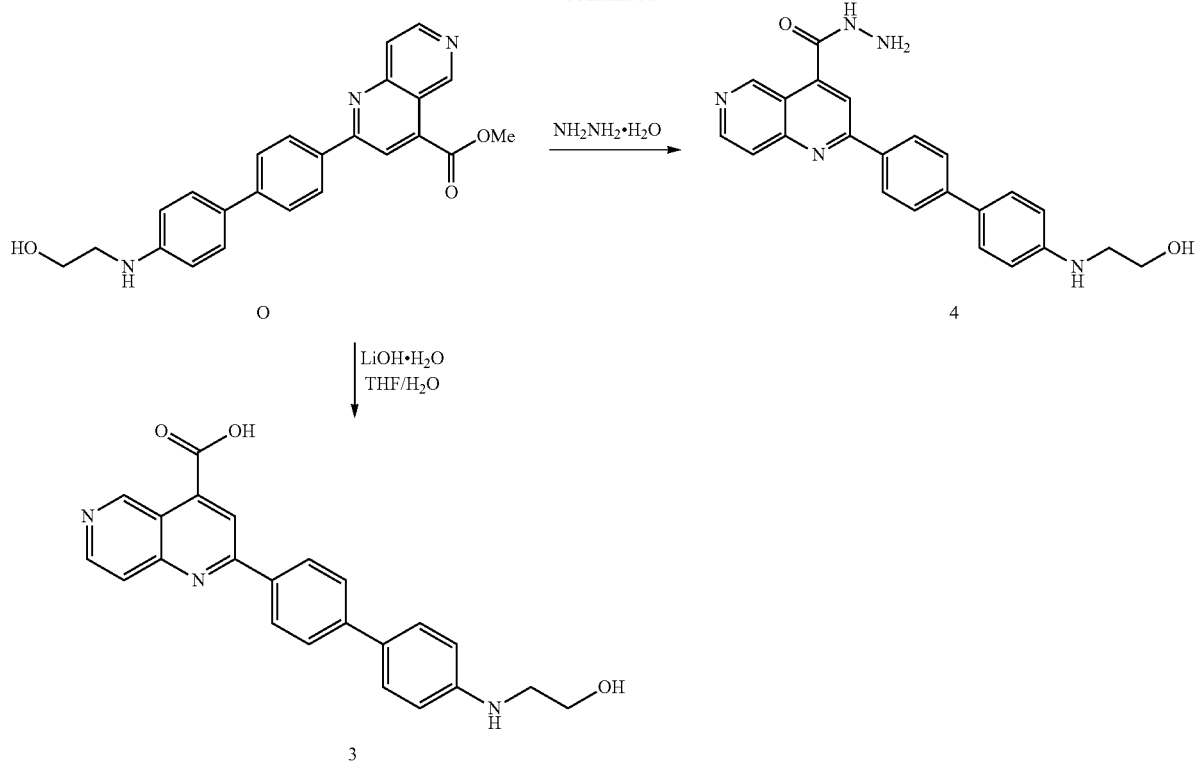

Example 3

2-(4'-((2-Hydroxyethyl)amino)-[1,1'-biphenyl]-4-yl)-1,6-naphthyridine-4-carboxylic acid (3)

To a stirred solution of acid D (50 mg, 0.15 mmol) in MeOH/Et$_2$O (1:4, 20 mL) was added freshly prepared diazomethane [N-nitroso-N-methylurea (78 mg, 0.75 mmol) in 40% aqueous KOH (10 mL)/Et$_2$O (20 mL)] at 0° C. and stirred for 1 h. After consumption of the starting material by TLC, the solvent was evaporated under reduced pressure. The obtained crude product was purified by silica gel column chromatography eluting with 8% MeOH/CH$_2$Cl$_2$ to afford ester N (40 mg, 76.9%) as an off-white solid. $^1$H NMR (500 MHz, CDCl$_3$): δ 10.15 (s, 1H), 8.84 (d, J=6.0 Hz, 1H), 8.47 (s, 1H), 8.13 (d, J=8.5 Hz, 2H), 8.00 (d, J=6.0 Hz, 1H), 7.71 (d, J=8.5 Hz, 2H), 4.12 (s, 3H). MS (ESI): m/z 342.9 [M$^+$+1].

To a stirred solution of ester N (0.4 g, 1.16 mmol) and 2-((4-(4,4,5-trimethyl-1,3,2-dioxaborolan-2-yl)phenyl)amino)ethanol (0.37 g, 1.40 mmol) in THF:H$_2$O (25 mL, 4:1) was added K$_2$CO$_3$ (0.484 g, 3.48 mmol) at RT under inert atmosphere. After purging with nitrogen over a period of 30 min, Pd(PPh$_3$)$_4$ (67 mg, 0.06 mmol) was added to reaction mixture and then stirred for 5 h at 80° C. Progress of the reaction was monitored by TLC. The reaction mixture was cooled to RT and filtered through a pad of Celite. The filtrate was concentrated under reduced pressure. The obtained residue was diluted with water (25 mL) and extracted with EtOAc (2×25 mL). The organic layer was dried over anhydrous Na$_2$SO$_4$ and concentrated under reduced pressure. The crude compound was purified by silica gel column chromatography eluting with 8% MeOH/CH$_2$Cl$_2$ to afford O (0.25 g, 53.6%) as a red solid. $^1$H NMR (500 MHz, DMSO-d$_6$): δ 9.91 (s, 1H), 8.82 (d, J=6.0 Hz, 1H), 8.62 (s, 1H), 8.36 (d, J=8.0 Hz, 2H), 8.03 (d, J=5.5 Hz, 1H), 7.81 (d, J=9.0 Hz, 2H), 7.57 (d, J=8.5 Hz, 2H), 6.72 (d, J=8.5 Hz, 2H), 5.88 (t, J=5.5 Hz, 1H), 4.71 (t, J=5.5 Hz, 1H), 4.07 (s, 3H), 3.58 (q, J=6.0 Hz, 2H), 3.17 (q, J=6.0 Hz, 2H). MS (ESI): m/z 400 [M$^+$+1]. HPLC: 97.49%.

To a stirred solution of 0 (0.1 g, 0.25 mmol) in THF/H$_2$O (4:1, 10 mL) was added LiOH H$_2$O (31 mg, 0.75 mmol) at RT and the reaction mixture was stirred for 2 h. After the consumption of the starting material by TLC, the volatiles were evaporated under reduced pressure. The residue was diluted with water and acidified to pH ~2 using 1N HCl. The precipitated solid was filtered, washed with H$_2$O and dried to afford 3 (75 mg, 78.1%) as a brown solid. $^1$H NMR (500 MHz, DMSO-d$_6$): δ 10.03 (s, 1H), 8.64 (d, J=6.0 Hz, 1H), 8.29 (d, J=8.5 Hz, 2H), 8.23 (s, 1H), 7.86 (d, J=6.0 Hz, 1H), 7.76 (d, J=8.5 Hz, 2H), 7.55 (d, J=8.5 Hz, 2H), 6.71 (d, J=9.0 Hz, 2H), 5.83 (bs, 1H), 4.72 (bs, 1H), 3.58 (t, J=6.0 Hz, 2H), 3.16 (t, J=6.0 Hz, 2H). MS (ESI): 386.2 [M$^+$+1]. HPLC: 97.41%.

Example 4

2-(4'-((2-Hydroxyethyl)amino)-[1,1'-biphenyl]-4-yl)-1,6-naphthyridine-4-carbohydrazide (4)

A mixture of O (0.1 g, 0.25 mmol) and hydrazine hydrate (NH$_2$—NH$_2$.H$_2$O; 2 mL) was heated at 90° C. for 5 h. After consumption of the starting material by TLC, the reaction mixture was concentrated in vacuo to remove the excess hydrazine hydrate. The crude material was purified by silica gel column chromatography eluting with 8% MeOH/CH$_2$Cl$_2$ to afford 4 (50 mg, 50%) as a yellow solid. $^1$H NMR (500 MHz, DMSO-d$_6$): δ 11.32 (s, 1H), 9.65 (s, 1H), 8.97 (d, J=6.1 Hz, 1H), 8.76 (d, J=8.0 Hz, 2H), 8.28 (s, 1H), 8.01 (d, J=6.0 Hz, 1H), 7.81 (d, J=8.0 Hz, 2H), 7.57 (d, J=9.0 Hz, 2H), 6.72 (d, J=8.5 Hz, 2H), 5.87 (bt, NH), 4.82 (bs, 2H), 4.72-4.6 (m, 1H), 3.74-3.73 (m, 2H), 3.23-3.22 (m, 2H). MS (ESI): 400.2 [M$^+$]. HPLC: 91.12%.

Scheme 4
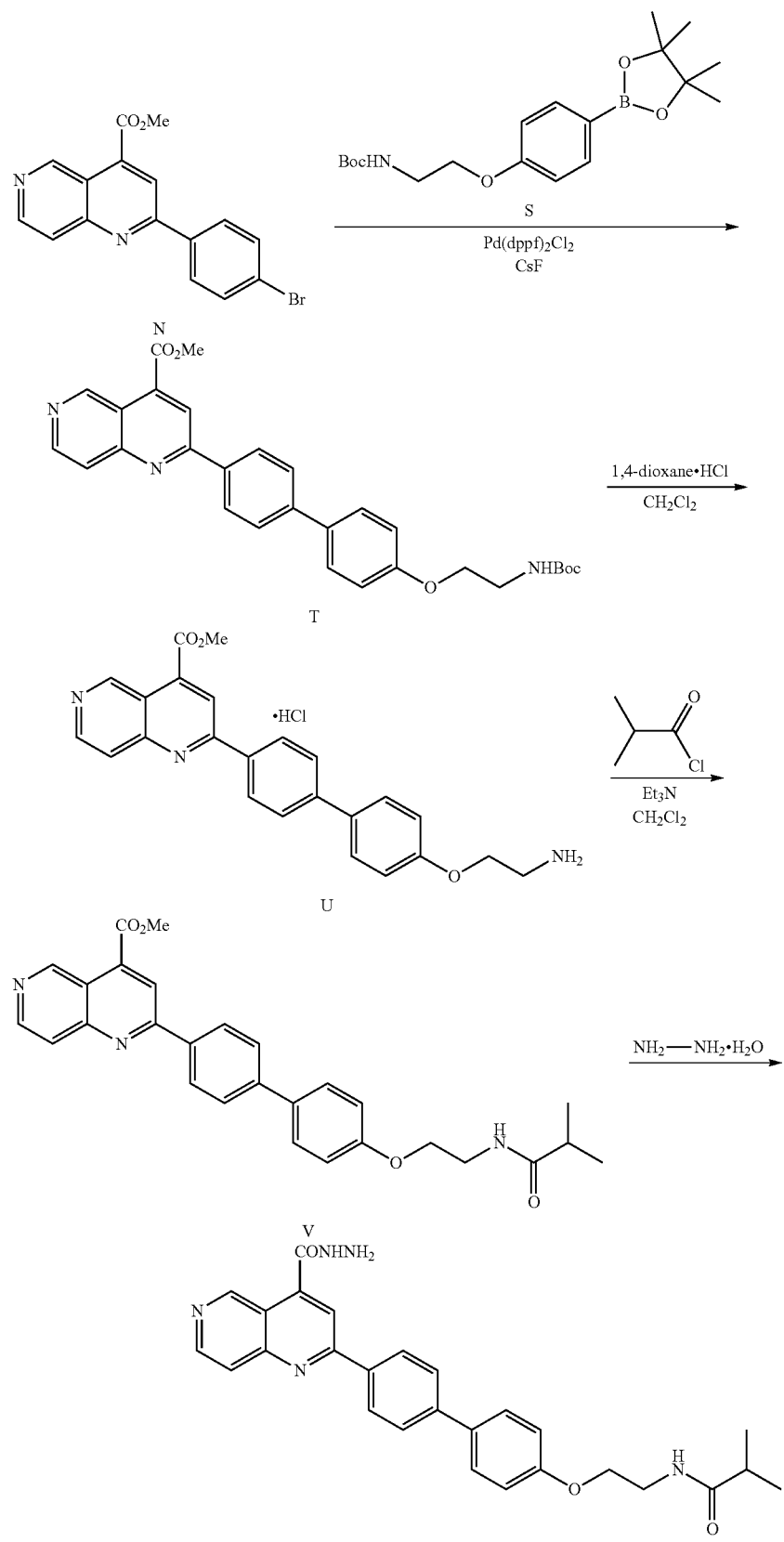

-continued

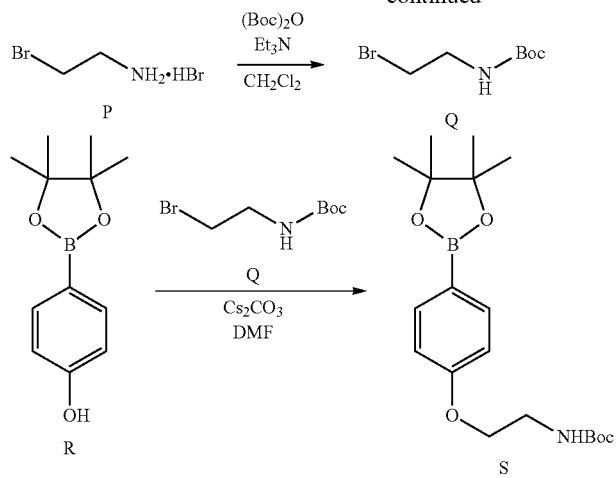

Example 5

N-(2-((4'-(4-(Hydrazinecarbonyl)-1,6-naphthyridin-2-yl)-[1,1'-biphenyl]-4-yl)oxy)ethyl)isobutyramide (5)

To a stirred solution of 2-bromoethanamine hydrobromide (P; 10.0 g, 48.78 mmol) in $CH_2Cl_2$ (30 mL) was added $Et_3N$ (17.1 mL, 121.95 mmol) followed by Boc-anhydride (12.7 g, 58.53 mmol) at 0° C. under inert atmosphere. The resulting reaction mixture was stirred for 3 h at RT. After complete consumption of the starting material (by TLC), the reaction mixture was extracted with $CH_2Cl_2$ (2×50 mL). The combined organic extracts were washed with water, brine, dried over anhydrous $Na_2SO_4$ and concentrated under reduced pressure to obtain the crude. The crude material was purified by silica gel column chromatography eluting with 20% EtOAc/hexane as eluent to afford Q (7.0 g, 31.23 mmol, 64%) as a white solid. $^1H$ NMR (500 MHz, $CDCl_3$): δ 4.98 (bs, NH), 3.54-3.53 (m, 2H), 3.46-3.45 (m, 2H), 1.45 (s, 9H).

To a stirred solution of 4-(4,4,5,5-tetramethyl-1,3,2-dioxaborolan-2-yl)phenol (R) (1.0 g, 4.54 mmol) in DMF (15 mL) was added $Cs_2CO_3$ (3.25 g, 9.99 mmol) at RT under inert atmosphere. After being stirred for 20 min, Q (1.52 g, 6.78 mmol) was added at RT and the resulting reaction mixture was heated to 65° C. and stirred for 12 h. Progress of the reaction was monitored by TLC. The reaction mixture was then allowed to RT, diluted with water (20 mL) and extracted with EtOAc (2×50 mL). The combined organic layer was dried over anhydrous $Na_2SO_4$ and concentrated under reduced pressure to furnish the crude. The crude material was purified by silica gel column chromatography eluting with 20% EtOAc/hexane as eluent to afford S (0.8 g, 2.20 mmol, 48%) as an off-white solid. $^1H$ NMR (500 MHz, $CDCl_3$): δ 7.74 (d, J=9.0 Hz, 2H), 6.88 (d, J=8.5 Hz, 2H), 4.98 (bs, 1H), 4.04 (t, J=5.0 Hz, 2H), 3.54-3.53 (m, 2H), 1.46 (s, 12H), 1.33 (s, 9H).

A solution of methyl 2-(4-bromophenyl)-1,6-naphthyridine-4-carboxylate (N; 2.8 g, 8.18 mmol) in THF/toluene (300 mL, 1:1 v/v) was degassed by purging with argon for 15 min. To the resulting reaction mixture were added boronate S (2.97 g, 8.18 mmol), CsF (3.7 g, 24.56 mmol) and $Pd(dppf)_2Cl_2$ (598 mg, 0.81 mmol) and degassed for another 5 min. The resulting reaction mixture was then stirred for 14 h at reflux. Progress of the reaction was monitored by TLC. The reaction mixture was filtered through a pad of Celite and the bed was washed with $CH_3OH$. The collected filtrate was concentrated under reduced pressure to obtain the crude. The crude was purified by silica gel column chromatography eluting with 30% EtOAc/hexane as eluent to afford T (2.8 g, 5.61 mmol, 70%) as a yellow solid. $^1H$ NMR (400 MHz, DMSO-$d_6$): δ 9.92 (s, 1H), 8.83 (d, J=5.6 Hz, 1H), 8.64 (s, 1H), 8.41 (d, J=8.4 Hz, 2H), 8.05 (d, J=5.6 Hz, 1H), 7.87 (d, J=8.8 Hz, 2H), 7.74 (d, J=8.8 Hz, 2H), 7.07 (d, J=8.8 Hz, 2H), 7.04 (t, J=6.0 Hz, NH), 4.08 (s, 3H), 4.03 (t, J=6.0 Hz, 2H), 3.34 (t, J=6.0 Hz, 2H), 1.40 (s, 9H). LC-MS: m/z 500 $[M+1]^+$ at 4.35 min (94.4% purity).

To a stirred solution of T (0.16 g, 0.32 mmol) in $CH_2Cl_2$ (5 mL) was added 4N hydrochloric acid (HCl) in 1,4-dioxane (3 mL) at 0° C. under inert atmosphere. The resulting reaction mixture was allowed to warm to RT and stirred for 2 h. Progress of the reaction was monitored by TLC. The volatiles were then evaporated under reduced pressure to afford amine U (0.12 g, crude) as a pink solid. The crude product was used in the next step without any further purification.

To a stirred solution of amine U (0.12 g, 0.30 mmol; crude) in $CH_2Cl_2$ (15 mL) were added $Et_3N$ (1.6 mL, 1.20 mmol) and isobutyryl chloride (38 mg, 0.36 mmol) at 0° C. under inert atmosphere. The resulting reaction mixture was allowed to warm to RT and stirred for 1 h. Progress of the reaction was monitored by TLC. The reaction mixture was then diluted with ice-cold water and extracted with $CH_2Cl_2$ (2×50 mL). The combined organic extracts were dried over anhydrous $Na_2SO_4$ and concentrated under reduced pressure to obtain the crude. The crude material was triturated with MeOH/diisopropyl ether to afford V (0.1 g, 0.21 mmol, 70.9%) as a yellow solid. The product was confirmed by LC-MS analysis and taken forward to the next step. LC-MS: m/z 470.6 $[M+1]^+$ at 3.73 min (96.1% purity).

A mixture of ester V (0.1 g, 0.21 mmol) and hydrazine hydrate (3 mL) was heated to 100° C. and stirred for 3 h. Progress of the reaction was monitored by TLC. The reaction mixture was allowed to cool to RT, diluted with ice-cold water and stirred for 5 min. The precipitated solid was filtered and dried under reduced pressure to obtain the crude. The crude material was purified by trituration with MeOH/diisopropyl ether to afford 5 (80 mg, 0.17 mmol, 80%) as an off-white solid. $^1H$ NMR (500 MHz, DMSO-$d_6$): δ 10.19

(bs, 1H), 9.63 (s, 1H), 8.79 (d, J=5.5 Hz, 1H), 8.43 (d, J=7.5 Hz, 2H), 8.33 (s, 1H), 8.01 (d, J=6.5 Hz, 2H), 7.88 (d, J=8.0 Hz, 2H), 7.75 (d, J=8.5 Hz, 2H), 7.09 (d, J=9.0 Hz, 2H), 4.78 (bs, 2H), 4.06 (t, J=5.5 Hz, 2H), 3.44 (t, J=5.5 Hz, 2H), 2.41-2.38 (m, 1H), 1.01 (d, J=7.0 Hz, 6H). MS (ESI): m/z 470 [M+1]$^+$. HPLC: 97.2%.

concentrated under reduced pressure to obtain the crude. The crude material was triturated with MeOH/diisopropyl ether to afford W (80 mg, 0.16 mmol, 44%) as a yellow solid. The obtained product was confirmed by LC-MS analysis and taken forward to the next reaction. LC-MS: m/z 478.5 [M+1]$^+$ at 3.60 min (82.7% purity).

Scheme 5

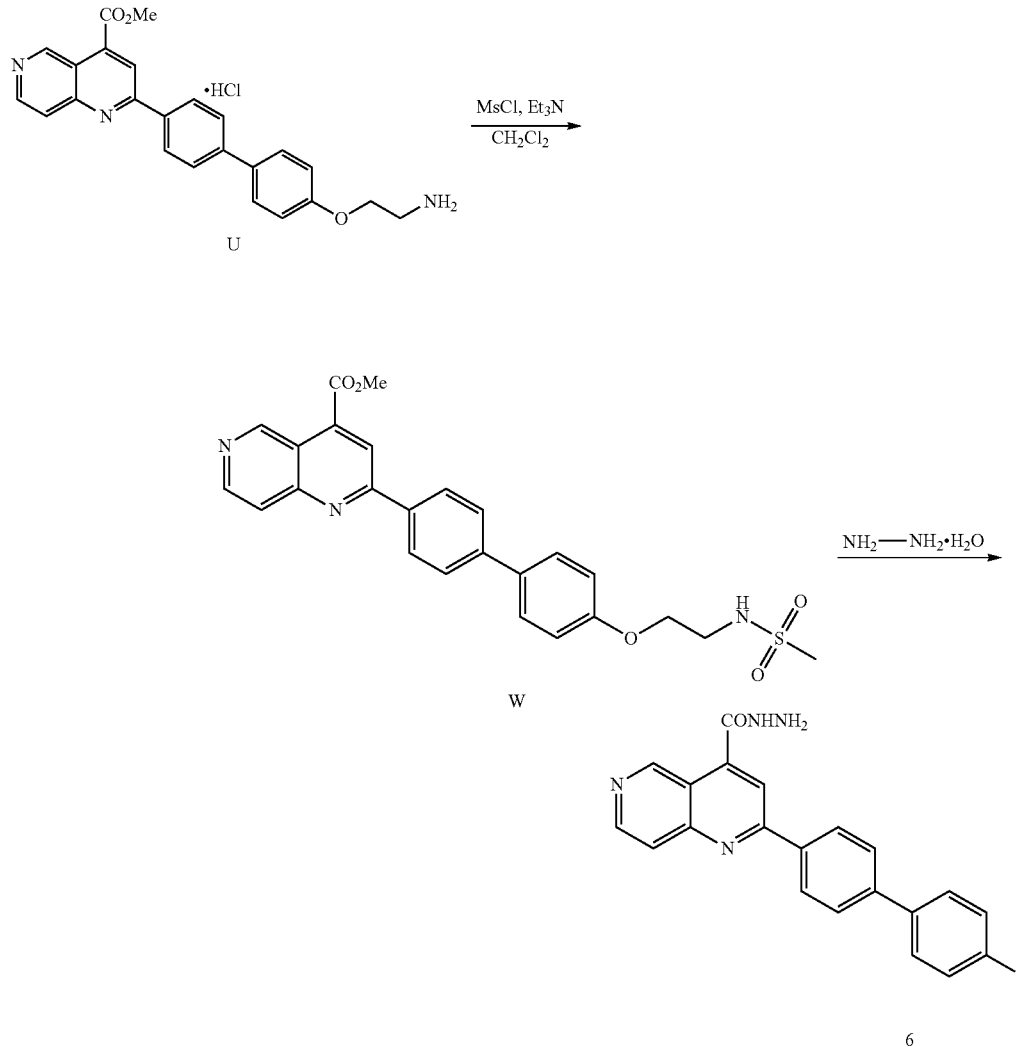

Example 6

N-(2-((4'-(4-(hydrazinecarbonyl)-1,6-naphthyridin-2-yl)-[1,1'-biphenyl]-4-yl)oxy)ethyl)methanesulfonamide (6)

To a stirred solution of methyl 2-(4'-(2-aminoethoxy)-[1,1'-biphenyl]-4-yl)-1,6-naphthyridine-4-carboxylate HCl salt (U; 0.15 g, 0.37 mmol) in CH$_2$Cl$_2$ (10 mL) was added Et$_3$N (0.16 mL, 1.12 mmol) followed by methanesulfonyl chloride (47 mg, 0.40 mmol) at 0° C. under inert atmosphere. The resulting reaction mixture was allowed to warm to RT and stirred for 1 h. Progress of the reaction was monitored by TLC. The reaction mixture was diluted with ice-cold water and extracted with CH$_2$Cl$_2$ (2×50 mL). The combined organic extracts were dried over anhydrous Na$_2$SO$_4$ and A mixture of W (80 mg, 0.16 mmol) and NH$_2$—NH$_2$H$_2$O (4 mL) was heated to 100° C. and stirred for 3 h. Progress of the reaction was monitored by TLC. The reaction mixture was then allowed to cool to RT, diluted with ice-cold water and stirred for 5 min. The precipitated solid was filtered and dried under reduced pressure to obtain the crude. The crude material was purified by trituration with MeOH/diisopropyl ether to afford 6 (70 mg, 0.14 mmol, 87%) as a yellow solid. $^1$H NMR (400 MHz, DMSO-d$_6$): δ 10.20 (bs, 1H), 9.64 (s, 1H), 8.80 (d, J=6.0 Hz, 1H), 8.44 (d, J=8.4 Hz, 2H), 8.34 (s, 1H), 8.02 (d, J=6.0 Hz, 1H), 7.90 (d, J=8.4 Hz, 2H), 7.78 (d, J=8.8 Hz, 2H), 7.32 (bs, 1H), 7.11 (d, J=8.8 Hz, 2H), 4.79 (bs, 2H), 4.12 (t, J=5.6 Hz, 2H), 3.38 (t, J=5.6 Hz, 2H), 2.98 (s, 3H). MS (ESI): m/z 478 [M+1]$^+$. HPLC: 96.7%.

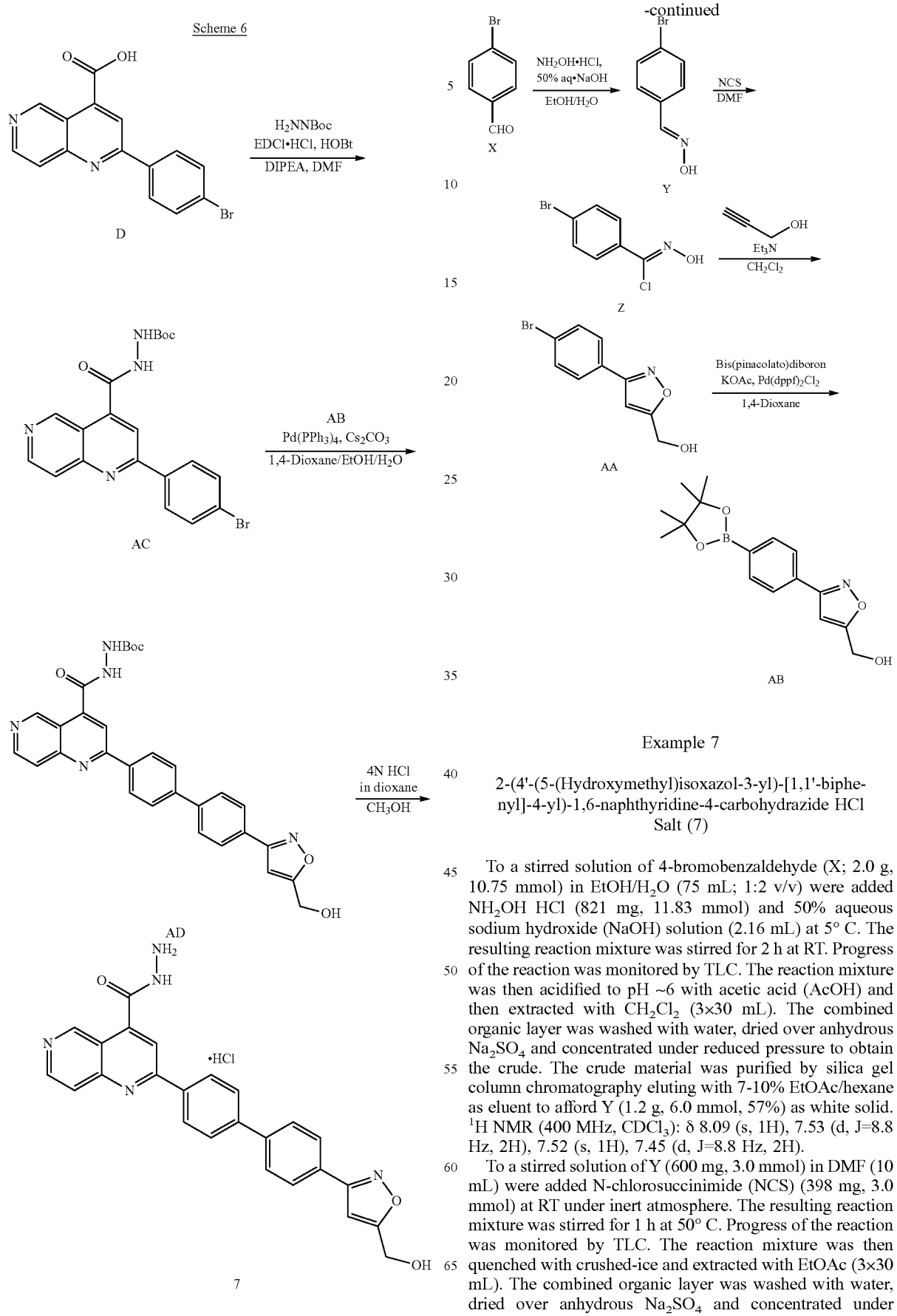

Example 7

2-(4'-(5-(Hydroxymethyl)isoxazol-3-yl)-[1,1'-biphenyl]-4-yl)-1,6-naphthyridine-4-carbohydrazide HCl Salt (7)

To a stirred solution of 4-bromobenzaldehyde (X; 2.0 g, 10.75 mmol) in EtOH/H$_2$O (75 mL; 1:2 v/v) were added NH$_2$OH HCl (821 mg, 11.83 mmol) and 50% aqueous sodium hydroxide (NaOH) solution (2.16 mL) at 5° C. The resulting reaction mixture was stirred for 2 h at RT. Progress of the reaction was monitored by TLC. The reaction mixture was then acidified to pH ~6 with acetic acid (AcOH) and then extracted with CH$_2$Cl$_2$ (3×30 mL). The combined organic layer was washed with water, dried over anhydrous Na$_2$SO$_4$ and concentrated under reduced pressure to obtain the crude. The crude material was purified by silica gel column chromatography eluting with 7-10% EtOAc/hexane as eluent to afford Y (1.2 g, 6.0 mmol, 57%) as white solid. $^1$H NMR (400 MHz, CDCl$_3$): δ 8.09 (s, 1H), 7.53 (d, J=8.8 Hz, 2H), 7.52 (s, 1H), 7.45 (d, J=8.8 Hz, 2H).

To a stirred solution of Y (600 mg, 3.0 mmol) in DMF (10 mL) were added N-chlorosuccinimide (NCS) (398 mg, 3.0 mmol) at RT under inert atmosphere. The resulting reaction mixture was stirred for 1 h at 50° C. Progress of the reaction was monitored by TLC. The reaction mixture was then quenched with crushed-ice and extracted with EtOAc (3×30 mL). The combined organic layer was washed with water, dried over anhydrous Na$_2$SO$_4$ and concentrated under reduced pressure to obtain the crude. The crude material was purified by silica gel column chromatography eluting with 7-10% EtOAc/hexane as eluent to afford Z (500 mg, 2.132 mmol, 71%) as white solid. $^1$H NMR (400 MHz, DMSO-d$_6$): δ 12.51 (s, 1H), 7.73-7.65 (m, 4H).

To a stirred solution of Z (500 mg, 2.132 mmol) in CH$_2$Cl$_2$ (10 ml) was added propargyl alcohol (120 mg, 2.132 mmol) and followed by Et$_3$N (0.34 ml 2.345 mmol) at 0° C. under inert atmosphere. The resulting reaction mixture was stirred for 12 h at RT. Progress of the reaction was monitored by TLC. The reaction mixture was then diluted with water and extracted with CH$_2$Cl$_2$ (3×30 mL). The combined organic layer was washed with water, dried over anhydrous Na$_2$SO$_4$ and concentrated under reduced pressure to obtain the crude. The crude material was purified by silica gel column chromatography eluting with 15-20% EtOAc/hexane as eluent to afford AA (400 mg, 1.57 mmol, 73%) as a white solid. $^1$H NMR (500 MHz, CDCl$_3$): δ 7.67 (d, J=8.5 Hz, 2H), 7.59 (d, J=8.5 Hz, 2H), 6.54 (s, 1H), 4.83 (d, J=4.5 Hz, 2H), 2.13 (bs, 1H). LC-MS: m/z 252 [M−2]$^−$ at 3.28 min (95.08% purity).

A stirred mixture of AA (200 mg, 0.787 mmol), bis(pinacalato)diboron (220 mg, 0.865 mmol) and anhydrous KOAc (231 mg, 2.36 mmol) in 1,4-dioxane (20 mL) was purged with argon for 30 min at RT. To the resulting reaction mixture was added Pd(dppf)$_2$Cl$_2$ (57 mg, 0.078 mmol) at RT and heated to 100° C. for 2 h. After completion of the starting material (by TLC), the reaction mass was brought to RT and filtered through a Celite pad. The filtrate was concentrated under reduced pressure and the crude material was purified by silica gel column chromatography eluting with 35-50% EtOAc/hexane as eluent to afford AB (300 mg, 0.67 mmol) as a colorless sticky solid. $^1$H NMR (400 MHz, CDCl$_3$): δ 7.89 (d, J=8 Hz, 2H), 7.80 (d, J=6.4 Hz, 2H), 6.60 (s, 1H), 4.83 (s, 2H), 4.15 (bs, 1H), 1.36 (s, 12H).

To a stirred solution of D (5.0 g, 15.24 mmol) in DMF (20 mL) was added DIPEA (8.5 mL, 45.72 mmol) followed by EDCI.HCl (4.4 g, 22.87 mmol) and HOBt (3.1 g, 22.87 mmol) at RT and continued stirring for another 20 min under inert atmosphere. To the resulting reaction mixture was added Boc-hydrazine (4.0 g, 30.48 mmol) at 0° C. and stirred for another 16 h at RT. After complete consumption of the starting material (by TLC), the reaction was quenched with ice-cold water and extracted with EtOAc (2×100 mL). The combined organic extracts were dried over anhydrous Na$_2$SO$_4$ and concentrated under reduced pressure to obtain the crude. The crude material was purified by silica gel column chromatography eluting with 3% CH$_3$OH/CH$_2$Cl$_2$ as eluent to afford AC (3.0 g, 6.77 mmol, 44%) as an off-white solid. $^1$H NMR (400 MHz, DMSO-d$_6$): δ 10.63 (bs, 1H), 9.70 (bs, 1H), 9.29 (s, 1H), 8.83 (d, J=5.6 Hz, 1H), 8.31 (d, J=8.4 Hz, 2H), 8.28 (s, 1H), 8.03 (d, J=5.6 Hz, 1H), 7.82 (d, J=8.4 Hz, 2H), 1.49 (s, 9H). LC-MS: m/z 445 [M+2]$^+$ at 3.66 min (99.6% purity).

To a stirred solution of AC (150 mg, 0.338 mmol) and AB (122 mg, 0.406 mmol) dissolved in a mixture of 1,4-dioxane (8 mL):EtOH (4 mL):H$_2$O (2 mL) was added Cs$_2$CO$_3$ (326 mg, 1.015 mmol) at RT. The reaction was degassed by purging with inert gas for 1 h. To the resulting reaction mixture was added Pd(PPh$_3$)$_4$ (39 mg, 0.033 mmol) and then stirred at reflux temperature for 4 h. After consumption of the starting material (by TLC), the reaction mixture was filtered through a pad of Celite and the pad was washed with CH$_2$Cl$_2$ (40 mL). The collected filtrate was dried over anhydrous Na$_2$SO$_4$ and concentrated under reduced pressure to furnish the crude. The crude material was purified by silica gel column chromatography eluting with 2-5% MeOH/CH$_2$Cl$_2$ as eluent to afford AD (25 mg, 0.046 mmol, 13%) as a yellow solid. $^1$H NMR (400 MHz, DMSO-d$_6$): δ 10.67 (s, 1H), 9.71 (s, 1H), 9.03 (s, 1H), 8.84 (d, J=6.0 Hz, 1H), 8.49 (d, J=7.6 Hz, 2H), 8.34 (s, 1H), 8.06-7.95 (m, 7H), 7.02 (s, 1H), 5.73 (t, J=6.0 Hz, OH), 4.64 (d, J=6.0 Hz, 2H), 1.50 (s, 9H). MS (ESI): m/z 537 [M]$^+$.

To a stirred solution of AD (20 mg, 0.037 mmol) in MeOH (5 mL) was added 4N HCl in 1,4-dioxane (5 mL) at 0° C. under inert atmosphere and continued stifling for another 12 h at RT. After complete consumption of the starting material (by LC-MS), the volatiles were removed under reduced pressure to obtain the crude. The crude material was triturated with diisopropyl ether (2×2 mL) followed by n-pentane (2 mL) to afford the HCl salt of 7 (17.4 mg) as a brownish solid. $^1$H NMR (400 MHz, DMSO-d$_6$): δ 11.95 (bs, 1H), 9.70 (s, 1H), 8.86 (d, J=6.0 Hz, 1H), 8.56 (s, 1H), 8.52 (d, J=8.4 Hz, 2H), 8.15 (d, J=6.0 Hz, 1H), 8.03-7.94 (m, 6H), 7.01 (s, 1H), 4.63 (s, 2H), 3.68 (bs, 3H). MS (ESI): m/z 437 [M]$^+$. HPLC: 90.5%.

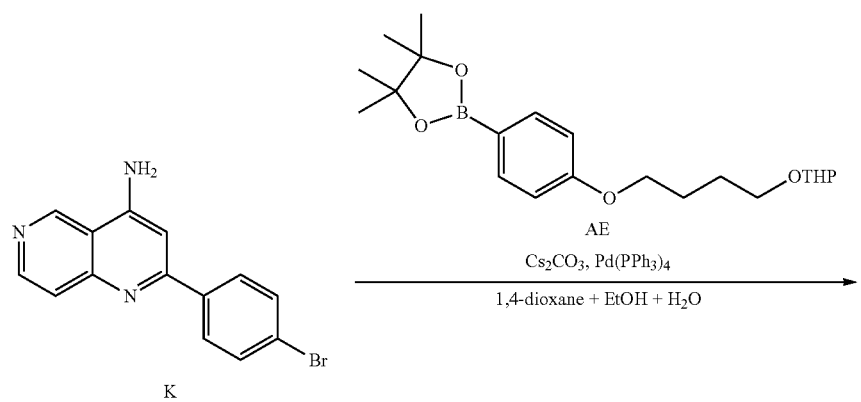

Scheme 7

-continued
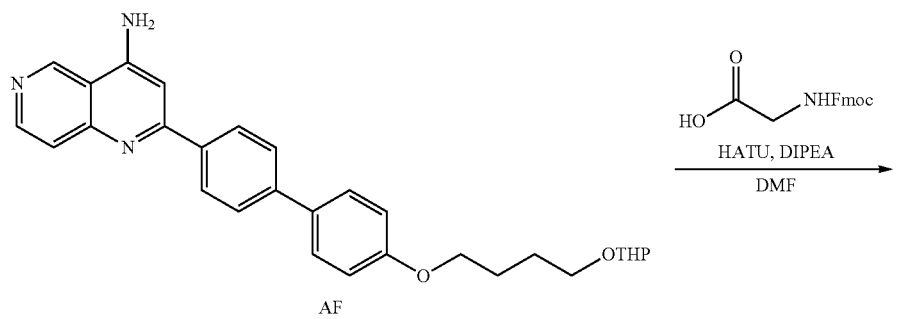
AF
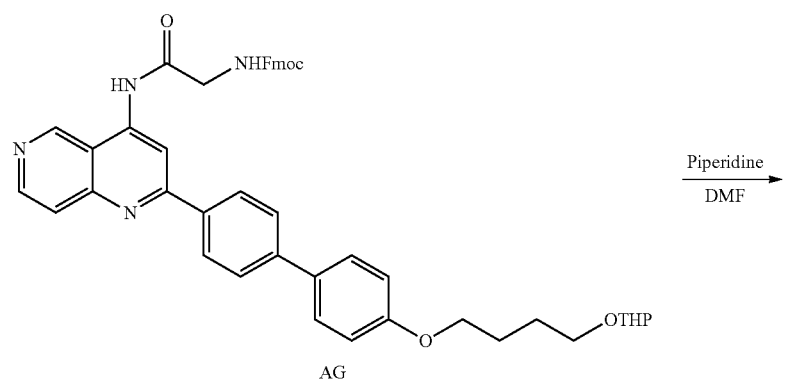
AG
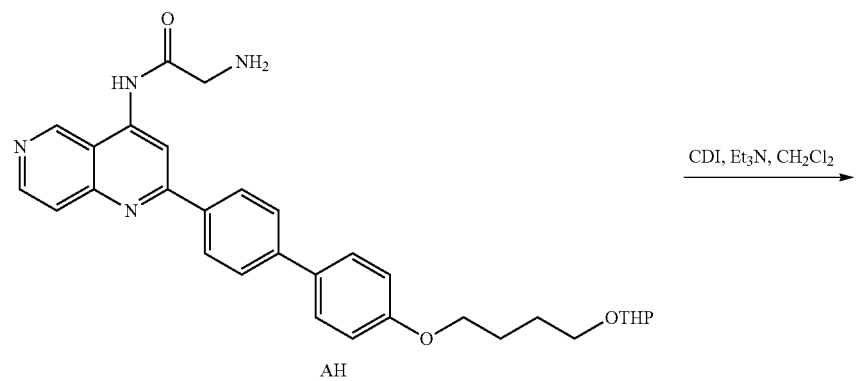
AH
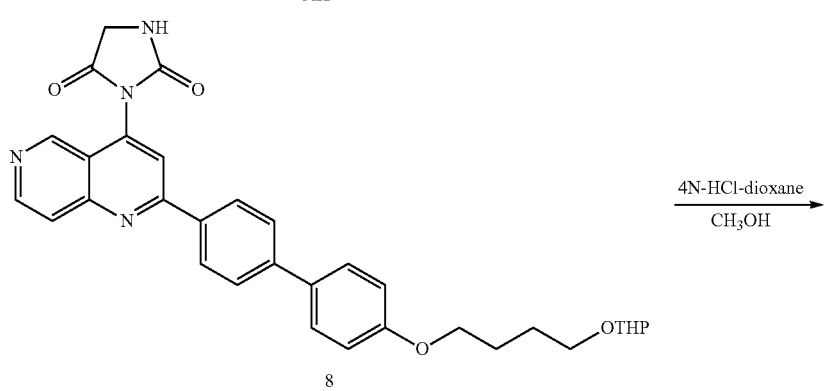
8

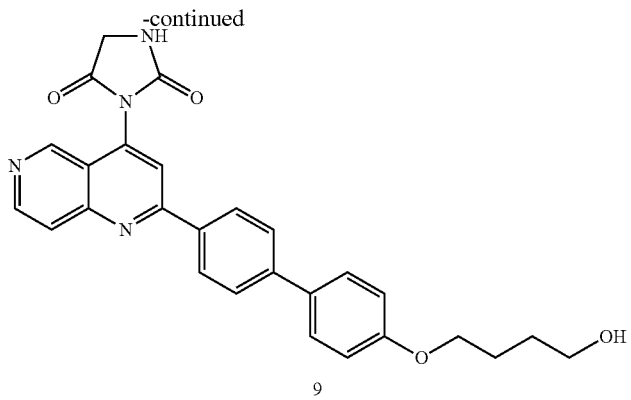

9

Example 8

3-(2-(4'-(4-((tetrahydro-2H-pyran-2-yl)oxy)butoxy)-[1,1'-biphenyl]-4-yl)-1,6-naphthyridin-4-yl)imidazolidine-2,4-dione (8)

To a stirred solution of 2-(4-bromophenyl)-1,6-naphthyridin-4-amine (K; 3.0 g, 10.03 mmol) in 1,4-dioxane (40 mL):EtOH (20 mL):$H_2O$ (8 mL) were added $Cs_2CO_3$ (9.8 g, 30.1 mmol), boronate AE (4.5 g, 12.04 mmol) and Pd(PPh$_3$)$_4$ (1.16 g, 1.003 mmol) at RT under inert atmosphere. The resulting reaction mixture was stirred for 16 h at reflux temperature. Progress of the reaction was monitored by TLC. The reaction mixture was allowed to RT, filtered through a Celite bed and the filtrate was concentrated under reduced pressure to obtain the crude. The crude material was purified by silica gel column chromatography eluting with 8% MeOH/$CH_2Cl_2$ as eluent to afford AF (2.6 g, 5.53 mmol, 55.3%) as a brownish solid. $^1$H NMR (500 MHz, DMSO-$d_6$): δ 9.54 (s, 1H), 8.55 (d, J=6.0 Hz, 1H), 8.17 (d, J=8.0 Hz, 2H), 7.78 (d, J=8.5 Hz, 2H), 7.69-7.61 (m, 3H), 7.37 (br s, 2H), 7.24 (s, 1H), 7.04 (d, J=8.0 Hz, 2H), 4.56 (s, 1H), 4.04 (t, J=6.5 Hz, 2H), 3.76-3.67 (m, 2H), 3.44-3.39 (m, 2H), 1.82-1.77 (m, 2H), 1.72-1.60 (m, 4H), 1.47-1.44 (m, 4H).

To a stirred solution of Fmoc-glycine (5.6 g, 18.8 mmol) in DMF (50 mL) was added DIPEA (90.4 mL, 56.4 mmol) followed by HATU (11.0 g, 28.2 mmol) at RT under inert atmosphere. The reaction mixture was then cooled to 0° C. and AF (2.64 g, 5.63 mmol) was added. The resulting reaction mixture was stirred for 72 h at RT. After consumption of the starting material by TLC, the reaction mixture was quenched with ice-cold water and extracted with EtOAc (3×50 mL). The combined organic layer was dried over anhydrous $Na_2SO_4$ and concentrated under reduced pressure to obtain the crude. The crude material was purified by silica gel column chromatography eluting with 5% MeOH/$CH_2Cl_2$ as eluent to afford AG (1.7 g, 2.26 mmol, 40.9%) as a brownish solid. $^1$H NMR (500 MHz, DMSO-$d_6$): δ 10.66 (s, 1H), 9.76 (s, 1H), 8.86 (s, 1H), 8.75-74 (m, 1H), 8.25 (d, J=8.0 Hz, 2H), 8.18 (br s, 1H), 7.91-7.84 (m, 5H), 7.88-7.71 (m, 5H), 7.44-7.34 (m, 4H), 7.06 (d, J=9.0 Hz, 2H), 4.57 (s, 1H), 4.37 (d, J=7.0 Hz, 1H), 4.28-4.26 (m, 2H), 4.13-4.06 (m, 1H), 3.76-3.60 (m, 2H), 3.43-3.41 (m, 2H), 3.16-3.11 (m, 2H), 1.81-1.59 (m, 6H), 1.47-1.45 (m, 4H). LCMS: m/z 749.0 [M$^+$+1] at 5.42 min (83.59% purity)

To a stirred solution of AG (1.7 g, 2.26 mmol) in DMF (50 mL) was added piperidine (1 mL, 11.34 mmol) at RT under inert atmosphere. The resulting reaction mixture was stirred for 30 min at RT. Progress of the reaction was monitored by TLC. The reaction mixture was quenched with ice-cold water and extracted with EtOAc (2×50 mL). The combined organic layers were dried over anhydrous $Na_2SO_4$ and concentrated under reduced pressure to obtain the crude. The crude material was purified by silica gel column chromatography eluting with 10% MeOH/$CH_2Cl_2$ as eluent to afford AH (0.7 g, 1.32 mmol, 58.8%) as a yellowish solid. $^1$H NMR (500 MHz, DMSO-$d_6$): δ 9.69 (s, 1H), 8.88 (s, 1H), 8.76 (d, J=5.5 Hz, 1H), 8.24 (d, J=8.0 Hz, 2H), 7.93 (d, J=6.0 Hz, 1H), 7.86 (d, J=7.5 Hz, 2H), 7.79-7.77 (m, 1H), 7.72 (d, J=8.5 Hz, 2H), 7.07 (d, J=8.5 Hz, 2H), 4.57 (s, 1H), 4.06 (t, J=6.5 Hz, 2H), 3.76-3.67 (m, 4H), 3.44-3.40 (m, 2H), 2.99 (t, J=5.5 Hz, 2H), 1.82-1.60 (m, 6H), 1.55-1.46 (m, 4H).

To a stirred solution of AH (0.3 g, 0.639 mmol) in $CH_2Cl_2$ (30 mL) were added $Et_3N$ (194 mg, 1.917 mmol) and N,N-carbonyl diimidazole (154 mg, 0.949 mmol) at 0° C. under inert atmosphere. The resulting reaction mixture was stirred for 45 min at 0° C. and then stirred for 3 h at RT. After consumption of the starting material by TLC, the reaction mixture was concentrated under reduced pressure, diluted with water and extracted with EtOAc (2×50 mL). The combined organic layer was washed with a brine solution, dried over anhydrous $Na_2SO_4$ and concentrated under reduced pressure to obtain the crude. The crude material was purified by silica gel column chromatography eluting with 5% MeOH/$CH_2Cl_2$ as eluent to afford 8 (110 mg, 0.22 mmol, 34.8%) as a pale-brown solid. $^1$H NMR (500 MHz, DMSO-$d_6$): δ 9.38 (s, 1H), 8.81 (d, J=5.5 Hz, 1H), 8.68 (s, 1H), 8.38 (s, 1H), 8.37 (d, J=8.5 Hz, 2H), 8.05 (d, J=6.0 Hz, 1H), 7.89 (d, J=8.5 Hz, 2H), 7.75 (d, J=9.0 Hz, 2H), 7.07 (d, J=9.0 Hz, 2H), 4.58-4.57 (m, 1H), 4.39 (d, J=17.5 Hz, 1H), 4.19 (d, J=17.5 Hz, 1H), 4.05 (t, J=6.5 Hz, 2H), 3.76-3.67 (m, 2H), 3.44-3.39 (m, 2H), 1.83-1.59 (m, 6H), 1.47-1.46 (m, 4H).

Example 9

3-(2-(4'-(4-hydroxybutoxy)-[1,1'-biphenyl]-4-yl)-1,6-naphthyridin-4-yl)imidazolidine-2,4-dione (13)

To a stirred solution of 8 (100 mg, 0.181 mmol) in $CH_3OH$ (4 mL) was added 4N HCl in 1,4-dioxane (1 mL) at 0° C. and stirring was continued for 30 min. After consumption of the starting material by TLC, the volatiles were evaporated under reduced pressure. The crude was triturated with 10% MeOH/$CH_2Cl_2$. The obtained solid was dissolved in $CH_2Cl_2$ and basified to pH~8 using $Et_3N$. The solid precipitate was filtered and dried under vacuum to afford 9 (60 mg, 0.128 mmol, 70.83%) as a yellowish solid.

¹H NMR (500 MHz, DMSO-d₆): δ 9.38 (s, 1H), 8.81 (d, J=6.0 Hz, 1H), 8.67 (br s, 1H), 8.38-8.36 (m, 3H), 8.05 (d, J=6.0 Hz, 1H), 7.89 (d, J=8.0 Hz, 2H), 7.75 (d, J=8.5 Hz, 2H), 7.07 (d, J=8.5 Hz, 2H), 4.39 (d, J=17.5 Hz, 1H), 4.20 (d, J=17.5 Hz, 1H), 4.05 (t, J=6.5 Hz, 2H), 3.47 (t, J=6.5 Hz, 2H), 3.33 (br s, 1H), 1.80-1.75 (m, 2H), 1.61-1.56 (m, 2H). LCMS: m/z 469 [M⁺+1] at 2.82 min (96.75% purity). HPLC: 97.07%.

Synthesis of intermediate

AE 4,4,5,5-tetramethyl-2-(4'-(4-((tetrahydro-2H-pyran-2-yl)oxy)butoxy)-[1,1'-biphenyl]-4-yl)-1,3,2-dioxaborolane To a stirred solution of 4-bromophenol (10 g, 57.80 mmol) in 1,4-dioxane (200 mL) was added bis(pinacolato)diborane (16.1 g, 63.38 mmol) followed by potassium acetate (16.9 g, 172.4 mmol) at RT and degassed by purging with N₂ for 15 min. To the resulting reaction mixture was added Pd(dppf)₂Cl₂ (4.2 g, 5.74 mmol) and then stirred at reflux temperature for 3 h. After consumption of the starting material (by TLC), the reaction mixture was filtered through pad of Celite and the pad was washed with EtOAc (30 mL). The collected filtrate was dried over anhydrous Na₂SO₄ and concentrated under reduced pressure to furnish the crude. The crude material was purified by silica gel column chromatography eluting with 20% EtOAc/hexane as eluent to afford 4-(4,4,5,5-tetramethyl-1,3,2-dioxaborolan-2-yl)phenol (10.0 g, 45.45 mmol, 79.3%) as a white solid. ¹H NMR (500 MHz, CDCl₃): δ 7.71 (d, J=8.5 Hz, 2H), 6.82 (d, J=8.5 Hz, 2H), 5.17 (brs, 1H), 1.33 (s, 12H). MS (ESI): m/z 218.9 [M⁺−1]

To a stirred solution of tetrahydrofuran (50 mL) was added 48% HBr (23 mL) dropwise over a period of 2 h at reflux temperature. The stifling was continued for another 1.3 h at reflux temperature and then cooled to RT. The reaction mixture was neutralized with a saturated NaHCO₃ solution, diluted with water and separated the organic layer. The organic layer was washed with brine, dried over anhydrous Na₂SO₄ and then concentrated under reduced pressure to afford 4-bromobutanol (20 g, crude) as a colorless liquid. ¹H NMR (500 MHz, CDCl₃): δ 3.67-3.65 (m, 2H), 3.47-3.44 (m, 2H), 1.99-1.93 (m, 2H), 1.74-1.68 (m, 2H).

To a stirred solution of 4-bromobutanol (1 g, 6.53 mmol) in CH₂Cl₂ (15 mL) was added 3,4-dihydro-2H-pyran (824 mg, 9.79 mmol) followed by p-TSA (124 mg, 0.65 mmol) at 0° C. under inert atmosphere. The resulting reaction mixture was stirred for 30 min at RT. After completion of the reaction (by TLC), the reaction mixture was diluted with water and extracted with CH₂Cl₂ (2×25 mL). The combined organic extracts were dried over anhydrous Na₂SO₄ and concentrated under reduced pressure to furnish the crude. The crude material was purified by silica gel column chromatography eluting with 5% EtOAc/hexane as eluent to afford 2-(4-bromobutoxyl)tetrahydro-2H-pyran (0.9 g, 3.79 mmol, 58.4%) as a colorless syrupy mass. ¹H NMR (500 MHz, CDCl₃): δ 4.57-4.56 (m, 1H), 3.87-3.74 (m, 2H), 3.51-3.40 (m, 4H), 2.00-1.94 (m, 2H), 1.84-1.68 (m, 4H), 1.61-1.51 (m, 4H).

To a stirred solution of 4-(4,4,5,5-tetramethyl-1,3,2-dioxaborolan-2-yl)phenol (4.0 g, 18.26 mmol) in DMF (10 mL) wad added K₂CO₃ (6.3 g, 45.65 mmol) at RT and stirred for 15 min. A solution of 2-(4-bromobutoxyl)tetrahydro-2H-pyran (5.6 g, 23.62 mmol) in DMF (10 mL) was added to the reaction mixture and stirring was continued for another 16 h at RT. After consumption of the starting material (by TLC), the reaction mixture was diluted with water and extracted with EtOAc (2×25 mL). The combined organic extracts were dried over anhydrous Na₂SO₄ and concentrated under reduced pressure to furnish the crude. The crude material was purified by silica gel column chromatography eluting with 20% EtOAc/hexane as eluent to afford 4,4,5,5-tetramethyl-2-(4-(4-((tetrahydro-2H-pyran-2-yl)oxy)butoxy)phenyl)-1,3,2-dioxaborolane (6.5 g, 17.3 mmol, 95.5%) as a colorless syrupy mass. ¹H NMR (500 MHz, CDCl₃): δ 7.73 (d, J=8.0 Hz, 2H), 6.88 (d, J=8.5 Hz, 2H), 4.60-4.58 (m, 1H), 4.02 (t, J=7.0 Hz, 2H), 3.88-3.78 (m, 2H), 3.51-3.43 (m, 2H), 1.90-1.69 (m, 4H), 1.60-1.58 (m, 4H), 1.57-1.52 (m, 2H), 1.33 (s, 12H).

To a stirred solution of 1-bromo-4-iodobenzene (14 g, 49.48 mmol) and 4,4,5,5-tetramethyl-2-(4-(4-((tetrahydro-2H-pyran-2-yl)oxy)butoxy)phenyl)-1,3,2-dioxaborolane (12.9 g, 34.6 mmol) dissolved in a mixture of toluene (250 mL):MeOH (40 mL) was added K₂CO₃ (20.4 g, 148.2 mmol) at RT. The reaction was degassed by purging with N₂ for 1 h. To the resulting reaction mixture was added Pd(PPh₃)₄ (2.9 g, 2.47 mmol) and then stirred at reflux temperature for 4 h. After consumption of the starting material (by TLC), the reaction mixture was filtered through a pad of Celite and the pad was washed with CH₂Cl₂ (40 mL). The collected filtrate was dried over anhydrous Na₂SO₄ and concentrated under reduced pressure to furnish the crude. The crude material was purified by silica gel column chromatography eluting with 10% EtOAc/hexane as eluent to afford 2-(4-((4'-bromo-[1,1'-biphenyl]-4-yl)oxy)butoxy)tetrahydro-2H-pyran (10 g, 24.69 mmol, 50%) as an off-white semi-solid. ¹H NMR (500 MHz, CDCl₃): δ 7.52 (d, J=8.5 Hz, 2H), 7.46 (d, J=9.0 Hz, 2H), 7.40 (d, J=8.0 Hz, 2H), 6.95 (d, J=8.5 Hz, 2H), 4.61-4.59 (m, 1H), 4.03 (t, J=6.0 Hz, 2H), 3.89-3.80 (m, 2H), 3.52-3.44 (m, 2H), 1.93-1.70 (m, 6H), 1.61-1.51 (m, 4H). MS (ESI): m/z 406 [M⁺+1].

To a stirred solution of 2-(4-((4'-bromo-[1,1'-biphenyl]-4-yl)oxy)butoxy)tetrahydro-2H-pyran (10 g, 24.67 mmol) in 1,4-dioxane (250 mL) at RT degassed by purging with argon for 15 min were added bis(pinacolato)diboron (6.9 g, 27.2 mmol) followed by potassium acetate (7.3 g, 74.1 mmol). The degassing was continued for another 1 h. To the resulting reaction mixture was added Pd(dppf)₂Cl₂ (1.8 g, 2.47 mmol) and then stirred at reflux temperature for 12 h. After consumption of the starting material (by TLC), the reaction mixture was filtered through a pad of Celite and the pad was washed with CH₂Cl₂ (50 mL). The collected filtrate was dried over anhydrous Na₂SO₄ and concentrated under reduced pressure to furnish the crude. The crude material was purified by silica gel column chromatography eluting with 15% EtOAc/hexane to afford desired boronate 4,4,5,5-tetramethyl-2-(4'-(4-((tetrahydro-2H-pyran-2-yl)oxy)butoxy)-[1,1'-biphenyl]-4-yl)-1,3,2-dioxaborolane (AE) (10 g, 22.1 mmol, 89%) as a white solid. ¹H NMR (500 MHz, CDCl₃): δ 7.85 (d, J=8.0 Hz, 2H), 7.56-7.53 (m, 4H), 6.96 (d, J=8.5 Hz, 2H), 4.61-4.60 (m, 1H), 4.04 (t, J=6.0 Hz, 2H), 3.89-3.80 (m, 2H), 3.52-3.45 (m, 2H), 1.92-1.70 (m, 7H), 1.56-1.52 (m, 3H), 1.33 (s, 12H). MS (ESI): m/z 452 [M⁺].

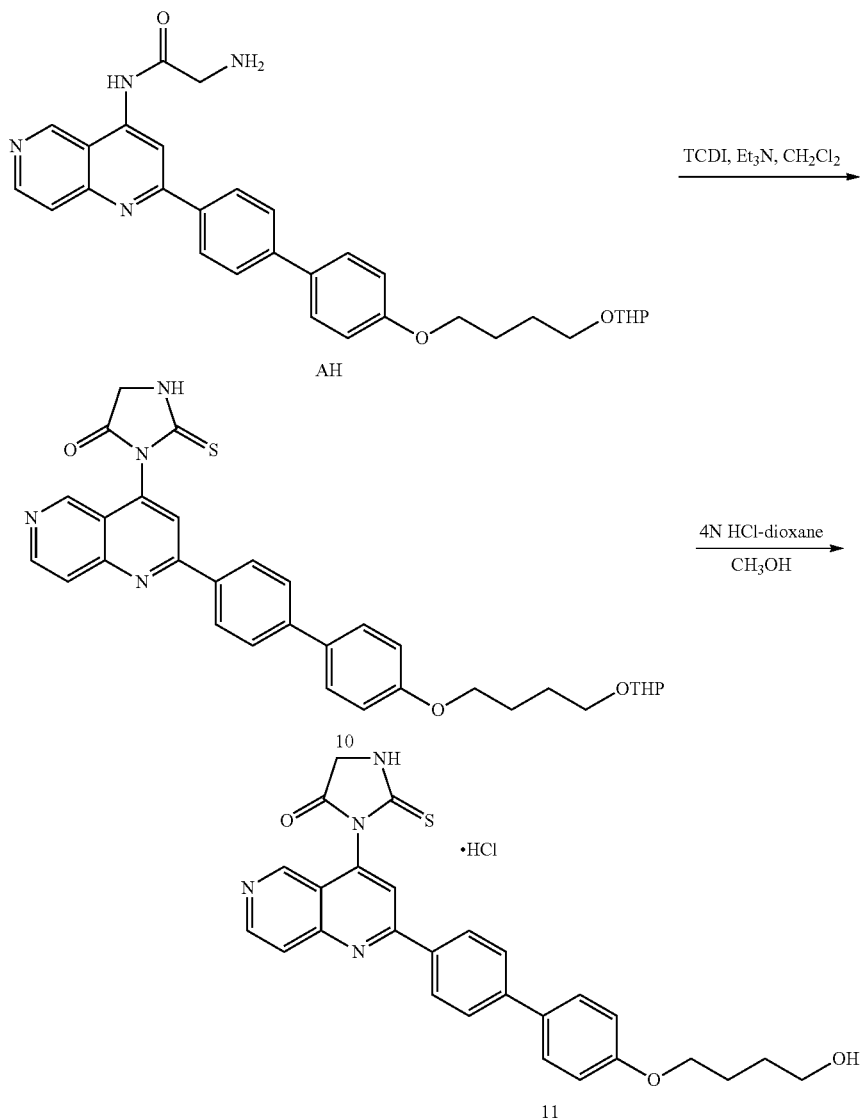

Example 10
3-(2-(4'-(4-((tetrahydro-2H-pyran-2-yl)oxy)butoxy)-[1,1'-biphenyl]-4-yl)-1,6-naphthyridin-4-yl)-2-thioxoimidazolidin-4-one (10)

To a stirred solution of AH (0.1 g, 0.213 mmol) in CH$_2$Cl$_2$ (10 mL) were added Et$_3$N (0.064 mg, 0.639 mmol) and thiocarbonyl diimidazole (TCDI) (56.9 mg, 0.319 mmol) at 0° C. under inert atmosphere. The reaction mixture was stirred for 2 h at RT. After consumption of the starting material by TLC, the reaction mixture was diluted with water and extracted with CH$_2$Cl$_2$ (3×30 mL). The combined organic layer was washed with water, dried over anhydrous Na$_2$SO$_4$ and concentrated under reduced pressure to obtain the crude. The crude material was purified by silica gel column chromatography eluting with 3% MeOH/CH$_2$Cl$_2$ as eluent to afford 10 (36.8 mg, 0.064 mmol, 30.6%) as a yellow solid. $^1$H NMR (500 MHz, DMSO-d$_6$): δ 10.78 (s, 1H), 9.38 (s, 1H), 8.81 (d, J=6.0 Hz, 1H), 8.42 (s, 1H), 8.37 (d, J=8.5 Hz, 2H), 8.05 (d, J=6.0 Hz, 1H), 7.89 (d, J=8.5 Hz, 2H), 7.75 (d, J=9.0 Hz, 2H), 7.07 (d, J=9.0 Hz, 2H), 4.58 (d, J=8.5 Hz, 2H), 4.44-4.40 (m, 1H), 4.07 (t, J=6.5 Hz, 2H), 3.76-3.67 (m, 2H), 3.44-3.40 (m, 2H), 2.01-1.99 (m, 1H), 1.82-1.80 (m, 2H), 1.72-1.68 (m, 3H), 1.63-1.60 (m, 1H), 1.49-1.47 (m, 3H).

Example 11
3-(2-(4'-(4-hydroxybutoxy)-[1,1'-biphenyl]-4-yl)-1,6-naphthyridin-4-yl)-2-thioxoimidazolidin-4-one HCl Salt (11)

To a stirred solution of 10 (30 mg, 0.052 mmol) in 10% CH$_3$OH/CH$_2$Cl$_2$ (5 mL) was added 4N HCl in 1,4-dioxane (0.5 mL) at 0° C. The reaction was stirred for 2 h. After consumption of the starting material by TLC, the volatiles were evaporated under reduced pressure and the crude was triturated with 10% MeOH/diethyl ether followed by n-pentane to obtain the HCl salt of 11 (15.5 mg) as a bright-yellow solid. $^1$H NMR (500 MHz, DMSO-d$_6$): δ 10.85 (s, 1H), 9.60 (br s, 1H), 8.86 (s, 1H), 8.55 (s, 1H), 8.40 (d, J=8.0 Hz, 2H), 8.24 (br s, 1H), 7.92 (d, J=8.0 Hz, 2H), 7.76 (d, J=8.5 Hz, 2H), 7.07 (d, J=8.5 Hz, 2H), 4.58 (d, J=20.0 Hz, 1H), 4.48 (d, J=20.0 Hz, 1H), 4.07-4.04 (m, 3H), 3.47 (t, J=6.5 Hz, 2H), 1.79-1.76 (m, 2H), 1.62-1.57 (m, 2H). MS (ESI): 485 [M$^+$+1]. HPLC: 95.23%.

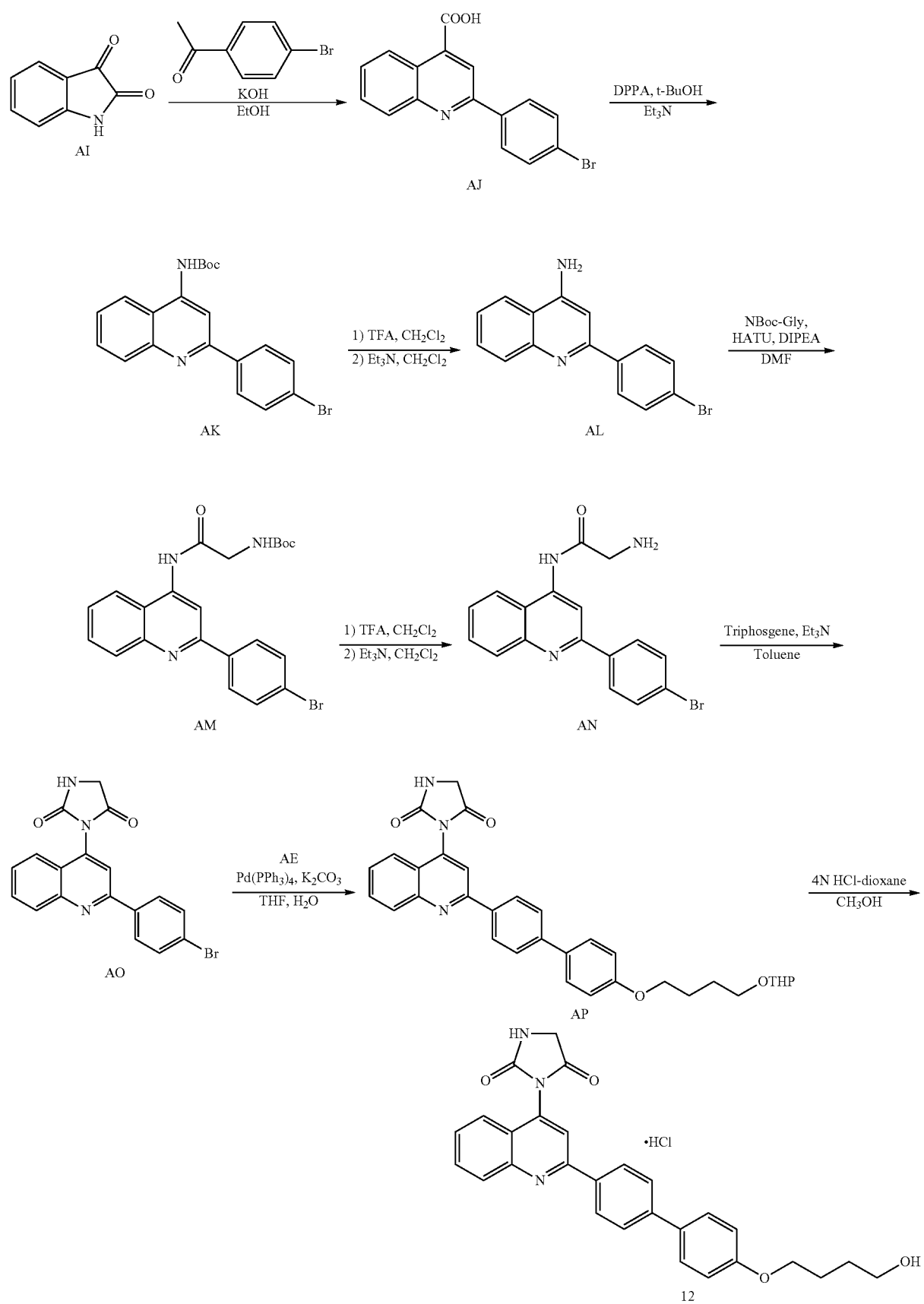

Example 12

3-(2-(4'-(4-hydroxybutoxy)-[1,1'-biphenyl]-4-yl)quinolin-4-yl)imidazolidine-2,4-dione HCl salt (12)

To a stirred solution of indoline-2,3-dione (AI; 10.0 g, 68.03 mmol) and 1-(4-bromophenyl)ethanone (12.2 g, 61.3 mmol) dissolved in a 1:1 mixture of EtOH/$H_2O$ (100 mL) was added KOH (15.3 g, 272.6 mmol) at RT. The resulting reaction mixture was heated at reflux and stirred for 2 h. After consumption of the starting material (by TLC), the volatiles were removed under reduced pressure and the aqueous layer was washed with $CH_2Cl_2$ (2×50 mL). The aqueous layer was separated and neutralized with acetic acid to precipitate the solid. The precipitated solid was filtered, azeotroped with toluene followed by drying the solid under reduced pressure to afford acid AJ (17.0 g, 51.8 mmol, 77%) as a pink solid. $^1$H NMR (500 MHz, DMSO-$d_6$): δ 8.63 (d, J=8.0 Hz, 1H), 8.31 (s, 1H), 8.24 (d, J=8.0 Hz, 2H), 8.11 (d, J=8.5 Hz, 1H), 7.80 (t, J=7.5 Hz, 1H), 7.75 (d, J=8.5 Hz, 2H), 7.64 (t, J=7.5 Hz, 1H). LCMS: m/z 328.8 [M$^+$+1] at 4.83 min (64.89%).

To a stirred solution of AJ (1.4 g, 4.28 mmol) in t-BuOH (20 mL) were added Et$_3$N (1.2 mL, 8.56 mmol) followed by diphenyl phosphorazidate (DPPA) (1.8 mL, 8.56 mmol) at RT. The resulting reaction mixture was heated to reflux and stirred for 12 h. After consumption of the starting material (by TLC), the reaction mixture was concentrated under reduced pressure, the residue dissolved in $CH_2Cl_2$ (30 mL) and washed with water (2×30 mL). The organic layer was dried over anhydrous $Na_2SO_4$ and concentrated under reduced pressure to furnish the crude. The crude material was purified by silica gel column chromatography eluting with 30% EtOAc/hexane as eluent to afford AK (1.8 g, 4.51 mmol) as a pale yellow solid. This contained a small amount of impurity (in $^1$H-NMR) and was used in the next step without further purification. $^1$H NMR (500 MHz, DMSO-$d_6$): δ 10.05 (br s, 1H), 8.54 (s, 1H), 8.45 (d, J=8.0 Hz, 1H), 8.10-8.06 (m, 3H), 7.83-7.78 (m, 2H), 7.61 (t, J=8.0 Hz, 1H), 7.33 (t, J=8.0 Hz, 1H), 1.57 (s, 9H). MS (ESI): m/z 399 [M$^+$+1]

To a stirred solution of AK (5.0 g, 12.5 mmol) in $CH_2Cl_2$ (20 mL) was added TFA (20 mL) at 0° C. The reaction mixture was slowly allowed to warm to RT and stirred for 8 h. After complete consumption of the starting material (by TLC), the reaction mixture was concentrated under reduced pressure and the residue was triturated with $CH_2Cl_2$. The obtained solid was dissolved in $CH_2Cl_2$ and basified by using Et$_3$N (15 mL). The solid precipitate was filtered, washed with pentane and dried under reduced pressure to afford amine AL (2.5 g, 8.35 mmol, 67.5 mmol) as a pale yellow solid. $^1$H NMR (500 MHz, DMSO-$d_6$): 8.15 (d, J=7.5 Hz, 1H), 8.04 (d, J=8.5 Hz, 2H), 7.83 (d, J=8.5 Hz, 1H), 7.70 (d, J=8.0 Hz, 2H), 7.62 (t, J=7.5 Hz, 1H), 7.39 (t, J=7.5 Hz, 1H), 7.10 (s, 1H), 6.87 (s, 2H). LCMS: m/z 300.5 [M$^+$+1] at 7.68 min (98.62%).

To a stirred solution N-Boc-glycine (1.7 g, 10.03 mmol) in DMF (20 mL) at 0° C. were added AL (1.0 g, 3.34 mmol) and HATU (5.9 g, 15.1 mmol) followed by DIPEA (2.59 g, 20.03 mmol) under inert atmosphere. The resulting reaction mixture was stirred for 12 h at RT. After complete consumption of the starting material (by TLC), the reaction mixture was diluted with EtOAc (20 mL) and washed with water (2×30 mL). The organic layer was dried over anhydrous $Na_2SO_4$ and concentrated under reduced pressure to furnish the crude. The crude material was purified by silica gel column chromatography eluting with 30% EtOAc/hexane as eluent to afford AM (0.7 g, 1.53 mmol) as a pale yellow solid. This contained a small amount of impurity and was used in the next step without further purification. $^1$H NMR (500 MHz, CDCl$_3$): δ 9.45 (br s, 1H), 8.82 (s, 1H), 8.15 (d, J=8.0 Hz, 1H), 8.06 (d, J=8.0 Hz, 2H), 7.96 (d, J=8.5 Hz, 1H), 7.73 (t, J=7.5 Hz, 1H), 7.63 (d, J=8.5 Hz, 2H), 7.54 (t, J=7.5 Hz, 1H), 5.41 (br s, 1H), 4.05 (d, J=6.5 Hz, 2H), 1.56 (s, 9H). MS (ESI): m/z 459.0 [M$^+$+2].

To a stirred solution of AM (0.7 g, 1.53 mmol) in $CH_2Cl_2$ (10 mL) was added TFA (5 mL) at 0° C. The reaction mixture was allowed to warm to RT and stirred for 4 h. After complete consumption of the starting material (by TLC), the reaction mixture was concentrated under reduced pressure. To the residue dissolved in $CH_2Cl_2$ (50 mL) was added Et$_3$N (10 mL, 136.3 mmol) at 0° C. and the solution was stirred for 30 min. The reaction mixture was diluted with $CH_2Cl_2$ (50 mL) and washed with water (3×50 mL). The organic layer was dried over anhydrous $Na_2SO_4$ and concentrated under reduced pressure to afford amine AN (0.35 g, 0.98 mmol, crude) as a yellow solid. This material was used in the next step without any further purification. $^1$H NMR (500 MHz, DMSO-$d_6$): δ 8.83 (s, 1H), 8.17-8.07 (m, 4H), 7.82 (t, J=7.5 Hz, 1H), 7.77 (d, J=8.5 Hz, 2H), 7.68 (t, J=7.5 Hz, 1H), 5.02 (br s, 2H), 3.50 (s, 2H). MS (ESI): m/z 358 [M$^+$+2].

To a stirred solution of AN (50 mg, 0.14 mmol) in toluene (10 mL) was added Et$_3$N (0.03 mL, 0.21 mmol) followed by triphosgene (42 mg, 0.14 mmol) at 0° C. under inert atmosphere. The stirring was continued for 45 min. The resulting reaction mixture was heated to reflux and stirred for 12 h. After complete consumption of the starting material (by TLC), the reaction mixture was concentrated under reduced pressure to furnish the crude. The crude material was purified by silica gel column chromatography eluting with 3% MeOH/$CH_2Cl_2$ as eluent to afford AO (30 mg, 0.078 mmol, 56.6%) as a pale yellow solid. $^1$H NMR (500 MHz, DMSO-$d_6$): δ 8.58 (s, 1H), 8.24-8.22 (m, 3H), 8.18 (d, J=8.5 Hz, 1H), 7.92 (d, J=8.5 Hz, 1H), 7.87 (t, J=7.5 Hz, 1H), 7.79 (d, J=8.5 Hz, 2H), 7.66 (t, J=7.5 Hz, 1H), 4.38 (d, J=18.0 Hz, 1H), 4.19 (d, J=18.0 Hz, 1H). LCMS: m/z 382 [M$^+$] at 4.03 min (94.19%).

To a stirred solution of AO (150 mg, 0.392 mmol) in THF (20 mL):water (2 mL) degassed by purging with argon for 30 min were added AE (176 mg, 0.471 mmol) and K$_2$CO$_3$ (162 mg, 1.178 mmol) at RT. The degassing was continued for another 30 min. To the resulting reaction mixture was added Pd(PPh$_3$)$_4$ (45 mg, 0.039 mmol) and the reaction was degassed for another 5 min. The reaction mixture was then slowly heated to reflux and stirred for 8.5 h. Progress of the reaction was monitored by TLC. The reaction mixture was then concentrated under reduced pressure and the obtained crude was purified by silica gel column chromatography eluting with 15% CH$_3$OH/CH$_2$Cl$_2$ as eluent to afford AP (30 mg, 0.054 mmol, 13.8%) as a white solid along with another 30 mg of product containing triphenylphosphine oxide as an impurity. $^1$H NMR (500 MHz, DMSO-$d_6$): δ 8.57 (s, 1H), 8.34 (d, J=8.5 Hz, 2H), 8.25 (s, 1H), 8.19 (d, J=8.5 Hz, 1H), 7.91 (d, J=8.0 Hz, 1H), 7.88-7.84 (m, 3H), 7.73 (d, J=8.0 Hz, 2H), 7.64 (t, J=7.5 Hz, 1H), 7.06 (d, J=9.0 Hz, 2H), 4.58-4.57 (m, 1H), 4.38 (d, J=17.5 Hz, 1H), 4.20 (d, J=17.5 Hz, 1H), 4.07 (t, J=6.5 Hz, 2H), 3.76-3.69 (m, 2H), 3.45-3.41 (m, 2H), 1.84-1.80 (m, 2H), 1.73-1.62 (m, 4H), 1.49-1.46 (m, 4H). LC-MS: m/z 552 [M$^+$+1] at 4.34 min (99.17% purity).

To a stirred solution of AP (30 mg, 0.054 mmol) in CH$_3$OH (1 mL) was added 4N HCl in 1,4-dioxane (0.5 mL) at 0° C. The stirring was continued for another 20 min. After complete consumption of the starting material (by TLC), the reaction mixture was concentrated under reduced pressure to furnish the crude. The crude material was triturated with diisopropyl ether to afford the HCl salt of 12 (25 mg) as a yellow solid. $^1$H NMR (500 MHz, DMSO-$d_6$): δ 8.57 (s, 1H), 8.34 (d, J=8.0 Hz, 2H), 8.25 (s, 1H), 8.19 (d, J=8.5 Hz, 1H), 7.91 (d, J=8.5 Hz, 1H), 7.88-7.84 (m, 3H), 7.73 (d, J=8.5 Hz, 2H), 7.64 (t, J=7.5 Hz, 1H), 7.06 (d, J=9.0 Hz, 2H), 4.38 (d, J=17.5 Hz, 1H), 4.20 (d, J=17.5 Hz, 1H), 4.06-4.03 (m, 3H), 3.47 (t, J=6.5 Hz, 2H), 1.81-1.76 (m, 2H), 1.62-1.56 (m, 2H). MS (ESI): m/z 468.6 [M$^+$+1]. HPLC: 99.74%.

Scheme 10

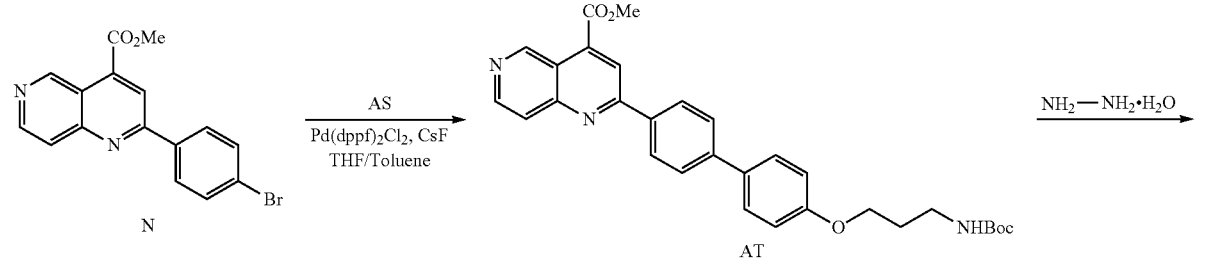

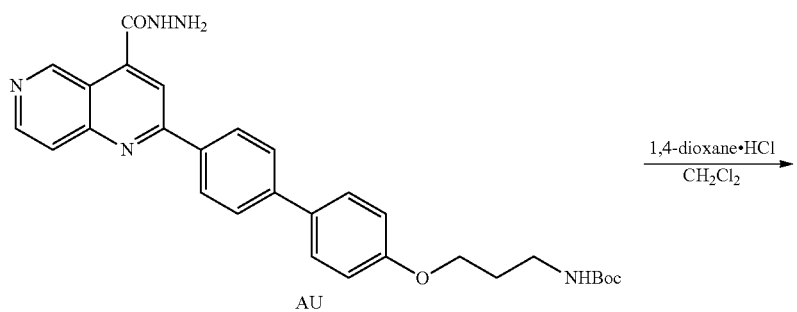

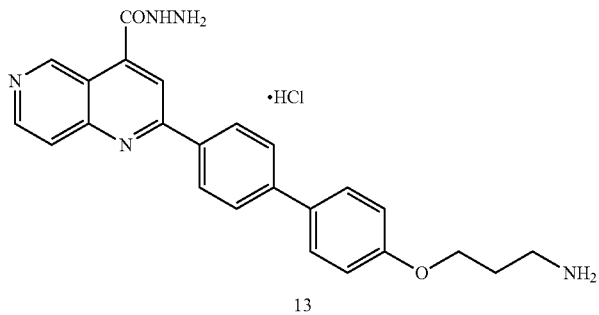

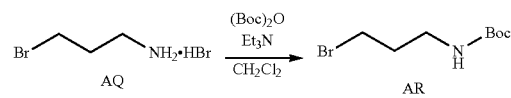

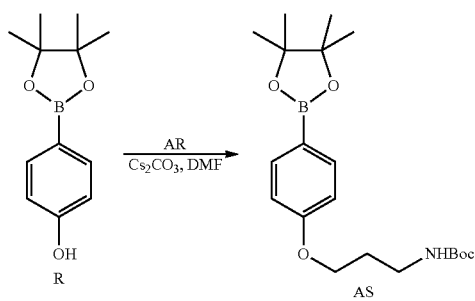

Example 13

2-(4'-(3-Aminopropoxy)-[1,1'-biphenyl]-4-yl)-1,6-naphthyridine-4-carbohydrazide HCl salt (13)

To a stirred solution of 3-bromopropan-1-amine hydrobromide (AQ; 1.0 g, 4.56 mmol) in $CH_2Cl_2$ (10 mL) was added $Et_3N$ (1.65 mL, 11.42 mmol) followed by Boc-anhydride (1.095 g, 5.02 mmol) at 0° C. under inert atmosphere. The resulting reaction mixture was stirred for 8 h at RT. After complete consumption of the starting material (by TLC), the reaction mixture was extracted with $CH_2Cl_2$ (2×30 mL). The combined organic extracts were washed with water, brine, dried over anhydrous $Na_2SO_4$ and concentrated under reduced pressure to obtain the crude. The crude material was purified by silica gel column chromatography eluting with 20% EtOAc/hexane as eluent to afford AR (0.8 g, 3.35 mmol, 74%) as a pale-brown liquid. $^1$H NMR (400 MHz, $CDCl_3$): δ 4.63 (bs, NH), 3.44 (t, J=6.4 Hz, 2H), 3.28 (t, J=6.4 Hz, 2H), 2.08-2.01 (m, 2H), 1.44 (s, 9H).

To a stirred solution of 4-(4,4,5,5-tetramethyl-1,3,2-dioxaborolan-2-yl)phenol (R; 5.4 g, 24.3 mmol) in DMF (54 mL) was added $Cs_2CO_3$ (17.4 g, 53.4 mmol) at RT under inert atmosphere. After being stirred for 20 min, AR (6.325 g, 26.56 mmol) was added to the above solution at RT. The resulting reaction mixture was heated to 65° C. and stirred for 12 h. Progress of the reaction was monitored by TLC. The reaction mixture was then allowed to RT, diluted with water (20 mL) and extracted with EtOAc (2×100 mL). The combined organic layer was washed with brine, dried over anhydrous $Na_2SO_4$ and concentrated under reduced pressure to furnish the crude. The crude material was purified by silica gel column chromatography eluting with 15% EtOAc/hexane as eluent to afford AS (6.7 g, 17.6 mmol, 72%) as an off-white solid. $^1$H NMR (400 MHz, $CDCl_3$): δ 7.74 (dd, J=6.8, 2.0 Hz, 2H), 6.88 (dd, J=6.8, 2.0 Hz, 2H), 4.73 (bs, NH), 4.04 (t, J=6.4 Hz, 2H), 3.33-3.31 (m, 2H), 2.05-1.94 (m, 2H), 1.43 (s, 9H), 1.33 (s, 12H).

To a solution of N (2.0 g, 5.83 mmol) in THF/toluene (100 mL, 1:1 v/v) were added boronate AS (2.2 g, 5.80 mmol), CsF (2.6 g, 17.19 mmol) at RT. The reaction was degassed by purging with inert gas for 10 min. To the resulting reaction mixture was added $Pd(dppf)_2Cl_2$ (426 mg, 0.58 mmol) and the reaction was degassed for another 15 min. The reaction mixture was then stirred for 24 h at reflux temperature. Progress of the reaction was monitored by TLC. The reaction mixture was then allowed to cool to RT and filtered through a pad of Celite. The Celite bed was washed with $CH_3OH$ and the collected filtrate was concentrated under reduced pressure to obtain the crude. The crude material was purified by silica gel column chromatography eluting with 50% EtOAc/hexane as eluent to afford AT (1.72 g, 2.80 mmol, 48%) as a yellow solid. $^1$H NMR (400 MHz, $CDCl_3$): δ 10.14 (s, 1H), 8.83 (d, J=6.0 Hz, 1H), 8.55 (s, 1H), 8.31 (d, J=8.4 Hz, 2H), 8.02 (dd, J=6.0 Hz, 1H), 7.76 (d, J=8.8 Hz, 2H), 7.62 (d, J=8.8 Hz, 2H), 7.01 (d, J=8.8 Hz, 2H), 4.76 (bs, NH), 4.11 (s, 3H), 4.09 (t, J=6.0 Hz, 2H), 3.38-3.34 (m, 2H), 2.02 (t, J=6.0 Hz, 2H), 1.45 (s, 9H). LC-MS: m/z 514 [M+1]$^+$ at 4.32 min (98.4% purity).

A mixture of ester AT (88 mg, 0.17 mmol) and hydrazine hydrate (3 mL) was heated to 100° C. and stirred for 2 h. Progress of the reaction was monitored by TLC. The reaction mixture was allowed to cool to 0° C., diluted with ice-cold water and stirred for 5 min. The precipitated solid was filtered and dried under reduced pressure to obtain the crude. The crude material was purified by trituration with IPA/pentane to afford AU (50 mg, 0.097 mmol, 56%) as a pale-green solid. $^1$H NMR (400 MHz, DMSO-$d_6$): δ 10.19 (s, 1H), 9.63 (s, 1H), 8.79 (d, J=6.0 Hz, 1H), 8.42 (d, J=8.4 Hz, 2H), 8.33 (s, 1H), 8.01 (d, J=6.0 Hz, 1H), 7.87 (d, J=8.4 Hz, 2H), 7.75 (d, J=8.8 Hz, 2H), 7.06 (d, J=8.8 Hz, 2H), 6.91 (bs, 1H), 4.78 (bs, 2H), 4.04 (t, J=6.4 Hz, 2H), 3.13-3.08 (m, 2H), 1.86 (t, J=6.4 Hz, 2H), 1.38 (s, 9H). LC-MS: m/z 514 [M+1]$^+$ at 3.54 min (79.1% purity).

To a stirred solution of AU (88 mg, 0.17 mmol) in $CH_3OH$ (1 mL) was added 4N HCl in 1,4-dioxane (2 mL) at 0° C. under inert atmosphere. The resulting reaction mixture was allowed to warm to RT and stirred for 2 h. Progress of the reaction was monitored by TLC. The volatiles were then evaporated under reduced pressure to obtain the crude. The crude product was triturated with diisopropylether followed by 10% $CH_3OH$/diisopropylether to afford the HCl salt of 13 (40 mg) as an orange colored solid. $^1$H NMR (400 MHz, DMSO-$d_6$): δ 12.01 (bs, 1H), 9.73 (s, 1H), 8.87 (d, J=6.0 Hz, 1H), 8.59 (s, 1H), 8.49 (d, J=8.4 Hz, 2H), 8.17 (d, J=6.0 Hz, 1H), 8.02 (bs, 3H), 7.91 (d, J=8.4 Hz, 2H), 7.79 (d, J=8.8 Hz, 2H), 7.10 (d, J=9.2 Hz, 2H), 4.15 (t, J=6.4 Hz, 2H), 3.01-2.96 (m, 2H), 2.09 (t, J=6.4 Hz, 2H). MS (ESI): m/z 412 [M−1]$^-$, 448 [M+HCl]. HPLC: 94.47%.

Scheme 11

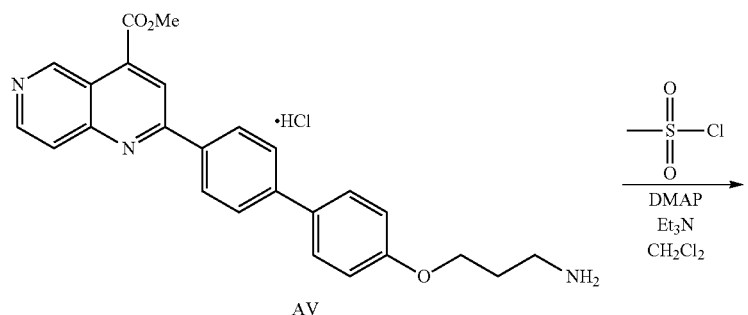

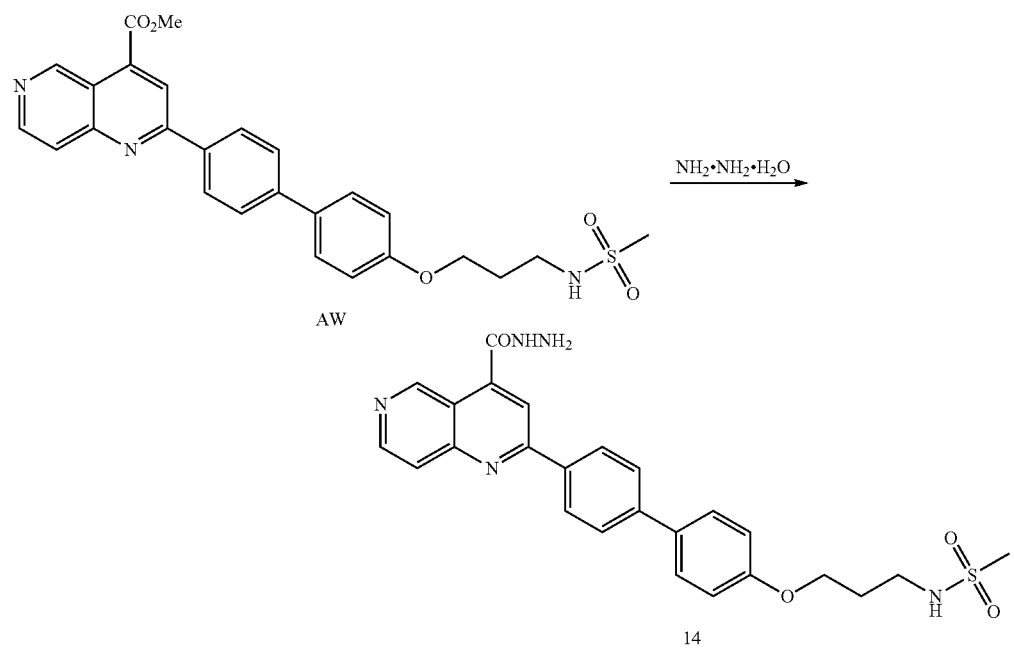

Example 14

N-(3-((4'-(4-(Hydrazinecarbonyl)-1,6-naphthyridin-2-yl)-[1,1'-biphenyl]-4-yl)oxy)propyl) methanesulfonamide (14)

To a stirred solution of methyl 2-(4'-(3-aminopropoxy)-[1,1'-biphenyl]-4-yl)-1,6-naphthyridine-4-carboxylate HCl salt (AV; 60 mg, 0.14 mmol) in $CH_2Cl_2$ (10 mL) was added $Et_3N$ (0.083 mL, 0.51 mmol) followed by DMAP (1.7 mg, 0.013 mmol) at 0° C. under inert atmosphere. After being stirred for 15 min, methanesulfonyl chloride (0.017 mL, 0.21 mmol) was added to the reaction mixture at 0° C. The resulting reaction mixture was stirred for 2 h at RT. Progress of the reaction was monitored by TLC. The reaction mixture was then diluted with ice-cold water and extracted with $CH_2Cl_2$ (2×30 mL). The combined organic extracts were washed with 10% $NaHCO_3$ solution followed by water, dried over anhydrous $Na_2SO_4$ and concentrated under reduced pressure to obtain the crude. The crude material was triturated with IPA/pentane to afford AW (27 mg, 0.054 mmol, 38%) as a pale-brown solid. $^1$H NMR (400 MHz, DMSO-$d_6$): δ 10.02 (bs, 1H), 8.89 (d, J=6.0 Hz, 1H), 8.75 (s, 1H), 8.47 (d, J=8.4 Hz, 2H), 8.24 (d, J=6.0 Hz, 1H), 7.91 (d, J=8.4 Hz, 2H), 7.77 (d, J=8.8 Hz, 2H), 7.09 (d, J=8.8 Hz, 2H), 7.08 (s, 1H), 4.11 (t, J=6.4 Hz, 2H), 3.16-3.13 (m, 2H), 2.91 (s, 3H), 2.32 (s, 3H), 1.98-1.90 (m, 2H). LC-MS: m/z 492.7 [M+1]$^+$ at 3.74 min (88.6% purity).

A mixture of AW (27 mg, 0.054 mmol) and $NH_2NH_2H_2O$ (2 mL) was heated to 100° C. and stirred for 1 h. Progress of the reaction was monitored by TLC. The reaction mixture was allowed to cool to RT, diluted with ice-cold water and stirred for 5 min. The precipitated solid was filtered and dried in vacuo to obtain the crude. The crude material was purified by trituration with MeOH/diisopropyl ether to afford 14 (9 mg, 0.018 mmol, 33%) as a pale-brown solid. $^1$H NMR (400 MHz, DMSO-$d_6$): δ 10.19 (bs, 1H), 9.63 (s, 1H), 8.79 (d, J=6.0 Hz, 1H), 8.43 (d, J=8.4 Hz, 2H), 8.33 (s, 1H), 8.01 (d, J=6.0 Hz, 1H), 7.88 (d, J=8.4 Hz, 2H), 7.76 (d, J=8.8 Hz, 2H), 7.09-7.07 (m, 3H), 4.78 (bs, 2H), 4.09 (t, J=6.4 Hz, 2H), 3.15 (t, J=6.4 Hz, 2H), 2.91 (s, 3H), 1.96 (t, J=6.4 Hz, 2H). MS (ESI): 492.7 [M+1]$^+$. HPLC: 90%.

Scheme 12

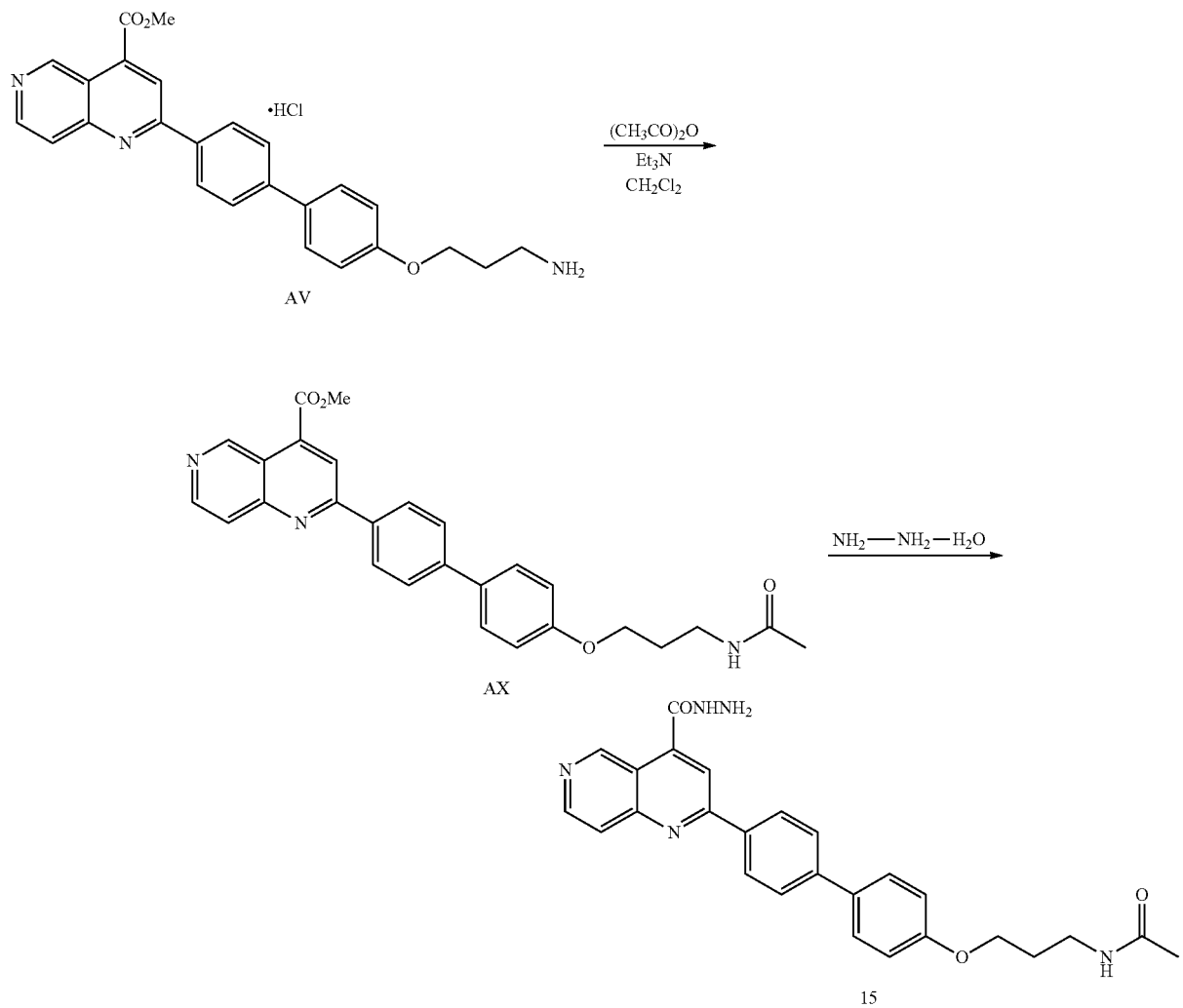

Example 15

N-(3-((4'-(4-(hydrazinecarbonyl)-1,6-naphthyridin-2-yl)-[1,1'-biphenyl]-4-yl)oxy)propyl) acetamide (15)

To a stirred solution of methyl 2-(4'-(3-aminopropoxy)-[1,1'-biphenyl]-4-yl)-1,6-naphthyridine-4-carboxylate HCl salt (AV; 0.15 g, 0.28 mmol) in CH$_2$Cl$_2$ (10 mL) was added Et$_3$N (0.16 mL, 1.12 mmol) followed by DMAP (3.4 mg, 0.027 mmol) at 0° C. under inert atmosphere. A solution of acetic anhydride (23 mg, 0.22 mmol) in CH$_2$Cl$_2$ (10 mL) was added to the reaction mixture dropwise at 0° C. The resulting reaction mixture was allowed to warm to RT and stirred for 1 h. Progress of the reaction was monitored by TLC. The reaction mixture was cooled to 0° C., diluted with 10% NaHCO$_3$ and the aqueous layer was extracted with CH$_2$Cl$_2$ (2×10 mL). The combined organic layers were washed with brine, dried over anhydrous Na$_2$SO$_4$ and concentrated under reduced pressure to obtain the crude. The crude material was triturated with IPA/pentane (4:1) to afford AX (0.1 g, 0.21 mmol, 83%) as a pale-green solid. $^1$H NMR (400 MHz, DMSO-d$_6$): δ 9.91 (s, 1H), 8.82 (d, J=6.0 Hz, 1H), 8.64 (s, 1H), 8.41 (d, J=8.4 Hz, 2H), 8.04 (dd, J=6.0 Hz, 1H), 7.89 (bs, 1H), 7.86 (d, J=8.8 Hz, 2H), 7.73 (d, J=8.8 Hz, 2H), 7.05 (d, J=8.8 Hz, 2H), 4.04 (s, 3H), 4.02 (t, J=6.4 Hz, 2H), 3.22-3.17 (m, 2H), 1.87 (t, J=6.4 Hz, 2H), 1.82 (s, 3H). LC-MS: m/z 456 [M+1]$^+$ at 3.40 min (98.8% purity).

A mixture of AX (0.03 g, 0.065 mmol) and hydrazine hydrate (2 mL) was heated to 100° C. and stirred for 1 h. Progress of the reaction was monitored by TLC. The reaction mixture was then allowed to cool to RT, diluted with ice-cold water and stirred for 5 min. The precipitated solid was dissolved in 30% MeOH/CH$_2$Cl$_2$ (15 mL), dried over anhydrous Na$_2$SO$_4$ and concentrated under reduced pressure to obtain the crude. The crude material was triturated with CH$_3$OH and diisopropyl ether to afford 15 (25 mg, 0.054 mmol, 83%) as an off-white solid. $^1$H NMR (400 MHz, DMSO-d$_6$): δ 10.20 (bs, 1H), 9.63 (s, 1H), 8.79 (d, J=6.0 Hz, 1H), 8.42 (d, J=8.4 Hz, 2H), 8.33 (s, 1H), 8.01 (d, J=6.0 Hz, 1H), 7.92-7.81 (m, 3H), 7.75 (d, J=8.8 Hz, 2H), 7.07 (d, J=8.8 Hz, 2H), 4.78 (bs, 2H), 4.05 (t, J=6.4 Hz, 2H), 3.25-3.15 (m, 2H), 1.87 (t, J=6.4 Hz, 2H), 1.81 (s, 3H). MS (ESI): 456.7 [M+1]$^+$. HPLC: 97.2%.

Scheme 13
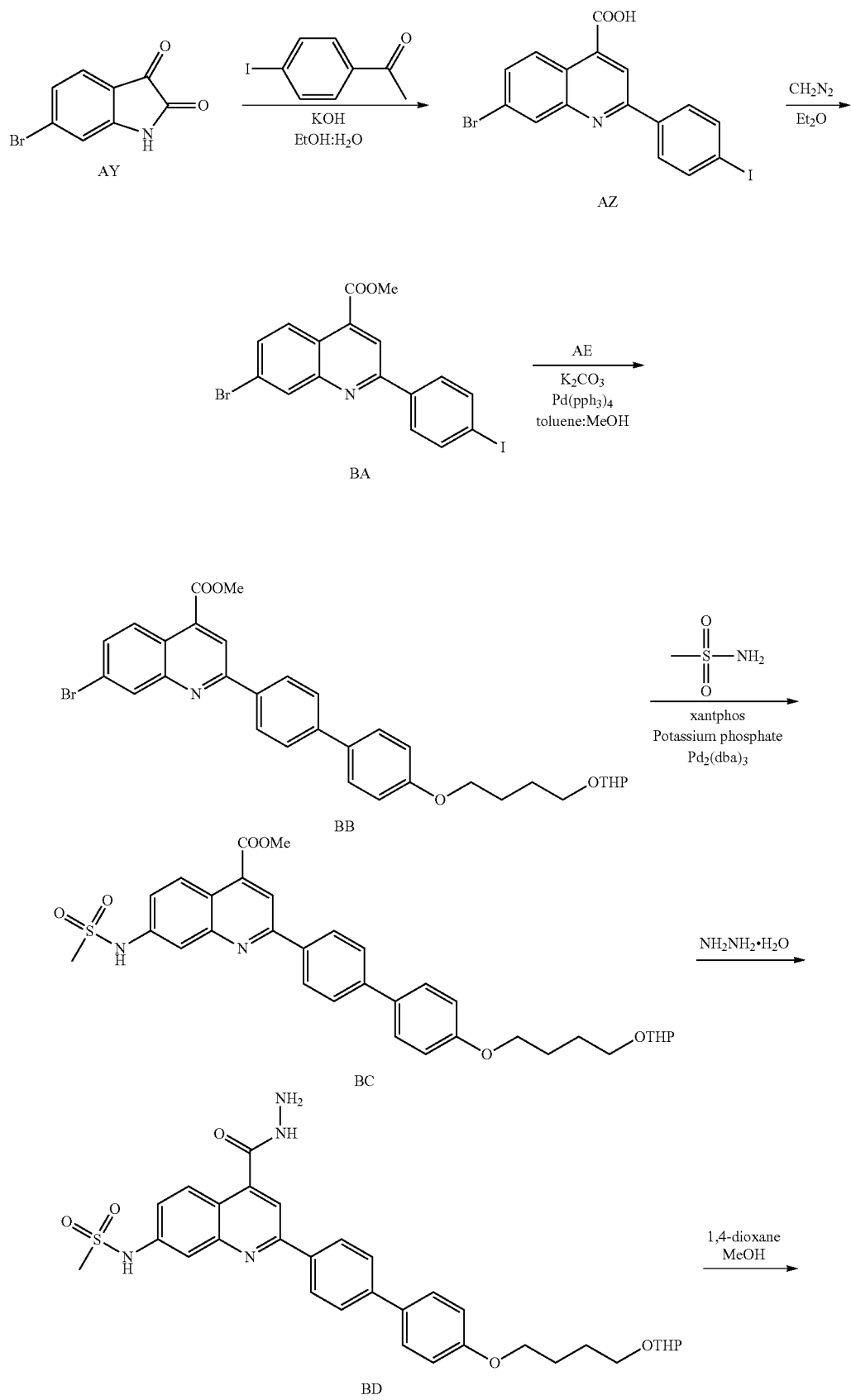

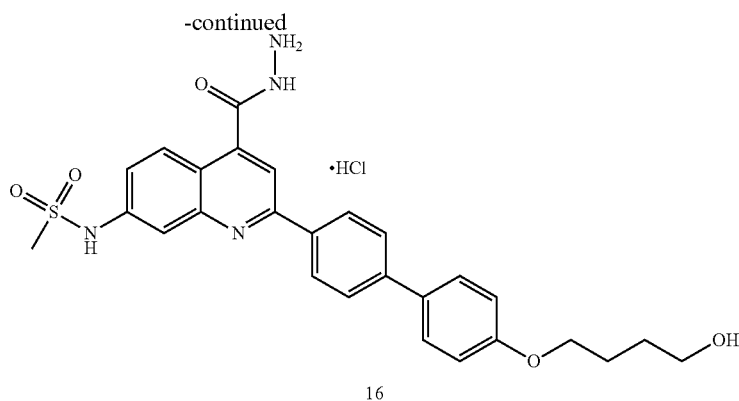

16

Example 16

N-(4-(Hydrazinecarbonyl)-2-(4'-(4-hydroxybutoxy)-[1,1'-biphenyl]-4-yl)quinolin-7-yl)methanesulfonamide HCl salt (16)

To a stirred solution of 6-bromoindoline-2,3-dione (AY; 5.0 g, 22.12 mmol) in EtOH:H$_2$O (100 mL, 1:1 v/v) were added 1-(4-iodophenyl)ethanone (5.4 g, 21.94 mmol) and KOH (4.96 g, 88.39 mmol) at RT under inert atmosphere. The resulting reaction mixture was stirred for 4 h at 110° C. Progress of the reaction was monitored by TLC. The reaction mixture was then cooled to RT and the volatiles were evaporated under reduced pressure. The residue obtained was diluted with CH$_2$Cl$_2$ (100 mL) and H$_2$O (50 mL). The aqueous layer was then separated, washed with CH$_2$Cl$_2$ (100 mL), and acidified to pH~2 using AcOH. After being stirred for 5 min, the precipitated solid was filtered, washed with water (50 mL) and dried under vacuum. To remove the water traces, the obtained solid residue was distilled twice with toluene (2×20 mL). The crude material was finally triturated with Et$_2$O and pentane to afford AZ (2.5 g, 5.50 mmol, 25%) as a pale-orange solid. $^1$H NMR (400 MHz, DMSO-d$_6$): δ 8.63 (d, J=9.2 Hz, 1H), 8.45 (s, 1H), 8.35 (d, J=2.0 Hz, 1H), 8.09 (d, J=8.8 Hz, 2H), 7.95 (d, J=8.8 Hz, 2H), 7.84 (dd, J=9.2, 2.0 Hz, 1H).

To a stirred solution of AZ (2.5 g, 5.50 mmol) in ether (100 mL) was added freshly prepared diazomethane [prepared by using dissolving NMU (2.8 g, 27.18 mmol) in a 1:1 mixture of 30% KOH solution (50 mL) and ether (50 mL) at 0° C. followed by separation and drying of the organic layer using KOH pellets] and stirred for 1 h at 0° C. The progress of the reaction was monitored by TLC. The reaction mixture was then concentrated under reduced pressure to obtain the crude. The crude material was purified by silica gel column chromatography eluting with 5-10% EtOAc/hexane as eluent to afford BA (2.4 g, 5.12 mmol, 96%) as a pale-green solid. $^1$H NMR (500 MHz, CDCl$_3$): δ 8.66 (d, J=9.0 Hz, 1H), 8.40 (d, J=2.0 Hz, 1H), 8.39 (s, 1H), 7.95 (d, J=8.5 Hz, 2H), 7.89 (d, J=9.0 Hz, 2H), 7.71 (dd, J=9.0, 2.0 Hz, 1H), 4.07 (s, 3H). LCMS: m/z 470 [M+2]$^+$ at 5.74 min (98.6%).

A stirred solution of BA (1.8 g, 3.84 mmol) in toluene/CH$_3$OH (100 mL, 4:1 v/v) was degassed by purging with argon for 15 min. To the resulting reaction mixture were added AE (1.44 g, 3.84 mmol), K$_2$CO$_3$ (1.59 g, 11.53 mmol) and Pd(PPh$_3$)$_4$ (0.44 g, 0.38 mmol) and degassed for another 5 min. The resulting reaction mixture was then stirred for 6 h at reflux temperature. Progress of the reaction was monitored by TLC. The reaction mixture was then cooled to RT, filtered through a pad of Celite and the bed was washed with EtOAc (2×20 mL). The collected filtrate was then concentrated under reduced pressure to obtain the crude. The crude material was purified by silica gel column chromatography eluting with 20% EtOAc/hexane as eluent to afford BB (0.62 g, 1.04 mmol, 27%) as a pale-brown thick syrup. $^1$H NMR (400 MHz, CDCl$_3$): δ 8.67 (d, J=9.2 Hz, 1H), 8.47 (s, 1H), 8.42 (s, 1H), 8.26 (d, J=8.8 Hz, 2H), 7.74-7.68 (m, 3H), 7.61 (d, J=8.8 Hz, 2H), 7.01 (d, J=8.8 Hz, 2H), 4.08-4.05 (m, 5H), 3.89-3.81 (m, 3H), 3.53-3.46 (m, 3H), 1.94-1.79 (m, 7H), 1.76-1.70 (m, 2H).

A stirred mixture of BB (0.62 g, 1.049 mmol), methane sulfonamide (119 mg, 1.25 mmol), potassium phosphate (0.33 g, 1.57 mmol), xantphos (32.6 mg, 0.062 mmol) and Pd$_2$(dba)$_3$ (28.8 mg, 0.031 mmol) in 1,4-dioxane (50 mL) at RT was degassed for 30 min by purging with nitrogen. The resulting reaction mixture was then heated to 100° C., and stirred for 12 h stirring. Progress of the reaction was monitored by TLC. The reaction mixture was then cooled to RT and the volatiles were evaporated under reduced pressure to obtain the crude. The crude compound was purified by silica gel column chromatography eluting with 30% EtOAc/hexane as eluent to afford BC (0.11 g, 0.18 mmol, 17.4%) as a pale-brown solid. $^1$H NMR (400 MHz, CDCl$_3$): δ 8.80 (d, J=9.2 Hz, 1H), 8.41 (s, 1H), 8.27 (d, J=8.4 Hz, 2H), 8.01 (d, J=2.0 Hz, 1H), 7.73 (d, J=8.4 Hz, 2H), 7.61 (d, J=8.8 Hz, 2H), 7.46 (dd, J=9.2, 2.0 Hz, 1H), 7.01 (d, J=8.8 Hz, 2H), 6.79 (bs, 1H), 4.61-4.60 (m, 1H), 4.08-4.05 (m, 5H), 3.91-3.82 (m, 2H), 3.81 (s, 1H), 3.53-3.46 (m, 2H), 3.16 (s, 3H), 2.04-2.01 (m, 4H), 1.94-1.89 (m, 3H), 1.84-1.79 (m, 2H). LCMS: m/z 605 [M+1]$^+$ at 4.62 min (92.5%).

A mixture of BC (0.11 g, 0.18 mmol) and hydrazine hydrate (2 mL) was heated to 100° C. and stirred for 1 h under inert atmosphere. Progress of the reaction was monitored by TLC. The reaction mixture was allowed to cool to RT, diluted with ice-cold water and extracted with 10% MeOH/EtOAc (2×10 mL). The combined organic layer was dried over anhydrous Na$_2$SO$_4$ and concentrated under reduced pressure to furnish the crude. The crude material was triturated with IPA/pentane to afford BD (82 mg, 0.13 mmol, 74%) as a pale brown-solid. $^1$H NMR (400 MHz, DMSO-d$_6$): δ 10.33 (bs, 1H), 10.02 (bs, 1H), 8.35 (d, J=8.4 Hz, 2H), 8.21 (d, J=8.8 Hz, 1H), 8.04 (s, 1H), 7.89 (d, J=2.0 Hz, 1H), 7.82 (d, J=8.4 Hz, 2H), 7.72 (d, J=8.8 Hz, 2H), 7.48 (dd, J=8.8, 2.0 Hz, 1H), 7.06 (d, J=8.8 Hz, 2H), 4.69 (bs, 2H), 4.58-4.57 (m, 1H), 4.08-4.05 (m, 2H), 3.78-3.67 (m, 2H), 3.45-3.39 (m, 2H), 3.15 (s, 3H), 1.74-1.59 (m, 6H), 1.59-1.45 (m, 4H).

To a stirred solution of BD (82 mg, 0.13 mmol) in MeOH (0.5 mL) was added 4N HCl in 1,4-dioxane (1 mL) at 0° C. under inert atmosphere. The resulting reaction mixture was allowed to warm to RT and stirred for 1.5 h. Progress of the reaction was monitored by TLC. The volatiles were then evaporated under reduced pressure. The crude material was triturated with MeOH/diisopropyl ether to afford 16 (75 mg, 0.14 mmol, 94%) as an orange colored solid. $^1$H NMR (400 MHz, DMSO-$d_6$): δ 11.48 (bs, 1H), 10.42 (bs, 1H), 8.37 (d, J=8.8 Hz, 2H), 8.20 (d, J=9.2 Hz, 1H), 8.16 (s, 1H), 7.93 (d, J=2.4 Hz, 1H), 7.85 (d, J=8.4 Hz, 2H), 7.72 (d, J=8.8 Hz, 2H), 7.54 (dd, J=2.0, 8.8 Hz, 2H), 4.05 (t, J=6.4 Hz, 2H), 3.54 (bs, 1H), 3.47 (t, J=6.4 Hz, 2H), 3.17 (s, 3H), 1.80-1.74 (m, 2H), 1.62-1.58 (m, 2H). MS (ESI): 521 [M+1]$^+$. HPLC: 95.03%.

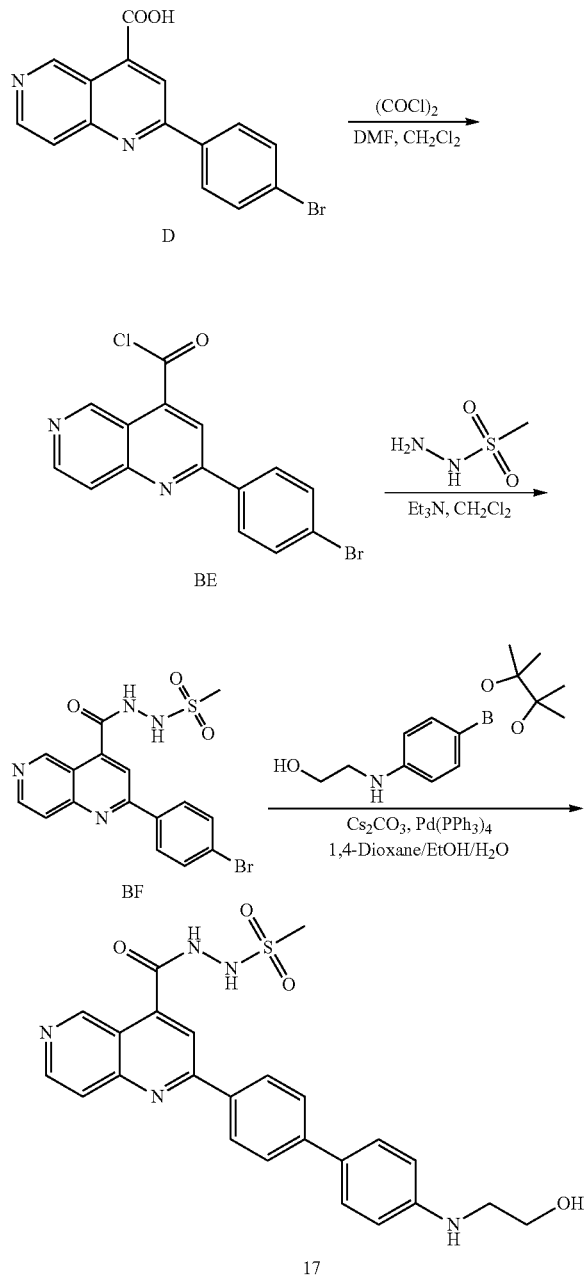

Scheme 14

Example 17

N'-(2-(4'-((2-Hydroxyethyl)amino)-[1,1'-biphenyl]-4-yl)-1,6-naphthyridine-4-carbonyl) methanesulfonohydrazide (17)

To a stirred solution of 2-(4-bromophenyl)-1,6-naphthyridine-4-carboxylic acid (D; 0.5 g, 1.52 mmol) in dry $CH_2Cl_2$ (20 mL) was added oxalyl chloride (0.54 mL, 6.08 mmol) followed by a catalytic amount of DMF at 0° C. and the reaction was stirred for 1 h at RT. After complete consumption of the starting material (by TLC), the volatiles were evaporated under reduced pressure to half the original volume. This was followed by the addition of dry $CH_2Cl_2$ (20 mL) and the mixture was concentrated to half the volume under reduced pressure to afford BE (416 mg, crude). This crude material was used directly in the next step without any further purification.

To a stirred solution of methanesulfonohydrazide (264 mg, 2.40 mmol) in $CH_2Cl_2$ (20 mL) was added $Et_3N$ (0.5 mL, 3.54 mmol) at 0° C. under inert atmosphere. A solution of BE (416 mg, 1.20 mmol) in $CH_2Cl_2$ (10 mL) was added to the above reaction mixture dropwise at 0° C. for 5 min. The resulting reaction mixture was allowed to warm to RT and stirred for 1 h. Progress of the reaction was monitored by TLC. The separated organic layer was washed with 10% a $NaHCO_3$ solution, brine, dried over anhydrous $Na_2SO_4$ and concentrated under reduced pressure to furnish the crude. The crude material was purified by silica gel column chromatography eluting with 5-10% MeOH/$CH_2Cl_2$ as eluent to afford BF (0.3 g, 0.71 mmol, 59%) as a pale yellow solid. $^1$H NMR (500 MHz, DMSO-$d_6$): δ 11.20 (bs, 1H), 9.94 (bs, 1H), 9.58 (s, 1H), 8.83 (d, J=6.0 Hz, 1H), 8.40 (s, 1H), 8.33 (d, J=8.5 Hz, 2H), 8.04 (d, J=6.0 Hz, 1H), 7.84 (d, J=8.5 Hz, 2H), 3.18 (s, 3H). MS (ESI): m/z 421 [M]$^+$.

To a mixture of BF (0.16 g, 0.37 mmol) and 2-((4-(4,4,5,5-tetramethyl-1,3,2-dioxaborolan-2-yl)phenyl)amino) ethanol (149 mg, 0.56 mmol) in 1,4-dioxane/EtOH/$H_2O$ (20 mL) was added $Cs_2CO_3$ (0.37 g, 1.13 mmol). The reaction mixture was degassed by purging with inert atmosphere for 20 min. To the resulting reaction mixture was added Pd(PPh$_3$)$_4$ (65.8 mg, 0.05 mmol) and the reaction was degassed for another 5 min. The resulting reaction mixture was stirred for 12 h at reflux temperature. Progress of the reaction was monitored by TLC. The volatiles were then evaporated under reduced pressure to obtain the crude. The crude was purified by silica gel column chromatography eluting with 8% MeOH/$CH_2Cl_2$ as eluent to afford 17 (12 mg, 0.025 mmol, 6.6%) as a brown solid. $^1$H NMR (500 MHz, DMSO-$d_6$): δ 11.22 (bs, 1H), 9.96 (bs, 1H), 9.55 (s, 1H), 8.81 (d, J=6.0 Hz, 1H), 8.39 (d, J=9.0 Hz, 2H), 8.02 (d, J=6.0 Hz, 1H), 7.82 (d, J=8.0 Hz, 2H), 7.59 (d, J=8.5 Hz, 2H), 6.72 (d, J=8.5 Hz, 2H), 5.90 (t, J=5.5 Hz, 1H), 4.73 (t, J=5.5 Hz, 2H), 3.60-3.56 (m, 2H), 3.19-3.14 (m, 5H). MS (ESI): 477 [M]$^+$. HPLC: 93.19%

Scheme 15

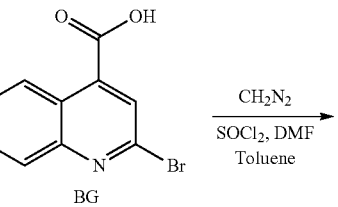

BG

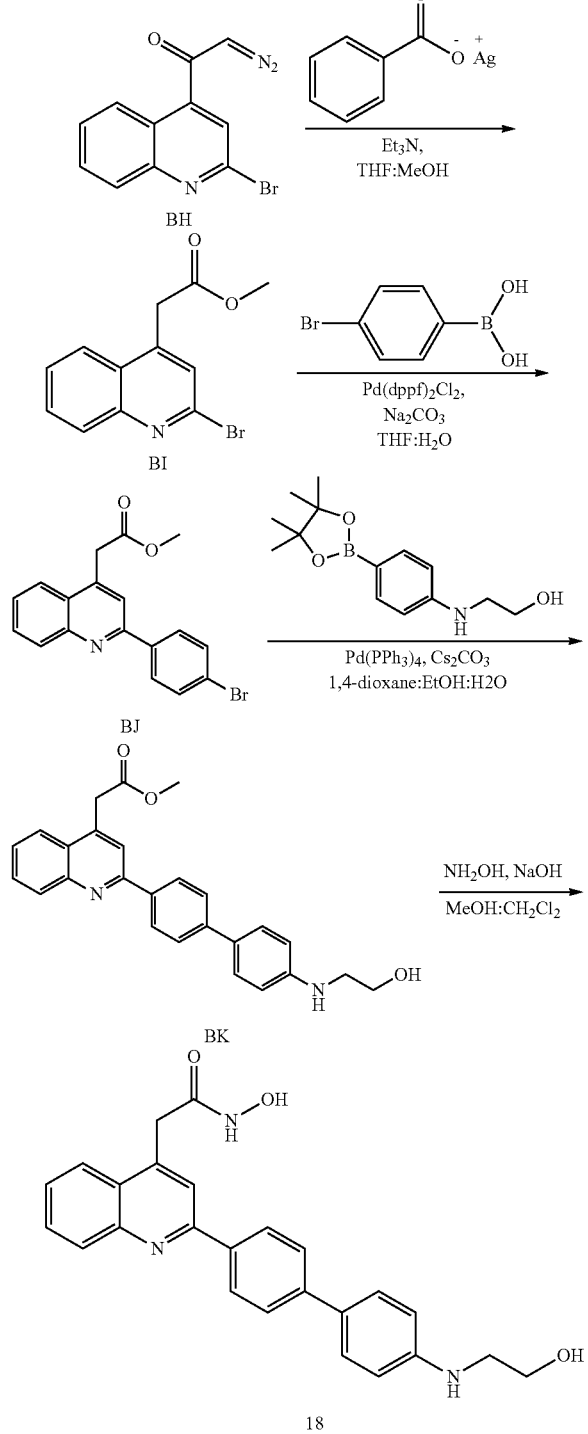

Example 18

N-hydroxy-2-(2-(4'-((2-hydroxyethyl)amino)-[1,1'-biphenyl]-4-yl)quinolin-4-yl)acetamide (18)

To a stirred solution of 2-bromoquinoline-4-carboxylic acid (BG; 200 mg, 0.79 mmol) in toluene (10 mL) under inert atmosphere were added thionyl chloride (0.22 mL, 3.17 mmol) and DMF (0.01 mL, catalytic) at RT. The reaction was heated to reflux for 1 h. The reaction was monitored by TLC. After complete consumption of the starting material, the volatiles were evaporated under reduced pressure. The residue was dissolved in toluene (10 mL) under inert atmosphere and diazomethane in ether (10 mL) was added at 0° C. and stirred for 30 min. After complete consumption of the starting material, the volatiles were evaporated under reduced pressure to obtain the crude. The crude was triturated with n-hexane (2×5 mL) to afford BH (170 mg, 80%) as a pale brown solid. $^1$H NMR (200 MHz, CDCl$_3$): δ 8.34-8.32 (m, 1H), 8.08 (d, J=8.0 Hz, 1H), 7.81 (t, J=8.0 Hz, 1H), 7.61 (t, J=8.0 Hz, 1H), 7.42 (s, 1H), 5.78 (br s, 1H).

To a stirred solution of BH (170 mg, 0.61 mmol) in THF:MeOH (1:1, 5 mL) under inert atmosphere was added a solution of silver benzoate (32.4 mg, 0.14 mmol) in triethylamine (0.3 mL, 1.97 mmol) dropwise at RT and stirred for 12 h. The reaction was monitored by TLC, after complete consumption of the starting material, the reaction mass was filtered through a Celite pad. The filtrate was concentrated under reduced pressure to obtain the crude. The crude was purified by silica gel column chromatography eluting with 10-15% EtOAc/hexanes to afford BI (110 mg, 64%) as a pale brown solid. $^1$H NMR (500 MHz, CDCl$_3$): δ 8.04 (d, J=8.5 Hz, 1H), 7.94 (d, J=8.5 Hz, 1H), 7.73 (t, J=8.0 Hz, 1H), 7.59 (t, J=8.0 Hz, 1H), 7.34 (s, 1H), 4.04 (s, 2H), 3.71 (s, 3H).

To a stirred solution of BI (100 mg, 0.35 mmol) in THF:H$_2$O (4:1, 20 mL) under inert atmosphere were added (4-bromophenyl) boronic acid (86 mg, 0.42 mmol) and sodium carbonate (150 mg, 1.42 mmol) at RT and purged with argon for 20 min. Then Pd(dppf)$_2$Cl$_2$ (39 mg, 0.05 mmol) was added to the reaction mixture and the reaction mixture was heated to reflux and stirred for 16 h. The reaction was monitored by TLC. After complete consumption of the starting material, the reaction mass was cooled to RT, diluted with water (10 mL) and the compound was extracted with EtOAc (2×10 mL). The combined organic extracts were washed with water (10 mL), dried over sodium sulfate, filtered and concentrated under reduced pressure to obtain the crude. The crude was purified by silica gel column chromatography eluting with 2-5% EtOAc/hexanes to afford BJ (50 mg, 39%) as an off-white solid. $^1$H NMR (500 MHz, CDCl$_3$): δ 8.22-8.17 (m, 1H), 8.06-7.98 (m, 3H), 7.85-7.70 (m, 3H), 7.65 (d, J=8.5 Hz, 2H), 4.15-4.13 (m, 2H), 3.72 (s, 3H).

To a stirred solution of BJ (100 mg, 0.28 mmol) in 1,4-dioxane:ethanol:water (3:1:1, 20 mL) under inert atmosphere were added 2-((4-(4,4,5,5-tetramethyl-1,3,2-dioxaborolan-2-yl)phenyl amino)ethanol (110 mg, 0.42 mmol) and cesium carbonate (366 mg, 1.12 mmol) at RT. Theb reaction mixture was purged with argon for 30 min. Then Pd(PPh$_3$)$_4$ (32 mg, 0.02 mmol) was added to the reaction mixture and the reaction mixture was heated to reflux and stirred for 12 h. The reaction was monitored by TLC. After complete consumption of the starting material, the reaction mass was cooled to RT and filtered through a Celite pad. The filtrate was concentrated under reduced pressure to obtain the crude. The crude was purified by silica gel column chromatography eluting with 40% EtOAc/hexanes to afford BK (20 mg, 13%) as an off-white solid. $^1$H NMR (500 MHz, DMSO-d$_6$): δ 8.29 (d, J=8.0 Hz, 2H), 8.10-8.05 (m, 3H), 7.79-7.70 (m, 3H), 7.60 (t, J=8.5 Hz, 1H), 7.54 (d, J=8.5 Hz, 2H), 6.70 (d, J=9.0 Hz, 2H), 5.80 (t, J=6.0 Hz, 1H), 4.70 (t, J=6.0 Hz, 1H), 3.60-3.57 (m, 2H), 3.17-3.14 (m, 2H), 2.79-2.77 (m, 3H).

To a stirred solution of BK (100 mg, 0.24 mmol) in MeOH:CH$_2$Cl$_2$ (3:1, 12 mL) under inert atmosphere was added 50% aq. hydroxyl amine solution (2.4 mL) at 0° C. and the reaction mixture was stirred for 10 min. Then a sodium hydroxide solution (77 mg in 1 mL water, 1.94 mmol) was added to the reaction mixture and stirred for 30 min. The reaction was warmed to RT and stirred for 2 h. After complete consumption of the starting material, the volatiles were evaporated under reduced pressure. The residue was diluted with water (20 mL) and the aqueous layer was acidified with acetic acid to pH~6. The compound was extracted with 20% MeOH/CH$_2$Cl$_2$ (2×20 mL). The combined organic extracts were washed with water (15 mL), dried over sodium sulfate, filtered and dried under reduced pressure to obtain the crude. The crude was purified by silica gel column chromatography (8-10% MeOH/CH$_2$Cl$_2$) to afford 18 (48 mg, 48%) as a pale brown solid. $^1$H NMR (500 MHz, DMSO-d$_6$): δ 10.86 (s, 1H), 8.95 (s, 1H), 8.27 (d, J=8.5 Hz, 2H), 8.16 (d, J=8.5 Hz, 1H), 8.09-8.06 (m, 2H), 7.76 (d, J=8.5 Hz, 3H), 7.60 (t, J=7.0 Hz, 2H), 7.55 (d, J=9.0 Hz, 1H), 6.71 (d, J=8.5 Hz, 2H), 5.79 (t, J=5.5 Hz, 1H), 4.70 (t, J=5.5 Hz, 1H), 3.92 (s, 2H), 3.60-3.57 (m, 2H), 3.18-3.14 (m, 2H). MS (ESI): m/z 414.2 [M+1]$^+$. HPLC Purity: 92.63%

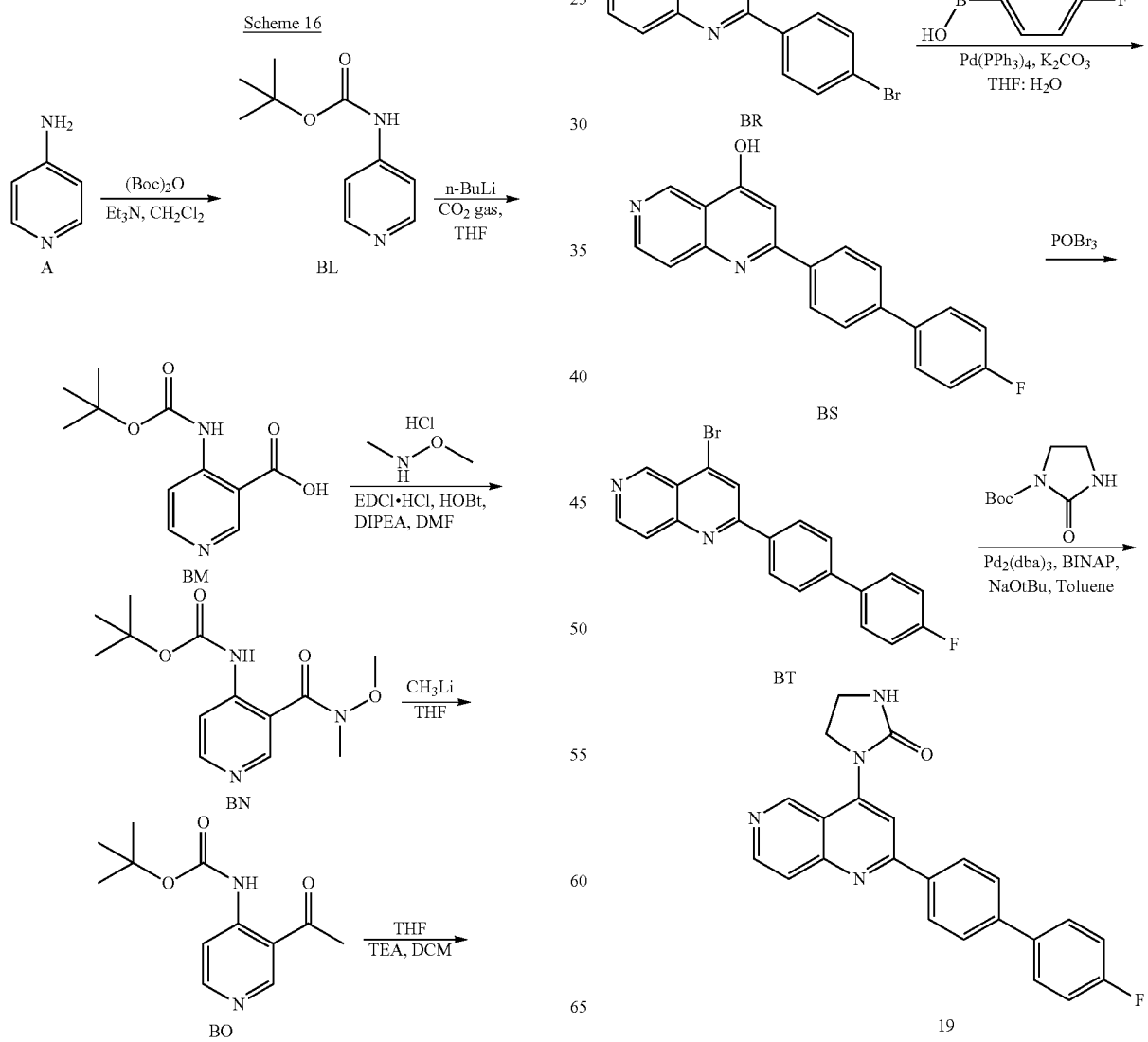

Example 19

1-(2-(4'-fluoro-[1,1'-biphenyl]-4-yl)-1,6-naphthyridin-4-yl)imidazolidin-2-one (19)

To a stirred solution of pyridin-4-amine (A; 100 g, 1.06 mol) in $CH_2Cl_2$ (1 L) under inert atmosphere were added triethylamine (161.47 g, 1.59 mol) and Boc-anhydride (255 g, 1.17 mol) at 0° C. The reaction was warmed to RT and stirred for 3 h. After complete consumption of the starting material, the reaction mixture was diluted with water (400 mL) and the compound was extracted with $CH_2Cl_2$ (2×500 mL). The combined organic extracts were washed with water (300 mL), dried over sodium sulfate, filtered and concentrated under reduced pressure to obtain the crude. The crude was purified through column chromatography eluting with 5% MeOH/$CH_2Cl_2$ to afford BL (190 g, 90%) as a white solid. $^1$H NMR (500 MHz, DMSO-$d_6$): δ 9.80 (s, 1H), 8.33 (d, J=5.5 Hz, 2H), 7.41 (d, J=6.5 Hz, 2H), 1.48 (s, 9H).

To a stirred solution of BL (12 g, 0.06 mol) in dry THF (200 mL) under inert atmosphere was added n-butyl lithium (79.12 mL, 0.18 mol) at −78° C. The reaction was warmed to 0° C. and stirred for 30 min. Carbon dioxide gas was added to the reaction mass at −78° C. for 1 h, then at RT for 1 h. The reaction was monitored by TLC. After complete consumption of the starting material, the reaction mass was diluted with water (200 mL) and washed with diethyl ether (2×150 mL). The aqueous layer was acidified with citric acid to pH~4. The obtained solid was filtered and dried under vacuum to afford BM (5.1 g, 35%) as a white solid. $^1$H NMR (400 MHz, DMSO-$d_6$): δ 11.76 (br s, 1H), 8.96 (s, 1H), 8.52 (d, J=15.0 Hz, 1H), 8.22 (d, J=15.0 Hz, 1H), 1.49 (s, 9H).

To a stirred solution of BM (5.1 g, 0.02 mol) in DMF (10 mL) under inert atmosphere were added EDCI.HCl (6.14 g, 0.03 mol), HOBt (4.33 g, 0.03 mol), diisopropylethyl amine (5.53 g, 0.04 mol) and N,O-dimethylhydroxylamine hydrochloride (4.18 g, 0.04 mol) at 0° C. The reaction was warmed to RT and stirred for 16 h. After complete consumption of the starting material, the reaction mixture was diluted with water (40 mL) and the compound was extracted with diethyl ether (3×40 mL). The combined organic extracts were washed with water (40 mL), dried over sodium sulfate, filtered and concentrated under reduced pressure to obtain the crude. The crude was purified through column chromatography eluting with 3% MeOH/$CH_2Cl_2$ to afford BN (2.5 g, 42%) as a yellow solid. $^1$H NMR (400 MHz, CDCl$_3$): δ 8.98 (br s, 1H), 8.74 (s, 1H), 8.47 (d, J=15.0 Hz, 1H), 8.25 (d, J=15.0 Hz, 1H), 3.58 (s, 3H), 3.41 (s, 3H), 1.52 (s, 9H).

To a stirred solution of BN (12 g, 42.70 mol) in THF (150 mL) under inert atmosphere was added methyl lithium (4.05 g, 0.19 mol) at −78° C. The reaction was warmed to RT and stirred for 1 h. After complete consumption of the starting material, the reaction mixture was diluted with a saturated ammonium chloride solution (80 mL) and the compound was extracted with diethyl ether (3×60 mL). The combined organic extracts were washed with water (60 mL), brine (60 mL), dried over sodium sulfate, filtered and concentrated under reduced pressure to obtain the crude. The crude was purified through column chromatography eluting with 40% EtOAc/hexanes to afford BO (11.5 g, 58%) as a pale yellow solid. $^1$H NMR (500 MHz, CDCl$_3$): δ 11.04 (br s, 1H), 9.03 (s, 1H), 8.53 (d, J=6.0 Hz, 1H), 8.38 (d, J=6.0 Hz, 1H), 2.68 (s, 3H), 1.53 (s, 9H).

To a stirred solution of BO (11.5 g, 48.72 mmol) in $CH_2Cl_2$ (120 mL) under inert atmosphere was added trifluoroacetic acid (55.8 mL, 730.8 mmol) at 0° C. The reaction was warmed to RT and stirred for 12 h. After complete consumption of the starting material, the volatiles were evaporated under reduced pressure, co-distilled with toluene (2×20 mL) and triturated with diethyl ether (2×20 mL). The residue was dissolved in $CH_2Cl_2$ (60 mL), triethylamine (60 mL) was added and stirred for 30 min. The volatiles were evaporated under reduced pressure and triturated with diethyl ether (2×40 mL) to obtain the crude. The crude was purified through column chromatography eluting with 60% EtOAc/hexanes to afford BP (4 g, 60%) as an off-white solid. $^1$H NMR (500 MHz, DMSO-$d_6$): δ 9.18 (br s, 1H), 9.06 (br s, 1H), 8.98 (s, 1H), 8.16 (d, J=7.0 Hz, 1H), 7.02 (d, J=7.0 Hz, 1H), 2.50 (s, 3H).

To a stirred solution of p-bromo benzoic acid (12 g, 59.70 mmol) in $CH_2Cl_2$ (50 mL) under inert atmosphere were added oxalyl chloride (6.5 mL, 71.64 mmol) and DMF (0.3 mL, catalytic) at 0° C. The reaction was warmed to RT and stirred for 1 h. The volatiles were evaporated under reduced pressure to obtain the acid chloride. To a stirred solution of BP (4 g, 29.41 mmol) in $CH_2Cl_2$ (25 mL) under inert atmosphere at −20° C. were added the freshly prepared acid chloride (12.9 g, 58.76 mmol) in $CH_2Cl_2$ (25 mL) dropwise for 15 min and triethylamine (12.7 mL, 88.24 mmol). The reaction was warmed to RT and and stirred for 2 h. After complete consumption of the starting material, the reaction mixture was diluted with saturated sodium bicarbonate solution (50 mL) and the compound was extracted with $CH_2Cl_2$ (3×50 mL). The combined organic extracts were washed with water (50 mL), brine (50 mL), dried over sodium sulfate, filtered and concentrated under reduced pressure to obtain the crude. The crude was purified through column chromatography eluting with 5% MeOH/$CH_2Cl_2$ to afford BQ (8 g, 85%) as a pale yellow solid. $^1$H NMR (500 MHz, CDCl$_3$): δ 12.80 (br s, 1H), 9.17 (s, 1H), 8.82 (d, J=6.0 Hz, 1H), 8.68 (d, J=6.0 Hz, 1H), 7.92 (d, J=9.0 Hz, 2H), 7.68 (d, J=9.0 Hz, 2H), 2.77 (s, 3H).

To a stirred solution of BQ (8 g, 25.07 mmol) in 1,4-dioxane (70 mL) under inert atmosphere was added sodium hydroxide (3.51 g, 87.75 mmol) at RT in a sealed tube. The reaction was heated at 100° C. and stirred for 2 h. After complete consumption of the starting material, the volatiles were evaporated under reduced pressure. The residue was diluted with water (50 mL) and washed with diethyl ether (2×40 mL). The aqueous layer was acidified with 2 N HCl to pH~6-7. The obtained solid was filtered, triturated with methanol (2×10 mL), diethyl ether (2×10 mL), pentane (2×10 mL) and dried under vacuum to afford BR (7 g, 93%) as a white solid. $^1$H NMR (500 MHz, DMSO-$d_6$): δ 12.03 (br s, 1H), 9.22 (s, 1H), 8.64 (d, J=6.0 Hz, 1H), 7.87-7.81 (m, 4H), 7.70-7.64 (m, 1H), 6.52 (br s, 1H).

To a stirred solution of BR (7 g, 23.25 mmol) in THF:water (3:1, 280 mL) under inert atmosphere were added p-fluoro benzene boronic acid (3.90 g, 27.87 mmol) and potassium carbonate (9.62 g, 69.71 mmol) at RT and purged under argon for 30 min. Then tetrakis(triphenylphosphino) palladium (0) (2.68 g, 2.32 mmol) was added to the reaction mass and again purged for 10 min. The reaction mixture was heated to reflux and stirred for 12 h. After complete consumption of the starting material, the reaction mass was filtered and washed with 50% MeOH:$CH_2Cl_2$ (2×40 mL). The aqueous layer was acidified with 2 N HCl to pH~6-7. The precipitate was filtered, triturated with methanol (2×10 mL), diethyl ether (2×10 mL), pentane (2×10 mL) and dried under vacuum to afford BS (5.2 g, 71%) as a pale yellow solid. $^1$H NMR (500 MHz, DMSO-$d_6$): δ 11.97 (br s, 1H), 9.22 (s, 1H), 8.64 (d, J=6.0 Hz, 1H), 7.96-7.82 (m, 6H), 7.64 (d, J=6.0 Hz, 1H), 7.35 (t, J=9.0 Hz, 2H), 6.56 (s, 1H).

A stirred solution of BS (1 g, 3.16 mmol) in phosphorous oxybromide (1.8 g, 9.49 mmol) under inert atmosphere was heated to 110° C. and stirred for 2 h. The reaction was monitored by TLC. After complete consumption of the starting material, the reaction mass was basified with solid sodium bicarbonate to pH~6-7. Then the reaction mass was diluted with water (30 mL) and the compound was extracted with $CH_2Cl_2$ (3×30 mL). The combined organic extracts were washed with water (30 mL), a brine solution (30 mL), dried over sodium sulfate, filtered and concentrated under reduced pressure to obtain the crude. The crude was purified through column chromatography eluting with 5% MeOH/$CH_2Cl_2$ to afford BT (550 mg, 46%) as a pale brown solid. $^1$H NMR (500 MHz, DMSO-$d_6$): δ 9.57 (s, 1H), 8.83 (d, J=6.0 Hz, 1H), 8.29 (s, 1H), 8.26 (d, J=8.5 Hz, 2H), 7.94 (d, J=6.0 Hz, 1H), 7.73 (d, J=8.5 Hz, 2H), 7.63 (t, J=9.0 Hz, 2H), 7.18 (t, J=9.0 Hz, 2H).

To a stirred solution of BT (100 mg, 0.26 mmol) in dry toluene (20 mL) under inert atmosphere were added tert-butyl 2-oxoimidazolidine-1-carboxylate (58 mg, 0.31 mmol), BINAP (25 mg, 0.03 mmol) and sodium tert-butoxide (38 mg, 0.39 mmol) at RT and purged under argon for 30 min. Then $Pd_2(dba)_3$ (12 mg, 0.013 mmol) was added to the reaction mass and again purged for 15 min. The reaction mass was heated to reflux and stirred for 20 h. The reaction was monitored by TLC. After complete consumption of the starting material, the volatiles were evaporated under reduced pressure. The residue was diluted with water (15 mL) and the compound was extracted with 10% MeOH:$CH_2Cl_2$ (3×15 mL). The combined organic extracts were washed with water (15 mL), brine (15 mL), dried over sodium sulfate, filtered and concentrated under reduced pressure to obtain the crude. The crude was purified through column chromatography eluting with 5-8% MeOH/$CH_2Cl_2$ to afford 19 (10 mg, 8%) as a pale brown liquid. $^1$H NMR (500 MHz, DMSO-$d_6$): δ 9.38 (br s, 1H), 8.67 (br s, 1H), 8.42 (d, J=8.5 Hz, 2H), 8.06 (s, 1H), 7.93-7.83 (m, 4H), 7.56 (s, 1H), 7.35 (t, J=9.0 Hz, 2H), 4.25 (t, J=7.5 Hz, 2H), 3.61 (t, J=7.5 Hz, 2H). Mass: m/z 385.7 [M+1]$^+$. HPLC Purity: 95.92%

Scheme 17

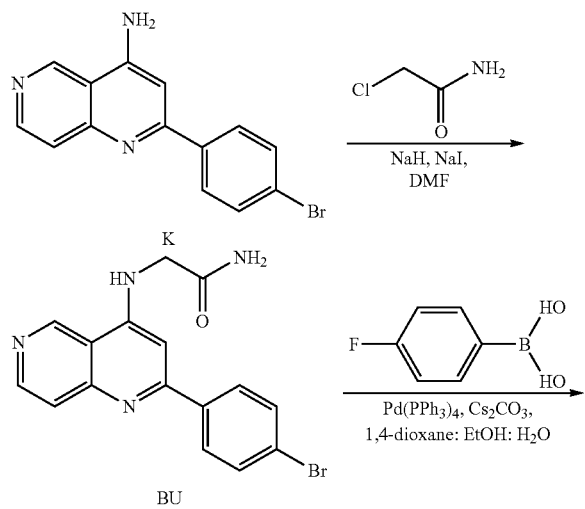

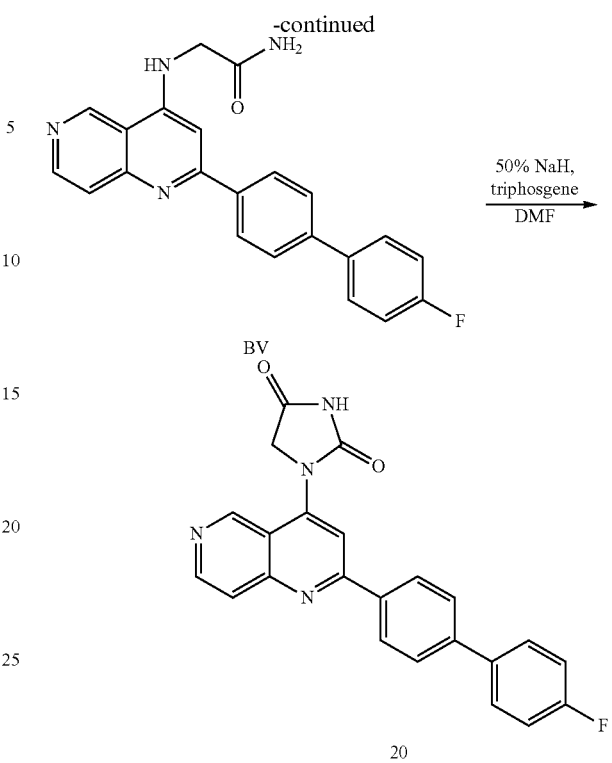

Example 20

1-(2-(4'-fluoro-[1,1'-biphenyl]-4-yl)-1,6-naphthyridin-4-yl)imidazolidine-2,4-dione (20)

To a stirred solution of 50% sodium hydride (0.8 g, 33.33 mmol) in DMF (60 mL) under inert atmosphere was added 2-(4-bromophenyl)-1,6-naphthyridin-4-amine (K; 2 g, 6.68 mmol) portionwise for 10 min at 0° C. The reaction was warmed to RT and stirred for 2 h. To the reaction mass cooled to 0° C. were added 2-chloro acetamide (1.87 g, 20.00 mmol) and sodium iodide (1.0026 g, 6.68 mmol). The reaction was then heated to 100° C. and stirred for 3 h. After complete consumption of the starting material, the reaction mass was diluted with ice cold water (40 mL) and the compound was extracted with EtOAc (2×40 mL). The combined organic extracts were washed with water (40 mL), dried over sodium sulfate, filtered and concentrated under reduced pressure to obtain the crude. The crude was purified through column chromatography eluting with 10% MeOH/$CH_2Cl_2$ to afford BU (510 mg, 21%) as a pale yellow solid. $^1$H NMR (500 MHz, DMSO-$d_6$): δ 9.56 (s, 1H), 8.58 (d, J=6.0 Hz, 1H), 8.23 (t, J=6.0 Hz, 1H), 8.13 (t, J=8.0 Hz, 2H), 7.73 (d, J=8.0 Hz, 2H), 7.67 (t, J=6.0 Hz, 2H), 7.22 (br s, 1H), 6.94 (s, 1H), 4.06 (d, J=6.0 Hz, 2H).

To a stirred solution of BU (510 mg, 1.43 mmol) in 1,4-dioxane:methanol:water (4:2:1, 50 mL) under inert atmosphere were added 4-fluorobenzeneboronic acid (240 mg, 1.71 mmol) and cesium carbonate (1.4 g, 4.29 mmol) After purging the reaction under argon for 30 min, tetrakis(triphenylphosphino) palladium(0) (160 mg, 0.13 mmol) was added to the reaction. The reaction was heated to 90° C. and stirred for 5 h. After complete consumption of the starting material, the volatiles were evaporated under reduced pressure to obtain the crude. The crude was purified by silica gel column chromatography eluting with 10%

MeOH/CH$_2$Cl$_2$ to afford BV (350 mg, 66%) as a pale brown solid. $^1$H NMR (500 MHz, DMSO-d$_6$): δ 9.57 (s, 1H), 8.59 (d, J=6.0 Hz, 1H), 8.25 (d, J=8.0 Hz, 2H), 8.19 (br s, 1H), 7.81 (t, J=8.0 Hz, 4H), 7.69 (d, J=6.0 Hz, 1H), 7.65 (s, 1H), 7.33 (t, J=8.5 Hz, 2H), 7.22 (s, 1H), 6.98 (s, 1H), 4.07 (d, J=7.0 Hz, 2H).

To a stirred solution of BV (250 mg, 0.67 mmol) in DMF (10 mL) under inert atmosphere was added 50% sodium hydride (129 mg, 2.68 mmol) portionwise for 5 min at 0° C. After stifling for 15 min, the reaction was warmed to RT and stirred for 30 min. Then triphosgene (398 mg, 1.34 mmol) was added at 0° C. and the reaction was stirred for 30 min at 0° C. and at RT for 30 min. The reaction was monitored by TLC. After complete consumption of the starting material, the reaction was diluted with ice cold water (20 mL) and the compound was extracted with EtOAc (2×20 mL). The combined organic extracts were washed with water (20 mL), dried over sodium sulfate, filtered and concentrated under reduced pressure to obtain the crude. The crude was purified through column chromatography eluting with 5% MeOH/CH$_2$Cl$_2$ to afford 20 (6 mg, 3%) as a pale brown solid. $^1$H NMR (500 MHz, DMSO-d$_6$): δ 11.53 (s, 1H), 9.48 (br s, 1H), 8.78 (br s, 1H), 8.44 (d, J=8.0 Hz, 1H), 8.40 (s, 1H), 8.00 (d, J=6.0 Hz, 1H), 7.91 (d, J=8.0 Hz, 2H), 7.86 (t, J=8.5 Hz, 2H), 7.35 (t, J=8.5 Hz, 2H), 4.85 (s, 2H). MS (ESI): m/z 399.4 [M+1]$^+$. HPLC Purity: 82.78%

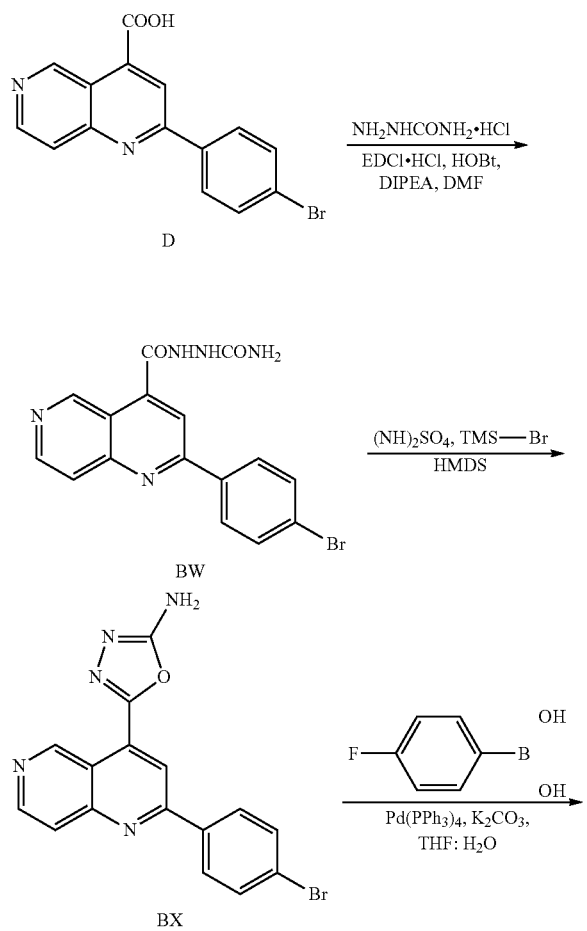

Scheme 18

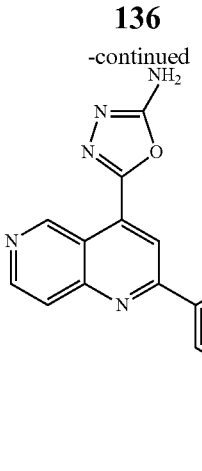

21

Example 21

5-(2-(4'-fluoro-[1,1'-biphenyl]-4-yl)-1,6-naphthyridin-4-yl)-1,3,4-oxadiazol-2-amine (21)

To a stirred solution of 2-(4-bromophenyl)-1,6-naphthyridine-4-carboxylic acid (D; 2 g, 6.09 mmol) in DMF (20 mL) under inert atmosphere were added EDCI.HCl (1.5 g, 7.85 mmol), HOBt (900 mg, 6.66 mmol) and diisopropylethyl amine (3.91 g, 30.22 mmol) at RT. The reaction was stirred for 30 min. Then semicarbazide hydrochloride (1.35 g, 12.10 mmol) was added to the reaction mass and again stirred at RT for 24 h. The reaction was monitored by TLC. After complete consumption of the starting material, the reaction mixture was diluted with water (40 mL) and the compound was extracted with EtOAc (2×40 mL). The combined organic extracts were washed with water (40 mL), dried over sodium sulfate, filtered and concentrated under reduced pressure to obtain the crude. The crude was purified via column chromatography eluting with 5% MeOH/CH$_2$Cl$_2$ to afford BW (1 g, 43%) as a pale yellow solid. $^1$H NMR (500 MHz, DMSO-d$_6$): δ 10.55 (s, 1H), 9.69 (s, 1H), 8.81 (d, J=6.0 Hz, 1H), 8.46 (br s, 1H), 8.32 (d, J=8.0 Hz, 1H), 8.24 (d, J=7.5 Hz, 1H), 8.15 (br s, 1H), 8.01 (d, J=6.0 Hz, 1H), 7.84 (d, J=8.5 Hz, 2H), 6.26 (br s, 2H).

To a stirred solution of BW (300 mg, 0.77 mmol) in HMDS (10 mL) under inert atmosphere were added TMS-bromide (1.19 g, 7.77 mmol) and ammonium sulphate (41 mg, 0.31 mmol) at RT. The reaction mixture was heated to reflux and stirred for 12 h. After complete consumption of the starting material, the volatiles were evaporated under reduced pressure to obtain the crude. The crude was purified via column chromatography eluting with 5% MeOH/CH$_2$Cl$_2$ to afford BX (100 mg, 35%) as an off-white solid. $^1$H NMR (500 MHz, DMSO-d$_6$): δ 10.41 (s, 1H), 8.86 (d, J=6.0 Hz, 1H), 8.42 (s, 1H), 8.25 (d, J=8.5 Hz, 2H), 8.04 (d, J=6.0 Hz, 1H), 7.84 (d, J=8.5 Hz, 2H), 7.77 (s, 2H).

To a stirred solution of BX (50 mg, 0.13 mmol) in THF:water (10:1, 11 mL) under inert atmosphere were added (4-fluorophenyl)boronic acid (28.6 mg, 0.20 mmol) and potassium carbonate (56 mg, 0.40 mmol) at RT. The reaction was purged under argon for 1 h. Then Pd(PPh$_3$)$_4$ (15.7 mg, 0.001 mmol) was added to the reaction mass and the reaction was heated to reflux and stirred for 8 h. The reaction was monitored by TLC. After complete consumption of the starting material, the volatiles were evaporated under reduced pressure to obtain the crude. The crude was purified through column chromatography eluting with 5%

MeOH/CH$_2$Cl$_2$ to afford 21 (25 mg, 48%) as a pale yellow solid. $^1$H NMR (500 MHz, DMSO-d$_6$): δ 10.41 (s, 1H), 8.85 (d, J=6.0 Hz, 1H), 8.46 (s, 1H), 8.38 (d, J=8.0 Hz, 2H), 8.05 (d, J=6.0 Hz, 1H), 7.92 (d, J=8.0 Hz, 2H), 7.85 (t, J=8.0 Hz, 2H), 7.77 (s, 2H), 7.35 (t, J=8.0 Hz, 2H). Mass: m/z 384.4 [M+1]$^+$. HPLC Purity: 99.10%

Scheme 19

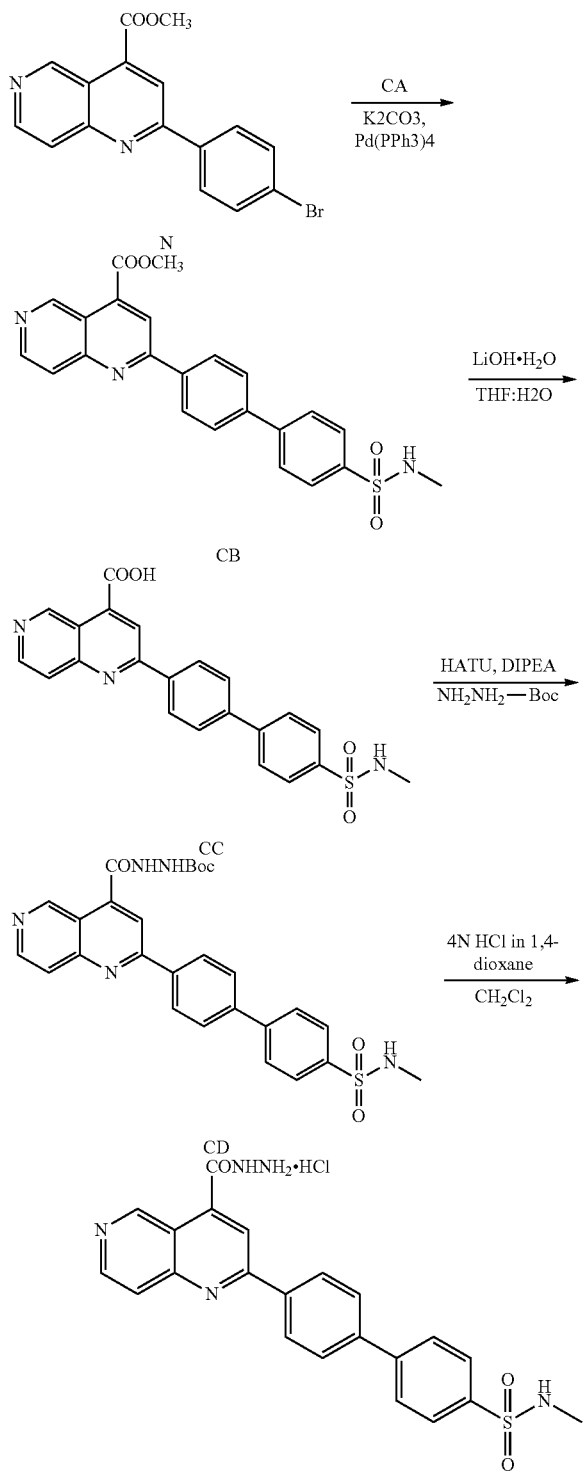

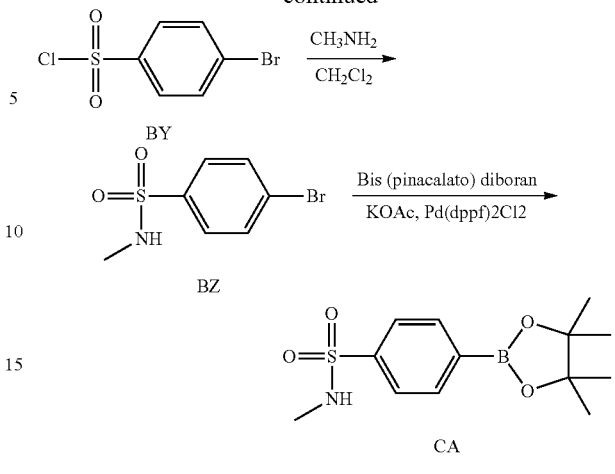

Example 22

4'-(4-(hydrazinecarbonyl)-1,6-naphthyridin-2-yl)-N-methyl-[1,1'-biphenyl]-4-sulfonamide hydrochloride (22)

To a stirred solution of 4-bromobenzene-1-sulfony chloride (BY; 2.5 g, 9.78 mmol) in CH$_2$Cl$_2$ (20 mL) under inert atmosphere was added 2M methylamine in THF (10 mL, 19.56 mmol) at 0° C. The reaction was then warmed to RT and stirred for 2 h. After complete consumption of the starting material, the volatiles were evaporated under reduced pressure. The residue was neutralized with saturated sodium bicarbonate solution (30 mL) and the compound was extracted with CH$_2$Cl$_2$ (3×25 mL). The combined organic extracts were washed with water (30 mL), dried over sodium sulfate, filtered and concentrated under reduced pressure to obtain the crude. The crude was triturated with diethyl ether/pentane (3×15 mL) to afford BZ (2 g, 94%) as a white solid. $^1$H NMR (500 MHz, DMSO-d$_6$): δ 7.83 (d, J=8.5 Hz, 2H), 7.70 (d, J=8.5 Hz, 2H), 7.54 (s, 1H), 2.41 (d, J=13.5 Hz, 3H). MS (ESI): m/z 250 [M+1]$^+$ To a stirred solution of BZ (500 mg, 2.00 mmol) in 1,4-dioxane (20 mL) under inert atmosphere were added bis(pinacalato)diboron (561 mg, 2.20 mmol) and fused potassium acetate (590 mg, 6.02 mmol) at RT. The reaction was purged with argon for 30 min. Then Pd(dppf)$_2$Cl$_2$ (146 mg, 0.2 mmol) was added to the reaction mixture and the reaction was heated to 100° C. and stirred for 12 h. The reaction was monitored by TLC. After complete consumption of the starting material, the reaction mass was cooled to RT and filtered through a Celite pad. The filtrate was concentrated under reduced pressure to obtain the crude. The crude was purified by silica gel column chromatography (30-40% EtOAc/hexanes) to afford CA (400 mg, 67%) as a white solid. $^1$H NMR (500 MHz, CDCl$_3$): δ 7.95 (d, J=8.0 Hz, 2H), 7.84 (d, J=8.5 Hz, 2H), 4.27 (d, J=5.5 Hz, 1H), 2.65 (d, J=5.5 Hz, 3H), 1.35 (s, 12H). MS (ESI): m/z 298 [M+1]$^+$ To a stirred solution N (370 mg, 1.07 mmol) in THF:H$_2$O (1:1, 10 mL) under inert atmosphere were added CA (384 mg, 1.29 mmol) and potassium carbonate (446 mg, 3.23 mmol) at RT. The reaction was purged with argon for 30 min. Then Pd(PPh$_3$)$_4$ (63 mg, 0.053 mmol) was added to the reaction mixture and the reaction was heated to reflux and stirred for 8 h. The reaction was monitored by TLC. After complete consumption of the starting material, the reaction mass was cooled to RT and filtered through a Celite pad. The filtrate was concentrated under reduced pressure to obtain the crude. The crude was purified by preparative HPLC to afford CB (250 mg, 54%) as a yellow solid. $^1$H NMR (500 MHz, DMSO-$d_6$): δ 9.94 (s, 1H), 8.85 (d, J=6.0 Hz, 1H), 8.69 (s, 1H), 8.51 (d, J=8.0 Hz, 2H), 8.08 (d, J=6.0 Hz, 1H), 8.04-8.00 (m, 4H), 7.91 (d, J=7.5 Hz, 2H), 7.55-7.52 (m, 1H), 4.08 (s, 3H), 2.47 (d, J=12.0 Hz, 3H). MS (ESI): m/z 434 [M+1]$^+$ To a stirred solution of CB (100 mg, 0.23 mmol) in THF:H$_2$O (1:1, 5 mL) under inert atmosphere was added lithium hydroxide monohydrate (40 mg, 0.69 mmol) at 0° C. The reaction was warmed to RT and stirred for 4 h. After complete consumption of the starting material, the volatiles were evaporated under reduced pressure to obtain the crude. The crude was diluted with water (10 mL) and acidified with a glacial acetic acid solution to pH~4 and then filtered. The obtained solid was triturated with toluene (2×5 mL) to afford CC (80 mg, 83%) as a yellow solid. $^1$H NMR (500 MHz, DMSO-$d_6$): δ 10.03 (s, 1H), 8.81 (d, J=5.5 Hz, 1H), 8.62 (s, 1H), 8.49 (d, J=7.5 Hz, 2H), 8.03 (d, J=7.5 Hz, 3H), 8.00 (d, J=8.0 Hz, 2H), 7.90 (d, J=7.5 Hz, 2H), 7.54 (s, 1H), 2.47 (d, J=13.5 Hz, 3H). MS (ESI): m/z 420 [M+1]$^+$ To a stirred solution of CC (80 mg, 0.18 mmol) in DMF (2 mL) under inert atmosphere were added HATU (144 mg, 0.36 mmol), diisopropyl ethyl amine (0.08 mL, 0.55 mmol) and Boc-hydrazine (48 mg, 0.36 mmol) at 0° C. The reaction was warmed to RT and stirred for 12 h. After complete consumption of the starting material, the reaction mixture was diluted with water (10 mL) and the compound was extracted with ethyl acetate (3×10 mL). The combined organic extracts were washed with water (10 mL), dried over sodium sulfate, filtered and concentrated under reduced pressure to obtain the crude. The crude was purified by preparative HPLC to afford CD (40 mg, 15%) as a pale yellow solid. $^1$H NMR (500 MHz, DMSO-$d_6$): δ 10.67 (s, 1H), 9.72 (s, 1H), 9.59 (s, 1H), 9.48 (s, 1H), 9.30 (s, 1H), 8.84 (d, J=5.5 Hz, 1H), 8.50 (d, J=7.5 Hz, 3H), 8.35-8.33 (m, 1H), 8.06-7.98 (m, 2H), 7.90 (d, J=8.0 Hz, 2H), 7.53 (d, J=4.5 Hz, 1H), 2.87 (s, 3H), 1.38 (s, 9H). MS (ESI): m/z 534 [M+1]$^+$ To a stirred solution of CD (20 mg, 0.03 mmol) in CH$_2$Cl$_2$ (5 mL) under inert atmosphere was added 4 N HCl in 1,4-dioxane (1 mL) at 0° C. The reaction was warmed to RT and stirred for 4 h. After complete consumption of the starting material, the volatiles were evaporated under reduced pressure to obtain the crude. The crude was triturated with IPA:diethyl ether (2×4 mL) followed by pentane (2×4 mL) to afford 22 (20 mg as HCl salt) as a brown solid. $^1$H NMR (500 MHz, DMSO-$d_6$): δ 12.10-11.90 (br s, 1H), 9.72 (s, 1H), 8.88 (d, J=6.0 Hz, 1H), 8.58 (s, 1H), 8.55 (d, J=8.5 Hz, 2H), 8.17 (d, J=6.0 Hz, 1H), 8.04 (t, J=8.5 Hz, 4H), 7.91 (d, J=8.5 Hz, 2H), 7.56 (s, 1H), 2.46 (d, J=13.0 Hz, 3H). MS (ESI): m/z 434 [M+1]$^+$. HPLC Purity: 96.02%

Scheme 20

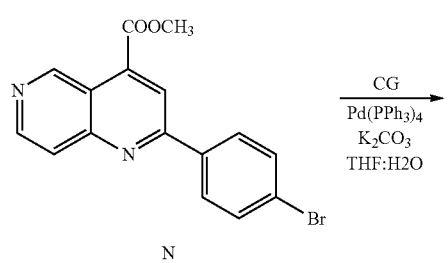

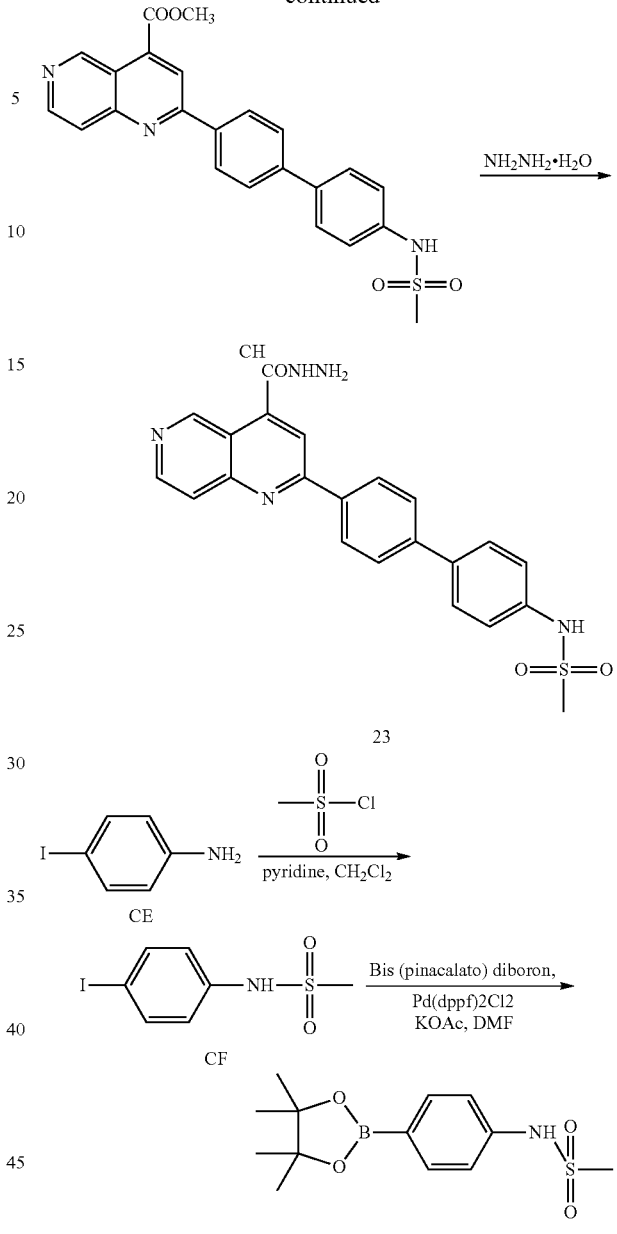

Example 23

N-(4'-(4-(hydrazinecarbonyl)-1,6-naphthyridin-2-yl)-[1,1'-biphenyl]-4-yl)methane sulfonamide (23)

To a stirred solution of 4-iodoaniline (CE; 2 g, 9.13 mmol) in CH$_2$Cl$_2$ (20 mL) under inert atmosphere were added pyridine (1.47 mL, 18.26 mmol), methane sulfonyl chloride (1.06 mL, 13.69 mmol) at 0° C. The reaction was warmed to RT and stirred for 1 h. After complete consumption of the starting material, the reaction mass was quenched with a 1 N HCl solution (30 mL) and the compound was extracted with EtOAc (2×30 mL). The combined organic extracts were washed with brine (30 mL), dried over sodium sulfate, filtered and concentrated under reduced pressure to obtain the crude. The crude was purified by silica gel column chromatography (20-30% EtOAc/hexanes) to afford CF (2.2 g, 81%) as a brown solid. ¹H NMR (500 MHz, CDCl₃): δ 7.67 (d, J=8.5 Hz, 2H), 6.99 (d, J=8.5 Hz, 2H), 3.68 (s, 1H), 3.02 (s, 3H).

To a stirred solution of CF (500 mg, 1.68 mmol) in DMF (20 mL) under inert atmosphere were added bis(pinacalato)diboron (470 mg, 1.85 mmol) and fused potassium acetate (495 mg, 5.05 mmol) at RT and purged with argon for 30 min. Then Pd(dppf)₂Cl₂ (123 mg, 0.16 mmol) was added to the reaction mixture and the reaction was heated to 100° C. and stirred for 4 h. The reaction was monitored by TLC. After complete consumption of the starting material, the reaction mass was cooled to RT, diluted with water (20 mL) and the compound was extracted with EtOAc (2×25 mL). The combined organic extracts were washed with brine (30 mL), dried over sodium sulfate, filtered and concentrated under reduced pressure to obtain the crude. The crude was purified by silica gel column chromatography (5% MeOH/CH₂Cl₂) to afford CG (320 mg, 64%) as a colorless sticky solid. ¹H NMR (500 MHz, CDCl₃): δ 8.01 (s, 1H), 7.78 (d, J=8.0 Hz, 2H), 7.21 (d, J=8.0 Hz, 2H), 2.95 (s, 3H), 1.33 (s, 12H).

To a stirred solution of N (150 mg, 0.43 mmol) in THF:H₂O (10:1, 11 mL) under inert atmosphere were added CG (300 mg, 1.00 mmol) and potassium carbonate (181 mg, 1.31 mmol) at RT. The reaction was purged with argon for 30 min. Then tetrakis(triphenyl phosphine) palladium(0) (50 mg, 0.04 mmol) was added to the reaction mixture and the reaction was heated to reflux and stirred for 4 h. The reaction was monitored by TLC. After complete consumption of the starting material, the reaction mass was cooled to RT and the volatiles were evaporated under reduced pressure to obtain the crude. The crude was purified by silica gel column chromatography (5% MeOH/CH₂Cl₂) to afford CH (100 mg, 52.9%) as a yellow solid. ¹H NMR (500 MHz, DMSO-d₆): δ 9.92 (s, 1H), 8.83 (d, J=6.0 Hz, 1H), 8.65 (s, 1H), 8.43 (d, J=8.0 Hz, 1H), 8.05 (d, J=6.0 Hz, 1H), 7.89 (d, J=8.0 Hz, 2H), 7.78 (d, J=9.0 Hz, 2H), 7.62-7.53 (m, 2H), 7.34 (d, J=8.5 Hz, 2H), 4.06 (s, 3H), 3.04 (s, 3H).

A stirred solution of CH (100 mg, 0.23 mmol) in hydrazine hydrate (4 mL) under inert atmosphere was heated to 70° C. and stirred for 30 min. The reaction was monitored by TLC. After complete consumption of the starting material, the reaction mass was cooled to RT and the reaction mass was diluted with water (15 mL). The compound was extracted with IPA/CH₂Cl₂ (3×20 mL) to afford 23 (15 mg, 15%) as an off-white solid. ¹H NMR (400 MHz, DMSO-d₆): δ 10.19 (br s, 1H), 9.80 (br s, 1H), 9.63 (s, 1H), 8.79 (d, J=6.0 Hz, 1H), 8.44 (d, J=8.8 Hz, 2H), 8.34 (s, 1H), 8.01 (d, J=6.4 Hz, 1H), 7.90 (d, J=8.4 Hz, 2H), 7.79 (d, J=8.4 Hz, 2H), 7.34 (d, J=8.4 Hz, 2H), 4.78 (s, 2H), 3.04 (s, 3H). MS (ESI): m/z 432.5 [M−1]⁺. HPLC Purity: 90.88%

Scheme 21

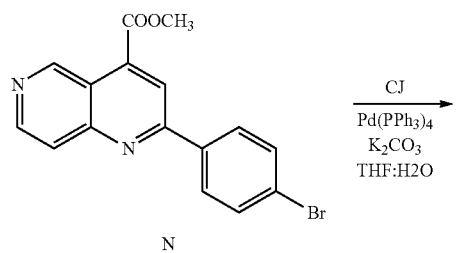

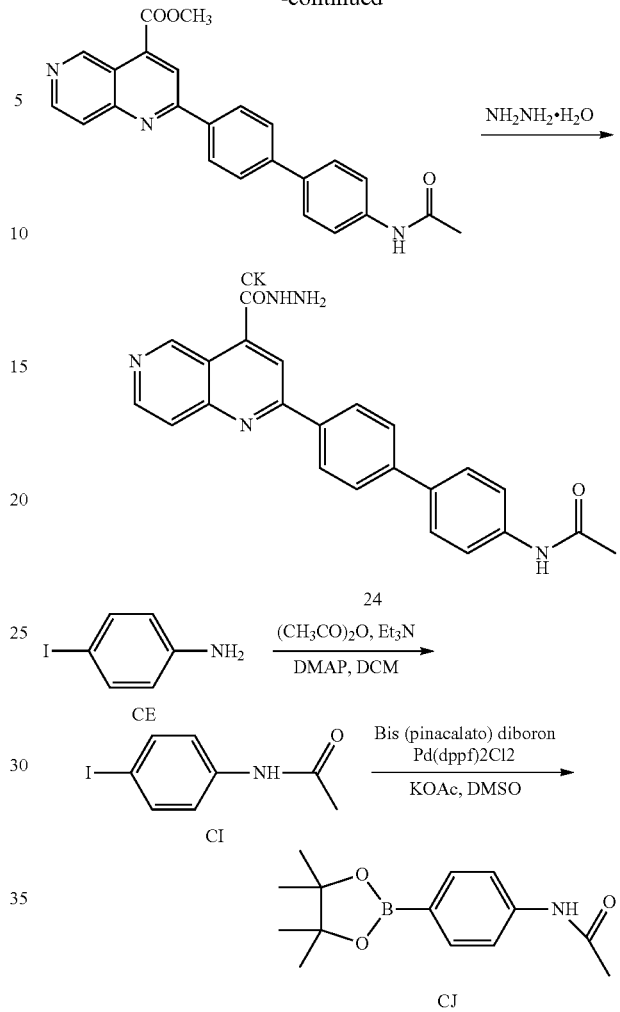

Example 24

N-(4'-(4-(hydrazinecarbonyl)-1,6-naphthyridin-2-yl)-[1,1'-biphenyl]-4-yl) acetamide (24)

To a stirred solution of 4-iodoaniline (CE; 1 g, 4.56 mmol) in CH₂Cl₂ (20 mL) under inert atmosphere were added triethylamine (1.6 mL, 11.41 mmol), p-dimethylaminopyridine (10 mg, catalytic) and acetic anhydride (0.51 mL, 5.47 mmol) at 0° C. After stirring for 2 h at 0° C., the reaction was warmed to RT and stirred for 2 h. The reaction was monitored by TLC. After complete consumption of the starting material, the reaction mass was diluted with water (30 mL) and the compound was extracted with CH₂Cl₂ (3×20 mL). The combined organic extracts were washed with water (20 mL), dried over sodium sulfate, filtered and concentrated under reduced pressure to obtain the crude. The crude was purified by silica gel column chromatography (20-30% EtOAc/hexanes) to afford CI (850 mg, 71%) as a solid. ¹H NMR (500 MHz, CDCl₃): δ 7.62 (d, J=9.0 Hz, 2H), 7.29 (d, J=9.0 Hz, 2H), 7.16 (br s, 1H), 2.17 (s, 3H). MS (ESI): m/z 262 [M+1]⁺

To a stirred solution of CI (300 mg, 1.14 mmol) in DMSO (15 mL) under inert atmosphere were added bis(pinacalato)diboron (321 mg, 1.26 mmol) and fused potassium acetate (338 mg, 3.44 mmol) at RT. The reaction was purged with argon for 30 min. Then Pd(dppf)$_2$Cl$_2$ (84 mg, 0.11 mmol) was added to the reaction mixture and the reaction was heated to 100° C. and stirred for 4 h. After complete consumption of the starting material, the reaction mass was cooled to RT, was diluted with water (20 mL), and was extracted with EtOAc (2×20 mL). The combined organic extracts were washed with water (20 mL), dried over sodium sulfate, filtered and concentrated under reduced pressure to obtain the crude. The crude was purified by silica gel column chromatography (5% MeOH/CH$_2$Cl$_2$) to afford CJ (150 mg, 50%) as a brown solid. $^1$H NMR (500 MHz, CDCl$_3$): δ 7.76 (d, J=8.0 Hz, 2H), 7.51 (d, J=8.0 Hz, 2H), 7.17 (br s, 1H), 2.18 (s, 3H), 1.33 (s, 12H). MS (ESI): m/z 262 [M+1]$^+$ To a stirred solution of N (150 mg, 0.43 mmol) in THF:H$_2$O (10:1, 11 mL) under inert atmosphere were added CJ (149 mg, 0.57 mmol) and potassium carbonate (181 mg, 1.31 mmol) at RT. The reaction was purged with argon for 30 min. Then tetrakis(triphenylphosphine) palladium(0) (50 mg, 0.04 mmol) was added to the reaction mixture and the reaction was heated to reflux and stirred for 4 h. After complete consumption of the starting material, the reaction mass was cooled to RT and the volatiles were evaporated under reduced pressure to obtain the crude. The crude was purified by silica gel column chromatography (3% MeOH/CH$_2$Cl$_2$) to afford CK (75 mg, 43%) as a yellow solid. $^1$H NMR (500 MHz, DMSO-d$_6$): δ 10.07 (s, 1H), 9.92 (s, 1H), 8.83 (d, J=6.0 Hz, 1H), 8.64 (s, 1H), 8.42 (d, J=8.5 Hz, 2H), 8.05 (d, J=6.0 Hz, 1H), 7.89 (d, J=8.5 Hz, 2H), 7.76-7.71 (m, 4H), 4.07 (s, 3H), 2.07 (s, 3H). MS (ESI): m/z 396.5 [M−1]$^+$ A stirred solution of CK (75 mg, 0.18 mmol) was dissolved in hydrazine hydrate (3 mL) under inert atmosphere. The reaction was heated to 90° C. and stirred for 30 min. After complete consumption of the starting material, the reaction mass was cooled to RT and the reaction mass was filtered under reduced pressure. The obtained solid was triturated with CH$_2$Cl$_2$ (2×5 mL) to afford 24 (35 mg, 47%) as an off-white solid. $^1$H NMR (500 MHz, DMSO-d$_6$): δ 10.20 (br s, 1H), 10.08 (s, 1H), 9.63 (s, 1H), 8.79 (d, J=6.0 Hz, 1H), 8.43 (d, J=8.0 Hz, 2H), 8.33 (s, 1H), 8.01 (d, J=6.0 Hz, 1H), 7.89 (d, J=8.0 Hz, 2H), 7.77-7.72 (m, 4H), 4.78 (br s, 2H), 2.08 (s, 3H). MS (ESI): m/z 398 [M+1]$^+$. HPLC Purity: 98.04%

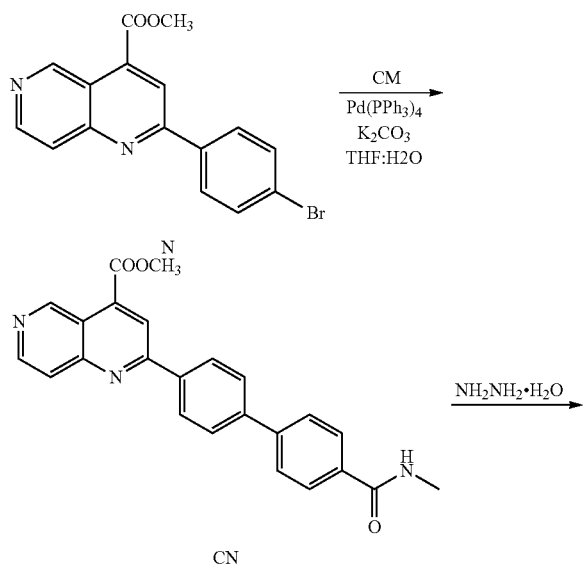

Scheme 22

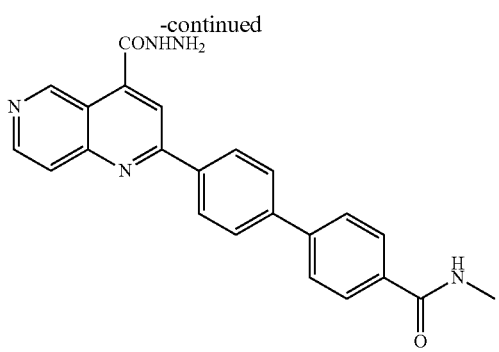

Example 25

4'-(4-(hydrazinecarbonyl)-1,6-naphthyridin-2-yl)-N-methyl-[1,1'-biphenyl]-4-carboxamide (25)

To a stirred solution of 4-boronobenzoic acid (CL; 1.5 g, 9.03 mmol) in CH$_2$Cl$_2$ (50 mL) under inert atmosphere were added DMF (1.5 mL) and oxalyl chloride (1.77 mL, 19.88 mmol) at 0° C. After stirring for 15 min at 0° C., the reaction was warmed to RT and stirred for 30 min. Then the reaction mixture was heated to 40° C. and stirred for 3 h. After complete consumption of the starting material, the volatiles were removed under reduced pressure. To the residue dissolved in DMF (5 mL) under inert atmosphere were added diisopropylamine (4.05 mL, 22.59 mmol) and methyl amine solution in 2 M THF (6 mL) at 0° C. The reaction was warmed to RT and stirred for 16 h. The reaction was monitored by TLC. After complete consumption of the starting material, the volatiles were removed under reduced pressure. The residue was diluted with water (25 mL) and the compound was extracted with EtOAc (2×20 mL). The combined organic extracts were washed with water (20 mL), 1 N HCl solution (10 mL), dried over sodium sulfate, filtered and concentrated under reduced pressure to obtain the crude CM (1.1 g, 68%) as a colorless sticky solid. $^1$H NMR (400 MHz, DMSO-d$_6$): δ 9.35 (br s, 1H), 8.42 (br s, 1H), 8.14 (s, 1H), 7.83-7.75 (m, 2H), 3.62-3.55 (m, 3H), 2.77-2.76 (m, 2H).

To a stirred solution of N (300 mg, 0.87 mmol) in THF:H$_2$O (10:1, 22 mL) under inert atmosphere were added CM (314 mg, 1.75 mmol) and potassium carbonate (363 mg, 2.63 mmol) at RT. The reaction was purged with argon for 30 min. Then tetrakis(triphenylphosphine) palladium(0) (101 mg, 0.08 mmol) was added to the reaction mixture and the reaction was heated to reflux and stirred for 12 h. The reaction was monitored by TLC. After complete consumption of the starting material, the reaction was cooled to RT, diluted with water (15 mL), and extracted with EtOAc (2×15 mL). The combined organic extracts were washed with water (15 mL), dried over sodium sulfate, filtered and concentrated under reduced pressure to obtain the crude. The crude was purified by silica gel column chromatography (5% MeOH/CH$_2$Cl$_2$) to afford CN (100 mg, 29%) as a white solid. $^1$H NMR (400 MHz, DMSO-d$_6$): δ 9.94 (s, 1H), 8.85 (d, J=6.0 Hz, 1H), 8.67 (s, 1H), 8.53-8.52 (m, 1H), 8.47 (d, J=8.4 Hz, 2H), 8.07 (d, J=6.4 Hz, 1H), 7.99 (d, J=8.4 Hz, 2H), 7.90 (d, J=8.8 Hz, 2H), 4.08 (s, 3H), 2.82 (s, 3H). MS (ESI): m/z 398 [M+1]$^+$ A stirred solution of CN (100 mg, 0.25 mmol) in hydrazine hydrate (3 mL) under inert atmosphere was heated to 90° C. and stirred for 30 min. The reaction was monitored by TLC After complete consumption of the starting material, the reaction mass was cooled to RT and the reaction mass was filtered under reduced pressure. The obtained solid was triturated with CH$_2$Cl$_2$ (2×5 mL) to afford 25 (90 mg, 90%) as an off-white solid. $^1$H NMR (400 MHz, DMSO-d$_6$): δ 10.21 (br s, 1H), 9.65 (s, 1H), 8.80 (d, J=6.0 Hz, 1H), 8.53-8.52 (m, 1H), 8.48 (d, J=8.4 Hz, 2H), 8.36 (s, 1H), 8.03-7.97 (m, 6H), 7.91 (d, J=8.4 Hz, 1H), 4.80-4.78 (m, 2H), 2.83-2.82 (m, 3H). MS (ESI): m/z 398 [M+1]$^+$. HPLC Purity: 97.04%

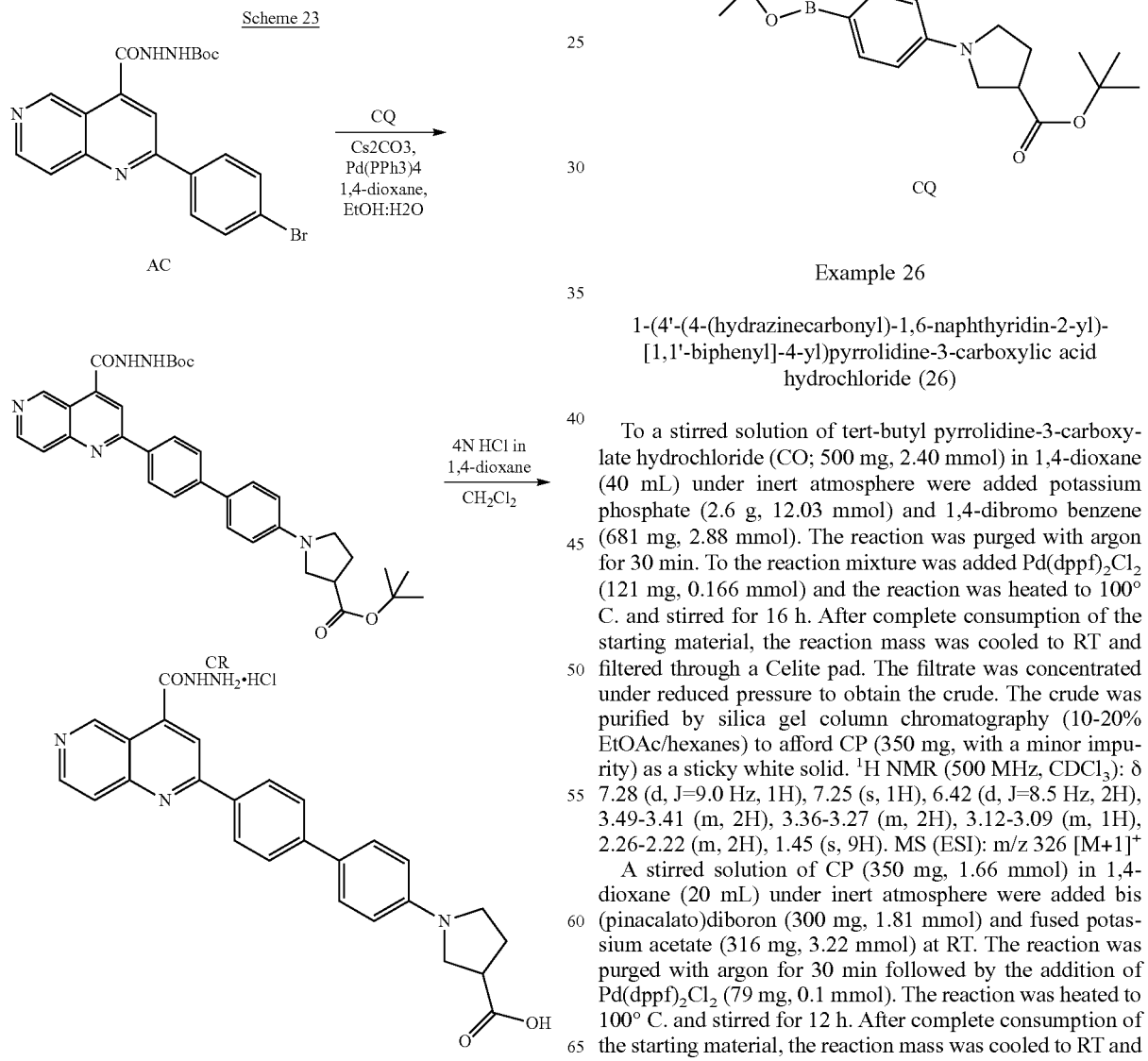

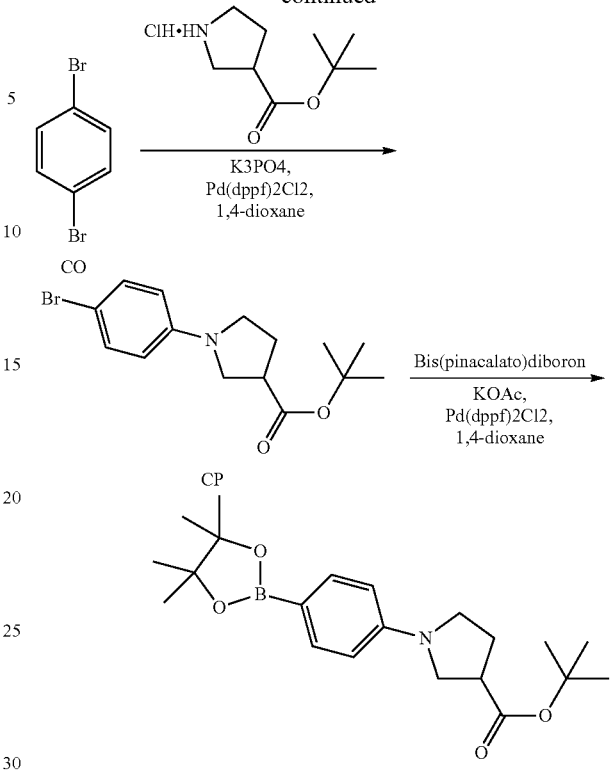

Example 26

1-(4'-(4-(hydrazinecarbonyl)-1,6-naphthyridin-2-yl)-[1,1'-biphenyl]-4-yl)pyrrolidine-3-carboxylic acid hydrochloride (26)

To a stirred solution of tert-butyl pyrrolidine-3-carboxylate hydrochloride (CO; 500 mg, 2.40 mmol) in 1,4-dioxane (40 mL) under inert atmosphere were added potassium phosphate (2.6 g, 12.03 mmol) and 1,4-dibromo benzene (681 mg, 2.88 mmol). The reaction was purged with argon for 30 min. To the reaction mixture was added Pd(dppf)$_2$Cl$_2$ (121 mg, 0.166 mmol) and the reaction was heated to 100° C. and stirred for 16 h. After complete consumption of the starting material, the reaction mass was cooled to RT and filtered through a Celite pad. The filtrate was concentrated under reduced pressure to obtain the crude. The crude was purified by silica gel column chromatography (10-20% EtOAc/hexanes) to afford CP (350 mg, with a minor impurity) as a sticky white solid. $^1$H NMR (500 MHz, CDCl$_3$): δ 7.28 (d, J=9.0 Hz, 1H), 7.25 (s, 1H), 6.42 (d, J=8.5 Hz, 2H), 3.49-3.41 (m, 2H), 3.36-3.27 (m, 2H), 3.12-3.09 (m, 1H), 2.26-2.22 (m, 2H), 1.45 (s, 9H). MS (ESI): m/z 326 [M+1]$^+$ A stirred solution of CP (350 mg, 1.66 mmol) in 1,4-dioxane (20 mL) under inert atmosphere were added bis(pinacalato)diboron (300 mg, 1.81 mmol) and fused potassium acetate (316 mg, 3.22 mmol) at RT. The reaction was purged with argon for 30 min followed by the addition of Pd(dppf)$_2$Cl$_2$ (79 mg, 0.1 mmol). The reaction was heated to 100° C. and stirred for 12 h. After complete consumption of the starting material, the reaction mass was cooled to RT and filtered through a Celite pad. The filtrate was concentrated under reduced pressure to obtain the crude, which was purified by silica gel column chromatography (20-30% EtOAc/hexanes) to afford CQ (170 mg, 43%) as a sticky brown solid. $^1$H NMR (500 MHz, CDCl$_3$): δ 7.67 (d, J=8.5 Hz, 2H), 6.53 (d, J=8.5 Hz, 2H), 3.55 (d, J=8.5 Hz, 1H), 3.49 (d, J=7.0 Hz, 1H), 3.45-3.42 (m, 1H), 3.35-3.33 (m, 1H), 3.12-3.09 (m, 1H), 2.60-2.21 (m, 2H), 1.54 (s, 9H), 1.34 (s, 12H). MS (ESI): m/z 374 [M+1]$^+$.

To a stirred solution of AC (181 mg, 0.41 mmol) in 1,4-dioxane:ethanol:H$_2$O (4:2:1) under inert atmosphere was added CQ (170 mg, 0.45 mmol) and cesium carbonate (405 mg, 1.24 mmol) at RT. The reaction was purged with argon for 30 min followed by the addition of Pd(PPh$_3$)$_4$ (48 mg, 0.04 mmol). The reaction was heated to reflux and stirred for 8 h. After complete consumption of the starting material, the reaction mass was cooled to RT and filtered through a Celite pad. The filtrate was concentrated under reduced pressure to obtain the crude, which was purified by preparative HPLC to afford CR (60 mg, 25%) as a pale yellow solid. $^1$H NMR (400 MHz, DMSO-d$_6$): δ 10.72 (br s, 1H), 9.74 (br s, 1H), 9.25 (br s, 1H), 8.79 (d, J=5.6 Hz, 1H), 8.37 (d, J=8.0 Hz, 2H), 8.29 (s, 1H), 8.00 (d, J=5.6 Hz, 1H), 7.84 (d, J=8.8 Hz, 2H), 7.67 (d, J=8.8 Hz, 2H), 6.68 (d, J=8.8 Hz, 2H), 4.01 (d, J=6.4 Hz, 1H), 3.54-3.46 (m, 1H), 3.44-3.42 (m, 1H), 3.38-3.33 (m, 1H), 3.22-3.18 (m, 1H), 2.26-2.12 (m, 2H), 1.86 (s, 9H), 1.52 (s, 9H). MS (ESI): m/z 610 [M+1]$^+$ To a stirred solution of CR (60 mg, 0.09 mmol) in CH$_2$Cl$_2$ (10 mL) under inert atmosphere was added 4N HCl solution in 1,4-dioxane (1 mL) at 0° C. The reaction was warmed to RT, stirred for 4 h. The reaction was monitored by TLC; after complete consumption of the starting material, the volatiles were evaporated under reduced pressure to obtain the crude. The crude was triturated with IPA:diethyl ether (2×10 mL) followed by pentane (2×5 mL) to afford 26 (42 mg as HCl salt) as a brown solid. $^1$H NMR (400 MHz, DMSO-d$_6$): δ 12.37 (br s, 1H), 9.77 (s, 1H), 8.89 (d, J=6.4 Hz, 1H), 8.65 (s, 1H), 8.48 (d, J=4.8 Hz, 2H), 8.26 (d, J=6.4 Hz, 1H), 7.88 (d, J=8.8 Hz, 2H), 7.70 (d, J=8.8 Hz, 2H), 6.69 (d, J=8.8 Hz, 2H), 3.56-3.46 (m, 2H), 3.39-3.34 (m, 2H), 3.25-3.21 (m, 1H), 2.26-2.17 (m, 2H). MS (ESI): m/z 510 [M+1]$^+$. HPLC Purity: 97.76%

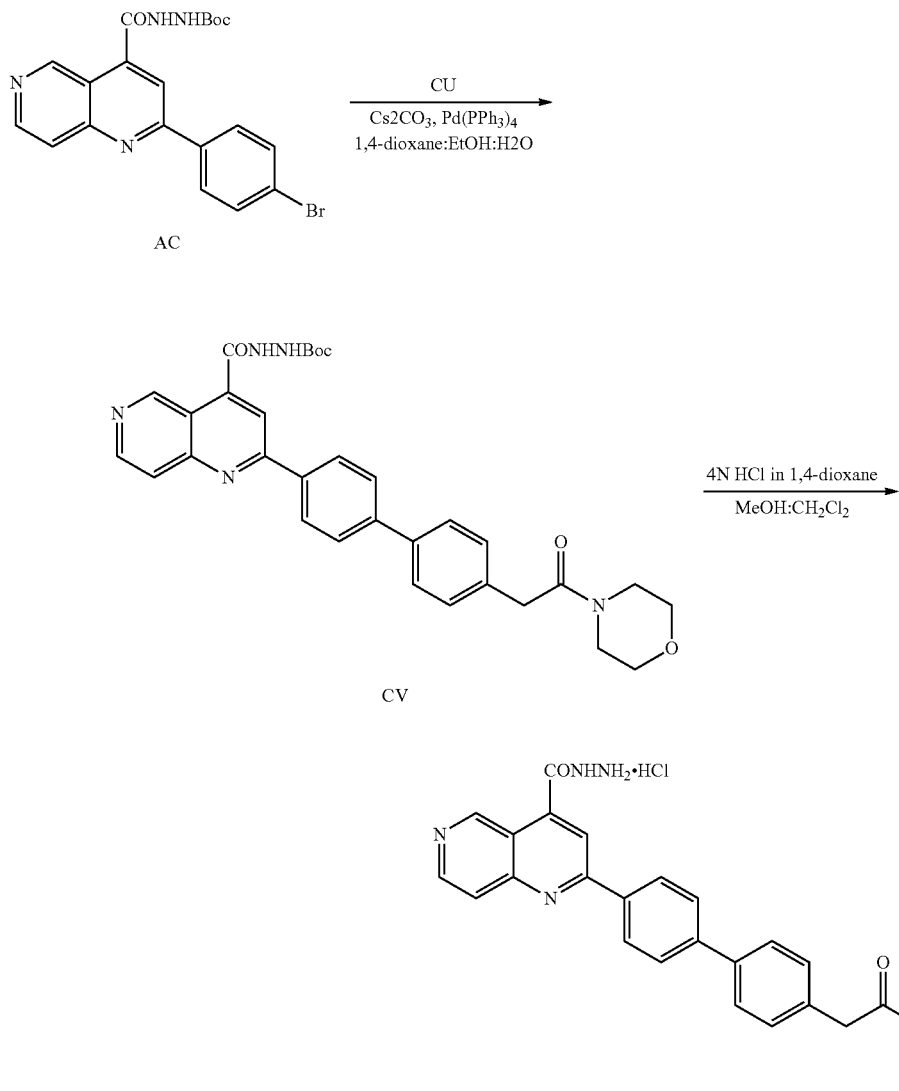

Scheme 24

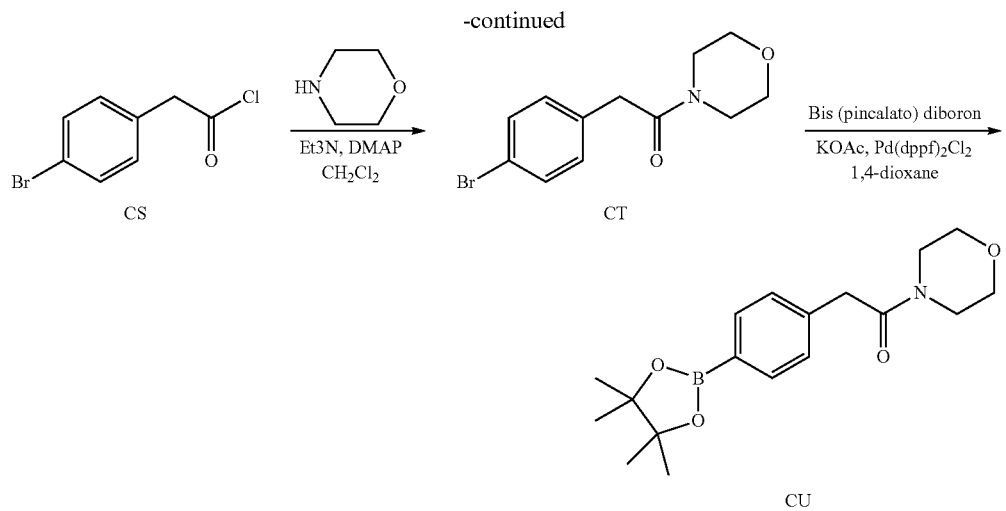

Example 27

2-(4'-(2-morpholino-2-oxoethyl)-[1,1'-biphenyl]-4-yl)-1,6-naphthyridine-4-carbohydrazide hydrochloride (27)

To a stirred solution of morpholine (1 g, 11.47 mmol) in CH$_2$Cl$_2$ (40 mL) under inert atmosphere was added triethylamine (2.3 g, 22.92 mmol) and p-dimethyl amino pyridine (140 mg, 1.14 mmol) at 0° C. To this was added 2-(4-bromophenyl) acetyl chloride (CS; 3.2 g, 13.77 mmol) in CH$_2$Cl$_2$ (10 mL) at 0° C. and the reaction was warmed to RT and stirred for 2 h. The reaction was monitored by TLC, after complete consumption of the starting material, the reaction mass was diluted with (30 mL) and the compound was extracted with CH$_2$Cl$_2$ (3×30 mL). The combined organic extracts were washed with water (30 mL), brine (30 mL), dried over sodium sulfate, filtered and concentrated under reduced pressure to obtain the crude. The crude was purified by silica gel column chromatography eluting with 1-2% MeOH/CH$_2$Cl$_2$ to afford CT (1.4 g, 45%) as an off-white solid. $^1$H NMR (500 MHz, CDCl$_3$): δ 7.45 (d, J=8.0 Hz, 2H), 7.11 (d, J=8.0 Hz, 2H), 3.66-3.64 (m, 6H), 3.54-3.52 (m, 2H), 3.43-3.42 (m, 2H).

To a stirred solution of CT (1.4 g, 5.68 mmol) in 1,4-dioxane (30 mL) under inert atmosphere were added bis(pinacalato)diboron (1.56 g, 6.14 mmol) and fused potassium acetate (1.51 g, 15.41 mmol) at RT. The reaction was purged with argon for 20 min followed by the addition of Pd(dppf)$_2$Cl$_2$ (370 mg, 0.50 mmol). The reaction was heated to reflux and stirred for 12 h. After complete consumption of the starting material, the reaction mass was cooled to RT and filtered through a Celite pad. The filtrate was concentrated under reduced pressure to obtain the crude, which was purified by silica gel column chromatography eluting with 50-70% EtOAc/hexanes to afford CU (1.1 g, 66%) as a pale brown solid. $^1$H NMR (400 MHz, CDCl$_3$): δ 7.76 (d, J=8.0 Hz, 2H), 7.25 (d, J=8.0 Hz, 2H), 3.75 (s, 2H), 3.63 (s, 4H), 3.43-3.41 (m, 2H), 3.39-3.38 (m, 2H), 1.34 (s, 12 H).

To a stirred solution of AC (300 mg, 0.67 mmol) in 1,4-dioxane:ethanol:H$_2$O (4:2:1; 21 mL) under inert atmosphere were added CU (260 mg, 0.78 mmol) and cesium carbonate (660 mg, 2.02 mmol) at RT. The reaction was then purged with argon for 20 min followed by the addition of Pd(PPh$_3$)$_4$ (78 mg, 0.06 mmol). The reaction was heated to reflux and stirred for 7 h. After complete consumption of the starting material, the volatiles were evaporated under reduced pressure to obtain the crude, which was purified by silica gel column chromatography eluting with 3-4% MeOH:CH$_2$Cl$_2$ to afford CV (260 mg, 68%) as a pale brown solid. $^1$H NMR (400 MHz, DMSO-d$_6$): δ 10.66 (br s, 1H), 9.70 (br s, 1H), 9.29 (br s, 1H), 8.83 (d, J=6.0 Hz, 1H), 8.45 (d, J=8.0 Hz, 2H), 8.32 (br s, 1H), 8.04 (d, J=6.0 Hz, 1H), 7.92 (d, J=8.8 Hz, 2H), 7.75 (d, J=8.4 Hz, 2H), 7.37 (d, J=8.0 Hz, 2H), 3.79 (s, 2H), 3.56-3.47 (m, 8H), 1.49 (s, 9H).

To a stirred solution of CV (150 mg, 0.26 mmol) in MeOH:CH$_2$Cl$_2$ (1:4, 2 mL) under inert atmosphere was added a 4N HCl solution in 1,4-dioxane (3 mL) at 0° C. The reaction was warmed to RT and stirred for 45 min. After complete consumption of the starting material, the volatiles were evaporated under reduced pressure to obtain the crude, which was triturated with diisopropyl ether (2×10 mL) to afford 27 (100 mg as an HCl salt) as an orange solid. $^1$H NMR (500 MHz, DMSO-d$_6$): δ 11.50 (br s, 1H), 9.67 (s, 1H), 8.84 (d, J=6.0 Hz, 1H), 8.47 (d, J=8.5 Hz, 3H), 8.10 (d, J=6.0 Hz, 1H), 7.94 (d, J=8.5 Hz, 2H), 7.75 (d, J=8.0 Hz, 2H), 7.37 (d, J=8.0 Hz, 2H), 3.79 (s, 2H), 3.55-3.52 (m, 6H), 3.48-3.46 (m, 2H). MS (ESI): m/z 468.3 [M+1]$^+$. HPLC Purity: 98.25%

Scheme 25

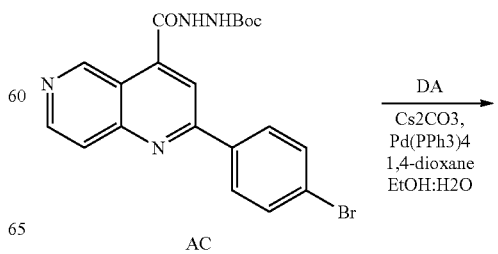

-continued

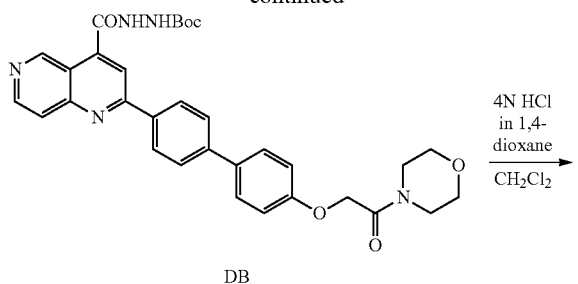

DB

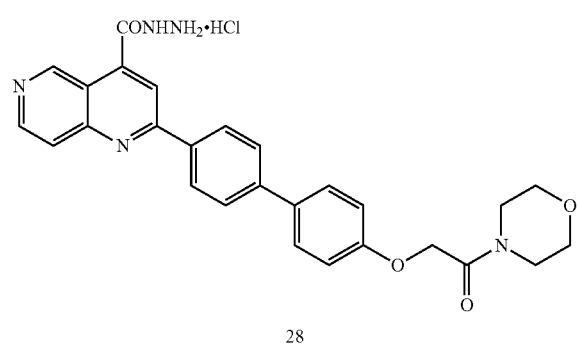

28

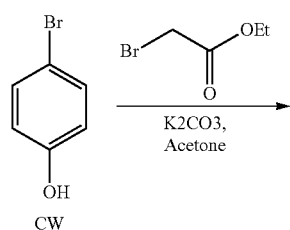

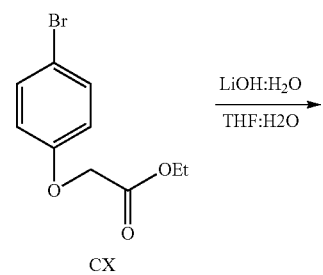

CX

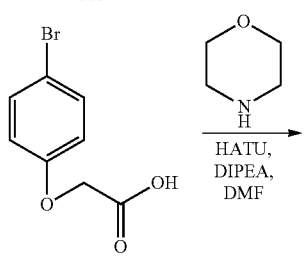

CY

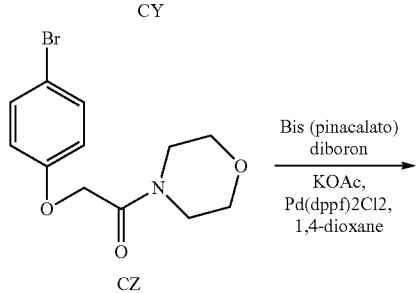

CZ

-continued

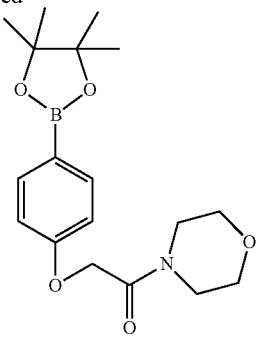

DA

Example 28

2-(4'-(2-morpholino-2-oxoethoxy)-[1,1'-biphenyl]-4-yl)-1,6-naphthyridine-4-carbohydrazide hydrochloride (28)

To a stirred solution of 4-bromophenol (CW; 10 g, 57.80 mmol) in acetone (150 mL) under inert atmosphere were added potassium carbonate (12 g, 86.70 mmol) and bromo ethyl acetate (7.7 mL, 69.40 mmol) at 0° C. The reaction was warmed to RT and stirred for 16 h. After complete consumption of the starting material, the volatiles were evaporated under reduced pressure. The residue was diluted with water (40 mL) and was extracted with diethyl ether (2×50 mL). The combined organic extracts were washed with an aqueous 10% NaOH solution (40 mL), water (40 mL), dried over sodium sulfate, filtered and concentrated under reduced pressure to obtain the crude. The crude was recrystallized with ethanol (20 mL) to afford CX (13 g, 86%) as a white solid. $^1$H NMR (500 MHz, CDCl$_3$): δ 7.38 (d, J=9.5 Hz, 2H), 6.89 (d, J=9.0 Hz, 2H), 4.58 (s, 2H), 4.29-4.24 (m, 2H), 1.31-1.28 (m, 3H). MS (ESI): m/z 260 [M+1]$^+$ To a stirred solution of CX (7 g, 27.02 mmol) in THF:H$_2$O (1:1, 50 mL) under inert atmosphere was added lithium hydroxide monohydrate (11.3 g, 41.90 mmol) at 0° C. The reaction was warmed to RT for 4 h. After complete consumption of the starting material, the volatiles were evaporated under reduced pressure. The residue was diluted with water (40 mL) and acidified with HCl to pH~2 and filtered. The obtained solid was triturated with toluene (2×30 mL) to afford CY (4.5 g, 73%) as a white solid. $^1$H NMR (400 MHz, DMSO-d$_6$): δ 13.03 (br s, 1H), 7.44 (d, J=6.8 Hz, 2H), 6.89 (d, J=6.8 Hz, 2H), 4.66 (s, 2H). MS (ESI): m/z 231 [M+1]$^+$ To a stirred solution of CY (500 mg, 2.16 mmol) in DMF (10 mL) under inert atmosphere were added HATU (2.1 g, 5.41 mmol) and diisopropylethylamine (0.04 mL, 0.27 mmol) at 0° C. After the addition of morpholine (282 mg, 3.24 mmol) at 0° C., the reaction was warmed to RT and stirred for 12 h. The reaction was monitored by TLC. After complete consumption of the starting material, the reaction mixture was diluted with water (15 mL) and extracted with EtOAc (2×20 mL). The combined organic extracts were washed with water (10 mL), dried over sodium sulfate, filtered and concentrated under reduced pressure to obtain the crude. The crude was purified by silica gel column chromatography (70-80% EtOAc/hexanes) to afford CZ (500 mg, 77%) as a white solid. $^1$H NMR (400 MHz, CDCl$_3$): δ 7.39 (d, J=7.0 Hz, 2H), 6.84 (d, J=7.0 Hz, 2H), 4.67 (s, 2H), 3.67-3.63 (m, 4H), 3.62-3.57 (m, 4H). MS (ESI): m/z 301 [M+1]$^+$ To a stirred solution of CZ (500 mg, 1.66 mmol) in 1,4-dioxane (20 mL) were added bis(pinacalato)diboron (634 mg, 2.49 mmol) and fused potassium acetate (489 mg, 4.99 mmol) at RT. After the reaction was purged with argon for 30 min, Pd(dppf)$_2$Cl$_2$ (121 mg, 0.166 mmol) was added to the reaction. The reaction mixture was then heated to 100° C. and stirred for 12 h. After complete consumption of the starting material, the reaction mass was cooled to RT and filtered through a Celite pad. The filtrate was concentrated under reduced pressure to obtain the crude, which was purified by silica gel column chromatography (50-70% EtOAc/hexanes) to afford DA (450 mg, 78%) as a sticky white solid. $^1$H NMR (500 MHz, CDCl$_3$): δ 7.75 (d, J=8.5 Hz, 2H), 6.93 (d, J=8.5 Hz, 2H), 4.71 (s, 2H), 3.64-3.60 (m, 8H), 1.26 (s, 12H). MS (ESI): m/z 348 [M+1]$^+$ To a stirred solution of AC (384 mg, 0.84 mmol) in 1,4-dioxane:ethanol:H$_2$O (4:2:1, 14 mL) under inert atmosphere were added DA (350 mg, 1.00 mmol) and cesium carbonate (808 mg, 2.52 mmol) at RT. After the reaction mixture was purged with argon for 30 min, Pd(PPh$_3$)$_4$ (97 mg, 0.08 mmol) was added. The reaction was heated to reflux and stirred for 8 h. After complete consumption of the starting material, the reaction mass was cooled to RT and filtered through a Celite pad. The filtrate was concentrated under reduced pressure to obtain the crude, which was purified by silica gel column chromatography (2-5% CH$_2$Cl$_2$/MeOH) to afford DB (200 mg, 52%) as a yellow solid. $^1$H NMR (400 MHz, DMSO-d$_6$): δ 10.65 (br s, 1H), 9.69 (br s, 1H), 9.29 (br s, 1H), 8.82 (d, J=6.0 Hz, 1H), 8.42 (d, J=8.0 Hz, 2H), 8.31 (s, 1H), 8.03 (d, J=6.0 Hz, 1H), 7.88 (d, J=8.4 Hz, 2H), 7.74 (d, J=8.8 Hz, 2H), 7.07 (d, J=8.8 Hz, 2H), 4.91 (s, 2H), 3.63-3.58 (m, 4H), 3.50-3.48 (m, 4H), 1.49 (s, 9H). MS (ESI): m/z 584 [M+1]$^+$ To a stirred solution of DB (100 mg, 0.17 mmol) in CH$_2$Cl$_2$ (10 mL) under inert atmosphere was added 4N HCl solution in 1,4-dioxane (1 mL) at 0° C. and stirred for 4 h. The reaction was monitored by TLC. After complete consumption of the starting material, the volatiles were evaporated under reduced pressure to obtain the crude. The crude was triturated with IPA:diethyl ether (2×10 mL) followed by pentane (2×5 mL) to afford 28 (28.7 mg as an HCl salt) as a brown solid. $^1$H NMR (400 MHz, DMSO-d$_6$): δ 12.20 (br s, 1H), 9.75 (s, 1H), 8.88 (d, J=6.0 Hz, 1H), 8.61 (s, 1H), 8.50 (d, J=8.4 Hz, 2H), 8.21 (d, J=6.0 Hz, 1H), 7.92 (d, J=8.4 Hz, 2H), 7.76 (d, J=8.8 Hz, 2H), 7.07 (d, J=8.4 Hz, 2H), 4.92 (s, 2H), 3.63-3.58 (m, 4H), 3.50-3.48 (m, 4H). MS (ESI): m/z 484 [M+1]$^+$. HPLC Purity: 96.37%

Scheme 26

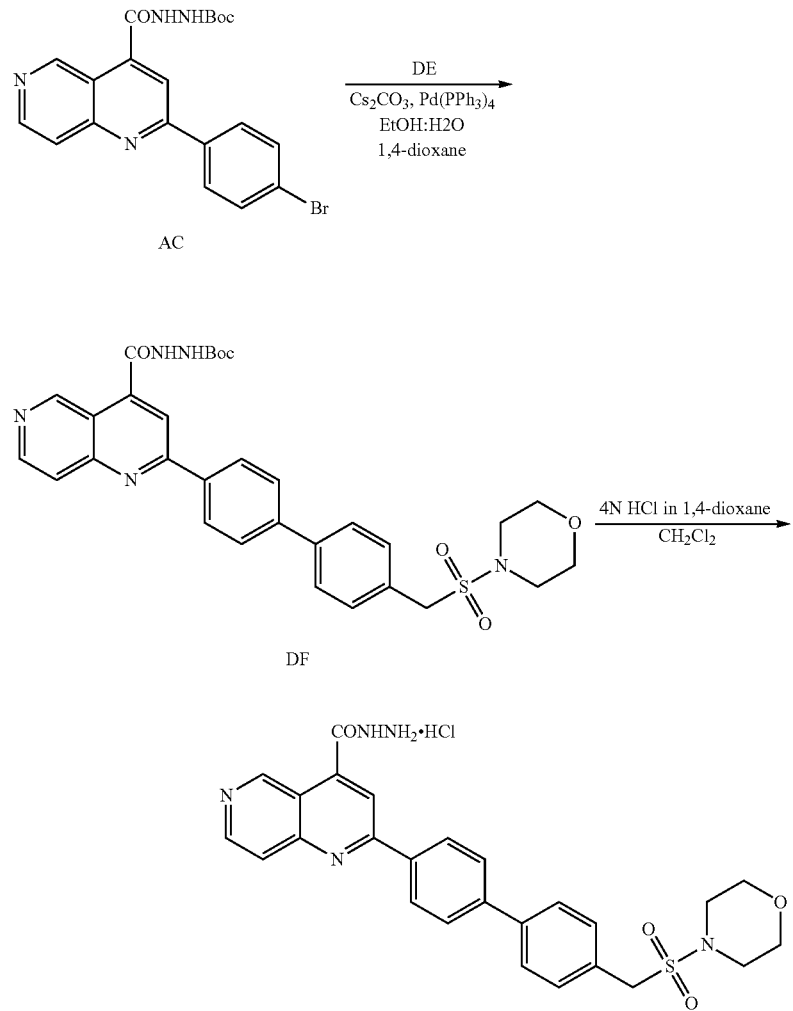

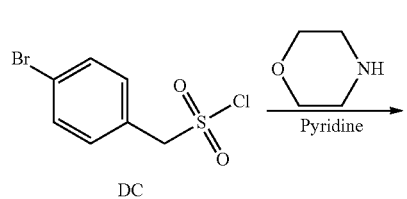

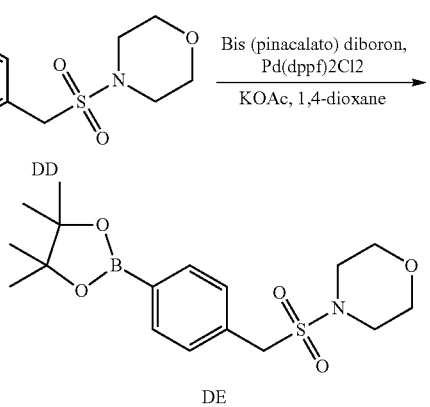

Example 29

2-(4'-((morpholinosulfonyl)methyl)-[1,1'-biphenyl]-4-yl)-1,6-naphthyridine-4-carbohydrazide hydrochloride (29)

To a stirred solution of (4-bromophenyl)methanesulfonyl chloride (DC; 500 mg, 1.85 mmol) in pyridine (10 mL) under inert atmosphere was added morpholine (712 mg, 2.22 mmol) at RT and stirred for 16 h. The reaction was monitored by TLC. After complete consumption of the starting material, the reaction mixture was diluted with water (30 mL) and was extracted with EtOAc (2×20 mL). The combined organic extracts were washed with water (15 mL), dried over sodium sulfate, filtered and concentrated under reduced pressure to obtain the crude. The crude was purified by silica gel column chromatography (20-30% EtOAc/hexanes) to afford DD (360 mg, 61%) as a white solid. $^1$H NMR (400 MHz, CDCl$_3$): δ 7.53 (d, J=8.8 Hz, 2H), 7.29 (d, J=8.8 Hz, 2H), 4.16 (s, 2H), 3.65 (t, J=4.8 Hz, 4H), 3.13 (t, J=4.8 Hz, 4H).

To a stirred solution of DD (250 mg, 0.78 mmol) in 1,4-dioxane (15 mL) under inert atmosphere were added bis(pinacalato)diboron (238 mg, 0.93 mmol) and fused potassium acetate (230 mg, 2.34 mmol) at RT. After the reaction was purged with argon for 30 min, Pd(dppf)$_2$Cl$_2$ (57 mg, 0.07 mmol) was added to the reaction mixture. The reaction was then heated to 90° C. and stirred for 16 h. After complete consumption of the starting material, the reaction mass was cooled to RT and filtered through a Celite pad. The filtrate was concentrated under reduced pressure to obtain the crude. The crude was purified by silica gel column chromatography (30-40% EtOAc/hexanes) to afford DE (210 mg, 52%) as a white solid. $^1$H NMR (400 MHz, CDCl$_3$): δ 7.82 (d, J=7.6 Hz, 2H), 7.41 (d, J=8.0 Hz, 2H), 4.25 (s, 2H), 3.60 (t, J=4.8 Hz, 4H), 3.08 (t, J=4.8 Hz, 4H), 1.35 (s, 12H).

To a stirred solution of AC (200 mg, 0.45 mmol) in 1,4-dioxane:ethanol:H$_2$O (20:10:3, 33 mL) under inert atmosphere were added DE (215 mg, 0.58 mmol) and cesium carbonate (442 mg, 1.35 mmol) at RT. After the reaction was purged with argon for 30 min, tetrakis(triphenylphosphine)paliadium(0) (52 mg, 0.05 mmol) was added to the reaction mixture. The reaction was heated to reflux and stirred for 5 h. After complete consumption of the starting material, the reaction mass was cooled to RT and filtered through a Celite pad. The filtrate was concentrated under reduced pressure to obtain the crude. The crude was purified by silica gel column chromatography (5-10% MeOH/CH$_2$Cl$_2$) to afford DF (110 mg, 40%) as a yellow solid. $^1$H NMR (500 MHz, DMSO-d$_6$): δ 10.65 (s, 1H), 9.69 (s, 1H), 9.29 (s, 1H), 8.82 (d, J=6.0 Hz, 1H), 8.46 (d, J=8.0 Hz, 2H), 8.32 (s, 1H), 8.04 (d, J=6.0 Hz, 1H), 7.96 (d, J=8.5 Hz, 2H), 7.84 (d, J=7.5 Hz, 2H), 7.56 (d, J=8.0 Hz, 2H), 4.52 (s, 2H), 3.60 (t, J=4.5 Hz, 4H), 3.14 (t, J=4.5 Hz, 4H), 1.48 (s, 9H).

To a stirred solution of DF (60 mg, 0.09 mmol) in CH$_2$Cl$_2$ (3 mL) under inert atmosphere was added 4N HCl in 1,4-dioxane (0.6 mL) at 0° C. The reaction mixture was warmed to RT and stirred for 4 h. After complete consumption of the starting material, the volatiles were evaporated under reduced pressure to obtain the crude. The crude was triturated with diethyl ether (2×5 mL) to afford 29 (40 mg as an HCl salt) as a yellow solid. $^1$H NMR (400 MHz, DMSO-d$_6$): δ 12.20 (br s, 1H), 9.75 (s, 1H), 8.89 (d, J=6.0 Hz, 1H), 8.63 (s, 1H), 8.54 (d, J=8.4 Hz, 2H), 8.22 (d, J=6.4 Hz, 1H), 8.00 (d, J=8.4 Hz, 2H), 7.87 (d, J=8.4 Hz, 2H), 7.58 (d, J=8.0 Hz, 2H), 4.53 (s, 2H), 3.62-3.60 (m, 4H), 3.17-3.15 (m, 4H). MS (ESI): m/z 504 [M+1]$^+$. HPLC Purity: 94.51%

Scheme 27

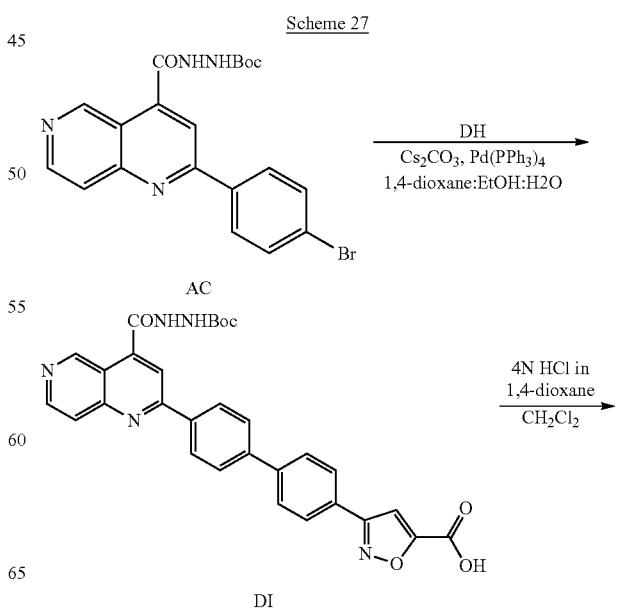

-continued

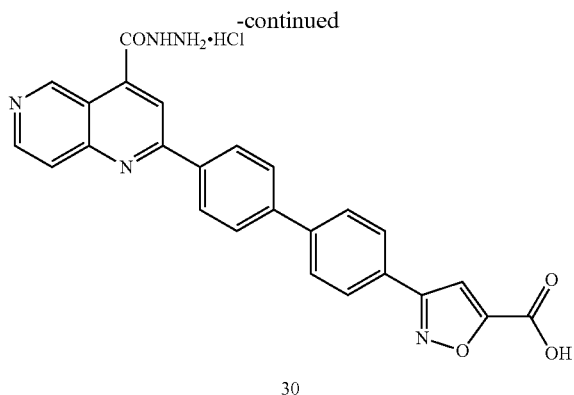

30

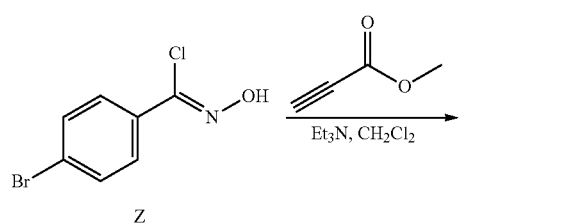

Z

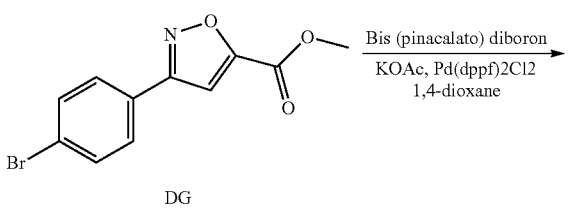

DG

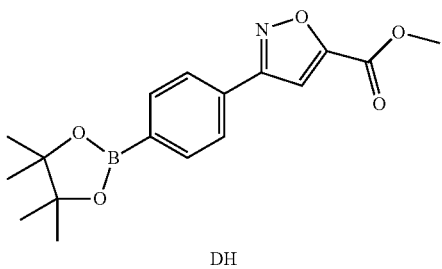

DH

Example 30

3-(4'-(4-(hydrazinecarbonyl)-1,6-naphthyridin-2-yl)-[1,1'-biphenyl]-4-yl)isoxazole-5-carboxylic acid hydrochloride (30)

To a stirred solution Z (8 g, 34.17 mmol) in dry CH$_2$Cl$_2$ (100 mL) under inert atmosphere were added triethylamine (5.38 mL, 101.19 mmol) and methylpropiolate (3.05 mL, 34.17 mmol) dropwise at 0° C. The reaction was warmed to RT and stirred for 12 h. After complete consumption of the starting material, the reaction mass was diluted with water (50 mL) and the compound was extracted with CH$_2$Cl$_2$ (3×50 mL). The combined organic extracts were washed with water (50 mL), dried over sodium sulfate, filtered and concentrated under reduced pressure to obtain the crude. The crude was purified by silica gel column chromatography eluting with 8-10% EtOAc/hexanes to afford DG (3.1 g, 32%) as an off-white solid. $^1$H NMR (400 MHz, CDCl$_3$): δ 7.70 (d, J=8.0 Hz, 2H), 7.62 (d, J=8.4 Hz, 2H), 7.23 (s, 1H), 4.00 (s, 3H).

To a stirred solution of DG (2 g, 7.08 mmol) in 1,4-dioxane (100 mL) under inert atmosphere were added bis (pinacalato)diboron (2.15 g, 8.50 mmol) and fused potassium acetate (2.08 g, 21.24 mmol) at RT. After the reaction mixture was purged with argon for 20 min, Pd(dppf)$_2$Cl$_2$ (518 mg, 0.70 mmol) was added. The reaction was then heated to 90° C. and stirred for 12 h. After complete consumption of the starting material, the reaction mass was cooled to RT and filtered through a Celite pad. The filtrate was concentrated under reduced pressure to obtain the crude, which was purified by silica gel column chromatography eluting with 8-10% EtOAc/hexanes to afford DH (1.4 g, 60%) as an off-white solid. $^1$H NMR (400 MHz, CDCl$_3$): δ 7.72 (d, J=8.0 Hz, 2H), 7.83 (d, J=8.4 Hz, 2H), 7.29 (s, 1H), 4.00 (s, 3H), 1.36 (s, 12H).

To a stirred solution of AC (1.5 g, 3.39 mmol) in 1,4-dioxane:EtOH:H$_2$O (4:2:1, 50 mL) were added DH (1.3 g, 4.06 mmol) and cesium carbonate (3.3 g, 10.17 mmol) at RT. After the reaction was purged with argon for 30 min, Pd(PPh$_3$)$_4$ (390 mg, 0.33 mmol) was added. The reaction was then heated to 90° C. and stirred for 12 h. After complete consumption of the starting material, the reaction mass was cooled to RT and the volatiles were evaporated under reduced pressure. The residue was diluted with water (40 mL) and the compound was extracted with ethyl acetate (3×30 mL). The aqueous layer was acidified with glacial acetic acid to pH~2 (20 mL) and the resulting solid was filtered under vacuum to afford DI (1.1 g, 59%) as a yellow solid. $^1$H NMR (400 MHz, DMSO-d$_6$): δ 10.68 (br s, 1H), 9.71 (s, 1H), 9.30 (s, 1H), 8.83 (d, J=6.0 Hz, 1H), 8.49 (d, J=8.0 Hz, 2H), 8.35 (s, 1H), 8.10-7.91 (m, 8H), 7.64 (s, 1H), 1.50 (s, 9H).

To a stirred solution of DI (70 mg, 0.12 mmol) in CH$_2$Cl$_2$ (3 mL) under inert atmosphere was added 4N HCl solution in 1,4-dioxane (1 mL) at 0° C. The reaction was warmed to RT and stirred for 1 h. After complete consumption of the starting material, the volatiles were evaporated under reduced pressure to obtain the crude. The crude was triturated with diisopropyl ether (2×8 mL) and pentane (2×8 mL) to afford 30 (50 mg as an HCl salt) as a yellow solid. $^1$H NMR (400 MHz, DMSO-d$_6$): δ 12.02 (br s, 1H), 9.73 (s, 1H), 8.88 (d, J=6.0 Hz, 1H), 8.60 (s, 1H), 8.55 (d, J=8.4 Hz, 2H), 8.18 (d, J=5.6 Hz, 1H), 8.12 (d, J=8.4 Hz, 2H), 8.06 (d, J=8.4 Hz, 2H), 8.00 (d, J=8.4 Hz, 2H), 7.90 (s, 1H). MS (ESI): m/z 452.3 [M+1]$^+$ Scheme 28

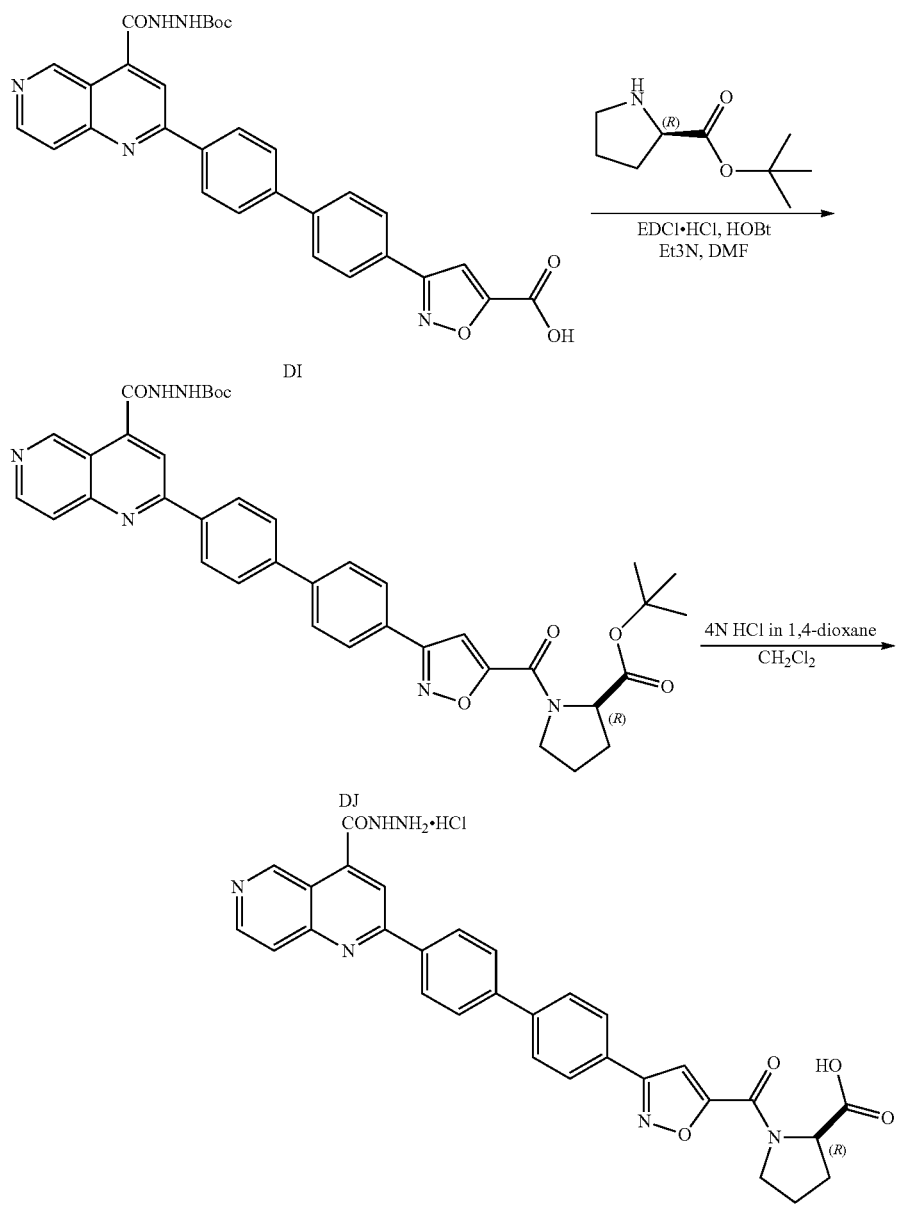

Example 31

(R)-1-(3-(4'-(4-(hydrazinecarbonyl)-1,6-naphthyridin-2-yl)-[1,1'-biphenyl]-4-yl)isoxazole-5-carbonyl)pyrrolidine-2-carboxylic acid hydrochloride (31)

To a stirred solution of DI (300 mg, 0.54 mmol) in DMF (10 mL) under inert atmosphere were added EDCI.HCl (260 mg, 1.36 mmol), HOBt (132 mg, 0.97 mmol), triethylamine (220 mg, 2.17 mmol) and (R)-tert-butyl pyrrolidine-2-carboxylate (226 mg, 1.08 mmol) at 0° C. The reaction was warmed to RT and stirred for 12 h. After complete consumption of the starting material, the reaction mass was diluted with water (20 mL) and extracted with EtOAc (2×30 mL). The combined organic extracts were washed with water (25 mL), a brine solution (25 mL), dried over sodium sulfate, filtered and concentrated under reduced pressure to obtain the crude. The crude was purified by silica gel column chromatography eluting with 2-4% MeOH/CH$_2$Cl$_2$ to afford DJ (115 mg, 39%) as a pale yellow solid. $^1$H NMR (400 MHz, DMSO-d$_6$): δ 10.67 (br s, 1H), 9.71 (s, 1H), 9.30 (s, 1H), 8.83 (d, J=6.0 Hz, 1H), 8.49 (d, J=7.6 Hz, 2H), 8.35 (s, 1H), 8.14-7.99 (m, 7H), 7.81 (s, 1H), 4.98-4.95 (m, 0.4H), 4.45-4.42 (m, 0.6H), 3.92 (t, J=6.8 Hz, 1H), 3.68-3.30 (m, 1H), 2.49-2.30 (m, 1H), 2.06-1.88 (m, 3H), 1.50 (s, 9H), 1.43 (s, 6H), 1.33 (s, 3H). MS (ESI): m/z 550.5 [M−1]$^+$ To a stirred solution of DJ (60 mg, 0.08 mmol) in CH$_2$Cl$_2$ (1 mL) under inert atmosphere was added 4N HCl solution in 1,4-dioxane (1 mL) at 0° C. The reaction was warmed to RT and stirred for 16 h. After complete consumption of the starting material, the volatiles were evaporated under reduced pressure to obtain the crude. The crude was triturated with isopropyl ether (2×5 mL), 20% isopropyl alcohol: CH$_2$Cl$_2$ (1:4, 2×5 mL):n-pentane (2×5 mL) to afford 31 (22 mg as an HCl salt) as a yellow solid. $^1$H NMR (400 MHz, DMSO-d$_6$): δ 11.61 (br s, 1H), 9.69 (s, 1H), 8.86 (d, J=6.0 Hz, 1H), 8.53 (d, J=5.6 Hz, 3H), 8.15-8.00 (m, 8H), 7.80 (s, 1H), 5.05-5.02 (m, 0.2H), 4.51-4.47 (m, 0.8H), 3.94-3.91 (m, 1H), 3.67-3.65 (m, 1H), 2.32-2.26 (m, 1H), 2.03-1.93 (m, 3H). MS (ESI): m/z 549.3 [M+1]$^+$. HPLC Purity: 92.71%

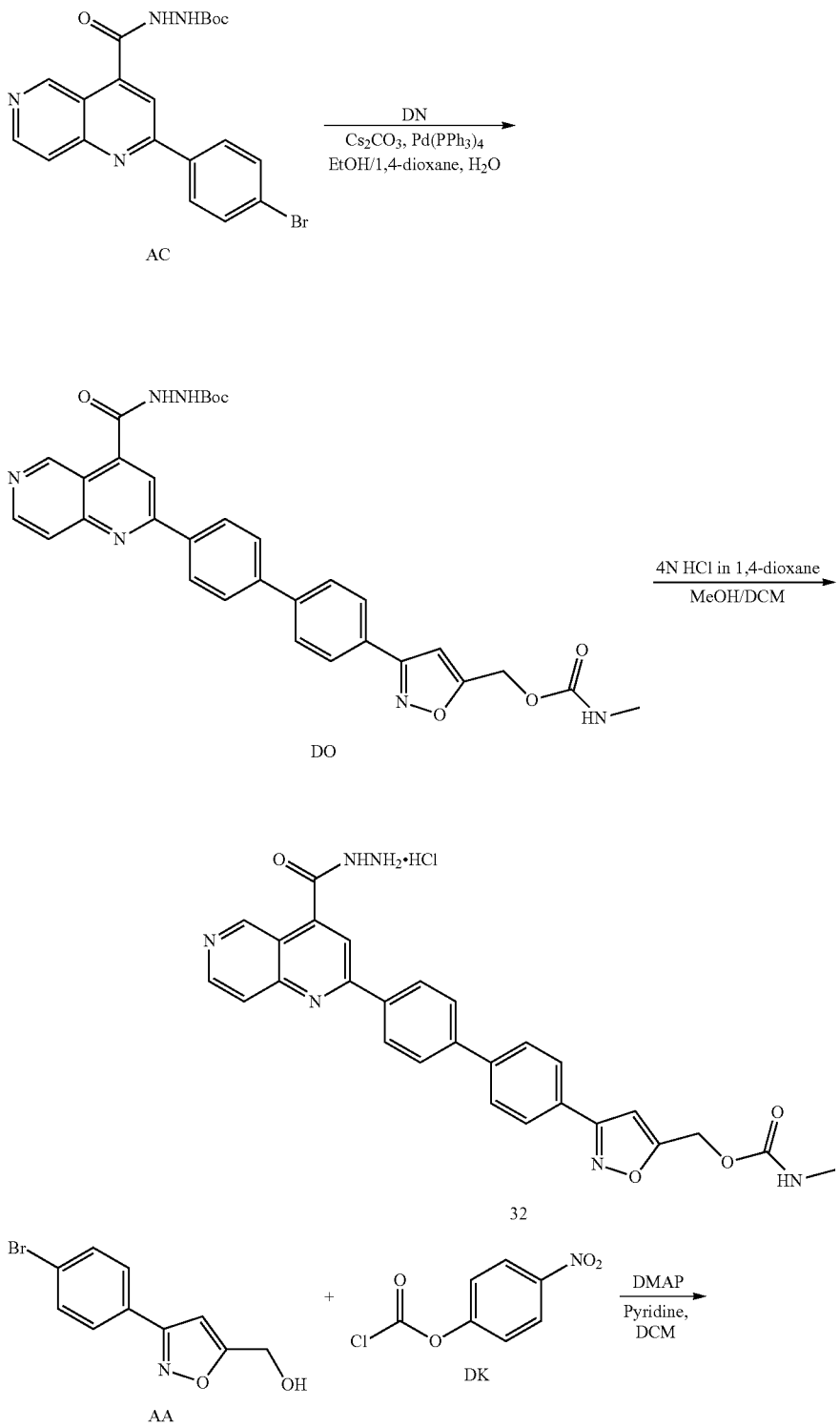

Scheme 29

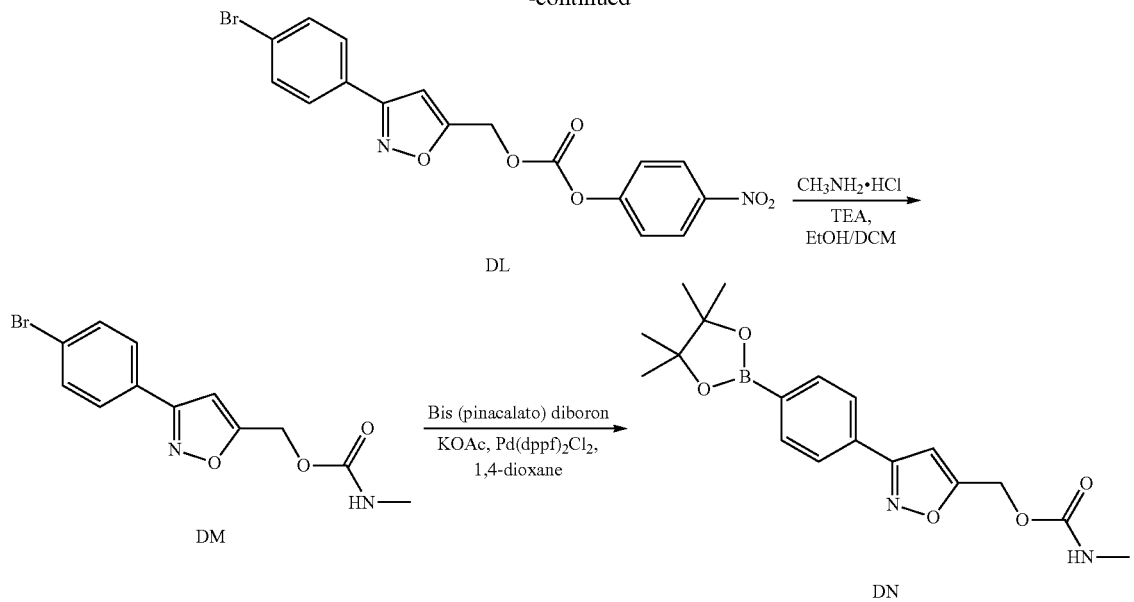

Example 32

(3-(4'-(4-(hydrazinecarbonyl)-1,6-naphthyridin-2-yl)-[1,1'-biphenyl]-4-yl)isoxazol-5-yl)methyl methylcarbamate hydrochloride (32)

To a stirred solution of (3-(4-bromophenyl)isoxazol-5-yl)methanol (AA; 0.5 g, 1.96 mmol) in CH$_2$Cl$_2$ (15 mL) under inert atmosphere were added pyridine (0.39 mL, 4.91 mmol) and p-dimethylaminopyridine (0.024 mg, 0.19 mmol) at 0° C. After the addition of 4-nitrophenyl carbonochloridate (DK; 0.39 g, 1.93 mmol) at 0° C., the reaction mixture was warmed to RT and stirred for 12 h. The reaction was monitored by TLC. After complete consumption of the starting material, the reaction mixture was diluted with a saturated ammonium chloride solution (20 mL) and the compound was extracted with CH$_2$Cl$_2$ (3×20 mL). The combined organic extracts were washed with water (20 mL), dried over sodium sulfate, filtered and concentrated under reduced pressure to obtain the crude. The crude was triturated with pentane (2×15 mL) to afford crude DL (710 mg) as an off-white solid. $^1$H NMR (500 MHz, CDCl$_3$): δ 8.30 (d, J=9.5 Hz, 2H), 8.17 (d, J=6.8 Hz, 1H), 7.70-7.59 (m, 5H), 7.40 (d, J=9.5 Hz, 2H), 6.91 (d, J=9.0 Hz, 1H), 6.73 (s, 1H), 5.43 (s, 2H), 5.34 (s, 1H).

To a stirred solution of DL (710 mg, 1.70 mmol) in CH$_2$Cl$_2$ (50 mL) under inert atmosphere were added methylamine hydrochloride (229 mg, 3.40 mmol) in ethanol (10 mL) and triethylamine (2.46 mL, 17.01 mmol) at RT. The reaction was stirred for 12 h. After complete consumption of the starting material, the reaction mass was diluted with a saturated ammonium chloride solution (30 mL) and was extracted with CH$_2$Cl$_2$ (3×30 mL). The combined organic extracts were washed with water (30 mL), a brine solution (30 mL), dried over sodium sulfate, filtered and concentrated under reduced pressure to obtain the crude. The crude material was purified by silica gel column chromatography eluting with 30% EtOAc/hexanes to afford DM (450 mg, 86%) as an off-white solid. $^1$H NMR (400 MHz, DMSO-d$_6$): δ 7.83 (d, J=8.8 Hz, 2H), 7.72 (d, J=6.8 Hz, 2H), 7.29-7.28 (m, 1H), 7.09 (s, 1H), 5.18 (s, 2H), 2.60-2.59 (m, 3H).

To a stirred solution of DM (420 mg, 1.34 mmol) in 1,4-dioxane (30 mL) under inert atmosphere were added fused potassium acetate (411 mg, 1.61 mmol), bis(pinacalato)diboron (393 mg, 4.02 mmol). After the reaction was purged with argon for 30 min, Pd(dppf)$_2$Cl$_2$ was added and the reaction was again purged with argon for 15 min. The reaction mixture was heated to 90° C. and stirred for 3 h. After complete consumption of the starting material, the volatiles were evaporated under reduced pressure to obtain the crude. The crude was purified by silica gel column chromatography eluting with 30% EtOAc/hexanes to afford DN (320 mg, 66%) as a colorless thick syrup. $^1$H NMR (400 MHz, CDCl$_3$): δ 7.88 (d, J=8.4 Hz, 2H), 7.80 (d, J=11.2 Hz, 2H), 6.64 (s, 1H), 5.22 (s, 2H), 2.84 (s, 3H), 1.36 (s, 12H). MS (ESI): m/z 359.3 [M+1]$^+$ To a stirred solution of AC (60 mg, 0.13 mmol) in 1,4-dioxane:ethanol (2:1, 30 mL) and water (1 mL) under inert atmosphere were added cesium carbonate (130 mg, 0.40 mmol) and DN (58 mg, 0.16 mmol) at RT. After the reaction was purged with argon for 20 min, Pd(PPh$_3$)$_4$ (15 mg, 0.013 mmol) was added. The reaction was heated to reflux and stirred for 6 h. After complete consumption of the starting material, the volatiles were evaporated under reduced pressure to obtain the crude, which was purified by silica gel column chromatography eluting with 3-4% MeOH/CH$_2$Cl$_2$ to afford DO (10 mg, 12%) as a pale yellow solid. $^1$H NMR (400 MHz, DMSO-d$_6$): δ 10.67 (s, 1H), 9.71 (s, 1H), 9.30 (s, 1H), 8.83 (d, J=5.6 Hz, 1H), 8.49 (d, J=7.6 Hz, 2H), 8.34 (s, 1H), 8.06-7.95 (m, 7H), 7.31-7.30 (m, 1H), 7.16 (s, 1H), 5.21 (s, 2H), 2.62 (s, 3H), 1.50 (s, 9H). MS (ESI): m/z 595.4 [M+1]$^+$ To a stirred solution of DO (7 mg, 0.011 mmol) in CH$_2$Cl$_2$ (1 mL) and methanol (0.2 mL) under inert atmosphere was added a 4N HCl solution in 1,4-dioxane (0.5 mL) at 0° C. The reaction was warmed to RT and stirred for 1 h. After complete consumption of the starting material, the volatiles were evaporated under reduced pressure to obtain the crude. The crude was triturated with diisopropyl ether (2×3 mL) and n-pentane (2×3 mL) to afford 32 (5 mg as an HCl salt) as an orange solid. $^1$H NMR (400 MHz, DMSO-d$_6$): δ 11.63 (br s, 1H), 9.69 (s, 1H), 8.86 (d, J=6.0 Hz, 1H), 8.52 (t, J=4.4 Hz, 3H), 8.13 (d, J=6.0 Hz, 1H), 8.03 (d, J=8.4 Hz, 4H), 7.97 (d, J=8.4 Hz, 2H), 7.29-7.28 (m, 1H), 7.15 (s, 1H), 5.22 (s, 2H), 2.60 (s, 3H). MS (ESI): m/z 495.2 [M+1]$^+$. HPLC Purity: 86.47%

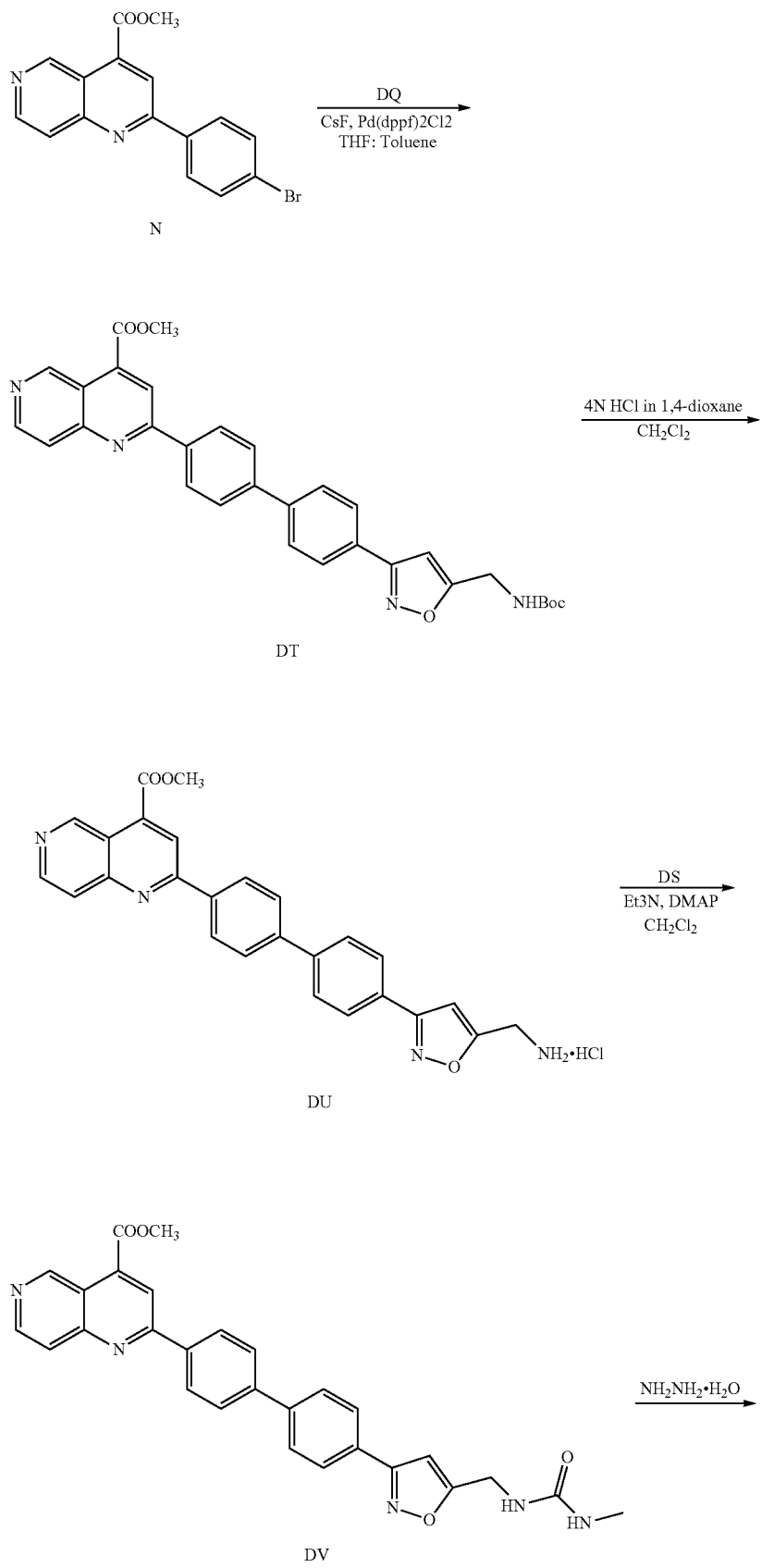

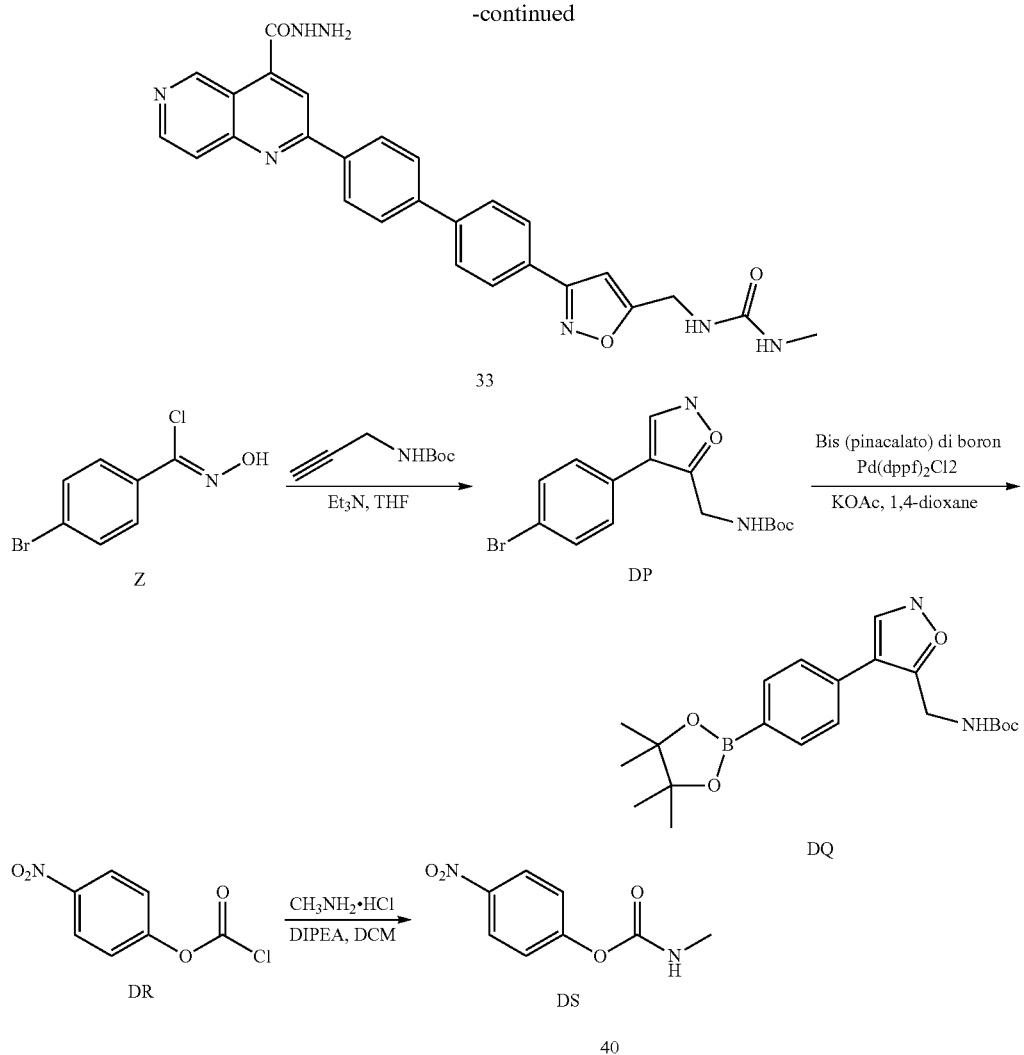

Example 33

1-((3-(4'-(4-(hydrazinecarbonyl)-1,6-naphthyridin-2-yl)-[1,1'-biphenyl]-4-yl)isoxazol-5-yl)methyl)-3-methylurea (33)

To a stirred solution Z (3 g, 12.93 mmol) in THF (40 mL) under inert atmosphere were added triethylamine (1.86 mL, 12.93 mmol) and tert-butylprop-2-yn-1-ylcarbamate (12 g, 12.93 mmol) at 0° C. The reaction was then warmed to RT and stirred for 12 h. After complete consumption of the starting material, the reaction mass was diluted with water (30 mL) and the compound was extracted with $CH_2Cl_2$ (3×30 mL). The combined organic extracts were washed with water (30 mL), dried over sodium sulfate, filtered and concentrated under reduced pressure to obtain the crude. The crude was purified by silica gel column chromatography (20-30% EtOAc/hexanes) to afford DP (3.2 g, 70%) as an off-white solid. $^1$H NMR (500 MHz, DMSO-$d_6$): δ 7.81 (d, J=8.5 Hz, 2H), 7.70 (d, J=8.5 Hz, 2H), 7.55-7.53 (m, 1H), 6.84 (s, 1H), 4.30-4.29 (m, 2H), 1.39 (s, 9H).

To a stirred solution of DP (2 g, 5.68 mmol) in 1,4-dioxane (30 mL) under inert atmosphere were added bis(pinacalato)diboron (1.73 g, 6.81 mmol) and fused potassium acetate (1.67 g, 17.04 mmol) at RT. After the reaction was purged with argon for 20 min, Pd(dppf)$_2$Cl$_2$ (415 mg, 0.56 mmol) was added. The reaction was heated to 90° C. and stirred for 12 h. After complete consumption of the starting material, the reaction mass was cooled to RT, filtered through a Celite pad and the filtrate was concentrated under reduced pressure. The residue was diluted with water (30 mL) and extracted with EtOAc (2×30 mL). The combined organic extracts were washed with water (30 mL), dried over sodium sulfate, filtered and concentrated under reduced pressure to obtain the crude. The crude was purified by silica gel column chromatography (20-30% EtOAc/hexanes) to afford DQ (1.6 g, 70%) as an off-white solid. $^1$H NMR (500 MHz, DMSO-$d_6$): δ 7.86 (d, J=7.5 Hz, 2H), 7.77 (d, J=8.0 Hz, 2H), 7.56-7.54 (m, 1H), 6.84 (s, 1H), 4.31-4.29 (m, 2H), 1.39 (s, 9H), 1.30 (s, 12H).

To a stirred solution of methylamine hydrochloride (3 g, 44.43 mmol) in $CH_2Cl_2$ (100 mL) under inert atmosphere were added diisopropylethylamine (24.56 mL, 132.55 mmol) and 4-nitrophenylchloroformate (DR; 10.74 g, 53.28 mmol) at 0° C. The reaction was then warmed to RT and stirred for 16 h. After complete consumption of the starting material, the reaction mass was diluted with ice cold water (40 mL) and the compound was extracted with $CH_2Cl_2$ (2×40 mL). The combined organic extracts were washed with water (40 mL), dried over sodium sulfate, filtered and concentrated under reduced pressure to obtain the crude. The crude was purified by silica gel column chromatography (15% EtOAc/hexanes) to afford DS (1.6 g, 18%) as a pale yellow solid. ¹H NMR (400 MHz, CDCl₃): δ 8.16 (d, J=6.8 Hz, 1H), 7.31 (d, J=6.8 Hz, 2H), 5.06 (br s, 1H), 2.93 (d, J=4.8 Hz, 3H).

To stirred solution of N (1 g, 2.92 mmol) in THF:toluene (1:1, 30 mL) under inert atmosphere were added DQ (1.2 g, 3.21 mmol) and cesium fluoride (1.3 g, 8.77 mmol) at RT. After the reaction was purged with argon for 20 min, Pd(dppf)₂Cl₂ (213 mg, 0.29 mmol) was added. The reaction was heated to 90° C. and stirred for 12 h. After complete consumption of the starting material, the reaction mass was cooled to RT and the volatiles were evaporated under reduced pressure to obtain the crude. The crude was purified by silica gel column chromatography (2-5% MeOH/CH₂Cl₂) to afford DT (520 mg, 33%) as an off-white solid. ¹H NMR (500 MHz, DMSO-d₆): δ 9.93 (s, 1H), 8.84 (d, J=5.5 Hz, 1H), 8.68 (s, 1H), 8.48 (d, J=8.5 Hz, 2H), 8.07 (d, J=5.5 Hz, 1H), 8.01-8.00 (m, 4H), 7.94 (d, J=8.0 Hz, 2H), 7.59-7.57 (m, 1H), 6.91 (s, 1H), 4.33-4.32 (m, 2H), 4.08 (s, 3H), 1.41 (s, 9H).

To a stirred solution of DT (1.6 g, 2.98 mmol) in CH₂Cl₂ (15 mL) under inert atmosphere was added 4N HCl in 1,4-dioxane (3 mL) at 0° C. The reaction was then warmed to RT and stirred for 3 h. After complete consumption of the starting material, the volatiles were evaporated under reduced pressure to obtain the crude DU (1.2 g) as an off-white solid. ¹H NMR (400 MHz, DMSO-d₆): δ 10.00 (s, 1H), 8.89 (d, J=6.0 Hz, 1H), 8.75-8.73 (m, 3H), 8.53 (d, J=8.4 Hz, 2H), 8.20 (d, J=6.0 Hz, 1H), 8.04-7.98 (m, 6H), 7.24 (s, 1H), 4.37-4.36 (m, 2H), 4.18 (s, 3H).

To a stirred solution of DU (100 mg, 0.22 mmol) in CH₂Cl₂ (5 mL) under inert atmosphere were added triethylamine (69 mg, 0.68 mmol), DS (54 mg, 0.68 mmol) at 0° C. After stirring for 5 min at 0° C., the reaction mixture was then warmed to RT and stirred for 12 h. The reaction was monitored by TLC. After complete consumption of the starting material, the reaction mass was diluted with water (10 mL) and the compound was extracted with EtOAc (2×15 mL). The combined organic extracts were washed with water (10 mL), dried over sodium sulfate, filtered and concentrated under reduced pressure to obtain the crude. The crude was purified by silica gel column chromatography (2-5% MeOH/CH₂Cl₂) to afford DV (45 mg, 40%) as an off-white solid. ¹H NMR (400 MHz, DMSO-d₆): δ 9.94 (s, 1H), 8.85 (d, J=6.0 Hz, 1H), 8.69 (s, 1H), 8.49 (d, J=8.4 Hz, 2H), 8.08 (d, J=5.6 Hz, 1H), 8.02-7.93 (m, 6H), 6.87 (s, 1H), 6.06 (t, J=6.0 Hz, 1H), 5.99-5.97 (m, 1H), 4.40 (d, J=5.6 Hz, 2H), 4.08 (s, 3H), 2.58 (d, J=4.8 Hz, 3H).

A mixture of DV (45 mg, 0.09 mmol) in hydrazine hydrate (2 mL) under inert atmosphere was heated to 100° C. and stirred for 1 h. The reaction was monitored by TLC. After complete consumption of the starting material, the volatiles were evaporated under reduced pressure to obtain the crude, which was triturated with water (10 mL) and dried under vacuum to afford the 33 (15 mg, 33%) as an off-white solid. ¹H NMR (400 MHz, DMSO-d₆): δ 10.20 (s, 1H), 9.05 (s, 1H), 8.80 (d, J=6.0 Hz, 1H), 8.49 (d, J=8.4 Hz, 2H), 8.36 (s, 1H), 8.03-7.94 (m, 6H), 6.87 (s, 1H), 6.60 (t, J=5.6 Hz, 1H), 5.99-5.98 (m, 1H), 4.41-4.39 (m, 2H), 2.58 (d, J=4.8 Hz, 3H). MS (ESI): m/z 494.3 [M+1]⁺. HPLC Purity: 85.01%

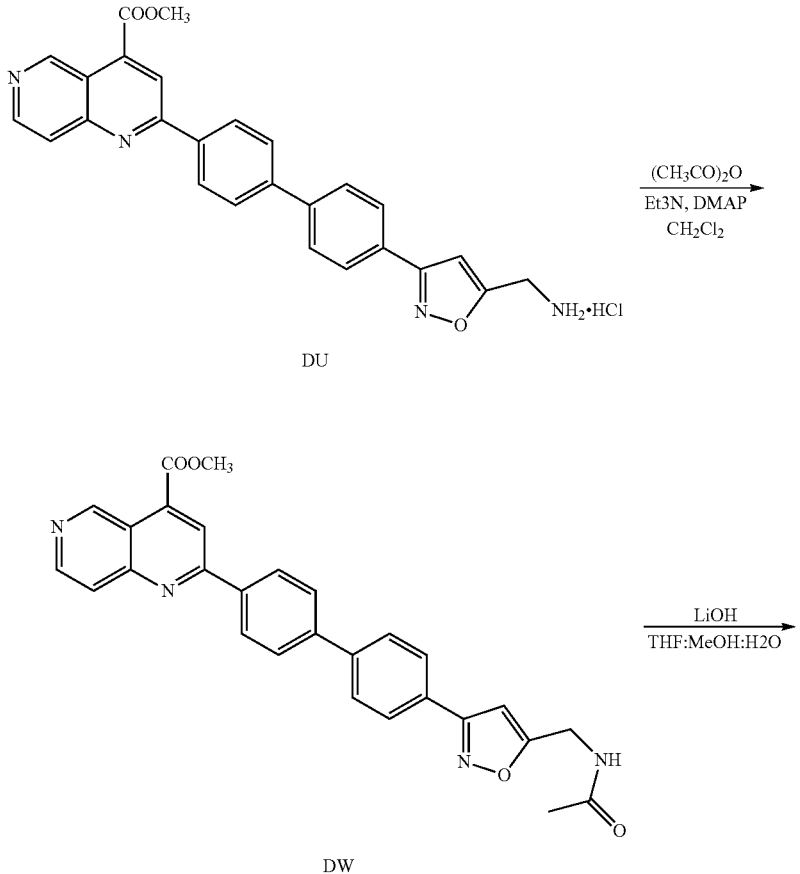

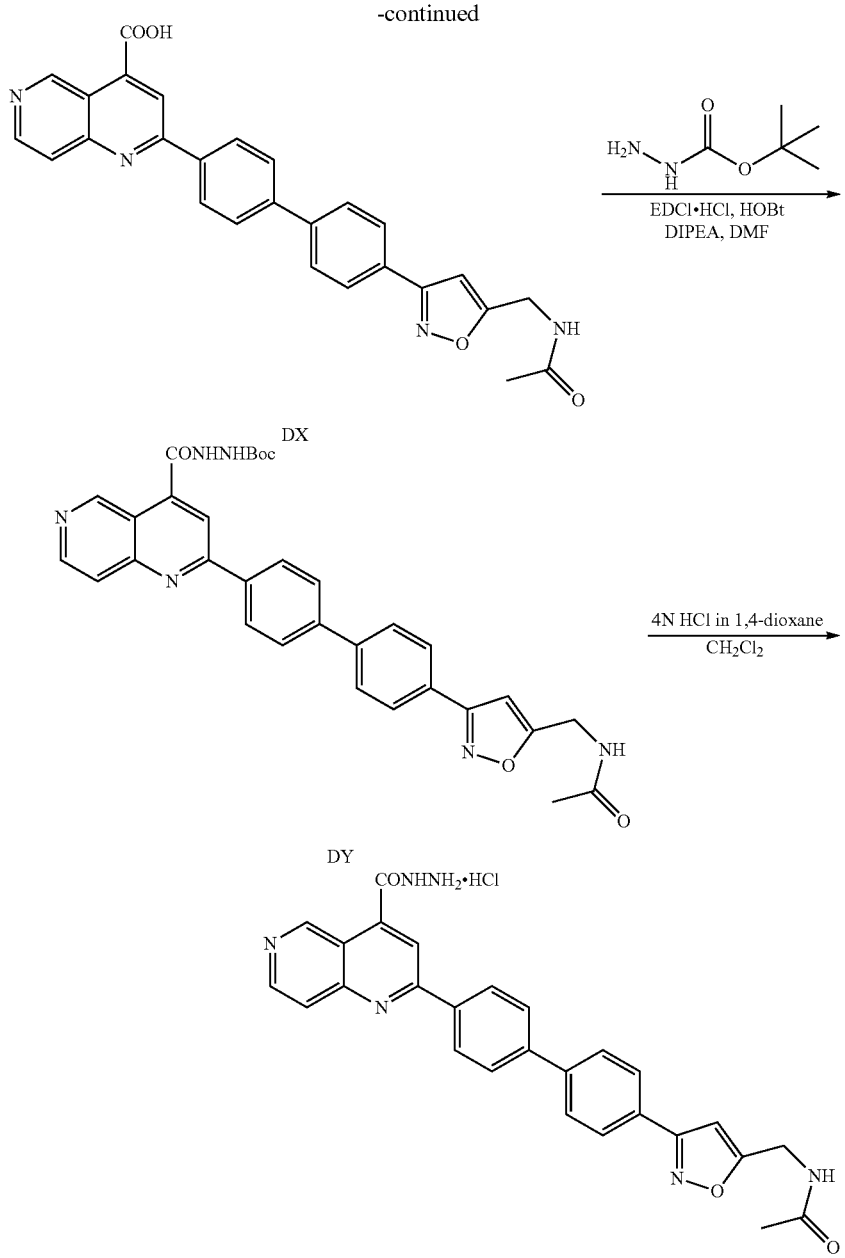

Example 34

N-((3-(4'-(4-(hydrazinecarbonyl)-1,6-naphthyridin-2-yl)-[1,1'-biphenyl]-4-yl)isoxazol-5-yl)methyl)acetamide hydrochloride (34)

To a stirred solution of DU (300 mg, 0.68 mmol) in $CH_2Cl_2$ (10 mL) under inert atmosphere were added triethylamine (0.29 mL, 2.06 mmol), dimethylaminopyridine (3 mg, catalytic) and acetic anhydride (84 mg, 0.82 mmol) at 0° C. The reaction was warmed to RT and stirred for 2 h. After complete consumption of the starting material, the reaction mass was diluted with water (20 mL) and the compound was extracted with $CH_2Cl_2$ (2×20 mL). The combined organic extracts were washed with water (30 mL), dried over sodium sulfate, filtered and concentrated under reduced pressure to obtain the crude. The crude was purified by silica gel column chromatography (2-5% MeOH/$CH_2Cl_2$) to afford DW (90 mg, 26%) as an off-white solid.

$^1$H NMR (500 MHz, DMSO-$d_6$): δ 9.93 (s, 1H), 8.84 (d, J=5.5 Hz, 1H), 8.67 (s, 1H), 8.57 (t, J=5.5 Hz, 1H), 8.47 (d, J=8.5 Hz, 1H), 8.07 (d, J=5.5 Hz, 1H), 8.01-7.99 (m, 4H), 7.95-7.93 (m, 3H), 6.95 (s, 1H), 4.45-4.44 (m, 2H), 4.07 (s, 3H), 1.90 (s, 3H).

To a stirred solution DW (120 mg, 0.25 mmol) in THF:MeOH:$H_2O$ (2:2:1, 10 mL) was added lithium hydroxide (32 mg, 0.75 mmol) at 0° C. The reaction was subsequently warmed to RT and stirred for 6 h. After complete consumption of the starting material, the volatiles were evaporated under reduced pressure to obtain the crude. The crude was diluted with water (10 mL) and acidified with 2N HCl solution to obtain the solid. The solid was filtered and dried under vacuum to afford DX (52 mg, 87%) as an off-white solid. $^1$H NMR (400 MHz, DMSO-$d_6$): δ 14.50 (br s, 1H), 10.06 (br s, 1H), 8.85 (br s, 1H), 8.67 (s, 1H), 8.59 (t, J=5.6 Hz, 1H), 8.49 (d, J=8.4 Hz, 2H), 8.01-8.09 (m, 1H), 8.01-7.94 (m, 6H), 6.96 (s, 1H), 4.46-4.45 (m, 2H), 1.91 (s, 3H).

To a stirred solution of DX (50 mg, 0.11 mmol) in DMF (2 mL) under inert atmosphere were added EDCI.HCl (41 mg, 0.21 mmol), HOBt (29 mg, 0.21 mmol) and diisopropylethylamine (42 mg, 0.32 mmol) at 0° C. and stirred for 5 min. Then tert-butylcarbazate was added to the reaction mixture and stirred for 12 h at RT. After complete consumption of the starting material, the reaction mass was diluted with water (10 mL) and the compound was extracted with EtOAc (2×10 mL). The combined organic extracts were washed with water (10 mL), dried over sodium sulfate, filtered and concentrated under reduced pressure to obtain the crude. The crude was purified by silica gel column chromatography (2-5% MeOH/CH$_2$Cl$_2$) to afford DY (90 mg, 26%) as an off-white solid. $^1$H NMR (400 MHz, DMSO-$d_6$): δ 10.67 (br s, 1H), 9.71 (br s, 1H), 9.30 (br s, 1H), 8.84-8.80 (m, 2H), 8.58 (t, J=5.6 Hz, 1H), 8.52-8.48 (m, 1H), 8.38 (s, 1H), 8.06-7.94 (m, 7H), 4.46-4.45 (m, 2H), 1.91 (s, 3H), 1.50 (s, 9H).

To a stirred solution of DY (30 mg, 0.05 mmol) in CH$_2$Cl$_2$ (3 mL) under inert atmosphere was added 4N HCl in 1,4-dioxane (0.2 mL) at 0° C. The reaction was warmed to RT and stirred for 3 h. After complete consumption of the starting material, the volatiles were evaporated under reduced pressure to obtain the crude. The crude was triturated with methanol (2×5 mL) and ether (2×5 mL) to afford 34 (20 mg as an HCl salt) as a yellow solid. $^1$H NMR (400 MHz, DMSO-$d_6$): δ 11.50 (br s, 1H), 9.69 (br s, 1H), 8.86 (d, J=5.6 Hz, 1H), 8.57 (t, J=4.0 Hz, 1H), 8.52-8.48 (m, 3H), 8.11 (d, J=6.0 Hz, 1H), 8.04-7.95 (m, 6H), 6.96 (s, 1H), 4.46-4.45 (m, 2H), 1.91 (s, 3H). MS (ESI): m/z 479.3 [M+1]$^+$. HPLC Purity: 87.08%

Scheme 32

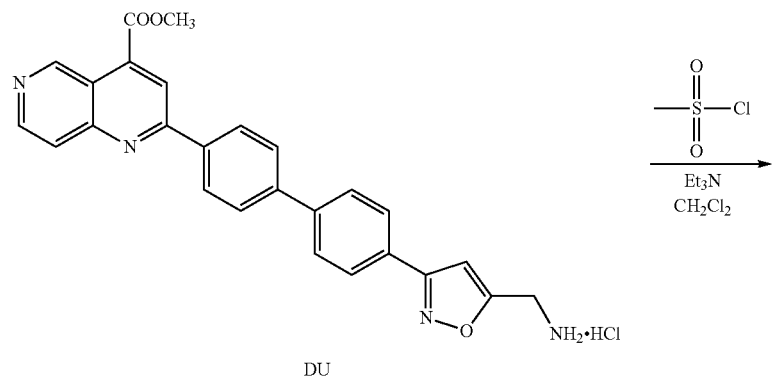

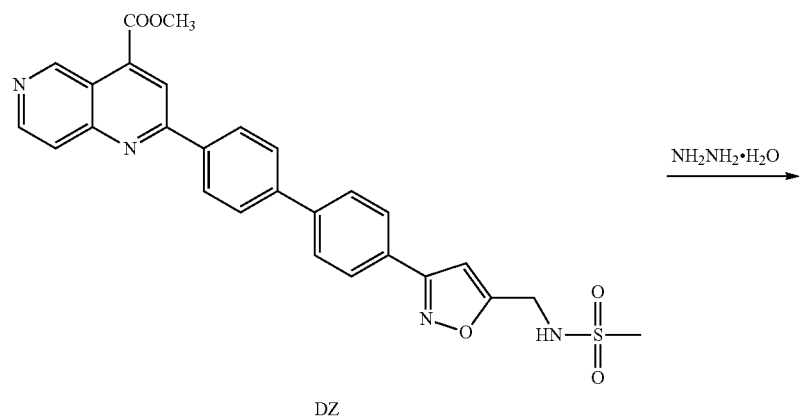

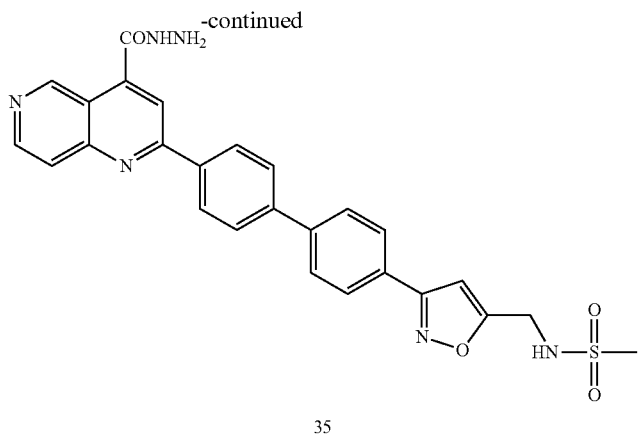

35

Example 35

N-((3-(4'-(4-(hydrazinecarbonyl)-1,6-naphthyridin-2-yl)-[1,1'-biphenyl]-4-yl)isoxazol-5-yl)methyl)methanesulfonamide (35)

To a stirred solution of DU (200 mg, 0.45 mmol) in $CH_2Cl_2$ (10 mL) under inert atmosphere were added triethylamine (0.1 mL, 1.37 mmol) and methanesulfonylchloride (52 mg, 0.45 mmol) at 0° C. The reaction was warmed to RT and stirred for 12 h. After complete consumption of the starting material, the reaction mass was diluted with water (20 mL) and extracted with $CH_2Cl_2$ (2×20 mL). The combined organic extracts were washed with water (20 mL), dried over sodium sulfate, filtered and concentrated under reduced pressure to obtain the crude. The crude was purified by silica gel column chromatography (50-60% EtOAc/hexanes) to afford DZ (20 mg, 17%) as an off-white solid. $^1$H NMR (400 MHz, DMSO-$d_6$): δ 9.94 (s, 1H), 8.85 (d, J=5.6 Hz, 1H), 8.68 (s, 1H), 8.49 (d, J=8.4 Hz, 2H), 8.08 (d, J=5.6 Hz, 2H), 8.02 (t, J=8.4 Hz, 2H), 7.96 (d, J=6.4 Hz, 3H), 7.90 (t, J=6.0 Hz, 2H), 7.07 (s, 1H), 4.42 (d, J=6.4 Hz, 2H), 4.08 (s, 3H), 3.30 (s, 3H).

A mixture of DZ (45 mg, 0.08 mmol) in hydrazine hydrate (1 mL) under inert atmosphere was heated to 100° C. and stirred for 1 h. The reaction was monitored by TLC. After complete consumption of the starting material, the volatiles were evaporated under reduced pressure to obtain the crude. The crude was triturated with water (10 mL) and dried under vacuum to afford 35 (15 mg, 33%) as a pale yellow solid. $^1$H NMR (400 MHz, DMSO-$d_6$): δ 10.21 (s, 1H), 9.65 (s, 1H), 8.80 (d, J=6.0 Hz, 1H), 8.49 (d, J=8.4 Hz, 2H), 8.37 (s, 1H), 8.04-7.94 (m, 7H), 7.90 (t, J=6.4 Hz, 1H), 7.07 (s, 1H), 4.82 (br s, 2H), 4.42 (d, J=6.0 Hz, 2H), 2.99 (s, 3H). MS (ESI): m/z 515.4 [M+1]$^+$. HPLC Purity: 92.98%

Scheme 33

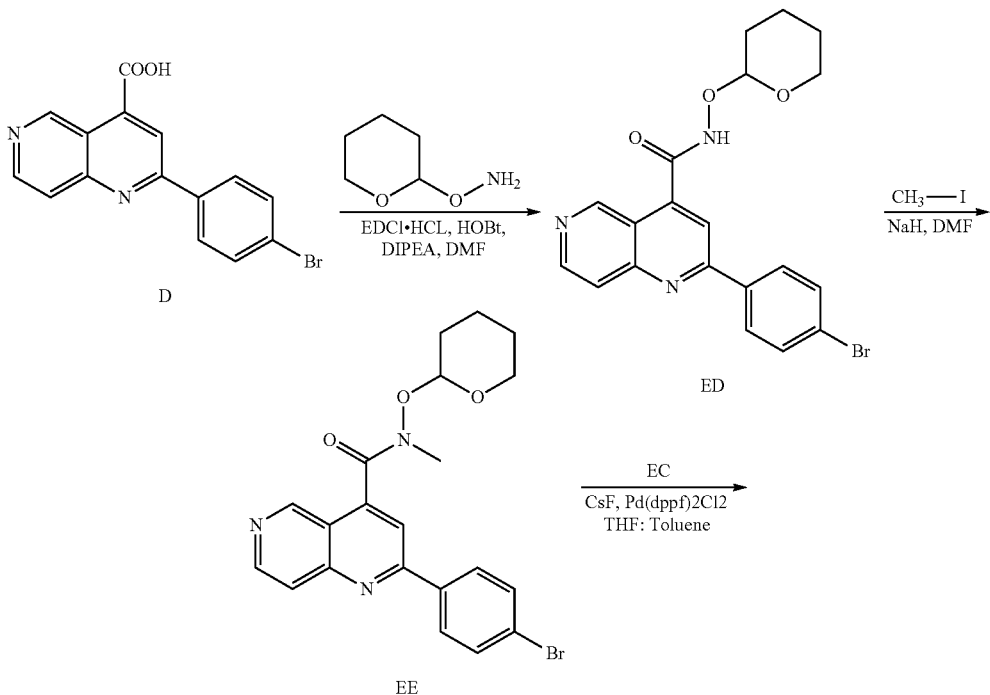

-continued
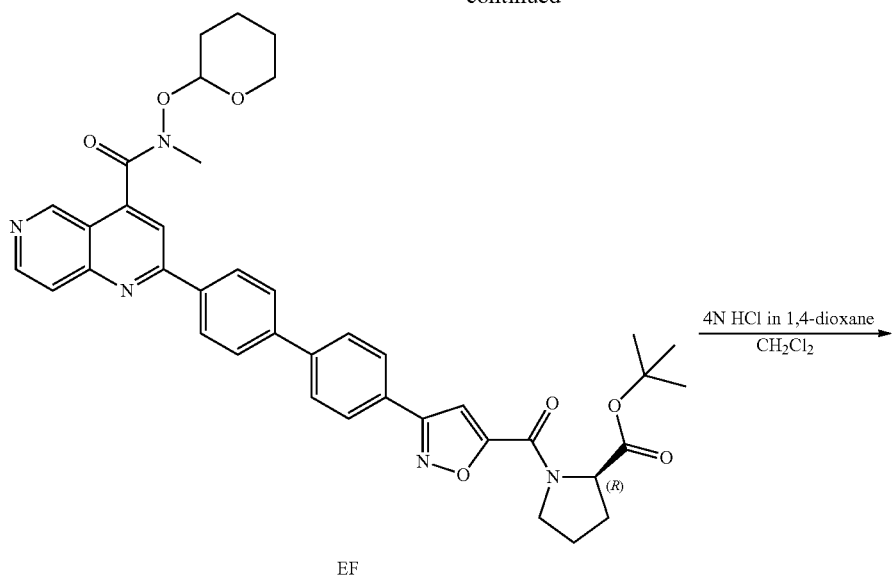
EF
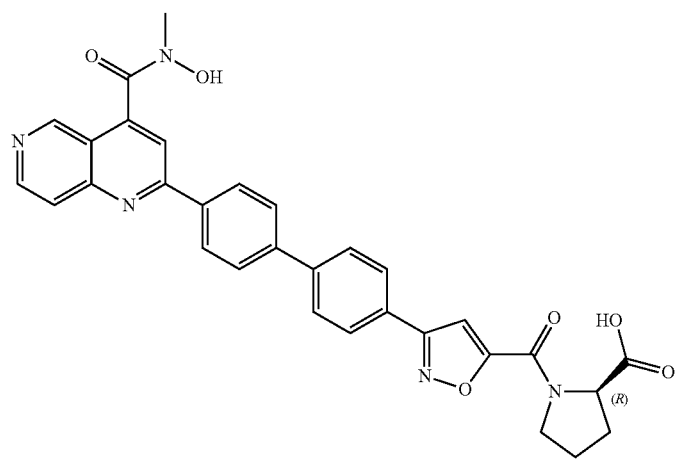
36
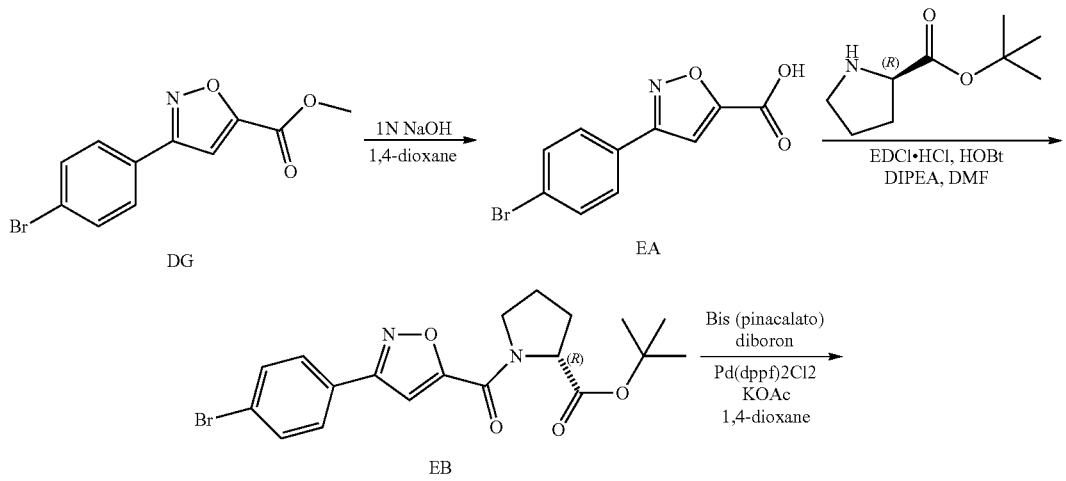

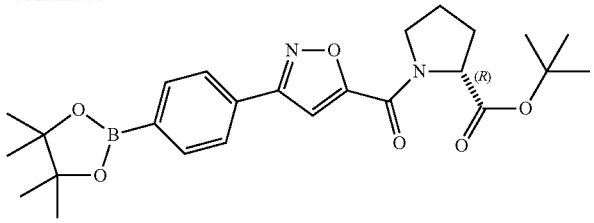

EC

Example 36

(R)-1-(3-(4'-(4-(hydroxy(methyl)carbamoyl)-1,6-naphthyridin-2-yl)-[1,1'-biphenyl]-4-yl)isoxazole-5-carbonyl)pyrrolidine-2-carboxylic acid (36)

To a stirred solution of DG (800 mg, 2.83 mmol) in DMF (25 mL) under inert atmosphere was added 1N NaOH solution (170 mg in 0.45 mL water, 4.25 mmol) at 0° C. The reaction was warmed to RT and stirred for 12 h. After complete consumption of the starting material, the volatiles were evaporated under reduced pressure. The residue was diluted with water (40 mL) and acidified with 1N HCl to pH~2 and filtered. The obtained solid was triturated with toluene (2×5 mL) and ether (2×5 mL) to afford EA (600 mg, 63%) as an off-white solid. $^1$H NMR (400 MHz, DMSO-d$_6$): δ 7.90 (d, J=8.5 Hz, 2H), 7.74 (d, J=8.5 Hz, 2H), 7.70 (s, 1H).

To a stirred solution of EA (100 mg, 0.37 mmol) in DMF (10 mL) under inert atmosphere were added EDCI.HCl (178 mg, 093 mmol), HOBt (90 mg, 0.66 mmol), diisopropylethylamine (0.2 mL, 1.16 mmol) and D-proline tertbutyl ester (154 mg, 0.74 mmol) at RT. The reaction was stirred for 14 h. After complete consumption of the starting material, the reaction mass was diluted with water (10 mL) and extracted with EtOAc (2×10 mL). The combined organic extracts were washed with water (10 mL), a brine solution (10 mL), dried over sodium sulfate, filtered and concentrated under reduced pressure to obtain the crude. The crude was purified by silica gel column chromatography eluting with 20% EtOAc/hexanes to afford EB (124 mg, 77%) as an off-white solid. $^1$H NMR (400 MHz, CDCl$_3$): δ 7.70-7.62 (m, 2H), 7.61-7.59 (m, 2H), 7.20 (d, J=7.2 Hz, 1H), 4.58-4.55 (m, 1H), 4.14-4.00 (m, 1H), 3.89-3.71 (m, 1H), 2.28-2.20 (m, 1H), 2.18-2.10 (m, 1H), 2.09-2.02 (m, 1H), 2.00-1.90 (m, 1H), 1.49-1.41 (m, 9H).

To a stirred solution of EB (120 mg, 0.28 mmol) in 1,4-dioxane (20 mL) under inert atmosphere were added bis(pinacalato)diboron (87 mg, 0.34 mmol) and fused potassium acetate (83 mg, 0.84 mmol) at RT. After the reaction mixture was purged with argon for 30 min, Pd(dppf)$_2$Cl$_2$ (20 mg, 0.02 mmol) was added. The reaction was then heated to reflux and stirred for 5 h. After complete consumption of the starting material, the volatiles were evaporated under reduced pressure to obtain the crude. The crude was purified by silica gel column chromatography eluting with 10-20% EtOAc/hexanes to afford EC (58 mg, 44%) as an off-white solid. $^1$H NMR (400 MHz, CDCl$_3$): δ 7.92-7.88 (m, 2H), 7.83-7.79 (m, 2H), 7.26-7.23 (m, 1H), 4.58-4.55 (m, 1H), 4.14-4.00 (m, 1H), 3.89-3.83 (m, 1H), 2.39-2.27 (m, 1H), 2.25-2.19 (m, 1H), 2.08-2.00 (m, 1H), 1.99-1.90 (m, 1H), 1.54 (s, 9H), 1.36 (s, 12H).

To a stirred solution of D (1 g, 3.03 mmol) in DMF (10 mL) under inert atmosphere were added EDCI.HCl (1.45 g, 7.56 mmol), HOBt (730 mg, 5.40 mmol), diisopropylethylamine (1.67 mL, 9.06 mmol) and o-(tetrahydro-2H-pyran-2-yl)hydroxylamine (712 mg, 6.07 mmol) at RT. The reaction was stirred for 14 h. After complete consumption of the starting material, the reaction mass was diluted with water (40 mL) and the compound was extracted with EtOAc (2×30 mL). The combined organic extracts were washed with water (30 mL), a brine solution (20 mL), dried over sodium sulfate, filtered and concentrated under reduced pressure to obtain the crude. The crude was purified by silica gel column chromatography eluting with 2-4% MeOH/CH$_2$Cl$_2$ to afford ED (1.1 g, 84%) as an off-white solid. $^1$H NMR (400 MHz, DMSO-d$_6$): δ 12.08 (s, 1H), 9.54 (s, 1H), 8.82 (d, J=6.0 Hz, 1H), 8.35 (s, 1H), 8.32 (d, J=6.8 Hz, 2H), 8.02 (d, J=5.6 Hz, 1H), 7.83 (d, J=8.8 Hz, 2H), 5.22 (s, 1H), 4.10-4.05 (m, 1H), 3.63-3.60 (m, 1H), 1.80-1.77 (m, 3H), 1.62-1.59 (m, 3H).

To a stirred solution of ED (1 g, 2.33 mmol) in DMF (15 mL) under inert atmosphere was added 50% sodium hydride (224 mg, 9.33 mmol) at 0° C. After being stirred for 15 min at 0° C., methyl iodide (0.03 mL, 0.46 mmol) was added and the reaction mixture was stirred for 30 min at RT. The reaction was monitored by TLC. After complete consumption of the starting material; the reaction mixture was cooled to 0° C., diluted with water (30 mL) and extracted with EtOAc (2×30 mL). The combined organic extracts were washed with water (30 mL), dried over sodium sulfate, filtered and concentrated under reduced pressure to obtain the crude. The crude was purified by silica gel column chromatography eluting with 2-3% MeOH/CH$_2$Cl$_2$ to afford EE (250 mg, 24%) as a thick brown syrup. $^1$H NMR (500 MHz, DMSO-d$_6$): δ 9.21 (s, 1H), 8.82-8.79 (m, 1H), 8.43 (s, 1H), 8.33-8.30 (m, 2H), 8.03-7.94 (m, 1H), 7.81-7.79 (m, 2H), 3.93-3.87 (m, 1H), 3.58-3.56 (m, 3H), 1.82-1.74 (m, 2H), 1.61-1.55 (m, 2H), 1.35-1.17 (m, 4H). MS (ESI): m/z 442 [M−2]$^+$. Rotameric isomers were observed by $^1$H NMR in the ratio of 4:1.

To a stirred solution of EE (100 mg, 0.22 mmol) in THF:toluene (1:1, 30 mL) under inert atmosphere were added EC (127 mg, 0.34 mmol) and cesium fluoride (102 mg, 0.67 mmol) at RT. After the reaction was purged with argon for 30 min, Pd(dppf)$_2$Cl$_2$ (16 mg, 0.02 mmol) was added. The reaction was heated to reflux and stirred for 5 h. After complete consumption of the starting material, the volatiles were evaporated under reduced pressure to obtain the crude, which was purified by silica gel column chromatography eluting with 4-6% MeOH/CH$_2$Cl$_2$ to obtain EF (60 mg, mixture of rotamers). The compound was further purified through preparative HPLC to afford (27 mg, 18%) as a pale brown solid. $^1$H NMR (400 MHz, DMSO-d$_6$): δ 9.22 (s, 1H), 8.81 (d, J=5.6 Hz, 1H), 8.51-8.50 (m, 3H), 8.14-7.97 (m, 7H), 7.81 (s, 1H), 4.98-4.95 (m, 0.5H), 4.45-4.42 (m, 0.5H), 3.91 (t, J=7.2 Hz, 2H), 3.59-3.50 (m, 4H), 2.31-2.29 (m, 1H), 2.03-1.98 (m, 4H), 1.43 (s, 6H), 1.33 (s, 9H).

To a stirred solution of EF (27 mg, 0.03 mmol) in CH$_2$Cl$_2$ (0.4 mL) under inert atmosphere was added a 4N HCl solution in 1,4-dioxane (1 mL) at 0° C. The reaction was then warmed to RT and stirred for 5 h. After complete consumption of the starting material, the volatiles were evaporated under reduced pressure to obtain the crude, which was triturated with isopropyl ether (2×5 mL) to afford 36 (15 mg as an HCl salt) as a yellow solid. $^1$H NMR (400 MHz, DMSO-d$_6$): δ 10.39 (br s, 1H), 9.29 (s, 1H), 8.81 (d, J=6.0 Hz, 1H), 8.51 (d, J=8.4 Hz, 2H), 8.40 (s, 1H), 8.14-8.08 (m, 4H), 8.03-7.98 (m, 4H), 7.80 (s, 1H), 5.05-5.02 (m, 0.4H), 4.51-4.47 (m, 0.6H), 3.93 (t, J=6.4 Hz, 1H), 3.47 (s, 3H), 2.03-1.94 (m, 4H). MS (ESI): m/z 562.4 [M−1]$^+$. HPLC Purity: 93.28%

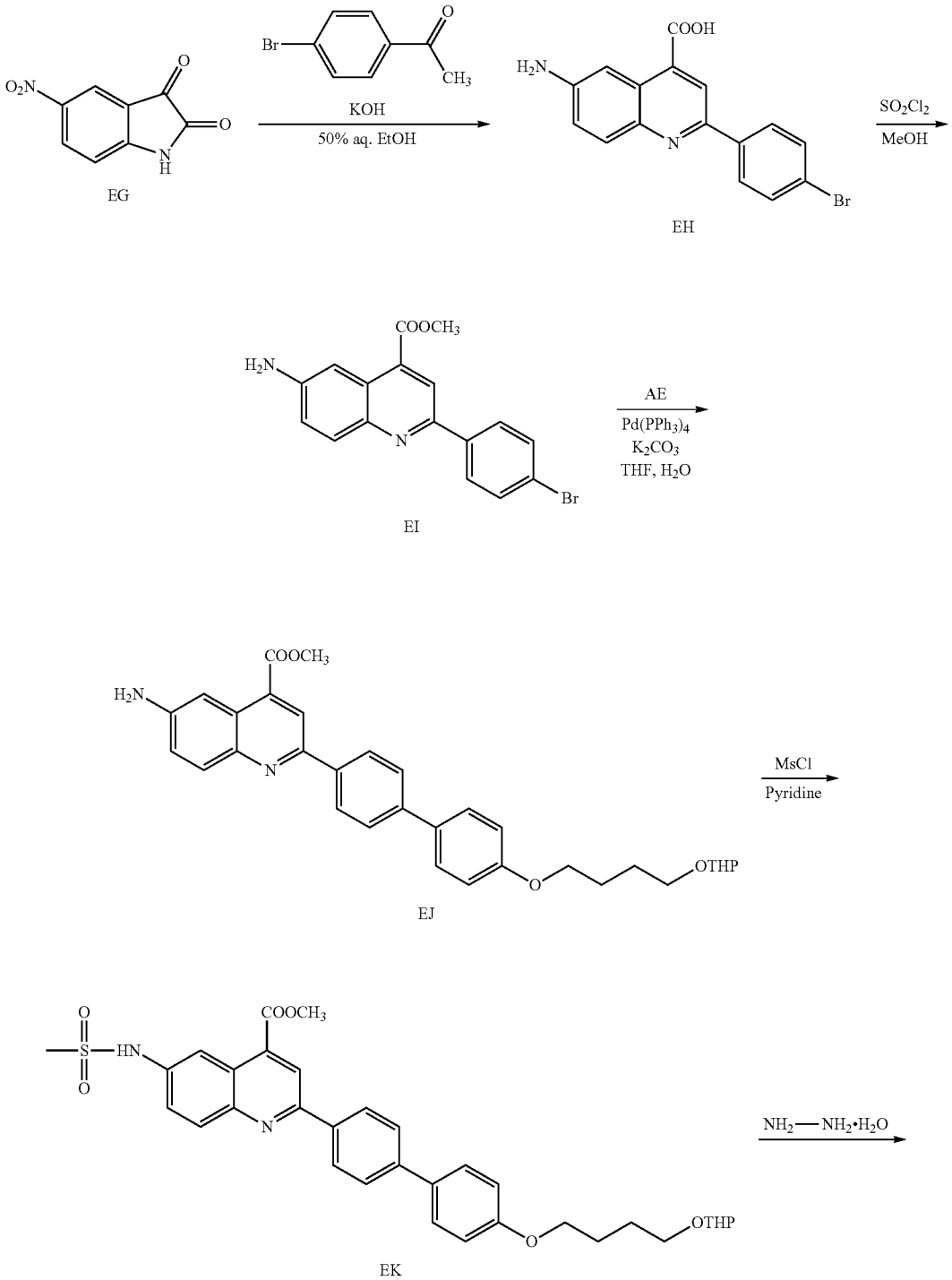

Scheme 34

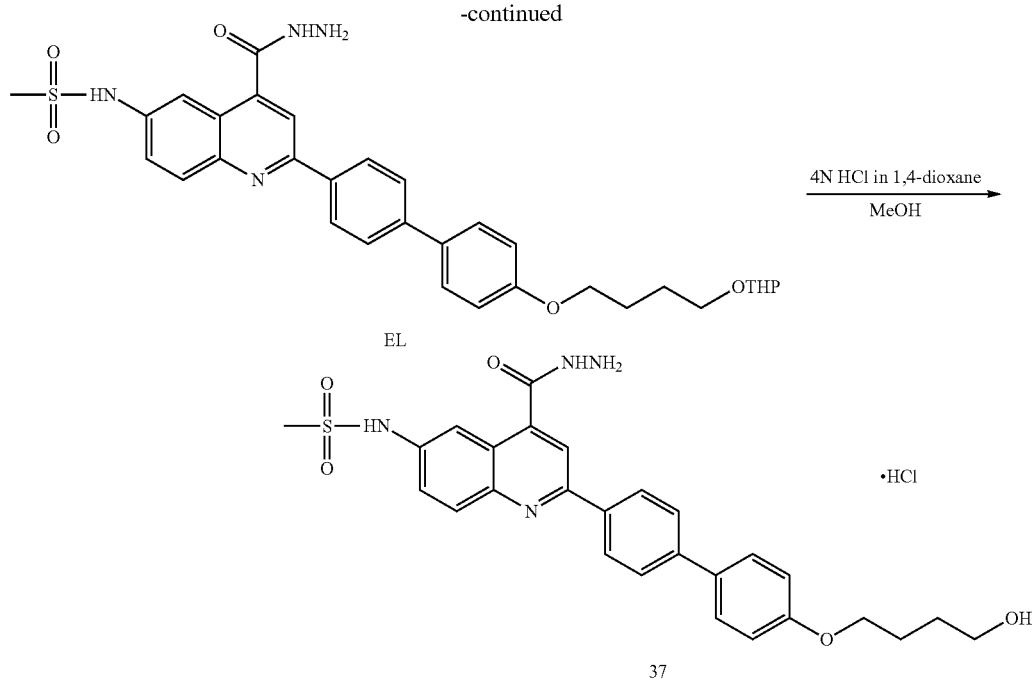

Example 37

N-(4-(hydrazinecarbonyl)-2-(4'-(4-hydroxybutoxy)-[1,1'-biphenyl]-4-yl)quinolin-6-yl)methanesulfonamide (37)

To a stirred solution of 5-nitroindoline-2,3-dione (EG; 1 g, 5.20 mmol) in aqueous ethanol (10 mL) under inert atmosphere were added 1-(4-bromophenyl)ethanone (1 g, 5.20 mmol) and potassium hydroxide (2.9 g, 52.04 mmol) at RT. The reaction mixture was heated to reflux and stirred for 2 h. After complete consumption of the starting material, the reaction mixture was cooled to RT and acidified with acetic acid. The obtained solid was filtered and the filtrate was concentrated under reduced pressure to obtain the crude EII (5 g) as an off-white solid. LCMS (ESI): 53%, m/z 343 [M+1]$^+$ To a stirred solution of EH (5 g, 14.61 mmol) in methanol (15 mL) under inert atmosphere was added sulfurylchloride (17.39 g, 146.17 mmol) at 0° C. The reaction mixture was then heated to reflux and stirred for 12 h. After complete consumption of the starting material, the volatiles were evaporated under reduced pressure. The residue was diluted with a saturated sodium bicarbonate solution (40 mL) and the compound was extracted with EtOAc (3×40 mL). The combined organic extracts were washed with water (40 mL), dried over sodium sulfate, filtered and concentrated under reduced pressure to obtain the crude. The crude was purified by silica gel column chromatography eluting with 20% EtOAc/hexanes to afford EI (300 mg, 7%) as an off-white solid. $^1$H NMR (500 MHz, DMSO-d$_6$): δ 8.27 (s, 1H), 8.12 (d, J=8.5 Hz, 1H), 7.83 (d, J=9.0 Hz, 1H), 7.69 (d, J=8.0 Hz, 1H), 7.54 (d, J=7.5 Hz, 2H), 7.35 (d, J=8.0 Hz, 1H), 7.25 (d, J=7.0 Hz, 1H), 6.04 (br s, 2H), 3.96 (s, 3H).

To a stirred solution of EI (200 mg, 56.17 mmol) in THF (15 mL) under inert atmosphere were added 4,4,5,5-tetramethyl-2-(4-(4-((tetrahydro-2H-pyran-2-yl)oxy)butoxy)phenyl)-1,3,2-dioxaborolane AE (252 mg, 67.20 mmol), potassium carbonate (232 mg, 1.60 mmol) and water (2 mL) at RT. After the reaction mixture was purged under argon for 15 min, Pd(PPh$_3$)$_4$ (32 mg, 0.028 mol) was added. The reaction as then heated to reflux and stirred for 4 h. After complete consumption of the starting material, the volatiles were evaporated under vacuum to obtain the crude, which was purified by silica gel column chromatography eluting with 30% EtOAc/hexanes to afford EJ (100 mg, 34%) as a yellow solid. $^1$H NMR (400 MHz, CDCl$_3$): δ 8.40 (s, 1H), 8.21 (d, J=8.0 Hz, 2H), 8.05 (d, J=8.0 Hz, 1H), 7.96 (s, 1H), 7.70 (d, J=8.5 Hz, 2H), 7.60 (d, J=8.5 Hz, 2H), 7.22-7.20 (m, 1H), 7.01 (d, J=8.5 Hz, 2H), 4.64-4.62 (m, 1H), 4.12-4.10 (m, 2H), 4.08-4.03 (m, 4H), 3.90-3.80 (m, 3H), 3.56-3.48 (m, 2H), 1.94-1.90 (m, 1H), 1.88-1.82 (m, 2H), 1.78-1.72 (m, 2H), 1.70-1.68 (m, 2H), 1.60-1.54 (m, 2H), 1.50-1.46 (m, 1H).

To a stirred solution of EJ (60 mg, 0.11 mmol) in pyridine (0.3 mL) under inert atmosphere was added methanesulfonylchloride (111 mg, 0.96 mmol) at 0° C. The reaction was warmed to RT and stirred for 12 h. After complete consumption of the starting material, the reaction mass was diluted with water (5 mL) and extracted with EtOAc (2×10 mL). The combined organic layers were washed with water (5 mL), dried over sodium sulfate, filtered and concentrated under reduced pressure to obtain the crude. The crude was purified by silica gel column chromatography eluting with 20% EtOAc/hexanes to afford EK (10 mg, 15%) as a yellow solid. $^1$H NMR (500 MHz, DMSO-d$_6$): δ 8.66 (br s, 1H), 8.52 (br s, 1H), 8.28-8.22 (m, 3H), 7.76-7.72 (m, 3H), 7.61 (d, J=8.0 Hz, 2H), 7.01 (d, J=8.0 Hz, 2H), 6.70 (s, 1H), 4.62-4.60 (m, 1H), 4.12-4.06 (m, 5H), 3.94-3.82 (m, 2H), 3.54-3.44 (m, 3H), 3.18 (s, 3H), 1.98-1.66 (m, 7H).

A stirred solution of EK (60 mg) in hydrazine hydrate (1 mL) under inert atmosphere was heated to 100° C. and stirred for 1 h. The reaction was monitored by TLC. After complete consumption of the starting material, the reaction mixture was diluted with water (5 mL) and extracted with 10% MeOH/CH$_2$Cl$_2$ (2×7 mL). The combined organic extracts were washed with water (5 mL), dried over sodium sulfate, filtered and concentrated under reduced pressure to obtain the crude. The crude was purified by silica gel column chromatography eluting with 10% MeOH/CH$_2$Cl$_2$ to afford EL (20 mg, 33%) as a yellow solid. $^1$H NMR (500 MHz, DMSO-d$_6$): δ 10.20 (br s, 1H), 10.06 (s, 1H), 8.34 (d, J=8.5 Hz, 2H), 8.13-8.09 (m, 3H), 7.82 (d, J=8.5 Hz, 2H), 7.72 (d, J=9.0 Hz, 2H), 7.69 (s, 1H), 7.06 (d, J=8.5 Hz, 2H), 4.71 (br s, 1H), 4.57 (s, 1H), 4.06 (t, J=6.5 Hz, 2H), 3.75-3.68 (m, 2H), 3.44-3.41 (m, 2H), 3.09 (s, 3H), 1.82-1.79 (m, 2H), 1.72-1.68 (m, 4H), 1.47-1.45 (m, 4H), 1.33 (s, 1H).

To a stirred solution of EL (20 mg) in methanol (5 mL) under inert atmosphere was added a 4N HCl solution in 1,4-dioxane (1 mL) at 0° C. The reaction was then warmed to RT and stirred for 1 h. After complete consumption of the starting material, the volatiles were evaporated under reduced pressure to obtain the crude, which was triturated with isopropyl alcohol (2×5 mL) and pentane (2×5 mL) to afford 37 (35 mg as an HCl salt) as a brick red solid. $^1$H NMR (500 MHz, DMSO-d$_6$): δ 11.80 (br s, 1H), 10.34 (s, 1H), 8.34 (d, J=8.0 Hz, 2H), 8.29 (s, 1H), 8.17-8.14 (m, 2H), 7.84 (d, J=8.5 Hz, 2H), 7.72-7.69 (m, 3H), 7.05 (d, J=8.5 Hz, 2H), 4.04 (t, J=7.0 Hz, 3H), 3.46 (t, J=7.0 Hz, 3H), 3.11 (s, 3H), 1.78-1.74 (m, 2H), 1.60-1.56 (m, 2H). Mass: m/z 521 [M+1]$^+$. HPLC Purity: 99.69%

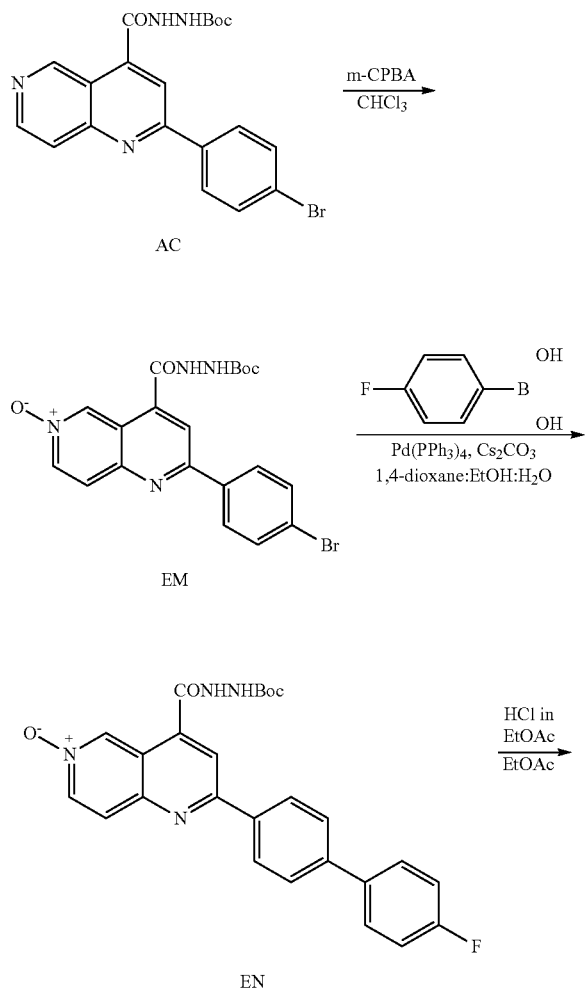

Scheme 35

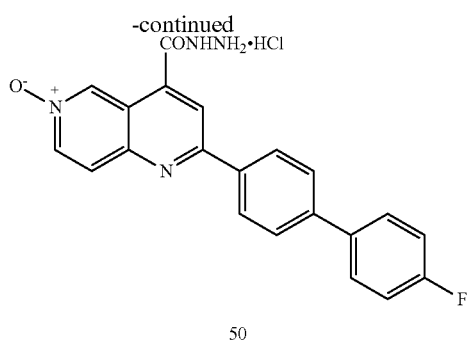

Example 50

2-(4'-fluoro-[1,1'-biphenyl]-4-yl)-4-(hydrazinecarbonyl)-1,6-naphthyridine 6-oxide hydrochloride (50)

To a stirred solution of tert-butyl 2-(2-(4-bromophenyl)-1,6-naphthyridine-4-carbonyl) hydrazinecarboxylate (AC; 120 mg, 0.27 mmol) in chloroform (10 mL) under inert atmosphere was added m-chloroperbenzoic acid (116 mg, 0.67 mmol) at 0° C. The reaction was warmed to RT and stirred for 2 h. After complete consumption of the starting material, the reaction mixture was diluted with a saturated sodium bicarbonate solution (15 mL) and extracted with CH$_2$Cl$_2$ (2×20 mL). The combined organic extracts were washed with water (15 mL), dried over sodium sulfate, filtered and concentrated under reduced pressure to obtain the crude. The crude was purified by silica gel column chromatography eluting with 2-5% MeOH/CH$_2$Cl$_2$ to afford EM (90 mg, 75%) as a yellow solid. $^1$H NMR (500 MHz, DMSO-d$_6$): δ 10.65 (br s, 1H), 9.26 (br s, 1H), 9.13 (br s, 1H), 8.45-8.43 (m, 1H), 8.30 (s, 1H), 8.25 (d, J=8.0 Hz, 1H), 8.07 (d, J=8.0 Hz, 1H), 7.79 (d, J=8.0 Hz, 2H), 1.27 (s, 9H).

To a stirred solution of EM (110 mg, 0.23 mmol) in 1,4-dioxane:EtOH:H$_2$O (4:2:1, 20 mL) under inert atmosphere were added (4-fluorophenyl)boronic acid (40 mg, 0.28 mmol) and cesium carbonate (230 mg, 0.71 mmol) at RT. After the reaction was purged with argon for 20 min, Pd(PPh$_3$)$_4$ (27 mg, 0.02 mmol) was added. The reaction was heated to reflux and stirred for 4 h. After complete consumption of the starting material, the reaction mass was cooled to RT and the volatiles were evaporated under reduced pressure. The residue was diluted with water (15 mL) and was extracted with CH$_2$Cl$_2$ (2×20 ml). The combined organic extracts were washed with water (15 mL), dried over sodium sulfate, filtered and concentrated under reduced pressure to obtain the crude. The crude was purified by silica gel column chromatography eluting with 2-4% MeOH/CH$_2$Cl$_2$ to afford EN (80 mg, 70%) as an off-white solid. $^1$H NMR (500 MHz, DMSO-d$_6$): δ 10.69 (br s, 1H), 9.28 (s, 1H), 9.16 (s, 1H), 8.46-8.31 (m, 4H), 8.09 (d, J=7.5 Hz, 1H), 7.91-7.84 (m, 4H), 7.35 (t, J=8.5 Hz, 2H), 1.48 (s, 9H).

To a stirred solution of EN (40 mg, 0.08 mmol) in ethyl acetate (2 mL) under inert atmosphere was added 2N HCl in ethyl acetate (5 mL) at 0° C. The reaction was warmed to RT and stirred for 1 h. After complete consumption of the starting material, the volatiles were evaporated under reduced pressure to obtain the crude, which was triturated with diisopropyl ether (2×5 mL) and pentane (2×5 mL) to afford 50 (26 mg of an HCl salt) as a yellow solid. $^1$H NMR (500 MHz, DMSO-d$_6$): δ 11.80 (br s, 1H), 9.15 (s, 1H), 8.50-8.42 (m, 4H), 8.11 (d, J=7.0 Hz, 1H), 7.91 (d, J=8.5 Hz, 2H), 7.87-7.84 (m, 2H), 7.35 (t, J=9.0 Hz, 2H). MS (ESI): m/z 375 [M+1]+. HPLC Purity: 94.93%

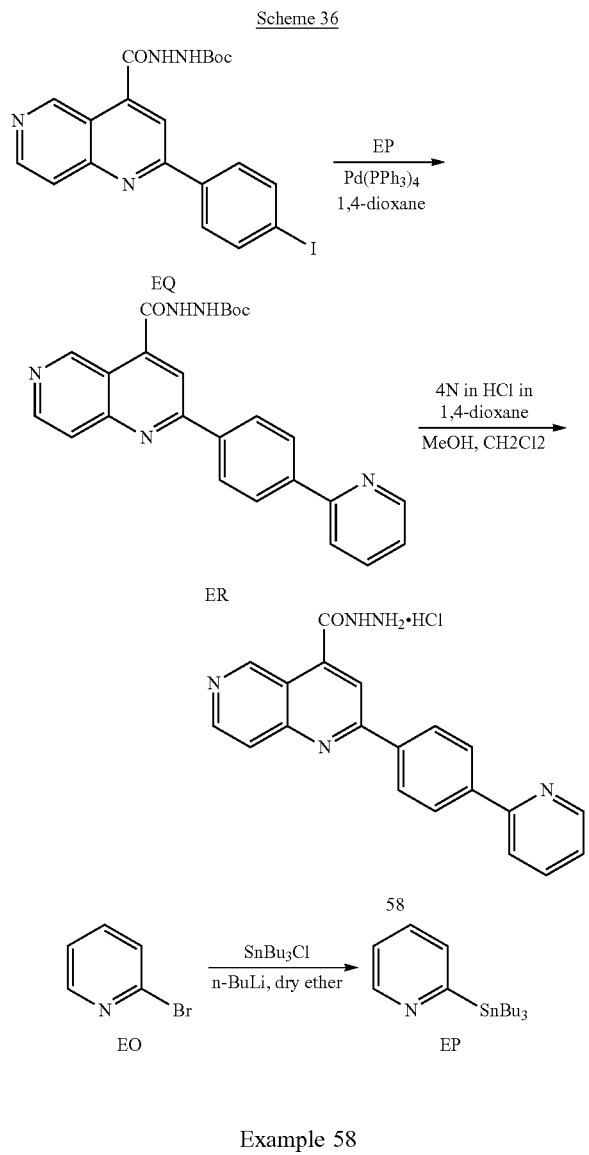

Example 58

2-(4-(pyridin-2-yl)phenyl)-1,6-naphthyridine-4-carbohydrazide hydrochloride (58)

To a stirred solution of 2-bromopyridine (EO; 1 g, 6.32 mmol) in dry ether (20 mL) under inert atmosphere was added n-butyl lithium (4.12 mL, 9.49 mmol) at −78° C. The reaction was stirred for 45 min at −78° C. After a solution of tributyltin chloride (2.57 mL, 9.49 mmol) was added, the reaction was heated to 50° C. and stirred for 30 min. The reaction was monitored by TLC. After complete consumption of the starting material, the crude was diluted with a saturated ammonium chloride solution (40 mL) and was extracted with EtOAc (2×40 mL). The combined organic extracts were washed with water (30 mL), dried over sodium sulfate, filtered and concentrated under reduced pressure to obtain the crude EP (3.2 g) as a sticky solid. $^1$H NMR (500 MHz, CDCl$_3$): δ 8.73 (s, 1H), 7.49 (d, J=7.5 Hz, 1H), 7.40 (d, J=7.5 Hz, 1H), 7.11 (t, J=6.0 Hz, 1H), 1.71-1.37 (m, 12H), 1.35-1.23 (m, 6H), 1.19-1.05 (m, 9H). MS (ESI): m/z 370 [M+1]+

A stirred solution of tert-butyl 2-(3-(4-iodophenyl)-1-naphthoyl)hydrazinecarboxylate (EQ; 150 mg, 0.30 mmol) in 1,4-dioxane (8 mL) was purged under argon for 15 min at RT. To this reaction mixture was added Pd(PPh$_3$)$_4$ (35 mg, 0.03 mmol) and purged with argon for 15 min. After the addition of EP (225 mg, 0.61 mmol), the reaction was heated to reflux and stirred for 12 h. The reaction was monitored by TLC. After complete consumption of the starting material, the volatiles were evaporated under reduced pressure. The residue was diluted with water (15 mL) and was extracted with EtOAc (2×15 mL). The combined organic extracts were washed with water (15 mL), dried over sodium sulfate, filtered and concentrated under reduced pressure to obtain ER (40 mg, 29%) as an off-white solid. $^1$H NMR (500 MHz, DMSO-d$_6$): δ 10.65 (br s, 1H), 9.69 (br s, 1H), 9.28 (br s, 1H), 8.82 (d, J=6.0 Hz, 1H), 8.72 (d, J=6.5 Hz, 1H), 8.48 (d, J=8.0 Hz, 2H), 8.33 (d, J=8.5 Hz, 3H), 8.10 (d, J=8.5 Hz, 1H), 8.05 (d, J=6.0 Hz, 1H), 7.94 (t, J=8.0 Hz, 1H), 7.41 (t, J=8.0 Hz, 1H), 1.35 (s, 9H). MS (ESI): m/z 442 [M+1]+

To a stirred solution of ER (35 mg, 0.07 mmol) in 10% methanol:CH$_2$Cl$_2$ (2 mL) under inert atmosphere was added a 4N HCl solution in 1,4-dioxane (2 mL) at 0° C. The reaction was then warmed to RT and stirred for 3 h. After complete consumption of the starting material, the volatiles were evaporated under reduced pressure to obtain the crude, which was triturated with n-pentane (2×2 mL) to afford 58 (30 mg as an HCl salt) as an off-white solid. $^1$H NMR (500 MHz, DMSO-d$_6$): δ 12.28 (br s, 1H), 9.78 (s, 1H), 8.90 (d, J=6.0 Hz, 1H), 8.77 (d, J=6.0 Hz, 1H), 8.68 (d, J=7.0 Hz, 1H), 8.58 (d, J=8.5 Hz, 2H), 8.37 (d, J=8.5 Hz, 2H), 8.26-8.20 (m, 2H), 8.08 (d, J=6.0 Hz, 1H), 7.56-7.55 (m, 1H). MS (ESI): m/z 342 [M+1]+. HPLC Purity: 96.95%

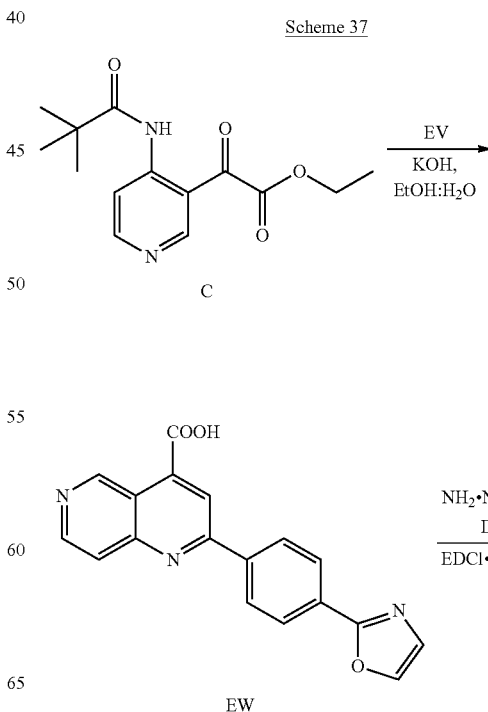

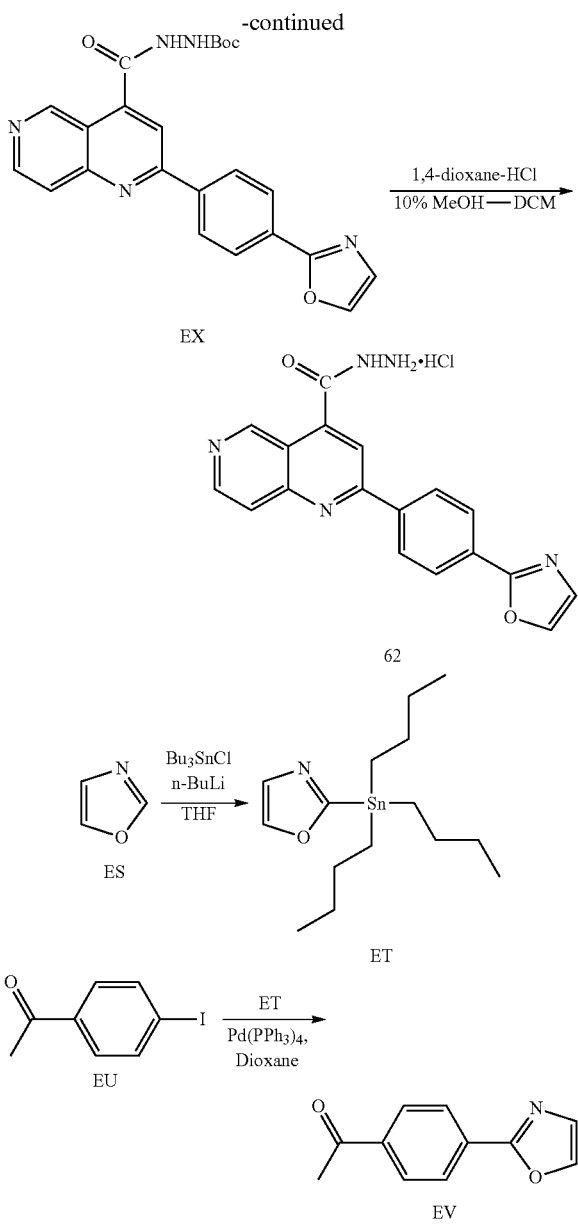

Example 62

2-(4-(oxazol-2-yl)phenyl)-1,6-naphthyridine-4-carbohydrazide hydrochloride (62)

To a stirred solution of oxazole (ES; 1 g, 14.71 mmol) in THF (25 mL) under inert atmosphere was added n-butyl lithium (7.3 mL, 14.71 mmol) dropwise for 10 min at −78° C. After stirring for 10 min at −78° C., tributyltin chloride (3.93 mL, 14.71 mmol) was added to the reaction mass and the reaction was stirred for 1 h at −78° C. The reaction was monitored by TLC. After complete consumption of the starting material, the reaction mixture was quenched with hexane (40 mL) and the volatiles were evaporated under reduced pressure to obtain crude ET (5.2 g) as a yellow liquid. $^1$H NMR (500 MHz, CDCl$_3$): δ 7.84 (s, 1H), 7.17 (s, 1H), 1.62-1.38 (m, 6H), 1.27-1.05 (m, 9H), 0.96-0.85 (m, 12H).

To a stirred solution of 1-(4-iodophenyl)ethanone (EU; 500 mg, 2.03 mmol) in 1,4-dioxane (5 mL) under inert atmosphere was added ET (1.1 g, 3.04 mmol) at RT in a sealed tube. After the reaction was purged under argon for 10 min, Pd(PPh$_3$)$_4$ (234 mg, 0.20 mmol) was added to the reaction mass. The reaction was then heated to 100° C. and stirred for 6 h. After complete consumption of the starting material, the reaction mass was filtered through Celite. The filtrate was diluted with water (20 mL) and was extracted with CH$_2$Cl$_2$ (2×20 mL). The combined organic extracts were washed with water (15 mL), dried over sodium sulfate, filtered and concentrated under reduced pressure to obtain crude EV (200 mg, 53%) as an off-white solid. $^1$H NMR (500 MHz, CDCl$_3$): δ 8.15 (d, J=8.5 Hz, 1H), 8.05 (d, J=9.0 Hz, 2H), 7.77 (s, 1H), 7.72 (d, J=8.5 Hz, 1H), 7.30 (s, 1H), 2.65 (s, 3H).

To a stirred solution of ethyl 2-oxo-2-(4-pivalamidopyridin-3-yl)acetate (C; 200 mg, 0.71 mmol) in ethanol:water (10:1, 11 mL) under inert atmosphere was added potassium hydroxide (201 mg, 3.59 mmol). The reaction was heated to reflux and stirred for 2 h. After the reaction mass was cooled to RT, EV (201 mg, 1.07 mmol) was added. The reaction was then heated to reflux and stirred for 12 h. After complete consumption of the starting material, the reaction mass was diluted with water (15 mL) and was extracted with CH$_2$Cl$_2$ (2×20 mL). The aqueous layer was acidified with acetic acid to pH~4. The obtained solid was filtered and co-distilled with toluene (2×5 mL) to obtain crude EW (250 mg) as a yellow solid. $^1$H NMR (500 MHz, DMSO-d$_6$): δ 12.00 (br s, 1H), 10.05 (d, J=10.0 Hz, 1H), 8.72 (d, J=6.0H, 1H), 8.49-8.41 (m, 3H), 8.30 (s, 1H), 8.18 (d, J=9.0 Hz, 1H), 8.04-7.95 (m, 2H), 7.46 (s, 1H).

To a stirred solution of EW (250 mg, 0.78 mmol) in DMF (5 mL) under inert atmosphere were added EDCI.HCl (226 mg, 1.18 mmol), HOBt (160 mg, 1.18 mmol), diisopropylethylamine (0.5 mL, 2.36 mmol) and Boc-hydrazine (310 mg, 2.36 mmol) at 0° C. The reaction was warmed to RT and stirred for 12 h. After complete consumption of the starting material, the reaction mass was diluted with water (25 mL) and the compound was extracted with EtOAc (3×20 mL). The combined organic extracts were washed with water (25 mL), dried over sodium sulfate, filtered and concentrated under reduced pressure to obtain the crude. The residue was purified via column chromatography eluting with 5% MeOH/CH$_2$Cl$_2$ to afford EX (50 mg, 14%) as a yellow solid. $^1$H NMR (500 MHz, DMSO-d$_6$): δ 10.66 (s, 1H), 9.72 (s, 1H), 9.30 (s, 1H), 8.85 (d, J=6.0 Hz, 1H), 8.53 (d, J=8.0 Hz, 2H), 8.33 (d, J=8.5 Hz, 2H), 8.21 (d, J=9.0 Hz, 2H), 8.06 (d, J=6.0 Hz, 1H), 7.47 (s, 1H), 1.49 (s, 9H).

To a stirred solution of EX (50 mg, 0.11 mmol) in CH$_2$Cl$_2$ (5 mL) under inert atmosphere was added 4N HCl in 1,4-dioxane (1 mL) at 0° C. The reaction was warmed to RT and stirred for 3 h. After complete consumption of the starting material, the volatiles were evaporated under reduced pressure to obtain the crude, which was triturated with diethyl ether (2×5 mL) and pentane (2×5 mL) to afford 62 (45 mg as an HCl salt) as a pale brown solid. $^1$H NMR (500 MHz, DMSO-d$_6$): δ 9.75 (s, 1H), 8.90 (d, J=6.0 Hz, 1H), 8.62 (s, 1H), 8.59 (d, J=8.5 Hz, 2H), 8.33 (s, 1H), 8.25-8.21 (m, 3H), 7.49 (s, 1H). MS (ESI): m/z 332 [M+1]$^+$. HPLC Purity: 96.37%

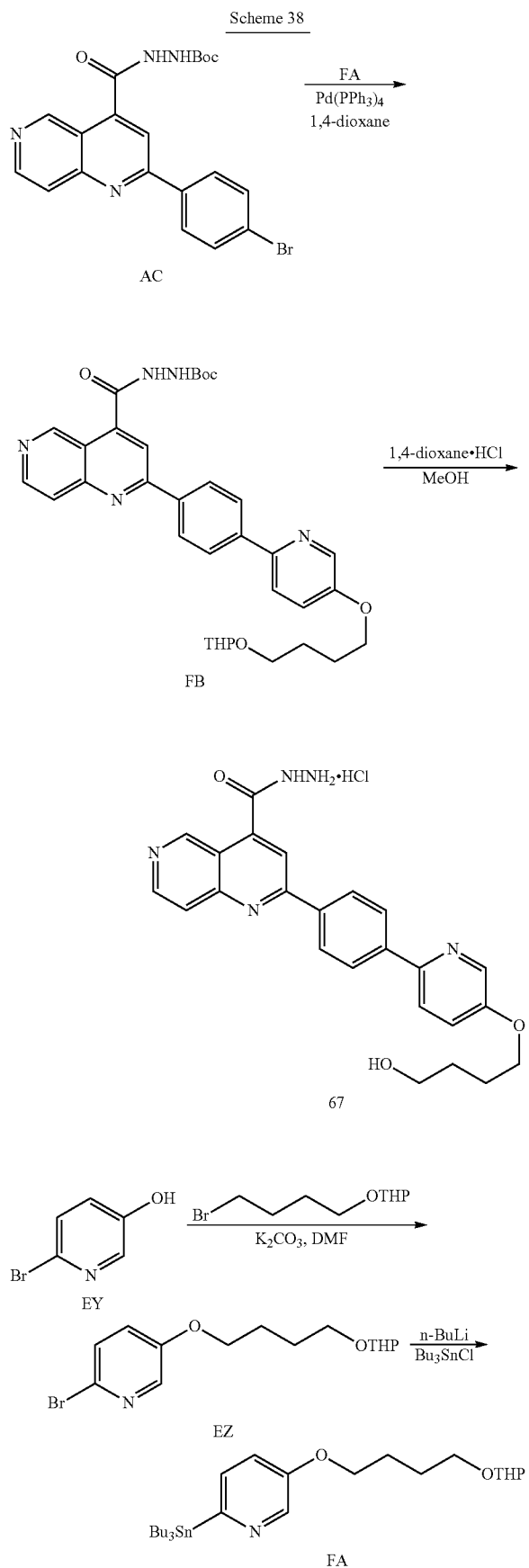

Example 67

2-(4-(5-(4-hydroxybutoxyl)pyridin-2-yl)phenyl)-1,6-naphthyridine-4-carbohydrazide hydrochloride (67)

To a stirred solution of 6-bromopyridin-3-ol (EY; 430 mg, 2.47 mmol) in DMF (5 mL) under inert atmosphere were added 2-(4-bromobutoxyl)tetrahydro-2H-pyran (762 mg, 3.21 mmol) and potassium carbonate at 0° C. The reaction was warmed to RT and stirred for 12 h. After complete consumption of the starting material, the reaction mixture was quenched with ice cold water (30 mL) and the compound was extracted with EtOAc (2×30 mL). The combined organic extracts were washed with water (25 mL), dried over sodium sulfate, filtered and concentrated under reduced pressure to obtain the crude. The crude material was purified via column chromatography eluting with 20% EtOAc/hexanes to afford EZ (660 mg, 80%) as a colorless liquid. MS (ESI): m/z 331 [M+1]$^+$ To a stirred solution of EZ (660 mg, 2.00 mmol) in dry ether (10 mL) under inert atmosphere was added n-butyl lithium (1.87 mL, 3.00 mmol) dropwise for 5 min at −78° C. After stirring for 1 h at −78° C., tributylchlorostannane (0.81 mL, 3.00 mmol) was added to the reaction mass and the reaction was stirred at −78° C. for 30 min. The reaction was monitored by TLC. After complete consumption of the starting material, the reaction mass was quenched with an aqueous ammonium chloride solution (30 mL) and was extracted with EtOAc (2×30 mL). The combined organic extracts were washed with water (25 mL), dried over sodium sulfate, filtered and concentrated under reduced pressure to obtain crude FA (1.4 g) as a colorless liquid. MS (ESI): m/z 541 [M+1]$^+$ To a stirred solution of FA (1 g, 1.85 mmol) in 1,4-dioxane (10 mL) under inert atmosphere was added AC (704 mg, 1.85 mmol) at RT. After the reaction was purged under argon for 15 min, Pd(PPh$_3$)$_4$ (214 mg, 0.18 mmol) was added. The reaction was then heated to reflux and stirred for 4 h. After complete consumption of the starting material, the volatiles were evaporated under reduced pressure to obtain the crude, which was purified via column chromatography eluting with 10% MeOH/CH$_2$Cl$_2$ to afford compound FB (200 mg, 18%) as a pale yellow solid. $^1$H NMR (500 MHz, DMSO-d$_6$): δ 10.66 (br s, 1H), 9.69 (br s, 1H), 9.29 (br s, 1H), 8.83 (d, J=6.0 Hz, 1H), 8.46-8.43 (m, 2H), 8.32 (s, 1H), 8.27 (d, J=8.5 Hz, 2H), 8.05 (t, J=9.0 Hz, 2H), 7.52 (d, J=6.0 Hz, 1H), 4.57 (d, J=4.0 Hz, 1H), 4.32 (d, J=4.0 Hz, 1H), 4.16 (t, J=6.0 Hz, 2H), 3.78-3.68 (m, 2H), 3.45-3.40 (m, 2H), 1.86-1.80 (m, 2H), 1.73-1.59 (m, 4H), 1.49-1.45 (m, 10H), 1.04-1.03 (m, 3H).

To a stirred solution of FB (100 mg, 0.16 mmol) in methanol (2 mL) under inert atmosphere was added 4N HCl in 1,4-dioxane (2 mL) at 0° C. The reaction was warmed to RT and stirred for 1 h. After complete consumption of the starting material, the volatiles were evaporated under reduced pressure to obtain the crude, which was triturated with diethyl ether (2×5 mL) and CH$_2$Cl$_2$ (2×5 mL) to afford 67 (56 mg as an HCl salt) as a yellow solid. $^1$H NMR (500 MHz, DMSO-d$_6$): δ 12.08 (br s, 1H), 9.73 (s, 1H), 8.88 (d, J=6.0 Hz, 1H), 8.59 (s, 1H), 8.52 (d, J=8.5 Hz, 2H), 8.44 (s, 1H), 8.30 (d, J=9.0 Hz, 2H), 8.20 (d, J=6.0 Hz, 1H), 8.10 (d, J=9.0 Hz, 1H), 7.57-7.55 (m, 1H), 4.15 (t, J=7.0 Hz, 2H), 3.48 (t, J=7.0 hz, 2H), 1.80 (t, J=8.0 Hz, 2H), 1.61 (t, J=8.0 Hz, 2H). Mass: m/z 430 [M+1]$^+$. HPLC Purity: 97.41%

Scheme 39
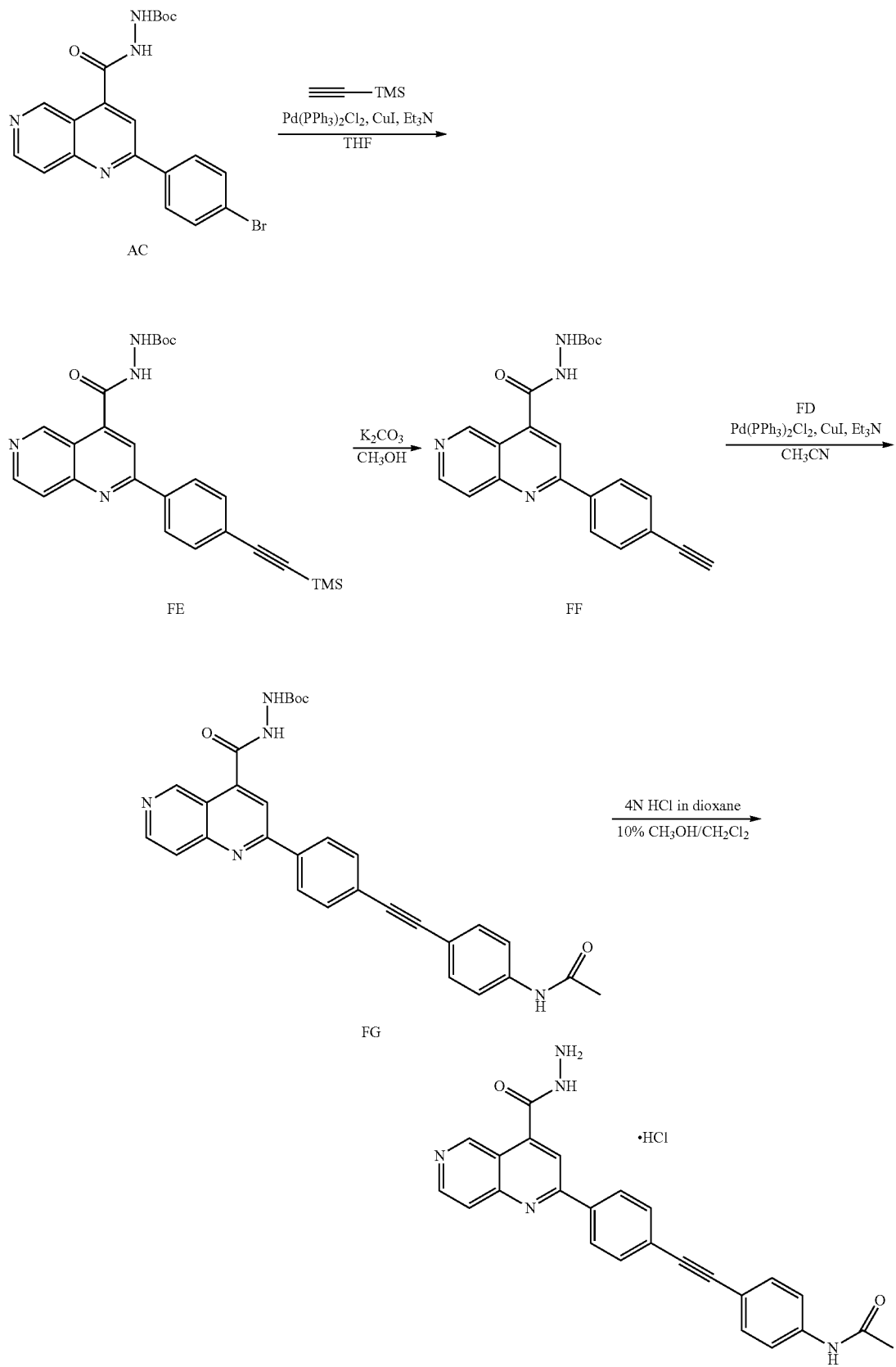

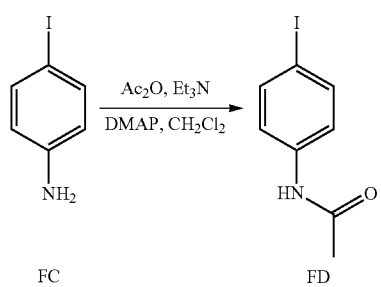

Example 116

N-(4-((4-(4-(hydrazinecarbonyl)-1,6-naphthyridin-2-yl)phenyl)ethynyl)phenyl)acetamide HCl Salt (116)

To a stirred solution of 4-iodoaniline (FC; 5.0 g, 22.83 mmol) in $CH_2Cl_2$ (50 mL) was added $Et_3N$ (8.0 mL, 57.06 mmol) followed by $Ac_2O$ (3.41 mL, 34.24 mmol) and DMAP (catalytic amount) at 0° C. under inert atmosphere. The reaction mixture was stirred for 2 h at 0° C. and then for 2 h at RT. Progress of the reaction was monitored by TLC. The reaction mixture was diluted with water and extracted with $CH_2Cl_2$ (2×100 mL). The combined organic layers were dried over anhydrous $Na_2SO_4$ and concentrated under reduced pressure to obtain the crude, which was purified by silica gel column chromatography eluting with 15% EtOAc/hexane as eluent to afford FD (3.5 g, 13.4 mmol, 59%) as a brownish solid. $^1H$ NMR (400 MHz, $CDCl_3$): δ 7.61 (d, J=8.4 Hz, 2H), 7.29 (d, J=8.8 Hz, 2H), 7.16 (bs, NH), 2.17 (s, 3H).

To a stirred solution of AC (2.0 g, 4.52 mmol) in THF (40 mL) were added TMS-acetylene (2.2 g, 22.6 mmol) and $Et_3N$ (6.34 mL, 45.2 mmol) at RT. After the reaction mixture was degassed by purging with argon for 20 min, CuI (86.15 mg, 0.45 mmol) and $Pd(PPh_3)_2Cl_2$ (317 mg, 0.45 mmol) were added at RT. The reaction was degassed for an additional 10 min. After stirring for 18 h at RT, the reaction mixture was then filtered through a pad of Celite and the filtrate was concentrated under reduced pressure to obtain the crude. The crude material was purified by silica gel column chromatography eluting with 2% $MeOH/CH_2Cl_2$ to afford FE (1.75 g, 3.8 mmol, 84%) as a brownish solid. $^1H$ NMR (500 MHz, DMSO-$d_6$): δ 10.64 (bs, 1H), 9.70 (bs, 1H), 9.29 (s, 1H), 8.83 (d, J=6.0 Hz, 1H), 8.38 (d, J=8.0 Hz, 2H), 8.30 (s, 1H), 8.03 (d, J=5.5 Hz, 1H), 7.69 (d, J=8.0 Hz, 2H), 1.49 (s, 9H), 0.27 (s, 9H). MS (ESI): m/z 461 [M+1]$^+$.

To a stirred solution of FE (1.0 g, 2.17 mmol) in $CH_3OH$ (20 mL) was added $K_2CO_3$ (899 mg, 6.52 mmol) at RT. After stirring for 3 h, the reaction mixture was filtered and concentrated under reduced pressure to obtain the crude. The crude material was purified by silica gel column chromatography eluting with 3% $CH_3OH/CH_2Cl_2$ as eluent to afford FF (250 mg, 0.64 mmol, 29%) as an off-white solid. $^1H$ NMR (400 MHz, DMSO-$d_6$): δ 10.64 (bs, 1H), 9.70 (bs, 1H), 9.29 (s, 1H), 8.83 (d, J=6.0 Hz, 1H), 8.38 (d, J=8.0 Hz, 2H), 8.30 (s, 1H), 8.03 (d, J=6.0 Hz, 1H), 7.71 (d, J=8.4 Hz, 2H), 4.43 (s, 1H), 1.49 (s, 9H). MS (ESI): m/z 389 [M+1]$^+$.

To a stirred solution of FF (150 mg, 0.38 mmol) in $CH_3CN$ (15 mL) were added FD (151 mg, 0.58 mmol) and $Et_3N$ (0.54 mL, 3.86 mmol) at RT. After the reaction was degassed by purging with argon for 20 min, CuI (7.36 mg, 0.038 mmol) and $Pd(PPh_3)_2Cl_2$ (27.0 mg, 0.038 mmol) were added at RT. The reaction mixture was degassed for an additional 10 min. After stirring for 3 h at reflux temperature, the reaction mixture was cooled to RT, filtered through a pad of Celite and the filtrate was concentrated under reduced pressure. The obtained residue was diluted with water and extracted with 10% MeOH/EtOAc. The combined organic extracts were dried over anhydrous $Na_2SO_4$ and concentrated under reduced pressure to obtain the crude. The crude material was purified by silica gel column chromatography eluting with 3% $MeOH/CH_2Cl_2$ to afford FG (100 mg, 0.19 mmol, 49%) as an off-white solid. $^1H$ NMR (500 MHz, DMSO-$d_6$): δ 10.65 (bs, 1H), 10.15 (bs, 1H), 9.70 (s, 1H), 9.29 (s, 1H), 8.84 (d, J=6.0 Hz, 1H), 8.41 (d, J=8.0 Hz, 2H), 8.32 (s, 1H), 8.04 (d, J=6.0 Hz, 1H), 7.76 (d, J=8.0 Hz, 2H), 7.67 (d, J=9.0 Hz, 2H), 7.54 (d, J=8.5 Hz, 2H), 2.07 (s, 3H), 1.49 (s, 9H). MS (ESI): m/z 522 [M+1]$^+$ To a stirred solution of FG (50 mg, 0.09 mmol) in 10% $CH_3OH/CH_2Cl_2$ (5 mL) was added 4N HCl in 1,4-dioxane (1.0 mL) at 0° C. under inert atmosphere. The resulting reaction mixture was stirred for 5 h at RT. After consumption of the starting material (by TLC), the volatiles were evaporated under reduced pressure to obtain the crude, which was triturated with 5% $CH_3OH/CH_2Cl_2$ to afford an HCl salt of 116 (12 mg) as a brownish solid. $^1H$ NMR (400 MHz, DMSO-$d_6$): δ 11.94 (bs, 1H), 10.21 (bs, 1H), 9.82 (s, 1H), 8.98-8.96 (m, 1H), 8.56 (s, 1H), 8.46 (d, J=8.4 Hz, 2H), 8.21-8.19 (m, 1H), 7.79 (d, J=8.4 Hz, 2H), 7.68 (d, J=8.8 Hz, 2H), 7.54 (d, J=8.4 Hz, 2H), 4.19 (bs, 2H), 2.08 (s, 3H). MS (ESI): m/z 422 [M+1]$^+$. HPLC: 93.6%.

Scheme 40

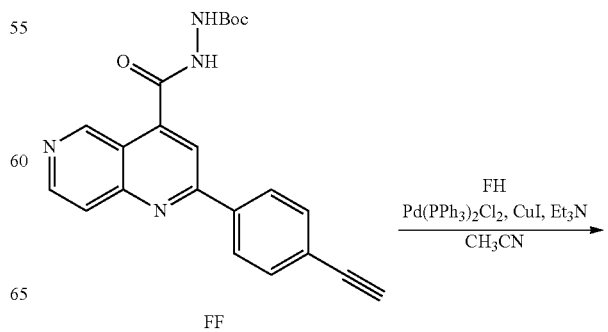

-continued

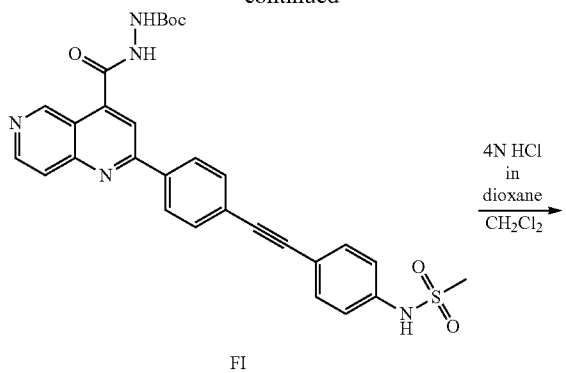

FI

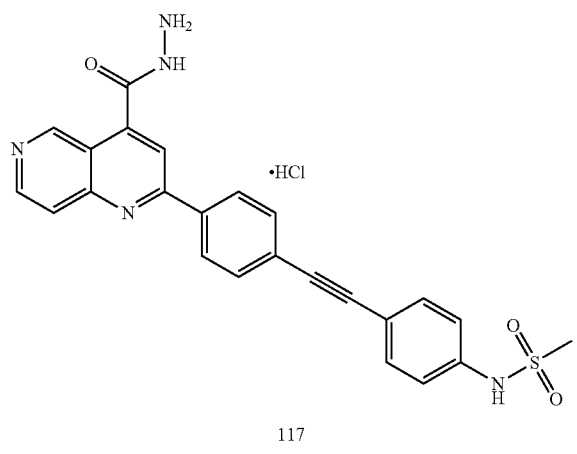

117

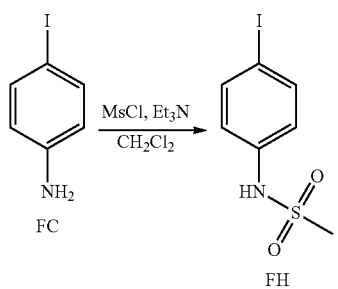

Example 117

N-(4-((4-(4-(hydrazinecarbonyl)-1,6-naphthyridin-2-yl)phenyl)ethynyl)phenyl)methanesulfonamide HCl salt (117)

To a stirred solution of 4-iodoaniline (FC; 2.0 g, 9.13 mmol) in $CH_2Cl_2$ (20 mL) was added pyridine (1.47 mL, 18.26 mmol) at RT. After the reaction was cooled to 0° C., methane sulfonyl chloride (1.06 mL, 13.69 mmol) was added under an inert atmosphere. The resulting solution was stirred for 1 h at RT. Progress of the reaction was monitored by TLC. The reaction was then quenched with 1N HCl and extracted with EtOAc (2×50 mL). The combined organic layers were washed with brine, dried over anhydrous $Na_2SO_4$ and concentrated under reduced pressure to obtain the crude. The crude material was purified by silica gel column chromatography eluting with 20% EtOAc/hexanes as eluent to afford FH (2.2 g, 7.40 mmol, 81%) as a brown solid.

$^1$H NMR (500 MHz, $CDCl_3$): δ 7.67 (d, J=8.5 Hz, 2H), 6.98 (d, J=8.5 Hz, 2H), 6.42 (bs, 1H), 3.01 (s, 3H).

To a stirred solution of FF (150 mg, 0.38 mmol) in $CH_3CN$ (15 mL) were added FH (172 mg, 0.58 mmol) and $Et_3N$ (0.54 mL, 3.86 mmol) at RT. The reaction was degassed by purging with argon for 20 min. To the resulting reaction mixture were added CuI (7.36 mg, 0.038 mmol) and $Pd(PPh_3)_2Cl_2$ (27.13 mg, 0.038 mmol) at RT and the reaction was degassed for an additional 10 min. The reaction mixture was then stirred for 3 h at reflux temperature. Progress of the reaction was monitored by TLC. The reaction mixture was then cooled to RT, filtered through a pad of Celite and the filtrate was concentrated under reduced pressure to obtain the crude. The crude material was purified by silica gel column chromatography eluting with 3% MeOH/$CH_2Cl_2$ to afford FI (40 mg, 0.07 mmol, 18%) as an off-white solid. $^1$H NMR (500 MHz, DMSO-$d_6$): δ 10.65 (bs, 1H), 10.16 (bs, 1H), 9.70 (s, 1H), 9.29 (s, 1H), 8.83 (d, J=6.0 Hz, 1H), 8.42 (d, J=8.5 Hz, 2H), 8.32 (s, 1H), 8.04 (d, J=6.0 Hz, 1H), 7.77 (d, J=8.5 Hz, 2H), 7.58 (d, J=8.5 Hz, 2H), 7.26 (d, J=8.5 Hz, 2H), 3.07 (s, 3H), 1.49 (s, 9H). LC-MS: m/z 558 [M+1]$^+$ at 3.12 min (85.2% purity).

To a stirred solution of FI (40 mg, 0.07 mmol) in $CH_2Cl_2$ (4 mL) was added 4N HCl in 1,4-dioxane (0.5 mL) at 0° C. under inert atmosphere. The resulting reaction mixture was stirred for 2 h at 0° C. and 1 h at RT. After consumption of the starting material (by TLC), the volatiles were evaporated under reduced pressure to obtain the crude, which was triturated with 5% $CH_3OH/CH_2Cl_2$ to afford an HCl salt of 117 (15 mg) as a red color solid. $^1$H NMR (400 MHz, DMSO-$d_6$): δ 11.80 (bs, 1H), 10.13 (s, 1H), 9.69 (s, 1H), 8.86 (d, J=6.0 Hz, 1H), 8.54 (s, 1H), 8.51-8.44 (m, 2H), 8.12 (d, J=6.0 Hz, 1H), 7.79 (d, J=8.4 Hz, 2H), 7.58 (d, J=8.4 Hz, 2H), 7.27 (d, J=8.8 Hz, 2H), 3.07 (s, 3H). MS (ESI): m/z 458 [M+1]$^+$. HPLC: 93.02%.

Scheme 41
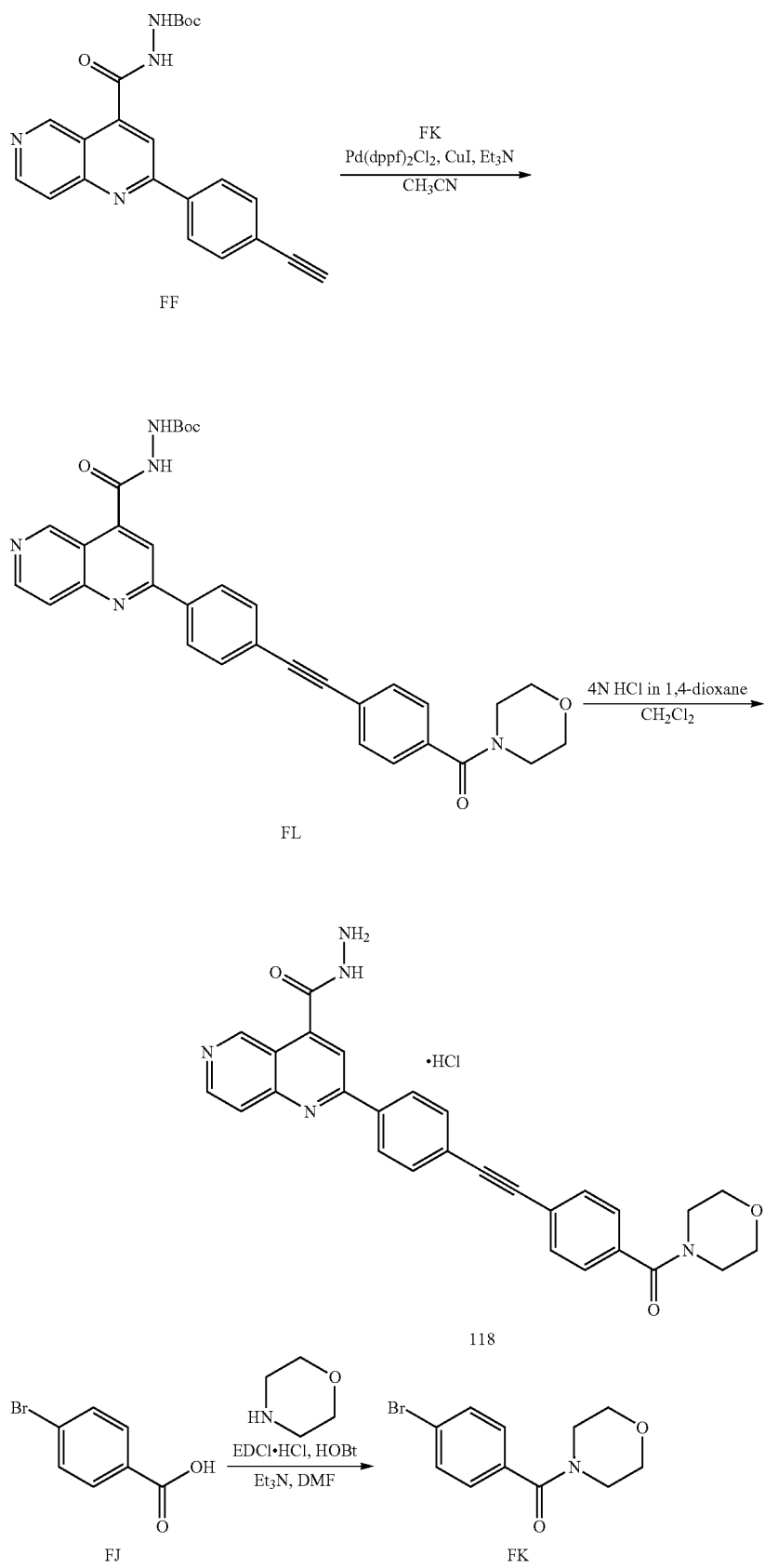

Example 118

2-(4-((4-(Morpholine-4-carbonyl)phenyl)ethynyl) phenyl)-1,6-naphthyridine-4-carbohydrazide HCl salt (118)

To a stirred solution of 4-bromobenzoic acid (FJ; 0.5 g, 2.5 mmol) in DMF (15 mL) were added EDCI.HCl (718.8 mg, 3.75 mmol), HOBt (506.6 mg, 3.75 mmol) and Et$_3$N (1.05 mL, 7.5 mmol) at RT under inert atmosphere. After being stirred for 10 min, morpholine (0.326 mL, 3.75 mmol) was added to the reaction mixture and stirring was continued for an additional 16 h at RT. Progress of the reaction was monitored (by TLC). The reaction mixture was then diluted with ice-cold water and extracted with EtOAc (2×50 mL). The combined organic extracts were dried over anhydrous Na$_2$SO$_4$ and concentrated under reduced pressure to obtain the crude, which was purified by silica gel column chromatography eluting with 2% CH$_3$OH/CH$_2$Cl$_2$ as eluent to afford FK (0.6 g, 2.22 mmol, 89%) as an off-white solid. $^1$H NMR (400 MHz, CDCl$_3$): δ 7.56 (d, J=8.8 Hz, 2H), 7.29 (d, J=8.8 Hz, 2H), 3.80-3.60 (m, 8H). MS (ESI): m/z 270 [M+1]$^+$.

To a stirred solution of FF (150 mg, 0.38 mmol) in CH$_3$CN (10 mL) were added FK (156 mg, 0.58 mmol) and Et$_3$N (0.54 mL, 3.86 mmol) at RT. After the reaction was degassed by purging with argon for 20 min, CuI (7.36 mg, 0.038 mmol) and Pd(PPh$_3$)$_2$Cl$_2$ (27.1 mg, 0.038 mmol) were added at RT and the reaction mixture was degassed for an additional 10 min. The reaction mixture was then stirred for 3 h at reflux temperature. Progress of the reaction was monitored by TLC. The reaction mixture was then cooled to RT, filtered through a pad of Celite and the filtrate was concentrated under reduced pressure to obtain the crude. The crude material was purified by silica gel column chromatography eluting with 7% MeOH/CH$_2$Cl$_2$ to afford FL (40 mg, 0.069 mmol, 17.9%) as an off-white solid. $^1$H NMR (500 MHz, DMSO-d$_6$): δ 10.65 (bs, 1H), 9.71 (s, 1H), 9.30 (s, 1H), 8.84 (d, J=6.0 Hz, 1H), 8.44 (d, J=8.0 Hz, 2H), 8.33 (s, 1H), 8.05 (d, J=6.0 Hz, 1H), 7.82 (d, J=8.0 Hz, 2H), 7.68 (d, J=7.5 Hz, 2H), 7.50 (d, J=8.5 Hz, 2H), 3.65-3.61 (m, 8H), 1.49 (s, 9H). LC-MS: m/z 578 [M+1]$^+$ at 3.89 min (89.3% purity).

To a stirred solution of FL (40 mg, 0.069 mmol) in CH$_2$Cl$_2$ (3 mL) was added 4N HCl in dioxane (0.3 mL) at 0° C. under inert atmosphere. The resulting reaction mixture was stirred for 3 h at RT. Progress of the reaction was monitored by TLC. The reaction mixture was then concentrated under reduced pressure to obtain the crude residue, which was purified via re-crystallization using CH$_3$OH/Et$_2$O to afford an HCl salt of 118 (20 mg) as a yellow solid. $^1$H NMR (400 MHz, DMSO-d$_6$): δ 11.98 (bs, 1H), 9.71 (s, 1H), 8.88 (d, J=6.0 Hz, 1H), 8.55 (s, 1H), 8.48 (d, J=8.4 Hz, 2H), 8.34 (s, 1H), 8.15 (d, J=6.0 Hz, 1H), 7.84 (d, J=8.4 Hz, 2H), 7.68 (d, J=8.0 Hz, 2H), 7.50 (d, J=8.4 Hz, 2H), 3.65-3.56 (m, 8H). MS (ESI): m/z 478 [M+1]$^+$. HPLC: 95.1%.

Scheme 42

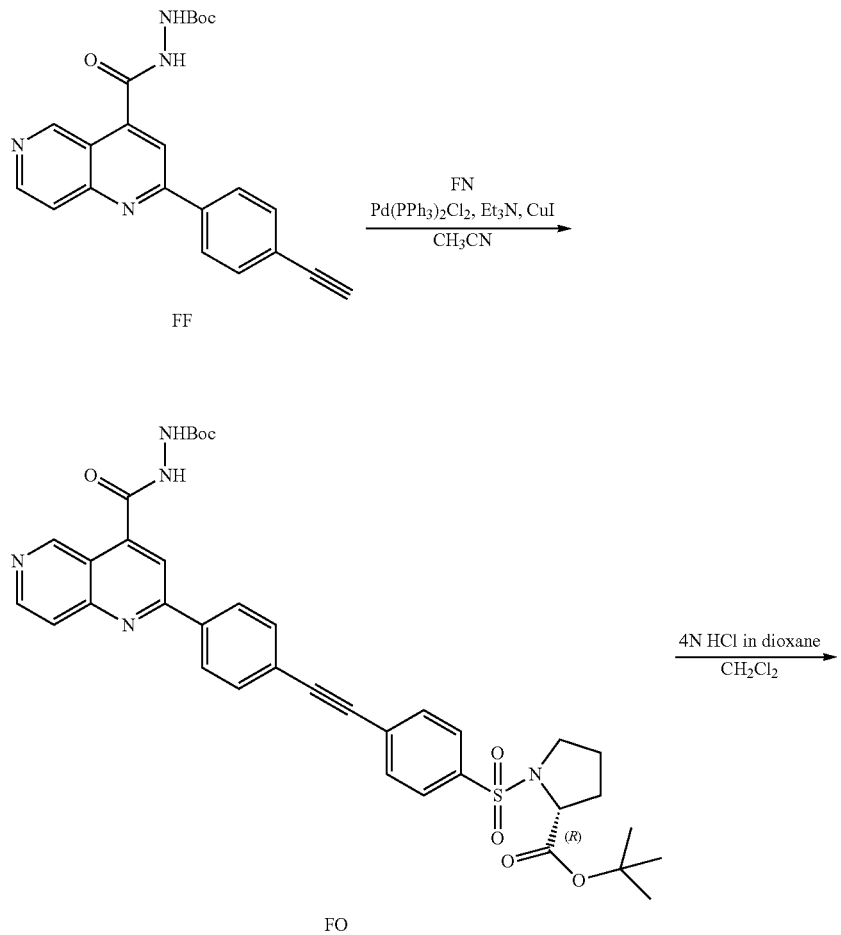

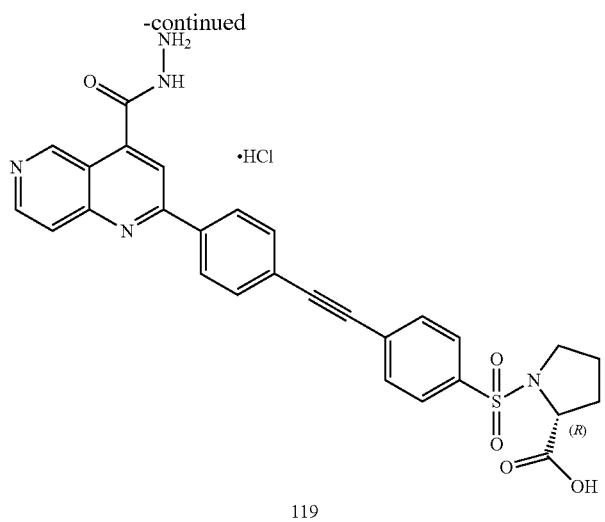

119

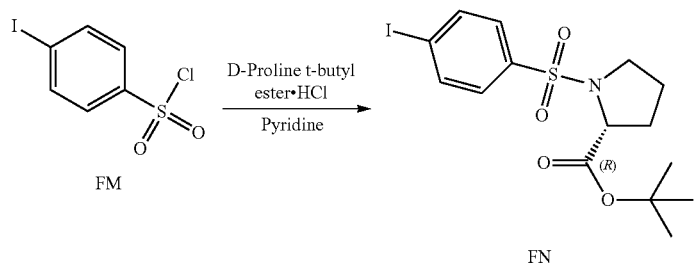

Example 119

(R)-1-((4-((4-(4-(hydrazinecarbonyl)-1,6-naphthyridin-2-yl)phenyl)ethynyl)phenyl)sulfonyl) pyrrolidine-2-carboxylic acid HCl salt (119)

To a stirred solution of the HCl salt of D-proline-tert-butyl ester (343 mg, 1.65 mmol) in pyridine (10 mL) was added 4-iodobenzene-1-sulfonyl chloride (FM; 500 mg, 1.65 mmol) at 0° C. under inert atmosphere. The resulting reaction mixture was stirred for 16 h at RT. Progress of the reaction was monitored by TLC. The reaction mixture was then diluted with water and extracted with EtOAc (3×30 mL). The combined organic extracts were dried over anhydrous $Na_2SO_4$ and concentrated under reduced pressure to obtain the crude. The crude material was purified by silica gel column chromatography eluting with 15% EtOAc/hexane as eluent to afford FN (550 mg, 1.25 mmol, 76%) as an orange color solid. $^1$H NMR (500 MHz, $CDCl_3$): δ 7.86 (d, J=8.0 Hz, 2H), 7.59 (d, J=8.0 Hz, 2H), 4.22 (dd, J=8.5, 3.0 Hz, 1H), 3.46-3.42 (m, 1H), 3.36-3.32 (m, 1H), 2.09-2.04 (m, 1H), 1.99-1.93 (m, 2H), 1.84-1.80 (m, 1H), 1.44 (s, 9H).

To a stirred solution of FF (150 mg, 0.38 mmol) in $CH_3CN$ (10 mL) were added FN (253 mg, 0.58 mmol) and $Et_3N$ (0.54 mL, 3.86 mmol) at RT. After the reaction was degassed by purging with argon for 20 min, CuI (7.36 mg, 0.038 mmol) and $Pd(PPh_3)_2Cl_2$ (27.1 mg, 0.038 mmol) were added at RT and the reaction mixture was degassed for an additional 10 min. The reaction mixture was then stirred for 4 h at reflux temperature with progress of the reaction being monitored by TLC. The reaction mixture was then cooled to RT, filtered through a pad of Celite and the filtrate was concentrated under reduced pressure to obtain the crude. The crude material was purified by silica gel column chromatography eluting with 5% $MeOH/CH_2Cl_2$ to afford FO (75 mg, 0.107 mmol, 27.8%) as a yellow solid. $^1$H NMR (400 MHz, DMSO-$d_6$): δ 10.66 (s, 1H), 9.72 (bs, 1H), 9.31 (s, 1H), 8.85 (d, J=4.8 Hz, 1H), 8.46 (d, J=8.0 Hz, 2H), 8.34 (s, 1H), 8.05 (d, J=4.8 Hz, 1H), 7.90-7.83 (m, 6H), 4.13 (dd, J=8.4, 3.2 Hz, 1H), 3.41-3.35 (m, 1H), 3.26-3.22 (m, 1H), 2.02-1.97 (m, 1H), 1.87-1.80 (m, 2H), 1.71-1.66 (m, 1H), 1.49 (s, 9H), 1.41 (s, 9H). LC-MS: m/z 696 [M−1]$^−$ at 4.42 min (95.3% purity).

To a stirred solution of FO (40 mg, 0.078 mmol) in $CH_2Cl_2$ (3 mL) was added 4N HCl in dioxane (0.5 mL) at 0° C. under inert atmosphere. The resulting reaction mixture was stirred for 12 h at RT with progress of the reaction being monitored by TLC. The reaction mixture was then concentrated under reduced pressure to obtain the crude material, which was purified by trituration using $CH_3CN$ to afford an HCl salt of 119 (20 mg) as a yellow solid. $^1$H NMR (400 MHz, DMSO-$d_6$): δ 12.30 (bs, 1H), 9.85 (bs, 1H), 8.98 (bs, 1H), 8.62 (s, 1H), 8.52 (d, J=8.4 Hz, 2H), 8.23 (s, 1H), 7.91-7.82 (m, 6H), 4.17 (dd, J=8.4, 3.6 Hz, 1H), 3.42-3.36 (m, 1H), 3.28-3.17 (m, 1H), 2.05-1.81 (m, 3H), 1.68-1.58 (m, 1H). MS (ESI): m/z 542 [M+1]$^+$. HPLC: 93.07%.

Scheme 43

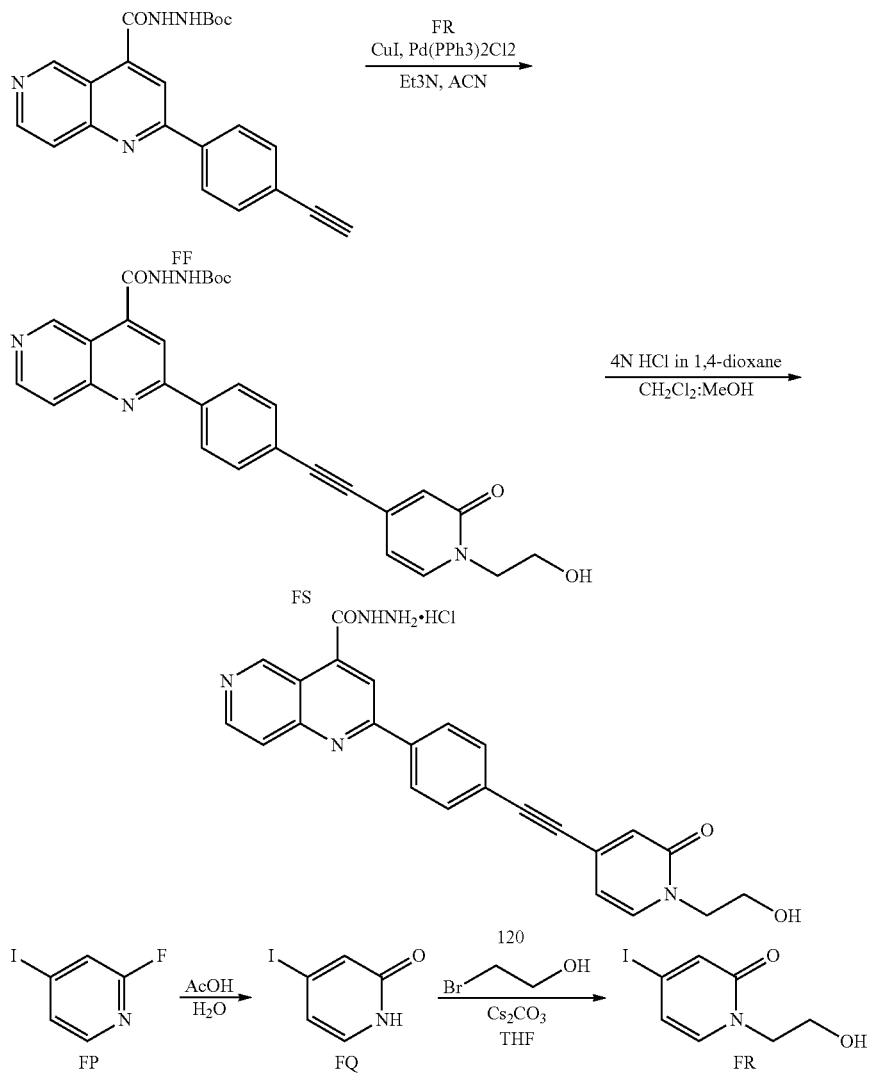

Example 120

2-(4-((1-(2-hydroxyethyl)-2-oxo-1,2-dihydropyridin-4-yl)ethynyl)phenyl)-1,6-naphthyridine-4-carbohydrazide hydrochloride (120)

To a stirred solution of 2-fluoro-4-iodopyridine (FP; 1 g, 4.42 mmol) in water (1.6 mL) was added acetic acid (3.3 mL) at RT. The reaction mixture was heated to 110-120° C. and stirred for 12 h. After complete consumption of the starting material (as monitored by TLC), the volatiles were evaporated under reduced pressure to obtain the crude material. The crude material was co-distilled with toluene (5 mL) and was triturated with ether (2×10 mL) to afford FQ (970 mg, 98%) as an off-white sold. $^1$H NMR (400 MHz, DMSO-$d_6$): δ 11.78 (br s, 1H), 7.13 (d, J=6.8 Hz, 1H), 6.86 (s, 1H), 6.49 (d, J=6.8 Hz, 1H).

To a stirred solution of FQ (500 mg, 2.26 mmol) in THF (20 mL) under inert atmosphere was added cesium carbonate (1.65 g, 5.06 mmol) at RT. After the reaction was stirred for 15 min, 2-bromoethanol was added to the reaction mixture. The reaction mixture was heated to reflux and stirred for 12 h. After complete consumption of the starting material, the reaction mixture was filtered under vaccum and the filtrate was concentrated under reduced pressure to obtain the crude material, which was purified by silica gel column chromatography eluting with 40-50% EtOAc/hexanes to afford FR (510 mg, 71%) as an off-white solid. $^1$H NMR (400 MHz, DMSO-$d_6$): δ 7.35 (d, J=7.2 Hz, 1H), 6.90 (s, 1H), 6.53 (d, J=7.2 Hz, 1H), 4.86 (t, J=5.2 Hz, 1H), 3.87 (t, J=5.6 Hz, 2H), 3.57 (t, J=5.6 Hz, 2H).

To a stirred solution of FF (150 mg, 0.38 mmol) in CH$_3$CN (20 mL) under inert atmosphere were added triethylamine (0.5 mL, 3.85 mmol) and FR (122 mg, 0.46 mmol) at 0° C. After the reaction was purged with argon for 30 min, copper iodide (7.3 mg, 0.03 mmol) and Pd(PPh$_3$)$_2$Cl$_2$ (27 mg, 0.03 mmol) were added. The reaction was then heated to reflux and stirred for 3 h. After complete consumption of the starting material, the reaction mass was cooled to RT and the volatiles were evaporated under reduced pressure to obtain the crude residue. The residue was purified by silica gel column chromatography eluting with 8-10% MeOH/

CH$_2$Cl$_2$ to afford FS (90 mg, 35%) as a pale yellow solid. $^1$H NMR (400 MHz, DMSO-d$_6$): δ 10.65 (br s, 1H), 9.71 (br s, 1H), 9.30 (br s, 1H), 8.84 (d, J=5.6 Hz, 1H), 8.45 (d, J=7.0 Hz, 2H), 8.33 (s, 1H), 8.05 (d, J=5.6 Hz, 1H), 7.83 (d, J=8.4 Hz, 2H), 7.66 (d, J=7.0 Hz, 1H), 6.62 (s, 1H), 6.34 (d, J=7.2 Hz, 1H), 4.90 (t, J=5.6 Hz, 1H), 3.95 (t, J=5.6 Hz, 2H), 3.64 (t, J=5.6 Hz 2H), 1.49 (s, 9H).

To a stirred solution of FS (45 mg, 0.08 mmol) in CH$_2$Cl$_2$ (1:1, 1 mL) under inert atmosphere was added 4N HCl solution in 1,4-dioxane (0.5 mL) at 0° C. The reaction was then warmed to RT and stirred for 1 h. After complete consumption of the starting material, the volatiles were evaporated under reduced pressure to obtain the crude material, which was triturated with CH$_3$CN (2×4 mL), diisopropyl ether (2×4 mL) and pentane (2×4 mL) to afford 120 (30 mg as an HCl salt) as a brown solid. $^1$H NMR (400 MHz, DMSO-d$_6$): δ 11.80 (br s, 1H), 9.71 (br s, 1H), 8.88-8.87 (m, 1H), 8.53 (s, 1H), 8.48 (d, J=8.4 Hz, 1H), 8.14 (d, J=5.6 Hz, 1H), 7.85 (d, J=8.4 Hz, 2H), 7.67 (d, J=7.0 Hz, 1H), 6.62 (s, 1H), 6.34 (d, J=7.0 Hz, 1H), 3.97-3.90 (m, 2H), 3.65-3.56 (m, 2H). Mass: m/z 426 [M+1]$^+$. HPLC Purity: 95.82%

Scheme 44

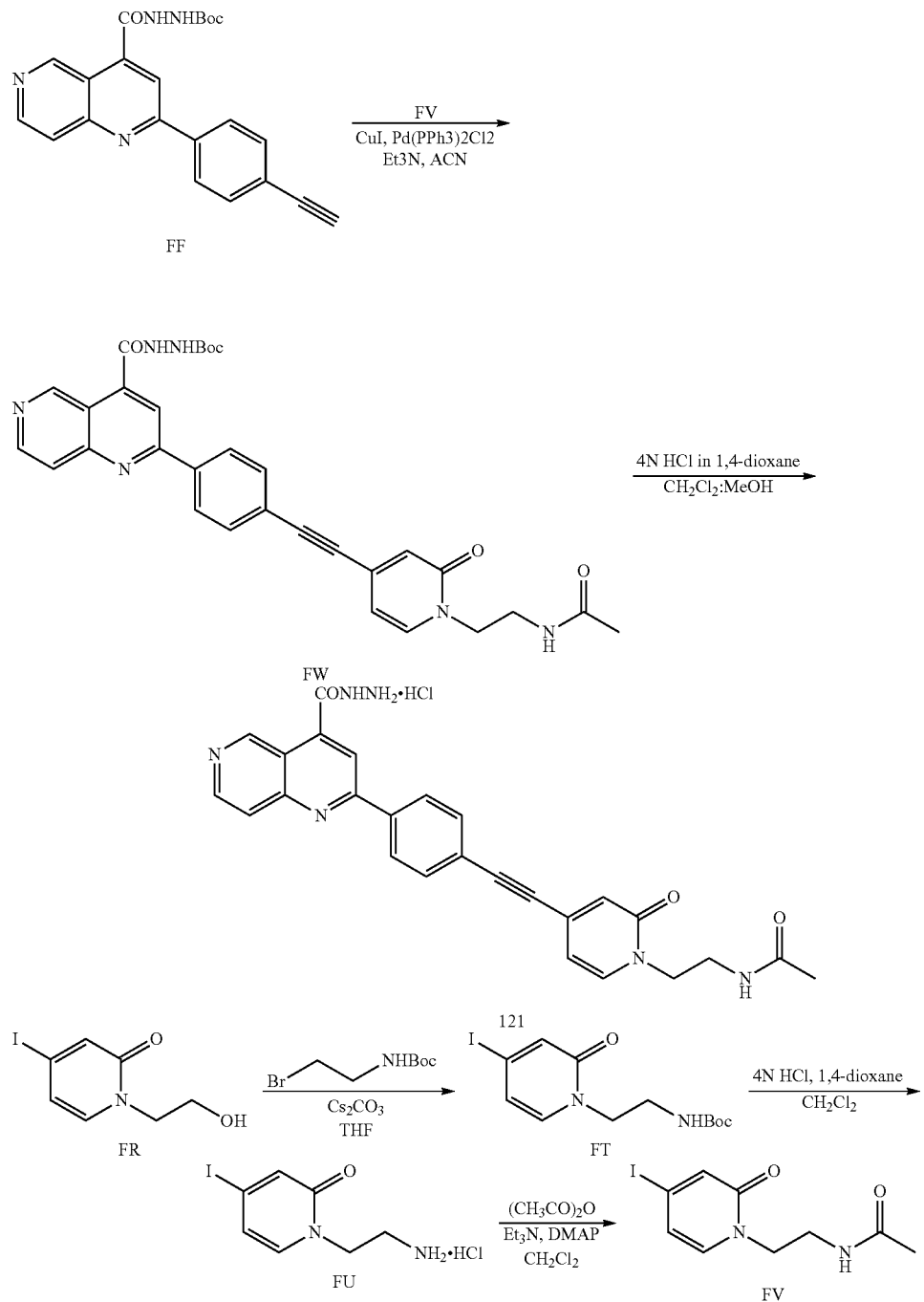

Example 121

N-(2-(4-((4-(4-(hydrazinecarbonyl)-1,6-naphthyridin-2-yl)phenyl)ethynyl)-2-oxopyridin-1(2H)-yl)ethyl)acetamide hydrochloride (121)

To a stirred solution of FR (1 g, 4.52 mmol) in THF (30 mL) under inert atmosphere was added cesium carbonate (1.27 g, 10.16 mmol) at RT. After stirring at RT for 15 min, tert-butyl (2-bromoethyl)carbamate was added to the reaction mixture and the reaction was heated to reflux and stirred for 12 h. After complete consumption of the starting material, the reaction mixture was filtered under vaccum and the filtrate was concentrated under reduced pressure to obtain the crude material. The crude material was purified by silica gel column chromatography eluting with 2-5% MeOH/$CH_2Cl_2$ to afford FT (750 mg, 45%) as an off-white solid. $^1$H NMR (500 MHz, DMSO-$d_6$): δ 7.22 (d, J=7.0 Hz, 1H), 6.89 (s, 1H), 6.86-6.84 (m, 1H), 6.54 (d, J=7.0 Hz, 1H), 3.84-3.82 (m, 2H), 3.19-3.17 (m, 2H), 1.33 (s, 9H).

To a stirred solution of FT (300 mg, 0.82 mmol) in $CH_2Cl_2$ (1 mL) under inert atmosphere was added 4N HCl solution in 1,4-dioxane (2 mL) at 0° C. After stifling for 2 h at RT, the volatiles were evaporated under reduced pressure to obtain the crude material, which was triturated with $CH_2Cl_2$ (2×7 mL) to afford FU (240 mg as an HCl salt) as an off-white solid. $^1$H NMR (400 MHz, DMSO-$d_6$): δ 7.44 (d, J=7.2 Hz, 1H), 7.07 (s, 1H), 6.87 (d, J=8.8 Hz, 1H), 6.64-6.62 (m, 2H), 3.84-3.82 (m, 2H), 3.19-3.08 (m, 2H).

To a stirred solution of FU (300 mg, 1.13 mmol) in $CH_2Cl_2$ (20 mL) under inert atmosphere were added triethylamine (286 mg, 2.83 mmol), p-dimethylaminopyridine (13.8 mg, 0.11 mmol) and acetic anhydride (138 mg, 1.35 mmol) at 0° C. After stirring for 2 h at RT, the reaction mixture was diluted with water (15 mL) and extracted with EtOAc (2×10 mL). The combined organic extracts were washed with water (15 mL), dried over sodium sulfate, filtered and concentrated under reduced pressure to obtain the crude residue. The crude residue was purified by silica gel column chromatography eluting with 3-5% MeOH/$CH_2Cl_2$ to afford FV (150 mg, 43%) as an off-white solid. $^1$H NMR (500 MHz, DMSO-$d_6$): δ 7.91 (br s, 1H), 7.26 (d, J=7.0 Hz, 1H), 6.91 (s, 1H), 6.54 (d, J=7.0 Hz, 1H), 3.86-3.84 (m, 2H), 3.30 (s, 2H), 1.76 (s, 3H).

To a stifled solution of FF (150 mg, 0.38 mmol) in $CH_3CN$ (30 mL) under inert atmosphere were added triethylamine (0.5 mL, 3.85 mmol) and FV (142 mg, 0.46 mmol) at 0° C. After the reaction was purged with argon for 30 min, copper iodide (7.3 mg, 0.03 mmol) and $Pd(PPh_3)_2Cl_2$ (27 mg, 0.03 mmol) were added. The reaction was then heated to reflux and stirred for 3 h. After complete consumption of the starting material, the reaction mass was cooled to RT and the volatiles were evaporated under reduced pressure to obtain the crude material, which was purified by silica gel column chromatography eluting with 8-10% MeOH/$CH_2Cl_2$ to afford FW (101 mg, 46%) as a pale yellow solid. $^1$H NMR (400 MHz, DMSO-$d_6$): δ 10.65 (br s, 1H), 9.71 (br s, 1H), 9.21 (br s, 1H), 8.84 (d, J=5.6 Hz, 1H), 8.45 (d, J=8.0 Hz, 2H), 8.33 (s, 1H), 8.05 (d, J=5.6 Hz, 1H), 7.94 (t, J=5.2 Hz, 1H), 7.82 (d, J=8.8 Hz, 2H), 7.57 (d, J=6.8 Hz, 1H), 6.61 (s, 1H), 6.35 (d, J=6.8 Hz, 1H), 3.91 (t, J=4.0 Hz, 2H), 3.31-3.30 (m, 2H), 1.78 (s, 3H), 1.49 (s, 9H).

To a stirred solution of FW (101 mg, 0.17 mmol) in $CH_2Cl_2$ (1 mL) under inert atmosphere was added 4N HCl solution in 1,4-dioxane (1 mL) at 0° C. After stifling for 4 h at RT, the volatiles were evaporated under reduced pressure to obtain the crude material. The crude material was triturated with $CH_2Cl_2$ (2×5 mL), $CH_3CN$ (2×5 mL) and pentane (2×5 mL) to afford 121 (12 mg as an HCl salt) as a yellow solid. $^1$H NMR (400 MHz, DMSO-$d_6$): δ 12.00 (br s, 1H), 9.74 (br s, 1H), 8.90 (br s, 1H), 8.55 (s, 1H), 8.49 (d, J=8.4 Hz, 2H), 8.17-8.15 (m, 1H), 7.99-7.97 (m, 1H), 7.85 (d, J=8.8 Hz, 2H), 7.58 (d, J=6.8 Hz, 1H), 6.61 (s, 1H), 6.34 (d, J=6.8 Hz, 1H), 3.94-3.91 (m, 2H), 3.34-3.33 (m, 2H), 1.78 (s, 3H). Mass: m/z 467.4 [M+1]$^+$. HPLC Purity: 97.84%

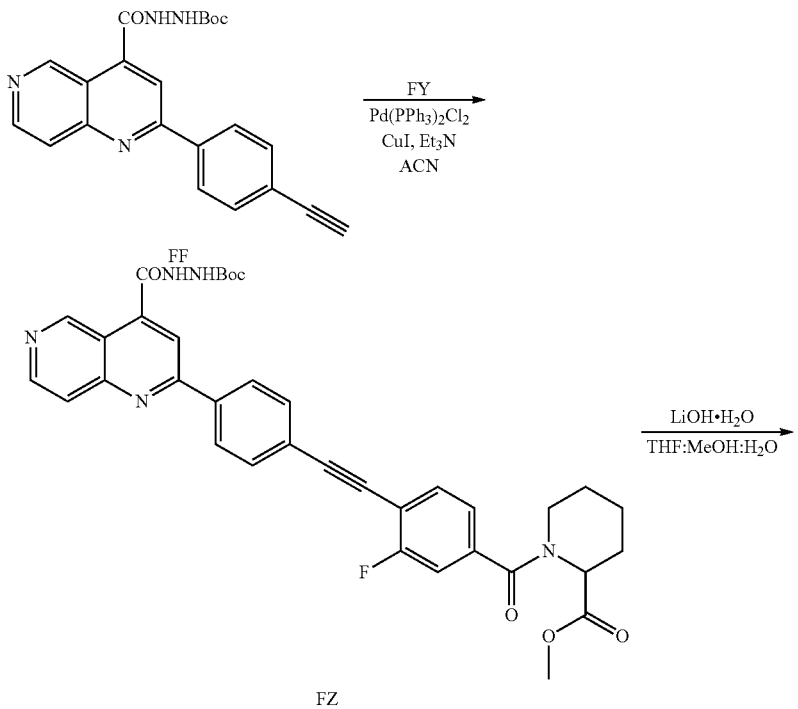

Scheme 45

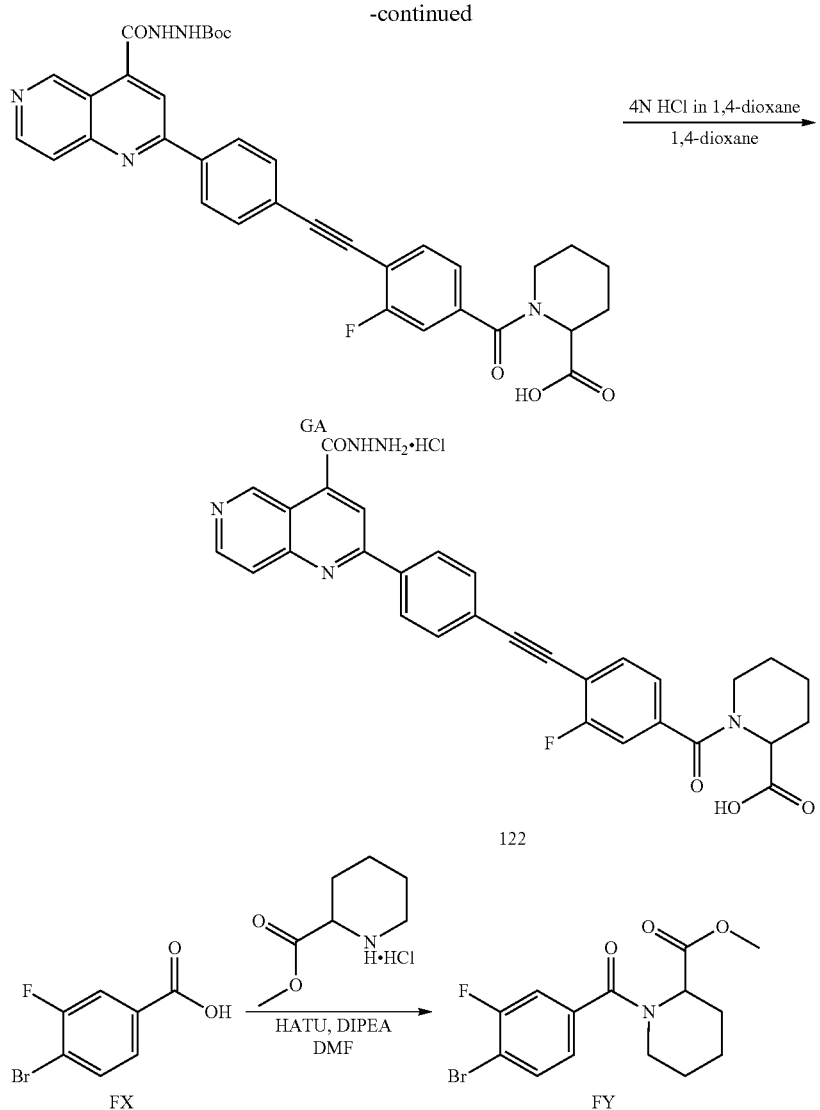

Example 122

2-(3-fluoro-4-((4-(4-(hydrazinecarbonyl)-1,6-naph-thyridin-2-yl)phenyl)ethynyl)benzoyl)cyclohexan-ecarboxylic acid hydrochloride (122)

To a stirred solution of 4-bromo-3-fluorobenzoic acid (FX; 500 mg, 2.28 mmol) in DMF (20 mL) under inert atmosphere were added methyl piperidine-2-carboxylate hydrochloride (282 mg, 3.24 mmol), HATU (1.3 g, 3.47 mmol) and diisopropylethylamine (1.68 mL, 9.12 mmol) at 0° C. The reaction was then warmed to RT and stirred for 14 h. After complete consumption of the starting material, the reaction mixture was diluted with water (15 mL) and extracted with EtOAc (2×20 mL). The combined organic extracts were washed with water (15 mL), brine (15 mL), dried over sodium sulfate, filtered and concentrated under reduced pressure to obtain the crude residue. The residue was purified by silica gel column chromatography (70-80% EtOAc/hexanes) to afford FY (500 mg, 77%) as a thick brown syrup. $^1$H NMR (400 MHz, CDCl$_3$): δ 7.64-7.58 (m, 1H), 7.22 (d, J=6.0 Hz, 1H), 7.10 (d, J=6.0 Hz, 1H), 3.80 (s, 3H), 3.60 (d, J=9.0 Hz, 1H), 3.29 (t, J=6.0 Hz, 1H), 2.38 (d, J=9.0 Hz, 1H), 1.80-1.72 (m, 2H), 1.66-1.60 (m, 2H), 1.48-1.38 (m, 2H).

To a stirred solution of FF (300 mg, 0.77 mmol) in CH$_3$CN (30 mL) under inert atmosphere were added triethylamine (1.1 mL, 7.70 mmol) and FY (2.2 g, 21.6 mmol) at 0° C. The reaction mixture was purged with argon for 30 min followed by the addition of copper iodide (14 mg, 0.07 mmol) and Pd(PPh$_3$)$_2$Cl$_2$ (54 mg, 0.07 mmol). After stirring at reflux for 3 h, the reaction was cooled to RT and filtered through a Celite pad. The filtrate was concentrated under reduced pressure to obtain the crude material, which was purified by silica gel column chromatography eluting with 2-4% MeOH/CH$_2$Cl$_2$ to afford FZ (59 mg, 11%) as an off-white solid. $^1$H NMR (400 MHz, DMSO-d$_6$): δ 10.65 (br s, 1H), 9.71 (br s, 1H), 9.29 (br s, 1H), 8.84 (d, J=5.2 Hz, 1H), 8.46 (d, J=8.0 Hz, 2H), 8.33 (br s, 1H), 8.05 (d, J=5.6 Hz, 1H), 7.84-7.79 (m, 3H), 7.40-7.29 (m, 2H), 5.27-5.25 (m, 1H), 4.46-4.44 (m, 1H), 3.75-3.73 (m, 4H), 3.51-3.48 (m, 1H), 3.17-3.15 (m, 1H), 1.72-1.69 (m, 2H), 1.49 (s, 12H).

To a stirred solution of FZ (60 mg, 0.09 mmol) in THF:MeOH:H$_2$O (4:1:1; 12 mL) was added lithium hydroxide monohydrate (9.6 mg, 230.4 mmol) at 0° C. The reaction was warmed to RT and stirred for 4 h. After consumption of the starting material, the volatiles were evaporated under reduced pressure to obtain the crude residue, which was diluted with water (10 mL) and acidified with glacial acetic acid (pH~4) (10 mL) to obtain a solid. The solid was filtered, dried and triturated with isopropyl alcohol:pentane (1:4, 2×5 mL) to afford crude GA (45 mg) as a pale yellow solid. $^1$H NMR (400 MHz, DMSO-$d_6$): δ 13.11 (br s, 1H), 10.66 (br s, 1H), 9.71 (br s, 1H), 9.29 (br s, 1H), 8.86-8.84 (m, 1H), 8.46-8.44 (m, 2H), 8.33 (s, 1H), 8.06-8.05 (m, 1H), 7.84-7.82 (m, 3H), 7.38-7.36 (m, 2H), 5.17-5.14 (m, 1H), 4.32-4.31 (m, 1H), 3.79-3.76 (m, 1H), 2.25-2.24 (m, 2H), 1.69-1.66 (m, 3H), 1.69 (s, 9H), 1.50-1.48 (m, 2H).

To a stirred solution of GA (45 mg, 0.07 mmol) in 1,4-dioxane (10 mL) under inert atmosphere was added 4N HCl in 1,4-dioxane (1 mL) at 0° C. After stifling for 2 h at RT, the volatiles were evaporated under reduced pressure to obtain the crude residue. The crude residue was triturated with isopropyl alcohol:CH$_3$CN (1:1, 2×5 mL) to afford 122 (30 mg as HCl salt) as an orange solid. $^1$H NMR (400 MHz, DMSO-$d_6$): δ 11.59 (br s, 1H), 9.69 (s, 1H), 8.85 (d, J=6.0 Hz, 1H), 8.48 (d, J=10.0 Hz, 3H), 8.10 (d, J=6.0 Hz, 1H), 7.85 (d, J=7.6 Hz, 2H), 7.78-7.77 (m, 1H), 7.39-7.37 (m, 1H), 7.29-7.28 (m, 1H), 5.18-5.16 (m, 1H), 4.32-4.30 (m, 2H), 3.22-3.19 (m, 1H), 2.22-2.20 (m, 2H), 1.68-1.67 (m, 2H), 1.56-1.54 (m, 1H), 1.47-1.45 (m, 1H), 1.31-1.29 (m, 1H). MS (ESI): m/z 538.4 [M+1]$^+$. HPLC Purity: 90.87%

Scheme 46

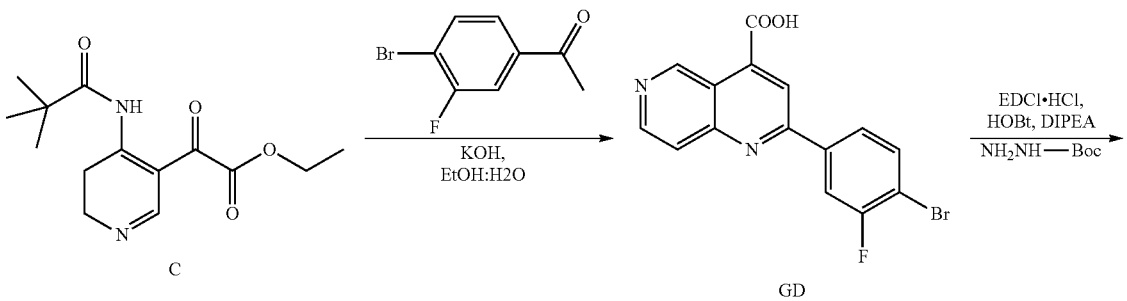

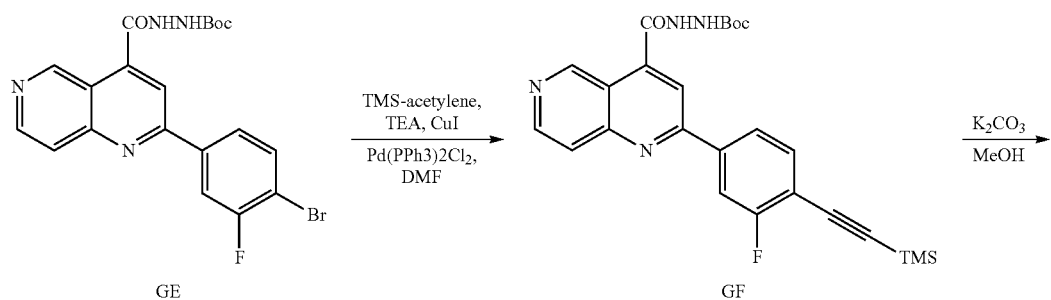

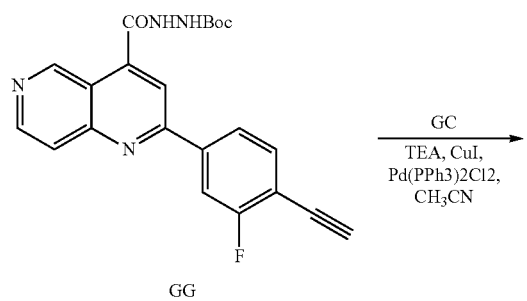

-continued
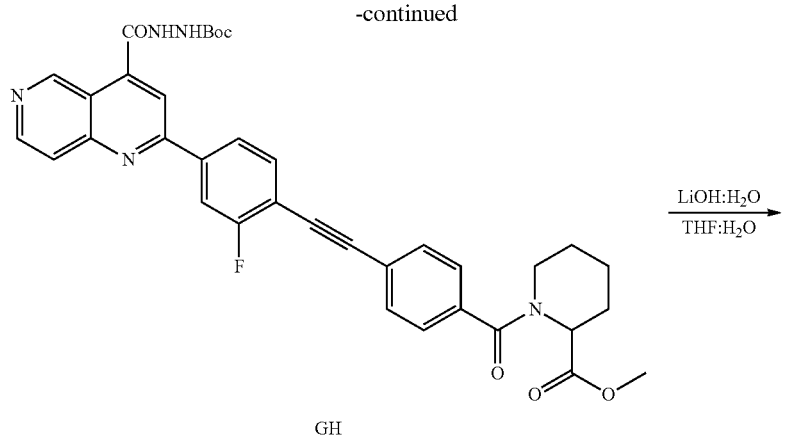
GH
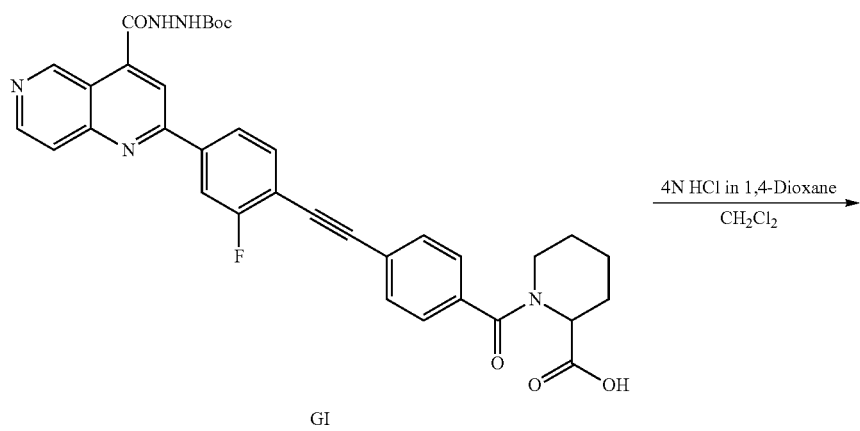
GI
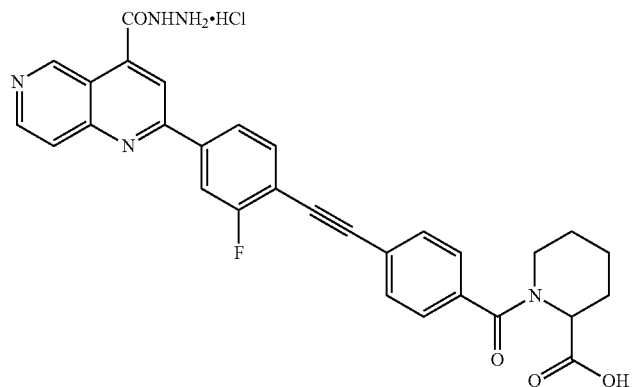
123
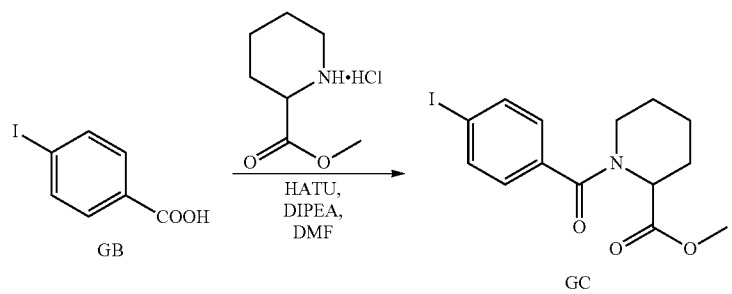

Example 123

1-(4-((2-fluoro-4-(4-(hydrazinecarbonyl)-1,6-naph-thyridin-2-yl)phenyl)ethynyl)benzoyl) piperidine-2-carboxylic acid hydrochloride (123)

To a stirred solution of 4-iodobenzoic acid (GB; 500 mg, 2.01 mmol) in DMF (30 mL) under inert atmosphere were added HATU (1.57 g, 4.03 mmol), diisopropylethylamine (1.1 mL, 6.04 mmol) and methyl piperidine-2-carboxylate hydrochloride (434 mg, 2.41 mmol) at 0° C. After stirring for 16 h at RT, the reaction mass was diluted with water (25 mL) and extracted with EtOAc (2×25 mL). The combined organic extracts were washed with water (20 mL), brine (20 mL), dried over sodium sulfate, filtered and concentrated under reduced pressure to obtain the crude residue. The crude residue was purified by silica gel column chromatography eluting with 30-50% EtOAc/exanes to afford GC (650 mg, 86%) as a pale yellow sticky solid. $^1$H NMR (500 MHz, CDCl$_3$): δ 7.76 (d, J=8.0 Hz, 2H), 7.18-7.12 (m, 2H), 5.47 (br s, 1H), 3.78-3.75 (m, 3H), 3.59 (d, J=13.0 Hz, 1H), 3.24 (t, J=13.0 Hz, 1H), 2.34 (d, J=12.5 Hz, 1H), 1.76 (d, J=11.0 Hz, 2H), 1.40-1.30 (m, 3H). MS (ESI): m/z 374 [M+1]$^+$ To a stirred solution of ethyl 2-oxo-2-(4-pivalamido-5,6-dihydropyridin-3-yl)acetate (C; 2 g, 7.19 mmol) in ethanol-water (1:1, 40 mL) was added potassium hydroxide (1.44 g, 28.70 mmol) at RT. After the reaction was heated at 90° C. for 2 h, the reaction mixture was cooled to RT at which point 1-(4-bromo-3-fluorophenyl)ethanone (1.9 g, 8.63 mmol) was added. The resulting reaction mixture was heated at reflux for 16 h. After complete consumption of the starting material, the reaction mass was cooled to RT, diluted with water (40 mL), and washed with CH$_2$Cl$_2$ (2×30 mL). The pH of the aqueous layer was adjusted to 4 with glacial acetic acid. The precipitate was filtered, washed with water, dried, and co distilled with toluene (2×15 mL) to afford GD (1.9 g, 83%) as a pale yellow solid. $^1$H NMR (500 MHz, DMSO-d$_6$): δ 10.01 (s, 1H), 8.83 (d, J=6.0 Hz, 1H), 8.61 (s, 1H), 8.33 (d, J=9.0 Hz, 1H), 8.16 (d, J=8.5 Hz, 1H), 8.04 (d, J=6.0 Hz, 1H), 7.94 (t, J=9.0 Hz, 1H). MS: m/z 346 [M+1]$^+$ To a stirred solution of GD (2 g, 5.78 mmol) in DMF (30 mL) under inert atmosphere were added EDCI.HCl (2.2 g, 11.56 mmol), HOBt (1.56 g, 11.56 mmol), diisopropylethylamine (3.2 mL, 17.34 mmol) and Boc-hydrazine (2.3 g, 17.34 mmol) at 0° C. The reaction was warmed to RT and stirred for 16 h. After complete consumption of the starting material, the reaction mass was diluted with water (30 mL) and extracted with EtOAc (2×30 mL). The combined organic extracts were washed with water (30 mL), brine (20 mL), dried over sodium sulfate, filtered and concentrated under reduced pressure to obtain the crude residue. The residue was purified by silica gel column chromatography eluting with 2-5% MeOH/CH$_2$Cl$_2$ to afford GE (1.8 g, 67%) as a pale yellow solid. $^1$H NMR (500 MHz, DMSO-d$_6$): δ 10.63 (s, 1H), 9.73 (br s, 1H), 9.31 (br s, 1H), 8.84 (d, J=5.5 Hz, 1H), 8.36 (br s, 2H), 8.18 (d, J=7.0 Hz, 1H), 8.05 (d, J=6.0 Hz, 1H), 7.96 (t, J=8.5 Hz, 1H), 1.49 (s, 9H). MS (ESI): m/z 462 [M+1]$^+$ To a stirred solution of GE (1 g, 2.16 mmol) in DMF (15 mL) under inert atmosphere were added triethylamine (3.2 mL, 21.60 mmol) and TMS-acetylene (2.2 g, 21.6 mmol) at RT. The reaction mixture was cooled to 0° C. and purged with argon for 30 min. Then copper iodide (41 mg, 0.21 mmol) and Pd(PPh$_3$)$_2$Cl$_2$ (152 mg, 0.21 mmol) were added to the reaction mass and the reaction was heated to 80° C. for 16 h. The reaction was monitored by TLC. After complete consumption of the starting material, the reaction mass was cooled to RT and filtered through a Celite pad. The filtrate was diluted with water (25 mL), extracted with EtOAc (2×30 mL), and the combined organic extracts were washed with water (20 mL), brine (20 mL), dried over sodium sulfate, filtered and concentrated under reduced pressure to obtain the crude material. The crude material was purified by silica gel column chromatography eluting with 2-5% MeOH/CH$_2$Cl$_2$ to afford GF (980 mg, with a minor impurity) as a brown solid. $^1$H NMR (500 MHz, DMSO-d$_6$): δ 10.63 (br s, 1H), 9.74 (br s, 1H), 9.31 (br s, 1H), 8.85 (br s, 1H), 8.36 (br s, 1H), 8.31-8.23 (m, 1H), 8.06 (br s, 1H), 7.78-7.77 (m, 1H), 7.62-7.55 (m, 1H), 1.49 (s, 9H), 0.28 (s, 9H). MS (ESI): m/z 479 [M+1]$^+$ To a stirred solution of GF (1 g, 2.09 mmol) in methanol (20 mL) under inert atmosphere was added potassium carbonate (1.4 g, 10.46 mmol) at 0° C. The reaction was warmed to RT and stirred for 2 h. After complete consumption of the starting material, the volatiles were evaporated under reduced pressure. The residue was diluted with water (30 mL), extracted with EtOAc (2×30 mL), and the combined organic layers were washed with water (20 mL), brine (20 mL), dried over sodium sulfate, filtered and concentrated under reduced pressure to obtain the crude material. The crude material was purified by silica gel column chromatography eluting with 5-10% MeOH/CH$_2$Cl$_2$ to afford GG (812 mg, 88%) as a brown solid. $^1$H NMR (500 MHz, DMSO-d$_6$): δ 10.62 (br s, 1H), 9.72 (br s, 1H), 9.30 (br s, 1H), 8.84 (d, J=6.0 Hz, 1H), 8.40-8.23 (m, 3H), 8.04 (d, J=5.5 Hz, 1H), 7.78 (t, J=8.5 Hz, 1H), 4.72 (s, 1H), 1.48 (s, 9H). MS (ESI): m/z 407 [M+1]$^+$ To a stirred solution of GG (300 mg, 0.73 mmol) in CH$_3$CN (20 mL) under inert atmosphere were added triethylamine (1.07 mL, 7.30 mmol) and GC (330 mg, 0.88 mmol) at RT. After the reaction was purged with argon for 30 min, copper iodide (14.1 mg, 0.07 mmol) and Pd(PPh$_3$)$_2$Cl$_2$ (54.3 mg, 0.07 mmol) were added. The reaction mixture was then heated at 80° C. for 4 h. After complete consumption of the starting material, the reaction mass was cooled to RT and filtered through a Celite pad. The filtrate was diluted with water (20 mL), extracted with EtOAc (2×20 mL), and the combined organic extracts were washed with water (20 mL), brine (20 mL), dried over sodium sulfate, filtered and concentrated under reduced pressure to obtain the crude residue. The crude material was purified by silica gel column chromatography eluting with 2-4% MeOH/CH$_2$Cl$_2$ to afford GH (17.0 mg, 35%) as a yellow solid. $^1$H NMR (400 MHz, DMSO-d$_6$): δ 10.64 (br s, 1H), 9.74 (br s, 1H), 9.31 (br s, 1H), 8.85 (d, J=5.6 Hz, 1H), 8.39-8.30 (m, 3H), 8.06 (d, J=6.0 Hz, 1H), 7.97-7.87 (m, 2H), 7.48-7.42 (m, 2H), 5.28 (br s, 1H), 3.74-3.66 (m, 3H), 2.22-2.18 (m, 2H), 1.72-1.68 (m, 4H), 1.60-1.56 (m, 2H), 1.48 (s, 9H), 1.43-1.40 (m, 1H). MS (ESI): m/z 650 [M−1]$^+$ To a stirred solution of GH (100 mg, 0.15 mmol) in THF:H$_2$O (1:1, 5 mL) was added lithium hydroxide monohydrate (69 mg, 1.50 mmol) at 0° C. After stifling at RT for 4 h, the volatiles were evaporated under reduced pressure. The resulting residue was diluted with water (15 mL) and extracted with diethyl ether (2×20 mL). The pH of the aqueous layer was adjusted with glacial acetic acid to~4. The precipitate was filtered, dried and co-distilled with toluene (2×5 mL) to afford GI (60 mg, 61%) as a pale yellow solid. $^1$H NMR (400 MHz, DMSO-d$_6$): δ 13.00 (br s, 1H), 10.64 (br s, 1H), 9.74 (br s, 1H), 9.32 (br s, 1H), 8.86 (br s, 1H), 8.39-8.30 (m, 3H), 8.08-8.06 (m, 1H), 7.91-7.89 (m, 1H), 7.72-7.62 (m, 2H), 7.55-7.45 (m, 2H), 5.18-5.17 (m, 1H), 4.39-4.27 (m, 1H), 3.45-3.41 (m, 1H), 3.21-3.16 (m, 1H), 2.20-2.17 (m, 1H), 1.77-1.75 (m, 2H), 1.68-1.57 (m, 2H), 1.41 (s, 9H). MS (ESI): m/z 636 [M−1]+

To a stirred solution of GI (40 mg, 0.06 mmol) in CH$_2$Cl$_2$ (2 mL) under inert atmosphere was added 4N HCl solution in 1,4-dioxane (1 mL) at 0° C. After stifling for 2 hr at RT, the volatiles were evaporated under reduced pressure to obtain the crude material. The crude material was triturated with isopropyl alcohol:CH$_3$CN (2×5 mL) to afford 123 (30 mg as an HCl salt) as a brown solid. $^1$H NMR (400 MHz, DMSO-d$_6$): δ 12.10 (br s, 1H), 9.91-9.86 (m, 1H), 9.06-9.04 (m, 1H), 8.61 (s, 1H), 8.40-8.33 (m, 2H), 8.21 (br s, 1H), 7.91 (t, J=7.0 Hz, 1H), 7.70-7.68 (m, 2H), 7.46-7.41 (m, 3H), 5.18-5.16 (m, 1H), 4.37-4.26 (m, 1H), 3.43-3.41 (m, 1H), 3.20-3.13 (m, 1H), 2.80-2.72 (m, 1H), 2.21-2.18 (m, 1H), 1.70-1.68 (m, 3H), 1.36-1.29 (m, 2H). MS (ESI): m/z 575 [M+1]+. HPLC Purity: 95.51%.

Scheme 47

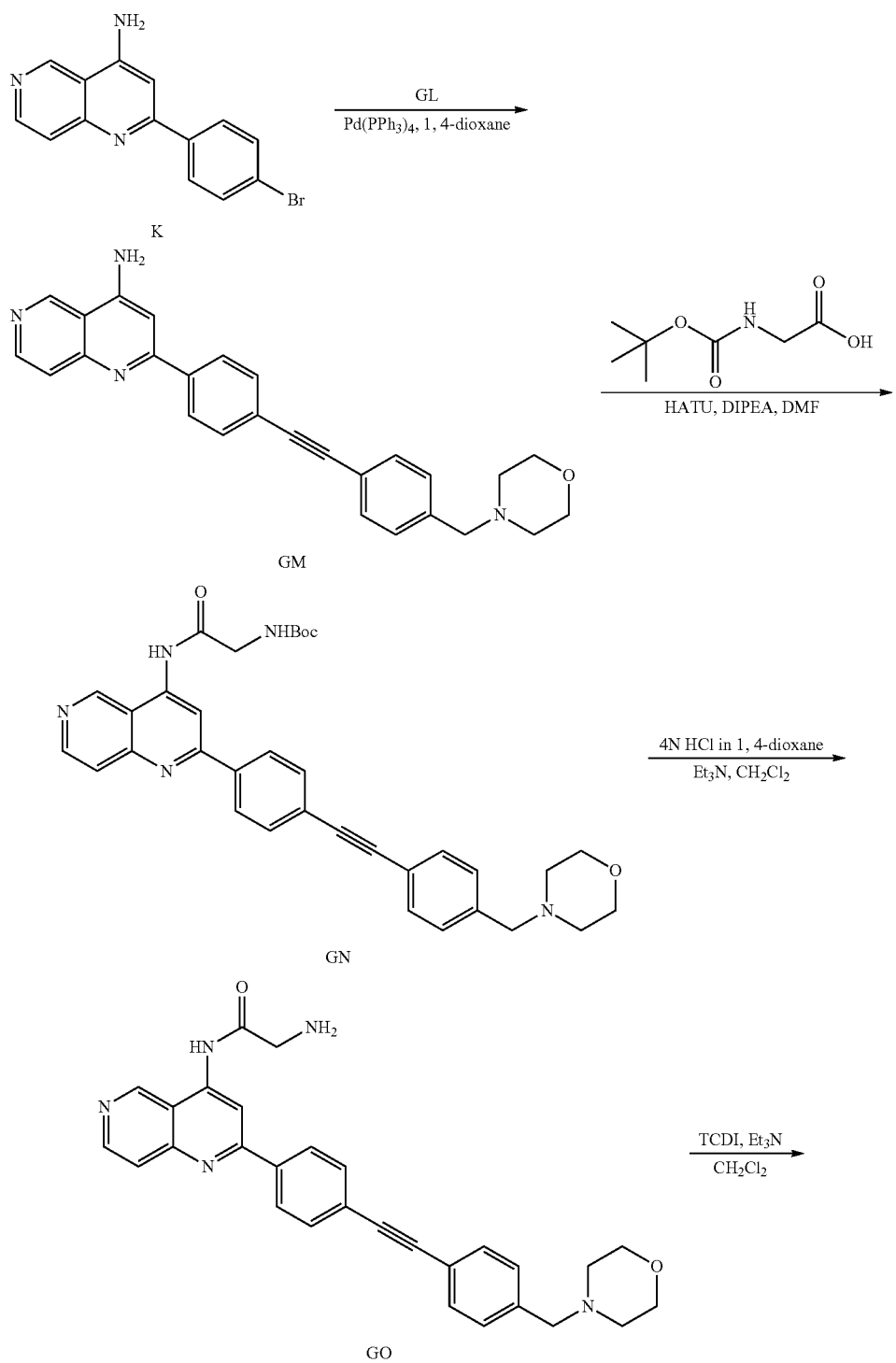

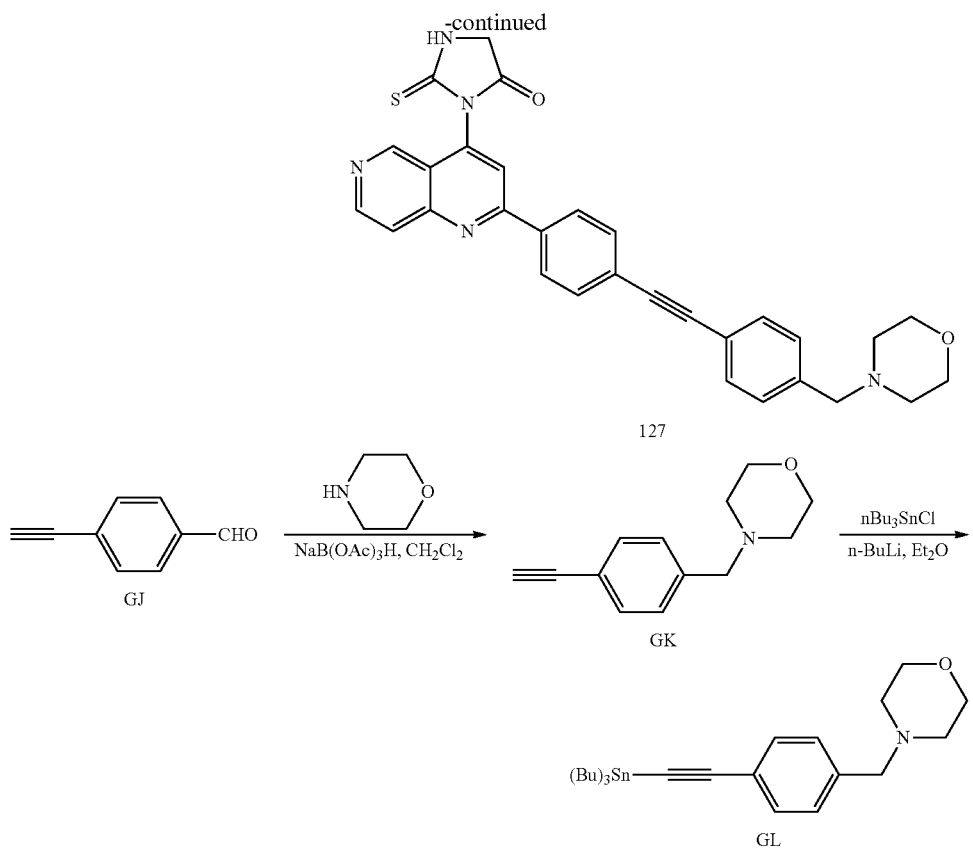

Example 127

3-(2-(4-((4-(morpholinomethyl)phenyl)ethynyl)phenyl)-1,6-naphthyridin-4-yl)-2-thioxoimidazolidin-4-one (127)

To a stirred solution of 4-ethynylbenzaldehyde (GJ; 1 g, 7.69 mmol) in CH$_2$Cl$_2$ (50 mL) under inert atmosphere were added morpholine (1.47 g, 16.90 mmol) and sodium triacetoxyborohydride (1.95 g, 9.20 mmol) at 0° C. After stirring at RT for 48 h, the reaction mixture was neutralized with a saturated NaHCO$_3$ solution (25 mL) and the compound was extracted with CH$_2$Cl$_2$ (2×30 mL). The combined organic extracts were washed with water (25 mL), brine (25 mL), dried over sodium sulfate, filtered and concentrated under reduced pressure to obtain the crude material. The crude material was purified via flash column chromatography eluting with 3% MeOH/CH$_2$Cl$_2$ to afford GK (600 mg, 39%) as a sticky solid. $^1$H NMR (500 MHz, CDCl$_3$): δ 7.44 (d, J=8.0 Hz, 2H), 7.29 (d, J=8.0 Hz, 2H), 3.71-3.66 (m, 4H), 3.48 (s, 2H), 3.05 (s, 1H), 2.44-2.42 (m, 4H).

To a stirred solution of GK (200 mg, 0.99 mmol) in dry ether (20 mL) under inert atmosphere was added n-butyl lithium (1.6M in hexane) (76.4 mg, 1.19 mmol) at 0° C. The reaction was stirred at RT for 1 h at which point tributyl tin chloride (485 mg, 1.49 mmol) was added and the reaction was stirred for 16 h. After complete consumption of the starting material; the reaction mixture was quenched with an ammonium chloride solution (20 mL) and was extracted with EtOAc (2×25 mL). The combined organic extracts were washed with water (20 mL), brine (20 mL), dried over sodium sulfate, filtered and concentrated under reduced pressure to obtain crude GL (600 mg) as a pale brown liquid. LCMS: 19.37%, MS (ESI): 491.8 [M+1]$^+$ To a stirred solution of 2-(4-bromophenyl)-1,6-naphthyridin-4-amine K (2.5 g, 8.36 mmol) in 1,4-dioxane (100 mL) under inert atmosphere was added GL (10.26 g, 20.89 mmol). After the reaction was purged under argon for 10 min, Pd(PPh$_3$)$_4$ (965 mg, 0.83 mmol) was added and the reaction was purged under argon for an additional 10 min. The reaction was then heated to reflux and stirred for 4 h. After complete consumption of the starting material, the volatiles were removed under reduced pressure to obtain the crude residue, which was purified through silica gel column chromatography eluting with 10% MeOH/CH$_2$Cl$_2$ to afford GM (2.9 g, 83%) as a pale yellow solid. $^1$H NMR (500 MHz, DMSO-d$_6$): δ 9.53 (s, 1H), 8.56-8.55 (m, 1H), 8.15 (d, J=8.0 Hz, 2H), 7.69 (d, J=8.0 Hz, 2H), 7.64 (d, J=5.0 Hz, 1H), 7.55 (d, J=7.5 Hz, 2H), 7.38 (d, J=7.5 Hz, 4H), 7.22 (s, 1H), 3.58 (s, 3H), 3.50 (s, 3H), 2.36 (s, 4H).

To a stirred solution of GM (120 mg, 0.28 mmol) in DMF (2 mL) under inert atmosphere were added 2-((tert-butoxycarbonyl)amino)acetic acid (100 mg, 0.57 mmol), diisopropylethyl amine (224 mg, 1.72 mmol) and HATU (440 mg, 1.12 mmol) at RT and the reaction was stirred for 12 h. After complete consumption of the starting material, the reaction mass was diluted with water (15 mL) and was extracted with EtOAc (2×20 mL). The combined organic extracts were washed with water (20 mL), brine (20 mL), dried over sodium sulfate, filtered and concentrated under reduced pressure to obtain the crude material. The crude material was purified through 5% MeOH/CH$_2$Cl$_2$ to afford GN (60 mg, 36%) as a yellow solid. $^1$H NMR (500 MHz, DMSO-d$_6$): δ 10.64 (s, 1H), 9.76 (s, 1H), 8.84 (s, 1H), 8.77-8.76 (m, 1H), 8.25 (d, J=7.5 Hz, 2H), 7.92 (d, J=5.5 Hz, 2H), 7.57 (d, J=7.5 Hz, 2H), 7.39 (d, J=7.5 Hz, 3H), 7.24-7.22 (m, 1H), 4.06-4.03 (m, 2H), 3.61-3.58 (m, 4H), 3.51 (s, 2H), 2.38-2.36 (m, 4H), 1.38 (s, 9H).

To a stirred solution of GN (400 mg, 0.69 mmol) in $CH_2Cl_2$ (10 mL) under inert atmosphere was added a 4N HCl solution in 1,4-dioxane (1 mL) at 0° C. After stirring at RT for 3 h, the volatiles were evaporated under reduced pressure to obtain the crude material. The crude material was triturated with diisopropyl ether (2×10 mL) to obtain 350 mg of material. The material was dissolved in $CH_2Cl_2$ followed by the addition of triethyl amine (0.5 mL). The obtained solid was filtered and dried under reduced pressure to afford GO (100 mg, 30%) as a yellow solid. $^1$H NMR (500 MHz, DMSO-$d_6$): δ 11.74 (br s, 1H), 11.40 (br s, 1H), 10.24 (br s, 1H), 8.94 (s, 1H), 8.85 (d, J=6.0 Hz, 1H), 8.41 (br s, 2H), 8.29 (d, J=8.0 Hz, 2H), 8.19 (br s, 1H), 7.83 (d, J=8.0 Hz, 2H), 7.70 (s, 3H), 4.37 (s, 3H), 4.20-4.19 (m, 2H), 3.94 (d, J=12.0 Hz, 2H), 3.81 (t, J=11.5 Hz, 2H), 3.56 (s, 1H), 3.23 (d, J=12.0 Hz, 2H).

To a stirred solution of GO (100 mg, 0.20 mmol) in $CH_2Cl_2$ (10 mL) under inert atmosphere were added triethylamine (63.5 mg, 0.62 mmol) and TCDI (56 mg, 0.31 mmol) at 0° C. and the reaction mixture was stirred for 30 min. After stirring for 1 h at RT, the reaction mass was diluted with water (10 mL) and the product was extracted with $CH_2Cl_2$ (2×20 mL). The combined organic extracts were washed with water (10 mL), brine (10 mL), dried over sodium sulfate, filtered and concentrated under reduced pressure to obtain the crude material. The crude material was purified through silica gel column chromatography eluting with 3% MeOH/$CH_2Cl_2$ and was further purified through preparative HPLC to afford 127 (5.4 mg, 5%) as a yellow solid. $^1$H NMR (500 MHz, DMSO-$d_6$): δ 10.80 (br s, 1H), 11.40 (s, 1H), 8.82 (d, J=8.0 Hz, 1H), 8.42 (s, 1H), 8.38 (d, J=8.4 Hz, 2H), 8.04 (d, J=8.0 Hz, 1H), 7.80 (d, J=8.4 Hz, 2H), 7.56 (d, J=8.4 Hz, 2H), 7.40 (d, J=8.4 Hz, 2H), 4.60 (d, J=12.0 Hz, 1H), 4.44 (d, J=12.0 Hz, 1H), 3.62-3.58 (m, 4H), 3.52 (s, 2H), 2.38-2.32 (m, 4H). MS (ESI): m/z 520 [M+1]$^+$. HPLC Purity: 96.48%

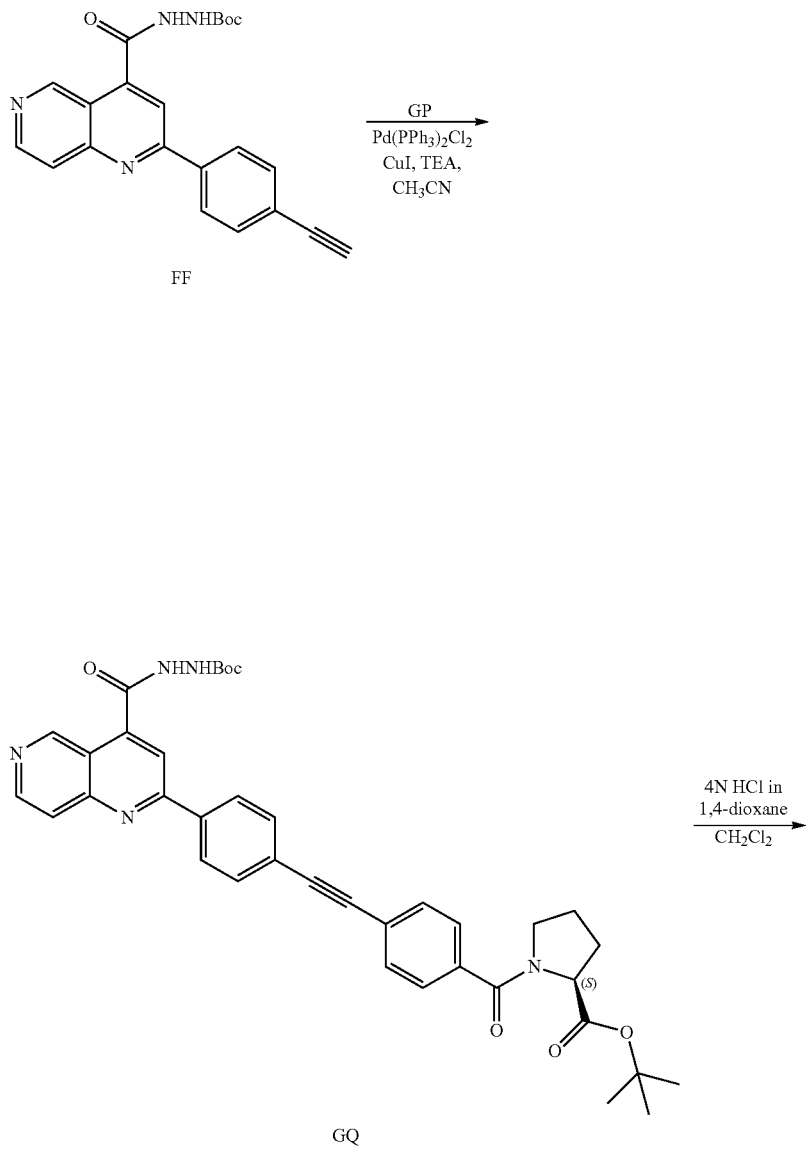

Scheme 48

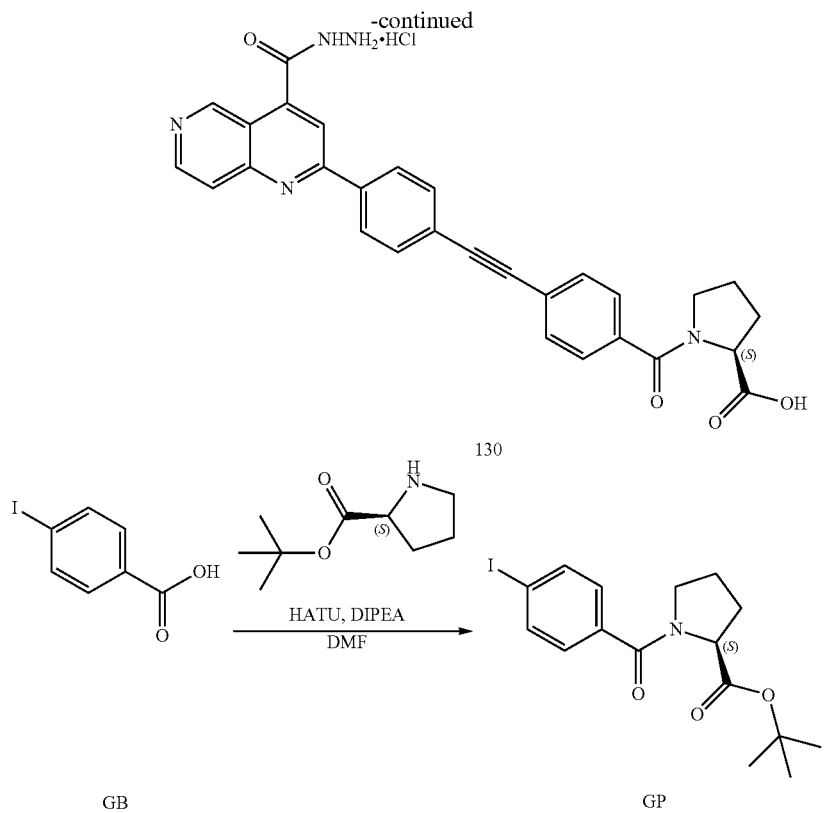

Example 130

(S)-1-(4-((4-(4-(hydrazinecarbonyl)-1,6-naphthyridin-2-yl)phenyl)ethynyl)benzoyl)pyrrolidine-2-carboxylic acid hydrochloride (130)

To a stirred solution of 4-iodobenzoic acid (GB; 500 mg, 2.01 mmol) in DMF (10 mL) under inert atmosphere were added HATU (1.17 g, 3.02 mmol) and diisopropylethylamine (1.08 mL, 6.04 mmol) at RT and the resulting reaction mixture was stirred for 15 min. After cooling to 0° C., (S)-tert-butyl pyrrolidine-2-carboxylate (379.6 mg, 2.21 mmol) was added to the reaction mass The reaction was stirred at RT for 24 h. After complete consumption of the starting material, the reaction mixture was diluted with ice cold water (25 mL) and the compound was extracted with EtOAc (2×25 mL). The combined organic extracts were washed with water (25 mL), dried over sodium sulfate, filtered and concentrated under reduced pressure to obtain the crude material. The crude material was purified through silica gel column chromatography eluting with 3% MeOH/CH$_2$Cl$_2$ to afford GP (700 mg, 87%) as an off-white solid. $^1$H NMR (400 MHz, CDCl$_3$): δ 7.76-7.70 (m, 2H), 7.29 (d, J=8.0 Hz, 2H), 4.54-4.51 (m, 1H), 2.80 (s, 1H), 2.33-2.21 (m, 1H), 2.04-1.94 (m, 3H), 1.90-1.84 (m, 1H), 1.49 (s, 9H).

To a stirred solution of tert-butyl 2-(2-(4-ethynylphenyl)-1,6-naphthyridine-4-carbonyl)hydrazine carboxylate FF (150 mg, 0.38 mmol) in CH$_3$CN (10 mL) under inert atmosphere were added GP (232 mg, 0.57 mmol), triethylamine (0.54 mL, 3.86 mmol), copper iodide (7.3 mg, 0.038mmol) and Pd(PPh$_3$)$_2$Cl$_2$ (27.1 mg, 0.038 mmol) at RT. After stirring at reflux for 4 h, the volatiles were evaporated under reduced pressure to obtain the crude material. The crude material was purified through silica gel column chromatography eluting with 3-5% MeOH/CH$_2$Cl$_2$ to afford GQ (50 mg, 20%) as a yellow solid. $^1$H NMR (400 MHz, DMSO-d$_6$): δ 10.66 (s, 1H), 9.80 (br s, 1H), 9.30 (s, 1H), 8.86 (br s, 1H), 8.45-8.34 (m, 3H), 8.26-7.79 (m, 2H), 7.78-7.41 (m, 5H), 4.40-4.36 (m, 1H), 3.65-3.49 (m, 2H), 3.10-3.07 (m, 1H), 2.30-2.26 (m, 1H), 1.90-1.83 (m, 2H), 1.49 (s, 9H), 1.43 (s, 9H).

To a stirred solution of GQ (50 mg, 0.07 mmol) in CH$_2$Cl$_2$ (4 mL) under inert atmosphere was added 4N HCl solution in 1,4-dioxane (0.5 mL) at 0° C. After stifling at RT for 4 h, the volatiles were evaporated under reduced pressure to obtain the crude material. The crude material was triturated with CH$_3$CN (2×5 mL) and was further purified through preparative chiral HPLC to afford 130 (10 mg as an HCl salt) as a yellow solid. $^1$H NMR (400 MHz, DMSO-d$_6$): δ 12.40 (br s, 1H), 9.80 (br s, 1H), 8.95 (br s, 1H), 8.62 (s, 1H), 8.50 (d, J=8.4 Hz, 2H), 8.22 (br s, 1H), 7.85 (d, J=8.0 Hz, 2H), 7.79 (d, J=8.0 Hz, 1H), 7.60 (d, J=8.0 Hz, 2H), 4.44-4.41 (m, 1H), 3.65-3.51 (m, 3H), 2.30-2.19 (m, 2H), 1.91-1.87 (m, 3H), 1.03 (d, J=6.0 Hz, 2H). MS (ESI): m/z 506.4 [M+1]$^+$. HPLC Purity: 90.68%

Scheme 49
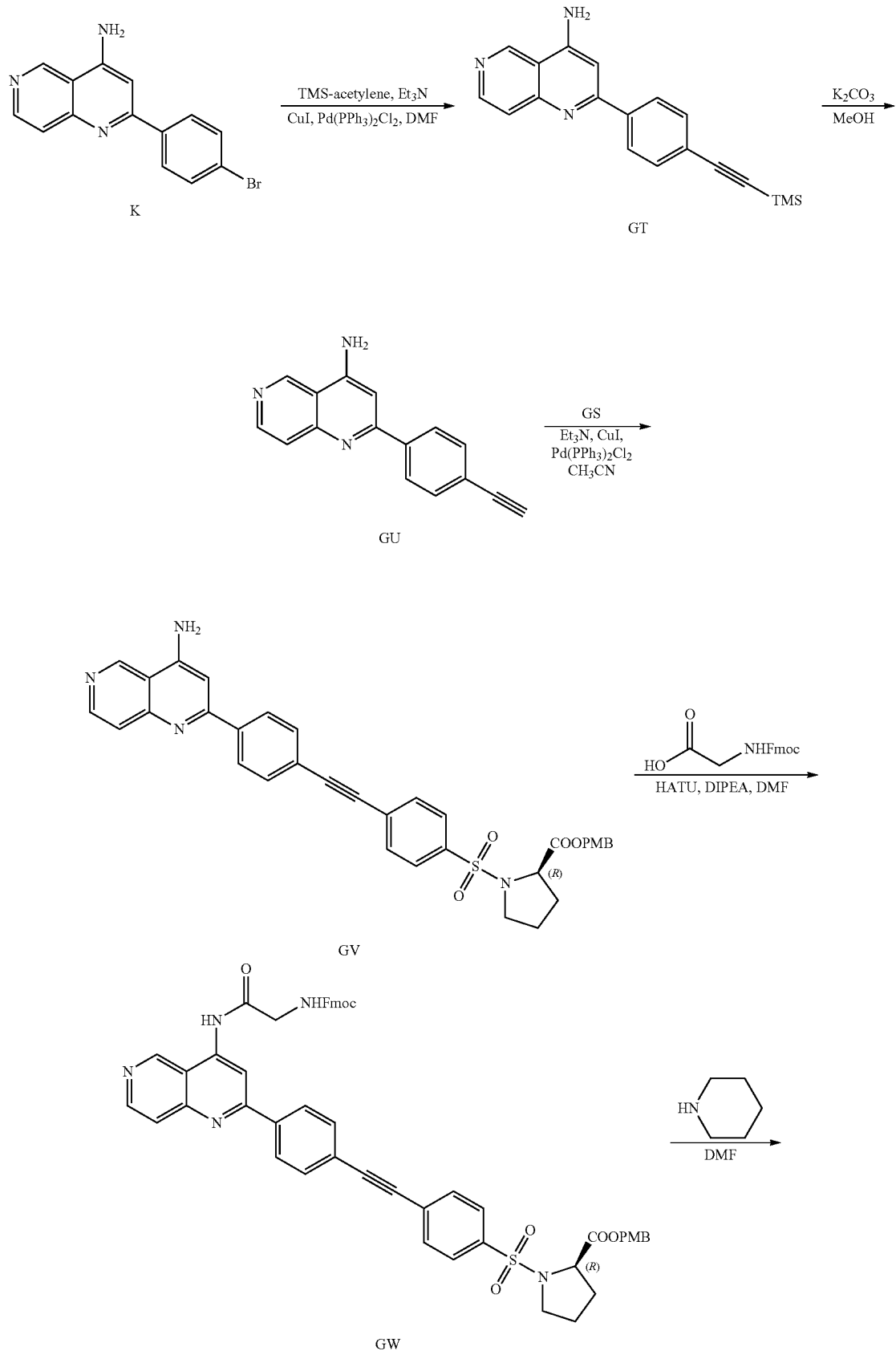

-continued
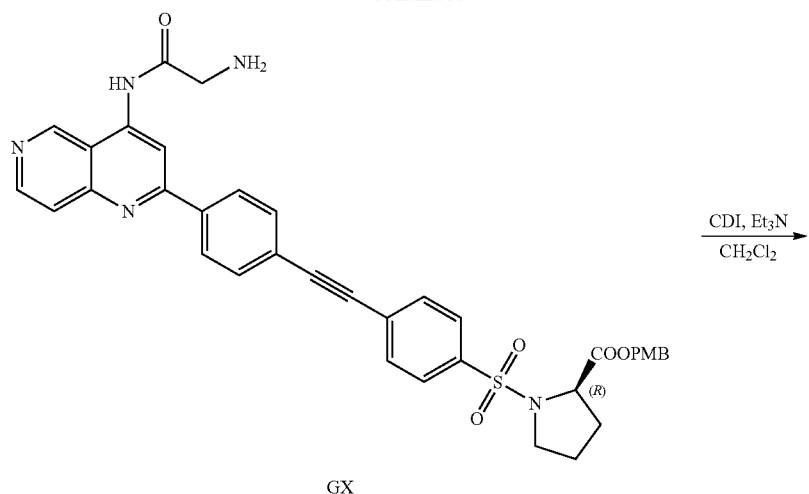
GX
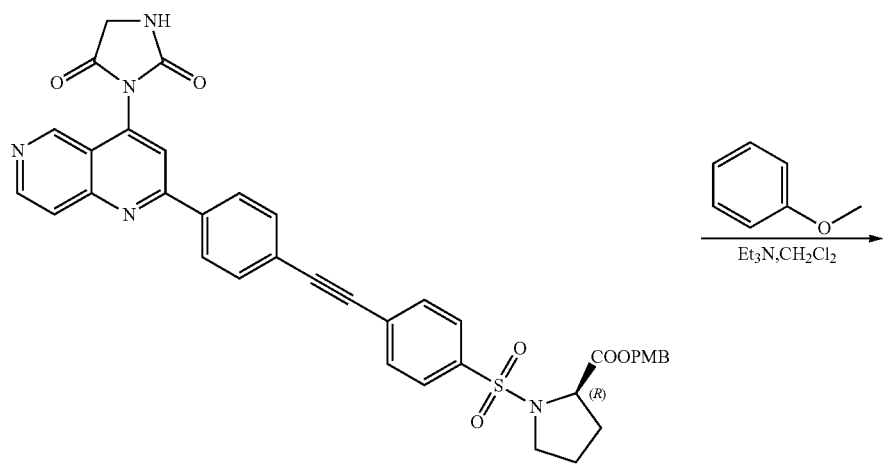
GY
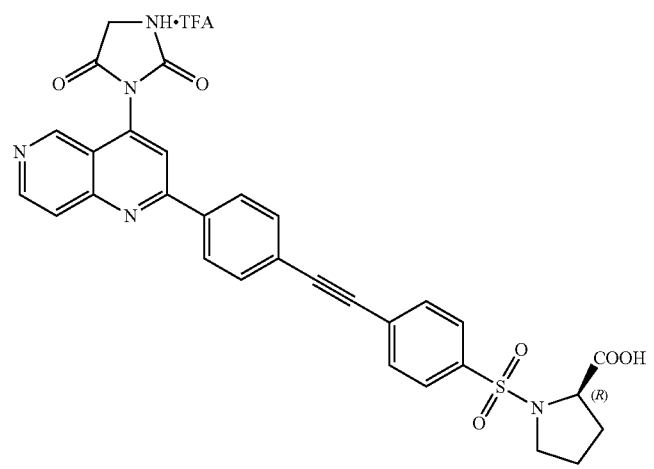

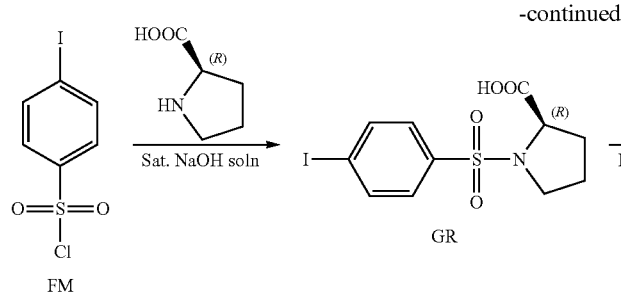 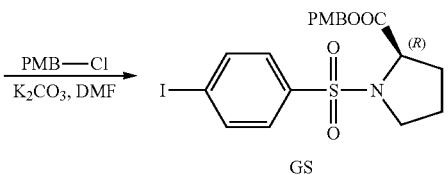

Example 152

(R)-1-((4-((4-(4-(2,5-dioxoimidazolidin-1-yl)-1,6-naphthyridin-2-yl)phenyl)ethynyl)phenyl)sulfonyl)pyrrolidine-2-carboxylic acid (152)

To a stirred solution of (R)-pyrrolidine-2-carboxylic acid (5 g, 43.43 mmol) in aq. sodium hydroxide (20 mL) was added 4-iodobenzene-1-sulfonyl chloride (FM; 13.2 g, 43.43 mmol) at 0° C. After stirring at RT for 12 h, the volatiles were removed under reduced pressure. The residue was diluted with 2N HCl solution to pH~2 and the obtained solids were filtered and dried under reduced pressure to afford GR (13.5 g, 82%) as a white solid. $^1$H NMR (500 MHz, DMSO-$d_6$): δ 12.75 (s, 1H), 8.00 (d, J=8.5 Hz, 2H), 7.58 (d, J=8.5 Hz, 2H), 4.12-4.10 (m, 1H), 3.37-3.31 (m, 1H), 3.18-3.14 (m, 1H), 1.97-1.93 (m, 1H), 1.87-1.78 (m, 2H), 1.63-1.60 (m, 1H).

To a stirred solution of GR (8.5 g, 22.37 mmol) in DMF (50 mL) under inert atmosphere were added potassium carbonate (15.4 g, 111.85 mmol) and p-methoxybenzyl chloride (4.2 g, 26.84 mmol) at 0° C. After stirring at 70-80° C. for 8 h, the reaction mixture was diluted with water (50 mL) and was extracted with EtOAc (3×50 mL). The combined organic extracts were washed with water (40 mL), brine (40 mL), dried over sodium sulfate, filtered and concentrated under reduced pressure to obtain the crude residue. The crude material was purified through silica gel column chromatography eluting with 5% EtOAc/hexanes to afford GS (10 g, 89%) as a white solid. $^1$H NMR (400 MHz, CDCl$_3$): δ 7.82 (d, J=8.5 Hz, 2H), 7.55 (d, J=8.5 Hz, 2H), 7.27 (d, J=8.5 Hz, 2H), 6.89 (d, J=8.5 Hz, 2H), 5.07-5.03 (m, 2H), 4.39-4.37 (m, 1H), 3.87 (s, 3H), 3.42-3.33 (m, 2H), 2.07-2.05 (m, 1H), 1.99-1.92 (m, 2H), 1.82-1.80 (m, 1H).

To a stirred solution of 2-(4-bromophenyl)-1,6-naphthyridin-4-amine (K; 200 mg, 0.66 mmol) in DMF (10 mL) under inert atmosphere were added TMS-acetylene (55 mg, 6.68 mmol) and triethylamine (1 mL, 6.68 mmol) at 0° C. After the reaction mixture was purged under argon for 15 min, copper iodide (12.7 mg, 0.06 mmol) and Pd(PPh$_3$)$_2$Cl$_2$ (46.9 mg, 0.06 mmol) were added at RT. The reaction was heated to 50° C. and stirred for 12 h. After complete consumption of the starting material, the volatiles were removed under reduced pressure to obtain the crude material, which was purified through silica gel column chromatography eluting with 5% MeOH/CH$_2$Cl$_2$ to afford GT (100 mg, 49%) as a yellow solid. $^1$H NMR (400 MHz, DMSO-$d_6$): δ 9.30 (br s, 2H), 8.10 (d, J=8.4 Hz, 2H), 7.72 (d, J=8.0 Hz, 1H), 7.50 (d, J=8.4 Hz, 2H), 7.40-7.38 (m, 2H), 7.22 (s, 1H), 0.26 (s, 9H).

To a stirred solution of GT (4 g, 12.62 mmol) in MeOH (100 mL) under inert atmosphere was added potassium carbonate (8.7 g, 63.09 mmol) at 0° C. and the resulting reaction mixture was stirred at RT for 4 h. After complete consumption of the starting material, the volatiles were removed under reduced pressure to obtain the crude material, which was purified through silica gel column chromatography eluting with 5% MeOH/CH$_2$Cl$_2$ to afford GU (1.5 g, 48%) as a yellow solid. $^1$H NMR (500 MHz, DMSO-$d_6$): δ 9.52 (s, 1H), 8.55 (d, J=6.0 Hz, 1H), 8.10 (d, J=8.0 Hz, 2H), 7.63-7.62 (m, 3H), 7.39 (s, 2H), 7.19 (s, 1H), 4.32 (s, 1H).

To a stirred solution of GU (650 mg, 2.66 mmol) in CH$_3$CN (50 mL) under inert atmosphere were added GS (1.6 g, 3.19 mmol) and triethyl amine (3.9 mL, 26.62 mmol) at 0° C. After purging under argon for 30 min, copper iodide (51 mg, 0.26 mmol) and Pd(PPh$_3$)$_2$Cl$_2$ (187 mg, 0.26 mmol) were added to the reaction mass at RT. The reaction mixture was then heated to reflux and stirred for 8 h. After complete consumption of the starting material, the volatiles were removed under reduced pressure to obtain crude GV (1 g) as a yellow solid. $^1$H NMR (500 MHz, CDCl$_3$): δ 9.61 (br s, 1H), 8.66 (br s, 1H), 8.13 (d, J=7.5 Hz, 2H), 7.89-7.73 (m, 7H), 7.32 (d, J=8.5 Hz, 2H), 7.21 (s, 1H), 6.95 (d, J=9.0 Hz, 2H), 5.11-5.05 (m, 2H), 4.34-4.31 (m, 1H), 3.76 (s, 3H), 3.40-3.38 (m, 1H), 3.24-3.20 (m, 1H), 3.11-3.07 (m, 2H), 1.20-1.97 (m, 1H), 1.87-1.80 (m, 2H), 1.66-1.64 (m, 1H).

To a stirred solution of 2-((((9H-fluoren-9-yl)methoxy)carbonyl)amino)acetic acid (2.4 g, 8.08 mmol) in DMF (100 mL) under inert atmosphere were added HATU (9.4 g, 24.26 mmol), diisopropylethyl amine (6 mL, 32.36 mmol) and GV (1 g, 1.60 mmol) at 0° C. After stirring at RT for 12 h, the reaction mixture was diluted with water (30 mL) and was extracted with EtOAc (2×30 mL). The combined organic extracts were washed with water (25 mL), dried over sodium sulfate, filtered and concentrated under reduced pressure to obtain the crude material. The crude material was purified through silica gel column chromatography eluting with 5% MeOH/CH$_2$Cl$_2$ to afford GW (500 mg, 34%) as a yellow solid. $^1$H NMR (400 MHz, DMSO-$d_6$): δ 10.70 (s, 1H), 9.78 (s, 1H), 8.87 (s, 1H), 8.77 (d, J=5.6 Hz, 1H), 8.28 (d, J=8.4 Hz, 2H), 7.94-7.87 (m, 5H), 7.83-7.75 (m, 5H), 7.74-7.71 (m, 1H), 7.45-7.41 (m, 2H), 7.37-7.30 (m, 2H), 6.95 (d, J=8.8 Hz, 2H), 5.11-5.04 (m, 2H), 4.38-4.25 (m, 5H), 4.14 (d, J=6.0 Hz, 2H), 3.78 (s, 3H), 3.39-3.36 (m, 1H), 3.25-3.20 (m, 1H), 3.02-1.97 (m, 1H), 1.90-1.78 (m, 2H), 1.67-1.64 (m, 1H), 1.03 (d, J=6.0 Hz, 3H).

To a stirred solution of GW (500 mg, 5.55 mmol) in DMF (15 mL) under inert atmosphere was added piperidine (0.3 mL, 2.78 mmol) at 0° C. Upon stirring at RT for 4 h, the reaction mixture was diluted with water (20 mL) and was extracted with EtOAc (2×20 mL). The combined organic extracts were washed with water (15 mL), dried over sodium sulfate, filtered and concentrated under reduced pressure to obtain the crude material. The crude material was purified through silica gel column chromatography eluting with 5%

MeOH/CH₂Cl₂ to afford GX (170 mg, 45%) as a yellow solid. ¹H NMR (500 MHz, DMSO-$d_6$): δ 9.64 (s, 1H), 8.93 (s, 1H), 8.77 (d, J=6.5 Hz, 1H), 8.28 (d, J=8.5 Hz, 2H), 7.94-7.80 (m, 7H), 7.31 (d, J=8.0 Hz, 2H), 6.95 (d, J=8.5 Hz, 2H), 5.90-5.64 (m, 2H), 5.07 (d, J=6.0 Hz, 2H), 4.33-4.31 (m, 1H), 3.76-3.73 (m, 3H), 3.55 (s, 2H), 3.42-3.38 (m, 1H), 3.12-3.08 (m, 2H), 2.02-1.99 (m, 1H), 1.84-1.78 (m, 2H), 1.66-1.62 (m, 1H).

To a stirred solution of GX (200 mg, 0.29 mmol) in CH₂Cl₂ (20 mL) under inert atmosphere were added triethylamine (0.13 mL, 0.88 mmol) and CDI (57.6 mg, 0.35 mmol) at 0° C. Upon stirring at RT for 6 h, the reaction mixture was diluted with water (15 mL) and was extracted with CH₂Cl₂ (2×15 mL). The combined organic extracts were washed with water (15 mL), brine (15 mL), dried over sodium sulfate, filtered and concentrated under reduced pressure to obtain the crude material. The crude material was purified through silica gel column chromatography eluting with 3% MeOH/CH₂Cl₂ to afford GY (100 mg, 48%) as a yellow solid. ¹H NMR (400 MHz, DMSO-$d_6$): δ 9.39 (s, 1H), 8.82 (d, J=6.0 Hz, 1H), 8.67 (s, 1H), 8.38 (d, J=8.4 Hz, 3H), 8.05 (d, J=6.0 Hz, 1H), 7.88-7.79 (m, 6H), 7.30 (d, J=8.4 Hz, 2H), 6.93 (d, J=8.4 Hz, 2H), 5.10-5.03 (m, 2H), 4.40-4.30 (m, 2H), 4.02-4.16 (m, 1H), 3.74 (s, 3H), 3.40-3.35 (m, 1H), 3.23-3.19 (m, 1H), 2.01-1.96 (m, 1H), 1.87-1.77 (m, 2H), 1.65-1.62 (m, 1H).

To a stirred solution of GY (20 mg, 0.02 mmol) in CH₂Cl₂ (5 mL) under inert atmosphere were added anisole (9.2 mg, 0.08 mmol) and trifluoroacetic acid (0.1 mL) at 0° C. After stirring at RT for 4 h, the volatiles were removed under reduced pressure to obtain the crude material, which was triturated with isopropyl alcohol (2×3 mL), diethyl ether (2×3 mL) and n-pentane (2×3 mL) to afford 152 (18 mg as a TFA salt) as a yellow solid. ¹H NMR (400 MHz, DMSO-$d_6$): δ 9.43 (br s, 1H), 8.84 (d, J=5.6 Hz, 1H), 8.69 (s, 1H), 8.42-9=8.39 (m, 3H), 8.08 (d, J=6.0 Hz, 1H), 7.91-7.83 (m, 6H), 4.41-4.37 (m, 1H), 4.22-4.15 (m, 2H), 3.42-3.36 (m, 1H), 3.25-3.19 (m, 1H), 2.02-1.95 (m, 1H), 1.92-1.77 (m, 2H), 1.64-1.58 (m, 1H). MS (ESI): m/z 581 [M−1]⁺. HPLC Purity: 97.44%

Scheme 50

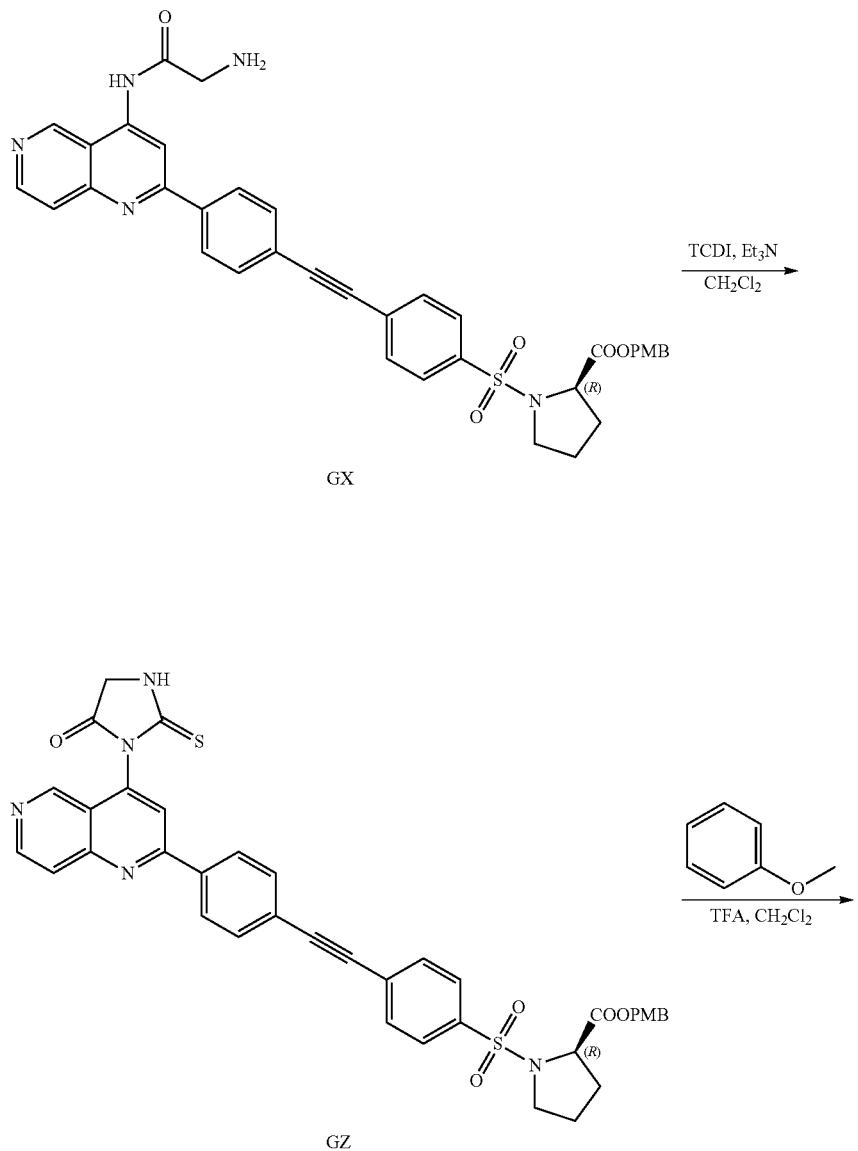

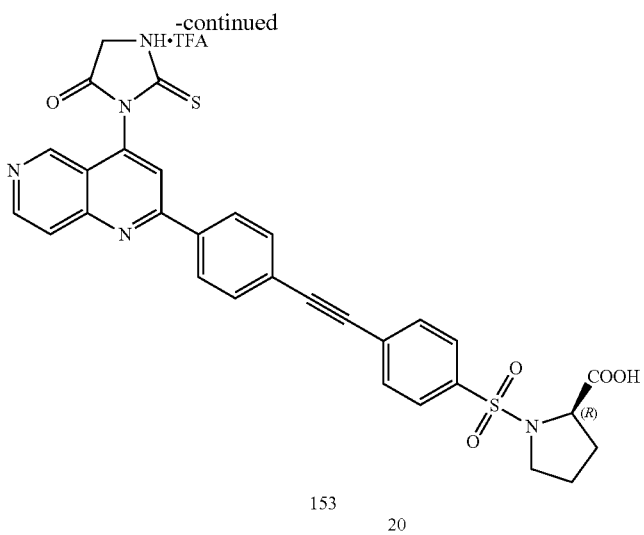

153

Example 153
(R)-1-((4-((4-(5-oxo-2-thioxoimidazolidin-1-yl)-1,6-naphthyridin-2-yl)phenyl)ethynyl)phenyl)sulfonyl)pyrrolidine-2-carboxylic acid (153)

To a stirred solution of GX (320 mg, 0.46 mmol) in CH$_2$Cl$_2$ (20 mL) under inert atmosphere were added triethylamine (0.11 mL, 1.42 mmol) and TCDI (101.4 mg, 0.56 mmol) at 0° C. After stirring at RT for 6 h, the reaction mixture was diluted with water (20 mL) and was extracted with CH$_2$Cl$_2$ (2×20 mL). The combined organic extracts were washed with water (20 mL), brine (20 mL), dried over sodium sulfate, filtered and concentrated under reduced pressure to obtain the crude residue. The crude residue was purified through silica gel column chromatography eluting with 3% MeOH/CH$_2$Cl$_2$ to afford GZ (35 mg, 10%) as a yellow solid. $^1$H NMR (400 MHz, DMSO-d$_6$): δ 0.79 (br s, 1H), 9.42 (s, 1H), 8.83 (d, J=6.0 Hz, 1H), 8.46 (s, 1H), 8.39 (d, J=8.8 Hz, 2H), 8.07 (d, J=6.8 Hz, 1H), 7.89-7.80 (m, 6H), 7.31 (d, J=8.8 Hz, 2H), 6.94 (d, J=8.8 Hz, 2H), 5.11-5.04 (m, 2H), 4.63-4.58 (m, 1H), 4.45-4.40 (m, 1H), 4.34-4.31 (m, 1H), 3.76 (s, 3H), 3.42-3.38 (m, 1H), 3.28-3.24 (m, 1H), 2.02-1.60 (m, 4H).

To a stirred solution of GZ (10 mg, 0.01 mmol) in CH$_2$Cl$_2$ (5 mL) under inert atmosphere were added anisole (4.5 mg, 0.04 mmol) and trifluoroacetic acid (0.1 mL) at 0° C. After stirring at RT for 4 h, the volatiles were removed under reduced pressure to obtain the crude material. The crude material was triturated with isopropyl alcohol (2×2 mL), diethyl ether (2×2 mL) and n-pentane (2×2 mL) to afford 153 (11 mg as a TFA salt) as a yellow solid. $^1$H NMR (400 MHz, DMSO-d$_6$): δ 12.90 (br s, 1H), 10.79 (s, 1H), 9.42 (s, 1H), 8.82 (s, 1H), 8.45 (s, 1H), 8.38 (d, J=7.6 Hz, 2H), 8.08-8.07 (m, 1H), 7.87-7.83 (m, 6H), 4.61-4.56 (m, 1H), 4.43-4.38 (m, 1H), 4.16-4.10 (m, 1H), 3.36 (s, 1H), 3.21-3.12 (m, 1H), 1.95-1.84 (m, 3H), 1.62-1.61 (m, 1H). MS (ESI): m/z 598.4 [M+1]$^+$. HPLC Purity: 99.55%

Scheme 51

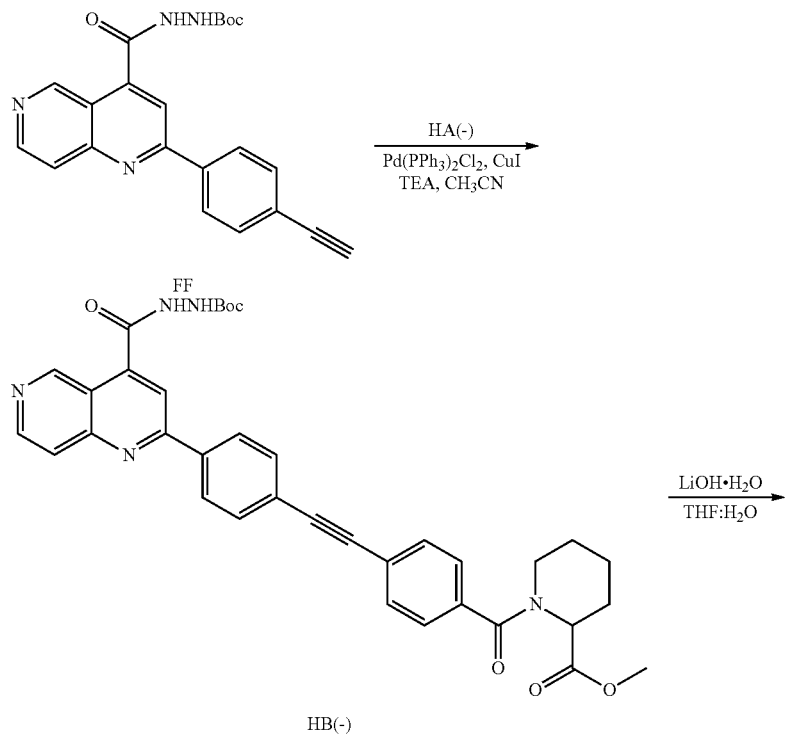

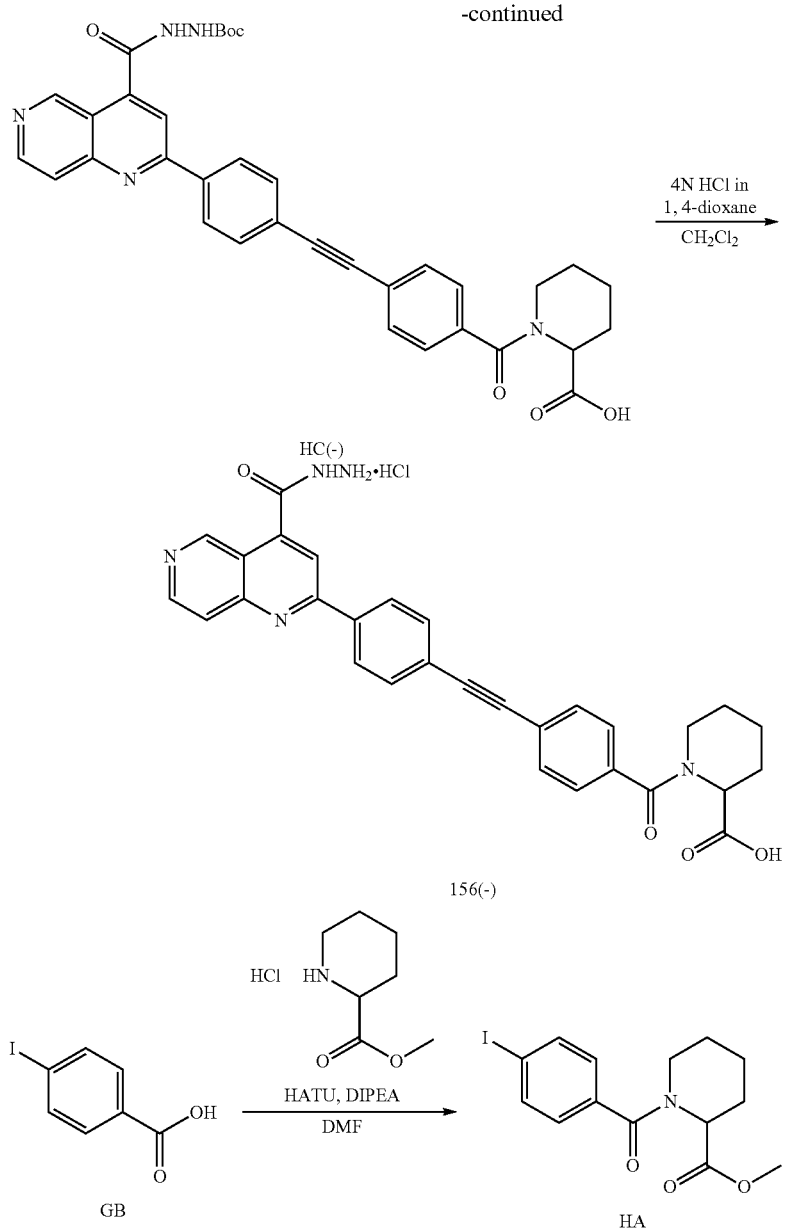

Examples 156(−)

1-(4-((4-(4-(hydrazinecarbonyl)-1,6-naphthyridin-2-yl)phenyl)ethynyl)benzoyl)piperidine-2-carboxylic acid hydrochloride (156(−))

To a stirred solution of 4-iodobenzoic acid (GB; 750 mg, 3.02 mmol) in DMF (10 mL) under inert atmosphere were added HATU (1.77 g, 4.53 mmol) and diisopropylethylamine (2.70 mL, 15.12 mmol) at RT. After stirring for 15 min at RT, methyl piperidine-2-carboxylate hydrochloride (651 mg, 3.62 mmol) was added to the reaction mass at 0° C. The reaction mixture was then stirred at RT for 16 h. After complete consumption of the starting material, the reaction mixture was diluted with ice cold water (30 mL) and was extracted with EtOAc (2×30 mL). The combined organic extracts were washed with water (30 mL), dried over sodium sulfate, filtered and concentrated under reduced pressure to obtain the crude material. The crude material was purified through silica gel column chromatography eluting with 2% MeOH/CH$_2$Cl$_2$ to afford HA (500 mg, racemic). $^1$H NMR (400 MHz, CDCl$_3$): 7.79-7.75 (m, 2H), 7.21-7.17 (m, 2H), 5.48 (br s, 1H), 3.80 (s, 3H), 3.60 (d, J=12.4 Hz, 1H), 3.25 (t, J=12.0 Hz, 1H), 2.37 (d, J=12.4 Hz, 1H), 1.80-1.72 (m, 3H), 1.48-1.34 (m, 2H).

The racemic HA was further purified through chiral preparative HPLC (with R$_t$ at 17.28 min, 19.98 min) (Chiralpak IC, 250×4.6 mm, 5μ); mobile phase (A) n-Hexane (B) Ethanol (A:B: 90:10); flow Rate: 1.0 mL/min) to afford HA(−) (220 mg) and HA(+) (250 mg) as off-white solids.

HA(−) Analytical Data:

$^1$H NMR (400 MHz, CDCl$_3$): δ 7.77 (d, J=8.0 Hz, 2H), 7.19 (d, J=8.0 Hz, 2H), 5.49 (br s, 1H), 3.80 (s, 3H), 3.62 (d, J=12.8 Hz, 1H), 3.26 (t, J=12.0 Hz, 1H), 2.36 (d, J=12.0 Hz, 1H), 1.79-1.74 (m, 2H), 1.64-1.58 (m, 1H), 1.45-1.40 (m, 2H); LC-MS: 98.16%; 374 (M$^+$+NH$_4$); (column; X-bridge C-18, 50×3.0 mm, 3.5 μm); R$_t$ 3.75 min 5 mM NH$_4$OAc (Aq): ACN; 0.8 mL/min; Chiral HPLC: 99.31%, R$_t$=17.39 min (Chiralpak IC, 250×4.6 mm, 5μ); mobile phase (A) n-Hexane (B) Ethanol (A:B: 90:10); flow Rate: 1.0 mL/min); Optical rotation [α]$_D^{20}$: −50.01° (c=0.25, CH$_2$Cl$_2$).

HA(+) Analytical Data:

$^1$H NMR (400 MHz, CDCl$_3$): δ 7.76 (d, J=8.0 Hz, 2H), 7.18 (d, J=8.0 Hz, 2H), 5.48 (br s, 1H), 3.78 (s, 3H), 3.59 (d, J=12.8 Hz, 1H), 3.24 (t, J=12.0 Hz, 1H), 2.34 (d, J=12.0 Hz, 1H), 1.77-1.75 (m, 2H), 1.61-1.58 (m, 1H), 1.42-1.38 (m, 2H); LC-MS: 99.69%; 374 (M$^+$+NH$_4$); (column; X-bridge C-18, 50×3.0 mm, 3.5 μm); R$_t$ 3.73 min 5 mM NH$_4$OAc (Aq): ACN; 0.8 mL/min; Chiral HPLC: 99.92%, R$_t$=20.17 min (Chiralpak IC, 250×4.6 mm, 5μ); mobile phase (A) n-Hexane (B) Ethanol (A:B: 90:10); flow Rate: 1.0 mL/min); Optical rotation [α]$_D^{20}$: +58.19° (c=0.25, CH$_2$Cl$_2$).

To a stirred solution of tert-butyl 2-(2-(4-ethynylphenyl)-1,6-naphthyridine-4-carbonyl)hydrazine carboxylate (FF; 135 mg, 0.34 mmol) in CH$_3$CN (10 mL) under inert atmosphere were added HA(−) (168.7 mg, 0.45 mmol) and triethylamine (0.48 mL, 3.47 mmol). After the reaction was purged under argon for 20 min, copper iodide (6.62 mg, 0.03 mmol) and Pd(PPh$_3$)$_2$Cl$_2$ (24.4 mg, 0.03 mmol) were added at RT. The reaction was heated at reflux for 4 h, at which point the reaction mixture was filtered through Celite. The filtrate was concentrated under reduced pressure to obtain the crude material, which was purified through silica gel column chromatography eluting with 3-5% MeOH/CH$_2$Cl$_2$ to afford HB(−) (100 mg with TEA impurity) as a yellow solid. $^1$H NMR (500 MHz, DMSO-d$_6$): δ 10.65 (br s, 1H), 9.71 (br s, 1H), 9.30 (br s, 1H), 8.84 (br s, 1H), 8.44 (d, J=8.0 Hz, 2H), 8.33 (s, 1H), 8.05 (d, J=6.0 Hz, 1H), 7.82 (d, J=8.0 Hz, 2H), 7.71-7.70 (m, 2H), 7.47-7.41 (m, 2H), 5.29-5.27 (m, 0.5H), 4.43-4.41 (m, 0.5H), 3.74 (s, 3H), 3.52-3.49 (m, 1H), 3.10-3.08 (m, 1H), 2.21-2.18 (m, 1H), 1.76-1.69 (m, 2H), 1.49 (s, 9H), 1.19-1.16 (m, 3H).

To a stirred solution of HB(−) (100 mg, 0.15 mmol) in THF:H$_2$O (4:1, 10 mL) was added lithium hydroxide monohydrate (33 mg, 0.78 mmol) at 0° C. and the resulting reaction mixture was stirred for 5 h at RT. After complete consumption of the starting material, the volatiles were evaporated under reduced pressure, the residue was neutralized with an acetic acid solution (1 mL), and was dried under reduced pressure to afford HC(−) (60 mg, 61%) as a yellow solid. $^1$H NMR (500 MHz, DMSO-d$_6$): δ 10.66 (br s, 1H), 9.70 (br s, 1H), 9.28 (br s, 1H), 8.83-8.81 (m, 1H), 8.42 (d, J=7.5 Hz, 2H), 8.32 (s, 1H), 8.04-8.02 (m, 1H), 7.79 (d, J=7.5 Hz, 2H), 7.58 (d, J=7.5 Hz, 2H), 7.44 (d, J=8.0 Hz, 2H), 4.93-4.91 (m, 0.5H), 4.32-4.30 (m, 0.5H), 3.81-3.79 (m, 1H), 2.95-2.93 (m, 1H), 2.16-2.14 (m, 1H), 1.60-1.58 (m, 1H), 1.48 (s, 9H), 1.34-1.32 (m, 2H), 1.26-1.23 (m, 2H).

To a stirred solution of HC(−) (60 mg, 0.09 mmol) in CH$_2$Cl$_2$ (5 mL) under inert atmosphere was added 4N HCl in 1,4-dioxane (0.6 mL) at 0° C. and the resulting mixture was stirred for 3 h at RT. After complete consumption of the starting material, the volatiles were evaporated under reduced pressure to obtain the crude material, which was washed with CH$_3$CN (2×5 mL) to afford 156(−) (15 mg as HCl salt) as a yellow solid. $^1$H NMR (400 MHz, DMSO-d$_6$): δ 12.20 (br s, 1H), 9.77 (s, 1H), 8.91-8.89 (m, 1H), 8.65 (s, 1H), 8.52 (d, J=8.4 Hz, 2H), 8.23 (d, J=6.0 Hz, 1H), 7.85 (d, J=8.0 Hz, 2H), 7.70 (d, J=7.2 Hz, 2H), 7.46-7.40 (m, 2H), 5.20-5.18 (m, 1H), 4.45-4.40 (m, 0.5H), 4.38-4.29 (m, 0.5H), 3.49-3.47 (m, 1H), 3.22-3.17 (m, 1H), 2.82-2.75 (m, 0.5H), 2.23-2.21 (m, 0.5H), 1.72-1.69 (m, 3H), 1.58-1.55 (m, 1H). MS (ESI): m/z 520.4 [M+1]$^+$. HPLC Purity: 95.11%

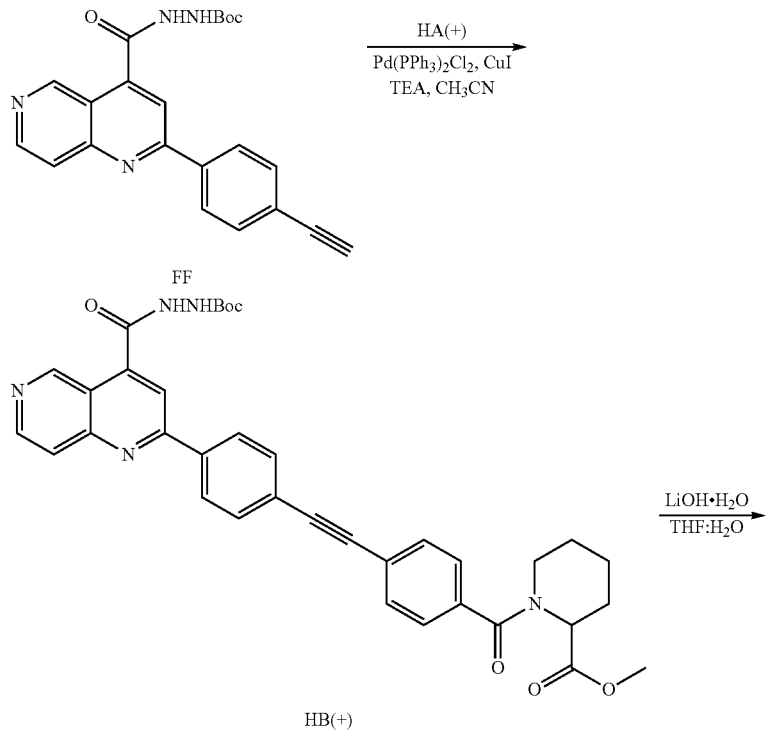

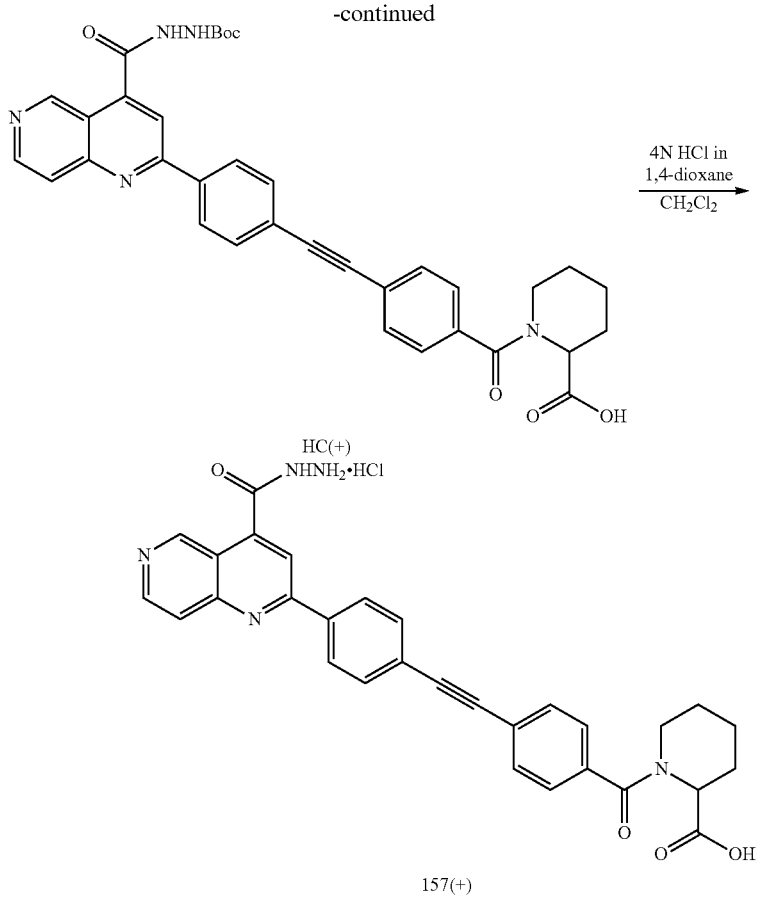

Example 157(+)

1-(4-((4-(4-(hydrazinecarbonyl)-1,6-naphthyridin-2-yl)phenyl)ethynyl)benzoyl)pyrrolidine-2-carboxylic acid hydrochloride (157(+))

To a stirred solution of tert-butyl 2-(2-(4-ethynylphenyl)-1,6-naphthyridine-4-carbonyl)hydrazine carboxylate (FF; 150 mg, 0.38 mmol) in $CH_3CN$ (10 mL) under inert atmosphere were added HA(+) (187 mg, 0.50 mmol) and triethylamine (0.54 mL, 3.86 mmol). After the reaction was purged under argon for 20 min, copper iodide (7.36 mg, 0.03 mmol) and $Pd(PPh_3)_2Cl_2$ (27.1 mg, 0.03 mmol) were added at RT. The reaction was heated at reflux for 4 h, at which point, the reaction mixture was filtered through Celite. The filtrate was concentrated under reduced pressure to obtain the crude material, which was purified through silica gel column chromatography eluting with 3-5% $MeOH/CH_2Cl_2$ to afford HB(+) (80 mg, 32%) as a yellow solid. $^1H$ NMR (400 MHz, DMSO-$d_6$): δ 10.65 (br s, 1H), 9.72 (br s, 1H), 9.30 (br s, 1H), 8.84 (br s, 1H), 8.44 (d, J=8.0 Hz, 2H), 8.33 (s, 1H), 8.05 (d, J=5.6 Hz, 1H), 7.82 (d, J=8.0 Hz, 2H), 7.71-7.70 (m, 2H), 7.47-7.41 (m, 2H), 5.29-5.27 (m, 0.5H), 4.44-4.43 (m, 0.5H), 3.74 (s, 3H), 3.52-3.49 (m, 1H), 3.10-3.08 (m, 1H), 2.21-2.18 (m, 1H), 1.76-1.69 (m, 2H), 1.53 (s, 9H), 1.19-1.16 (m, 3H).

To a stirred solution of HB(+) (80 mg, 0.12 mmol) in $THF:H_2O$ (4:1, 10 mL) was added lithium hydroxide monohydrate (26.5 mg, 0.63 mmol) at 0° C. and the resulting reaction mixture was stirred for 5 h at RT. After complete consumption of the starting material, the volatiles were evaporated under reduced pressure, the residue was neutralized with an acetic acid solution (1 mL), and was filtered and dried under reduced pressure to afford crude HC(+) (65 mg) as a yellow solid. $^1H$ NMR (400 MHz, DMSO-$d_6$): δ 10.66 (br s, 1H), 9.89 (br s, 1H), 9.24 (br s, 1H), 8.81-8.80 (m, 1H), 8.42 (d, J=8.0 Hz, 2H), 8.38 (s, 1H), 8.02-8.01 (m, 1H), 7.80 (d, J=7.6 Hz, 2H), 7.58 (d, J=7.6 Hz, 2H), 7.46 (d, J=7.6 Hz, 2H), 4.80-4.79 (m, 0.5H). 4.34-4.31 (m, 0.5H), 3.79-3.77 (m, 1H), 2.97-2.94 (m, 1H), 2.16-2.14 (m, 1H), 1.60-1.59 (m, 1H), 1.49 (s, 9H), 1.34-1.32 (m, 2H), 1.26-1.23 (m, 2H).

To a stirred solution of HC(+) (30 mg, 0.04 mmol) in $CH_2Cl_2$ (3 mL) under inert atmosphere was added 4N HCl in 1,4-dioxane (0.4 mL) at 0° C. and the reaction mixture was stirred for 3 h at RT. After complete consumption of the starting material, the volatiles were evaporated under reduced pressure to obtain the crude material, which was washed with $CH_3CN$ (2×3 mL) to afford 157(+) (15 mg as an HCl salt) as a yellow solid. $^1H$ NMR (400 MHz, DMSO-$d_6$): δ 12.00 (br s, 1H), 9.73 (br s, 1H), 8.89-8.87 (m, 1H), 8.56 (s, 1H), 8.49 (d, J=8.8 Hz, 2H), 8.16 (d, J=6.0 Hz, 1H), 7.84 (d, J=8.0 Hz, 2H), 7.70 (d, J=7.2 Hz, 2H), 7.46-7.41 (m, 2H), 5.20-5.18 (m, 1H), 4.45-4.40 (m, 0.5H), 4.38-4.29 (m, 0.5H), 3.49-3.47 (m, 1H), 3.22-3.16 (m, 1H), 2.81-2.69 (m, 0.5H), 2.23-2.20 (m, 0.5H), 1.72-1.69 (m, 3H), 1.58-1.55 (m, 1H). MS: m/z 518.4 [M−1]$^+$. HPLC Purity: 94.48%

Scheme 53
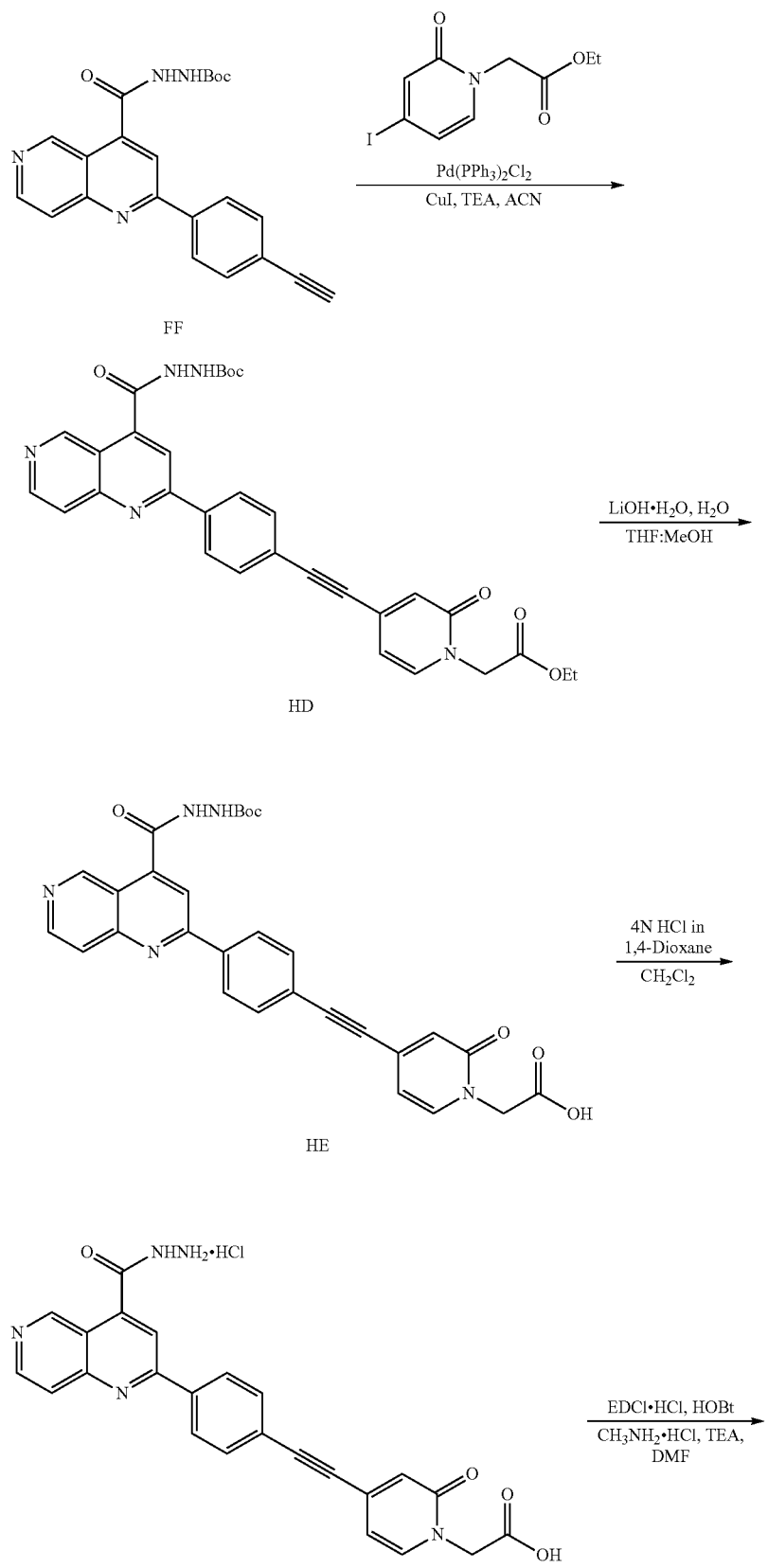

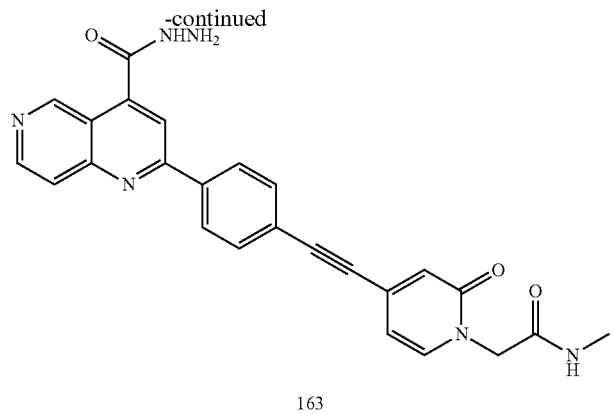

163

Examples 162 and 163

2-(4-((4-(4-(hydrazinecarbonyl)-1,6-naphthyridin-2-yl)phenyl)ethynyl)-2-oxopyridin-1(2H)-yl)acetic acid hydrochloride (162)

To a stirred solution of tert-butyl 2-(2-(4-ethynylphenyl)-1,6-naphthyridine-4-carbonyl) hydrazine carboxylate (FF; 400 mg, 1.02 mmol) in CH₃CN (30 mL) under inert atmosphere were added ethyl 2-(4-iodo-2-oxopyridin-1(2H)-yl) acetate (379 mg, 1.23 mmol) and triethylamine (1.48 mL, 10.29 mmol) at RT. After the reaction was purged under argon for 15 min, copper iodide (19 mg, 0.10 mmol) and Pd(PPh₃)₂Cl₂ (72 mg, 0.10 mmol) were added. The reaction was heated at reflux for 3 h, at which point, the volatiles were evaporated under reduced pressure to obtain the crude material. The crude material was purified through silica gel column chromatography eluting with 4-5% MeOH/CH₂Cl₂ to afford HD (211 mg, 36%) as a pale brown solid. ¹H NMR (400 MHz, DMSO-d₆): δ 10.65 (br s, 1H), 9.71 (br s, 1H), 9.30 (br s, 1H), 8.84 (d, J=6.0 Hz, 1H), 8.46 (d, J=8.0 Hz, 2H), 8.34 (br s, 1H), 8.05 (d, J=6.0 Hz, 1H), 7.84 (d, J=8.0 Hz, 2H), 7.75 (d, J=7.2 Hz, 1H), 6.67 (s, 1H), 6.42 (d, J=7.2 Hz, 1H), 4.72 (s, 2H), 4.18-4.13 (q, 2H), 1.49 (s, 9H), 1.23-1.21 (m, 3H).

To a stirred solution of HD (211 mg, 0.37 mmol) in THF/MeOH (4:1, 10 mL) under inert atmosphere were added lithium hydroxide monohydrate (311 mg, 7.41 mmol) and water (1.5 mL) at 0° C. After stirring at RT for 3 h, the volatiles were evaporated under reduced pressure, the residue was diluted with water (25 mL), and acidified with acetic acid to pH~4. The obtained solid was filtered, co-distilled with toluene (2×5 mL) and dried under reduced pressure to obtain crude HE (170 mg) as a yellow solid.

To a stirred solution of HE (30 mg, 0.06 mmol) in CH₂Cl₂ (1 mL) under inert atmosphere was added 4N HCl solution in 1,4-dioxane (0.5 mL) at 0° C. After stirring for 30 min at RT, the volatiles were evaporated under reduced pressure to obtain the crude material, which was triturated with isopropyl alcohol:n-pentane (1:4, 5 mL) to afford 162 (20 mg as an HCl salt) as a yellow solid. ¹H NMR (400 MHz, DMSO-d₆): δ 11.64 (br s, 1H), 9.69 (s, 1H), 8.86 (d, J=6.0 Hz, 1H), 8.51-8.46 (m, 3H), 8.11 (d, J=6.0 Hz, 1H), 7.85 (d, J=8.4 Hz, 2H), 7.74 (d, J=6.8 Hz, 1H), 6.65 (s, 1H), 6.41-6.38 (m, 1H), 4.64 (s, 2H). MS (ESI): m/z 453.2 [M+1]⁺. HPLC Purity: 94.24%

2-(4-((4-(4-(hydrazinecarbonyl)-1,6-naphthyridin-2-yl)phenyl)ethynyl)-2-oxopyridin-1(2H)-yl)-N-methylacetamide (163)

To a stirred solution of 162 (30 mg, 0.06 mmol) in DMF (10 mL) under inert atmosphere were added EDCI.HCl (32 mg, 0.16 mol), HOBt (16 mg, 0.12 mol), triethylamine (0.03 mL, 0.27 mmol) and methylamine hydrochloride (9 mg, 0.13 mol) at 0° C. After stirring at RT for 12 h, the reaction mixture was diluted with ice cold water (20 mL) and was extracted with 20% MeOH/CH₂Cl₂ (2×20 mL). The combined organic extracts were washed with water (20 mL), dried over sodium sulfate, filtered and concentrated under reduced pressure to obtain the crude material. The crude material was purified through silica gel column chromatography containing neutral alumina using 4-8% MeOH/CH₂Cl₂ to afford 163 (16 mg, 51%) as a yellow solid. ¹H NMR (400 MHz, DMSO-d₆): δ 9.62 (s, 1H), 8.99-8.98 (m, 1H), 8.80 (d, J=6.0 Hz, 1H), 8.46 (d, J=8.4 Hz, 2H), 8.40 (s, 1H), 8.10-8.09 (m, 1H), 8.02 (d, J=6.0 Hz, 1H), 7.83 (d, J=8.4 Hz, 2H), 7.67 (d, J=6.8 Hz, 1H), 6.61 (s, 1H), 6.38-6.35 (m, 1H), 4.52 (s, 2H), 2.94 (d, J=4.8 Hz, 3H), 2.62 (d, J=4.8 Hz, 2H). MS (ESI): m/z 440.3 [M+1]⁺

Scheme 54

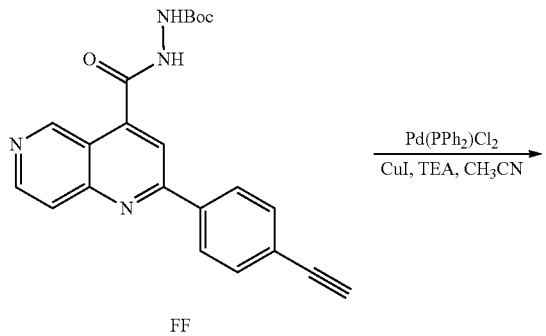

FF

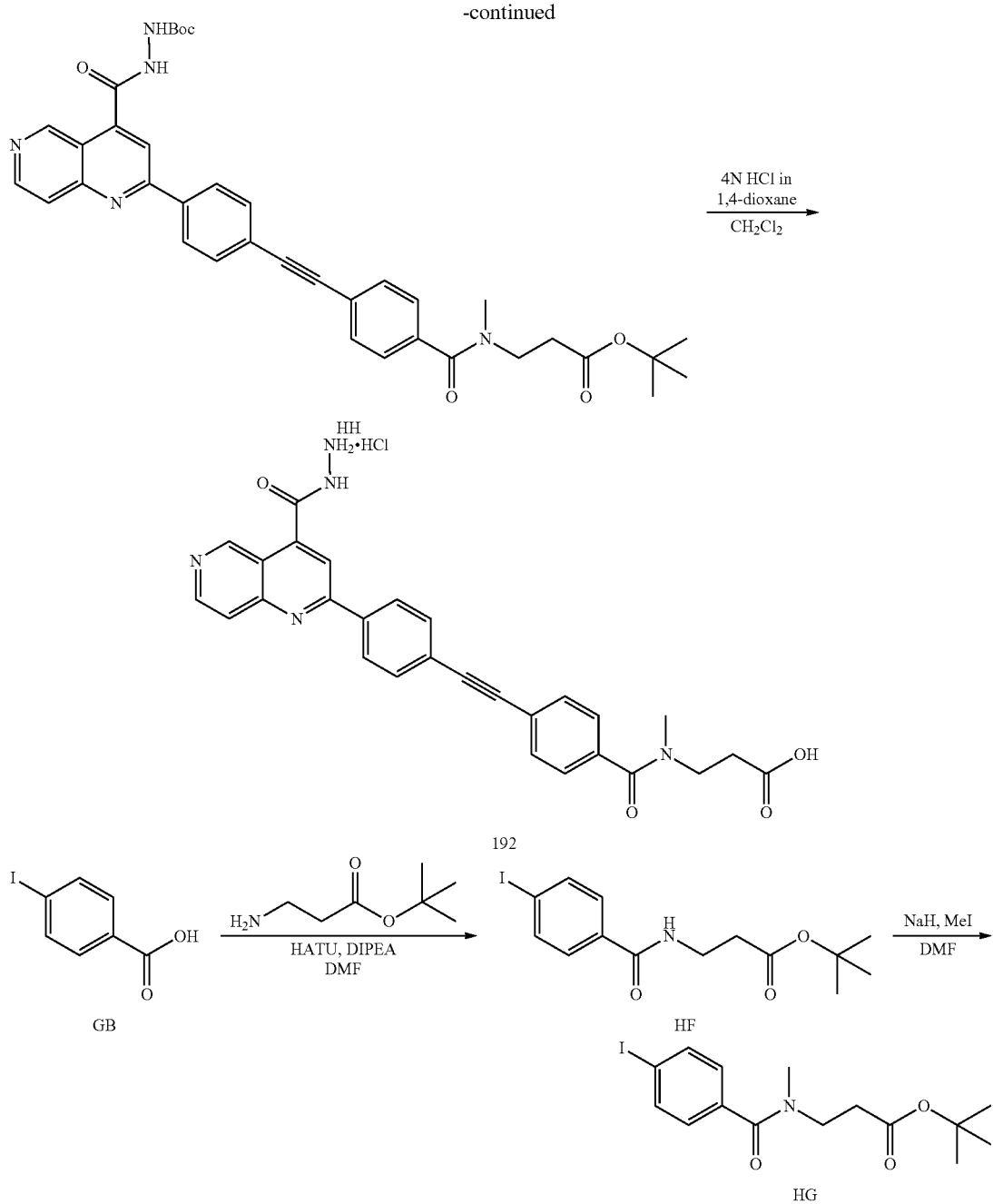

Example 192

3-(4-((4-(4-(hydrazinecarbonyl)-1,6-naphthyridin-2-yl)phenyl)ethynyl)-N-methylbenzamido)propanoic acid hydrochloride (192)

To a stirred solution of 4-iodobenzoic acid (GB; 500 mg, 2.01 mmol) in DMF (10 mL) under inert atmosphere were added HATU (1.14 g, 3.02 mmol), diisopropylethylamine (1.10 mL, 6.04 mmol) at 0° C. After stirring for 15 min, tert-butyl 3-aminopropanoate (439 mg, 2.41 mmol) was added to the reaction at 0° C. The reaction mixture was stirred for 12 h at RT, at which point, the reaction mixture was diluted with water (25 mL) and was extracted with EtOAc (2×25 mL). The combined organic extracts were washed with water (25 mL), dried over sodium sulfate, filtered and concentrated under reduced pressure to obtain the crude residue. The crude residue was purified through flash column chromatography eluting with 15% EtOAc/hexanes to afford HF (550 mg, 73%) as an off-white solid. $^1$H NMR (500 MHz, DMSO-$d_6$): δ 8.57-8.55 (m, 1H), 7.85 (d, J=8.5 Hz, 2H), 7.59 (d, J=8.5 Hz, 2H), 3.45-3.41 (m, 2H), 2.50-2.46 (m, 2H), 1.38 (s, 9H).

To a stirred solution of HF (300 mg, 0.80 mmol) in DMF (10 mL) under inert atmosphere was added sodium hydride (38.4 mg, 1.60 mmol) at 0° C. After stirring at RT for 15 min, methyl iodide (170 mg, 1.20 mmol) was added at 0° C. The reaction was then stirred for 2 h at RT, at which point, the reaction mixture was diluted with ice cold water (20 mL) and was extracted with EtOAc (2×20 mL). The combined organic extracts were washed with water (20 mL), dried over sodium sulfate, filtered and concentrated under reduced pressure to obtain the crude material. The crude material was purified through flash column chromatography eluting with 20% EtOAc/hexanes to afford HG (250 mg, 64%) as a yellow solid. $^1$H NMR (500 MHz, DMSO-$d_6$): δ 7.80 (d, J=7.0 Hz, 2H), 7.16 (d, J=7.0 Hz, 2H), 3.66-3.58 (m, 1H), 3.44-3.38 (m, 1H), 2.95-2.86 (m, 5H), 1.40 (s, 9H).

To a stirred solution of tert-butyl 2-(2-(4-ethynylphenyl)-1,6-naphthyridine-4-carbonyl) hydrazinecarboxylate (FF; 200 mg, 0.51 mmol) in CH$_3$CN (20 mL) under inert atmosphere were added HG (240 mg, 0.61 mmol), triethylamine (0.74 mL, 5.15 mmol), and copper iodide (9.9 mg, 0.051 mmol) at RT. After the reaction was purged under argon for 15 min, Pd(PPh$_3$)$_2$Cl$_2$ (36 mg, 0.051 mmol) was added and the reaction was heated at reflux for 4 h. After complete consumption of the starting material, the volatiles were evaporated under reduced pressure to obtain the crude material, which was purified through flash column chromatography eluting with 3-5% MeOH/CH$_2$Cl$_2$ to afford HH (20 mg, 6%) as a yellow solid. $^1$H NMR (400 MHz, DMSO-$d_6$): δ 10.65 (br s, 1H), 9.30 (br s, 1H), 8.90-8.76 (m, 1H), 8.45 (d, 2H), 8.33-8.31 (m, 1H), 8.08-8.06 (m, 1H), 7.98-7.96 (m, 1H), 7.82-7.80 (m, 2H), 7.78-7.73 (m, 2H), 7.64-7.61 (m, 2H), 7.59-7.54 (m, 1H), 7.49-7.44 (m, 2H), 3.66-3.64 (m, 1H), 3.17-3.16 (m, 1H), 3.10-2.91 (m, 4H), 2.55-2.52 (m, 1H), 1.49 (s, 9H), 1.41-1.37 (m, 9H).

To a stirred solution of HH (20 mg, 0.03 mmol) in CH$_2$Cl$_2$ (2 mL) under inert atmosphere was added 4N HCl solution in 1,4-dioxane (0.5 mL) at 0° C. After stifling at RT for 6 h, the volatiles were evaporated under reduced pressure to obtain the crude material, which was triturated with 20% MeOH/CH$_3$CN (2×2 mL) to afford 192 (14 mg as an HCl salt) as a yellow solid. $^1$H NMR (400 MHz, DMSO-$d_6$): δ 9.71 (s, 1H), 8.88-8.87 (m, 1H), 8.53 (s, 1H), 8.48 (d, J=8.4 Hz, 2H), 8.14 (d, J=6.0 Hz, 1H), 7.84 (d, J=8.4 Hz, 2H), 7.67 (d, J=8.0 Hz, 2H), 7.46 (d, J=8.0 Hz, 2H), 3.71-3.66 (m, 2H), 3.51-3.46 (m, 2H), 2.92 (br s, 3H). MS (ESI): m/z 494.6 [M+1]$^+$. HPLC Purity: 97.03%.

Scheme 55

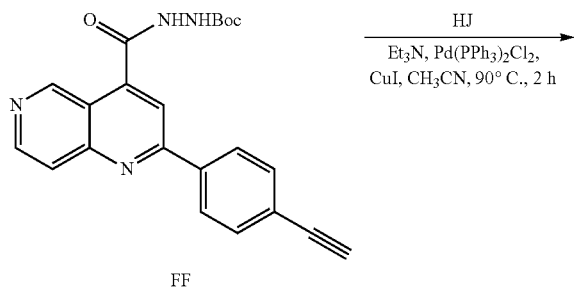

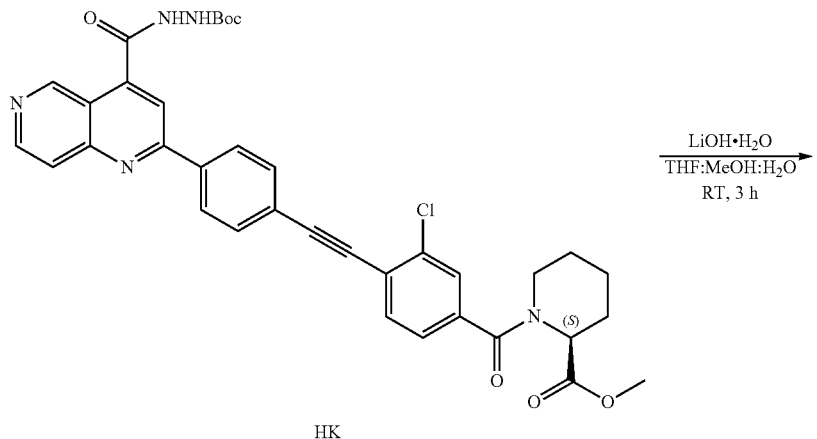

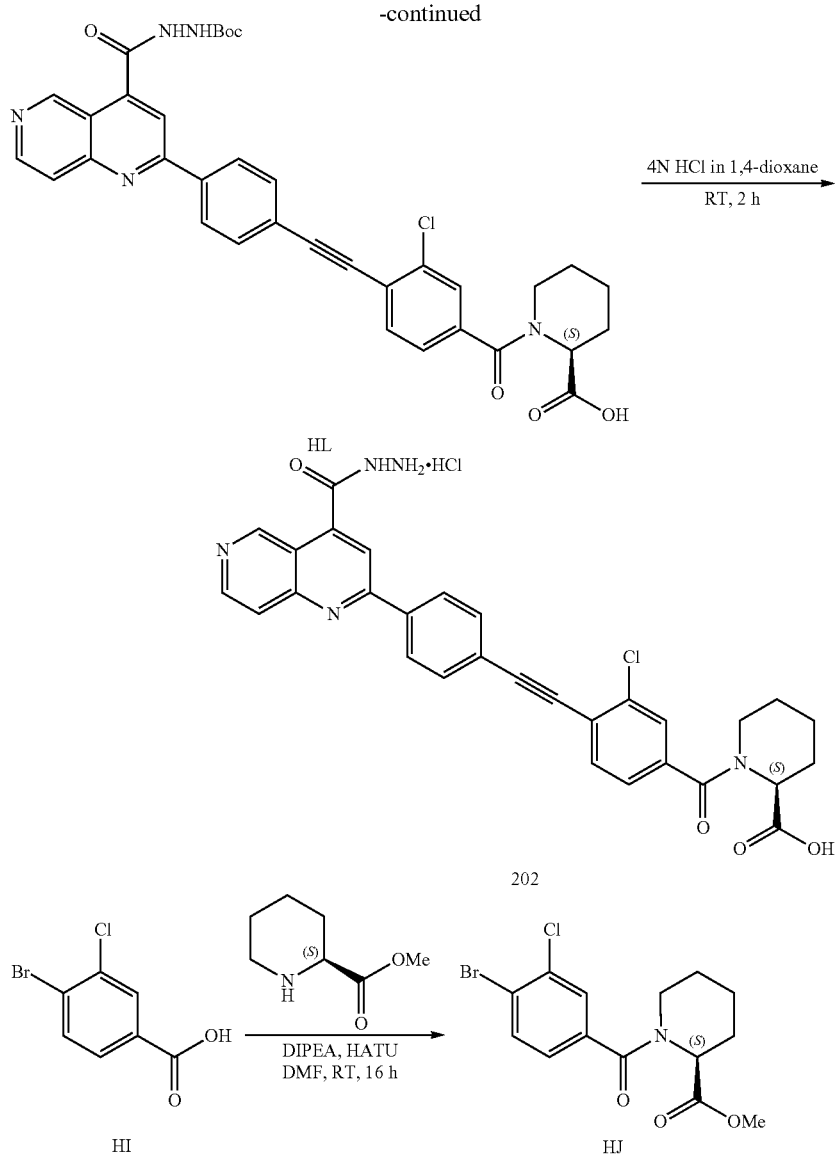

Example 202

(S)-1-(3-chloro-4-((4-(4-(hydrazinecarbonyl)-1,6-naphthyridin-2-yl)phenyl)ethynyl)benzoyl)piperidine-2-carboxylic acid hydrochloride (202)

To a stirred solution of 4-bromo-3-chlorobenzoic acid (HI; 6.5 g, 27.60 mmol) in DMF (50 mL) under nitrogen atmosphere were added HATU (15.74 g, 41.40 mmol), DIPEA (14.4 mL, 82.81 mmol) and (S)-methyl piperidine-2-carboxylate hydrochloride (5.34 g, 29.74 mmol) at RT and the reaction mixture was stirred for 16 h. After complete consumption of the starting material (by TLC), the reaction was diluted with water (100 mL) and the compound was extracted with EtOAc (2×100 mL). The combined organic extracts were washed with water (2×100 mL), brine (2×75 mL), dried over sodium sulfate, filtered and concentrated under reduced pressure. The crude product was purified by silica gel chromatography eluting with 30% EtOAc/hexanes to afford compound HJ (8.9 g, 90%) as a yellow thick syrup.

$^1$H-NMR (DMSO-d$_6$, 500 MHz): δ 7.89-7.84 (m, 1H), 7.61-7.56 (m, 1H), 7.28 (d, J=7.5 Hz, 1H), 5.24 (br s, 1H), 4.44-4.37 (m, 1H), 3.73 (s, 3H), 3.45 (d, J=12.5 Hz, 1H), 3.12 (t, J=12.5 Hz, 1H), 2.67-2.64 (m, 1H), 1.70-1.67 (m, 2H), 1.53-1.40 (m, 2H). MS (ESI): m/z 360.63 [M+1]$^+$

To a stirred solution of compound FF (250 mg, 0.64 mmol) in CH$_3$CN (20 mL) under argon atmosphere were added compound HJ (311 mg, 0.64 mmol) and TEA (1 mL, 6.44 mmol). The reaction was purged with argon for 10 min followed by the addition of copper iodide (12 mg, 0.06 mmol) and Pd(PPh$_3$)$_2$Cl$_2$ (45 mg, 0.06 mmol). The reaction was heated to 90° C. and stirred for 2 h. After complete consumption of the starting material (by TLC), the reaction mixture was concentrated under reduced pressure. The crude product was purified by silica gel column chromatography eluting with 2-5% MeOH/DCM to afford compound HK (120 mg, 28%) as a pale brown solid. The compound was carried forward into the next step without further purification. MS (ESI): m/z 668.15 [M+1]$^+$ To a stirred solution of compound HK (120 mg, 0.17 mmol) in THF:H$_2$O (5 mL:5 mL) was added lithium hydroxide monohydrate (75 mg, 1.79 mmol) at 0° C. The reaction was allowed to warm to RT and was stirred for 3 h. After complete consumption of the starting material (by TLC), the volatiles were evaporated under reduced pressure. The reaction residue was diluted with water (5 mL), washed with DCM (5 mL) and the pH was adjusted to 3 using an acetic acid solution (0.2 mL). The solid precipitate was filtered, dried under reduced pressure, and washed with $CH_3CN$ (2 mL) to afford compound HL (61 mg, 52%) as a pale yellow solid. The compound was carried forward without further purification. MS (ESI): m/z 655[M+1]$^+$ To a stirred solution of compound HL (60 mg, 0.09 mmol) in DCM (4 mL) under nitrogen atmosphere was added 4N HCl in 1,4-dioxane (1 mL) at 0° C. The reaction was allowed to warm to RT and was stirred for 2 h. After complete consumption of the starting material (by TLC), the volatiles were evaporated under reduced pressure. The crude product was triturated with $CH_3CN$ (2 mL) to afford 202 (38 mg as an HCl salt) as a yellow solid. $^1$H-NMR (400 MHz, DMSO-$d_6$): δ 12.1 (brs, 1H), 9.71 (brs, 1H), 8.86 (brs, 1H), 8.55 (s, 1H), 8.48 (d, J=8.0 Hz, 2H), 8.18-8.14 (m, 1H), 7.84-7.78 (m, 3H), 7.56-7.52 (m, 2H), 7.41-7.31 (m, 1H), 5.14 (brs, 0.6H), 4.41-4.32 (m, 0.4H), 3.48-3.41 (m, 0.4H), 3.17 (t, J=10 Hz, 0.6H), 2.76-2.68 (m, 0.5H), 2.24-2.14 (m, 1H), 2.09-2.01 (m, 0.5 H), 1.72-1.62 (m, 3H), 1.44-1.22 (m, 2H). MS (ESI): m/z 554.5 and 555.3 [M+1]$^+$ (Chloro pattern is observed in the mass spectrum). HPLC Purity: 93.36%

Scheme 56

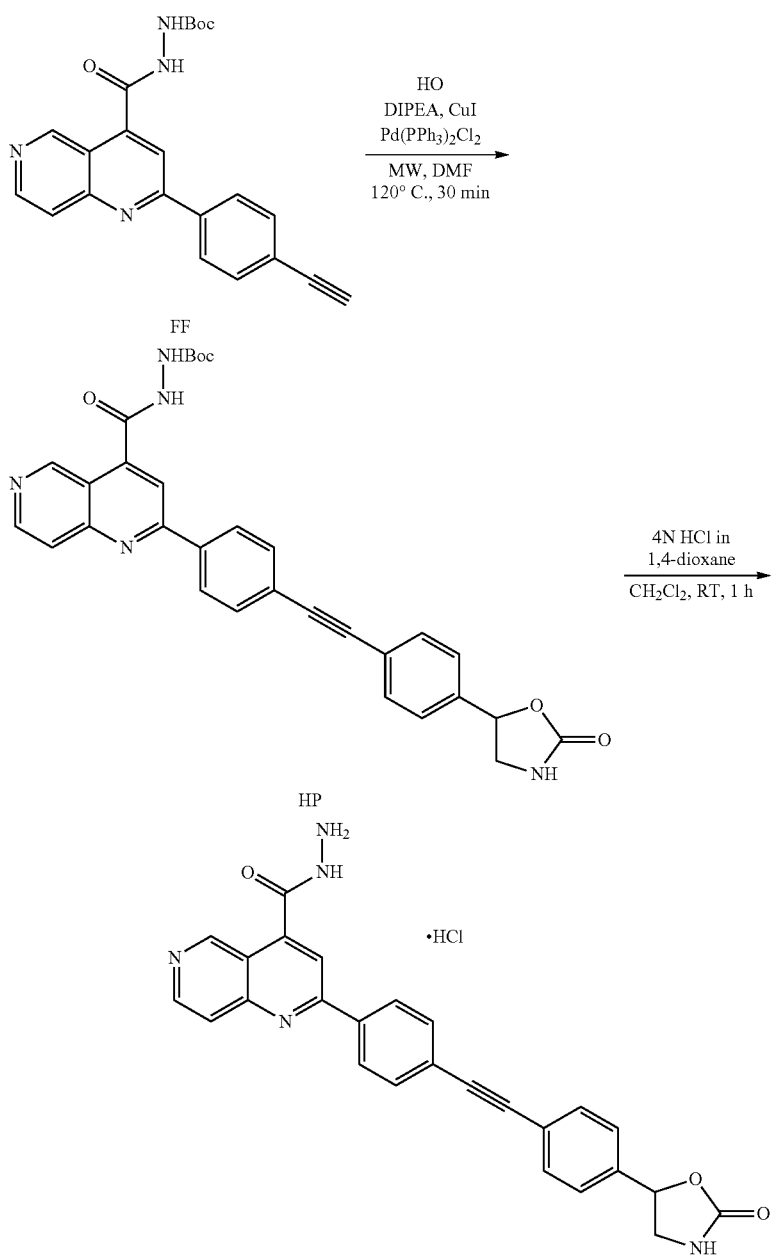

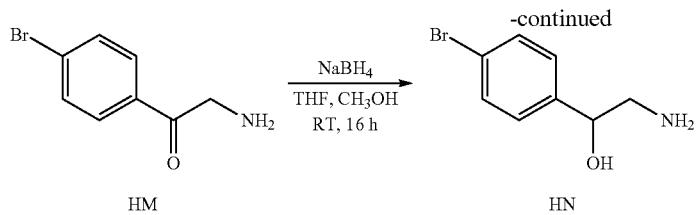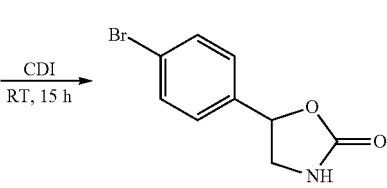

Example 211

2-(4-((4-(2-oxooxazolidin-5-yl)phenyl)ethynyl)phenyl)-1,6-naphthyridine-4-carbohydrazide hydrochloride (211)

To a stirred solution of 2-amino-1-(4-bromophenyl)ethan-1-one (HM; 2.5 g, 11.68 mmol) in MeOH:THF (20 mL:20 mL) under nitrogen atmosphere was added NaBH$_4$ (1.33 g, 35.04 mmol) portionwise at 0° C. The reaction was allowed to warm to RT and was stirred for 16 h. After complete consumption of the starting material (by TLC), the reaction was diluted with cold water (15 mL) and concentrated under reduced pressure. The crude was diluted with water (30 mL) and extracted with 10% MeOH:DCM (2×100 mL). The combined organic extracts were dried over sodium sulfate, filtered and concentrated under reduced pressure to afford compound HN (1.1 g, 43.6) as an off white solid. $^1$H NMR (400 MHz, DMSO-d$_6$): δ 7.50 (d, J=8.4 Hz, 2H), 7.27 (d, J=8.4 Hz, 2H), 5.16-5.08 (m, 1H), 4.44-4.41 (m, 1H), 3.60 (m, 1H), 2.67-2.63 (m, 2H). MS (ESI): m/z 217.08 [M+1]$^+$ To a stirred solution of compound HN (1 g, 4.62 mmol) in DCM (20 mL) under nitrogen atmosphere was added CDI (825 mg, 5.09 mmol) portionwise at 0° C. The reaction was allowed to warm to RT and was stirred for 15 h. After complete consumption of the starting material (by TLC), the reaction was diluted with cold water (20 mL) and extracted with DCM (2×50 mL). The combined organic extracts were dried over sodium sulfate, filtered and concentrated under reduced pressure to afford compound HO (750 mg, 67%) as a white solid.

$^1$H NMR (400 MHz, CDCl$_3$): δ 7.56-7.53 (m, 2H), 7.27-7.24 (m, 2H), 5.58 (t, J=8.0 Hz, 1H), 5.34 (br s, 1H), 4.00-3.96 (m, 1H), 3.51-3.47 (m, 1H). MS (ESI): m/z 243.07 [M+1]$^+$

To a stirred solution of compound FF (200 mg, 0.51 mmol) in DMF (5 mL) under argon atmosphere were added compound HO (133 mg, 0.51 mmol) and DIPEA (0.93 mL, 5.15 mmol) at RT. The reaction was purged under argon for 20 min followed by addition of copper iodide (9.8 mg, 0.05 mmol) and Pd(PPh$_3$)$_2$Cl$_2$ (36 mg, 0.05 mmol). The reaction was heated in the MW to 120° C. and stirred for 30 min. After complete consumption of the starting material (by TLC), the reaction mixture was filtered through Celite and the Celite pad was washed with ethyl acetate (15 mL). The filtrate was concentrated under reduced pressure. The crude was purified by silica gel column chromatography eluting with 3% MeOH:DCM to afford compound HP (70 mg, 25%) as a yellow solid. $^1$H NMR (400 MHz, DMSO-d$_6$): δ 10.82 (br s, 1H), 9.70 (s, 1H), 9.29 (s, 1H), 8.84 (d, J=6.0 Hz, 1H), 8.43 (d, J=8.0 Hz, 2H), 8.32 (s, 1H), 8.05 (d, J=5.6 Hz, 1H), 7.80 (d, J=8.0 Hz, 2H), 7.73 (s, 1H), 7.67 (d, J=8.4 Hz, 2H), 7.48 (d, J=8.0 Hz, 2H), 5.67 (t, J=7.2 Hz, 1H), 3.92 (t, J=8.8 Hz, 1H), 3.35 (t, J=9.2 Hz, 1H), 1.49 (s, 9H). MS (ESI): m/z 550.59 [M+1]$^+$ To a stirred solution of compound HP (25 mg, 0.04 mmol) in DCM (1 mL) under nitrogen atmosphere was added 4N HCl in 1,4-dioxane (0.5 mL) at 0° C. The reaction was allowed to warm to RT and was stirred for 1 h. After complete consumption of the starting material (by TLC), the volatiles were evaporated under reduced pressure. The crude was triturated with diethylether (2 mL) to afford 211 (13 mg as an HCl salt) as a yellow solid. $^1$H-NMR (DMSO-d$_6$, 400 MHz): δ 12.04 (s, 1H), 9.72 (s, 1H), 8.88 (d, J=6.0 Hz, 1H), 8.56 (s, 1H), 8.48 (d, J=8.4 Hz, 2H), 8.16 (d, J=6.0 Hz, 1H), 7.83 (d, J=8.4 Hz, 2H), 7.74 (s, 1H), 7.67 (d, J=8.4 Hz, 2H), 7.48 (d, J=8.0 Hz, 2H), 5.67 (t, J=7.2 Hz, 1H), 3.92 (t, J=8.8 Hz, 1H), 3.38-3.33 (m, 1H). MS (ESI): m/z 450.47 [M+1]$^+$. UPLC Purity: 93.22%.

Scheme 57

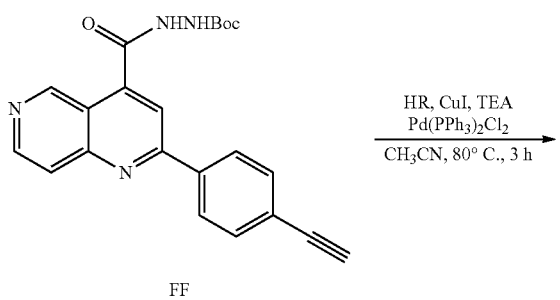

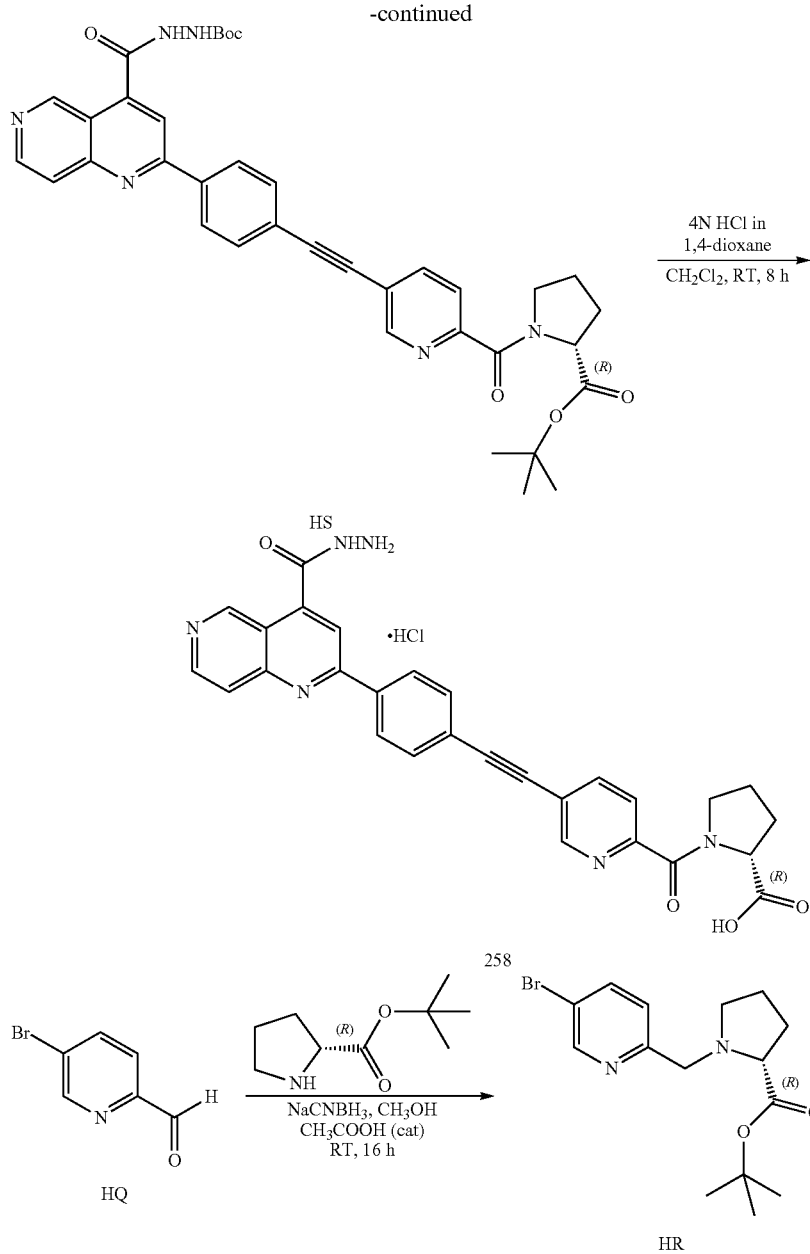

Example 258

((5-((4-(4-(hydrazinecarbonyl)-1,6-naphthyridin-2-yl)phenyl)ethynyl)pyridin-2-yl)methyl)-D-proline hydrochloride (258)

To a stirred solution of 5-bromo-2-formylpyridine (HQ; 760 mg, 4.09 mmol) in MeOH (15 mL) under nitrogen atmosphere was added D-proline tert-butylester (700 mg, 4.09 mmol) at 0° C. The reaction was allowed to warm to RT and was stirred for 2 h. Then NaCNBH$_3$ (1.28 g, 20.46 mmol) and acetic acid (0.2 mL) were added at 0° C. The reaction was allowed to warm to RT and was stirred for 16 h. After complete consumption of the starting material (by TLC), the reaction was concentrated under reduced pressure. The crude was diluted with water (30 mL) and extracted with EtOAc (2×50 mL). The combined organic extracts were dried over sodium sulfate, filtered and concentrated under reduced pressure to afford compound HR (600 mg, crude) as a colorless liquid. $^1$H NMR (400 MHz, DMSO-d$_6$): δ 8.58 (s, 1H), 8.01-7.98 (m, 1H), 7.43 (d, J=8.4 Hz, 1H), 3.91 (d, J=14.0 Hz, 1H), 3.68 (d, J=14.4 Hz, 1H), 3.27-3.24 (m, 1H), 2.91-2.86 (m, 1H), 2.44 (t, J=8.0 Hz, 1H), 2.08-1.98 (m, 1H), 1.82-1.70 (m, 3H), 1.36 (s, 9H). MS (ESI): m/z 342.25 [M+1]$^+$ To a stirred solution of compound FF (300 mg, 0.77 mmol) in CH$_3$CN (25 mL) under argon atmosphere were added compound HR (263 mg, 0.77 mmol) and TEA (1.09 mL, 7.73 mmol) at RT. The reaction was purged under argon for 20 min followed by addition of copper iodide (14.7 mg, 0.07 mmol) and Pd(PPh$_3$)$_2$Cl$_2$ (54 mg, 0.07 mmol). The reaction was heated to 80° C. and stirred for 3 h. After complete consumption of the starting material (by TLC), the reaction mixture was filtered through Celite and the Celite bed was washed with ethyl acetate (15 mL). The filtrate was concentrated under reduced pressure. The crude was purified by silica gel column chromatography eluting with 3% MeOH:DCM to afford compound HS (140 mg, 28%) as a yellow solid. $^1$H NMR (400 MHz, DMSO-$d_6$): δ 10.65 (s, 1H), 9.71 (s, 1H), 9.30 (s, 1H), 9.01 (s, 1H), 8.84 (d, J=5.6 Hz, 1H), 8.70 (s, 2H), 8.45 (d, J=7.6 Hz, 1H), 8.05-7.99 (m, 2H), 7.82 (d, J=8.4 Hz, 1H), 7.56-7.35 (m, 2H), 4.14-4.00 (m, 1H), 3.77 (m, 1H), 2.91-2.86 (m, 1H), 2.08-1.97 (m, 2H), 1.68-1.59 (m, 1H), 1.84-1.75 (m, 3H), 1.49 (s, 9H), 1.39 (s, 9H). MS (ESI): m/z 649.76 [M+1]$^+$ To a stirred solution of compound HS (30 mg, 0.04 mmol) in DCM (1 mL) under nitrogen atmosphere was added 4N HCl in 1,4-dioxane (0.5 mL) at 0° C. The reaction was allowed to warm to RT and was stirred for 8 h. After complete consumption of the starting material (by TLC), the volatiles were evaporated under reduced pressure. The crude material was triturated with CH$_3$CN (2 mL) to afford 258 (16 mg as an HCl salt) as a yellow solid. $^1$H-NMR (DMSO-$d_6$, 400 MHz): δ 12.06 (s, 1H), 9.72 (s, 1H), 8.87 (t, J=6.0 Hz, 2H), 8.56 (s, 1H), 8.51 (d, J=8.8 Hz, 2H), 8.17-8.13 (m, 2H), 7.87 (d, J=8.4 Hz, 2H), 7.65 (d, J=7.6 Hz, 1H), 4.76-4.49 (m, 2H), 3.64 (d, J=7.6 Hz, 2H), 3.35-3.28 (m, 1H), 2.60-2.49 (m, 1H), 2.11-1.93 (m, 3H). MS (ESI): m/z 493.5 [M+1]$^+$. HPLC Purity: 87.07%

Scheme 58

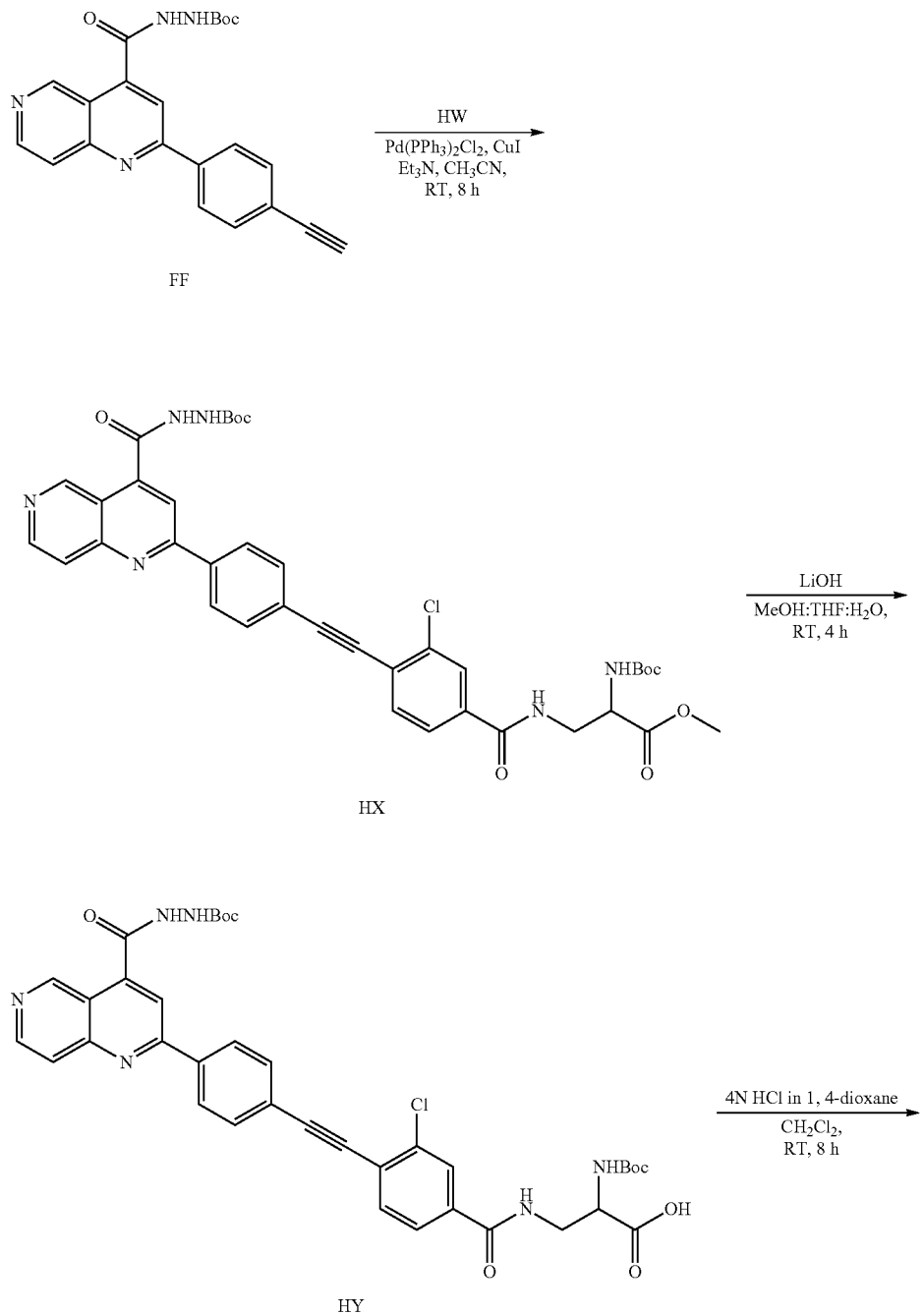

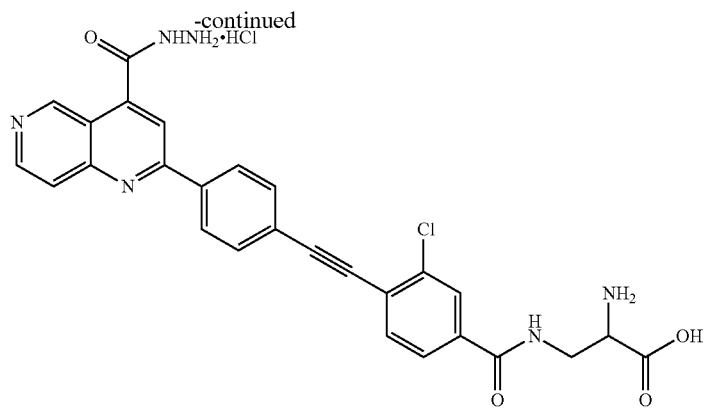

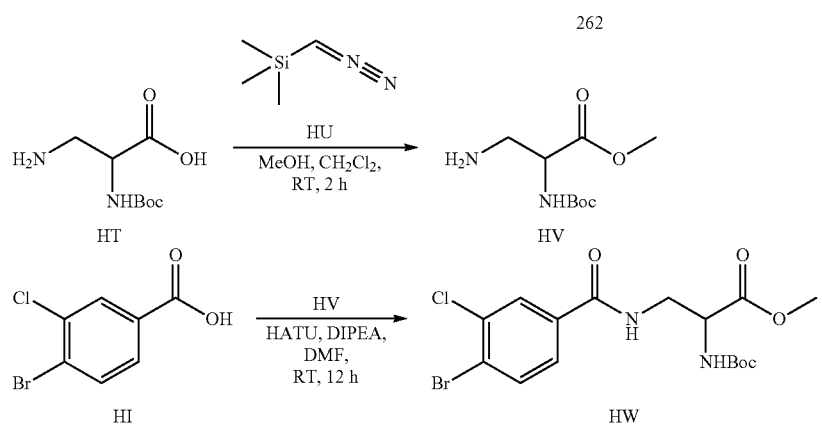

Example 262

2-amino-3-(3-chloro-4-((4-(4-(hydrazinecarbonyl)-1, 6-naphthyridin-2-yl)phenyl) ethynyl)benzamido) propanoic acid hydrochloride (262)

To a stirred solution of 3-amino-2-((tert-butoxycarbonyl) amino)propanoic acid (HT; 100 mg, 0.49 mmol) in DCM (5 mL) under nitrogen atmosphere were added (diazomethyl) trimethylsilane (0.26 mL, 0.53 mmol) and MeOH (0.5 mL). The reaction was stirred at RT for 2 h. After complete consumption of the starting material (by TLC), the reaction mixture was concentrated under reduced pressure to obtain compound HV (80 mg, 75%) as a colorless oil. $^1$H NMR (500 MHz, DMSO-$d_6$): δ 7.13-7.12 (m, 1H), 3.97-3.93 (m, 1H), 3.61 (s, 3H), 2.80-2.77 (m, 2H), 1.75 (br s, 1H), 1.41 (s, 9H). MS (ESI): m/z 219.4 [M+1]$^+$ To a stirred solution of 4-bromo-3-chlorobenzoic acid HI (500 mg, 2.12 mmol) in DMF (10 mL) under nitrogen atmosphere were added HATU (1.2 g, 3.18 mmol), DIPEA (1.56 mL, 8.49 mmol) and compound HV (510 mg, 2.33 mmol) at 0° C. The reaction was allowed to warm to RT and was stirred for 12 h. After complete consumption of the starting material (by TLC), the reaction was diluted with water (100 mL) and the compound was extracted with EtOAc (2×100 mL). The combined organic extracts were washed with water (100 mL), brine (50 mL), dried over sodium sulfate, filtered and concentrated under reduced pressure. The crude was purified by silica gel chromatography eluting with 20% EtOAc/hexane to afford compound HW (600 mg, 65%) as a pale yellow syrup. $^1$H NMR (500 MHz, DMSO-$d_6$): δ 8.71-8.70 (m, 1H), 8.00 (s, 1H), 7.90 (d, J=8.5 Hz, 1H), 7.68 (d, J=8.0 Hz, 1H), 7.24 (d, J=8.0 Hz, 1H), 4.25 (d, J=7.0 Hz, 1H), 3.60 (s, 3H), 3.57 (d, J=6.0 Hz, 2H), 1.39 (s, 9H). MS (ESI): m/z 436.3 [M+1]$^+$ To a stirred solution of compound FF (250 mg, 0.64 mmol) in CH$_3$CN (20 mL) under argon atmosphere were added compound HW (308 mg, 0.70 mmol) and TEA (0.92 mL, 6.44 mmol). The reaction was purged with argon for 10 min followed by the addition of copper iodide (12 mg, 0.06 mmol) and Pd(PPh$_3$)$_2$Cl$_2$ (45 mg, 0.06 mmol). The reaction was heated to 90° C. and stirred for 4 h. After complete consumption of the starting material (by TLC), the reaction mixture was concentrated under reduced pressure. The crude was purified by silica gel column chromatography eluting with 2-5% MeOH/DCM to afford compound HX (150 mg, 31%) as a yellow solid. $^1$H-NMR (500 MHz, DMSO-$d_6$): δ 10.66 (br s, 1H), 9.72 (s, 1H), 9.29 (s, 1H), 8.84 (d, J=6.0 Hz, 1H), 8.74 (t, J=7.0 Hz, 1H), 8.47 (d, J=8.0 Hz, 2H), 8.05 (d, J=6.0 Hz, 1H), 8.00 (s, 1H), 7.87-7.83 (m, 3H), 7.26 (d, J=8.0 Hz, 1H), 4.27 (q, 1H), 3.62-3.56 (m, 5H), 1.49 (s, 9H), 1.37 (s, 9H). MS (ESI): m/z 744.7 [M+1]$^+$ To a stirred solution of compound HX (50 mg, 0.06 mmol) in MeOH:THF:H$_2$O (4 mL:4 mL:2 mL) was added lithium hydroxide monohydrate (14 mg, 0.33 mmol) at 0° C. The reaction was allowed to warm to RT and was stirred for 4 h. After complete consumption of the starting material (by TLC), the volatiles were evaporated under reduced pressure. The crude was diluted with water and the pH was adjusted to ~3 using an acetic acid solution (0.2 mL). The solid precipitate was filtered and dried under reduced pressure to afford compound HY (35 mg, 71%) as a yellow solid. $^1$H-NMR (500 MHz, DMSO-$d_6$): δ 10.67 (br s, 1H), 9.73 (br s, 1H), 9.29 (s, 1H), 9.12 (s, 1H), 8.83 (d, J=6.0 Hz, 1H), 8.46 (d, J=8.5 Hz, 2H), 8.35 (s, 1H), 8.05 (d, J=6.0 Hz, 1H), 7.94 (s, 1H), 7.84-7.77 (m, 4H), 6.07 (s, 1H), 3.62-3.56 (m, 2H), 3.21-3.20 (m, 1H), 1.49 (s, 9H), 1.37 (s, 9H). MS (ESI): m/z 730.5 [M+1]⁺

To a stirred solution of compound HY (35 mg, 0.04 mmol) in DCM (3 mL) under nitrogen atmosphere was added 4N HCl in 1,4-dioxane (0.5 mL) at 0° C. The reaction was allowed to warm to RT and stir for 2 h. After complete consumption of the starting material (by TLC), the volatiles were evaporated under reduced pressure. The crude residue was triturated with CH$_3$CN (2 mL) to afford 262 (18 mg as an HCl salt) as a yellow solid. $^1$H-NMR (400 MHz, DMSO-d$_6$): δ 12.44-12.39 (m, 1H), 9.70 (s, 1H), 9.28 (s, 1H), 9.06 (d, J=5.6 Hz, 1H), 8.88 (d, J=6.0 Hz, 1H), 8.65 (s, 1H), 8.55 (d, J=8.4 Hz, 1H), 8.50-8.45 (m, 2H), 7.94-7.85 (m, 3H), 4.16-4.12 (m, 1H), 3.71-3.67 (m, 1H), 3.50-3.47 (m, 1H). MS (ESI): m/z 529.4 [M+1]⁺. UPLC Purity: 94.04%

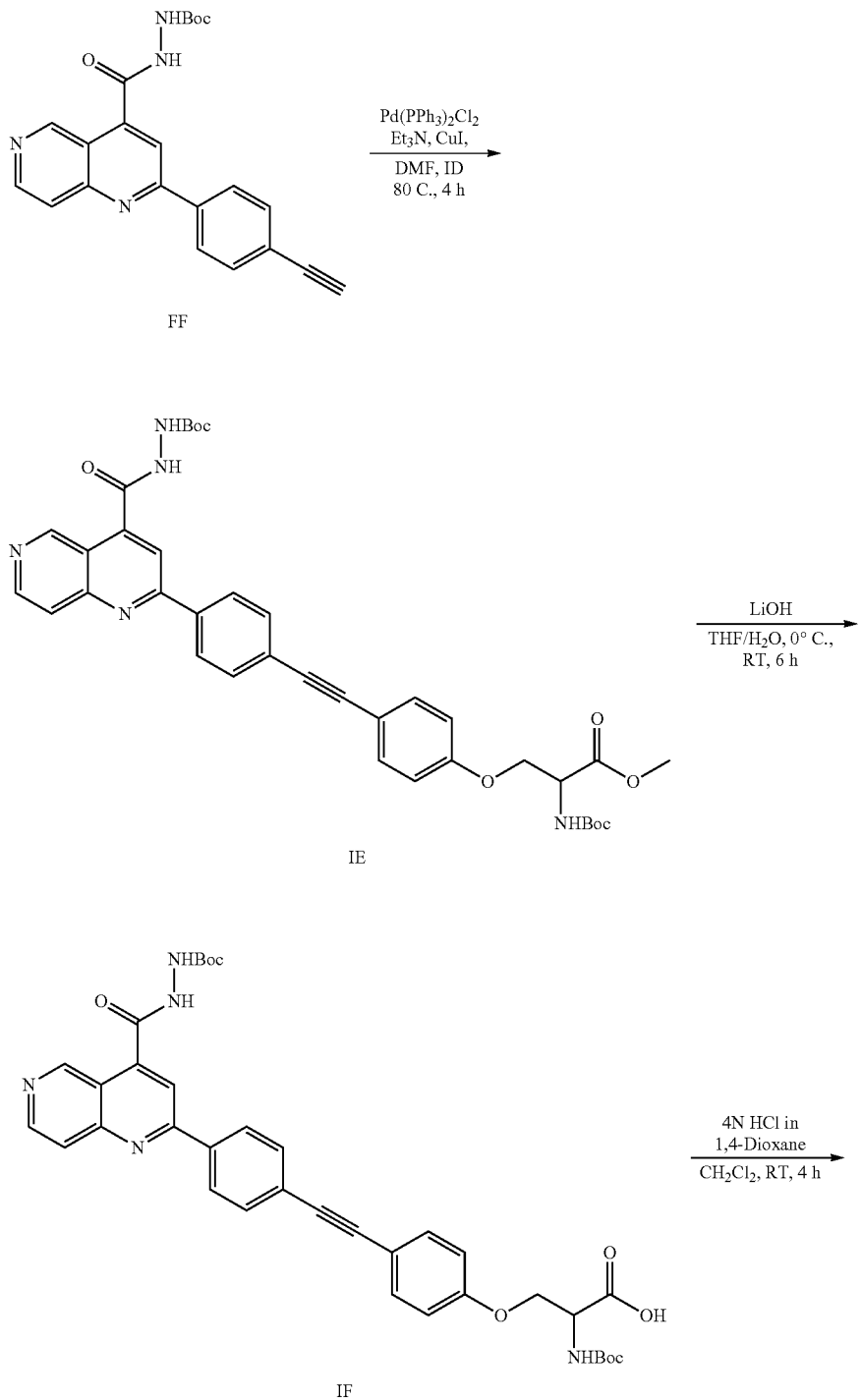

Scheme 59

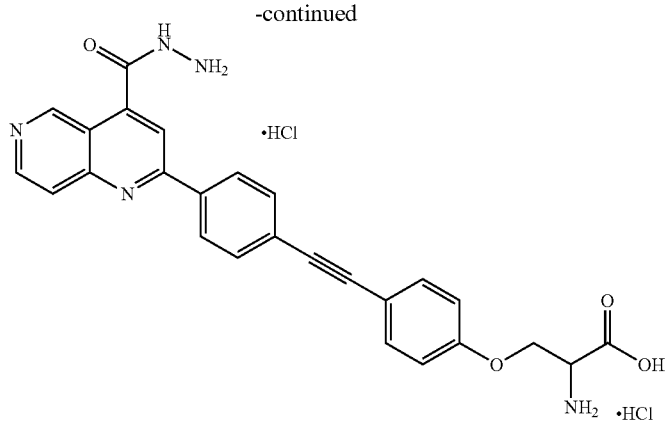

277

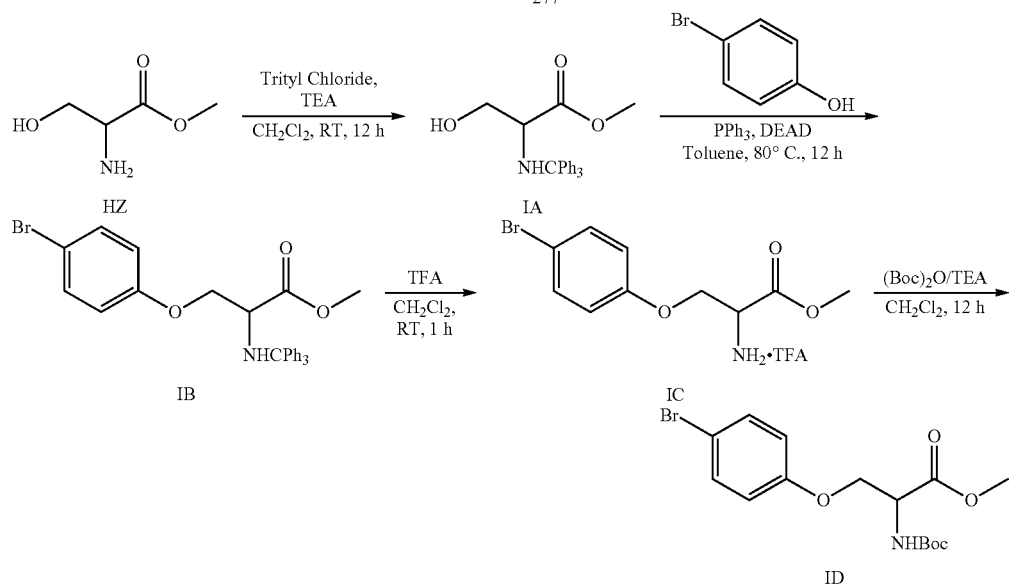

Example 277

O-(4-((4-(4-(hydrazinecarbonyl)-1,6-naphthyridin-2-yl)phenyl)ethynyl)phenyl)serine dihydrochloride (277)

To a stirred solution of DL-serine methyl ester HCl (HZ; 200 mg, 1.28 mmol) in DCM (10 mL) under nitrogen atmosphere were added TEA (0.9 mL, 6.40 mmol) and trityl chloride (442 mg, 1.53 mmol) at 0° C. The reaction was allowed to warm to RT and was stirred for 12 h. After complete consumption of the starting material (by TLC), the reaction was diluted with water (15 mL) and extracted with EtOAc (2×20 mL). The combined organic extracts were dried over sodium sulfate, filtered and concentrated under reduced pressure. The crude material was purified by silica gel column chromatography eluting with 1% MeOH:DCM to afford compound IA (300 mg, 65%) as a white solid. $^1$H NMR (400 MHz, DMSO-$d_6$): δ 7.41 (d, J=7.2 Hz, 6H), 7.27 (t, J=7.6 Hz, 6H), 7.19 (t, J=7.2 Hz, 3H), 4.91 (s, 1H), 3.61-3.57 (m, 1H), 3.44-3.39 (m, 1H), 3.19 (s, 3H), 2.80 (d, J=8.0 Hz, 1H), 2.50-2.47 (m, 1H)

To a stirred solution of triphenylphosphine (302 mg, 1.15 mmol) in toluene (10 mL) was added DEAD (200 mg, 1.15 mmol) under nitrogen atmosphere at 0° C. After stirling for 10 min, compound IA (200 mg, 1.15 mmol) in toluene (2 mL) and 4-bromophenol (415 mg, 1.15 mmol) in toluene (2 mL) were added dropwise. After stirring for 10 min, the reaction was heated to 80° C. and stirred for 48 h. After complete consumption of the starting material (by TLC), the reaction was diluted with water (20 mL) and extracted with EtOAc (2×20 mL). The combined organic extracts were dried over sodium sulfate, filtered and concentrated under reduced pressure. The crude was purified by silica gel column chromatography eluting with 10% EtOAc:hexane to afford compound IB (250 mg, 42%) as a white solid. $^1$H NMR (500 MHz, DMSO-$d_6$): δ 7.42-7.38 (m, 5H), 7.33-7.17 (m, 14H), 6.82 (d, J=8.5 Hz, 1H), 4.13-4.10 (m, 1H), 4.03-3.99 (m, 1H), 3.50-3.48 (m, 1H), 3.16 (s, 3H), 3.08 (d, J=10.0 Hz, 1H). MS (ESI): m/z 516.43 [M+1]$^+$ To a stirred solution of compound IB (900 mg, 1.74 mmol) in DCM (10 mL) under nitrogen atmosphere was added TFA (1.98 g, 17.42 mmol) at 0° C. and the reaction was stirred for 10 min. The reaction was allowed to warm to RT and was stirred for 1 h. After complete consumption of the starting material (by TLC), the volatiles were evaporated under reduced pressure to obtain compound IC (800 mg, TFA salt) as a yellow solid.

To a stirred solution of compound IC (800 mg, 2.06 mmol) in DCM (10 mL) under nitrogen atmosphere was added TEA (2 mL, 14.47 mmol) at 0° C. Boc anhydride (1.35 mL, 6.18 mmol) was added dropwise at 0° C. and the reaction was stirred for 10 min. The reaction was allowed to warm to RT and was stirred for 12 h. After complete consumption of the starting material (by TLC), the reaction was diluted with water (20 mL) and extracted with DCM (2×30 mL). The combined organic extracts were washed with water (2×20 mL), brine (2×15 mL), dried over sodium sulfate, filtered and concentrated under reduced pressure. The crude residue was purified by silica gel column chromatography eluting with 15% EtOAc:hexane to afford compound ID (250 mg, 42%) as a viscous liquid. $^1$H NMR (500 MHz, DMSO-$d_6$): δ 7.43 (d, J=9.0 Hz, 3H), 6.89 (d, J=9.0 Hz, 2H), 4.45-4.42 (m, 1H), 4.19 (d, J=5.5 Hz, 2H), 3.66 (s, 3H), 1.38 (s, 9H). MS (ESI): m/z 374.23 [M+1]$^+$ To a stirred solution of compound FF (300 mg, 0.77 mmol) in CH$_3$CN (15 mL) under argon atmosphere were added compound ID (345 mg, 0.92 mmol) and TEA (1.1 mL, 7.73 mmol) at RT. The reaction was purged under argon for 20 min followed by the addition of copper iodide (14.7 mg, 0.07 mmol) and Pd(PPh$_3$)$_2$Cl$_2$ (54 mg, 0.07 mmol). The reaction was heated to 70° C. and stirred for 4 h. After complete consumption of the starting material (by TLC), the reaction was diluted with water (20 mL) and extracted with DCM (2×30 mL). The combined organic extracts were washed with water (2×20 mL), brine (2×15 mL), dried over sodium sulfate, filtered and concentrated under reduced pressure. The crude was purified by silica gel column chromatography eluting with 3% MeOH:DCM and further purified by preparative HPLC to afford compound IE (30 mg, 6%) as a yellow solid. $^1$H NMR (500 MHz, DMSO-$d_6$): δ 10.63 (s, 1H), 9.69 (s, 1H), 9.28 (s, 1H), 8.82 (d, J=5.5 Hz, 1H), 8.40 (d, J=8.5 Hz, 2H), 8.31 (s, 1H), 8.03 (d, J=5.5 Hz, 1H), 7.75 (d, J=8.0 Hz, 2H), 7.54 (d, J=8.5 Hz, 2H), 7.46 (d, J=8.0 Hz, 1H), 7.00 (d, J=8.5 Hz, 2H), 4.48 (d, J=7.0 Hz, 1H), 4.26 (s, 2H), 3.68 (s, 3H), 1.49 (s, 9H), 1.40 (s, 9H). MS (ESI): m/z 681.75 [M+1]$^+$ To a stirred solution of compound IE (25 mg, 0.03 mmol) in THF:MeOH:H$_2$O (2 mL:2 mL:1 mL) were added lithium hydroxide monohydrate (7.7 mg, 0.18 mmol) at 0° C. The reaction was allowed to warm to RT and was stirred for 6 h. After complete consumption of the starting material (by TLC), the reaction mixture was concentrated under reduced pressure. The crude was diluted with water and acidified with acetic acid to pH~3. The precipitate was filtered and dried under reduced pressure to afford compound IF (20 mg, crude) as a yellow solid. $^1$H NMR (500 MHz, DMSO-$d_6$): δ 10.65 (s, 1H), 10.00 (br s, 1H), 9.70 (s, 1H), 9.29 (s, 1H), 8.83 (d, J=5.0 Hz, 1H), 8.40-8.31 (m, 4H), 8.04 (d, J=5.0 Hz, 1H), 7.79-7.72 (m, 2H), 7.54-7.42 (m, 2H), 6.99 (d, J=8.5 Hz, 1H), 6.83 (d, J=8.5 Hz, 1H), 4.22-4.15 (m, 3H), 1.49 (s, 9H), 1.39 (s, 9H). MS (ESI): m/z 667.26 [M+1]$^+$ To a stirred solution of compound IF (20 mg, crude) in DCM (2 mL) under nitrogen atmosphere was added 4N HCl in 1,4-dioxane (1 mL) at 0° C. The reaction was allowed to warm to RT and was stirred for 4 h. After complete consumption of the starting material (by TLC), the volatiles were evaporated under reduced pressure. The crude material was triturated with CH$_3$CN (3 mL) and further purified through preparative HPLC to afford 277 (8 mg as an HCl salt) as a yellow solid. $^1$H NMR (500 MHz, DMSO-$d_6$): δ 11.00 (s, 1H), 9.65 (s, 1H), 8.83 (d, J=6.0 Hz, 1H), 8.52 (s, 3H), 8.41 (t, J=8.0 Hz, 3H), 8.05 (d, J=6.0 Hz, 1H), 7.76 (d, J=8.0 Hz, 2H), 7.58 (d, J=9.0 Hz, 2H), 7.07 (d, J=8.5 Hz, 2H), 4.52-4.47 (m, 3H), 4.35 (d, J=8.0 Hz, 2H). MS (ESI): m/z 468.3 [M+1]$^+$. UPLC Purity: 99.26%

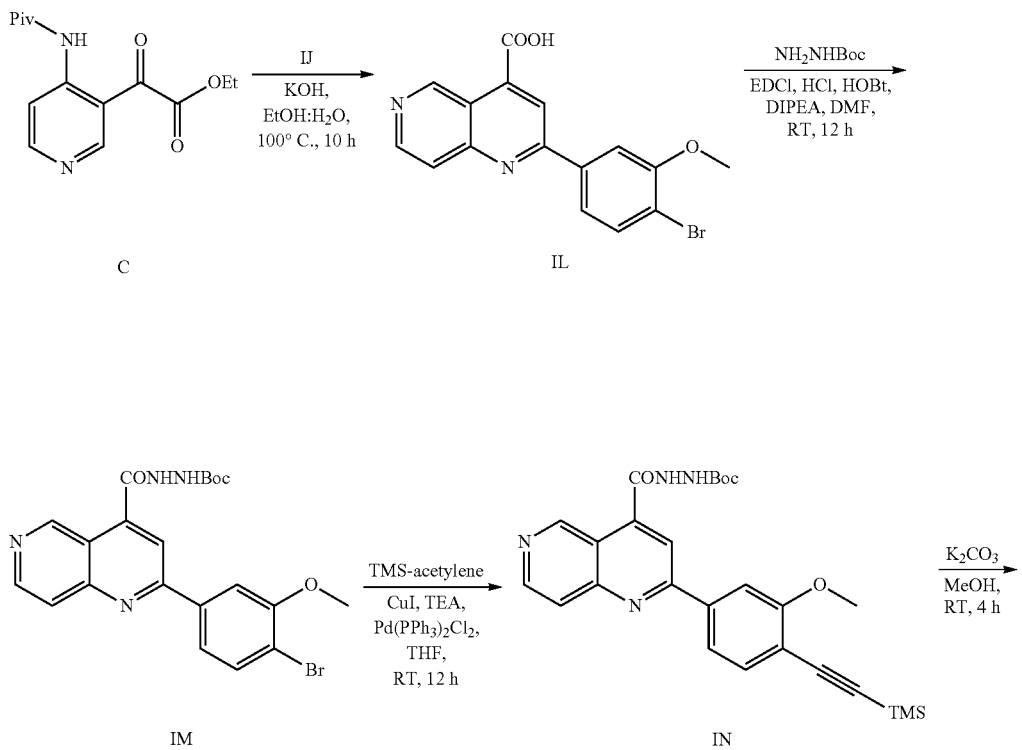

Scheme 60

-continued
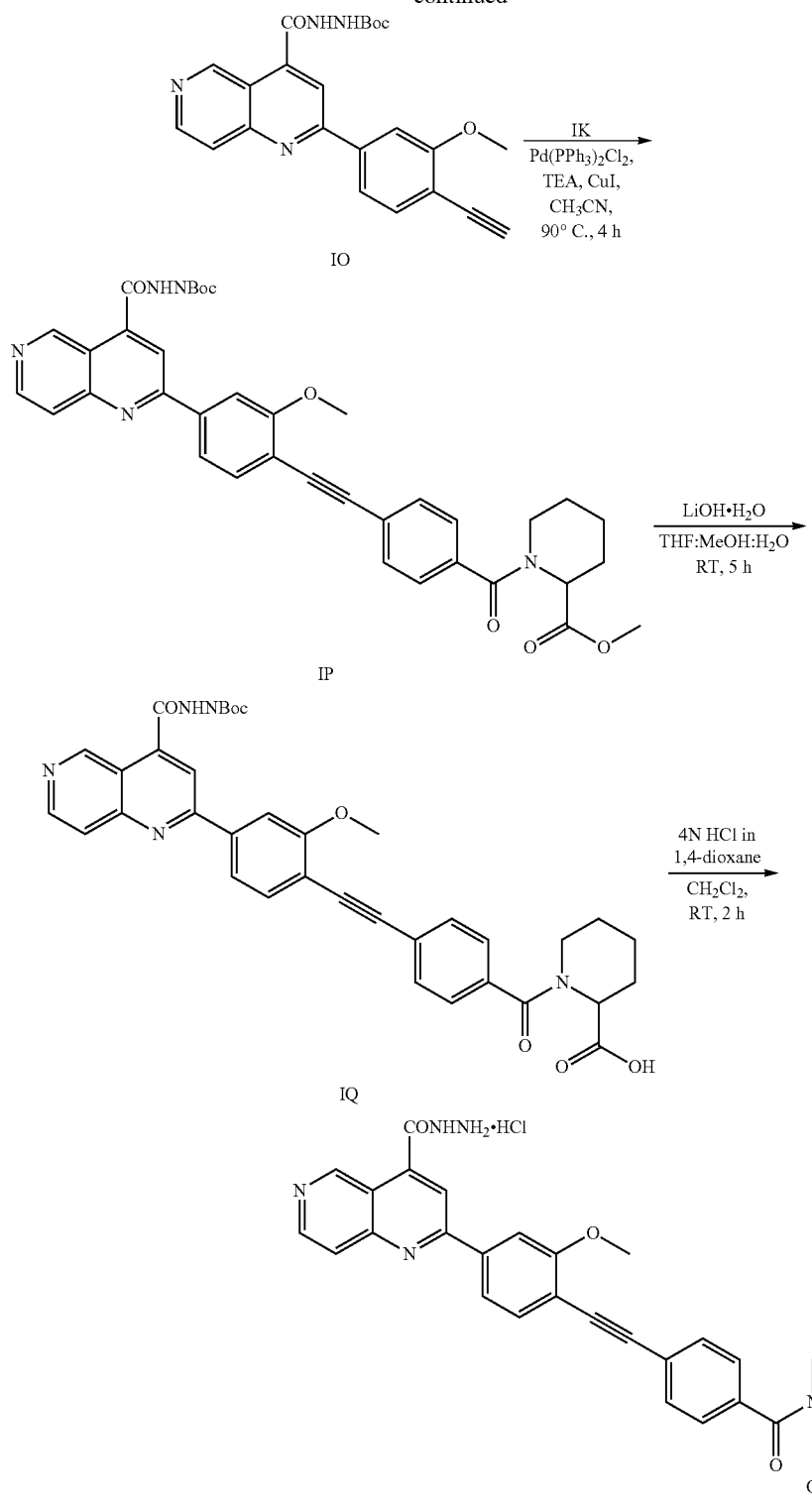
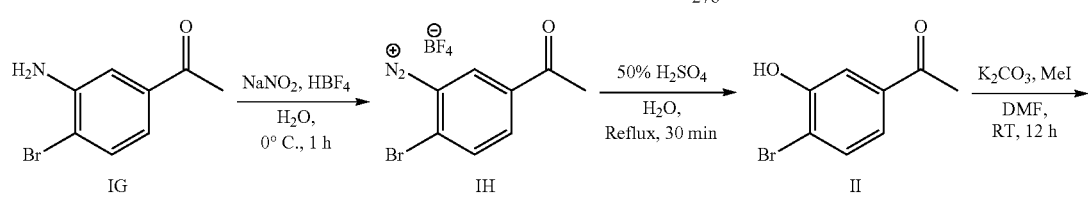

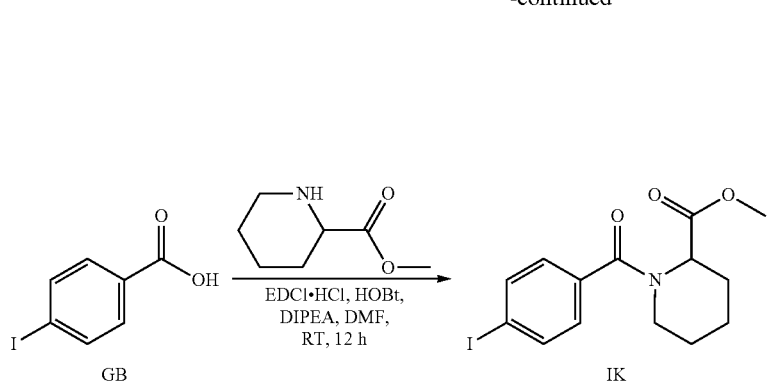

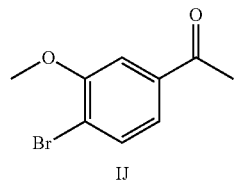

Example 278

1-(4-((4-(4-(hydrazinecarbonyl)-1,6-naphthyridin-2-yl)-2-methoxyphenyl)ethynyl)benzoyl)piperidine-2-carboxylic acid hydrochloride (278)

To a stirred solution of 1-(3-amino-4-bromophenyl)ethan-1-one (IG; 3 g, 14.01 mmol) in H$_2$O (15 mL) were added sodium nitrate (1.93 g, 28.03 mmol) and 51-57% HBF$_4$ in diethyl ether (3 mL) at 0° C. The reaction was allowed to warm to RT and was stirred for 1 h. After complete consumption of the starting material (by TLC), the reaction mixture was filtered. The obtained solid was washed with water (2×5 mL) and dried under reduced pressure to afford compound IH (150 mg, crude) as an orange solid. The crude product was carried forward without further purification.

To a stirred solution of compound IH (3 g, 13.33 mmol) in H$_2$O (6 mL) under nitrogen atmosphere was added 50% sulphuric acid (39 mL) at RT. The reaction was heated to reflux and stirred for 30 min. After complete consumption of the starting material (by TLC), the reaction mixture was extracted with EtOAc (2×40 mL). The combined organic extracts were dried over sodium sulfate, filtered and concentrated under reduced pressure. The crude was purified by silica gel column chromatography eluting with 15-20% EtOAc/hexane to afford compound II (700 mg, 24%) as a yellow solid. $^1$H-NMR (500 MHz, DMSO-d$_6$): δ 10.63 (s, 1H), 7.64 (d, J=8.0 Hz, 1H), 7.45 (s, 1H), 7.33 (d, J=8.0 Hz, 1H), 2.50 (d, J=9.5 Hz, 3H). MS (ESI): m/z 216.2 [M+1]$^+$ To a stirred solution of compound II (500 mg, 2.33 mmol) in DMF (10 mL) under nitrogen atmosphere were added potassium carbonate (967 mg, 7.00 mmol) and methyl iodide (995 mg, 7.00 mmol) at 0° C. The reaction was allowed to warm to RT and was stirred for 12 h. After complete consumption of the starting material (by TLC), the reaction mixture was diluted with water (25 mL) and extracted with EtOAc (2×30 mL). The combined organic extracts were dried over sodium sulfate, filtered and concentrated under reduced pressure. The crude was purified by silica gel chromatography to afford compound IJ (500 mg, 93%) as a pale yellow liquid. $^1$H-NMR (500 MHz, CDCl$_3$): δ 7.62 (d, J=8.5 Hz, 1H), 7.48 (s, 1H), 7.38 (d, J=8.5 Hz, 1H), 3.95 (s, 3H), 2.59 (s, 3H). MS (ESI): m/z 230.4 [M+1]$^+$ To a stirred solution of 4-iodobenzoic acid GB (500 mg, 2.01 mmol) in DMF (10 mL) under nitrogen atmosphere were added methyl piperidine-2-carboxylate (343 mg, 2.41 mmol), EDCI.HCl (967 mg, 5.04 mmol), HOBt (493 mg, 3.62 mmol), and DIPEA (1.3 g, 10.08 mmol) at RT. The reaction was stirred for 12 h. After complete consumption of the starting material (by TLC), the reaction mixture was diluted with water (25 mL) and extracted with EtOAc (2×35 mL). The combined organic extracts were dried over sodium sulfate, filtered and concentrated under reduced pressure. The crude material was purified by silica gel chromatography to afford compound IK (600 mg, 80%) as an off-white solid. $^1$H-NMR (500 MHz, CDCl$_3$): δ 7.74 (d, J=7.5 Hz, 2H), 7.16 (d, J=8.0 Hz, 2H), 5.46 (br s, 1H), 4.41-4.38 (m, 1H), 3.91-3.88 (m, 1H), 3.78-3.75 (m, 3H), 3.60-3.57 (m, 1H), 3.32 (br s, 1H), 3.26-3.22 (m, 1H), 2.40 (br s, 1H), 1.25-1.22 (m, 2H). MS (ESI): m/z 374.5 [M+1]$^+$ To a stirred solution of ethyl 2-oxo-2-(4-pivalamidopyridin-3-yl)acetate (C; 500 mg, 1.79 mmol) in EtOH:H$_2$O (1:1, 20 mL) were added compound IJ (494 mg, 2.15 mmol) and potassium hydroxide (402 mg, 7.19 mmol) at 0° C. The reaction was heated to reflux and stirred for 12 h. The reaction mixture was concentrated under reduced pressure. The crude was diluted with water (25 mL) and acidified with acetic acid to pH~4. The precipitate was filtered and dried under reduced pressure to afford compound IL (510 mg, 65%) as a yellow solid. $^1$H-NMR (500 MHz, DMSO-d$_6$): δ 9.98 (s, 1H), 8.78 (d, J=6.0 Hz, 1H), 8.53 (s, 1H), 8.01 (d, J=6.0 Hz, 1H), 7.97 (s, 1H), 7.84 (d, J=8.0 Hz, 1H), 7.78 (d, J=8.5 Hz, 2H), 4.02 (s, 3H). MS (ESI): m/z 360.1 [M+1]$^+$ To a stirred solution of compound IL (500 mg, 1.38 mmol) in DMF (15 mL) under nitrogen atmosphere were added tert-butyl carbazate (548 mg, 4.15 mmol), EDCI.HCl (664 mg, 3.46 mmol), HOBt (339 mg, 2.49 mmol), and DIPEA (714 mg, 5.54 mmol) at 0° C. The reaction was allowed to warm to RT and was stirred for 12 h. After complete consumption of the starting material (by TLC), the reaction mixture was diluted with water (25 mL) and extracted with EtOAc (2×25 mL). The combined organic extracts were dried over sodium sulfate, filtered and concentrated under reduced pressure. The crude material was purified by flash chromatography to afford compound IM (430 mg, 66%) as an off-white solid. $^1$H-NMR (500 MHz, DMSO-d$_6$): δ 10.62 (br s, 1H), 9.70 (s, 1H), 9.28 (s, 1H), 8.82 (d, J=6.0 Hz, 1H), 8.32 (s, 1H), 8.03 (d, J=6.0 Hz, 1H), 7.99 (s, 1H), 7.87 (d, J=8.0 Hz, 1H), 7.80 (d, J=8.0 Hz, 1H), 4.03 (s, 3H), 1.49 (s, 9H). MS (ESI): m/z 474.5 [M+1]$^+$ To a stirred solution of compound IM (430 mg, 0.91 mmol) in THF (15 mL) under nitrogen atmosphere were added TMS-acetylene (890 mg, 9.11 mmol) and TEA (920 mg, 9.11 mmol) at 0° C. The reaction was purged with argon for 10 min followed by the addition of Pd(PPh$_3$)$_2$Cl$_2$ (63 mg, 0.09 mmol) and copper iodide (17 mg, 0.09 mmol) at RT. The reaction was stirred for 12 h. After complete consumption of the starting material (by TLC), the reaction mixture was concentrated under reduced pressure. The crude was purified by silica gel chromatography to afford compound IN (320 mg, 84%) as a yellow solid. $^1$H-NMR (500 MHz, DMSO-d$_6$): δ 10.62 (s, 1H), 9.70 (br s, 1H), 9.28 (br s, 1H), 8.82 (br s, 1H), 8.32 (s, 1H), 7.99 (s, 1H), 7.95 (s, 1H), 7.91 (d, J=6.5 Hz, 1H), 7.60-7.54 (m, 1H), 3.99 (s, 3H), 1.48 (s, 9H), 0.26 (s, 9H). MS (ESI): m/z 491.2 [M+1]$^+$ To a stirred solution of compound IN (200 mg, 0.40 mmol) in MeOH (10 mL) under nitrogen atmosphere was added potassium carbonate (168 mg, 1.22 mmol) at RT and the reaction was stirred for 4 h. After complete consumption of the starting material (by TLC), the reaction mixture was diluted with water (25 mL) and extracted with EtOAc (2×25 mL). The combined organic extracts were dried over sodium sulfate, filtered and concentrated under reduced pressure. The crude material was purified by silica gel chromatography to afford compound IO (150 mg, 88%) as a yellow solid. $^1$H-NMR (500 MHz, DMSO-d$_6$): δ 10.62 (s, 1H), 9.70 (s, 1H), 9.28 (s, 1H), 8.82 (d, J=6.0 Hz, 1H), 8.32 (s, 1H), 8.03 (d, J=6.0 Hz, 1H), 7.95-7.91 (m, 2H), 7.62 (d, J=7.5 Hz, 1H), 4.45 (s, 1H), 4.00 (s, 3H), 1.49 (s, 9H). MS (ESI): m/z 419.6 [M+1]$^+$ To a stirred solution of compound IO (150 mg, 0.35 mmol) in CH$_3$CN (20 mL) under nitrogen atmosphere were added compound IK (162 mg, 0.43 mmol) and TEA (0.5 mL, 3.58 mmol) at RT. The reaction was purged under argon for 10 min followed by the addition of copper iodide (6.8 mg, 0.03 mmol) and Pd(PPh$_3$)$_2$Cl$_2$ (25 mg, 0.03 mmol). The reaction was heated to 90° C. and stirred for 4 h. After complete consumption of the starting material (by TLC), the reaction mixture was concentrated under reduced pressure. The crude was purified by silica gel chromatography to afford compound IP (200 mg, 63%) as a yellow solid. $^1$H-NMR (500 MHz, DMSO-d$_6$): δ 10.66 (s, 1H), 9.73 (br s, 1H), 9.31 (s, 1H), 8.85 (br s, 1H), 8.37 (s, 1H), 8.07-8.00 (m, 4H), 7.82-7.55 (m, 3H), 7.45-7.40 (m, 1H), 5.28 (br s, 1H), 4.44-4.43 (m, 1H), 4.06 (s, 3H), 3.74-3.70 (m, 2H), 3.52-3.50 (m, 1H), 3.16-3.15 (m, 1H), 2.20-2.19 (m, 1H), 1.99-1.98 (m, 1H), 1.72-1.69 (m, 2H), 1.55 (s, 9H). MS (ESI): m/z 664.4 [M+1]$^+$ To a stirred solution of compound IP (100 mg, 0.15 mmol) in MeOH:THF:H$_2$O (2:2:1, 10 mL) was added lithium hydroxide monohydrate (32 mg, 0.75 mmol) at 0° C. The reaction was allowed to warm to RT and stir for 5 h. After complete consumption of the starting material (by TLC), the volatiles were evaporated under reduced pressure. The crude was diluted with water and the pH was adjusted to 3 using an acetic acid solution (0.2 mL). The precipitate was filtered and dried under reduced pressure to afford compound IQ (55 mg, 57%) as a yellow solid. $^1$H-NMR (500 MHz, DMSO-d$_6$): δ 10.64 (s, 1H), 9.71 (s, 1H), 9.28 (s, 1H), 8.82 (br s, 1H), 8.35 (s, 1H), 8.04-8.00 (m, 3H), 7.72-7.59 (m, 4H), 7.41-7.40 (m, 2H), 4.05 (s, 3H), 3.46-3.45 (m, 1H), 2.99-2.98 (m, 1H), 2.84-2.82 (m, 2H), 2.21-2.20 (m, 1H), 2.09-2.08 (m, 1H), 2.00-1.99 (m, 1H), 1.68-1.67 (m, 3H), 1.49-1.48 (m, 2H), 1.33-1.32 (m, 2H). MS (ESI): m/z 650.5 [M+1]$^+$ To a stirred solution of compound IQ (25 mg, 0.038 mmol) in DCM (2 mL) under nitrogen atmosphere was added 4N HCl in 1,4-dioxane (0.5 mL) at 0° C. The reaction was allowed to warm to RT and was stirred for 2 h. After complete consumption of the starting material (by TLC), the volatiles were evaporated under reduced pressure. The crude was triturated with 10% MeOH/CH$_3$CN (2×5 mL) to afford 278 (13 mg as an HCl salt) as a yellow solid. $^1$H-NMR (500 MHz, DMSO-d$_6$): δ 12.01 (br s, 1H), 9.84 (br s, 1H), 8.98 (br s, 1H), 8.59 (s, 1H), 8.19 (br s, 1H), 8.09 (s, 1H), 8.04 (d, J=7.5 Hz, 1H), 7.76 (d, J=8.0 Hz, 1H), 7.66-7.65 (m, 2H), 7.44 (d, J=7.5 Hz, 1H), 7.40 (br s, 1H), 5.19 (br s, 1H), 4.32-4.31 (m, 1H), 4.29-4.28 (m, 1H), 4.07 (s, 3H), 3.50-3.47 (m, 1H), 3.19-3.17 (m, 1H), 2.20-2.18 (m, 1H), 2.06-2.02 (m, 1H), 1.72-1.70 (m, 3H), 1.44-1.41 (m, 2H). MS (ESI): m/z 550.5 [M+1]$^+$. HPLC: 90.91%

Scheme 61

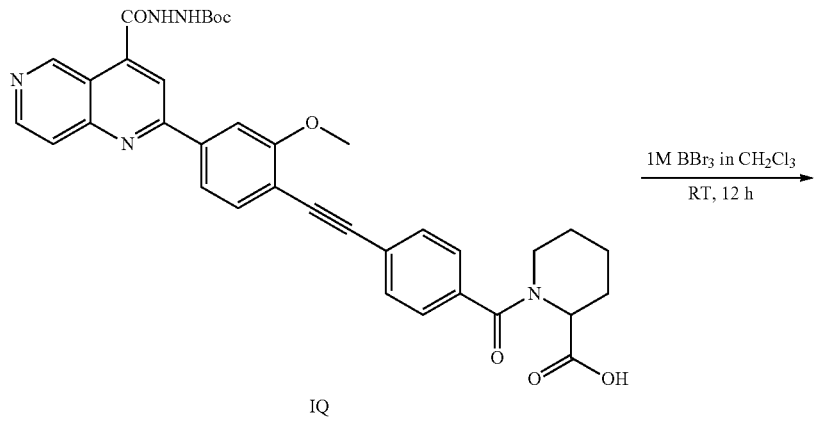

1M BBr$_3$ in CH$_2$Cl$_2$
RT, 12 h

IQ

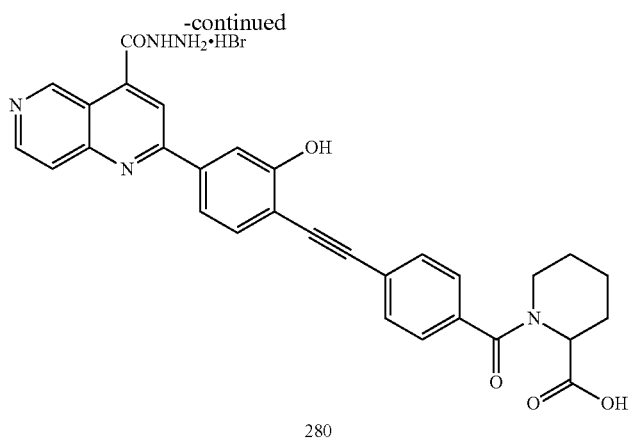

280

Example 280

1-(4-((4-(4-(hydrazinecarbonyl)-1,6-naphthyridin-2-yl)-2-hydroxyphenyl)ethynyl)benzoyl)piperidine-2-carboxylic acid HBr salt (280)

To a stirred solution of compound IQ (20 mg, 0.03 mmol) in DCM (2 mL) was added 1M BBr₃ in DCM (45 mg, 0.18 mmol) at −78° C. The reaction was allowed to warm to RT and was stirred for 12 h. After complete consumption of the starting material (by TLC), the reaction mixture was quenched with MeOH (5 mL) and stirred for 2 h. The volatiles were evaporated in vacuo. The crude material was purified by preparative HPLC to afford 280 (4 mg, 21% as an HBr salt) as a yellow solid. ¹H-NMR (400 MHz, CD₃OD-d₄): δ 9.73 (br s, 1H), 8.79-8.76 (m, 1H), 8.32 (s, 1H), 8.17 (s, 1H), 7.97 (s, 1H), 7.81 (d, J=7.6 Hz, 1H), 7.67 (d, J=8.8 Hz, 2H), 7.62 (d, J=8.0 Hz, 1H), 7.47 (d, J=8.0 Hz, 2H), 5.38-5.37 (m, 1H), 4.57-4.45 (m, 1H), 3.67-3.55 (m, 1H), 2.99-2.94 (m, 1H), 2.40-2.22 (m, 1H), 1.81-1.78 (m, 2H), 1.67-1.56 (m, 1H), 1.51-1.44 (m, 2H). MS (ESI): m/z 536.6 [M+1]⁺. UPLC Purity: 83.89%

Scheme 62

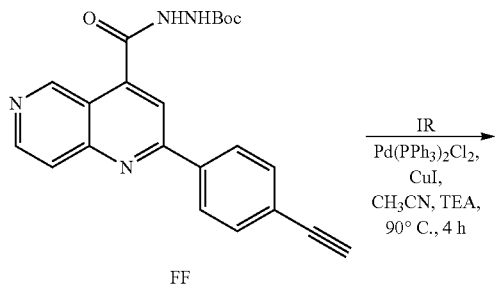

FF

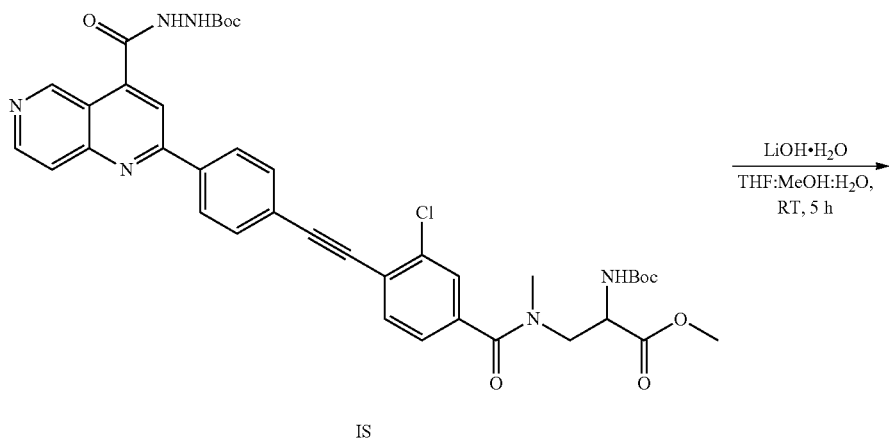

IS

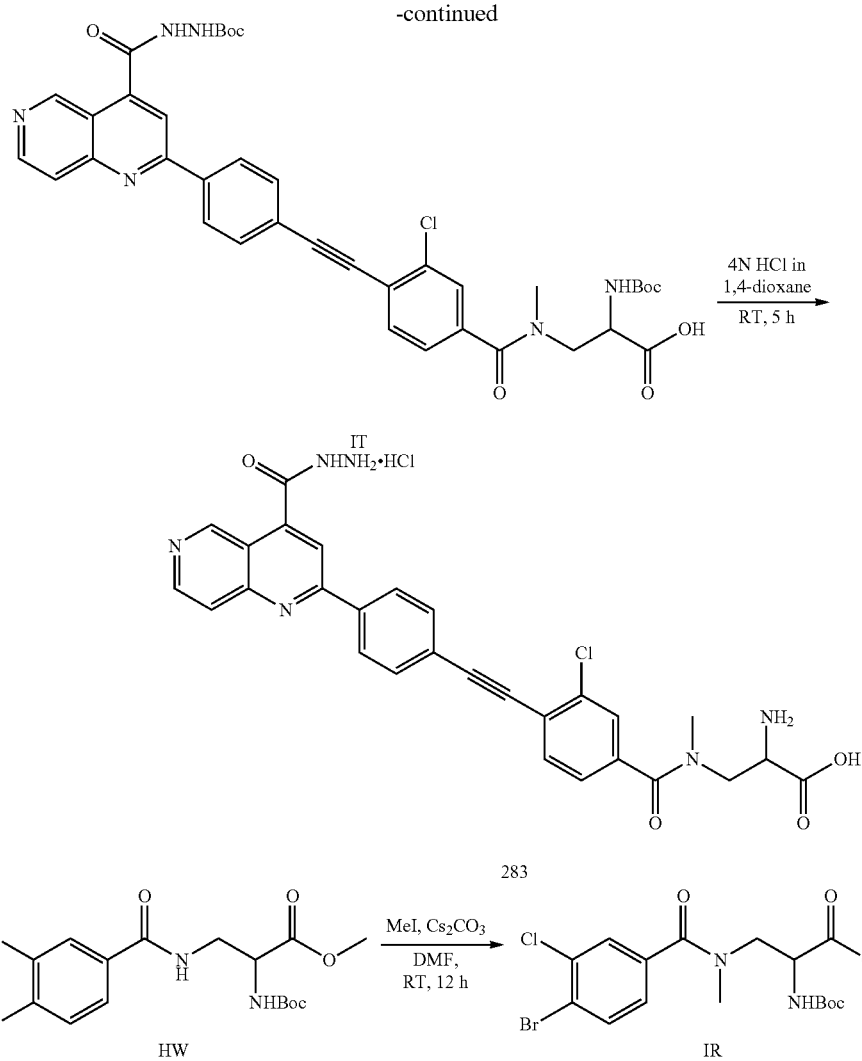

Example 283

2-amino-3-(3-chloro-4-((4-(4-(hydrazinecarbonyl)-1,6-naphthyridin-2-yl)phenyl) ethynyl)-N-methylbenzamido)propanoic acid hydrochloride (283)

To a stirred solution of methyl 3-(4-bromo-3-chlorobenzamido)-2-((tert-butoxycarbonyl)amino) propanoate (HW; 700 mg, 1.61 mmol) in DMF (15 mL) under nitrogen atmosphere were added cesium carbonate (1.57 g, 4.83 mmol) and methyl iodide (687 mg, 4.83 mmol) at 0° C. The reaction was allowed to warm to RT and was stirred for 12 h. After complete consumption of the starting material (by TLC), the reaction mixture was diluted with water (30 mL) and extracted with EtOAc (2×40 mL). The combined organic extracts were dried over sodium sulfate, filtered and concentrated under reduced pressure. The crude was purified through preparative HPLC to afford compound IR (350 mg, 48%) as a colorless syrup. $^1$H NMR (500 MHz, CDCl$_3$): δ 7.65 (d, J=8.5 Hz, 1H), 7.51 (s, 1H), 7.16 (d, J=7.5 Hz, 1H), 5.47 (br s, 1H), 4.65 (br s, 1H), 4.09-4.08 (m, 1H), 3.78 (s, 3H), 3.67-3.64 (m, 1H), 3.03 (s, 3H), 1.45 (s, 9H). MS (ESI): m/z 450.5 [M+1]$^+$ To a stirred solution of tert-butyl 2-(2-(4-ethynylphenyl)-1,6-naphthyridine-4-carbonyl)hydrazine-1-carboxylate (FF; 173 mg, 0.44 mmol) in CH$_3$CN:TEA (1:1, 20 mL) under nitrogen atmosphere was added compound IR (100 mg, 0.22 mmol). The reaction was degassed under argon for 10 min followed by the addition of copper iodide (4.2 mg, 0.044 mmol) and Pd(PPh$_3$)$_2$Cl$_2$ (15.6 mg, 0.022 mmol). The reaction was heated to 90° C. and stirred for 4 h. After complete consumption of the starting material (by TLC), the volatiles were removed under reduced pressure. The crude was purified by silica gel chromatography to afford compound IS (103 mg, 61%) as a yellow solid. $^1$H NMR (500 MHz, DMSO-d$_6$): δ 10.66 (s, 1H), 9.71 (br s, 1H), 9.30 (s, 1H), 8.85 (br s, 1H), 8.47-8.46 (m, 2H), 8.34 (s, 1H), 8.07-8.06 (m, 1H), 7.82 (d, J=9.0 Hz, 2H), 7.70-7.33 (m, 2H), 7.18-7.13 (m, 2H), 4.50-4.49 (m, 1H), 4.15-4.14 (m, 1H), 4.07-4.06 (m, 1H), 3.67-3.53 (m, 3H), 2.97-2.89 (m, 3H), 1.40 (s, 9H), 1.24 (s, 9H). MS (ESI): m/z 756.2 [M+1]$^+$ To a stirred solution of compound IS (50 mg, 0.066 mmol) in THF:MeOH:H$_2$O (2:2:1, 10 mL) under nitrogen atmosphere was added lithium hydroxide monohydrate (8.3 mg, 0.19 mmol) at 0° C. The reaction was allowed to warm to RT and was stirred for 5 h. After complete consumption of the starting material (by TLC), the reaction mixture was concentrated under reduced pressure. The crude was diluted with water (5 mL) and acidified with acetic acid. The precipitate was filtered and dried under reduced pressure to afford compound IT (28 mg, 57%) as a yellow solid. ¹H-NMR (500 MHz, DMSO-d₆): δ 12.80 (br s, 2H), 10.66 (br s, 1H), 9.71 (s, 1H), 9.30 (s, 1H), 8.84 (d, J=6.0 Hz, 1H), 8.46 (d, J=7.0 Hz, 1H), 8.34 (s, 1H), 8.06-8.05 (m, 1H), 7.84-7.76 (m, 2H), 7.64-7.55 (m, 2H), 7.41-7.36 (m, 2H), 4.34-4.33 (m, 1H), 3.90-3.88 (m, 2H), 3.60-3.58 (m, 2H), 1.30 (s, 9H), 1.22 (s, 9H). MS (ESI): m/z 744.7 [M+1]⁺

To a stirred solution of compound IT (25 mg, 0.033 mmol) in DCM (3 mL) under nitrogen atmosphere was added 4N HCl in 1,4-dioxane (0.5 mL) at 0° C. The reaction was allowed to warm to RT and was stirred for 5 h. After complete consumption of the starting material (by TLC), the volatiles were evaporated under reduced pressure. The crude was triturated with 10% MeOH/CH₃CN (2×5 mL) to afford 283 (12 mg as an HCl salt) as a yellow solid. ¹H-NMR (400 MHz, DMSO-d₆): δ 12.09-11.99 (m, 1H), 9.71 (br s, 1H), 8.87 (d, J=5.6 Hz, 1H), 8.55 (s, 1H), 8.51-8.49 (m, 3H), 8.38-8.37 (m, 1H), 8.13 (d, J=5.6 Hz, 1H), 7.83 (t, J=4.8 Hz, 3H), 7.75 (s, 1H), 7.51 (d, J=7.6 Hz, 1H), 4.27 (br s, 1H), 4.03-3.99 (m, 2H), 3.77-3.75 (m, 1H), 2.95-2.92 (m, 4H). MS (ESI): m/z 543.6 [M+1]⁺. UPLC Purity: 90.09%

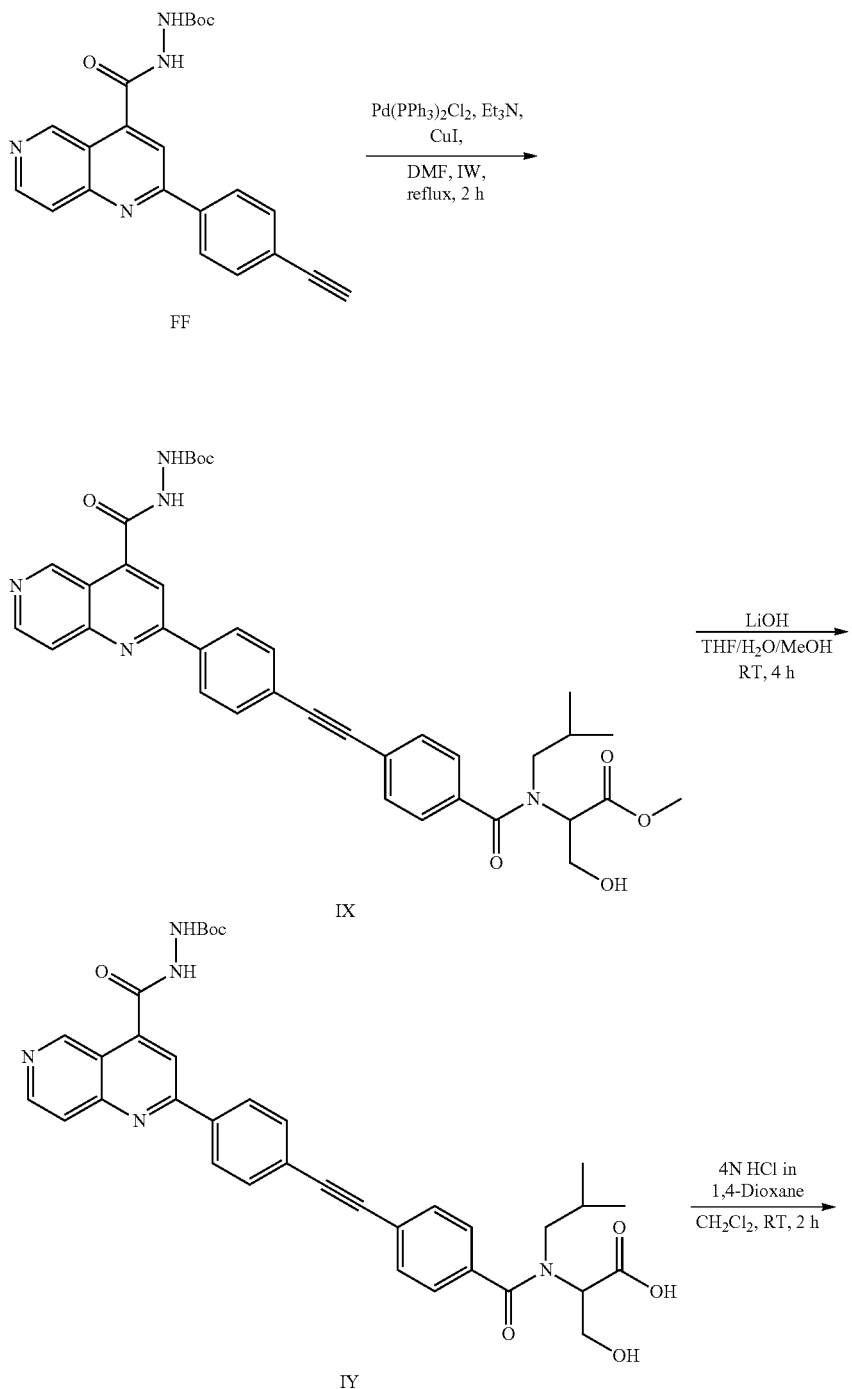

Scheme 63

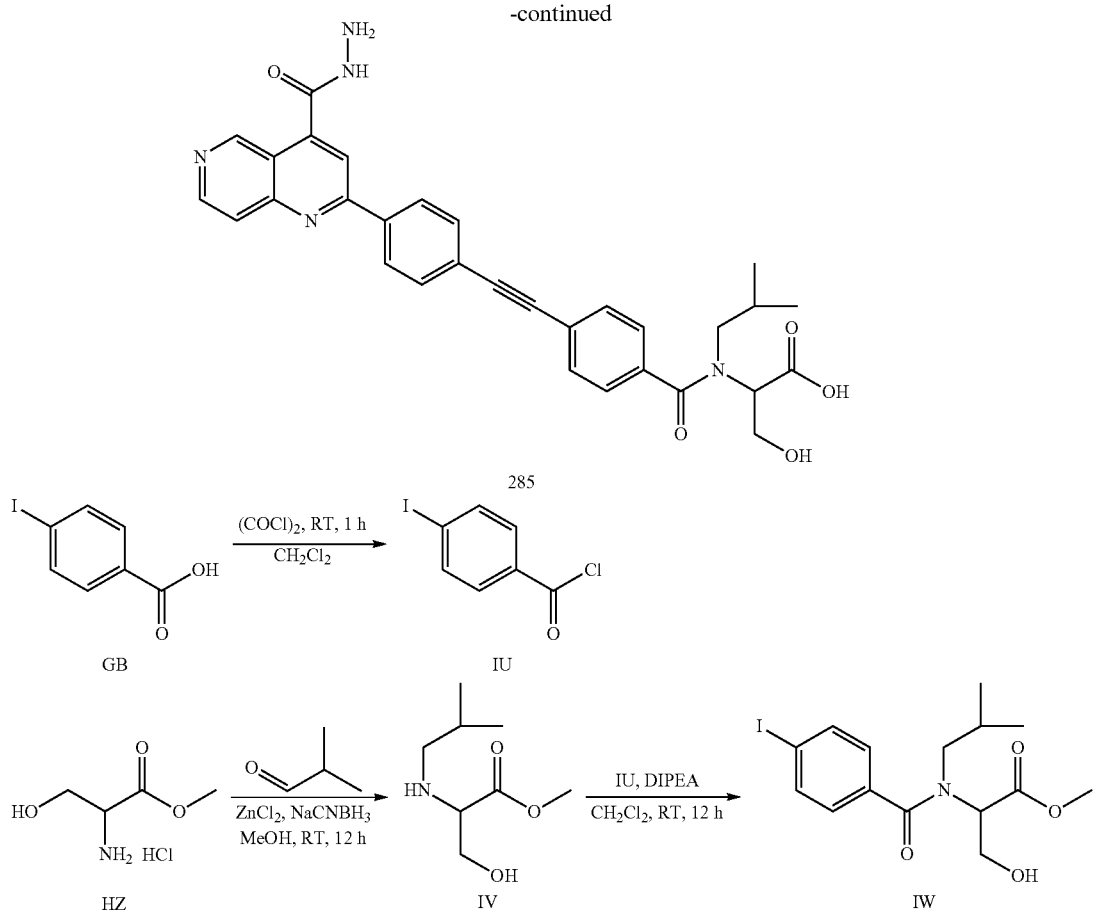

Example 285 tert-butyl 2-(2-(4-((4-((3-hydroxy-1-methoxy-1-oxopropan-2-yl)(isobutyl)carbamoyl)phenyl)ethynyl)phenyl)-1,6-naphthyridine-4-carbonyl)hydrazine-1-carboxylate (285)

To a stirred solution of DL-serine methylester HCl (HZ; 2 g, 12.85 mmol) in MeOH (20 mL) under nitrogen atmosphere were added isobutyraldehyde (1.4 g, 19.27 mmol) and ZnCl$_2$ (874 mg, 6.42 mmol) at 0° C. The reaction was allowed to warm to RT and was stirred for 30 min. Then NaCNBH$_3$ (2.43 g, 38.55 mmol) was added portionwise at 0° C. The reaction was allowed to warm to RT and was stirred for 12 h. After complete consumption of the starting material (by TLC), the reaction was diluted with water (30 mL) and extracted with EtOAc (2×50 mL). The combined organic extracts were dried over sodium sulfate, filtered and concentrated under reduced pressure. The crude was purified by silica gel column chromatography eluting with 3% MeOH:DCM to afford compound IV (850 mg, 38%) as a colorless liquid. $^1$H NMR (400 MHz, DMSO-d$_6$): δ 4.77 (t, J=5.6 Hz, 1H), 3.62 (s, 3H), 3.57-3.51 (m, 2H), 3.21 (t, J=5.2 Hz, 1H), 2.35-2.31 (m, 1H), 2.23-2.18 (m, 1H), 1.84 (br s, 1H), 1.62-1.56 (m, 1H), 0.84 (d, J=6.4 Hz, 6H).

To a stirred solution of 4-iodo benzoic acid GB (300 mg, 1.20 mmol) in DCM (5 mL) under nitrogen atmosphere were added oxalyl chloride (307 mg, 2.42 mmol) and DMF (0.01 mL) at 0° C. and the reaction was stirred for 10 min. The reaction was then allowed to warm to RT and was stirred for 1 h. After complete consumption of the starting material (by TLC), the volatiles were evaporated under reduced pressure to obtain compound IU (320 mg, crude) as a pale yellow solid.

To a stirred solution of compound IV (423 mg, 2.4 mmol) in DCM (10 mL) under nitrogen atmosphere was added DIPEA (2 mL, 12.0 mmol) at 0° C. Then compound IU (320 mg, crude) in DCM (5 mL) was added under nitrogen atmosphere at 0° C. The reaction was allowed to warm to RT and was stirred for 12 h. After complete consumption of the starting material (by TLC), the reaction was diluted with water (20 mL) and extracted with DCM (2×30 mL). The combined organic extracts were washed with water (2×20 mL), brine (2×15 mL), dried over sodium sulfate, filtered and concentrated under reduced pressure. The crude was purified by silica gel column chromatography eluting with 30% EtOAc:hexane to afford compound IW (340 mg, crude) as an off white solid. $^1$H NMR (500 MHz, DMSO-d$_6$): δ 7.83-7.79 (m, 2H), 7.21-7.13 (m, 2H), 3.63 (s, 3H), 3.13 (d, J=6.5 Hz, 2H), 2.96-2.88 (m, 2H), 1.86-1.80 (m, 1H), 1.33-1.23 (m, 2H), 0.77 (d, J=6.5 Hz, 6H). MS (ESI): m/z 405.23 [M+1]$^+$ To a stirred solution of compound FF (200 mg, 0.51 mmol) in CH$_3$CN (10 mL) under argon atmosphere were added compound IW (250 mg, 0.61 mmol) and TEA (0.71 mL, 5.15 mmol). The reaction was purged under argon for 20 min followed by the addition of copper iodide (9.5 mg, 0.05 mmol) and Pd(PPh$_3$)$_2$Cl$_2$ (36 mg, 0.05 mmol). The reaction was heated to reflux and stirred for 2 h. After complete consumption of the starting material (by TLC), the reaction mixture was filtered through Celite and the Celite bed was washed with ethyl acetate. The filtrate was concentrated under reduced pressure. The crude was purified by silica gel column chromatography eluting with 3% MeOH:DCM and further purified by preparative HPLC to afford compound IX (80 mg, 23%) as a yellow solid. $^1$H NMR (400 MHz, DMSO-d$_6$): δ 9.74 (br s, 1H), 9.29 (br s, 1H), 8.84 (d, J=5.6 Hz, 1H), 8.44 (d, J=8.0 Hz, 3H), 8.34 (s, 1H), 8.04 (d, J=6.0 Hz, 1H), 7.81 (d, J=8.4 Hz, 2H), 7.69 (d, J=8.0 Hz, 2H), 7.49-7.41 (m, 2H), 5.02 (s, 1H), 4.18-3.98 (m, 3H), 3.65 (s, 3H), 3.17 (d, J=5.2 Hz, 3H), 1.49 (s, 9H), 0.72 (d, J=7.2 Hz, 6H). MS (ESI): m/z 665.75 [M+1]$^+$ To a stirred solution of compound IX (80 mg, 0.11 mmol) in THF:MeOH:H$_2$O (4 mL:2 mL:4 mL) was added lithium hydroxide monohydrate (12.6 mg, 0.30 mmol) at 0° C. The reaction was allowed to warm to RT and was stirred for 4 h. After complete consumption of the starting material (by TLC), the reaction mixture was concentrated under reduced pressure. The crude was diluted with water and neutralized with acetic acid. The precipitate was filtered, washed with water and dried under reduced pressure to afford compound IY (62 mg, 79%) as a yellow solid. $^1$H NMR (400 MHz, DMSO-d$_6$): δ 12.20 (s, 1H), 10.66 (s, 1H), 9.71 (s, 1H), 9.31 (s, 1H), 8.84 (d, J=5.6 Hz, 1H), 8.44 (d, J=8.0 Hz, 1H), 8.33 (s, 1H), 8.05-7.99 (m, 1H), 7.81 (d, J=8.0 Hz, 1H), 7.69 (d, J=7.6 Hz, 2H), 7.61 (t, J=8.8 Hz, 2H), 7.49-7.33 (m, 2H), 4.08-3.97 (m, 2H), 3.88-3.67 (m, 2H), 3.13-3.09 (m, 2H), 1.90-1.87 (m, 2H), 1.49 (s, 9H), 0.87-0.71 (m, 6H). MS (ESI): m/z 651.72 [M+1]$^+$ To a stirred solution of compound IY (60 mg, 0.092 mmol) in DCM (2 mL) under nitrogen atmosphere was added 4N HCl in 1,4-dioxane (1 mL) at 0° C. The reaction was allowed to warm to RT and was stirred for 2 h. After complete consumption of the starting material (by TLC), the volatiles were evaporated under reduced pressure. The crude was purified through preparative HPLC to afford 285 (10 mg as an HCl salt) as a yellow solid. $^1$H NMR (400 MHz, DMSO-d$_6$): δ 11.0 (s, 1H), 9.67 (s, 1H), 8.83 (s, 1H), 8.54 (s, 1H), 8.44 (t, J=8.0 Hz, 2H), 8.06 (d, J=4.0 Hz, 1H), 7.82 (d, J=7.6 Hz, 2H), 7.41 (d, J=4.8 Hz, 2H), 7.26-7.01 (m, 3H), 4.31 (s, 1H), 4.07-3.98 (m, 2H), 3.70-3.62 (m, 1H), 3.30-3.16 (m, 2H), 2.06-1.88 (m, 1H), 0.91-0.73 (m, 6H). MS (ESI): m/z 552.5 [M+1]$^+$. UPLC Purity: 91.19%

Scheme 64

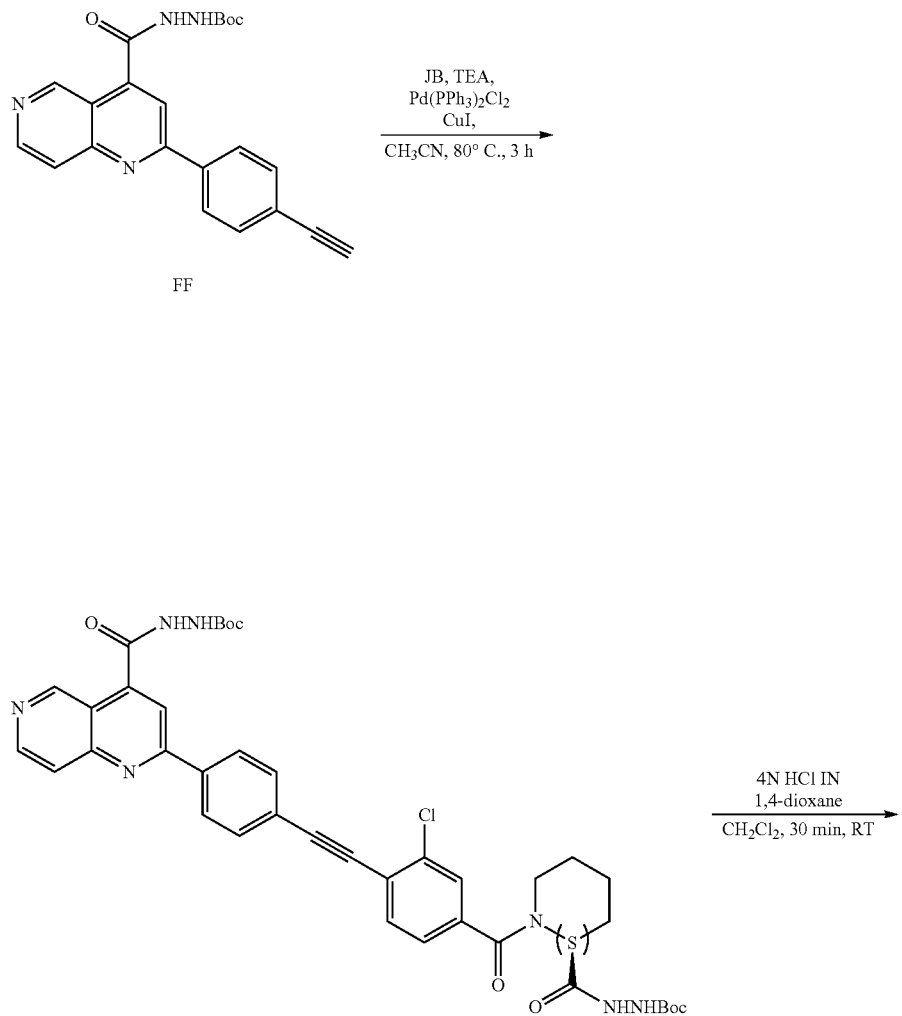

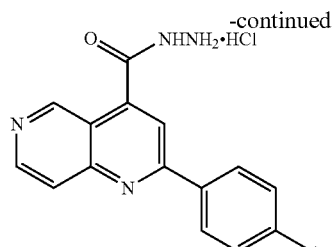
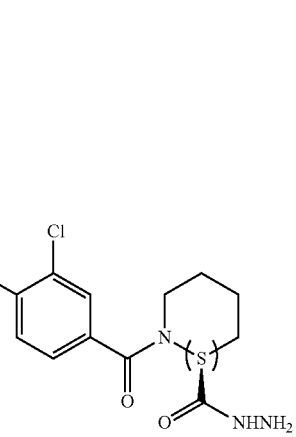
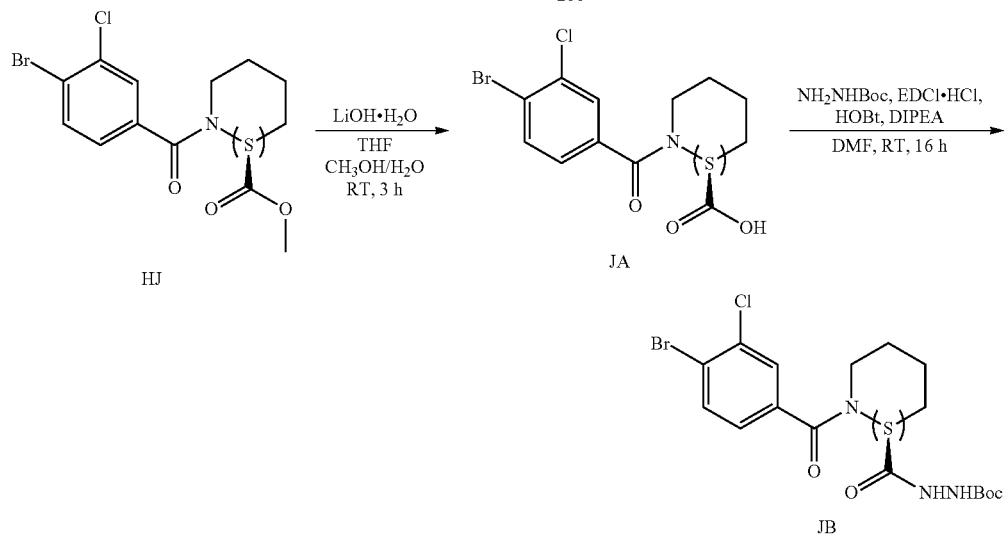

Example 286

(S)-2-(4-((2-chloro-4-(2-(hydrazinecarbonyl)piperidine-1-carbonyl)phenyl) ethynyl)phenyl)-1,6-naphthyridine-4-carbohydrazide dihydrochloride (286)

To a stirred solution of compound HJ (500 mg, 1.36 mmol) in THF:MeOH:H$_2$O (8 mL:4 mL:4 mL) was added lithium hydroxide monohydrate (175 mg, 4.16 mmol) at 0° C. The reaction was allowed to warm to RT and was stirred for 3 h. After complete consumption of the starting material (by TLC), the volatiles were evaporated under reduced pressure. The crude was diluted with water and the pH was adjusted to 3 using an acetic acid solution (0.2 mL). The crude compound was extracted with 10% MeOH/DCM (2×10 mL), dried over sodium sulfate, filtered and concentrated under reduced pressure to afford compound JA (450 mg, 94%) as a gummy colorless solid. $^1$H NMR (500 MHz, DMSO-d$_6$): δ 12.35 (brs, 1H), 7.86-7.82 (m, 1H), 7.58-7.49 (m, 1H), 7.25-7.20 (m, 1H), 5.12 (brs, 1H), 4.35-4.33 (m, 1H), 3.41-3.39 (m, 1H), 3.16-3.11 (m, 1H), 2.18-2.16 (m, 2H), 1.76-1.65 (m, 3H).

To a stirred solution of compound JA (450 mg, 1.29 mmol) in DMF (5 mL) under nitrogen atmosphere were added DIPEA (1.16 mL, 6.48 mmol), EDCI·HCl (498 mg, 2.59 mmol), HOBt (350 mg, 2.59 mmol) and tert-butyl carbazate (513 mg, 3.89 mmol) at 0° C. The reaction was allowed to warm to RT and was stirred for 16 h. After complete consumption of the starting material (by TLC), the reaction was diluted with water (50 mL) and the compound was extracted with EtOAc (2×50 mL). The combined organic extracts were washed with water (2×20 mL), brine (2×25 mL), dried over sodium sulfate, filtered and concentrated under reduced pressure. The crude was purified by silica gel chromatography eluting with 2% MeOH/DCM to afford compound JB (350 mg, 59%) as a sticky colorless solid. $^1$H NMR (400 MHz, DMSO-d$_6$): δ 9.67 (s, 1H), 8.80 (s, 1H), 7.95 (s, 2H), 7.36 (d, J=7.6 Hz, 1H), 5.13 (br s, 1H), 4.41-4.15 (m, 1H), 3.89 (s, 1H), 3.41-3.37 (m, 1H), 3.15-2.98 (m, 1H), 2.23 (d, J=10.0 Hz, 1H), 1.79 (s, 1H), 1.61-1.58 (m, 2H), 1.41 (s, 9H). MS (ESI): m/z 461.75 [M+1]$^+$ To a stirred solution of compound FF (200 mg, 0.51 mmol) in CH$_3$CN (20 mL) under argon atmosphere were added compound JB (142 mg, 0.30 mmol) and TEA (0.72 mL, 5.15 mmol). The reaction was purged under argon for 20 min followed by the addition of CuI (9.8 mg, 0.05 mmol) and Pd(PPh$_3$)$_2$Cl$_2$ (36 mg, 0.05 mmol). The reaction was heated to 80° C. and stirred for 3 h. After complete consumption of the starting material (by TLC), the reaction mixture was filtered through Celite, the Celite bed was washed with EtOAc (10 mL). The filtrate was concentrated under reduced pressure. The crude material was purified by silica gel column chromatography eluting with 3% MeOH:

DCM to afford compound JC (70 mg, 18%) as a yellow solid. ¹H NMR (400 MHz, DMSO-$d_6$): δ 10.66 (s, 1H), 9.69 (s, 1H), 9.30 (s, 1H), 8.80 (s, 1H), 8.46 (d, J=6.4 Hz, 3H), 8.18-8.12 (m, 1H), 7.83 (d, J=6.4 Hz, 1H), 7.51-7.39 (m, 3H), 5.15 (s, 1H), 4.51-4.36 (m, 1H), 3.61-3.57 (m, 2H), 2.26 (t, J=4.4 Hz, 1H), 2.16-2.11 (m, 1H), 1.64-1.50 (m, 2H), 1.49 (s, 9H), 1.41 (s, 9H), 1.03 (d, J=6.0 Hz, 1H). MS (ESI): m/z 769.27 [M+1]⁺

To a stirred solution of compound JC (35 mg, 0.04 mmol) in DCM (0.5 mL) under nitrogen atmosphere was added 4N HCl in 1,4-dioxane (0.02 mL) at 0° C. The reaction was stirred for 15 min. After complete consumption of the starting material (by TLC), the volatiles were evaporated under reduced pressure. The crude was purified through preparative HPLC to afford 286 (15 mg as an HCl salt) as a yellow solid. ¹H-NMR (DMSO-$d_6$, 400 MHz): δ 10.92 (s, 1H), 9.80 (s, 1H), 8.98 (br s, 1H), 8.46 (t, J=8.4 Hz, 4H), 8.11 (br s, 1H), 7.84 (d, J=8.4 Hz, 4H), 7.68 (s, 1H), 7.48 (d, J=4.4 Hz, 1H), 5.22 (br s, 1H), 4.55-4.38 (m, 1H), 3.71-3.66 (m, 1H), 3.50-3.46 (m, 1H), 2.28-2.10 (m, 1H), 1.69-1.58 (m, 2H), 1.51-1.38 (m, 2H). MS (ESI): m/z 568.6 [M+1]⁺. UPLC Purity: 96.41%

Scheme 65

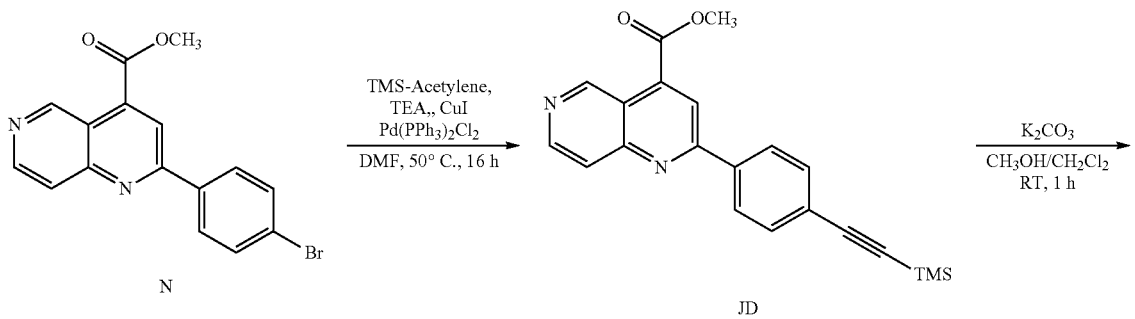

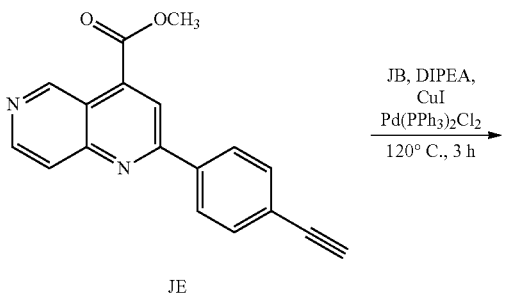

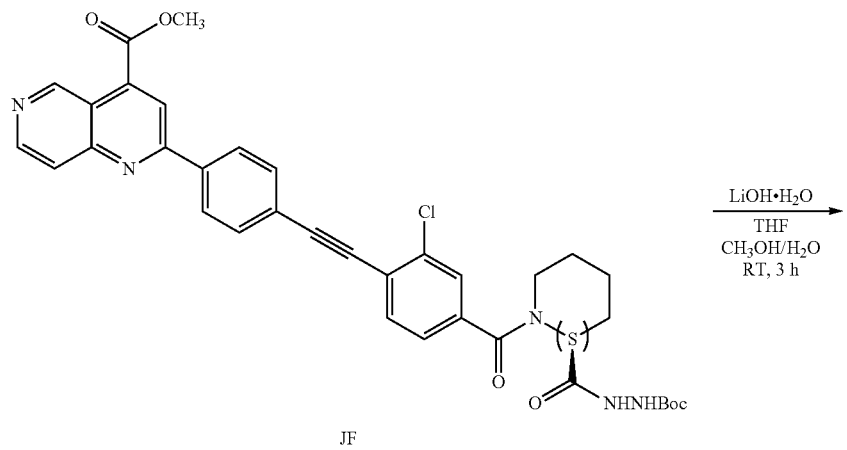

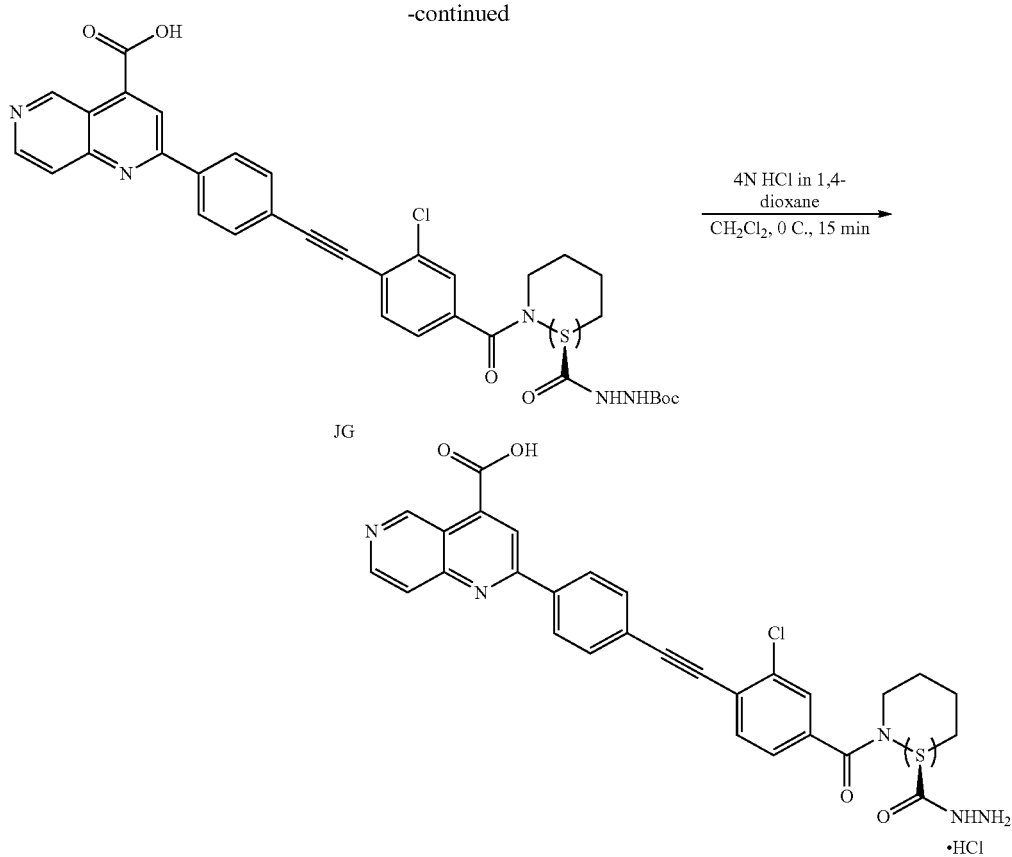

Example 287

2-(4-((4-(2-oxooxazolidin-5-yl)phenyl)ethynyl)phenyl)-1,6-naphthyridine-4-carbohydrazide HCl salt (287)

To a stirred solution of compound N (2 g, 5.84 mmol) in DMF (20 mL) under argon atmosphere were added TMS-acetylene (5.7 g, 58.4 mmol) and TEA (8.2 mL, 58.4 mmol). The reaction was purged under argon for 20 min followed by the addition of copper iodide (111 mg, 0.58 mmol) and Pd(PPh$_3$)$_2$Cl$_2$ (410 mg, 0.58 mmol). The reaction was heated to 50° C. and stirred for 16 h. After complete consumption of the starting material (by TLC), the reaction mixture was diluted with ice cold water (100 mL) and extracted with EtOAc (2×100 mL). The combined organic extracts were washed with water (2×100 mL), dried over sodium sulfate, filtered and concentrated under reduced pressure. The crude was purified by silica gel column chromatography eluting with 20% EtOAc:hexane to afford compound JD (1.3 g, 62%) as a yellow solid. $^1$H NMR (400 MHz, CDCl$_3$): δ 10.16 (s, 1H), 8.84 (s, 1H), 8.50 (s, 1H), 8.22 (d, J=8.4 Hz, 2H), 8.02 (d, J=5.2 Hz, 1H), 7.66 (d, J=8.4 Hz, 2H), 4.13 (s, 3H), 0.29 (s, 9H). MS (ESI): m/z 361.49 [M+1]$^+$ To a stirred solution of compound JD (1.3 g, 3.61 mmol) in MeOH:DCM (10 mL:10 mL) under nitrogen atmosphere was added K$_2$CO$_3$ (1.49 g, 10.83 mmol) portionwise at 0° C. The reaction was allowed to warm to RT and was stirred for 1 h. After complete consumption of the starting material (by TLC), the reaction mixture was filtered through Celite and the Celite bed was washed with DCM (30 mL). The filtrate was concentrated under reduced pressure. The crude was diluted with cold water (20 mL) and extracted with DCM (2×50 mL). The combined organic extracts were dried over sodium sulfate, filtered and concentrated under reduced pressure to afford compound JE (800 mg, 77%) as a yellow solid. $^1$H NMR (400 MHz, DMSO-d$_6$): δ 9.94 (s, 1H), 8.85 (d, J=6.0 Hz, 1H), 8.63 (s, 1H), 8.37 (d, J=8.4 Hz, 2H), 8.06 (d, J=5.6 Hz, 1H), 7.71 (d, J=8.4 Hz, 2H), 4.44 (s, 1H), 4.06 (s, 3H). MS (ESI): m/z 289.3 [M+1]$^+$ To a stirred solution of compound JE (200 mg, 0.69 mmol) in DMF (5 mL) under argon atmosphere were added compound JB (191 mg, 0.41 mmol) and DIPEA (0.97 mL, 6.94 mmol). The solution was purged under argon for 20 min followed by the addition of copper iodide (13 mg, 0.06 mmol) and Pd(PPh$_3$)$_2$Cl$_2$ (49 mg, 0.06 mmol). The reaction was heated to 120° C. and stirred for 3 h. After complete consumption of the starting material (by TLC), the reaction mixture was diluted with ice cold water (30 mL) and the compound was extracted with EtOAc (2×30 mL). The combined organic extracts were washed with water (2×30 mL), dried over sodium sulfate, filtered and concentrated under reduced pressure. The crude was purified by silica gel column chromatography eluting with 3% MeOH:DCM to afford compound JF (100 mg, 22%) as a yellow solid. $^1$H NMR (400 MHz, DMSO-d$_6$): δ 9.47 (s, 1H), 8.88 (s, 1H), 8.70 (s, 1H), 8.46 (d, J=8.4 Hz, 2H), 8.20 (s, 1H), 7.83 (d, J=8.4 Hz, 2H), 7.72-7.66 (m, 3H), 7.41-7.36 (m, 2H), 5.01 (s, 1H), 4.25-4.12 (m, 2H), 3.31 (s, 3H), 1.90-1.81 (m, 2H), 1.41 (s, 9H), 1.64 (d, J=5.2 Hz, 2H), 1.28-1.23 (m, 2H). MS (ESI): m/z 669.15 [M+1]$^+$ To a stirred solution of compound JF (100 mg, 0.14 mmol) in THF/MeOH/H$_2$O (4 mL/2 mL/2 mL) were added LiOH H$_2$O (19 mg, 0.44 mmol) at 0° C. The reaction was allowed to warm to RT and stir for 3 h. After complete consumption of the starting material (by LC-MS), the volatiles were evaporated under reduced pressure. The crude material was diluted with water and the pH was adjusted to ~3 by using AcOH. The resulting solids were filtered and washed with water, dried under reduced pressure to afford compound JG (40 mg, 41%) as a yellow solid. MS (ESI): m/z 655.12 [M+1]$^+$ To a stirred solution of compound JG (40 mg, 653 mmol) in DCM (0.5 mL) under nitrogen atmosphere was added 4N HCl in 1,4-dioxane (0.5 mL) at 0° C. The reaction was stirred for 15 min. After complete consumption of the starting material (by TLC), the volatiles were evaporated under reduced pressure. The crude material was purified by preparative HPLC to afford 287 (4 mg as an HCl salt) as a yellow solid. $^1$H-NMR (400 MHz, CD$_3$OD): δ 10.50 (br s, 1H), 8.97 (d, J=10.0 Hz, 1H), 8.51 (d, J=8.4 Hz, 2H), 7.85-7.76 (m, 3H), 7.71 (s, 2H), 7.68-7.42 (m, 2H), 5.35 (s, 1H), 4.23 (d, J=4.4 Hz, 2H), 2.35-2.10 (m, 1H), 1.99-1.85 (m, 1H), 1.72-1.65 (m, 2H), 1.64-1.55 (m, 2H). MS (ESI): m/z 555 [M+1]$^+$. UPLC Purity: 98.85%

Scheme 66

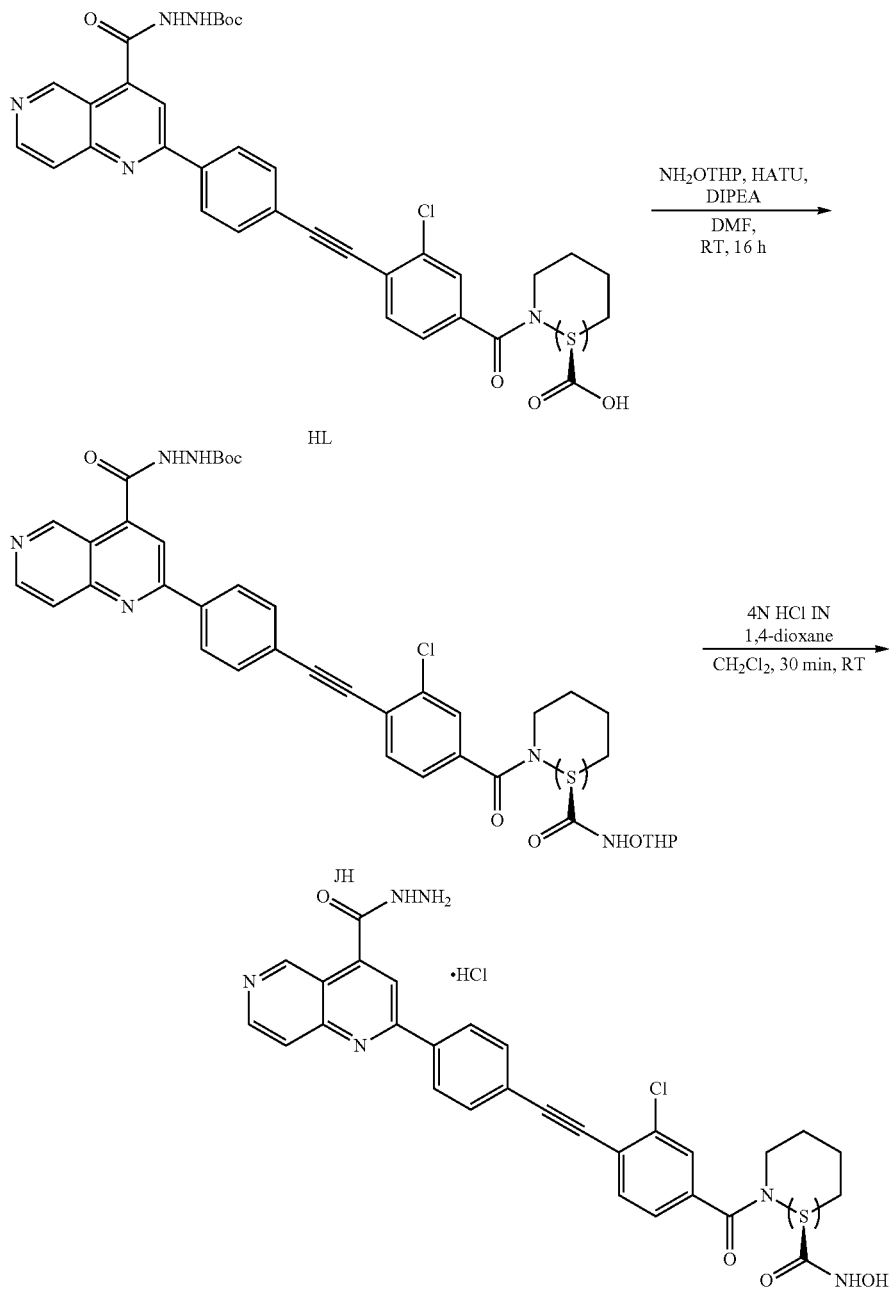

Example 288

(S)-1-(3-chloro-4-((4-(4-(hydrazinecarbonyl)-1,6-naphthyridin-2-yl)phenyl)ethynyl)benzoyl)-N-hydroxypiperidine-2-carboxamide hydrochloride (288)

To a stirred solution of compound HL (55 mg, 0.084 mmol) in DMF (2 mL) under nitrogen atmosphere were added DIPEA (0.04 mL, 0.25 mmol), NH$_2$OTHP (19.5 mg, 0.168 mmol) and HATU (49 mg, 0.126 mmol) at 0° C. The reaction was allowed to warm to RT and was stirred for 16 h. After complete consumption of the starting material (by TLC), the reaction was diluted with water (20 mL) and the compound was extracted with EtOAc (2×30 mL). The combined organic extracts were washed with water (2×30 mL), brine (2×25 mL), dried over sodium sulfate, filtered and concentrated under reduced pressure to afford compound JH (30 mg, crude) as a yellow solid. $^1$H NMR (400 MHz, DMSO-d$_6$): δ 11.22 (br s, 1H), 10.80 (s, 1H), 9.74 (s, 1H), 9.29 (s, 1H), 8.84 (d, J=6.0 Hz, 1H), 8.47-8.39 (m, 2H), 8.34 (s, 1H), 8.05 (d, J=5.2 Hz, 1H), 7.83 (d, J=8.0 Hz, 1H), 7.73-7.67 (m, 2H), 7.66-7.46 (m, 2H), 5.07 (s, 1H), 4.22 (t, J=6.4 Hz, 2H), 4.01 (d, J=6.4 Hz, 1H), 3.53 (d, J=11.2 Hz, 2H), 1.68-1.60 (m, 6H), 1.53-1.50 (m, 2H), 1.49 (s, 9H), 1.42-1.34 (m, 4H). MS (ESI): m/z 754.25 [M+1]$^+$ To a stirred solution of compound JH (30 mg, 0.039 mmol, crude) in DCM (0.5 mL) under nitrogen atmosphere was added 4N HCl in 1,4-dioxane (0.02 mL) at 0° C. The reaction was allowed to warm to RT and was stirred for 30 min. After complete consumption of the starting material (by TLC), the volatiles were evaporated under reduced pressure to afford 288 (15 mg as an HCl salt) as a yellow solid. $^1$H NMR (400 MHz, DMSO-d$_6$): δ 12.30 (br s, 1H), 10.70 (br s, 1H), 9.70 (s, 1H), 8.88 (d, J=6.0 Hz, 1H), 8.51 (t, J=10.0 Hz, 3H), 8.14 (d, J=6.0 Hz, 1H), 7.87-7.80 (m, 2H), 7.73-7.69 (m, 1H), 7.68-7.47 (m, 2H), 7.38-7.15 (m, 2H), 5.12 (s, 1H), 4.22 (t, J=6.8 Hz, 1H), 4.01 (d, J=6.8 Hz, 1H), 3.44-3.29 (m, 2H), 2.30-2.19 (m, 1H), 2.01-1.85 (m, 1H), 1.40-1.34 (m, 3H). MS (ESI): 90.12%, m/z 569.5 [M+1]$^+$ Scheme 67

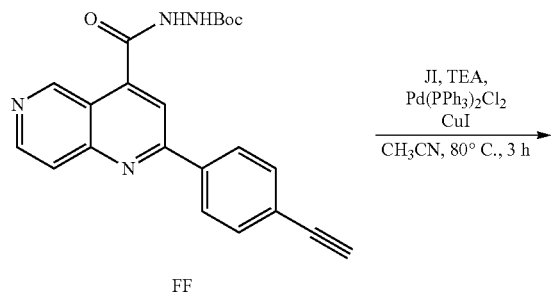

FF

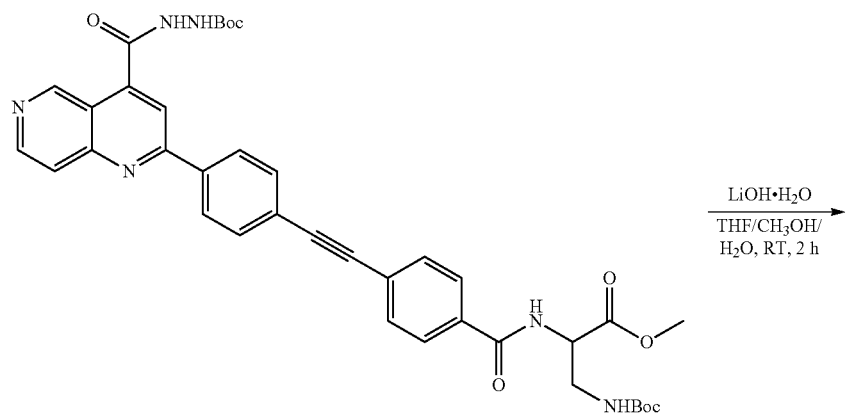

JJ

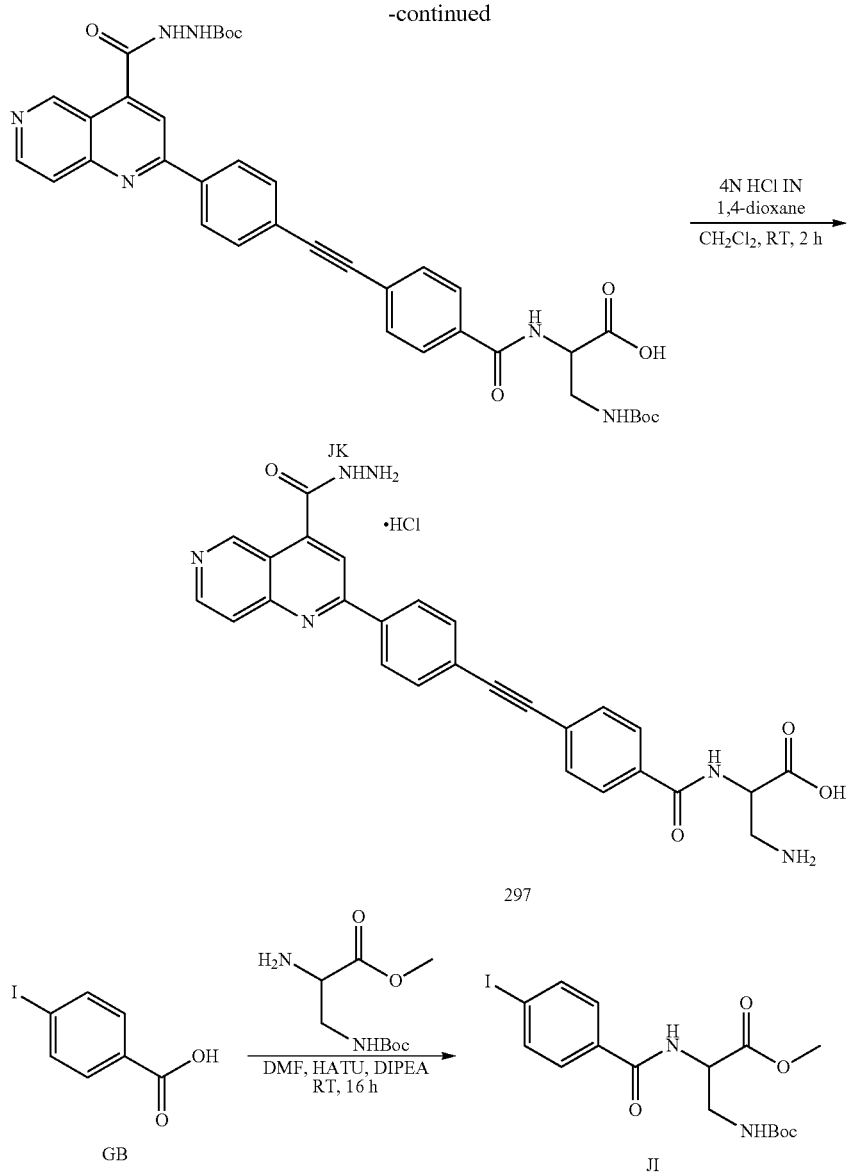

Example 297

3-amino-2-(4-((4-(4-(hydrazinecarbonyl)-1,6-naph-thyridin-2-yl)phenyl)ethynyl)benzamido)propanoic acid hydrochloride (297)

To a stirred solution of 4-iodobenzoic acid (GB; 100 mg, 0.40 mmol) in DMF (5 mL) under nitrogen atmosphere were added DIPEA (0.2 mL, 1.20 mmol), methyl 2-amino-3-((tert-butoxycarbonyl)amino)propanoate (88 mg, 0.40 mmol) and HATU (235 mg, 0.60 mmol). The reaction was stirred at RT for 16 h. After complete consumption of the starting material (by TLC), the reaction was diluted with water (10 mL) and the compound was extracted with EtOAc (2×30 mL). The combined organic extracts were washed with water (2×20 mL), brine (2×25 mL), dried over sodium sulfate, filtered and concentrated under reduced pressure. The crude was purified by silica gel chromatography eluting with 40% EtOAc/hexane to afford compound JI (120 mg, crude) as an off white solid. $^1$H NMR (400 MHz, CDCl$_3$): δ 8.01 (s, 2H), 7.78 (d, J=8.8 Hz, 1H), 7.58 (d, J=8.4 Hz, 2H), 4.73-4.62 (m, 1H), 3.78 (s, 3H), 3.68-3.57 (m, 1H), 2.80 (s, 2H), 1.42 (s, 9H). MS (ESI): m/z 449.26 [M+1]$^+$ To a stirred solution of compound FF (100 mg, 0.25 mmol) in CH$_3$CN (10 mL) under argon atmosphere were added compound JI (115 mg, 0.25 mmol) and TEA (0.36 mL, 2.57 mmol). The solution was purged under argon for 20 min followed by the addition of copper iodide (5 mg, 0.025 mmol) and Pd(PPh$_3$)$_2$Cl$_2$ (18 mg, 0.025 mmol). The reaction was heated to 80° C. and stirred for 3 h. After complete consumption of the starting material (by TLC), the reaction mixture was filtered through Celite and the Celite bed was washed with EtOAc (10 mL). The filtrate was concentrated under reduced pressure. The crude residue was purified by silica gel column chromatography eluting with 2% MeOH:DCM to afford compound JJ (50 mg, 25%) as a yellow solid. $^1$H NMR (400 MHz, DMSO-d$_6$): δ 10.65 (s, 1H), 9.72 (s, 1H), 9.30 (br s, 1H), 8.89-8.73 (m, 2H), 8.70-8.63 (m, 1H), 8.62-8.50 (m, 1H), 8.48-8.34 (m, 1H), 8.05 (d, J=5.6 Hz, 2H), 7.98-7.73 (m, 2H), 7.70-7.61 (m, 2H), 7.07-7.04 (m, 1H), 4.53-4.49 (m, 1H), 3.63 (s, 3H), 3.62-3.58 (m, 1H), 3.45 (d, J=6.4 Hz, 2H), 1.49 (s, 9H), 1.37 (s, 9H). MS (ESI): m/z 709.77 [M+1]+

To a stirred solution of compound JJ (50 mg, 0.06 mmol) in THF/MeOH/H$_2$O (4 mL/4 mL/2 mL) was added LiOH H$_2$O (5.5 mg, 0.13 mmol) at 0° C. The reaction was allowed to warm to RT and was stirred for 2 h. After complete consumption of the starting material (by TLC), the volatiles were evaporated under reduced pressure. The crude was diluted with water and the pH was adjusted to pH~3 with AcOH. The precipitate was filtered, washed with water, and dried under reduced pressure to afford compound JK (35 mg, 71%) as a yellow solid. $^1$H-NMR (DMSO-d$_6$, 400 MHz): δ 10.65 (s, 1H), 9.71 (s, 1H), 9.29 (s, 1H), 8.83 (s, 1H), 8.45-8.33 (m, 4H), 8.05 (d, J=6.4 Hz, 1H), 7.91 (d, J=7.6 Hz, 2H), 7.83 (d, J=8.4 Hz, 2H), 7.73-7.56 (m, 2H), 6.89 (br s, 1H), 4.25 (br s, 1H), 3.40-3.32 (m, 2H), 1.49 (s, 9H), 1.36 (s, 9H). MS (ESI): m/z 695.75 [M+1]+

To a stirred solution of compound JK (35 mg, 0.05 mmol) in DCM (2 mL) under nitrogen atmosphere was added 4N HCl in 1,4-dioxane (0.5 mL) at 0° C. The reaction was allowed to warm to RT and was stirred for 2 h. After complete consumption of the starting material (by TLC), the volatiles were evaporated under reduced pressure to afford 297 (25 mg as an HCl salt) as a yellow solid. $^1$H-NMR (DMSO-d$_6$, 400 MHz): δ 11.98 (s, 1H), 9.76 (br s, 1H), 9.06 (d, J=8.0 Hz, 1H), 8.92 (s, 1H), 8.55 (s, 1H), 8.49 (d, J=8.4 Hz, 2H), 8.20-8.14 (m, 2H), 8.02 (d, J=8.4 Hz, 2H), 7.85 (d, J=8.4 Hz, 2H), 7.76 (d, J=8.0 Hz, 2H), 4.78-4.72 (m, 1H), 3.35 (t, J=6.0 Hz, 1H), 3.24 (d, J=5.6 Hz, 1H). MS (ESI): m/z 495.4 [M+1]+. UPLC Purity: 92.01%

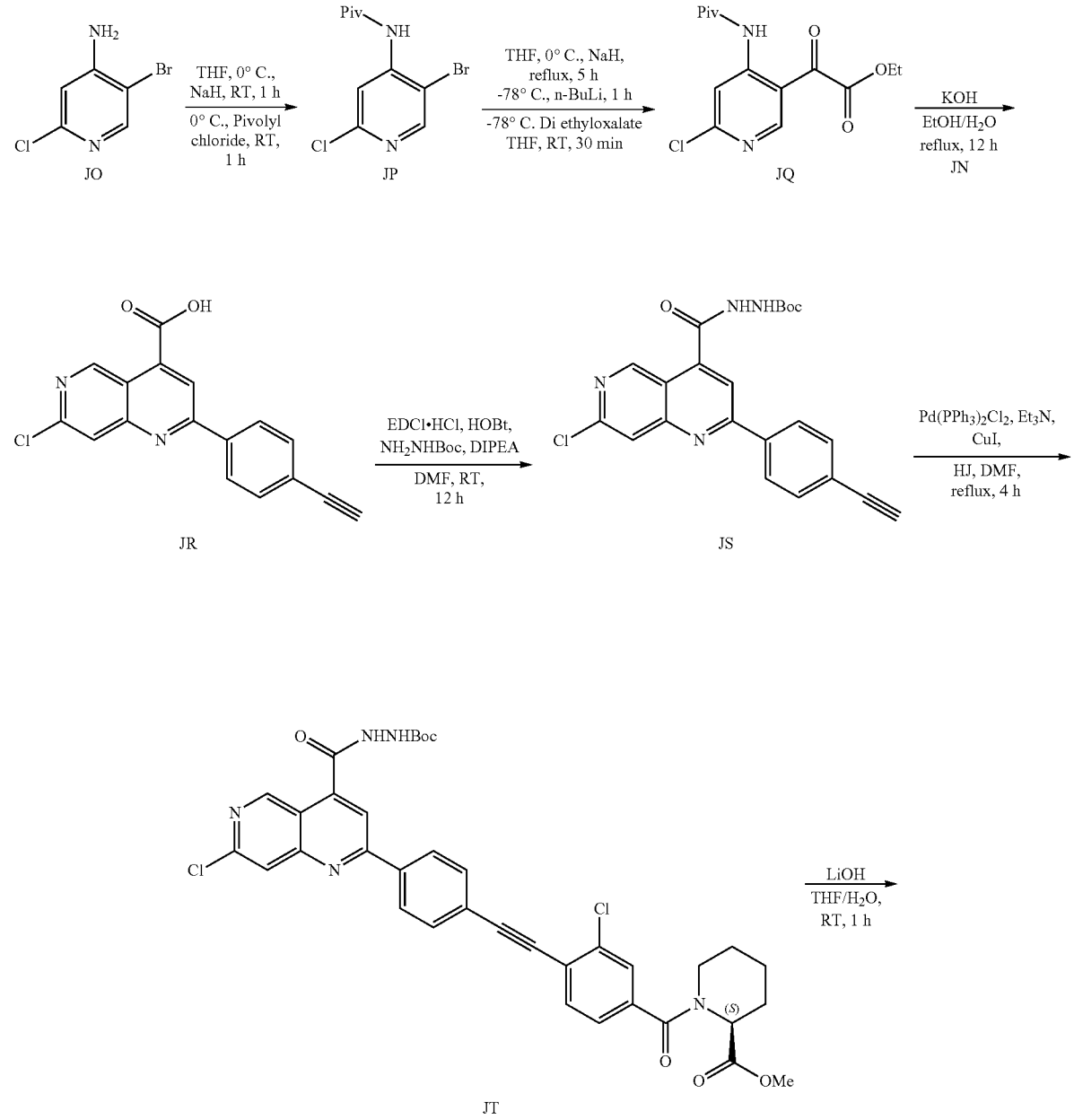

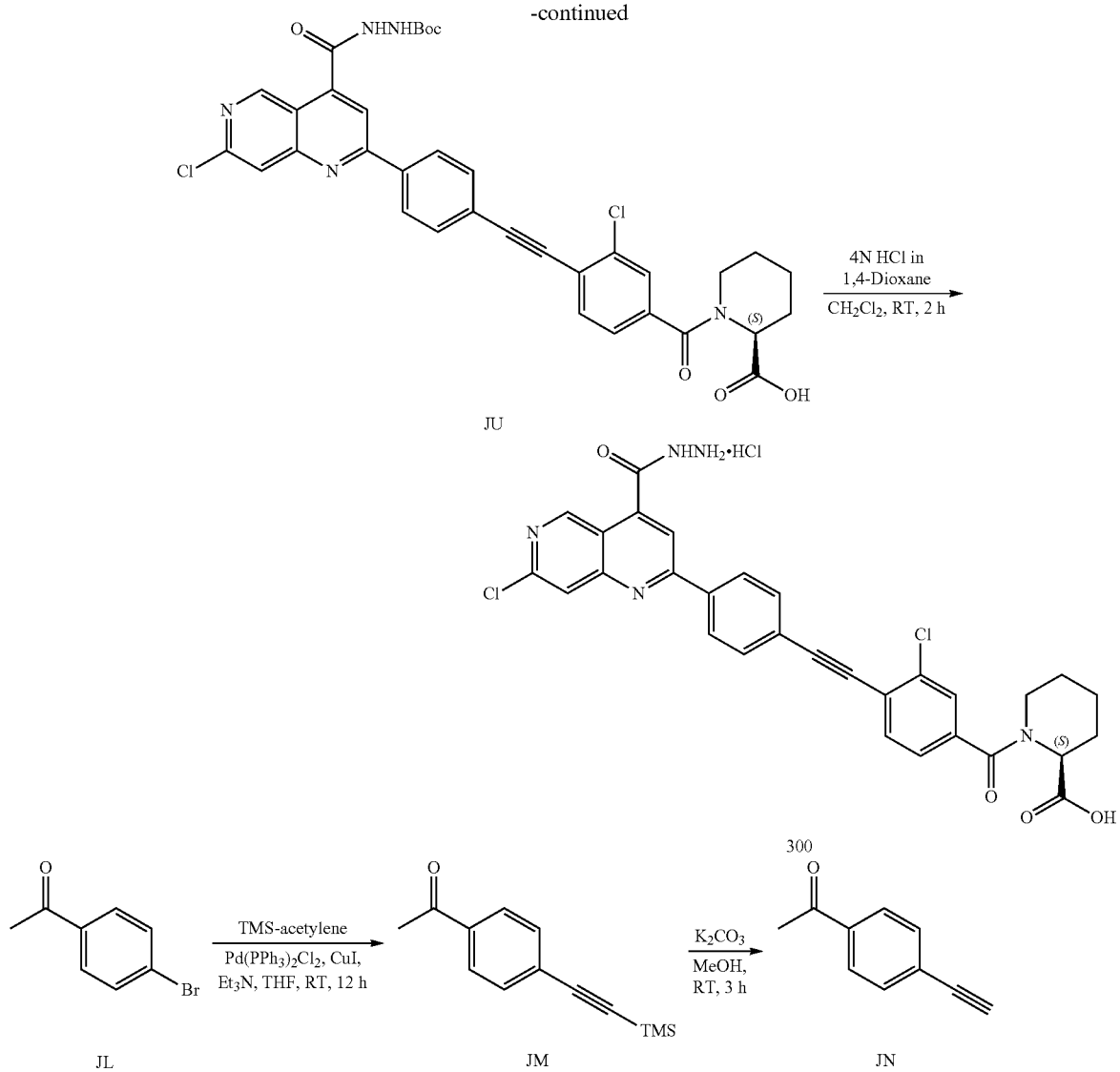

Example 300

(S)-1-(3-chloro-(4-((4-(7-chloro-4-(hydrazinecarbonyl)-1,6-naphthyridin-2-yl)phenyl)ethynyl)benzoyl) piperidine-2-carboxylic acid hydrochloride (300)

To a stirred solution of 1-(4-bromophenyl)ethan-1-one (JL; 5 g, 25.12 mmol) in THF (50 mL) under argon atmosphere were added TMS-acetylene (24.6 g, 251.2 mmol) and TEA (17.5 mL, 125.6 mmol) at 0° C. The solution was purged under argon for 30 min followed by the addition of Pd(PPh$_3$)$_2$Cl$_2$ (1.76 g, 2.51 mmol) and CuI (478 mg, 2.51 mmol). The reaction was allowed to warm to RT and was stirred for 12 h. After complete consumption of the starting material (by TLC), the reaction mixture was filtered through Celite and the Celite bed was washed with ethyl acetate. The filtrate was concentrated under reduced pressure. The crude material was purified by silica gel column chromatography eluting with 5% EtOAc/hexane to afford compound JM (4.8 g, 88%) as a brown liquid. $^1$H NMR (400 MHz, CDCl$_3$): δ 7.88 (d, J=8.4 Hz, 2H), 7.53 (d, J=8.4 Hz, 2H), 2.59 (s, 3H), 0.26 (s, 9H). MS (ESI): m/z 216.36 [M+1]$^+$ To a stirred solution of compound JM (500 mg, 2.31 mmol) in MeOH (5 mL) under nitrogen atmosphere was added anhydrous K$_2$CO$_3$ (958 mg, 6.94 mmol) at 0° C. The reaction was allowed to warm to RT and was stirred for 3 h. After complete consumption of the starting material (by TLC), the volatiles were evaporated under reduced pressure. The reaction was diluted with water (10 mL) and the compound was extracted with EtOAc (2×20 mL). The combined organic extracts were washed with water (10 mL), dried over sodium sulfate, filtered and concentrated under reduced pressure. The crude was purified by silica gel column chromatography eluting with 5% EtOAc/hexane to afford compound JN (280 mg, 84%) as a yellow solid. $^1$H NMR (400 MHz, CDCl$_3$): δ 7.92-7.90 (m, 2H), 7.58-7.56 (m, 2H), 3.24 (s, 1H), 2.60 (s, 3H). MS (ESI): m/z 144.17 [M+1]$^+$ To a stirred solution of 5-bromo-2-chloropyridin-4-amine (JO; 41 g, 197.63 mmol) in THF (600 mL) under nitrogen atmosphere was added NaH (20 g, 494.07 mmol) portionwise at 0° C. The reaction was allowed to warm to RT and was stirred for 1 h. Then pivaloyl chloride (29.16 mL, 237.16 mmol) in THF (20 mL) was added dropwise at 0° C.

The reaction was allowed to warm to RT and was stirred for 1 h. After complete consumption of the starting material (by TLC), the reaction was diluted with water (500 mL) and the compound was extracted with EtOAc (2×500 mL). The combined organic extracts were washed with water (2×200 mL), brine (2×100 mL), dried over sodium sulfate, filtered and concentrated under reduced pressure. The crude was purified by silica gel chromatography eluting with 10% EtOAc/hexane to afford compound JP (46.25 g, 81%) as an off white solid. $^1$H-NMR (DMSO-$d_6$, 500 MHz): δ 8.93 (s, 1H), 8.61 (s, 1H), 7.96 (s, 1H), 1.27 (s, 9H). MS (ESI): m/z 291.57 [M+1]$^+$ To a stirred solution of compound JP (5.5 g, 19.03 mmol) in THF (75 mL) under argon atmosphere was added NaH (3 g, 76.12 mmol) portionwise at 0° C. The reaction was heated to reflux and was stirred for 5 h. Then n-BuLi (15.3 mL, 38.06 mmol) was added dropwise at −78° C. and stirred for 2 h. Diethyl oxalate (5.55 g, 38.06 mmol) was then added dropwise at −78° C. over 30 min. The reaction was allowed to warm to RT and was stirred for 30 min. After complete consumption of the starting material (by TLC), the reaction was diluted with an NH$_4$Cl solution (100 mL) and the compound was extracted with EtOAc (2×100 mL). The combined organic extracts were washed with water (50 mL), brine (50 mL), dried over sodium sulfate, filtered and concentrated under reduced pressure. The crude was purified by silica gel column chromatography eluting with 5-7% EtOAc/hexane to afford compound JQ (4.8 g, 40.3%) as a white solid. $^1$H-NMR (DMSO-$d_6$, 500 MHz): δ 10.70 (s, 1H), 8.70 (s, 1H), 8.11 (s, 1H), 4.31 (q, 2H), 1.28 (t, J=7.5 Hz, 3H), 1.21 (s, 9H). MS (ESI): m/z 312.75 [M+1]$^+$ To a stirred solution of compound JQ (1 g, 3.20 mmol) in EtOH/H$_2$O (20 mL/20 mL) was added KOH (719 mg, 12.82 mmol). The reaction was heated to reflux and was stirred for 2 h. Then 4-acetylene acetophenone JN (923 mg, 6.41 mmol) was added at RT and the reaction was heated to refluxed for 12 h. After complete consumption of the starting material (by LC-MS), the volatiles were evaporated under reduced pressure. The crude material was diluted with water (15 mL) and acidified using AcOH. The obtained solid was filtered and dried under reduced pressure to afford compound JR (801 mg, 81%) as a yellow solid. $^1$H NMR (400 MHz, DMSO-$d_6$): δ 9.95 (s, 1H), 8.40 (s, 1H), 8.31 (d, J=8.0 Hz, 2H), 8.06 (s, 1H), 7.67 (d, J=8.0 Hz, 2H), 4.41 (s, 1H). MS (ESI): m/z 308.72 [M+1]$^+$ To a stirred solution of compound JR (250 mg, 0.81 mmol) in DMF (5 mL) under nitrogen atmosphere were added DIPEA (0.5 mL, 2.43 mmol), tert-butyl hydrazine carboxylate (320 mg, 2.43 mmol) and HATU (634 mg, 1.62 mmol). The reaction was stirred at RT for 12 h. After complete consumption of the starting material (by TLC), the reaction was diluted with water (20 mL) and extracted with EtOAc (2×50 mL). The combined organic extracts were washed with water (2×20 mL), brine (2×25 mL), dried over sodium sulfate, filtered and concentrated under reduced pressure. The crude was purified by silica gel chromatography 2% MeOH/DCM to afford compound JS (380 mg, 55%) as a yellow solid. $^1$H NMR (400 MHz, DMSO-$d_6$): δ 10.68 (s, 1H), 9.58 (s, 1H), 9.32 (s, 1H), 8.37 (t, J=7.6 Hz, 3H), 8.20 (s, 1H), 7.72 (d, J=8.0 Hz, 2H), 4.45 (s, 1H), 1.48 (s, 9H). MS (ESI): m/z 422.87 [M+1]$^+$ To a stirred solution of compound JS (300 mg, 0.71 mmol) in CH$_3$CN (20 mL) under argon atmosphere were added HJ (383 mg, 1.06 mmol) and TEA (1 mL, 7.11 mmol). The solution was purged under argon for 20 min followed by the addition of copper iodide (13.5 mg, 0.071 mmol) and Pd(PPh$_3$)$_2$Cl$_2$ (50 mg, 0.071 mmol). The reaction was heated to reflux and stirred for 4 h. After complete consumption of the starting material (by TLC), the reaction mixture was filtered through Celite and the Celite bed was washed with ethyl acetate. The filtrate was concentrated under reduced pressure. The crude material was purified by silica gel column chromatography eluting with 2% MeOH/DCM to afford compound JT (180 mg, 36%) as a yellow solid. $^1$H NMR (400 MHz, DMSO-$d_6$): δ 10.70 (s, 1H), 9.59 (s, 1H), 9.33 (s, 1H), 8.47 (d, J=8.0 Hz, 3H), 8.22 (s, 1H), 7.85 (t, J=9.2 Hz, 2H), 7.64-7.54 (m, 3H), 5.26 (s, 1H), 4.46-4.38 (m, 1H), 3.74 (s, 3H), 3.50-3.31 (m, 1H), 2.21-2.08 (m, 1H), 1.78-1.69 (m, 2H), 1.58-1.54 (m, 1H), 1.49 (s, 9H), 1.33-1.24 (m, 2H). MS (ESI): m/z 702.59 [M+1]$^+$ To a stirred solution of compound JT (100 mg, 0.14 mmol) in THF:H$_2$O (5 mL:5 mL) was added lithium hydroxide monohydrate (60 mg, 1.42 mmol) at 0° C. The reaction was allowed to warm to RT and was stirred for 1 h. After complete consumption of the starting material (by TLC), the volatiles were evaporated under reduced pressure. The crude material was diluted with water and neutralized with an acetic acid solution (0.2 mL) to obtain the solid, which was filtered, washed with water, and dried under reduced pressure to afford compound JU (62 mg, 63%) as a yellow solid. $^1$H NMR (400 MHz, DMSO-$d_6$): δ 10.72 (s, 1H), 9.59 (s, 1H), 9.33 (s, 1H), 8.45 (d, J=6.4 Hz, 2H), 8.38 (s, 1H), 8.21 (s, 1H), 7.89-7.76 (m, 3H), 7.62-7.58 (m, 2H), 7.40 (s, 1H), 4.31-4.22 (m, 1H), 4.10-3.99 (m, 1H), 3.41-3.31 (m, 1H), 2.24-2.12 (m, 1H), 1.65-1.54 (m, 2H), 1.49 (s, 9H), 1.10-1.01 (m, 3H). MS (ESI): m/z 688.46 [M+1]$^+$ To a stirred solution of compound JU (60 mg, 0.087 mmol) in DCM (2 mL) under nitrogen atmosphere was added 4N HCl in 1,4-dioxane (0.5 mL) at 0° C. The reaction was allowed to warm to RT and was stirred for 2 h. After complete consumption of the starting material (by TLC), the volatiles were evaporated under reduced pressure. The crude was triturated with 20% IPA:CH$_3$CN (3 mL) to afford 300 (30 mg as an HCl salt) as a yellow solid. $^1$H NMR (400 MHz, DMSO-$d_6$): δ 10.97 (s, 1H), 9.54 (s, 1H), 8.47 (d, J=8.0 Hz, 3H), 8.21 (s, 1H), 7.90-7.81 (m, 3H), 7.59-7.55 (m, 1H), 7.42-7.04 (m, 1H), 5.17 (s, 1H), 4.41-4.31 (m, 1H), 3.46 (d, J=12.8 Hz, 1H), 3.18 (t, J=12.8 Hz, 1H), 2.19-2.05 (m, 1H), 1.71-1.55 (m, 2H), 1.46-1.22 (m, 2H). MS (ESI): m/z 624.90 [M+1]$^+$. UPLC Purity: 92.04%

Scheme 69
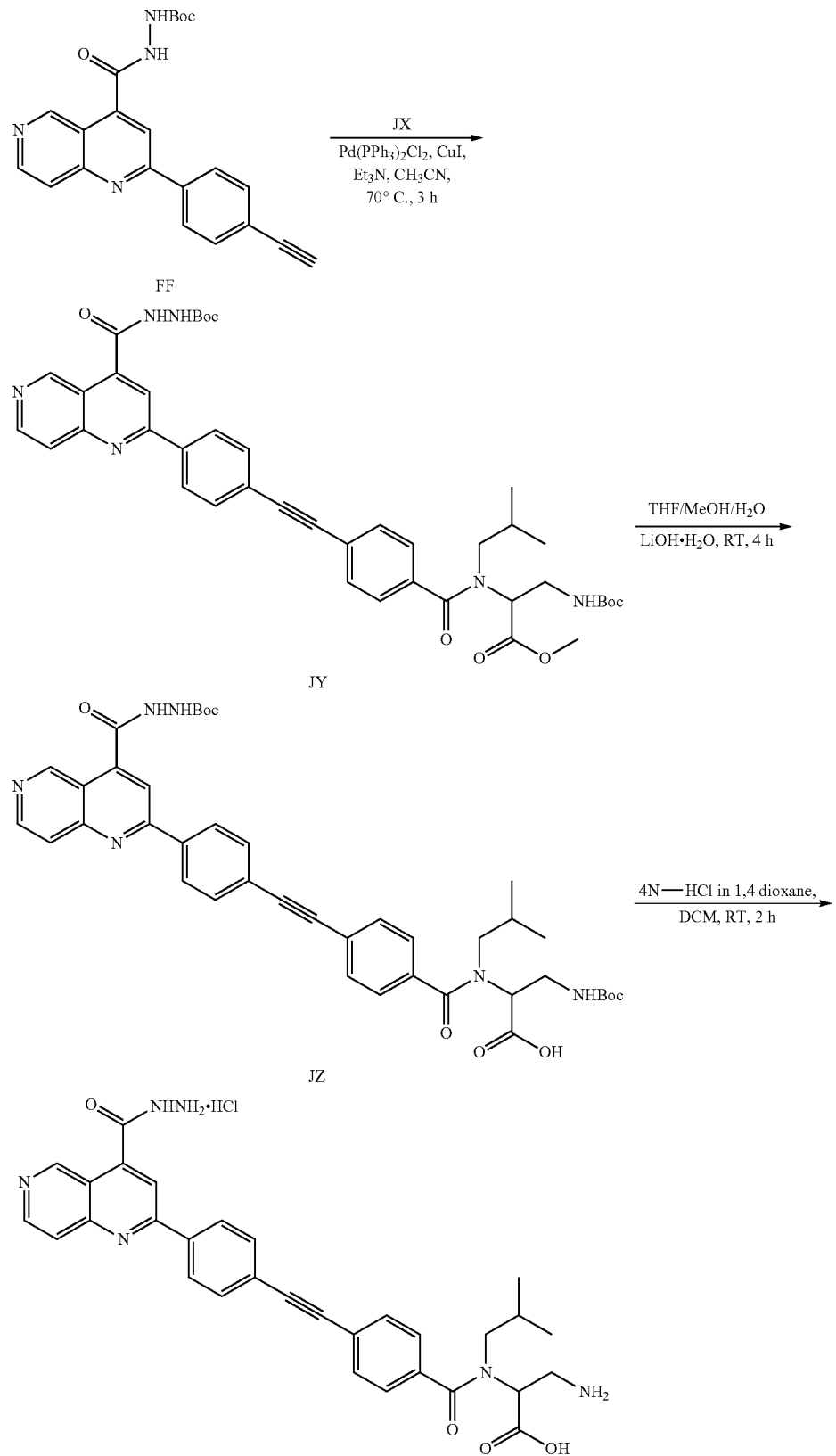

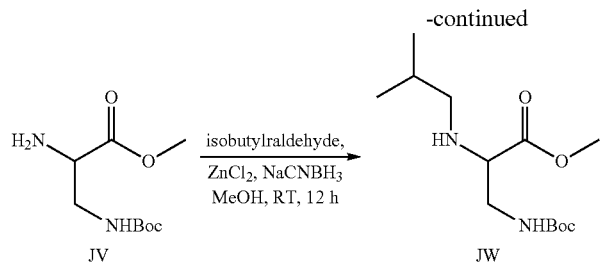
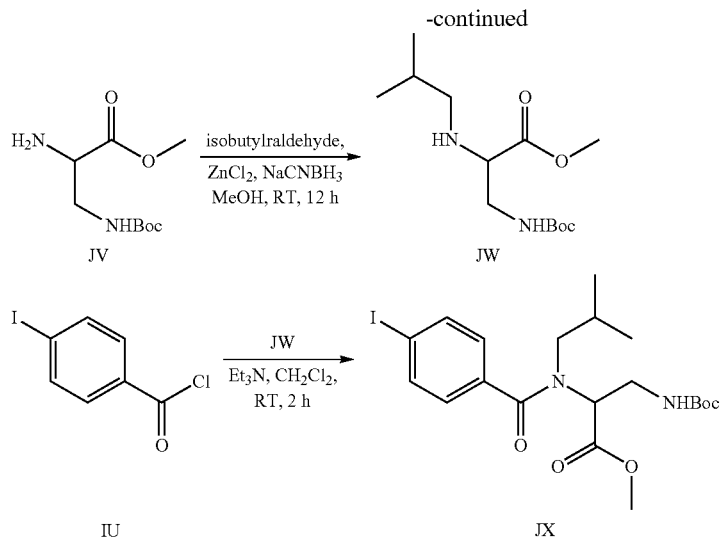

Example 301

3-amino-2-(4-((4-(4-(hydrazinecarbonyl)-1,6-naphthyridin-2-yl)phenyl)ethynyl)-N-isobutylbenzamido)propanoic acid (301)

To a stirred solution of methyl 2-amino-3-((tert-butoxycarbonyl)amino)propanoate (JV; 1 g, 4.58 mmol) in MeOH (20 mL) under nitrogen atmosphere were added isobutyraldehyde (0.71 mL, 6.84 mmol) and $ZnCl_2$ (311 mg, 2.28 mmol) at RT. After stifling for 1 h at RT, $NaCNBH_3$ (865 mg, 13.73 mmol) was added portionwise at 0° C. The reaction was allowed to warm to RT and was stirred for 12 h. After complete consumption of the starting material (by TLC), the reaction mixture was concentrated under reduced pressure. The crude material was diluted with water (5 mL) and the pH was adjusted to pH~8 by using a $NaHCO_3$ solution. The solution was extracted with EtOAc (2×50 mL) and the combined organic extracts were washed with water (50 mL), brine (50 ml), dried over sodium sulfate, filtered and concentrated under reduced pressure to afford compound JW (1 g, 80%) as a yellow solid. $^1$H-NMR (DMSO-$d_6$, 400 MHz): δ 6.81 (br s, 1H), 3.59 (s, 3H), 3.25-3.18 (m, 1H), 3.15-3.08 (m, 2H), 2.32-2.14 (m, 2H), 1.87 (br s, 1H), 1.60-1.51 (m, 1H), 1.36 (s, 9H), 0.84 (d, J=6.4 Hz, 6H). MS (ESI): m/z 275.36 [M+1]$^+$ To a stirred solution of JW (308 mg, 1.12 mmol) in DCM (5 mL) was added compound IU (300 mg, 1.12 mmol) in 5 mL DCM dropwise at 0° C. The reaction was allowed to warm to RT and was stirred for 2 h. After complete consumption of the starting material (by TLC), the reaction mixture was diluted with water (10 mL) and the compound was extracted with DCM (2×10 mL). The combined organic extracts were washed with a 10% $NaHCO_3$ solution (10 mL), dried over sodium sulfate, filtered and concentrated under reduced pressure. The crude was purified by silica gel column chromatography eluting with 20% EtOAc/hexane to afford compound JX (360 mg, 59%) as allow melting white solid. $^1$H NMR (400 MHz, $CDCl_3$): δ 7.75-7.73 (m, 2H), 7.09 (d, J=7.6 Hz, 2H), 5.21 (br s, 1H), 3.88 (s, 2H), 3.75 (s, 3H), 3.71-3.65 (m, 1H), 3.20-3.08 (m, 2H), 1.93 (t, J=6.8 Hz, 1H), 1.44 (s, 9H), 0.93 (d, J=6.4 Hz, 3H), 0.84 (d, J=6.4 Hz, 3H). MS (ESI): m/z 505.37 [M+1]$^+$ To a stirred solution of compound FF (250 mg, 0.64 mmol) in $CH_3CN$ (15 mL) under argon atmosphere were added compound JX (357 mg, 0.70 mmol) and $Et_3N$ (0.9 mL, 6.44 mmol) at 0° C. The solution was purged under argon for 30 min followed by the addition of $Pd(PPh_3)_2Cl_2$ (4.5 mg, 0.06 mmol) and CuI (12.2 mg, 0.06 mmol). The reaction was purged under argon for 10 min and then heated to 70° C. and stirred for 3 h. After complete consumption of the starting material (by TLC), the reaction mixture was filtered through Celite. The filterate was concentrated under reduced pressure. The resulting crude residue was purified by silica gel column chromatography eluting with 5% MeOH/DCM and further triturated with IPA:pentane (1 mL/4 mL) to afford compound JY (240 mg, 51%) as a brown solid. $^1$H NMR (400 MHz, DMSO-$d_6$): δ 10.65 (br s, 1H), 9.71 (br s, 1H), 9.30 (br s, 1H), 8.84 (d, J=5.6 Hz, 1H), 8.44 (d, J=8.0 Hz, 2H), 8.33 (s, 1H), 8.05 (d, J=6.4 Hz, 1H), 7.96 (s, 1H), 7.83-7.62 (m, 3H), 7.44 (d, J=8.4 Hz, 2H), 7.14 (s, 1H), 4.08 (s, 1H), 3.67 (s, 3H), 3.63-3.57 (m, 2H), 3.13 (d, J=10.4 Hz, 1H), 3.01-2.96 (m, 1H), 1.80-1.71 (m, 1H), 1.49 (s, 9H), 1.41 (s, 9H), 0.77 (d, J=6.0 Hz, 3H), 0.72 (d, J=6.4 Hz, 3H). MS (ESI): m/z 765.88 [M+1]$^+$ To a stirred solution of compound JY (80 mg, 0.10 mmol) in THF:MeOH:$H_2O$ (4 mL:1 mL:1 mL) was added lithium hydroxide monohydrate (22 mg, 0.52 mmol) at 0° C. The reaction was allowed to warm to RT and was stirred for 4 h. After complete consumption of the starting material (by TLC), the volatiles were evaporated under reduced pressure. The crude was diluted with water (5 mL) and the pH was adjusted to pH~3 by using an acetic acid solution (0.2 mL). The product was extracted with 20% MeOH/DCM (2×10 mL) and the combined organic extracts were dried over sodium sulfate, filtered, and concentrated under reduced pressure. The resulting residue was further triturated with IPA:pentane (2 mL/4 mL) to afford compound JZ (60 mg, 80%) as a brown solid. $^1$H-NMR (DMSO-$d_6$, 400 MHz): δ 9.71 (br s, 1H), 9.29 (br s, 1H), 8.84 (d, J=5.6 Hz, 1H), 8.44 (d, J=7.6 Hz, 2H), 8.33 (s, 1H), 8.05 (d, J=5.6 Hz, 1H), 7.81 (d, J=8.0 Hz, 1H), 7.68 (d, J=7.6 Hz, 2H), 7.64-7.52 (m, 3H), 7.42 (d, J=8.0 Hz, 2H), 7.07 (s, 1H), 4.33 (d, J=3.2 Hz, 1H), 3.95-3.77 (m, 2H), 3.64-3.56 (m, 1H), 3.03-2.97 (m, 2H), 1.83-1.79 (m, 1H), 1.49 (s, 9H), 1.41 (s, 9H), 0.77 (d, J=6.4 Hz, 3H), 0.72 (d, J=6.4 Hz, 3H). MS (ESI): m/z 751.85 [M+1]$^+$ To a stirred solution of compound JZ (60 mg, 0.07 mmol) in DCM (2 mL) under nitrogen atmosphere was added 4N HCl in 1,4-dioxane (1 mL) at 0° C. The reaction was allowed to warm to RT and was stirred for 2 h. After complete consumption of the starting material (by TLC), the volatiles were evaporated under reduced pressure. The crude material was triturated with MeOH:CH$_3$CN (1 mL: 3 mL) to afford 301 (20 mg as an HCl salt) as a pale brown solid. $^1$H-NMR (DMSO-d$_6$, 400 MHz): δ 11.64 (s, 1H), 9.70 (br s, 1H), 8.87 (br s, 1H), 8.48 (t, J=4.0 Hz, 3H), 8.10 (t, J=6.4 Hz, 4H), 7.83 (d, J=8.4 Hz, 2H), 7.71 (d, J=8.0 Hz, 2H), 7.53 (d, J=8.4 Hz, 2H), 4.30 (t, J=6.4 Hz, 2H), 3.19 (d, J=6.8 Hz, 3H), 1.92-1.85 (m, 1H), 0.78 (d, J=6.4 Hz, 3H), 0.71 (d, J=6.4 Hz, 3H). MS (ESI): m/z 551.8 [M+1]$^+$. UPLC: 87.77%

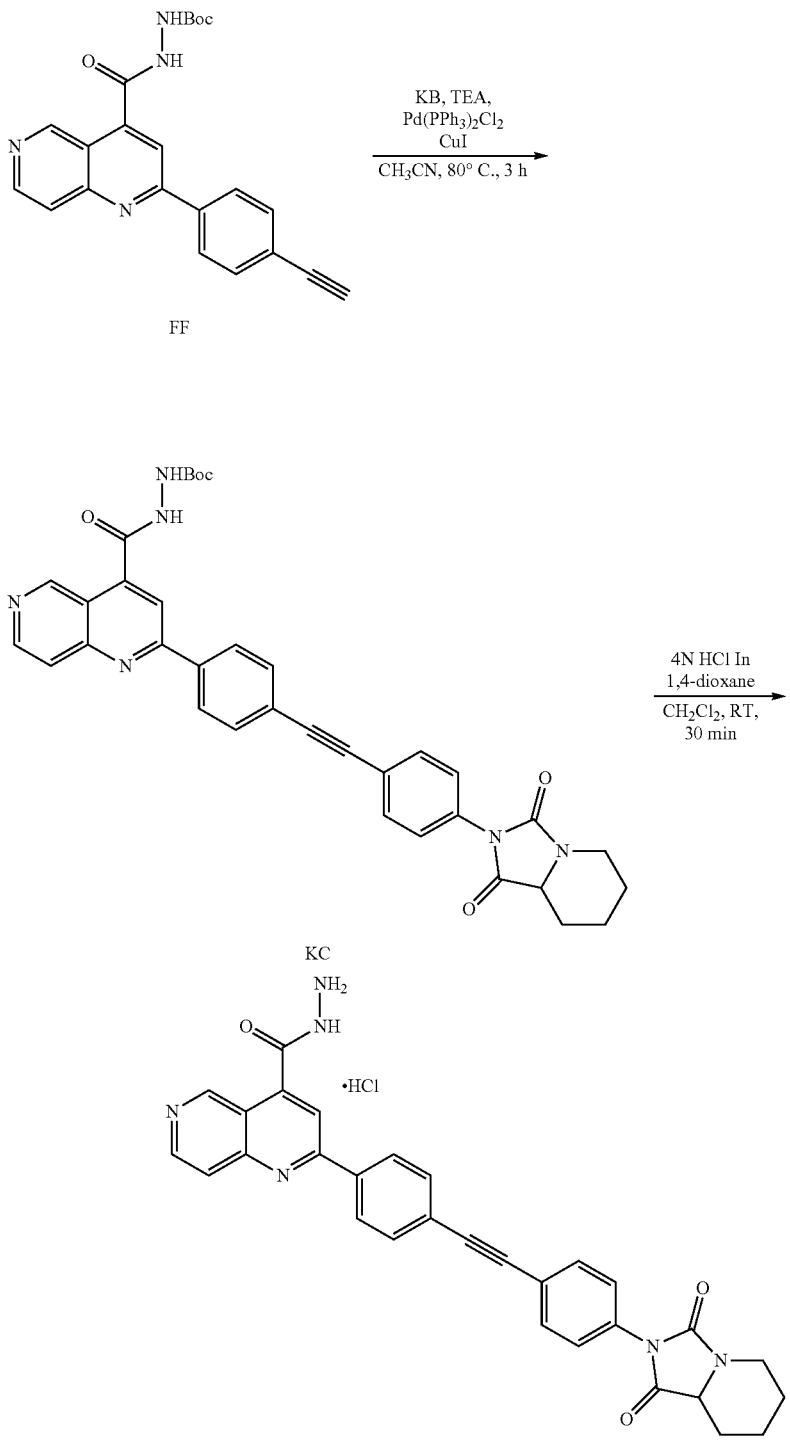

Scheme 70

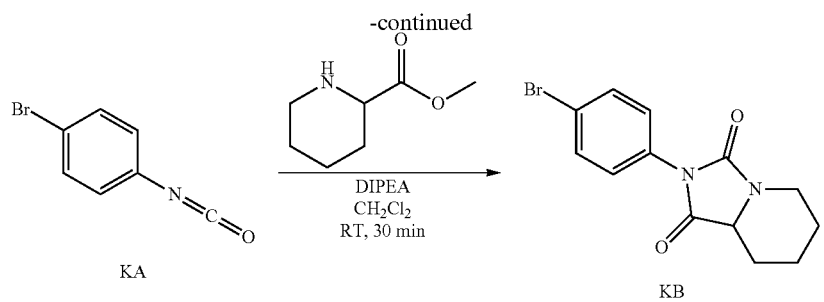

Example 304

2-(4-((4-(1,3-dioxohexahydroimidazo[1,5-a]pyridin-2(3H)-yl)phenyl)ethynyl)phenyl)-1,6-naphthyridine-4-carbohydrazide hydrochloride (304)

To a stirred solution of compound KA (500 mg, 3.49 mmol) in DCM (15 mL) under nitrogen atmosphere was added DIPEA (1.25 mL, 6.99 mmol) at 0° C. followed by the addition of methyl piperidine-2-carboxylate (690 mg, 3.49 mmol) at 0° C. The reaction was allowed to warm to RT and was stirred for 30 min. After complete consumption of the starting material (by TLC), the reaction mixture was concentrated under reduced pressure to afford compound KB (650 mg, crude) as a white solid. $^1$H NMR (400 MHz, DMSO-$d_6$): δ 7.67 (d, J=8.4 Hz, 2H), 7.35 (d, J=8.8 Hz, 2H), 4.12-4.08 (m, 1H), 4.02-3.97 (m, 1H), 2.92-2.85 (m, 1H), 2.05 (d, J=10.0 Hz, 1H), 1.89 (d, J=12.4 Hz, 1H), 1.70 (d, J=12.8 Hz, 1H), 1.54-1.45 (m, 2H), 1.37-1.23 (m, 1H). MS (ESI): m/z 310.16 [M+1]$^+$ To a stirred solution of compound FF (200 mg, 0.51 mmol) in CH$_3$CN (20 mL) under argon atmosphere was added compound KB (158 mg, 0.51 mmol) and Et$_3$N (0.72 mL, 5.15 mmol). The solution was purged under argon for 20 min followed by the addition of copper iodide (9.8 mg, 0.05 mmol) and Pd(PPh$_3$)$_2$Cl$_2$ (36 mg, 0.05 mmol). The reaction was heated to 80° C. and stirred for 3 h. After complete consumption of the starting material (by TLC), the reaction mixture was filtered through Celite and the Celite bed was washed with EtOAc (10 mL). The filtrate was concentrated under reduced pressure and the residue was purified by silica gel column chromatography eluting with 2% MeOH:DCM to afford compound KC (60 mg, 19%) as a yellow solid. $^1$H NMR (400 MHz, DMSO-$d_6$): δ 10.66 (br s, 1H), 9.30 (br s, 1H), 8.44 (d, J=3.6 Hz, 2H), 7.98-7.89 (m, 2H), 7.80-7.61 (m, 6H), 7.59-7.43 (m, 2H), 4.15-4.11 (m, 2H), 2.94-2.87 (m, 1H), 2.07 (t, J=4.0 Hz, 1H), 1.88-1.69 (m, 1H), 1.49 (s, 9H), 1.38-1.22 (m, 4H). MS (ESI): m/z 617.68 [M+1]$^+$ To a stirred solution of compound KC (60 mg, 0.09 mmol) in DCM (2 mL) under nitrogen atmosphere was added 4N HCl in 1,4-dioxane (0.5 mL) at 0° C. The reaction was allowed to warm to RT and was stirred for 1 h. After complete consumption of the starting material (by TLC), the volatiles were evaporated under reduced pressure. The crude material was triturated with CH$_3$CN (3 mL) to afford 304 (22 mg as an HCl salt) as a yellow solid. $^1$H-NMR (DMSO-$d_6$, 400 MHz): δ 11.96 (br s, 1H), 9.74 (br s, 1H), 8.89 (br s, 1H), 8.56 (s, 1H), 8.48 (d, J=8.4 Hz, 2H), 8.17 (s, 1H), 7.84 (d, J=8.0 Hz, 2H), 7.73-7.62 (m, 2H), 7.49 (t, J=8.4 Hz, 2H), 4.14 (t, J=4.0 Hz, 1H), 4.04-3.99 (m, 1H), 2.95-2.88 (m, 1H), 2.08-1.89 (m, 2H), 1.71 (d, J=12.4 Hz, 1H), 1.56-1.23 (m, 3H). MS (ESI): m/z 517.58 [M+1]$^+$. UPLC Purity: 92.41%

Scheme 71

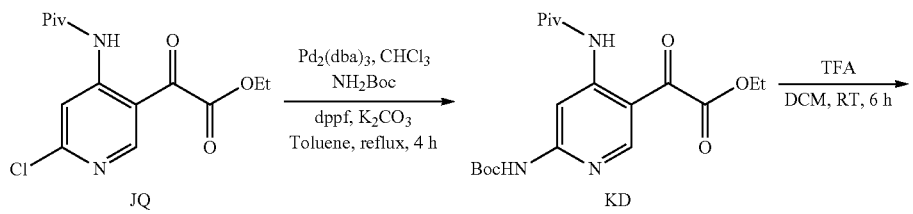

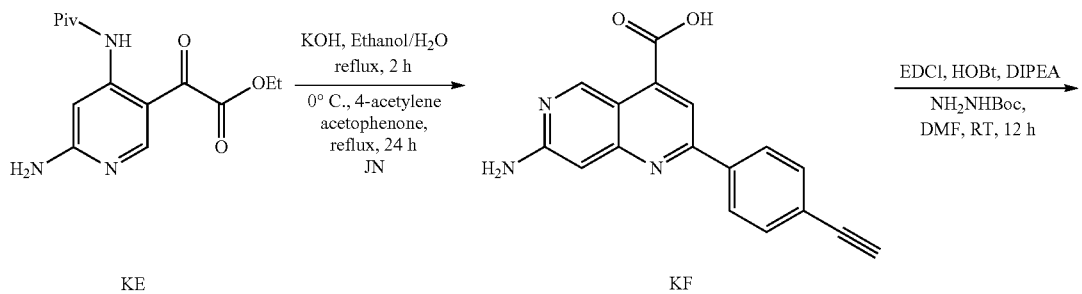

-continued
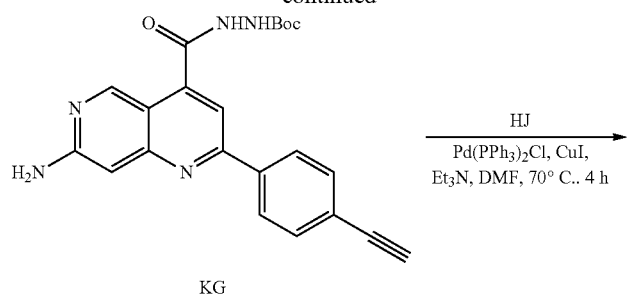
KG
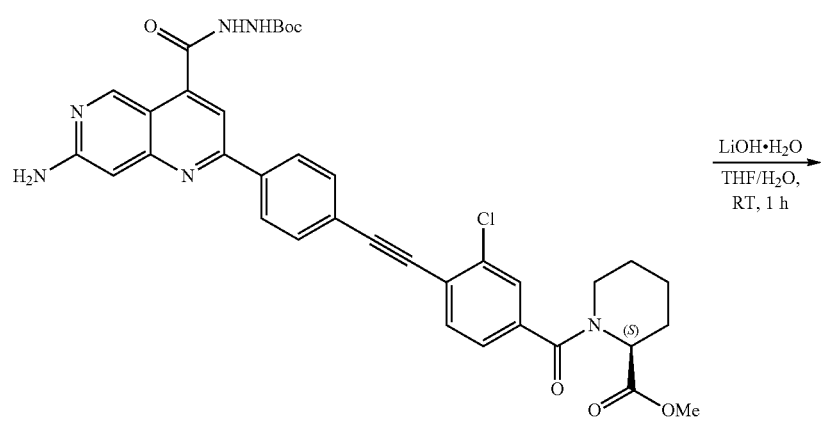
KH
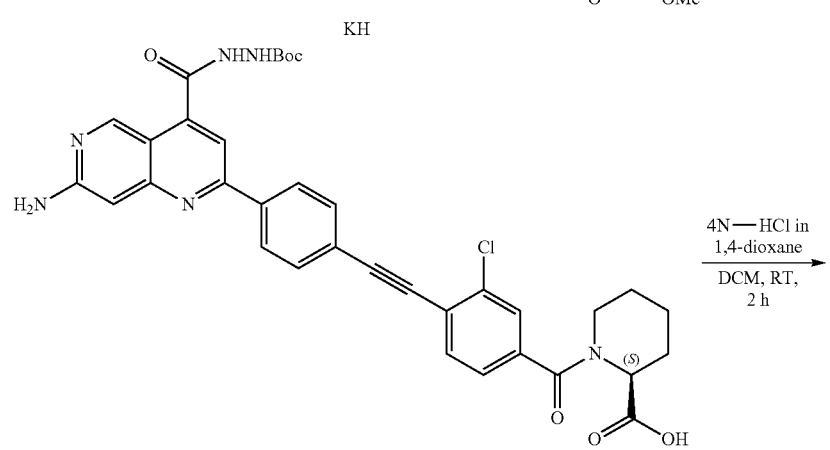
KI
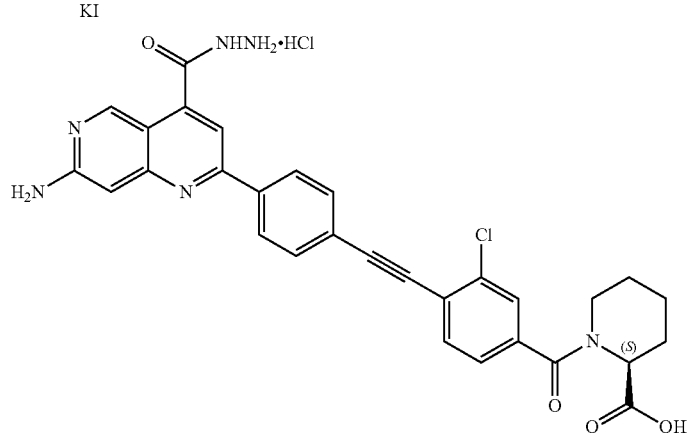

Example 306

(S)-1-(4-((4-(4-(hydrazinecarbonyl)-1,6-naphthyridin-2-yl)phenyl)ethynyl)benzoyl) pyrrolidine-2-carboxylic acid hydrochloride (306)

To a stirred solution of compound JQ (500 mg, 1.60 mmol) in toluene (20 mL) under argon atmosphere were added tert-butyl carbamate (281 mg, 2.40 mmol) and potassium carbonate (662 mg, 4.80 mmol). The mixture was purged under argon for 10 min followed by the addition of 1,1'-bis(diphenylphosphino)ferrocene (44.3 mg, 0.08 mmol) and Pd$_2$(dba)$_3$CHCl$_3$ (83 mg, 0.08 mmol). The reaction was heated to reflux and was stirred for 4 h. After complete consumption of the starting material (by TLC), the reaction mixture was filtered through Celite and the Celite bed was washed with ethyl acetate. The filtrate was concentrated under reduced pressure and the resulting residue was purified by silica gel column chromatography eluting with 20% EtOAc/hexane to afford compound KD (220 mg, 35%) as a pale yellow solid. $^1$H-NMR (DMSO-d$_6$, 400 MHz): δ 11.22 (s, 1H), 10.45 (s, 1H), 9.04 (s, 1H), 8.61 (s, 1H), 4.40 (q, 2H), 1.49 (s, 9H), 1.31 (t, J=9.0 Hz, 3H), 1.25 (s, 9H). MS (ESI): m/z 393.44 [M+1]$^+$ To a stirred solution of compound KD (785 mg, 1.99 mmol) in DCM (5 mL) under nitrogen atmosphere was added TFA (5 mL) at 0° C. The reaction was allowed to warm to RT and was stirred for 6 h. After complete consumption of the starting material (by TLC), the volatiles were evaporated under reduced pressure and the resulting residue was triturated with Et$_2$O (15 mL). The obtained solid was diluted with DCM (15 mL), basified with TEA, and washed with water (50 mL), brine (50 mL), dried over sodium sulfate, filtered and concentrated under reduced pressure. The crude material was purified by silica gel column chromatography eluting with 50% EtOAc/hexane to afford compound KE (500 mg, 85%) as a yellow solid. $^1$H-NMR (DMSO-d$_6$, 500 MHz): δ 11.41 (s, 1H), 8.29 (s, 1H), 7.66 (s, 1H), 7.46 (s, 2H), 4.37 (q, 2H), 1.29 (t, J=7.0 Hz, 3H), 1.24 (s, 9H). MS (ESI): m/z 293.32 [M+1]$^+$ To a stirred solution of compound KE (500 mg, 1.70 mmol) in EtOH/H$_2$O (40 mL/8 mL) was added NaOH (682 mg, 17.06 mmol). The reaction was heated to reflux and was stirred for 2 h. After cooling to RT, JN (489 mg, 3.30 mmol) was added, and the reaction mixture was heated at reflux for 24 h. After complete consumption of the starting material (by LC-MS), the volatiles were evaporated under reduced pressure and the residue was triturated with DCM (15 mL). The obtained solid was suspended in water and the pH was adjusted to pH~3 by using AcOH. The solid was filtered, washed with water, and dried under reduced pressure to afford compound KF (385 mg, 78%) as a yellow solid. $^1$H-NMR (DMSO-d$_6$, 400 MHz): δ 9.51 (s, 1H), 8.24 (d, J=8.0 Hz, 2H), 7.99 (s, 1H), 7.64 (d, J=8.4 Hz, 2H), 6.81 (s, 1H), 6.51-6.45 (m, 2H), 4.37 (s, 1H). MS (ESI): m/z 289.29 [M+1]$^+$ To a stirred solution of compound KF (380 mg, 1.31 mmol) in DMF (4 mL) under nitrogen atmosphere were added EDCI.HCl (502 mg, 2.62 mmol), HOBt (354 mg, 2.62 mmol), DIPEA (0.68 mL, 3.93 mmol), and tert-butyl carbazate (516 mg, 3.93 mmol) at 0° C. The reaction was allowed to warm to RT and was stirred for 16 h. After complete consumption of the starting material (by TLC), the reaction mixture was diluted with ice cold water (20 mL) and was extracted with EtOAc (2×20 mL). The combined organic extracts were washed with water (20 mL), brine (20 ml), dried over sodium sulfate, filtered and concentrated under reduced pressure. The crude material was purified by silica gel column chromatography eluting with 2% MeOH/DCM to afford compound KG (280 mg, 53%) as a yellow solid. $^1$H-NMR (DMSO-d$_6$, 400 MHz): δ 10.47 (br s, 1H), 9.18 (br s, 2H), 8.25 (d, J=8.0 Hz, 2H), 7.71 (s, 1H), 7.68 (d, J=8.0 Hz, 1H), 7.65 (s, 1H), 6.80 (s, 1H), 6.52-6.49 (m, 1H), 6.44-6.42 (m, 1H), 4.38 (s, 1H), 1.47 (s, 9H). MS (ESI): m/z 403.44 [M+1]$^+$ To a stirred solution of compound KG (100 mg, 0.24 mmol) in DMF (5 mL) under argon atmosphere were added compound HJ (130 mg, 0.36 mmol) and TEA (0.33 mL, 2.4 mmol). The solution was purged with argon for 10 min followed by the addition of copper iodide (4.56 mg, 0.024 mmol) and Pd(PPh$_3$)$_2$Cl$_2$ (16.9 mg, 0.024 mmol). The reaction was then heated to 70° C. and was stirred for 4 h. After complete consumption of the starting material (by TLC), the reaction mixture was diluted with ice cold water (20 mL) and extracted with EtOAc (2×30 mL). The combined organic extracts were washed with water (2×20 mL), dried over sodium sulfate, filtered and concentrated under reduced pressure. The crude material was purified by silica gel column chromatography eluting with 2-5% MeOH/DCM to afford compound KH (100 mg, 61%) as a yellow solid. $^1$H-NMR (DMSO-d$_6$, 400 MHz): δ 10.49 (s, 1H), 9.18 (s, 2H), 8.90-8.82 (m, 1H), 8.33 (d, J=8.0 Hz, 1H), 8.15 (d, J=8.4 Hz, 1H), 7.82 (d, J=8.0 Hz, 2H), 7.78 (d, J=8.0 Hz, 1H), 7.61 (d, J=8.4 Hz, 2H), 7.57-7.54 (m, 1H), 6.81-6.77 (m, 1H), 6.52-6.50 (m, 1H), 5.34-5.26 (m, 1H), 4.55-4.45 (m, 1H), 3.75-3.74 (m, 2H), 3.50-3.47 (m, 1H), 3.32-3.31 (m, 1H), 3.13-3.10 (m, 2H), 1.61-1.74 (m, 2H), 1.47 (s, 9H), 1.28-1.17 (m, 2H). MS (ESI): m/z 683.16 [M+1]$^+$ To a stirred solution of compound KH (100 mg, 0.14 mmol) in THF:H$_2$O (5 mL:5 mL) was added lithium hydroxide monohydrate (33 mg, 0.44 mmol) at 0° C. The reaction was allowed to warm to RT and was stirred for 4 h. After complete consumption of the starting material (by TLC), the volatiles were evaporated under reduced pressure. The solid was suspended in water and the pH was adjusted to pH~3 by using an acetic acid solution (0.2 mL). The solid was filtered and dried under reduced pressure to afford compound KI (50 mg, crude) as a yellow solid. $^1$H-NMR (DMSO-d$_6$, 400 MHz): δ 10.50 (br s, 1H), 9.18 (br s, 2H), 8.32 (br s, 1H), 8.14 (br s, 1H), 7.77-7.73 (m, 3H), 7.58 (s, 2H), 7.40-7.38 (m, 2H), 6.81 (s, 1H), 6.77-6.72 (m, 2H), 5.34-5.10 (m, 1H), 4.05 (d, J=6.8 Hz, 1H), 2.90-2.84 (m, 1H), 2.18-2.10 (m, 1H), 1.67-1.65 (m, 3H), 1.35 (s, 9H), 1.29-1.23 (m, 2H). MS (ESI): m/z 669.13 [M+1]$^+$ To a stirred solution of compound KI (50 mg, 0.07 mmol) in DCM (2 mL) under nitrogen atmosphere was added 4N HCl in 1,4-dioxane (1 mL) at 0° C. The reaction was allowed to warm to RT and was stirred for 2 h. After complete consumption of the starting material (by TLC), the volatiles were evaporated under reduced pressure. The crude was triturated with IPA:CH$_3$CN (5 mL) to afford 306 (40 mg as an HCl salt) as a brown solid. $^1$H-NMR (DMSO-d$_6$, 400 MHz): δ 13.16 (s, 1H), 9.20 (s, 2H), 8.96 (s, 2H), 8.72 (s, 1H), 8.59 (s, 1H), 8.36 (d, J=8.4 Hz, 2H), 7.81-7.76 (m, 3H), 7.58-7.54 (m, 2H), 7.41-7.34 (m, 1H), 5.17 (br s, 1H), 4.41-4.31 (m, 1H), 3.46 (d, J=11.6 Hz, 1H), 3.18 (t, J=12.0 Hz, 1H), 2.77-2.76 (m, 1H), 2.21 (d, J=12.0 Hz, 1H), 1.71-1.69 (m, 2H), 1.45-1.30 (m, 2H). MS (ESI): m/z 569.6 [M+1]$^+$. UPLC Purity: 95.32%

Scheme 72
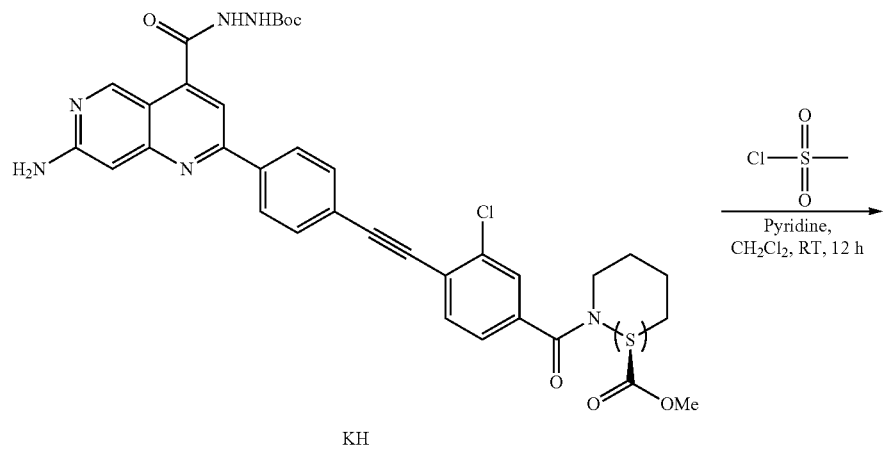
KH
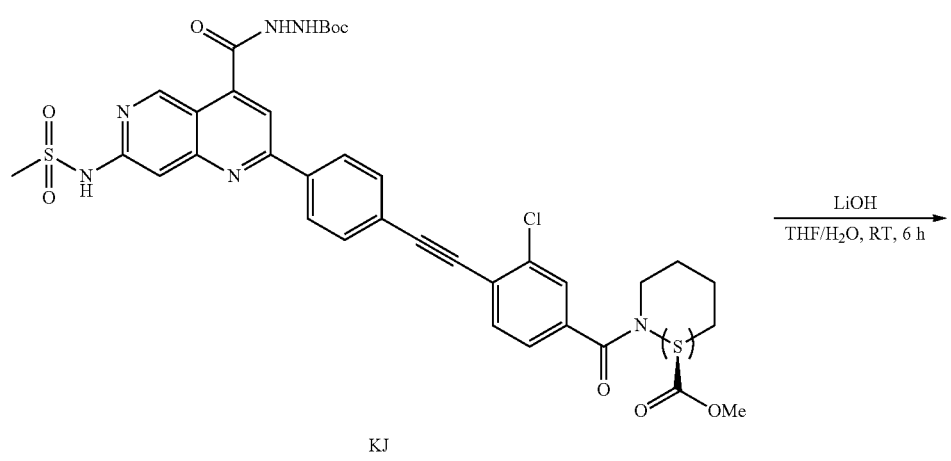
KJ
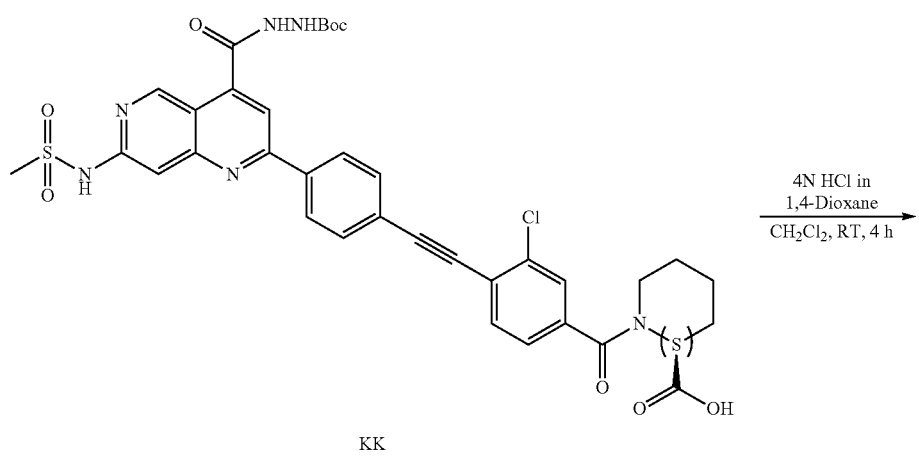
KK

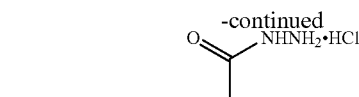

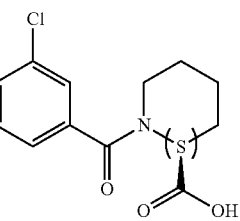

309

Example 309

(S)-1-(3-chloro-(4-((4-(4-(hydrazinecarbonyl)-7-(methylsulfonamido)-1,6-naphthyridin-2-yl)phenyl)ethynyl)benzoyl)piperidine-2-carboxylic acid hydrochloride (309)

To a stirred solution of compound KH (100 mg, 0.14 mmol) in DCM (5 mL) under nitrogen atmosphere were added pyridine (0.02 mL, 0.29 mmol) and MeSO$_2$Cl (0.02 mL, 0.17 mmol) at 0° C. The reaction was allowed to warm to RT and was stirred for 12 h. After complete consumption of the starting material (by TLC), the volatiles were evaporated under reduced pressure. The crude material was purified by silica gel column chromatography eluting with 1% MeOH/DCM and further purified by preparative HPLC to afford compound KJ (50 mg, 20%) as a yellow solid. $^1$H NMR (400 MHz, DMSO-d$_6$): δ 10.99 (br s, 1H), 10.60 (br s, 1H), 9.48 (s, 1H), 9.26 (s, 1H), 8.43 (d, J=8.0 Hz, 2H), 8.09 (br s, 1H), 7.81 (d, J=8.0 Hz, 3H), 7.60-7.58 (m, 1H), 7.43 (s, 1H), 7.41-7.38 (m, 1H), 5.26 (br s, 1H), 4.49-4.45 (m, 1H), 3.74 (s, 3H), 3.49 (d, J=13.6 Hz, 1H), 3.22-3.13 (m, 1H), 2.70-2.62 (m, 1H), 2.24-2.20 (m, 1H), 1.98 (s, 3H), 1.80-1.72 (m, 2H), 1.67-1.64 (m, 1H), 1.49 (s, 9H). MS (ESI): m/z 761.25 [M+1]$^+$ To a stirred solution of compound KJ (10 mg, 0.013 mmol) in THF:H$_2$O (3 mL:2 mL) was added lithium hydroxide monohydrate (1.10 mg, 0.026 mmol) at 0° C. The reaction was allowed to warm to RT and was stirred for 6 h. After complete consumption of the starting material (by TLC), the volatiles were evaporated under reduced pressure. The crude material was diluted with water and the pH was adjusted to pH ~3 by using an acetic acid solution (0.02 mL). The precipitate was filtered and dried under reduced pressure to afford compound KK (8 mg, 82%) as a yellow solid. MS (ESI): m/z 747.22 [M+1]$^+$ To a stirred solution of compound KK (8 mg, 0.01 mmol) in DCM (2 mL) under nitrogen atmosphere was added 4N HCl in 1,4-dioxane (0.1 mL) at 0° C. The reaction was allowed to warm to RT and was stirred for 4 h. After complete consumption of the starting material (by TLC), the volatiles were evaporated under reduced pressure. The crude material was triturated with 10% IPA:CH$_3$CN (3 mL) to afford 309 (7 mg as an HCl salt) as a yellow solid. $^1$H NMR (400 MHz, DMSO-d$_6$): δ 11.00 (br s, 1H), 9.46 (s, 1H), 8.45 (d, J=8.0 Hz, 2H), 8.27 (s, 1H), 7.90-7.82 (m, 3H), 7.57-7.49 (m, 2H), 7.40 (s, 1H), 5.17 (s, 1H), 4.38-4.31 (m, 1H), 3.39-3.16 (m, 1H), 3.01 (s, 3H), 2.81-2.70 (m, 1H), 1.69-1.56 (m, 3H), 1.48-1.30 (m, 2H). MS (ESI): m/z 647.7.4 [M+1]$^+$. UPLC Purity: 90.20%

Scheme 73

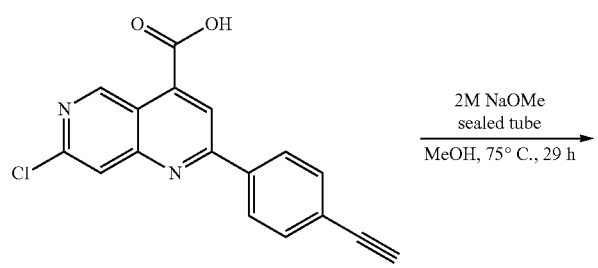

JR

-continued
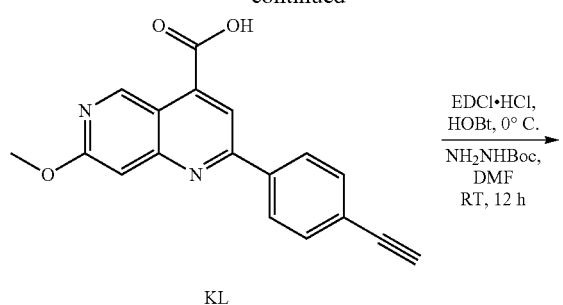
KL
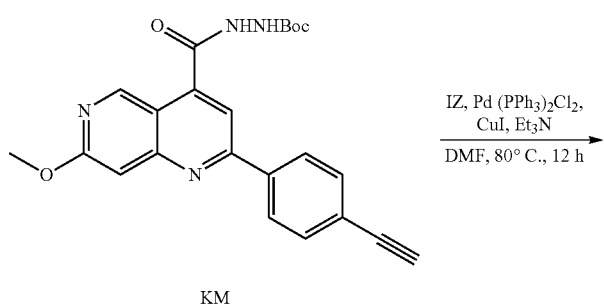
KM
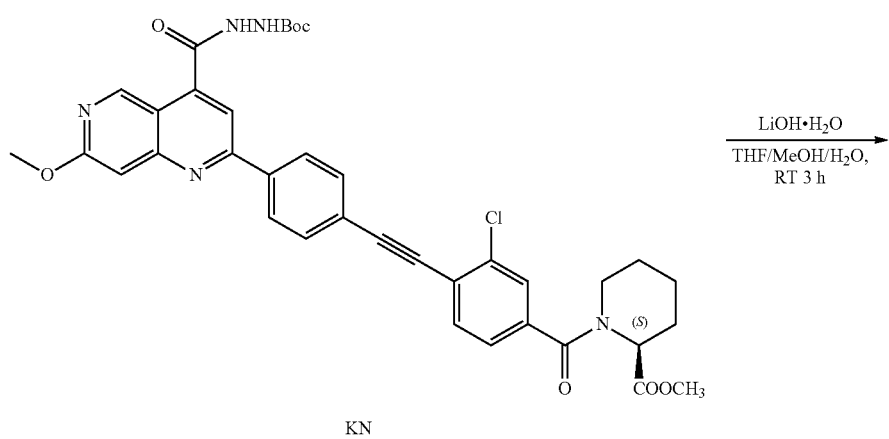
KN
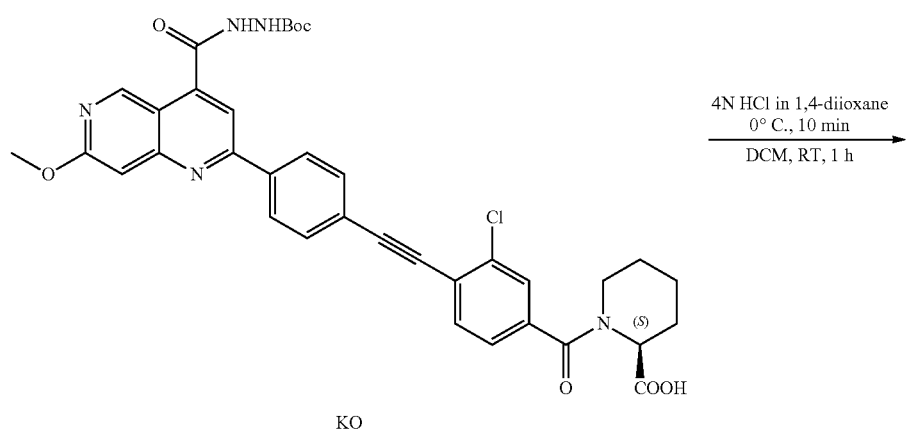
KO

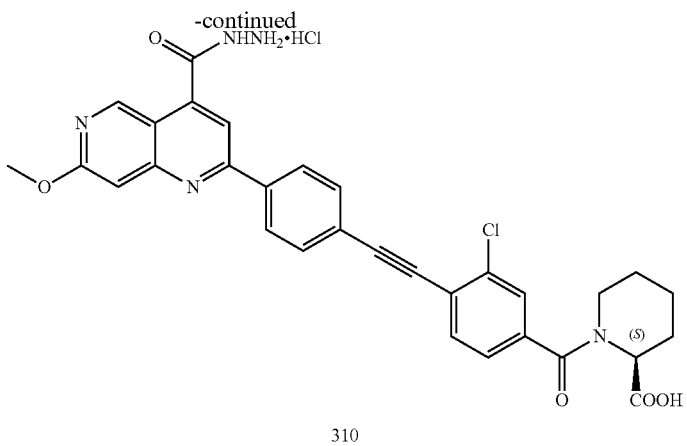

310

Example 310

(S)-1-(3-chloro-4-((4-(4-(hydrazinecarbonyl)-7-methoxy-1,6-naphthyridin-2-yl)phenyl) ethynyl) benzoyl)piperidine-2-carboxylic acid hydrochloride (310)

To a stirred solution of compound JR (1 g, 3.24 mmol) in MeOH (1 mL) was added 2M NaOMe (4 mL, 8.1 mmol) at 0° C. The reaction was heated to 75° C. and was stirred for 12 h. The reaction was cooled to RT, at which point, compound 9 (692 mg, 4.80 mmol) was added. The reaction was heated to 100° C. for 29 h in sealed tube. After complete consumption of the starting material (by TLC), the reaction was diluted with cold water (10 mL) and the volatiles were evaporated under reduced pressure. The crude material was diluted with water and the pH was adjusted to pH~4 by using AcOH. The precipitate was filtered, washed with water, and dried under reduced pressure to afford compound KL (880 mg crude) as a yellow solid. MS (ESI): m/z 305.31 [M+1]$^+$ To a stirred solution of compound KL (880 mg, 2.89 mmol) in DMF (10 mL) under nitrogen atmosphere were added DIPEA (1.50 mL, 8.67 mmol), EDCI.HCl (1.10 g, 5.78 mmol), HOBt (780 mg, 5.78 mmol), and tert-butyl carbazate (757 mg, 5.78 mmol) at 0° C. The reaction was allowed to warm to RT and was stirred for 12 h. After complete consumption of the starting material (by TLC), the reaction mixture was diluted with ice cold water (50 mL) and was extracted with EtOAc (2×50 mL). The combined organic extracts were washed with water (50 mL), brine (50 ml), dried over sodium sulfate, filtered and concentrated under reduced pressure. The crude material was purified by silica gel column chromatography eluting with 30% EtOAc/hexane to afford compound KM (300 mg, crude). Preparative HPLC purification afforded compound KM (110 mg) as a pale yellow solid. $^1$H-NMR (DMSO-d$_6$, 400 MHz): δ 10.59 (s, 1H), 9.45 (s, 1H), 9.27 (s, 1H), 8.34 (d, J=8.0 Hz, 2H), 8.06 (s, 1H), 7.69 (d, J=8.0 Hz, 2H), 7.34 (s, 1H), 4.42 (s, 1H), 4.03 (s, 3H), 1.48 (s, 9H). MS (ESI): m/z 419.45 [M+1]$^+$ IZ was synthesized from 3-chloro-4-iodobenzoic acid and (S)-methyl piperidine-2-carboxylate hydrochloride following a similar procedure used to synthesize HJ.

To a stirred solution of compound KM (80 mg, 0.19 mmol) in CH$_3$CN (10 mL) under argon atmosphere were added compound IZ (85 mg, 0.20 mmol) and TEA (0.26 mL, 1.91 mmol). The solution was purged under argon for 20 min followed by the addition of copper iodide (3 mg, 0.01 mmol) and Pd(PPh$_3$)$_2$Cl$_2$ (13 mg, 0.01 mmol). The reaction was heated to 80° C. and was stirred for 2 h. After complete consumption of the starting material (by TLC), the reaction was concentrated under reduced pressure and the resulting residue was purified by silica gel column chromatography eluting with 2% MeOH:DCM and further triturated with IPA:pentane (3 mL:2 mL) to afford compound KN (15 mg, 30%) as a yellow solid. $^1$H NMR (400 MHz, DMSO-d$_6$): δ 10.61 (s, 1H), 9.46 (s, 1H), 9.27 (s, 1H), 8.43 (d, J=8.0 Hz, 2H), 8.10 (s, 1H), 7.82 (d, J=8.0 Hz, 3H), 7.55 (s, 1H), 7.37 (s, 2H), 5.26 (s, 1H), 4.02 (s, 3H), 3.74 (s, 3H), 3.51-3.47 (m, 1H), 3.15 (t, J=11.6 Hz, 1H), 2.21-2.18 (m, 1H), 1.72-1.68 (m, 3H), 1.58-1.54 (m, 1H), 1.49 (s, 9H), 1.03 (d, J=6.0 Hz, 1H). MS (ESI): m/z 699.17 [M+1]$^+$ To a stirred solution of compound KN (30 mg, 0.04 mmol) in THF:MeOH:H$_2$O (2 mL:1 mL:1 mL) was added lithium hydroxide monohydrate (2 mg, 0.06 mmol) at 0° C. The reaction was allowed to warm to RT and was stirred for 3 h. After complete consumption of the starting material (by TLC), the reaction mixture was concentrated under reduced pressure. The crude material was diluted with water (5 mL) and the pH was adjusted to pH~3 by using AcOH (0.1 mL). The product was extracted with 20% MeOH/DCM (2×10 mL) and the combined organic extracts were dried over sodium sulfate, filtered and concentrated under reduced pressure. The residue was triturated with 10% MeOH:DCM (2 mL) to afford compound KO (18 mg, 62%) as a yellow solid. $^1$H NMR (400 MHz, DMSO-d$_6$): δ 13.10 (s, 1H), 10.61 (s, 1H), 9.46 (s, 1H), 9.27 (s, 1H), 8.43 (d, J=7.6 Hz, 2H), 8.10 (s, 1H), 7.82 (d, J=7.6 Hz, 3H), 7.58 (s, 1H), 7.41-7.36 (m, 2H), 5.15 (s, 1H), 4.17 (s, 3H), 3.46-3.43 (m, 1H), 3.23-3.17 (m, 1H), 2.83-2.76 (m, 1H), 2.22-2.07 (m, 1H), 1.67-1.52 (m, 4H), 1.49 (s, 9H). MS (ESI): m/z 685.15 [M+1]$^+$ To a stirred solution of compound KO (13 mg, 0.01 mmol) in DCM (0.4 mL) under nitrogen atmosphere was added 4N HCl in 1,4-dioxane (0.1 mL) at 0° C. and the reaction was stirred for 2 h. After complete consumption of the starting material (by TLC), the volatiles were evaporated under reduced pressure and the resulting solids were triturated with 30% CH$_3$OH:CH$_3$CN (0.5 mL) to afford 310 (10 mg as an HCl salt) as a brown solid. $^1$H NMR (400 MHz, DMSO-d$_6$): δ 11.27 (s, 1H), 9.39 (s, 1H), 8.44 (d, J=8.0 Hz, 2H), 8.21 (s, 1H), 7.83 (d, J=8.0 Hz, 3H), 7.58 (s, 1H), 7.37 (s, 2H), 5.17-4.38 (s, 1H), 4.40 (m, 0.5H), 4.38 (m, 0.5H), 4.31 (m, 3H), 4.03 (m, 0.5H), 3.36 (m, 0.5H), 2.76-2.72 (m, 0.5H), 2.22-2.05 (m, 1H), 1.71-1.55 (m, 3H), 1.35-1.23 (m, 2H). MS (ESI): m/z 584.8 [M+1]+. HPLC Purity: 87.38%

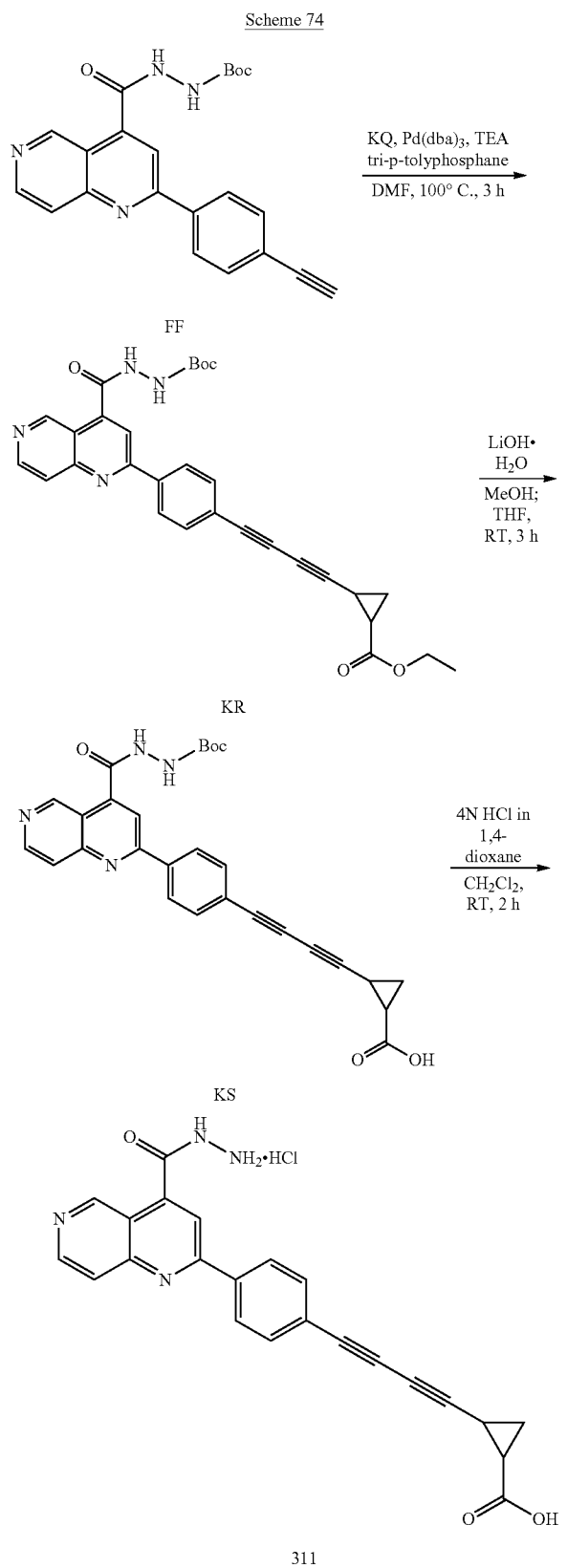

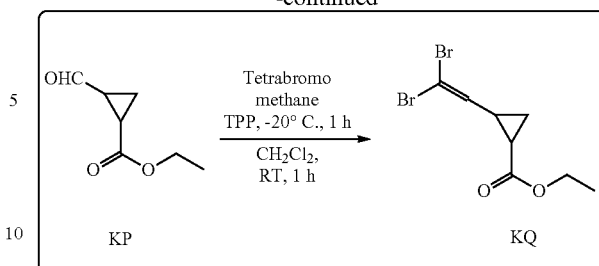

Example 311

2-((4-(4-(hydrazinecarbonyl)-1,6-naphthyridin-2-yl) phenyl)buta-1,3-diyn-1-yl)cyclopropane-1-carboxylic acid hydrochloride (311)

To a stirred solution of tetrabromomethane (934 mg, 2.81 mmol) in DCM (5 mL) under nitrogen atmosphere was added triphenylphosphine (1.47 g, 5.63 mmol) in DCM (5 mL) dropwise over 10 min at −20° C. Then ethyl 2-formylcyclopropane-1-carboxylate (KP; 200 mg, 1.40 mmol) in DCM (4 mL) was added dropwise over 10 min at −70° C. and was stirred for 30 min. The reaction was allowed to slowly warm to RT over 1 h. After complete consumption of the starting material (by TLC), the reaction mixture was concentrated under reduced pressure. The crude material was purified by column chromatography eluting with 15% EtOAc/hexane to afford compound KQ (250 mg, 59%) as a colorless liquid. $^1$H NMR (500 MHz, CDCl$_3$): δ 5.86 (d, J=9.0 Hz, 1H), 4.17-4.13 (m, 2H), 2.23-2.19 (m, 1H), 1.78-1.74 (m, 1H), 1.50-1.46 (m, 1H), 1.33-1.26 (m, 1H), 1.06-1.02 (m, 3H).

To a stirred solution of carboxylate KQ (100 mg, 0.33 mmol) in DMF (4 mL) under nitrogen atmosphere were added FF (130 mg, 0.33 mmol), TEA (0.14 mL, 0.99 mmol), Pd$_2$(dba)$_3$ (30 mg, 0.033 mmol) and tri-p-tolylphosphine (5 mg, 0.01 mmol). The reaction was heated to 100° C. and was stirred for 3 h. After complete consumption of the starting material (by TLC), the reaction mixture was diluted with ice cold water (20 mL) and the compound was extracted with EtOAc (2×20 mL). The combined organic extracts were washed with water (2×20 mL), dried over sodium sulfate, filtered and concentrated under reduced pressure. The crude material was purified by silica gel column chromatography eluting with 2% MeOH/DCM to afford compound KR (60 mg, 35%) as a yellow solid. $^1$H NMR (400 MHz, DMSO-d$_6$): δ 10.64 (br s, 1H), 9.71 (br s, 1H), 9.29 (br s, 1H), 8.84 (d, J=6.0 Hz, 1H), 8.39 (d, J=7.6 Hz, 2H), 8.31 (s, 1H), 8.03 (d, J=5.6 Hz, 1H), 7.78-7.70 (m, 2H), 4.14-4.08 (m, 2H), 2.34 (d, J=10.8 Hz, 1H), 2.32-2.19 (m, 2H), 2.18-1.97 (m, 1H), 1.49 (s, 9H), 1.41-1.32 (m, 3H).

To a stirred solution of compound KR (60 mg, 0.11 mmol) in THF/MeOH (1:1, 6 mL) were added lithium hydroxide monohydrate (9.6 mg, 0.22 mmol) and water (2 mL) at 0° C. The reaction was allowed to warm to RT and was stirred for 3 h. After complete consumption of the starting material (by TLC), the volatiles were evaporated under reduced pressure. The residue was dissolved in water (5 mL) and acidified with acetic acid to pH~4. The precipitate was filtered and dried under reduced pressure to obtain compound KS (15 mg, 27%) as a yellow solid. $^1$H NMR (400 MHz, DMSO-d$_6$): δ 10.66 (br s, 1H), 9.70 (s, 1H), 9.29 (s, 1H), 8.83 (d, J=5.6 Hz, 1H), 8.38 (d, J=8.4 Hz, 2H), 8.30 (s, 1H), 8.03 (d, J=6.0 Hz, 1H), 7.77-7.70 (m, 2H), 1.85 (d, J=7.6 Hz, 2H), 1.48 (s, 9H), 1.30-1.22 (m, 1H), 0.96-0.99 (m, 1H). MS (ESI): 19.37%, m/z 491.8 [M+1]⁺

To a stirred solution of compound KS (15 mg, 0.03 mmol) in DCM (2 mL) under nitrogen atmosphere was added 4N HCl in 1,4-dioxane (0.2 mL) at 0° C. The reaction was allowed to warm to RT and was stirred for 2 h. After complete consumption of the starting material (by TLC), the volatiles were evaporated under reduced pressure. The crude material was triturated with 20% CH₃OH/CH₃CN (4 mL) to afford 311 (10 mg as an HCl salt) as a yellow solid. ¹H NMR (400 MHz, DMSO-d₆): δ 11.79 (br s, 1H), 9.69 (s, 1H), 8.86 (d, J=6.0 Hz, 1H), 8.50 (s, 1H), 8.42 (d, J=8.4 Hz, 2H), 8.12 (d, J=6.0 Hz, 1H), 7.79 (d, J=8.8 Hz, 2H), 2.08-2.00 (m, 2H), 1.36 (t, J=8.0 Hz, 2H). HPLC Purity: 91.30%

Scheme 75

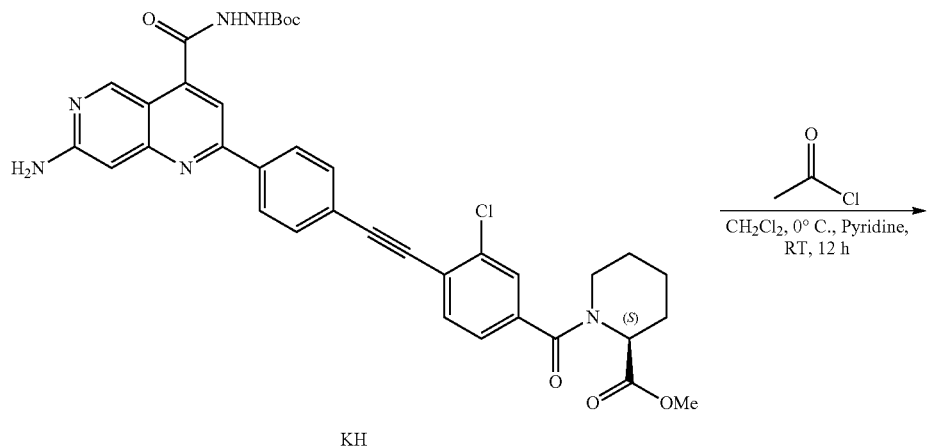

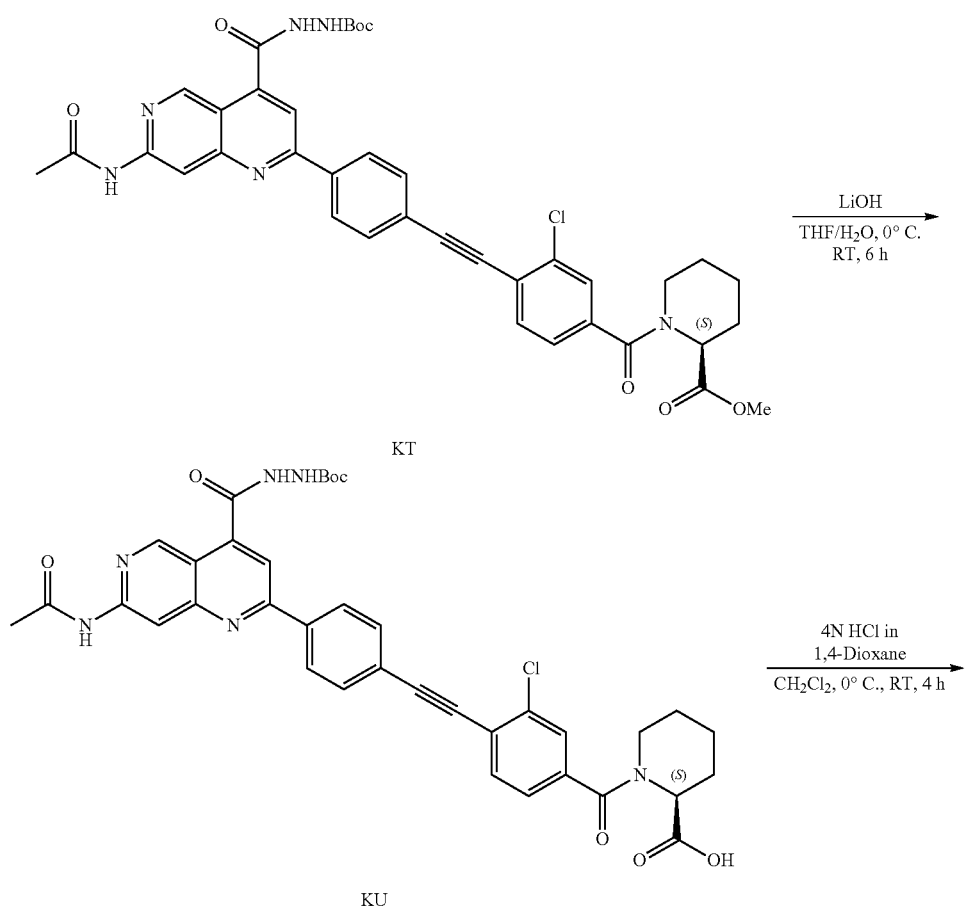

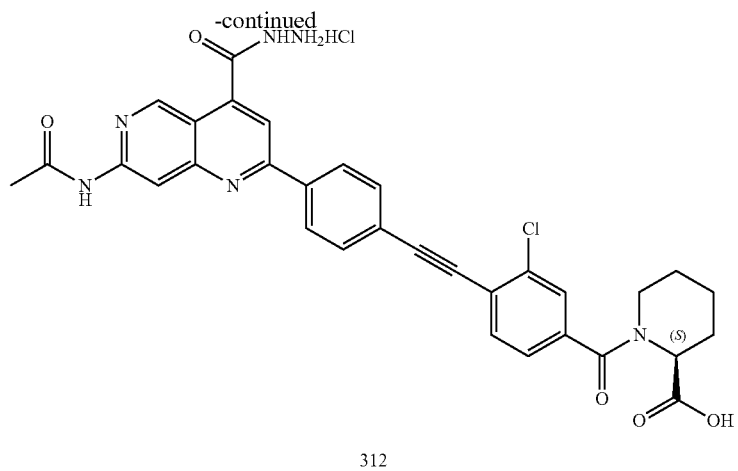

312

Example 312

(S)-1-(4-((4-(7-acetamido-4-(hydrazinecarbonyl)-1,6-naphthyridin-2-yl)phenyl)ethynyl)-3-chlorobenzoyl)piperidine-2-carboxylic acid hydrochloride (312)

To a stirred solution of compound KH (100 mg, 0.14 mmol) in DCM (2 mL) under nitrogen atmosphere were added pyridine (0.03 mL, 0.28 mmol) and acetyl chloride (0.02 mL, 0.22 mmol) at 0° C. The reaction was allowed to warm to RT and was stirred for 4 h. After complete consumption of the starting material (by TLC), the volatiles were concentrated under reduced pressure. The crude material was purified by preparative TLC to afford compound KT (30 mg, 30%) as a yellow solid. $^1$H NMR (400 MHz, DMSO-$d_6$): δ 10.90 (s, 1H), 10.65 (s, 1H), 9.50 (s, 1H), 9.26 (s, 1H), 8.68 (s, 1H), 8.44 (d, J=8.0 Hz, 2H), 8.16 (s, 1H), 7.82 (d, J=7.6 Hz, 2H), 7.60 (s, 1H), 7.42 (d, J=7.2 Hz, 1H), 5.26 (br s, 1H), 4.45-4.39 (m, 1H), 3.74 (s, 3H), 3.37-3.36 (m, 1H), 3.12 (s, 1H), 2.19 (s, 3H), 2.10-2.04 (m, 1H), 1.76-1.72 (m, 2H), 1.48 (s, 9H), 1.34-1.30 (m, 2H). MS (ESI): m/z 725.20 [M+1]$^+$ To a stirred solution of compound KT (70 mg, 0.096 mmol) in THF:H$_2$O (4 mL:2 mL) was added lithium hydroxide monohydrate (8.1 mg, 0.193 mmol) at 0° C. The reaction was allowed to warm to RT and was stirred for 4 h. After complete consumption of the starting material (by TLC), the volatiles were evaporated under reduced pressure. The residue was diluted with water (3 mL) and neutralized with an acetic acid solution (0.03 mL) and the resulting precipitate was filtered and dried under reduced pressure to afford compound KU (25 mg, 37%) as a yellow solid. $^1$H NMR (400 MHz, DMSO-$d_6$): δ 10.90 (s, 1H), 10.66 (s, 1H), 9.50 (s, 1H), 9.26 (s, 1H), 8.68 (s, 1H), 8.44 (d, J=7.2 Hz, 2H), 8.25 (d, J=7.6 Hz, 1H), 7.82-7.72 (m, 3H), 7.58 (s, 1H), 7.40-7.39 (m, 1H), 5.12 (br s, 1H), 4.37 (d, J=10.4 Hz, 1H), 3.33-3.32 (m, 1H), 2.86-2.82 (m, 1H), 2.19 (s, 3H), 2.16-2.00 (m, 1H), 1.68-1.66 (m, 2H), 1.49 (s, 9H), 1.30-1.26 (m, 2H). MS (ESI): m/z 711.17 [M+1]$^+$ To a stirred solution of compound KU (40 mg, 0.056 mmol) in DCM (2 mL) under nitrogen atmosphere was added 4N HCl in 1,4-dioxane (0.4 mL) at 0° C. The reaction was allowed to warm to RT and was stirred for 3 h. After complete consumption of the starting material (by TLC), the volatiles were evaporated under reduced pressure. The crude material was triturated with 30% MeOH:ACN (2 mL) to afford 312 (25 mg as an HCl salt) as a brown solid. $^1$H NMR (400 MHz, DMSO-$d_6$): δ 12.20 (s, 1H), 10.94 (s, 1H), 9.45 (s, 1H), 8.69 (s, 1H), 8.47 (d, J=8.0 Hz, 2H), 8.37-8.33 (m, 1H), 7.84-7.82 (m, 3H), 7.58-7.55 (m, 1H), 7.40-7.36 (m, 1H), 5.17 (br s, 1H), 4.40-4.31 (m, 1H), 3.46 (d, J=10.8 Hz, 1H), 3.18 (t, J=12.0 Hz, 1H), 2.79-2.76 (m, 2H), 2.19 (s, 3H), 2.07-2.04 (m, 1H), 1.71-1.69 (m, 3H), 1.42-1.30 (m, 2H). MS (ESI): m/z 613.5 [M+2]$^+$. UPLC Purity: 80.05%

Scheme 76

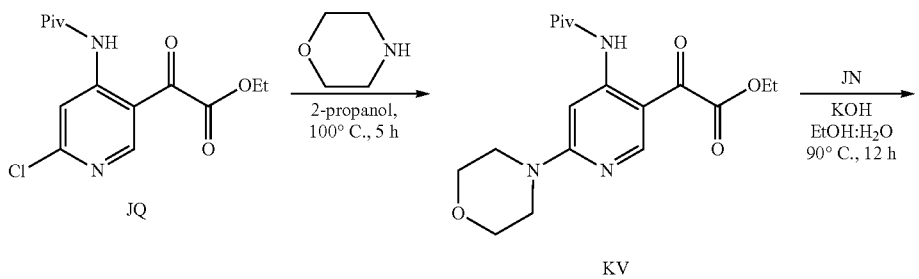

-continued
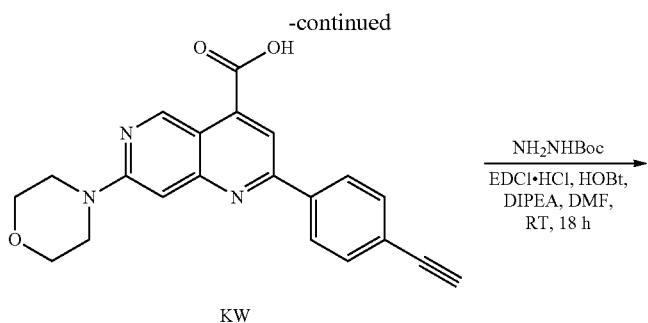
KW
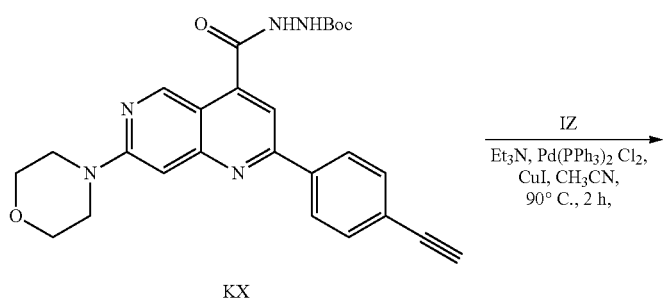
KX
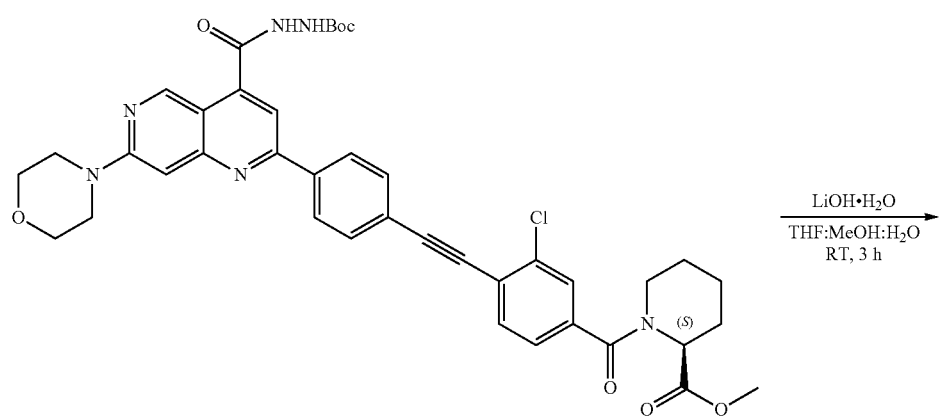
KY
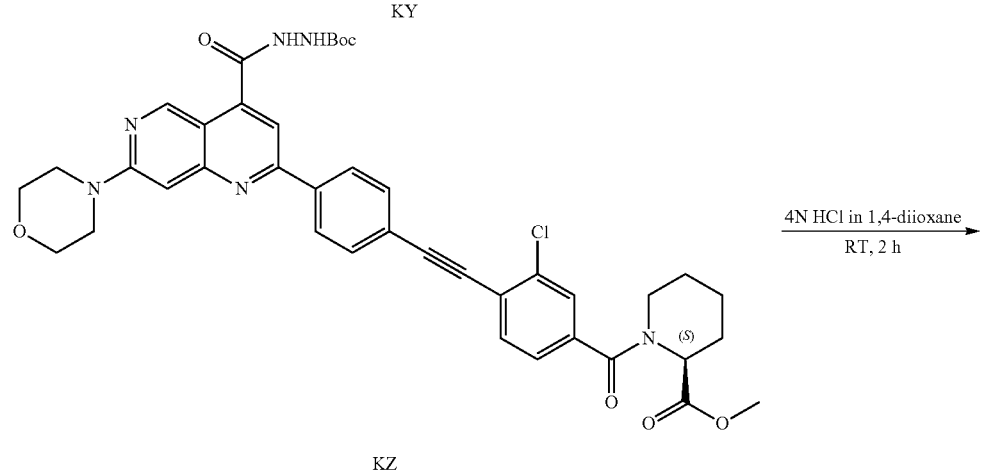
KZ

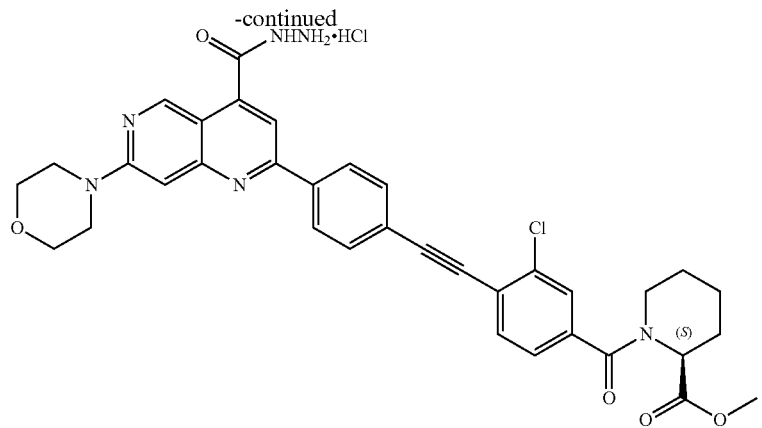

313

Example 313

(S)-1-(3-chloro-4-((4-(4-(hydrazinecarbonyl)-7-morpholino-1,6-naphthyridin-2-yl)phenyl)ethynyl)benzoyl)piperidine-2-carboxylic acid hydrochloride (313)

To a stirred solution of ethyl 2-(6-chloro-4-pivalamidopyridin-3-yl)-2-oxoacetate JQ (1 g, 3.20 mmol) in 2-propanol (15 mL) under nitrogen atmosphere was added morpholine (826 mg, 9.61 mmol). The reaction was heated to 100° C. in a sealed tube and was stirred for 5 h. After complete consumption of the starting material (by TLC), the reaction mixture was concentrated under reduced pressure. The resulting residue was purified by silica gel column chromatography eluting with 20% EtOAc/hexanes to afford compound KV (800 mg, 69%) as a yellow solid. $^1$H-NMR (500 MHz, DMSO-$d_6$): δ 11.46 (s, 1H), 8.49-8.44 (m, 1H), 7.99 (s, 1H), 4.40 (q, 2H), 3.8 (br s, 8H), 1.5 (t, 3H), 1.26 (s, 9H). MS (ESI): m/z 364.4 [M+1]$^+$ To a stirred solution of compound KV (800 mg, 2.20 mmol) in EtOH:H$_2$O (10 mL:10 mL) was added potassium hydroxide (495 mg, 8.83 mmol) at 0° C. The reaction was heated to 90° C. and was stirred for 2 h. The reaction was then cooled to 0° C. at which point JN (477 mg, 3.31 mmol) was added. The reaction was heated to 90° C. for 12 h. After complete consumption of the starting material (by TLC), the reaction mixture was concentrated under reduced pressure. The crude material was diluted with water (1 mL) and the pH was adjusted to pH~3 using an acetic acid solution (0.2 mL). The precipitate was filtered and dried under reduced pressure to afford compound KW (600 mg, 75%) as a yellow solid. $^1$H-NMR (500 MHz, DMSO-$d_6$): δ 9.67 (s, 1H), 8.29 (d, J=8.5 Hz, 1H), 8.17 (d, J=10.0 Hz, 2H), 7.67 (d, J=8.5 Hz, 1H), 7.41-7.38 (m, 2H), 7.15 (s, 1H), 5.86 (s, 1H), 4.39 (s, 1H), 3.76-3.75 (m, 2H), 3.66-3.62 (m, 2H), 3.50-3.48 (m, 2H), 3.33-3.30 (m, 1H). MS (ESI): m/z 360.4 [M+1]$^+$ To a stirred solution of compound KW (200 mg, 0.55 mmol) in DMF (10 mL) under nitrogen atmosphere were added tert-butyl hydrazine carboxylate (220 mg, 1.67 mmol), EDCI.HCl (213 mg, 1.11 mmol), HOBt (151 mg, 1.11 mmol), and DIPEA (215 mg, 1.67 mmol) at 0° C. The reaction was allowed to warm to RT and was stirred for 18 h. After complete consumption of the starting material (by TLC), the reaction mixture was diluted with water (25 mL) and extracted with EtOAc (2×30 mL). The combined organic extracts were dried over sodium sulfate, filtered, concentrated under reduced pressure, and the resulting residue was purified by silica gel column chromatography eluting with 30% EtOAc/hexanes to afford compound KX (60 mg, 23%) as a yellow solid. $^1$H-NMR (400 MHz, DMSO-$d_6$): δ 10.52 (s, 1H), 9.37 (s, 1H), 9.22 (s, 1H), 8.29 (d, J=8.0 Hz, 2H), 7.85 (s, 1H), 7.68 (d, J=8.4 Hz, 2H), 7.13 (s, 1H), 4.40 (s, 1H), 3.76 (t, J=4.8 Hz, 4H), 3.63 (t, J=4.8 Hz, 4H), 1.47 (s, 9H). MS (ESI): m/z 474.3 [M+1]$^+$ To a stirred solution of compound KX (100 mg, 0.21 mmol) in CH$_3$CN (15 mL) under nitrogen atmosphere were added IZ (94 mg, 0.23 mmol) and TEA (0.3 mL, 2.11 mmol) at RT. After the reaction was purged under argon for 10 min, copper iodide (4 mg, 0.02 mmol) and Pd(PPh$_3$)$_2$Cl$_2$ (15 mg, 0.02 mmol) were added. The reaction was then heated to 90° C. and stirred for 2 h. After complete consumption of the starting material (by TLC), the reaction mixture was concentrated under reduced pressure. The crude material was purified by silica gel column chromatography eluting with 50% EtOAc/hexanes to afford compound KY (54 mg, 34%) as a yellow solid. $^1$H-NMR (400 MHz, DMSO-$d_6$): δ 10.54 (s, 1H), 9.38 (s, 1H), 9.23 (s, 1H), 8.38 (d, J=7.6 Hz, 2H), 7.88 (s, 2H), 7.80 (d, J=7.6 Hz, 2H), 7.60 (s, 1H), 7.15-7.13 (m, 1H), 5.26 (br s, 1H), 4.43 (br s, 1H), 3.78-3.71 (m, 7H), 3.67-3.63 (m, 4H), 3.50-3.48 (m, 1H), 3.20-3.17 (m, 1H), 1.80-1.72 (m, 3H), 1.60-1.54 (m, 2H), 1.46 (s, 9H). MS (ESI): m/z 754.1 [M+1]$^+$ To a stirred solution of compound KY (50 mg, 0.06 mmol) in MeOH:THF:H$_2$O (2:2:1, 5 mL) was added lithium hydroxide monohydrate (5.5 mg, 0.13 mmol) at 0° C. The reaction was allowed to warm to RT and was stirred for 3 h. After complete consumption of the starting material (by TLC), the volatiles were evaporated under reduced pressure. The crude material was diluted with water and the pH was adjusted to pH~3 using an acetic acid solution (0.2 mL). The precipitate was filtered and dried under reduced pressure to afford compound KZ (28 mg, 57%) as a yellow solid. $^1$H-NMR (400 MHz, DMSO-$d_6$): δ 10.55 (br s, 1H), 9.37 (s, 1H), 9.22 (s, 1H), 8.37 (d, J=7.6 Hz, 2H), 7.89 (s, 1H), 7.79 (d, J=7.6 Hz, 2H), 7.71 (d, J=8.0 Hz, 1H), 7.62 (s, 1H), 7.56-7.55 (m, 1H), 7.41 (d, J=8.0 Hz, 1H), 7.16-7.13 (m, 1H), 4.93 (br s, 1H), 4.31-4.29 (m, 1H), 3.78-3.76 (m, 4H), 3.64-3.62 (m, 4H), 2.91-2.89 (m, 1H), 2.20-2.17 (m, 1H), 1.61-1.58 (m, 2H), 1.50 (s, 9H), 1.40-1.34 (m, 3H). MS (ESI): m/z 740.5 [M+1]$^+$ To a stirred solution of compound KZ (28 mg, 0.03 mmol) in DCM (3 mL) under nitrogen atmosphere was added 4N HCl in 1,4-dioxane (0.5 mL) at 0° C. The reaction was allowed to warm to RT and was stirred for 2 h. After complete consumption of the starting material (by TLC), the volatiles were evaporated under reduced pressure. The crude residue was triturated with 10% MeOH:CH$_3$CN (2 mL) to afford 313 (11 mg as an HCl salt) as a yellow solid. $^1$H-NMR (400 MHz, CD$_3$OD-d$_4$): δ 8.66 (s, 1H), 8.59 (s, 1H), 8.25 (d, J=8.4 Hz, 2H), 7.81-7.71 (m, 4H), 7.65-7.59 (m, 1H), 7.41-7.37 (m, 1H), 5.35-5.34 (m, 1H), 4.55-4.40 (m, 1H), 3.91-3.85 (m, 4H), 3.74-3.72 (m, 1H), 3.60 (s, 3H), 3.59-3.58 (m, 1H), 2.95-2.92 (m, 1H), 2.40-2.27 (m, 1H), 1.79 (d, J=12.0 Hz, 2H), 1.67-1.64 (m, 2H), 1.54-1.43 (m, 2H). MS (ESI): 86.62%, m/z 639.7 [M+1]$^+$ Scheme 77

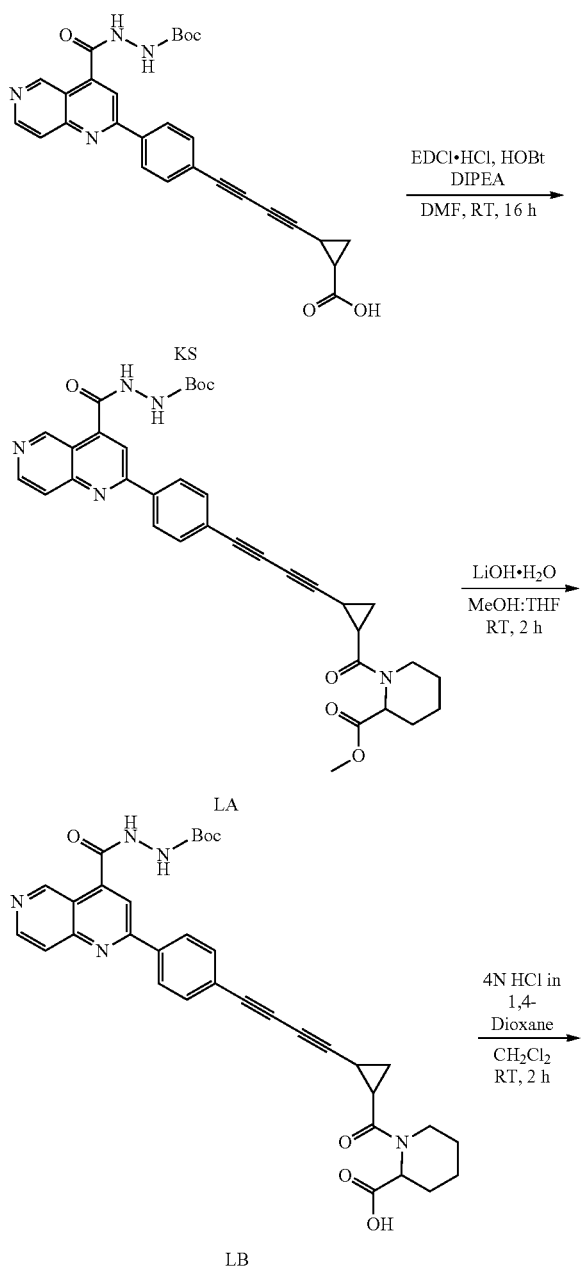

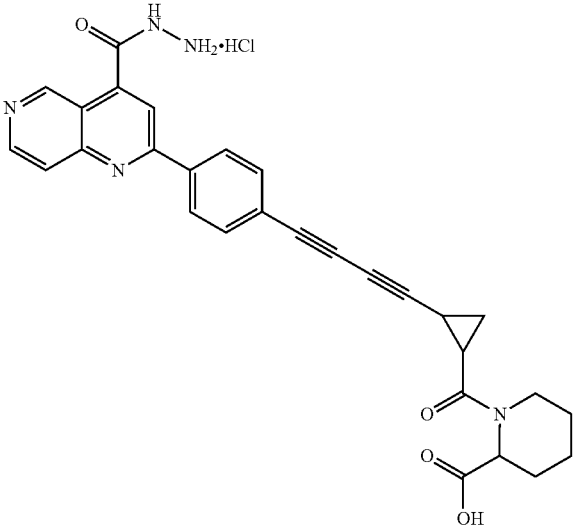

314

Example 314

1-(2-((4-(4-(hydrazinecarbonyl)-1,6-naphthyridin-2-yl)phenyl)buta-1,3-diyn-1-yl)cyclopropane-1-carbonyl)piperidine-2-carboxylic acid hydrochloride (314)

To a stirred solution of compound KS (25 mg, 0.05 mmol) in DMF (2 mL) under nitrogen atmosphere were added DIPEA (0.04 mL, 0.25 mmol), EDCI.HCl (14.3 mg, 0.075 mmol), HOBt (10 mg, 0.075 mmol) and methyl piperidine-2-carboxylate hydrochloride (9.81 mg, 0.055 mmol) at 0° C. The reaction was allowed to warm to RT and was stirred for 16 h. After complete consumption of the starting material (by TLC), the reaction mixture was diluted with ice cold water (5 mL) and was extracted with EtOAc (2×10 mL). The combined organic extracts were washed with water (10 mL), dried over sodium sulfate, filtered and concentrated under reduced pressure to obtain compound LA (30 mg) as a yellow solid. MS (ESI): m/z 622.6 [M+1]$^+$ To a stirred solution of compound LA (30 mg, 0.048 mmol) in THF/MeOH/H$_2$O (1 mL:1 mL:0.5 mL) was added lithium hydroxide monohydrate (6 mg, 0.14 mmol) at 0° C. The reaction was allowed to warm to RT and was stirred for 2 h. After complete consumption of the starting material (by TLC), the volatiles were evaporated under reduced pressure. The residue was diluted with water (2 mL) and acidified with acetic acid to pH~4 The obtained solid was filtered and triturated with CH$_3$CN (3 mL) to obtain compound LB (10 mg, 34%) as a yellow solid. MS (ESI): m/z 608.6 [M+1]$^+$ To a stirred solution of compound LB (10 mg, 0.016 mmol) in DCM (0.5 mL) under nitrogen atmosphere was added 4N HCl in 1,4-dioxane (0.1 mL) at 0° C. The reaction was allowed to warm to RT and was stirred for 1 h. After complete consumption of the starting material (by TLC), the volatiles were evaporated under reduced pressure to afford 314 (6 mg as an HCl salt) as a yellow solid. $^1$H NMR (400 MHz, DMSO-d$_6$): δ 11.66 (s, 1H), 9.68 (s, 1H), 8.85 (d, J=5.6 Hz, 1H), 8.48 (s, 1H), 8.42 (d, J=8.4 Hz, 2H), 8.08 (d, J=6.0 Hz, 1H), 7.78 (d, J=8.4 Hz, 2H), 7.40 (s, 1H), 7.10 (s, 1H), 5.03 (d, J=4.8 Hz, 2H), 4.28-4.19 (m, 1H), 3.27-3.21 (m, 1H), 2.24-2.01 (m, 1H), 1.91-1.86 (m, 1H), 1.84-1.79 (m, 2H), 1.69-1.53 (m, 4H), 1.48-1.23 (m, 2H). MS (ESI): m/z 508.9 [M+1]$^+$ Scheme 78
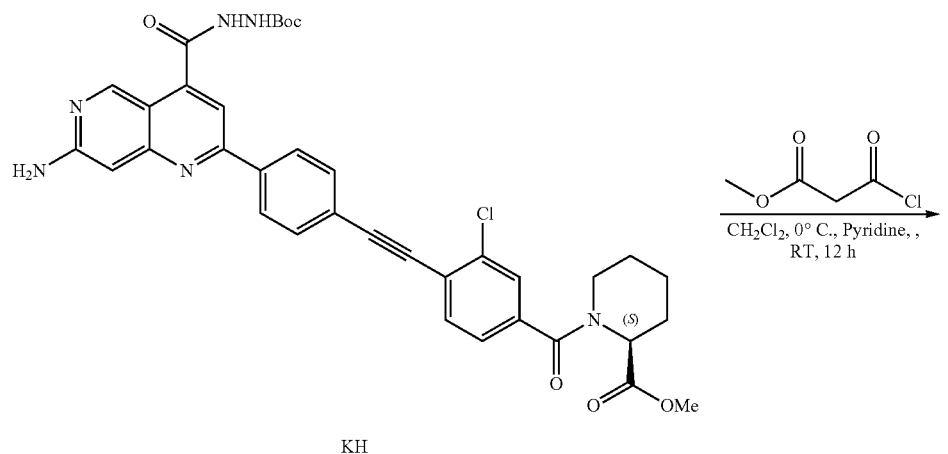
KH
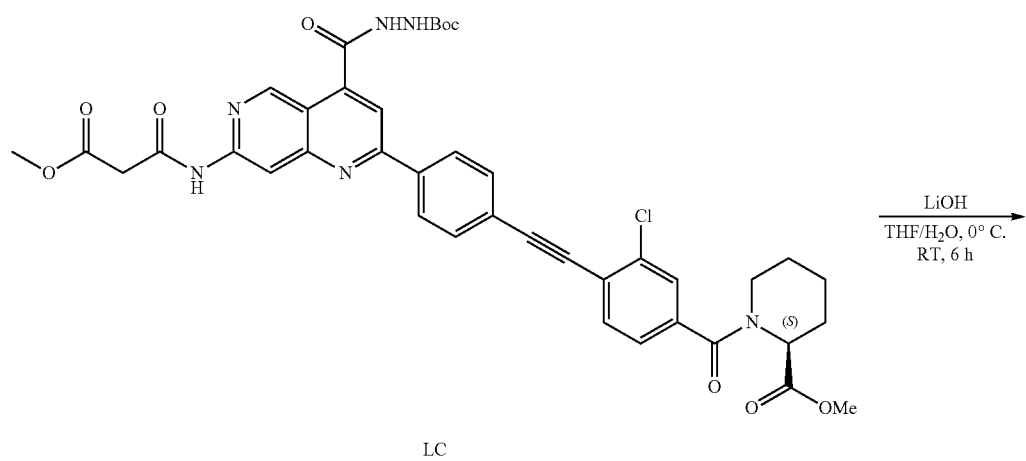
LC
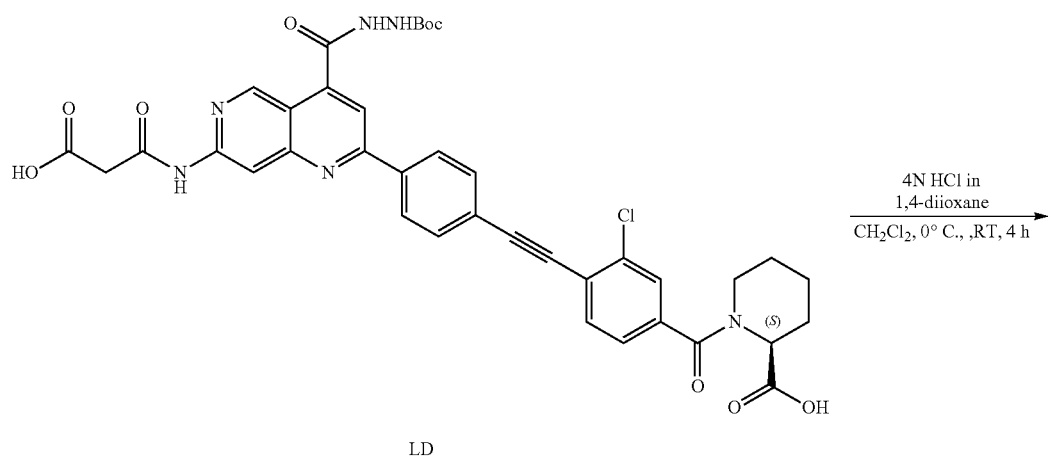
LD

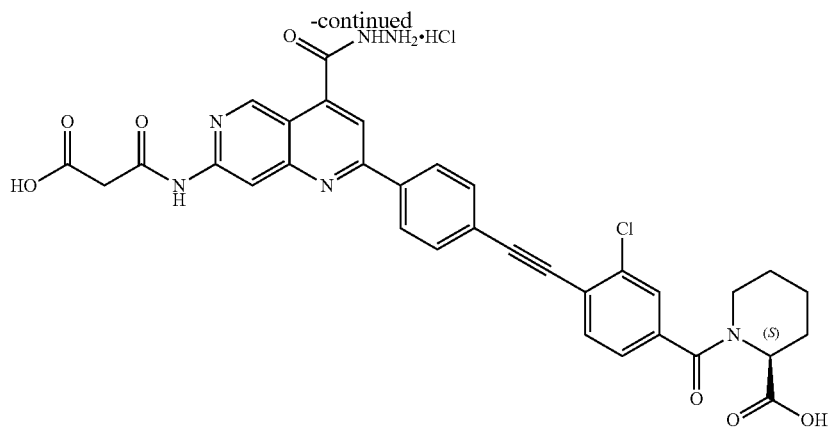

315

Example 315

(S)-1-(4-((4-(7-(2-carboxyacetamido)-4-(hydrazinecarbonyl)-1,6-naphthyridin-2-yl)phenyl)ethynyl)-3-chlorobenzoyl)piperidine-2-carboxylic acid hydrochloride (315)

To a stirred solution of compound KH (90 mg, 0.13 mmol) in DCM (5 mL) under nitrogen atmosphere were added pyridine (0.03 mL, 0.39 mmol) and methyl 3-chloro-3-oxopropanoate (0.02 mL, 0.14 mmol) at 0° C. The reaction was allowed to warm to RT and was stirred for 4 h. After complete consumption of the starting material (by TLC), the reaction mixture was diluted with ice cold water (5 mL) and the compound was extracted with DCM (2×5 mL). The combined organic extracts were washed with water (2×5 mL), dried over sodium sulfate, filtered and concentrated under reduced pressure. The crude material was purified by preparative HPLC to afford compound LC (50 mg, 20%) as a pale yellow solid. $^1$H NMR (400 MHz, CDCl$_3$): δ 9.74 (br s, 1H), 9.42 (s, 1H), 8.72 (s, 1H), 8.39 (br s, 1H), 8.22 (d, J=8.4 Hz, 2H), 7.99 (s, 1H), 7.72 (d, J=8.4 Hz, 2H), 7.62 (d, J=8.0 Hz, 1H), 7.53-7.52 (m, 1H), 7.32 (d, J=7.2 Hz, 1H), 6.94 (br s, 1H), 5.47 (br s, 1H), 4.63-4.42 (m, 1H), 3.83 (s, 6H), 3.63-3.59 (m, 3H), 3.28 (t, J=11.2 Hz, 1H), 2.36 (d, J=12.8 Hz, 1H), 1.78-1.72 (m, 2H), 1.60 (s, 9H), 1.43-1.37 (m, 2H). MS (ESI): m/z 783.24 [M+1]$^+$ To a stirred solution of compound LC (15 mg, 0.019 mmol) in THF:H$_2$O (4 mL:1 mL) were added lithium hydroxide monohydrate (2.4 mg, 0.05 mmol) at 0° C. The reaction was allowed to warm to RT and was stirred for 2 h. After complete consumption of the starting material (by TLC), the volatiles were evaporated under reduced pressure. The crude material was diluted with water and the pH was adjusted to pH~3 by using an acetic acid solution (0.02 mL). The precipitate was filtered and dried under reduced pressure to afford compound LD (10 mg, 71%) as a yellow solid. $^1$H NMR (400 MHz, DMSO-d$_6$): δ 13.01 (s, 1H), 11.67 (s, 1H), 10.66 (s, 1H), 9.51 (s, 1H), 9.27 (s, 1H), 9.18 (s, 1H), 8.67 (s, 1H), 8.45 (d, J=7.2 Hz, 2H), 8.16 (s, 1H), 7.99-7.81 (m, 3H), 7.73-7.58 (m, 1H), 7.25-7.16 (m, 1H), 6.51-6.42 (m, 1H), 5.16 (s, 1H), 4.39-4.22 (m, 2H), 3.42-3.39 (m, 2H), 2.23-2.18 (m, 1H), 2.08 (d, J=9.6 Hz, 3H), 1.48 (s, 9H), 1.21-1.10 (m, 1H). MS (ESI): m/z 755.18 [M+1]$^+$ To a stirred solution of compound LD (10 mg, 0.013 mmol) in DCM (1 mL) under nitrogen atmosphere was added 4N HCl in 1,4-dioxane (0.2 mL) at 0° C. The reaction was allowed to warm to RT and was stirred for 4 h. After complete consumption of the starting material (by TLC), the volatiles were evaporated under reduced pressure. The crude material was triturated with 10% IPA:CH$_3$CN (2 mL) to afford 315 (8 mg as an HCl salt) as a yellow solid. $^1$H NMR (400 MHz, CD$_3$OD): δ 9.48 (s, 1H), 8.79 (s, 1H), 8.67-8.61 (m, 2H), 8.37 (d, J=8.4 Hz, 1H), 7.81-7.73 (m, 2H), 7.59-7.55 (m, 2H), 7.42-7.38 (m, 4H), 5.36 (d, J=6.0 Hz, 1H), 4.41 (s, 2H), 3.66-3.52 (m, 3H), 2.95-2.90 (m, 1H), 2.40-2.23 (m, 1H), 1.81-1.65 (m, 4H), 1.55-1.43 (m, 3H). MS (ESI): m/z 692.52 [M+1]$^+$. UPLC Purity: 90.68%

Scheme 79

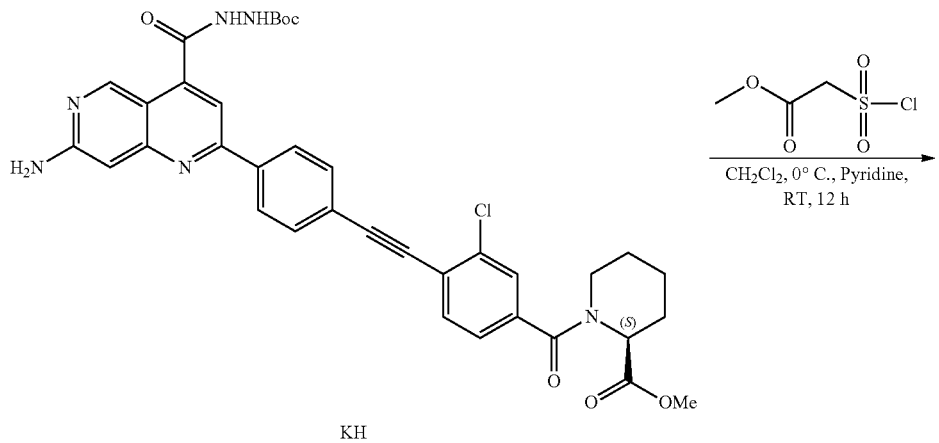

KH

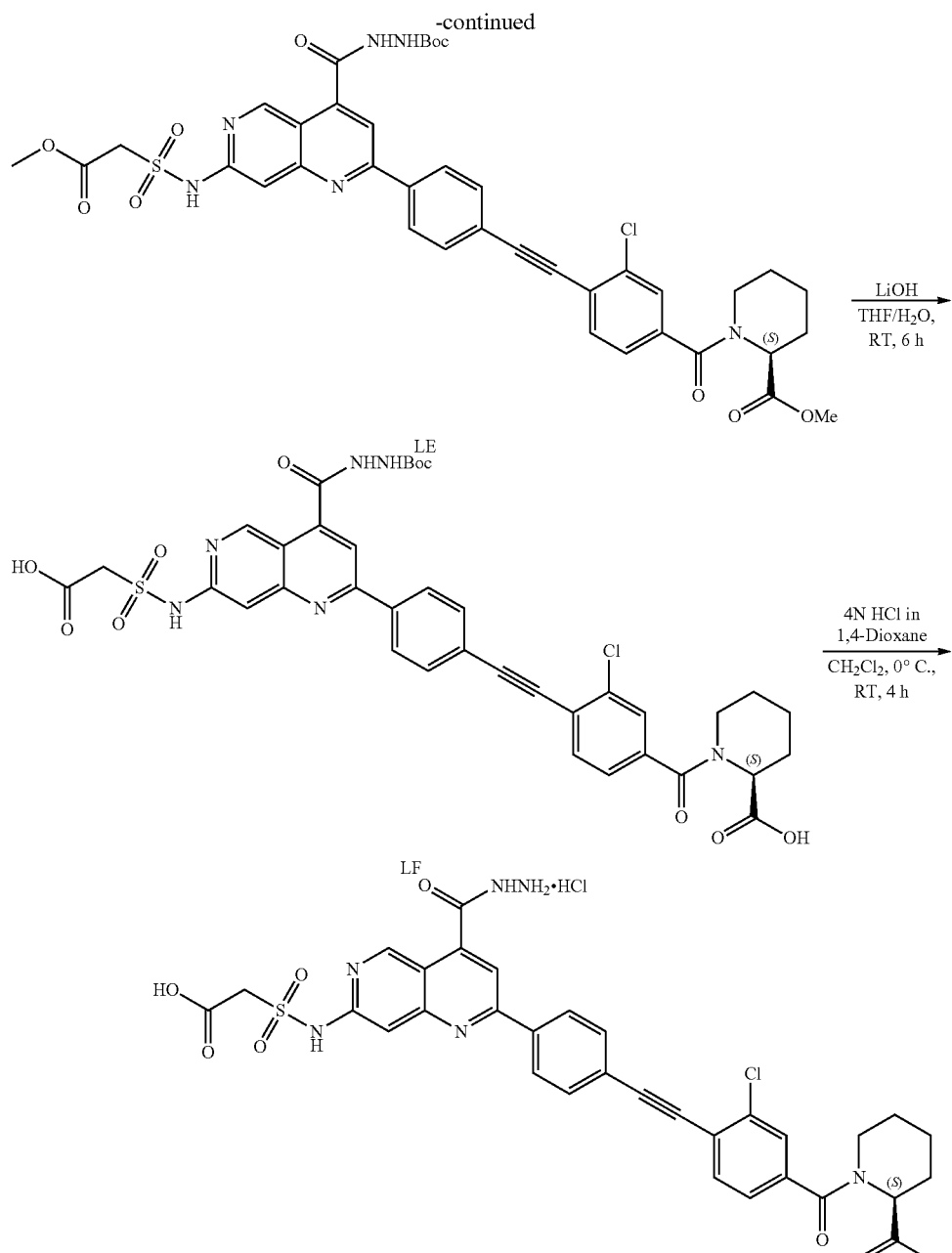

316

Example 316

(S)-1-(4-((4-(7-((carboxymethyl) sulfonamido)-4-(hydrazinecarbonyl)-1,6-naphthyridin-2-yl)phenyl) ethynyl)-3-chlorobenzoyl)piperidine-2-carboxylic acid hydrochloride (316)

To a stirred solution of compound KH (50 mg, 0.073 mmol) in DCM (5 mL) under nitrogen atmosphere were added pyridine (0.03 mL, 0.36 mmol) and methyl 2-(chlorosulfonyl)acetate (31 mg, 0.18 mmol) at 0° C. The reaction was allowed to warm to RT and was stirred for 6 h. After complete consumption of the starting material (by TLC), the volatiles were concentrated under reduced pressure. The crude material was purified by silica gel column chromatography eluting with 3% MeOH:DCM to afford compound LE (33 mg, 55%) as a yellow solid. $^1$H NMR (400 MHz, DMSO-$d_6$): δ 11.45 (s, 1H), 10.64 (s, 1H), 9.50 (s, 1H), 9.28 (s, 1H), 8.45 (d, J=8.0 Hz, 2H), 8.16 (s, 1H), 7.82-7.62 (m, 3H), 7.60-7.35 (m, 5H), 5.26 (s, 1H), 4.72 (s, 2H), 4.45-4.39 (m, 1H), 3.74 (s, 3H), 3.65 (s, 3H), 3.19-3.12 (m, 1H), 1.72-1.68 (m, 1H), 1.49 (s, 9H), 1.38-1.33 (m, 3H). MS (ESI): m/z 819.28 [M+1]$^+$ To a stirred solution of compound LE (33 mg, 0.04 mmol) in THF:H$_2$O (3 mL:1 mL) was added lithium hydroxide monohydrate (3.4 mg, 0.08 mmol) at 0° C. The reaction was allowed to warm to RT and was stirred for 4 h. After complete consumption of the starting material (by TLC), the volatiles were evaporated under reduced pressure. The residue was diluted with water (3 mL), neutralized with an acetic acid solution (0.03 mL), and the resulting solids were filtered and dried under reduced pressure to afford compound LF (28 mg, 90%) as a yellow solid. $^1$H NMR (400 MHz, DMSO-$d_6$): δ 13.00 (s, 2H), 10.64 (s, 1H), 9.50 (s, 1H), 9.28 (s, 1H), 8.45 (d, J=7.6 Hz, 2H), 8.15 (s, 1H), 7.81 (d, J=6.4 Hz, 3H), 7.64-7.58 (m, 2H), 7.41-7.36 (m, 2H), 5.17 (s, 1H), 4.54 (s, 2H), 4.35-4.28 (m, 1H), 3.78-3.60 (m, 1H), 2.80-2.78 (m, 1H), 2.22-2.16 (m, 1H), 2.08-1.97 (m, 1H), 1.71-1.69 (m, 3H), 1.49 (s, 9H). MS (ESI): m/z 791.23 [M+1]$^+$ To a stirred solution of compound LF (25 mg, 0.031 mmol) in DCM (3 mL) under nitrogen atmosphere was added 4N HCl in 1,4-dioxane (0.3 mL) at 0° C. The reaction was allowed to warm to RT and was stirred for 4 h. After complete consumption of the starting material (by TLC), the volatiles were evaporated under reduced pressure. The crude material was triturated with 30% MeOH:ACN (2 mL) to afford 316 (19 mg as an HCl salt) as a yellow solid. $^1$H NMR (400 MHz, DMSO-$d_6$): δ 11.31 (br s, 2H), 9.46 (s, 1H), 8.45 (d, J=8.4 Hz, 2H), 8.26 (s, 1H), 7.83 (d, J=8.0 Hz, 3H), 7.58-7.55 (m, 2H), 7.41 (d, J=7.2 Hz, 1H), 5.17 (br s, 1H), 4.61 (s, 2H), 4.39-4.31 (m, 1H), 3.21-3.19 (m, 1H), 2.79-2.76 (m, 1H), 2.22-2.19 (m, 1H), 1.71-1.69 (m, 3H), 1.35-1.30 (m, 1H). MS (ESI): m/z 691.5 [M+1]$^+$. UPLC Purity: 82.47%

Scheme 80

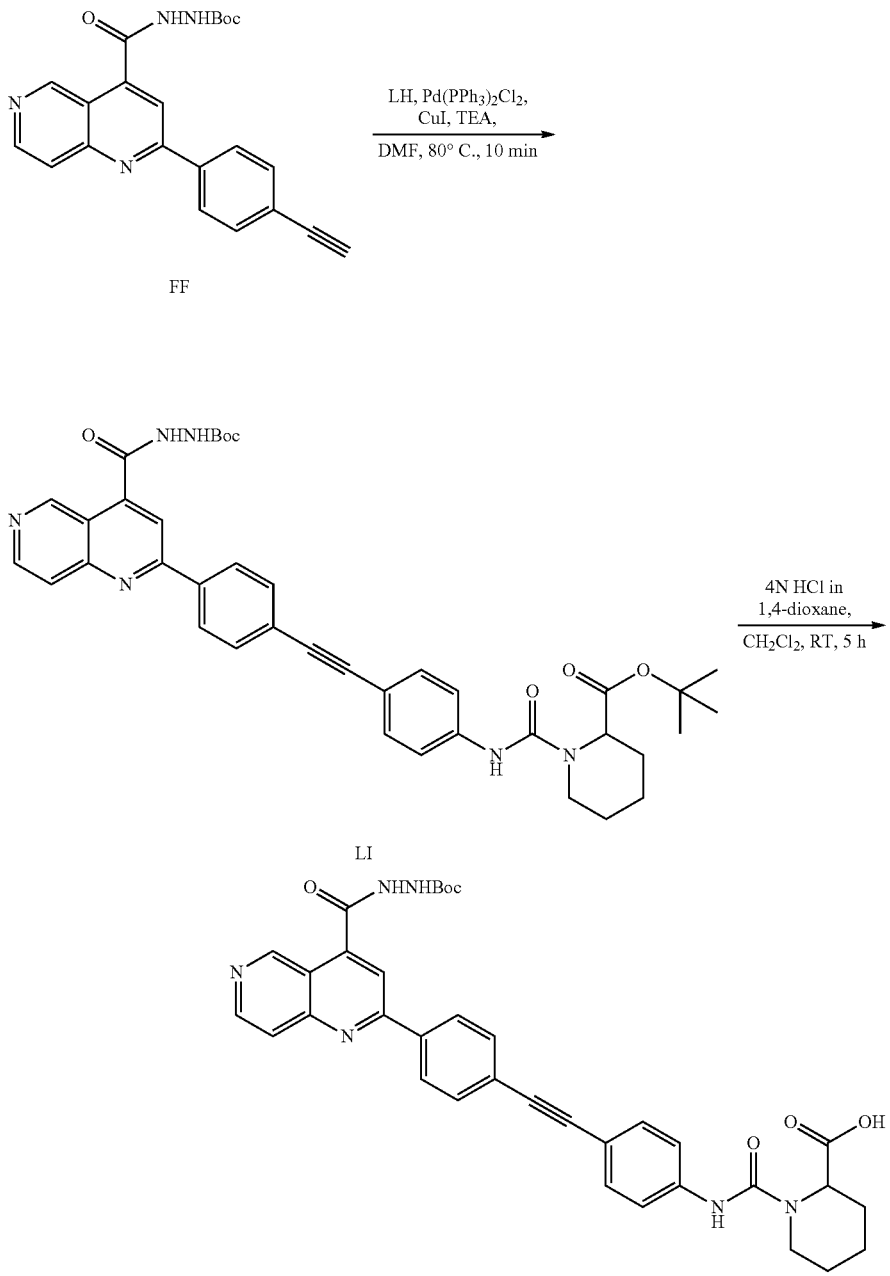

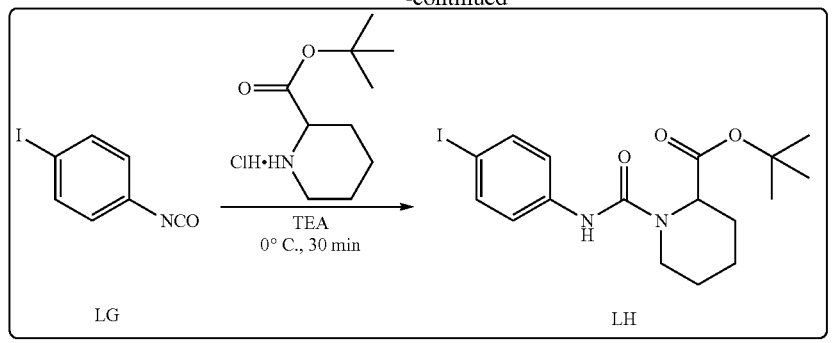

Example 317

1-((4-((4-(4-(hydrazinecarbonyl)-1,6-naphthyridin-2-yl)phenyl)ethynyl)phenyl) carbamoyl)piperidine-2-carboxylic acid hydrochloride (317)

To a stirred solution of tert-butyl piperidine-2-carboxylate hydrochloride (500 mg, 2.25 mmol) in DCM (20 mL) under nitrogen atmosphere were added TEA (0.31 mL, 2.25 mmol) and 1-iodo-4-isocyanatobenzene (LG; 551 mg, 2.25 mmol) at 0° C. After the reaction mixture was stirred for 30 min, the reaction mixture was washed with water (15 mL), dried over sodium sulfate, filtered and concentrated under reduced pressure. The crude material was purified by silica gel column chromatography eluting with 3% MeOH/DCM to afford compound LH (550 mg, 57%) as an off-white solid. $^1$H NMR (500 MHz, CDCl$_3$): δ 7.45 (d, J=8.0 Hz, 2H), 7.14 (d, J=8.5 Hz, 2H), 6.55 (s, 1H), 4.91 (d, J=4.5 Hz, 1H), 3.72 (d, J=12.0 Hz, 1H), 3.25-3.19 (m, 1H), 2.23 (d, J=14.0 Hz, 1H), 1.73-1.67 (m, 3H), 1.54-1.50 (m, 1H), 1.46 (s, 9H), 1.39-1.33 (m, 1H).

To a stirred solution of FF (100 mg, 0.25 mmol) in DMF (3 mL) under nitrogen atmosphere were added compound LH (107 mg, 0.25 mmol), TEA (0.35 mL, 2.57 mmol), copper iodide (7.3 mg, 0.025 mmol) and Pd(PPh$_3$)$_2$Cl$_2$ (27.1 mg, 0.025 mmol). The reaction mixture was heated in a microwave at 80° C. and stirred for 10 min. After complete consumption of the starting material (by TLC), the reaction mixture was diluted with ice cold water (20 mL) and the compound was extracted with EtOAc (2×20 mL). The combined organic extracts were washed with water (2×20 mL), dried over sodium sulfate, filtered and concentrated under reduced pressure. The crude was purified by silica gel column chromatography eluting with 3-5% MeOH/DCM and further purified by preparative HPLC to afford compound LI (18 mg, 10%) as a yellow solid. $^1$H NMR (400 MHz, DMSO-d$_6$): δ 10.65 (s, 1H), 9.70 (s, 1H), 9.30 (s, 1H), 8.83 (d, J=6.0 Hz, 1H), 8.77 (s, 1H), 8.41 (d, J=8.0 Hz, 2H), 8.32 (s, 1H), 8.04 (d, J=5.6 Hz, 1H), 7.75 (d, J=8.4 Hz, 2H), 7.56 (d, J=8.8 Hz, 2H), 7.48 (d, J=8.8 Hz, 2H), 4.83 (d, J=3.6 Hz, 1H), 3.97 (d, J=12.4 Hz, 1H), 3.03-2.97 (m, 1H), 2.12 (d, J=13.2 Hz, 1H), 1.67-1.59 (m, 4H), 1.49 (s, 9H), 1.41 (s, 9H), 1.28-1.15 (m, 1H)

To a stirred solution of compound LI (18 mg, 0.026 mmol) in DCM (1 mL) under nitrogen atmosphere was added 4N HCl in 1,4-dioxane (0.2 mL) at 0° C. The reaction was allowed to warm to RT and was stirred for 5 h. After complete consumption of the starting material (by TLC), the volatiles were evaporated under reduced pressure. The crude material was triturated with CH$_3$CN (3 mL) to afford 317 (12 mg as an HCl salt) as a yellow solid. $^1$H NMR (400 MHz, DMSO-d$_6$): δ 12.00 (s, 1H), 9.74 (s, 1H), 8.89 (d, J=6.0 Hz, 1H), 8.60 (s, 1H), 8.50 (d, J=8.8 Hz, 2H), 8.19 (d, J=6.0 Hz, 1H), 7.84 (d, J=8.4 Hz, 2H), 7.73-7.71 (m, 2H), 7.52-7.49 (m, 2H), 4.16-4.12 (m, 1H), 4.04-3.99 (m, 1H), 2.95-2.87 (m, 1H), 2.06 (t, J=4.4 Hz, 1H), 1.91 (t, J=2.8 Hz, 1H), 1.71 (d, J=12.4 Hz, 1H), 1.56-1.48 (m, 2H), 1.47-1.34 (m, 1H). HPLC Purity: 88.01%

Scheme 81

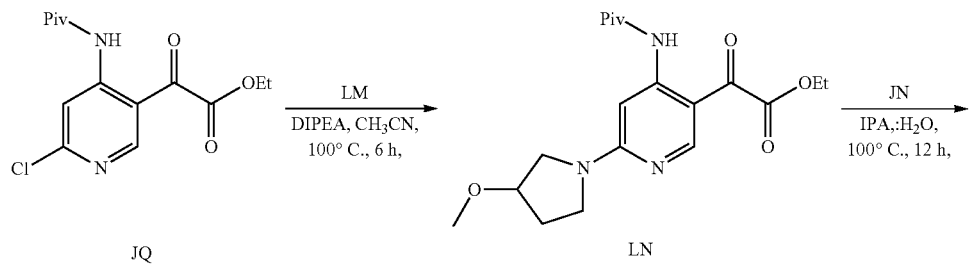

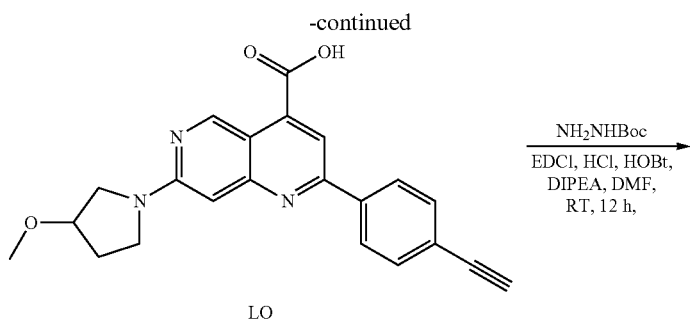
LO
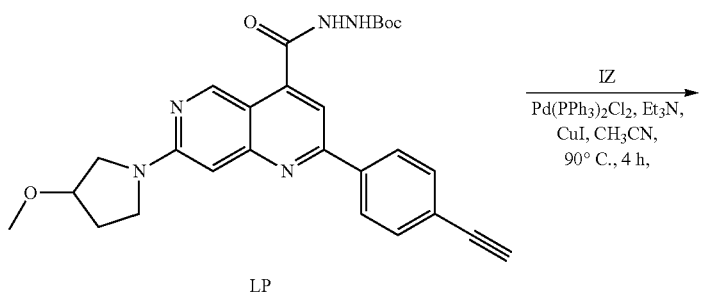
LP
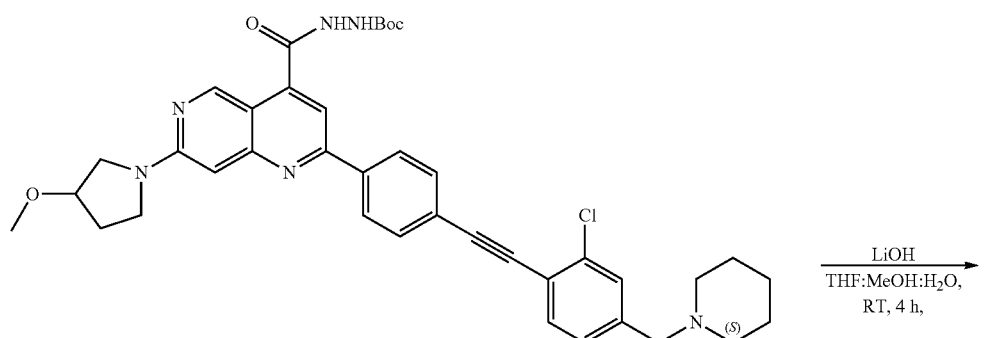
LQ
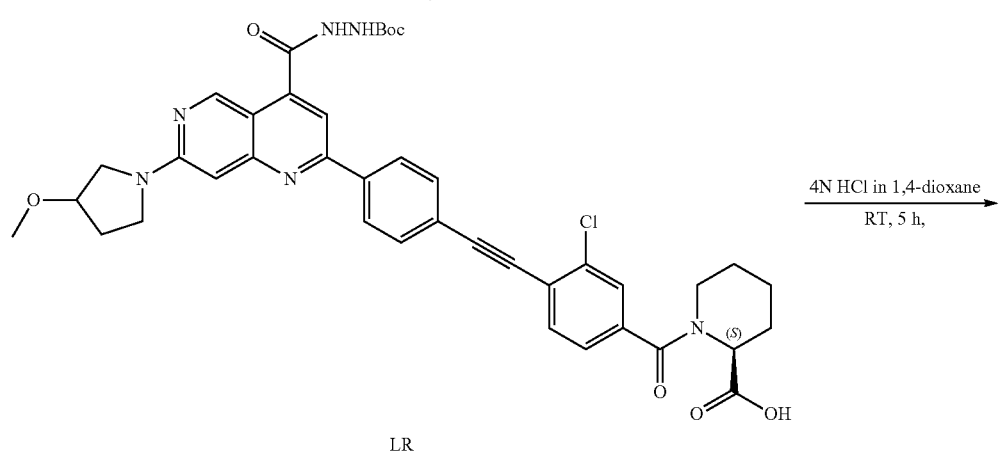
LR

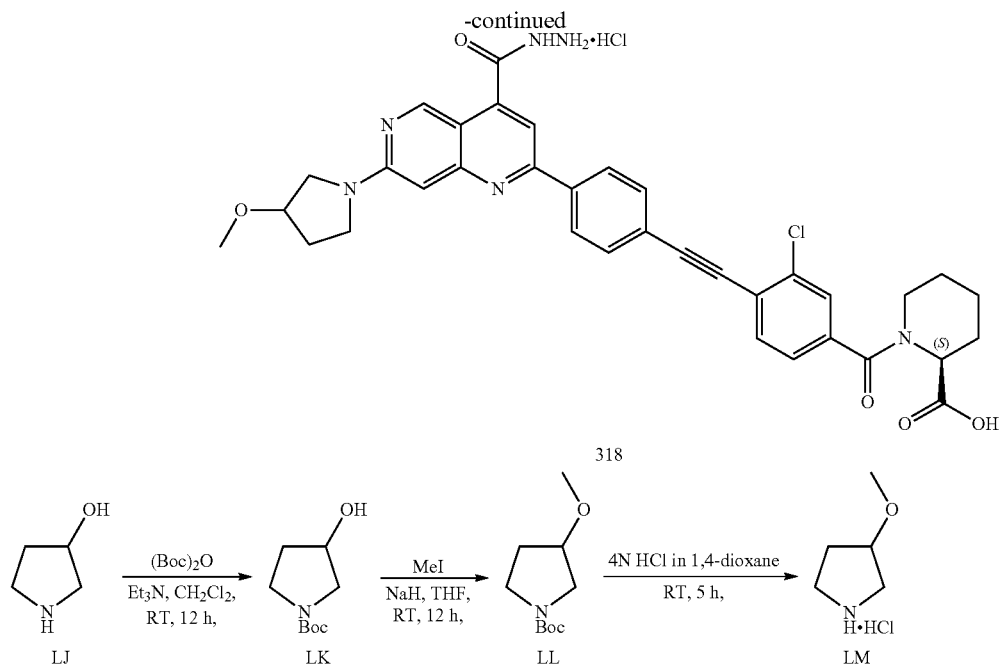

Example 318

(2S)-1-(3-chloro-4-((4-(4-(hydrazinecarbonyl)-7-(3-methoxypyrrolidin-1-yl)-1,6-naphthyridin-2-yl)phenyl)ethynyl)benzoyl)piperidine-2-carboxylic acid hydrochloride (318)

To a stirred solution of pyrrolidin-3-ol (LJ; 1 g, 11.47 mmol) in DCM (20 mL) under nitrogen atmosphere were added TEA (3.31 mL, 22.95 mmol) and Boc anhydride (1.48 g, 12.62 mmol) at 0° C. The reaction was allowed to warm to RT and was stirred for 12 h. After complete consumption of the starting material (by TLC), the reaction was diluted with water (100 mL) and was extracted with 10% MeOH/DCM (2×100 mL). The combined organic extracts were washed with brine (50 mL), dried over sodium sulfate, filtered and concentrated under reduced pressure. The crude material was purified by silica gel column chromatography eluting with 5% MeOH/DCM to afford compound LK (1.2 g, 56%) as a yellow oil. $^1$H NMR (500 MHz, DMSO-$d_6$): δ 4.89-4.88 (m, 1H), 4.21 (br s, 1H), 3.33 (s, 3H), 3.11-3.09 (m, 1H), 1.84-1.81 (m, 2H), 1.39 (s, 9H).

To a stirred solution of compound LK (350 mg, 1.87 mmol) in THF (10 mL) under nitrogen atmosphere was added sodium hydride (54 mg, 2.24 mmol) at 0° C. The mixture was stirred for 15 minutes, then methyl iodide (0.13 mL, 2.24 mmol) was added and the reaction was stirred at RT for 12 h. After complete consumption of the starting material (by TLC), the reaction was quenched with ice cold water (10 mL) and the compound was extracted with DCM (2×10 mL). The combined organic extracts were dried over sodium sulfate, filtered and concentrated under reduced pressure. The crude material was purified by silica gel column chromatography eluting with 5% MeOH/DCM to afford compound LL (300 mg, 80%) as a colorless liquid. $^1$H NMR (400 MHz, DMSO-$d_6$): δ 3.98 (br s, 1H), 3.31 (s, 3H), 3.29-3.25 (m, 1H), 3.22 (s, 3H), 1.89-1.88 (m, 2H), 1.39 (s, 9H).

To a stirred solution of compound LL (300 mg, 1.49 mmol) in DCM (10 mL) under nitrogen atmosphere was added 4N HCl in 1,4-dioxane (1.5 mL) at 0° C. The reaction was allowed to warm to RT and was stirred for 5 h. After complete consumption of the starting material (by TLC), the volatiles were evaporated under reduced pressure. The crude material was triturated with ether (2 mL) to afford compound LM (110 mg as an HCl salt) as an off-white solid. $^1$H NMR (500 MHz, DMSO-$d_6$): δ 9.61 (br s, 1H), 9.29 (br s, 1H), 4.07-4.05 (m, 1H), 3.34 (s, 3H), 3.23-3.05 (m, 3H), 2.04-2.00 (m, 1H), 1.92-1.85 (m, 1H).

To a stirred solution of compound JQ (500 mg, 1.60 mmol) in CH$_3$CN (10 mL) under nitrogen atmosphere were added DIPEA (1.77 mL, 9.61 mmol) and compound LM (329 mg, 2.40 mmol). The reaction mixture was stirred at 100° C. for 6 h in a sealed tube. After complete consumption of the starting material (by TLC), the reaction was diluted with water (20 mL) and the compound was extracted with EtOAc (2×20 mL). The combined organic extracts were dried over sodium sulfate, filtered and concentrated under reduced pressure. The crude material was purified by silica gel column chromatography eluting with 20% EtOAc/hexanes to afford compound LN (500 mg, 83%) as a colorless liquid. $^1$H-NMR (DMSO-$d_6$, 500 MHz): δ 11.52 (s, 1H), 8.45 (s, 1H), 7.69 (s, 1H), 4.42-4.37 (m, 2H), 3.81-3.79 (m, 1H), 3.80-3.61 (m, 3H), 3.31 (s, 3H), 3.28-3.29 (m, 1H), 2.08-2.06 (m, 2H), 1.32 (t, J=7.5 Hz, 3H), 1.26 (s, 9H).

To a stirred solution of compound LN (500 mg, 1.32 mmol) in IPA:H$_2$O (10 mL:10 mL) was added sodium hydroxide (530 mg, 13.26 mmol) at 0° C. The reaction mixture was heated to 100° C. for 2 h. The reaction was cooled to 0° C., JN (530 mg, 13.26 mmol) was added, and then the reaction was heated to 100° C. for 12 h. After complete consumption of the starting material (by TLC), the volatiles were evaporated under reduced pressure. The crude material was diluted with water and the pH was adjusted to pH~3 by using an acetic acid solution (0.2 mL). The precipitate was filtered, washed with ether (2 mL) and dried under reduced pressure to afford compound LO (350 mg, 71%) as a yellow solid. ¹H-NMR (DMSO-d₆, 400 MHz): δ 9.70 (s, 1H), 8.20 (d, J=8.0 Hz, 2H), 7.72 (s, 1H), 7.62 (d, J=8.4 Hz, 2H), 6.61 (s, 1H), 4.47 (s, 1H), 3.60-3.46 (m, 7H), 1.66 (s, 3H).

To a stirred solution of compound LO (350 mg, 0.93 mmol) in DMF (10 mL) under nitrogen atmosphere were added EDCI.HCl (360 mg, 1.87 mmol), HOBt (255 mg, 1.87 mmol) and DIPEA (0.52 mL, 2.81 mmol) at 0° C. The reaction was stirred for 5 min, tert-butyl hydrazinecarboxylate (371 mg, 2.81 mmol) was added, and the reaction was stirred at RT for 12 h. After complete consumption of the starting material (by TLC), the reaction mixture was diluted with water (20 mL) and the compound was extracted with EtOAc (2×20 mL). The combined organic extracts were dried over sodium sulfate, filtered and concentrated under reduced pressure. The crude material was purified by silica gel column chromatography eluting with 30% EtOAc/hexanes to afford compound LP (160 mg, 35%) as a yellow solid. ¹H-NMR (DMSO-d₆, 500 MHz): δ 10.50 (s, 1H), 9.48-9.21 (m, 2H), 8.29 (d, J=8.0 Hz, 2H), 7.72 (s, 1H), 7.67 (d, J=8.0 Hz, 1H), 6.75 (s, 1H), 4.39 (s, 1H), 4.14 (s, 1H), 3.90 (br s, 1H), 3.64-3.62 (m, 3H), 3.50-3.49 (m, 1H), 2.14-2.12 (m, 2H), 1.79 (s, 2H), 1.47 (s, 9H).

To a stirred solution of compound LP (160 mg, 0.32 mmol) in CH₃CN (15 mL) under nitrogen atmosphere were added IZ (147 mg, 0.36 mmol) and TEA (0.47 mL, 3.28 mmol). The solution was purged with argon for 10 min followed by the addition of copper iodide (6.25 mg, 0.03 mmol) and Pd(PPh₃)₂Cl₂ (23 mg, 0.32 mmol). The reaction was heated to 90° C. and stirred for 4 h. After complete consumption of the starting material (by TLC), the volatiles were concentrated under reduced pressure. The crude material was purified by silica gel column chromatography eluting with 4% MeOH/DCM to afford compound LQ (84 mg, 33%) as a yellow solid. ¹H NMR (400 MHz, DMSO-d₆): δ 10.51 (s, 1H), 9.47 (s, 1H), 9.32 (s, 1H), 9.21 (s, 1H), 8.63 (s, 1H), 8.36 (d, 2H), 7.80-7.76 (m, 4H), 6.76 (s, 1H), 5.26-5.24 (m, 1H), 4.41-4.38 (m, 1H), 4.15-4.11 (m, 1H), 3.74-3.72 (m, 5H), 3.69-3.64 (m, 3H), 3.51-3.47 (m, 2H), 3.17-3.13 (m, 1H), 2.17-2.14 (m, 4H), 1.79 (s, 4H), 1.48 (s, 9H).

To a stirred solution of compound LQ (80 mg, 0.10 mmol) in THF:MeOH:H₂O (5 mL:5 mL:5 mL) was added lithium hydroxide monohydrate (13 mg, 0.31 mmol) at 0° C. The reaction was allowed to warm to RT and was stirred for 4 h. After complete consumption of the starting material (by TLC), the volatiles were evaporated under reduced pressure. The crude material was diluted with water and the pH was adjusted to pH~3 by using an acetic acid solution (0.2 mL). The precipitate was filtered, washed with ether (2 mL) and dried under reduced pressure to afford compound LR (64 mg, 82%) as a yellow solid. MS (ESI): m/z 753 [M+1]⁺.

To a stirred solution of compound LR (20 mg, 0.02 mmol) in DCM (3 mL) under nitrogen atmosphere was added 4N HCl in 1,4-dioxane (0.5 mL) at 0° C. The reaction was allowed to warm to RT and was stirred for 3 h. After complete consumption of the starting material (by TLC), the volatiles were evaporated under reduced pressure. The crude material was triturated with CH₃CN (2 mL) to afford 318 (9 mg as an HCl salt) as a yellow solid. ¹H-NMR (DMSO-d₆, 400 MHz): δ 13.18 (s, 1H), 9.37 (s, 1H), 8.83-8.60 (m, 2H), 8.40-8.27 (m, 2H), 7.94-7.74 (m, 3H), 7.49-7.33 (m, 4H), 6.80 (s, 1H), 5.16 (br s, 1H), 4.86-4.69 (m, 1H), 4.37-4.03 (m, 3H), 3.80-3.69 (m, 2H), 3.30-3.29 (m, 2H), 3.20-3.18 (m, 1H), 3.10 (s, 1H), 2.26-2.09 (m, 3H), 1.99-1.71 (m, 3H), 1.68-1.29 (m, 2H). MS (ESI): m/z 569.6 [M+1]⁺. UPLC Purity: 95.32%

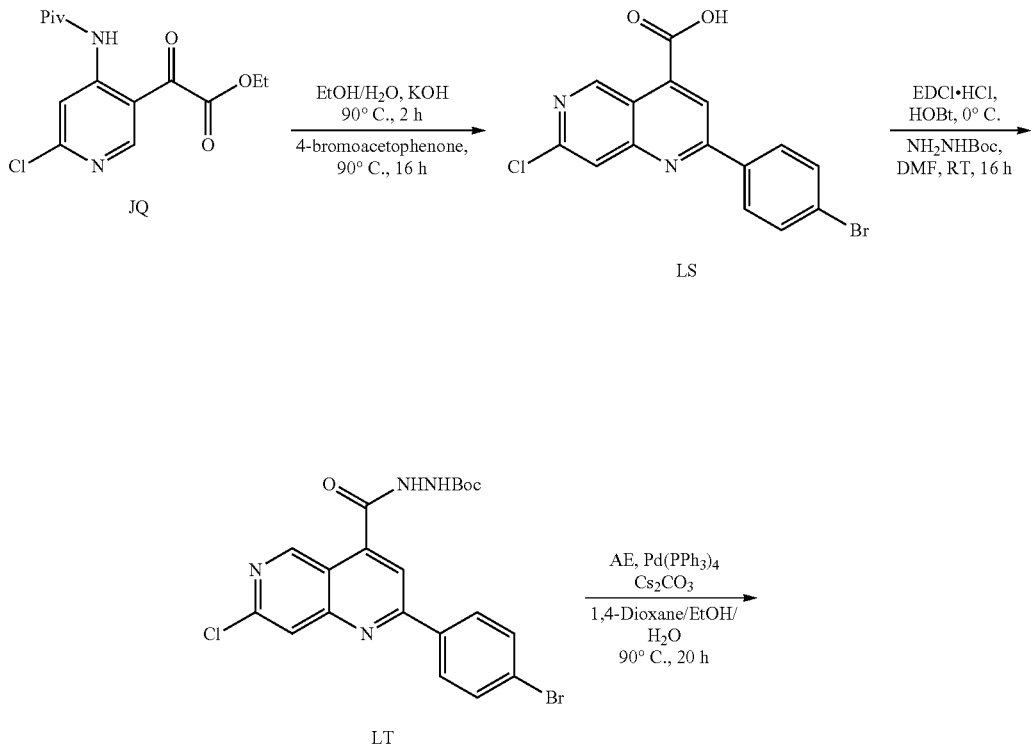

Scheme 82

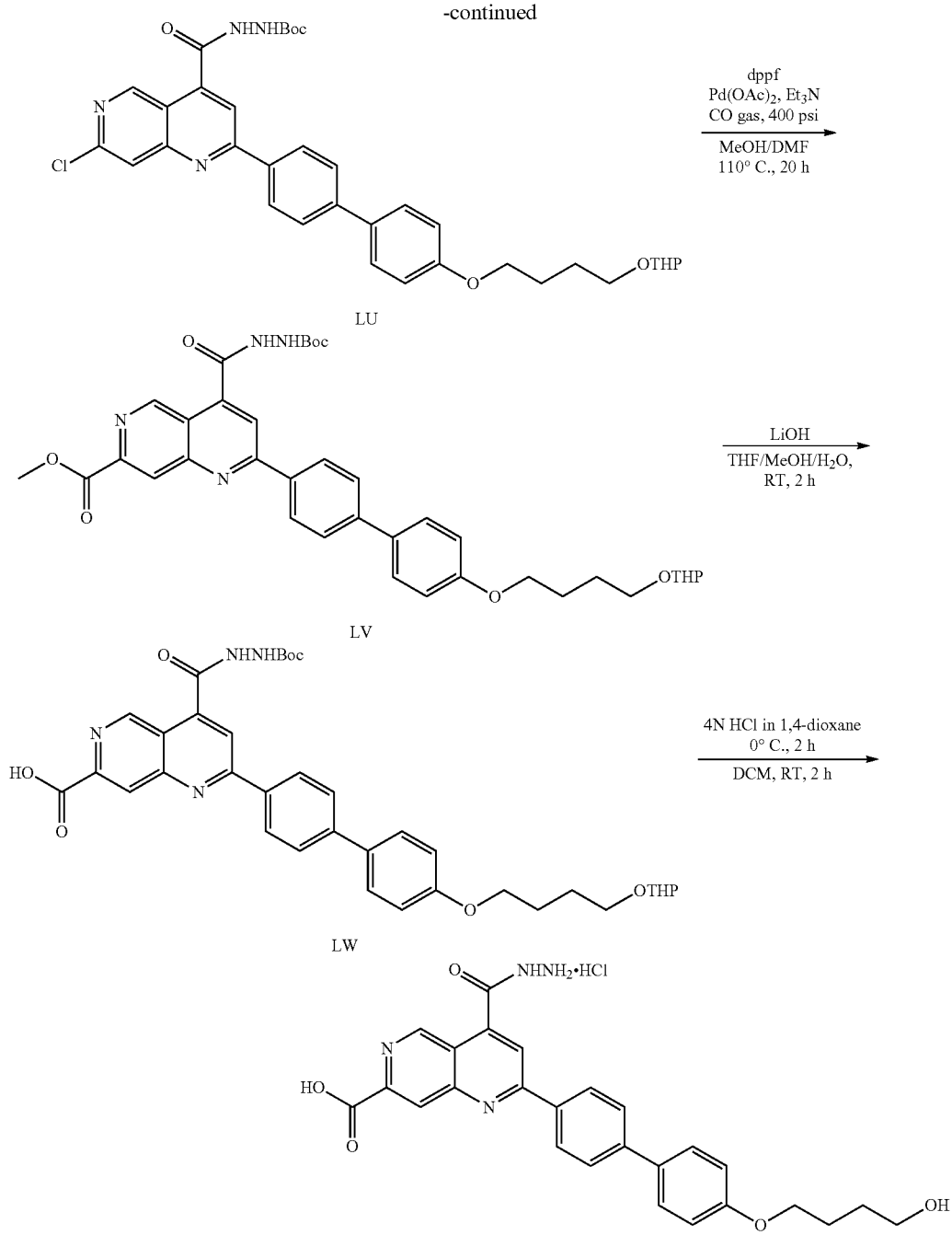

Example 319

4-(hydrazinecarbonyl)-2-(4'-(4-hydroxybutoxy)-[1,1'-biphenyl]-4-yl)-1,6-naphthyridine-7-carboxylic acid hydrochloride (319)

To a stirred solution of compound JQ (4 g, 12.82 mmol) in EtOH/H$_2$O (40 mL/10 mL) was added KOH (2.87 g, 51.28 mmol). The reaction was heated to 90° C. and was stirred for 2 h. The reaction was cooled to RT, 4-bromo acetophenone (5.11 g, 25.64 mmol) was added, and the reaction was heated to 90° C. for 16 h. After complete consumption of the starting material (by TLC), the volatiles were evaporated under reduced pressure. The crude was triturated with diethylether (30 mL). The obtained solid was diluted with water and the pH was adjusted to pH~3 using AcOH. The precipitate was filtered, washed with water, and dried under reduced pressure to afford compound LS (3.7 g, 79%) as an off-white solid. $^1$H-NMR (DMSO-d$_6$, 400 MHz): δ 9.96 (s, 1H), 8.36 (s, 1H), 8.26-8.20 (m, 2H), 8.05 (s, 1H), 7.80-7.76 (m, 2H). MS (ESI): m/z 364.59 [M+1]$^+$ To a stirred solution of compound LS (3.7 g, 10.17 mmol) in DMF (30 mL) under nitrogen atmosphere were added EDCI.HCl (3.90 g, 20.34 mmol), HOBt (2.76 g, 20.34 mmol), DIPEA (5.3 mL, 30.52 mmol) and tert-butyl carbazate (4.02 g, 30.52 mmol) at 0° C. The reaction was allowed to warm to RT and was stirred for 16 h. After complete consumption of the starting material (by TLC), the reaction mixture was diluted with ice cold water (50 mL) and the compound was extracted with EtOAc (2×50 mL). The combined organic extracts were washed with water (50 mL), brine (50 ml), dried over sodium sulfate, filtered and concentrated under reduced pressure. The crude material was purified by silica gel column chromatography eluting with 2% MeOH/DCM to afford compound LT (3.5 g, 72%) as a pale yellow solid. $^1$H-NMR (DMSO-d$_6$, 400 MHz): δ 10.68 (s, 1H), 9.58 (s, 1H), 9.32 (s, 1H), 8.36 (d, J=5.2 Hz, 2H), 8.3 (s, 1H), 8.19 (s, 1H), 7.84-7.79 (m, 2H), 1.48 (s, 9H). MS (ESI): m/z 478.74 [M+1]$^+$ To a stirred solution of compound LT (1 g, 2.09 mmol) in 1,4-dioxane:EtOH:H$_2$O (10 mL:5 mL:2.5 mL) under argon atmosphere were added compound AE (1.18 g, 3.13 mmol) and Cs$_2$CO$_3$ (2.38 g, 7.30 mmol). The solution was purged under argon for 20 min followed by the addition of Pd(PPh$_3$)$_4$ (240 mg, 0.20 mmol). The reaction was heated to 90° C. and stirred for 20 h. After complete consumption of the starting material (by TLC), the reaction was concentrated under reduced pressure. The crude material was purified by silica gel column chromatography eluting with 35% EtOAc/hexane to afford compound LU (700 mg with 64% HPLC purity). Preparative HPLC purification gave LU (300 mg, 22%) as a yellow solid. $^1$H NMR (500 MHz, DMSO-d$_6$): δ 10.71 (s, 1H), 9.57 (s, 1H), 9.33 (s, 1H), 8.46-8.28 (m, 3H), 8.19 (s, 1H), 7.90-7.85 (m, 2H), 7.74 (t, J=8.5 Hz, 2H), 7.08 (t, J=15.0 Hz, 2H), 4.57 (s, 1H), 4.10-4.05 (m, 1H), 3.76-3.67 (m, 2H), 3.41 (t, J=6.5 Hz, 2H), 1.82-1.68 (m, 8H), 1.62-1.50 (m, 2H), 1.49 (s, 9H), 1.06-1.01 (m, 1H). MS (ESI): m/z 648.17 [M+1]$^+$ To a stirred solution of compound LU (80 mg, 0.12 mmol) in MeOH:DMF (9 mL:1 mL) under argon atmosphere were added TEA (0.08 mL, 0.61 mmol), dppf (34 mg, 0.06 mmol), and Pd(OAc)$_2$ (1 mg, 0.06 mmol). The solution was purged under argon in a steel bomb for 20 min followed by pressurizing the system with CO gas (at 200 psi). The reaction was heated to 100° C. and stirred for 20 h. After complete consumption of the starting material (by TLC), the reaction mixture was filtered through Celite and the Celite bed was washed with 10% MeOH:DCM. The filtrate was concentrated under reduced pressure. The crude material was purified by silica gel column chromatography eluting with 3% MeOH:DCM and further triturated with 5% IPA:pentane (3 mL) to afford compound LV (35 mg, 42%) as a brown solid. $^1$H NMR (400 MHz, DMSO-d$_6$): δ 10.72 (s, 1H), 9.78 (s, 1H), 9.34 (s, 1H), 8.63 (s, 1H), 8.47-8.09 (m, 2H), 8.06 (t, J=4.4 Hz, 1H), 7.91-7.72 (m, 2H), 7.60 (s, 1H), 7.53-7.30 (m, 1H), 7.07 (d, J=8.8 Hz, 2H), 4.58 (d, J=4.0 Hz, 1H), 3.98 (s, 3H), 3.77-3.67 (m, 3H), 3.45-3.41 (m, 3H), 1.81-1.59 (m, 10H), 1.50 (s, 9H). MS (ESI): m/z 671.76 [M+1]$^+$ To a stirred solution of compound LV (30 mg, 0.04 mmol) in THF:MeOH:H$_2$O (2 mL:0.5 mL:0.5 mL) was added lithium hydroxide monohydrate (3 mg, 0.07 mmol) at 0° C. The reaction was allowed to warm to RT and was stirred for 2 h. After complete consumption of the starting material (by TLC), the reaction mixture was concentrated under reduced pressure. The crude material was triturated with diethylether (2 mL). The obtained solid was diluted with water and the pH was adjusted to pH~3 by using AcOH. The precipitate was filtered, washed with water and dried under reduced pressure. The solid was triturated with diethylether:CH$_3$CN (2 mL:0.5 mL) to afford compound LW (16 mg, 55%) as a pale yellow solid. $^1$H NMR (400 MHz, DMSO-d$_6$): δ 13.00 (s, 1H), 10.71 (s, 1H), 9.77 (s, 1H), 9.33 (s, 1H), 8.59 (s, 2H), 8.51-8.44 (m, 1H), 7.90 (d, J=7.6 Hz, 2H), 7.75 (d, J=8.4 Hz, 2H), 7.55-7.48 (m, 1H), 7.07 (d, J=8.4 Hz, 2H), 4.57-4.49 (m, 2H), 4.21-4.05 (m, 2H), 3.77-3.66 (m, 2H), 3.44-3.30 (m, 2H), 1.81-1.69 (m, 8H), 1.68-1.50 (m, 1H), 1.49 (s, 9H). MS (ESI): m/z 657.74 [M+1]$^+$ To a stirred solution of compound LW (16 mg, 0.02 mmol) in DCM (1 mL) under nitrogen atmosphere was added 4N HCl in 1,4-dioxane (1 mL) at 0° C. for 2 h. The reaction was allowed to warm to RT and was stirred for 2 h. After complete consumption of the starting material (by TLC), the volatiles were evaporated under reduced pressure. The solid was triturated with 10% CH$_3$OH:CH$_3$CN (1 mL) to afford 319 (9 mg as an HCl salt) as a brick red solid. $^1$H NMR (400 MHz, DMSO-d$_6$): δ 11.34 (s, 1H), 9.71 (s, 1H), 8.61 (s, 1H), 8.54 (s, 1H), 8.47 (d, J=8.0 Hz, 2H), 7.91 (d, J=8.4 Hz, 2H), 7.76 (d, J=8.8 Hz, 2H), 7.07 (d, J=8.8 Hz, 2H), 4.05 (t, J=6.4 Hz, 2H), 3.47 (t, J=6.4 Hz, 2H), 1.81-1.74 (m, 2H), 1.62-1.55 (m, 2H). MS (ESI): 81.30%, m/z 473.4 [M+1]$^+$ Scheme 83

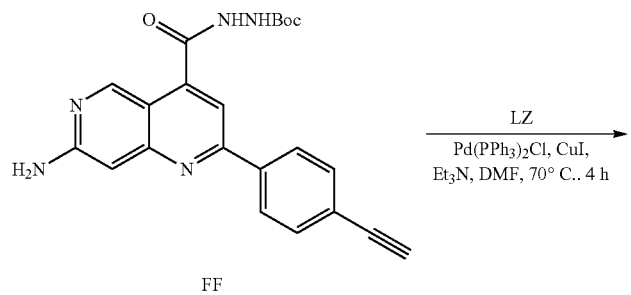

FF

-continued
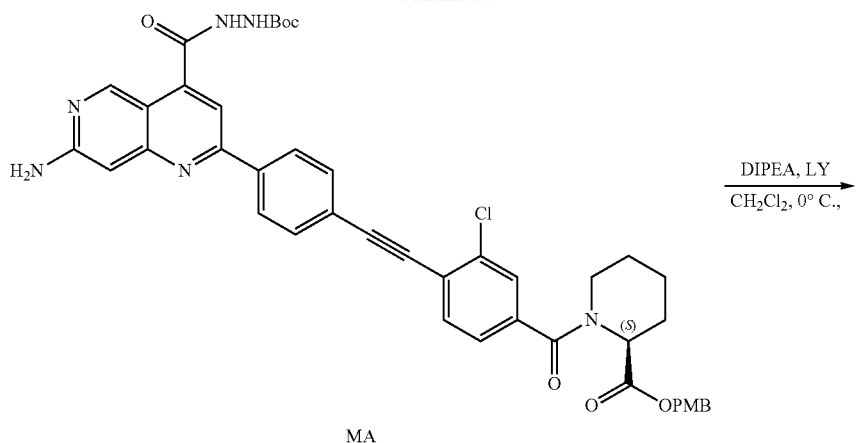
MA
DIPEA, LY
CH₂Cl₂, 0° C.,
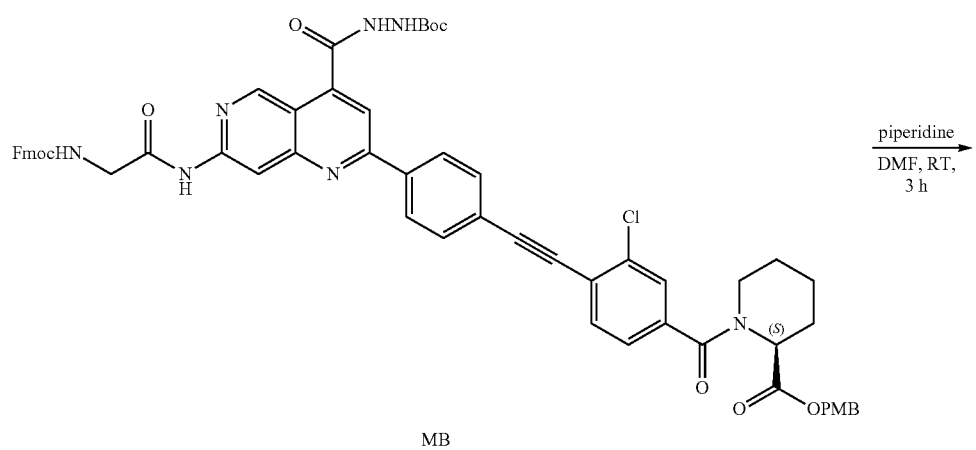
MB
piperidine
DMF, RT,
3 h
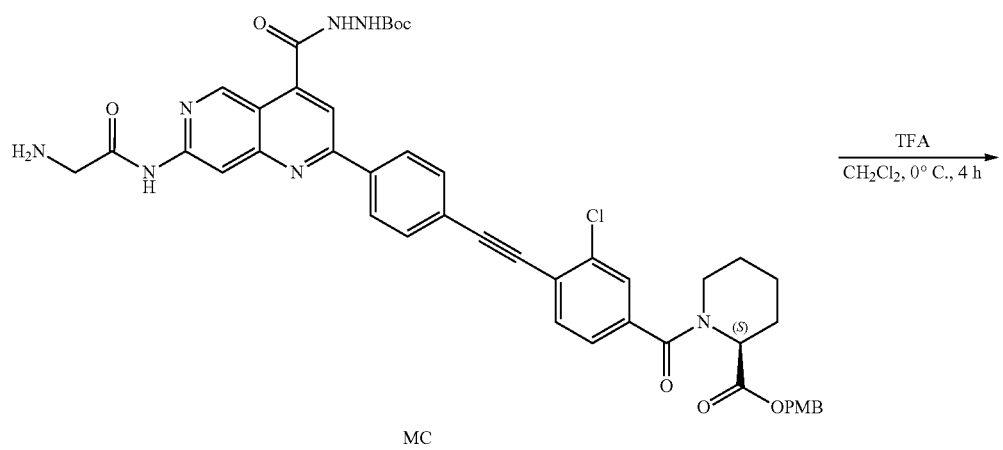
MC
TFA
CH₂Cl₂, 0° C., 4 h

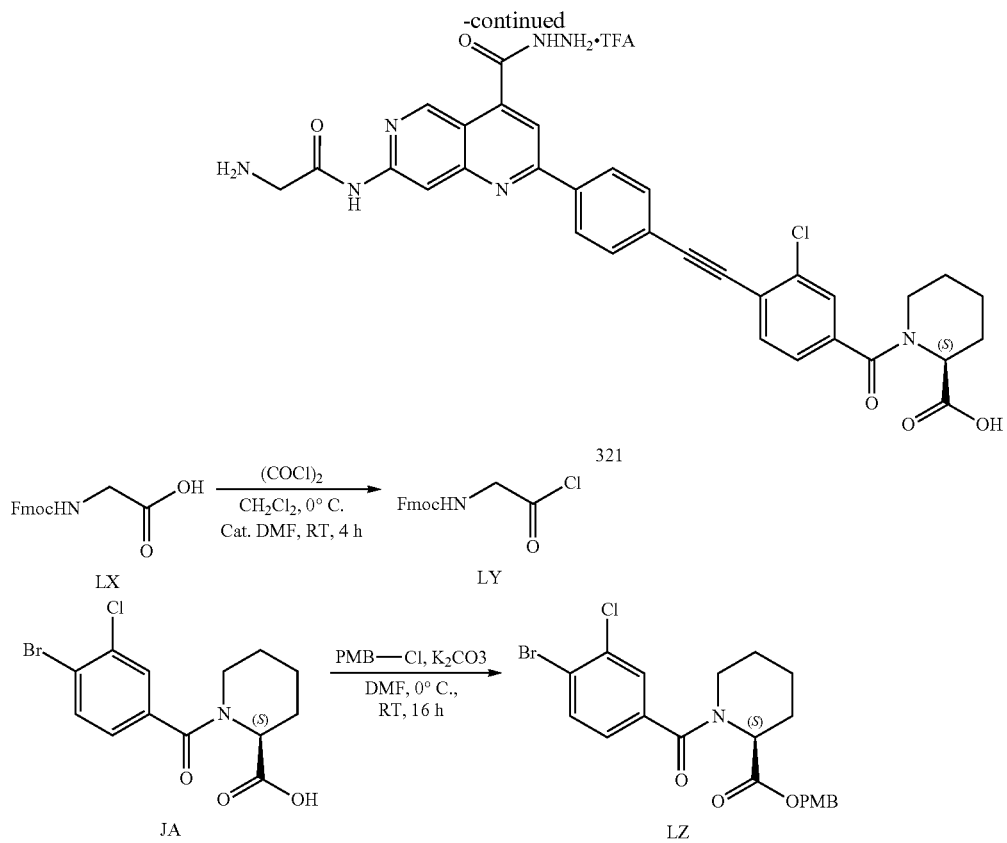

Example 321

(S)-1-(4-((4-(7-(2-aminoacetamido)-4-(2-(2,2,2-trifluoroacetyl)-2l4-diazane-1-carbonyl)-1,6-naphthyridin-2-yl)phenyl)ethynyl)-3-chlorobenzoyl)piperidine-2-carboxylic acid (321)

To a stirred solution of compound LX (370 mg, 1.24 mmol) in DCM:DMF (5 mL:0.01 mL) was added oxalyl chloride (315 mg, 2.48 mmol) at 0° C. The reaction was allowed to warm to RT and was stirred for 3 h. After complete consumption of the starting material (by TLC), the volatiles were evaporated under reduced pressure to afford compound LY (370 mg, crude). To a stirred solution of compound JA (850 mg, 2.45 mmol) in DCM (5 mL) under nitrogen atmosphere were added potassium carbonate (1.01 g, 7.35 mmol) and PMB-Cl (769 mg, 4.90 mmol) at 0° C. The reaction was heated to 80° C. and was stirred for 8 h. After complete consumption of the starting material (by TLC), the reaction was diluted with water (30 mL) and extracted with EtOAc (50 mL). The organic layer was dried over sodium sulfate, filtered and concentrated under reduced pressure. The crude material was purified by silica gel column chromatography eluting with 10% EtOAc:hexane to afford compound LZ (1 g, 88%) as a white sticky liquid. $^1$H NMR (400 MHz, CDCl$_3$): δ 7.62 (d, J=8.0 Hz, 1H), 7.53 (d, J=5.2 Hz, 1H), 7.43-7.28 (m, 2H), 7.10 (d, J 7.6 Hz, 1H), 6.92-6.87 (m, 2H), 5.22-5.10 (m, 1H), 4.62 (s, 2H), 3.81 (s, 3H), 3.53-3.15 (m, 1H), 2.38-2.20 (m, 1H), 1.40-1.29 (m, 6H). MS (ESI): m/z 466.76 [M+1]$^+$ To a stirred solution of compound FF (170 mg, 0.42 mmol) in DMF (10 mL) under argon atmosphere were added compound LZ (393 mg, 0.84 mmol) and TEA (0.61 mL, 4.21 mmol) at RT. The reaction was purged under argon for 20 min followed by the addition of copper iodide (8 mg, 0.04 mmol) and Pd(PPh$_3$)$_2$Cl$_2$ (29 mg, 0.04 mmol). The reaction was heated to 70° C. and was stirred for 4 h. After complete consumption of the starting material (by TLC), the reaction was diluted with water (20 mL) and extracted with DCM (2×30 mL). The combined organic extracts were washed with water (2×20 mL), brine (2×15 mL), dried over sodium sulfate, filtered and concentrated under reduced pressure. The crude material was purified by silica gel column chromatography eluting with 3% MeOH:DCM and further purified by preparative HPLC to afford compound MA (140 mg, 41%) as a yellow solid. $^1$H NMR (500 MHz, DMSO-d$_6$): δ 10.49 (s, 1H), 9.18 (s, 1H), 8.33 (d, J=8.0 Hz, 2H), 7.78 (d, J=8.0 Hz, 2H), 7.73-7.70 (m, 2H), 7.69-7.68 (m, 2H), 7.54-7.51 (m, 2H), 7.34-7.31 (m, 4H), 6.92 (s, 1H), 6.50 (br s, 2H), 5.28 (br s, 1H), 5.15 (s, 2H), 4.44-4.40 (m, 1H), 4.13-4.12 (m, 1H), 3.77 (s, 3H), 3.43-3.41 (m, 1H), 3.14-3.10 (m, 1H), 2.21-2.18 (m, 1H), 1.69-1.66 (m, 2H), 1.47 (s, 9H). MS (ESI): m/z 789.29 [M+1]$^+$ To a stirred solution of compound MA (140 mg, 0.177 mmol) in DCM (10 mL) and DIPEA (0.3 ml, 1.7 mmol) was added compound LY (370 mg, 1.17 mmol (crude) in 5 mL DCM dropwise at 0° C. The reaction was allowed to warm to RT and was stirred for 12 h. After complete consumption of the starting material (by TLC), the reaction mixture was diluted with water (10 mL) and the compound was extracted with DCM (2×10 mL). The combined organic extracts were washed with water (15 mL), brine (10 mL), dried over sodium sulfate, filtered and concentrated under reduced pressure. The crude material was purified by silica gel column chromatography eluting with 2% MeOH/DCM to afford compound MB (20 mg, 11%) as a pale yellow solid. $^1$H NMR (400 MHz, DMSO-d$_6$): δ 10.90 (br s, 1H), 10.65 (br s, 1H), 9.51 (s, 1H), 9.26 (s, 1H), 8.65 (s, 1H), 8.44 (d, J=7.2 Hz, 1H), 8.16 (s, 1H), 7.90 (d, J=7.6 Hz, 2H), 7.81 (d, J=8.0 Hz, 3H), 7.75-7.73 (m, 3H), 7.70-7.65 (m, 3H), 7.46-7.33 (m, 6H), 6.95 (d, J=8.4 Hz, 2H), 5.26-5.20 (br s, 1H), 5.14 (s, 2H), 4.34-4.32 (m, 2H), 4.28-4.26 (m, 2H), 3.98-3.96 (m, 2H), 3.76 (s, 3H), 3.50-3.46 (m, 1H), 3.09-3.05 (m, 1H), 2.20-2.10 (m, 2H), 1.68 (d, J=12.8 Hz, 3H), 1.48 (s, 9H). MS (ESI): m/z 1068.58 [M+1]$^+$ To a stirred solution of compound MB (20 mg, 0.018 mmol) in DMF (3 mL) under argon atmosphere was added piperidine (4.78 mg, 0.056 mmol) at 0° C. The reaction was allowed to warm to RT and was stirred for 4 h. After complete consumption of the starting material (by TLC), the reaction was diluted with water (10 mL) and extracted with EtOAc (2×10 mL). The combined extractions were washed with water (3×10 mL), dried over sodium sulfate, filtered and concentrated under reduced pressure. The crude material was purified by silica gel column chromatography eluting with 5% MeOH/DCM to afford compound MC (10 mg, 88%) as a pale yellow solid. MS (ESI): m/z 846.34 [M+1]$^+$ To a stirred solution of compound MC (10 mg, 0.01 mmol) in DCM (2 mL) under nitrogen atmosphere was added TFA (1 mL) at 0° C. The reaction was allowed to warm to RT and was stirred for 4 h. After complete consumption of the starting material (by TLC), the volatiles were evaporated under reduced pressure. The crude material was triturated with 10% IPA:MeOH (2 mL) to afford 321 (8 mg as a TFA salt) as a yellow solid. $^1$H NMR (400 MHz, DMSO-d$_6$): δ 13.15 (s, 1H), 11.50 (br s, 1H), 9.50 (s, 1H), 8.63 (s, 1H), 8.46-8.24 (m, 3H), 7.83-7.76 (m, 4H), 7.59-7.55 (m, 2H), 7.40-7.35 (m, 2H), 5.17 (s, 1H), 4.38-4.30 (m, 1H), 3.92 (s, 2H), 3.31-3.29 (m, 1H), 2.70-2.61 (m, 1H), 2.23-2.19 (m, 2H), 2.00-1.95 (m, 3H), 1.71-1.43 (m, 2H). MS (ESI): m/z 626.6 [M+1]$^+$. UPLC Purity: 71.45%

Scheme 84

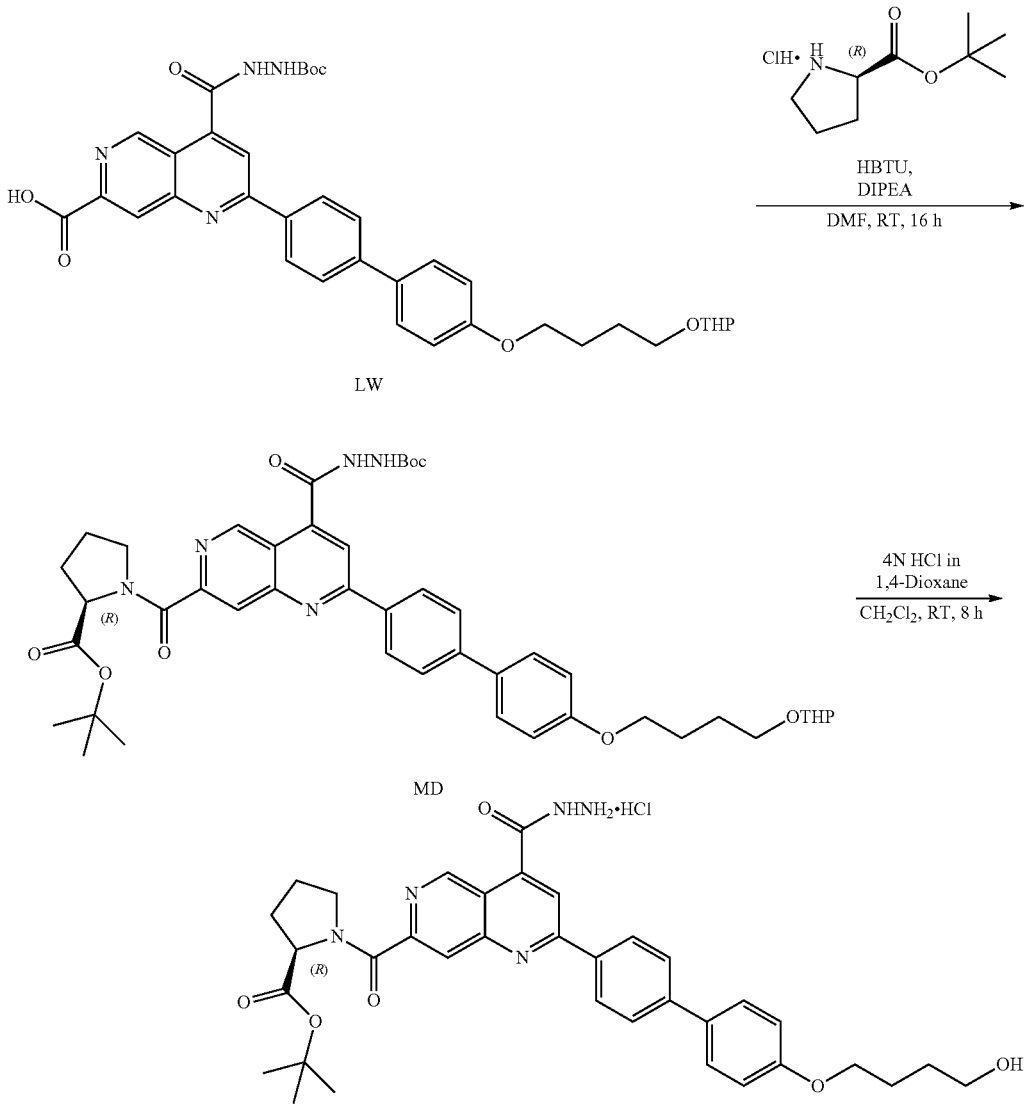

Example 323

(4-(hydrazinecarbonyl)-2-(4'-(4-hydroxybutoxy)-[1,1'-biphenyl]-4-yl)-1,6-naphthyridine-7-carbonyl)-D-proline hydrochloride (323)

To a stirred solution of compound LW (40 mg, 0.06 mmol) in DMF (2 mL) under nitrogen atmosphere were added DIPEA (0.04 mL, 0.24 mmol) and HBTU (27 mg, 0.07 mmol). The solution was stirred for 15 min at which point D-proline t-butylester.HCl (19 mg, 0.09 mmol) was added at 0° C. The reaction was allowed to warm to RT and was stirred for 16 h. After complete consumption of the starting material (by TLC), the reaction mixture was diluted with ice cold water (10 mL) and was extracted with 10% MeOH:EtOAc (2×20 mL). The combined organic extracts were washed with water (5 mL), brine (5 ml), dried over sodium sulfate, filtered and concentrated under reduced pressure. The crude material was purified by silica gel column chromatography eluting with 2% MeOH/DCM and was further triturated with DCM:pentane (1 mL:4 mL) to afford compound MD (20 mg, 41%) as a brown solid. $^1$H NMR (400 MHz, DMSO-$d_6$): δ 10.70 (d, J=12.4 Hz, 1H), 9.71 (s, 1H), 9.38 (s, 1H), 8.80 (s, 1H), 8.46-8.38 (m, 3H), 7.89 (d, J=8.0 Hz, 2H), 7.75 (d, J=8.8 Hz, 2H), 7.07 (d, J=8.8 Hz, 2H), 4.96 (d, J=6.0 Hz, 1H), 4.57 (s, 1H), 4.48 (d, J=4.8 Hz, 1H), 4.09-4.05 (m, 1H), 3.82-3.68 (m, 2H), 3.50-3.60 (m, 2H), 3.45-3.41 (m, 2H), 2.28-2.21 (m, 1H), 1.96-1.90 (m, 7H), 1.88-1.59 (m, 6H), 1.50 (s, 9H), 1.49 (s, 9H). MS (ESI): m/z 810.96 [M+1]$^+$ To a stirred solution of compound MD (18 mg, 0.02 mmol) in DCM (1 mL) under nitrogen atmosphere was added 4N HCl in 1,4-dioxane (2.5 mL) at 0° C. The reaction was allowed to warm to RT and was stirred for 8 h. After complete consumption of the starting material (by TLC), the volatiles were evaporated under reduced pressure and the resulting solid was triturated with 10% CH$_3$OH:CH$_3$CN (1 mL) to afford 323 (10 mg as an HCl salt) as a brick red solid. $^1$H NMR (400 MHz, DMSO-$d_6$): δ 11.0 (s, 1H), 9.66 (s, 1H), 8.48-8.45 (m, 4H), 8.40 (s, 1H), 7.89 (t, J=4.4 Hz, 2H), 7.75 (d, J=8.8 Hz, 2H), 7.07 (d, J=8.8 Hz, 2H), 5.12-5.09 (m, 1H), 4.53-4.50 (m, 1H), 4.05 (t, J=6.4 Hz, 2H), 3.74 (d, J=7.2 Hz, 2H), 3.47 (t, J=6.4 Hz, 2H), 1.93 (d, J=6.4 Hz, 4H), 1.81-1.55 (m, 4H). MS (ESI): 82.21%, m/z 570.5 [M+1]$^+$

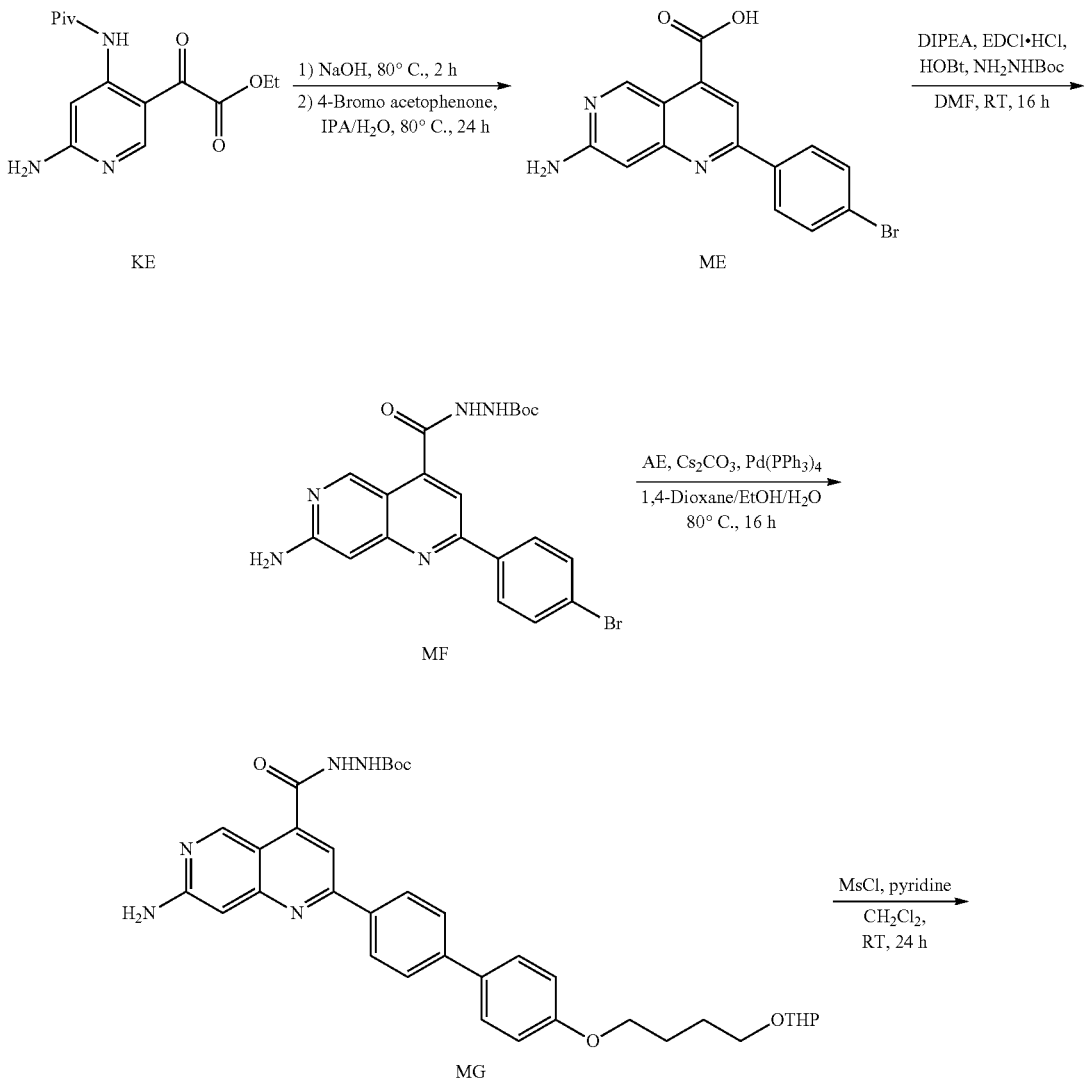

Scheme 85

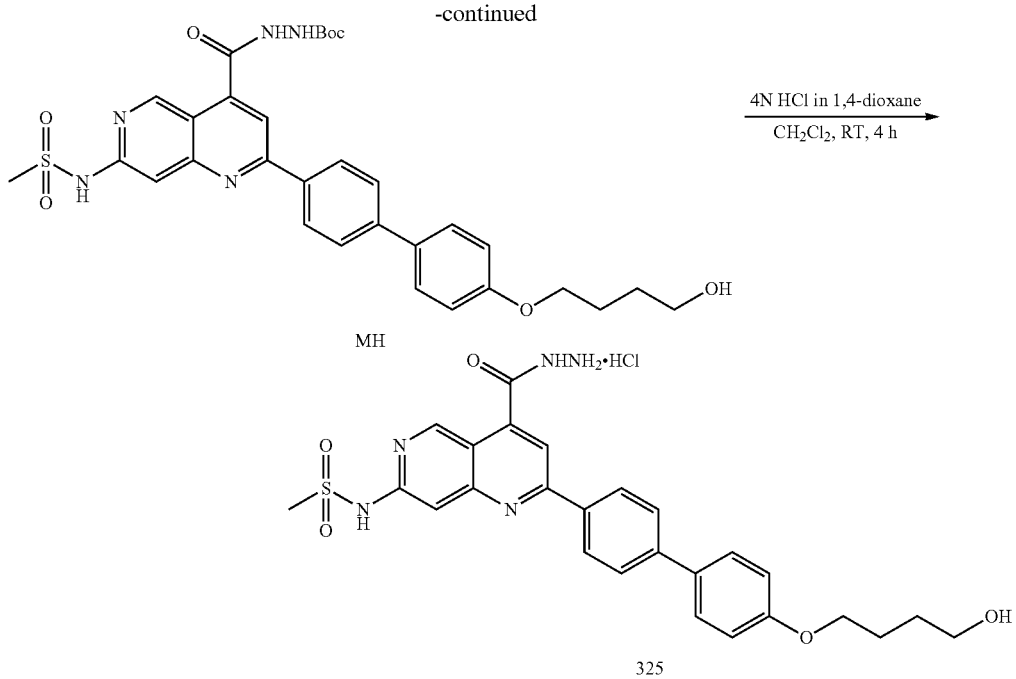

Example 325

N-(4-(hydrazinecarbonyl)-2-(4'-(4-hydroxybutoxy)-[1,1'-biphenyl]-4-yl)-1,6-naphthyridin-7-yl) methanesulfonamide hydrochloride (325)

To a stirred solution of compound KE (4 g, 13.65 mmol) in IPA/H$_2$O (80 mL/20 mL) was added NaOH (5.4 g, 27.30 mmol) at 0° C. The reaction was heated to 80° C. and was stirred for 2 h. The reaction was cooled to RT, 4-bromo acetophenone (5.4 g, 27.30 mmol) was added, and the reaction was heated to 80° C. for 24 h. After complete consumption of the starting material (by LC-MS), the volatiles were evaporated under reduced pressure. The crude material was triturated with diethylether (50 mL), the obtained solid was diluted with water, and the pH was adjusted to pH~4 by using AcOH. The precipitate was filtered, washed with water and dried under reduced pressure to afford compound ME (4 g, 86%) as a yellow solid. $^1$H-NMR (DMSO-d$_6$, 500 MHz): δ 12.00 (br s, 1H), 9.53 (s, 1H), 8.15 (d, J=8.0 Hz, 2H), 7.77 (s, 1H), 7.73 (d, J=8.0 Hz, 2H), 6.74 (s, 1H), 6.24 (s, 2H). MS (ESI): m/z 345.17 [M+1]$^+$ To a stirred solution of compound ME (4.5 g, 13.11 mmol) in DMF (25 mL) under nitrogen atmosphere were added EDCI.HCl (5 g, 26.23 mmol), HOBt (3.54 g, 26.23 mmol), DIEPA (6.8 mL, 39.35 mmol), and tert-butyl carbazate (5.1 g, 39.35 mmol) at 0° C. The reaction was allowed to warm to RT and was stirred for 16 h. After complete consumption of the starting material (by TLC), the reaction mixture was diluted with ice cold water (100 mL) and was extracted with EtOAc (2×100 mL). The combined organic extracts were washed with water (2×100 mL), brine (100 ml), dried over sodium sulfate, filtered and concentrated under reduced pressure. The crude material was purified by silica gel column chromatography eluting with 2% MeOH/DCM to afford compound MF (3.5 g, 58%) as a yellow solid. $^1$H-NMR (DMSO-d$_6$, 500 MHz): δ 10.47 (s, 1H), 9.18 (s, 1H), 8.19 (d, J=8.0 Hz, 2H), 7.95 (s, 2H), 7.77 (d, J=8.5 Hz, 1H), 7.67 (d, J=9.0 Hz, 1H), 6.80 (s, 1H), 6.49 (s, 2H), 1.48 (s, 9H). MS (ESI): m/z 459.32 [M+1]$^+$ To a stirred solution of compound MF (1 g, 2.18 mmol) in 1,4-dioxane:EtOH:H$_2$O (20 mL:10 mL:5 mL) under argon atmosphere were added compound AE (1.23 g, 3.28 mmol) and cesium carbonate (2.5 g, 7.65 mmol). The mixture was purged with argon for 10 min followed by the addition of Pd(PPh$_3$)$_4$ (253 mg, 0.21 mmol). The reaction was heated to 80° C. and was stirred for 16 h. After complete consumption of the starting material (by TLC), the reaction mixture was filtered through Celite and the Celite bed was washed with ethyl acetate (50 mL). The filtrate was concentrated under reduced pressure and the residue was purified by silica gel column chromatography eluting with 2% MeOH/DCM to afford compound MG (300 mg, 22%) as a pale yellow solid. $^1$H-NMR (DMSO-d$_6$, 500 MHz): δ 10.49 (s, 1H), 9.17 (s, 2H), 8.30 (d, J=7.5 Hz, 2H), 7.83 (d, J=8.5 Hz, 2H), 7.73 (d, J=8.0 Hz, 2H), 7.07 (d, J=8.5 Hz, 2H), 6.81 (s, 2H), 6.46 (s, 2H), 4.57 (s, 1H), 4.07 (t, J=6.5 Hz, 2H), 3.75-3.69 (m, 2H), 3.43 (t, J=6.5 Hz, 2H), 1.83-1.73 (m, 4H), 1.71-1.62 (m, 6H), 1.48 (s, 9H). MS (ESI): m/z 628.74 [M+1]$^+$ To a stirred solution of compound MG (80 mg, 0.12 mmol) in DCM (5 mL) under nitrogen atmosphere were added pyridine (99 mg, 1.27 mmol) and methanesulfonylchloride (0.02 mL, 0.25 mmol) at 0° C. The reaction was allowed to warm to RT and was stirred for 24 h. After complete consumption of the starting material (by TLC), the reaction mixture was diluted with ice cold water (10 mL) and was extracted with DCM (2×10 mL). The combined organic extracts were washed with water (2×20 mL), brine (20 ml), dried over sodium sulfate, filtered and concentrated under reduced pressure. The crude product was purified by silica gel column chromatography eluting with 2% MeOH/DCM to afford compound MH (30 mg, with some impurities) as a yellow solid. $^1$H-NMR (DMSO-d$_6$, 400 MHz): δ

11.00 (s, 1H), 10.65 (s, 1H), 9.49 (s, 1H), 9.27 (s, 1H), 8.39 (d, J=8.4 Hz, 2H), 8.00 (t, J=6.4 Hz, 2H), 7.86 (d, J=7.6 Hz, 3H), 7.73 (d, J=8.4 Hz, 1H), 7.06 (d, J=8.4 Hz, 2H), 4.05 (t, J=6.4 Hz, 2H), 3.46 (t, J=6.4 Hz, 2H), 3.38 (s, 3H), 1.77 (t, J=7.2 Hz, 2H), 1.58 (t, J=8.0 Hz, 2H), 1.48 (s, 9H). MS (ESI): m/z 622.71 [M+1]$^+$

To a stirred solution of compound MH (30 mg, impure) in DCM (2 mL) under nitrogen atmosphere was added 4N HCl in 1,4-dioxane (0.3 mL) at 0° C. The reaction was allowed to warm to RT and and was stirred for 4 h. After complete consumption of the starting material (by TLC), the volatiles were evaporated under reduced pressure. The crude product was triturated with CH$_3$CN (2 mL) to afford 325 (15 mg as an HCl salt) as a brown solid. $^1$H-NMR (DMSO-d$_6$, 400 MHz): δ 11.53 (s, 1H), 10.98 (s, 1H), 9.43 (s, 1H), 8.41 (d, J=8.4 Hz, 2H), 8.26 (s, 1H), 7.87 (d, J=8.4 Hz, 2H), 7.74 (d, J=8.8 Hz, 2H), 7.55 (s, 1H), 7.07 (d, J=8.8 Hz, 2H), 4.05 (s, 2H), 3.47 (t, J=6.4 Hz, 2H), 3.39 (s, 3H), 1.81-1.74 (m, 2H), 1.62-1.55 (m, 2H). MS (ESI): m/z 522.59 [M+1]$^+$. HPLC: 92.29%

Scheme 86

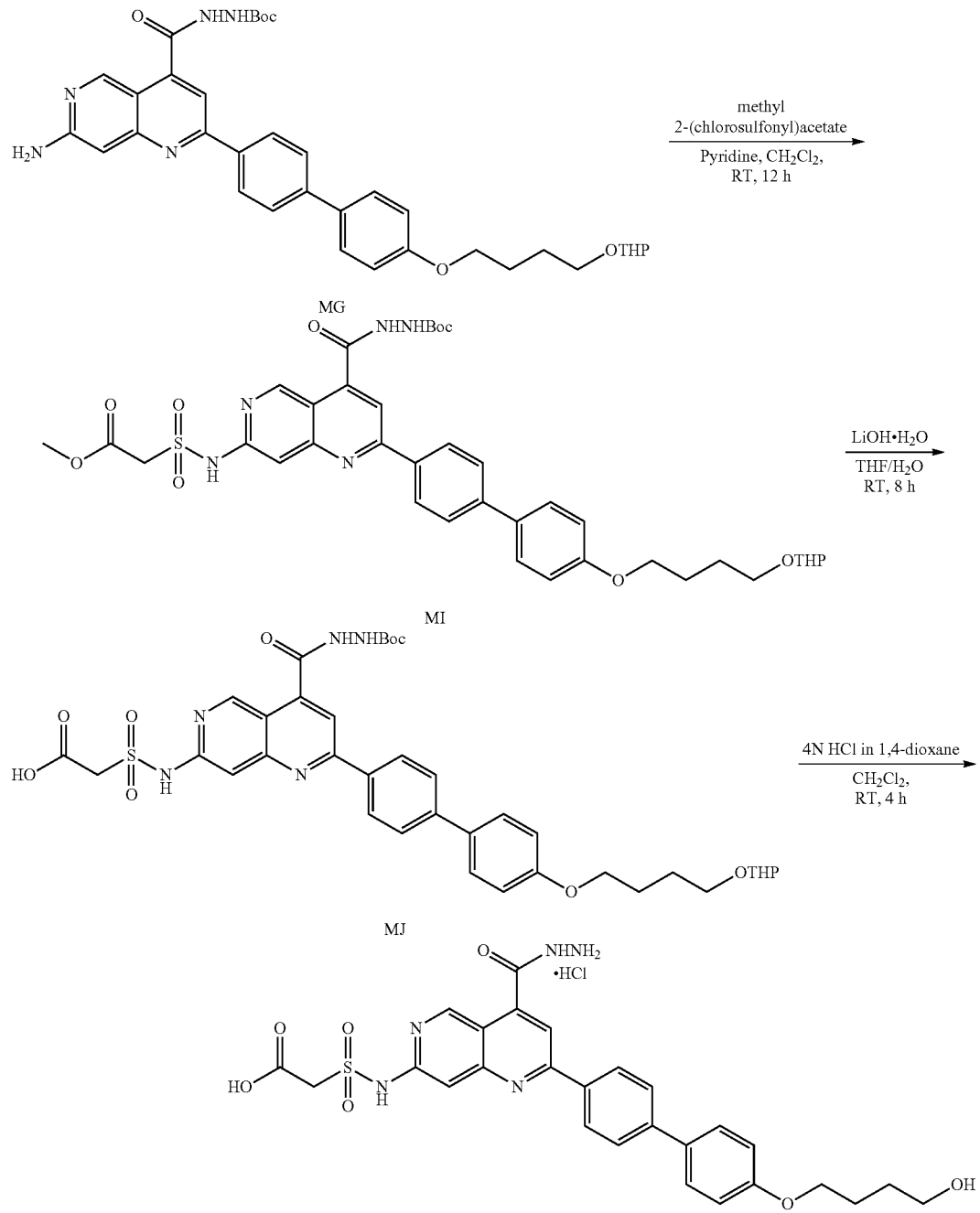

326

Example 326

2-(N-(4-(hydrazinecarbonyl)-2-(4'-(4-hydroxybutoxy)-[1,1'-biphenyl]-4-yl)-1,6-naphthyridin-7-yl)sulfamoyl)acetic acid hydrochloride (326)

To a stirred solution of compound MG (100 mg, 0.15 mmol) in DCM (5 mL) under nitrogen atmosphere were added pyridine (0.14 mL, 1.59 mmol) and methyl 2-(chlorosulfonyl)acetate (69 mg, 0.39 mmol) at 0° C. The reaction was allowed to warm to RT and was stirred for 12 h. After complete consumption of the starting material (by TLC), the reaction mixture was diluted with ice cold water (10 mL) and the compound was extracted with DCM (2×10 mL). The combined organic extracts were washed with water (2×20 mL), brine (20 ml), dried over sodium sulfate, filtered and concentrated under reduced pressure. The crude material was purified by silica gel column chromatography eluting with 2% MeOH/DCM to afford compound MI (30 mg, 25%) as a yellow solid. $^1$H-NMR (DMSO-$d_6$, 400 MHz): δ 11.40 (br s, 1H), 10.64 (br s, 1H), 9.48 (s, 1H), 9.27 (s, 1H), 8.40 (d, J=8.4 Hz, 2H), 8.14 (s, 1H), 7.86 (d, J=8.4 Hz, 2H), 7.74 (d, J=8.8 Hz, 2H), 7.52 (s, 1H), 7.07 (d, J=8.8 Hz, 2H), 4.73 (s, 2H), 4.58 (d, J=4.0 Hz, 1H), 4.07 (t, J=6.4 2H), 3.78-3.67 (m, 2H), 3.65 (s, 3H), 3.46-3.39 (m, 2H), 1.81-1.78 (m, 4H), 1.73-1.58 (m, 6H), 1.49 (s, 9H). MS (ESI): m/z 764.86 [M+1]$^+$ To a stirred solution of compound MI (30 mg, 0.03 mmol) in THF:H$_2$O (5 mL:1 mL) were added lithium hydroxide monohydrate (6.6 mg, 0.15 mmol) at 0° C. The reaction was allowed to warm to RT and was stirred for 8 h. After complete consumption of the starting material (by TLC), the volatiles were evaporated under reduced pressure. The crude material was diluted with water and the pH was adjusted to pH~4 by using an acetic acid solution (0.1 mL). The precipitate was filtered and dried under reduced pressure to afford compound MJ (15 mg, 52%) as a yellow solid. $^1$H-NMR (DMSO-$d_6$, 400 MHz): δ 10.61 (br s, 1H), 9.48 (s, 1H), 9.44 (s, 1H), 9.25 (s, 1H), 8.39 (d, J=7.6 Hz, 2H), 8.12 (s, 1H), 8.08 (s, 1H), 7.85 (d, J=8.0 Hz, 2H), 7.73 (d, J=8.4 Hz, 2H), 7.54 (d, J=12.4 Hz, 1H), 7.06 (d, J=8.4 Hz, 2H), 4.58 (d, J=3.6 Hz, 1H), 4.07 (t, J=6.4 Hz, 1H), 3.77-3.67 (m, 4H), 3.45-3.38 (m, 3H), 1.79 (t, J=6.4 Hz, 4H), 1.73-1.59 (m, 6H), 1.49 (s, 9H). MS (ESI): m/z 750.84 [M+1]$^+$ To a stirred solution of compound MJ (15 mg, 0.02 mmol) in DCM (2 mL) under nitrogen atmosphere was added 4N HCl in 1,4-dioxane (0.2 mL) at 0° C. The reaction was allowed to warm to RT and was stirred for 4 h. After complete consumption of the starting material (by TLC), the volatiles were evaporated under reduced pressure. The crude material was triturated with CH$_3$CN (2 mL) to afford 326 (5 mg as an HCl salt) as a yellow solid. $^1$H-NMR (DMSO-$d_6$, 400 MHz): δ 11.28 (br s, 1H), 10.99 (s, 1H), 9.43 (s, 1H), 8.41 (d, J=8.4 Hz, 2H), 8.23 (s, 1H), 7.87 (d, J=8.4 Hz, 2H), 7.74 (d, J=8.4 Hz, 2H), 7.53 (s, 1H), 7.06 (d, J=8.8 Hz, 2H), 4.06 (s, 2H), 4.05 (t, J=6.8 Hz, 2H), 3.47 (t, J=6.4 Hz, 2H), 1.80-1.75 (m, 2H), 1.62-1.57 (m, 2H). MS (ESI): m/z 566.6 [M+1]$^+$. HPLC: 74.97%

Scheme 87

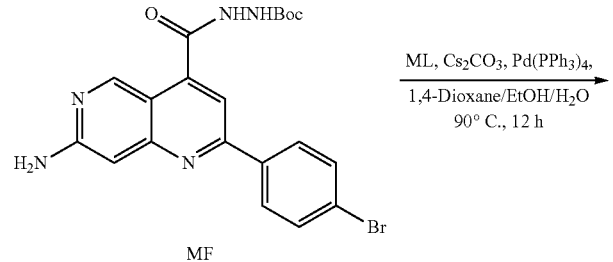

MF

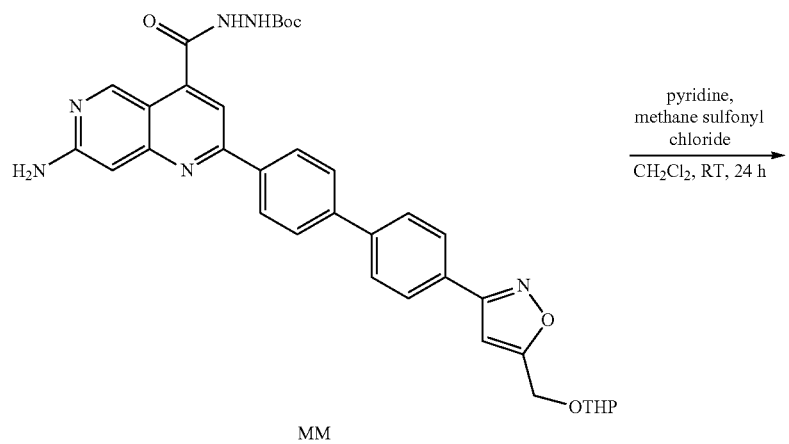

MM

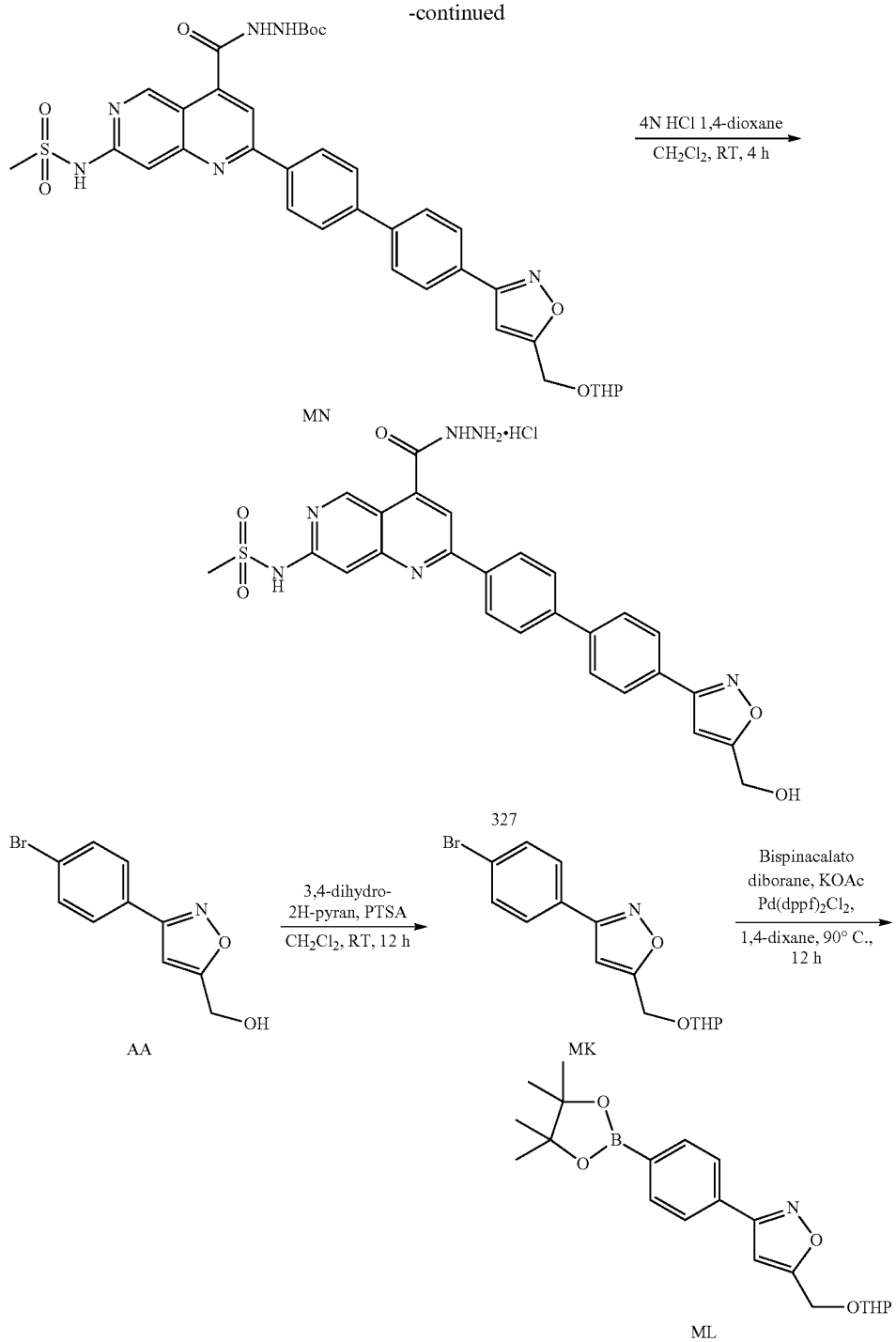

Example 327

N-(4-(hydrazinecarbonyl)-2-(4'-(5-(hydroxymethyl) isoxazol-3-yl)-[1,1'-biphenyl]-4-yl)-1,6-naphthyridin-7-yl) methanesulfonamide hydrochloride (327)

To a stirred solution of compound AA (500 mg, 1.97 mmol) in DCM (20 mL) under nitrogen atmosphere were added 3,4-dihydro-2H-pyran (249 mg, 2.96 mmol) and p-TSA (187 mg, 0.98 mmol) at 0° C. for 15 min. The reaction was allowed to warm to RT and was stirred for 12 h. After complete consumption of the starting material (by TLC), the reaction mixture was diluted with ice cold water (25 mL) and the compound was extracted with DCM (2×25 mL). The combined organic extracts were washed with water (2×30 mL) dried over sodium sulfate, filtered and concentrated under reduced pressure. The crude compound was purified by silica gel column chromatography eluting with 8% EtOAc/hexane to afford compound MK (310 mg, 46%) as a colorless thick syrup. $^1$H-NMR (DMSO-$d_6$, 400 MHz): δ 7.85-7.82 (m, 2H), 7.74-7.70 (m, 2H), 7.10 (s, 1H), 4.80 (s, 2H), 4.76-4.69 (m, 1H), 3.80-3.72 (m, 1H), 3.48-

3.40 (m, 1H), 1.78-1.61 (m, 2H), 1.56-1.42 (m, 4H). MS (ESI): m/z 338 [M]⁺, 340 [M+2]⁺

To a stirred solution of compound MK (300 mg, 0.89 mmol) in 1,4-dioxane (10 mL) under argon atmosphere were added bispinacalatodiborane (271 mg, 1.06 mmol) and potassium acetate (261 mg, 2.67 mmol). The solution was purged with argon for 10 min followed by the addition of Pd(dppf)$_2$Cl$_2$ (65 mg, 0.08 mmol). The reaction was heated to 90° C. and was stirred for 12 h. After complete consumption of the starting material (by TLC), the reaction mixture was filtered through Celite and the Celite bed washed with ethyl acetate (25 mL). The filtrate was concentrated under reduced pressure. The crude material was purified by silica gel column chromatography eluting with 10% EtOAc/hexane to afford compound ML (220 mg, 64%) as an off-white solid. ¹H-NMR (DMSO-d$_6$, 500 MHz): δ 7.91 (d, J=8.5 Hz, 2H), 7.80 (d, J=7.5 Hz, 2H), 7.11 (s, 1H), 4.80 (s, 2H), 4.78-4.67 (m, 1H), 3.81-3.76 (m, 1H), 3.52-3.49 (m, 1H), 1.76-1.65 (m, 2H), 1.55-1.49 (m, 4H), 1.23 (s, 12H). MS (ESI): m/z 386.27 [M+1]⁺

To a stirred solution of compound MF (500 mg, 1.09 mmol) in 1,4-dioxane:EtOH:H$_2$O (12 mL:3 mL:1 mL) under argon atmosphere were added compound ML (631 mg, 1.64 mmol) and cesium carbonate (1.25 g, 3.82 mmol). The solution was purged with argon for 10 min followed by the addition of Pd(PPh$_3$)$_4$ (126 mg, 0.10 mmol). The reaction was heated to 90° C. and was stirred for 12 h. After complete consumption of the starting material (by TLC), the reaction mixture was filtered through Celite and the Celite bed washed with ethyl acetate (25 mL). The filtrate was concentrated under reduced pressure. The crude material was purified by silica gel column chromatography eluting with 2% MeOH/DCM to afford compound MM (210 mg, 30%) as a yellow solid. ¹H-NMR (DMSO-d$_6$, 400 MHz): δ 10.57 (s, 1H), 9.18 (s, 2H), 8.36 (d, J=8.0 Hz, 2H), 8.03 (d, J=8.4 Hz, 2H), 7.95 (t, J=8.0 Hz, 4H), 7.57-7.55 (m, 1H), 7.16 (s, 1H), 6.80 (s, 1H), 6.47 (s, 2H), 4.83 (s, 2H), 4.78 (t, J=4.8 Hz, 1H), 3.83-3.77 (m, 1H), 3.54-3.49 (m, 1H), 1.77-1.64 (m, 2H), 1.56-1.50 (m, 4H), 1.48 (s, 9H). MS (ESI): m/z 637.7 [M+1]⁺

To a stirred solution of compound MM (50 mg, 0.07 mmol) in DCM (3 mL) under nitrogen atmosphere were added pyridine (18.6 mg, 0.23 mmol) and methanesulfonylchloride (22.4 mg, 0.19 mmol) at 0° C. The reaction was allowed to warm to RT and was stirred for 24 h. After complete consumption of the starting material (by TLC), the reaction mixture was diluted with ice cold water (10 mL) and the compound was extracted with DCM (2×10 mL). The combined organic extracts were washed with water (2×20 mL), brine (20 ml), dried over sodium sulfate, filtered and concentrated under reduced pressure. The crude material was purified by silica gel column chromatography eluting with 2% MeOH/DCM to afford compound MN (26 mg, 52%) as a yellow solid. ¹H-NMR (DMSO-d$_6$, 400 MHz): δ 10.98 (s, 1H), 10.64 (s, 1H), 9.51 (s, 1H), 9.28 (s, 1H), 8.54-8.45 (m, 2H), 8.16 (d, J=7.6 Hz, 1H), 8.05-7.90 (m, 5H), 7.64-7.51 (m, 2H), 7.16 (s, 1H), 4.83 (s, 2H), 4.72-4.64 (m, 1H), 3.83-3.75 (m, 1H), 3.54-3.49 (m, 1H), 3.43 (s, 3H), 1.77-1.68 (m, 2H), 1.66-1.53 (m, 4H), 1.49 (s, 9H). MS (ESI): 80% m/z 715.79 [M+1]⁺

To a stirred solution of compound MN (23 mg, 0.03 mmol) in DCM (2 mL) under nitrogen atmosphere was added 4N HCl in 1,4-dioxane (0.5 mL) at 0° C. The reaction was allowed to warm to RT and was stirred for 4 h. After complete consumption of the starting material (by TLC), the volatiles were evaporated under reduced pressure. The crude material was triturated with CH$_3$CN:pentane (2 mL:2 mL) to afford 327 (11 mg as an HCl salt) as a yellow solid. ¹H-NMR (DMSO-d$_6$, 400 MHz): δ 11.62 (s, 1H), 11.00 (s, 1H), 9.46 (s, 1H), 8.49 (d, J=8.4 Hz, 2H), 8.31 (s, 1H), 8.03-7.94 (m, 6H), 7.58 (s, 1H), 7.01 (s, 1H), 4.64 (s, 2H), 3.39 (s, 3H). MS (ESI): 80%; m/z 531.56 [M+1]⁺

Scheme 88

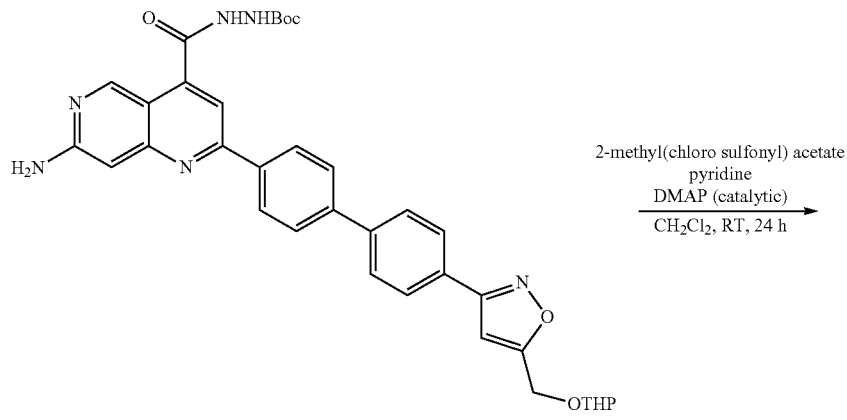

MM 2-methyl(chloro sulfonyl) acetate
pyridine
DMAP (catalytic)
CH$_2$Cl$_2$, RT, 24 h

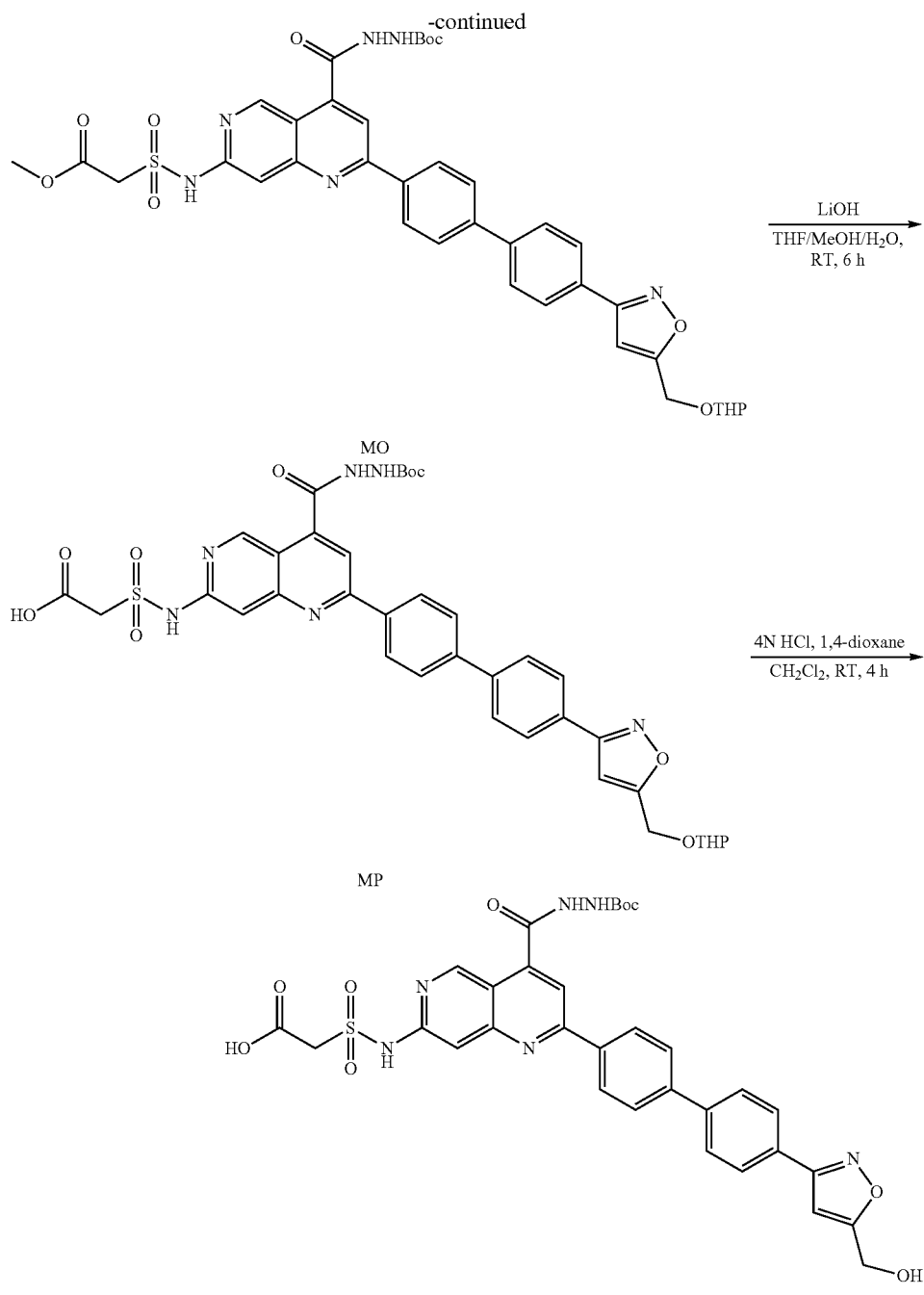

Example 328

2-(N-(4-(hydrazinecarbonyl)-2-(4'-(5-(hydroxymethyl)isoxazol-3-yl)-[1,1'-biphenyl]-4-yl)-1,6-naphthyridin-7-yl)sulfamoyl)acetic acid hydrochloride (328)

To a stirred solution of compound MM (300 mg, 0.47 mmol) in DCM (15 mL) under nitrogen atmosphere were added pyridine (372 mg, 4.7 mmol), DMAP (catalytic) and 2-methyl(chloro sulfonyl)acetate (203 mg, 1.17 mmol) at 0° C. The reaction was allowed to warm to RT and was stirred for 24 h. After complete consumption of the starting material (by TLC), the reaction mixture was diluted with ice cold water (10 mL) and was extracted with DCM (2×30 mL). The combined organic extracts were washed with water (2×20 mL), brine (20 ml), dried over sodium sulfate, filtered and concentrated under reduced pressure. The crude material was purified by silica gel column chromatography eluting with 2% MeOH/DCM to afford compound MO (45 mg) as a yellow solid. MS (ESI): 70% m/z 773.83 [M+1]$^+$ To a stirred solution of compound MO (45 mg, impure material) in THF:MeOH:H$_2$O (2 mL:1 mL:1 mL) were added lithium hydroxide monohydrate (7.3 mg, 0.17 mmol) at 0° C. The reaction was allowed to warm to RT and was stirred for 6 h. After complete consumption of the starting material (by TLC), the volatiles were evaporated under reduced pressure. The crude product mixture was diluted with water and the pH was adjusted to pH~4 by using an acetic acid solution (0.1 mL). The precipitate was filtered and dried under reduced pressure to afford compound MP (35 mg, 0.04 mmol, 10% over two steps) as a yellow solid. $^1$H-NMR (DMSO-$d_6$, 400 MHz): δ 10.60 (br s, 1H), 9.34 (s, 1H), 9.22 (d, J=11.6 Hz, 1H), 8.43 (t, J=7.6 Hz, 2H), 8.04-7.94 (m, 6H), 7.57-7.50 (m, 1H), 7.16 (s, 1H), 4.83 (s, 2H), 4.79-4.68 (m, 1H), 3.83-3.77 (m, 2H), 3.38 (s, 2H), 1.75-1.68 (m, 4H), 1.56-1.53 (m, 2H), 1.49 (s, 9H). MS (ESI): m/z 759.80 [M+1]$^+$ To a stirred solution of compound MP (35 mg, 0.04 mmol) in DCM (2 mL) under nitrogen atmosphere was added 4N HCl in 1,4-dioxane (0.5 mL) at 0° C. The reaction was allowed to warm to RT and was stirred for 4 h. After complete consumption of the starting material (by TLC), the volatiles were evaporated under reduced pressure. The crude material was triturated with CH$_3$CN (2 mL) to afford 328 (15 mg as an HCl salt) as a yellow solid. $^1$H-NMR (DMSO-$d_6$, 400 MHz): δ 11.34 (s, 2H), 9.45 (s, 1H), 8.48 (d, J=8.4 Hz, 2H), 8.30 (s, 1H), 8.03-7.94 (m, 6H), 7.56 (s, 1H), 7.01 (s, 1H), 4.62 (d, J=11.6 Hz, 4H). MS (ESI): 81.1%; m/z 575.57 [M+1]$^+$

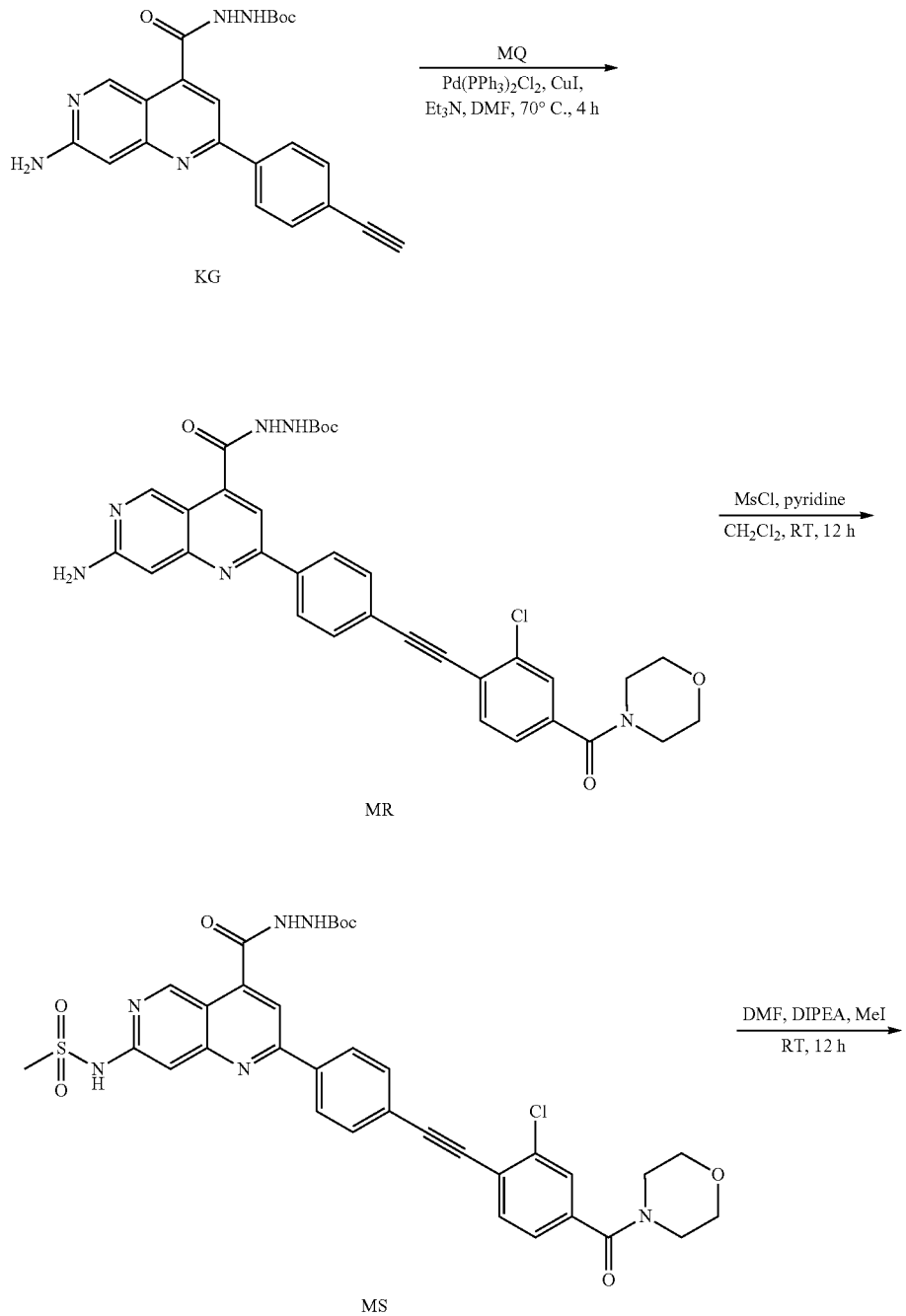

Scheme 89

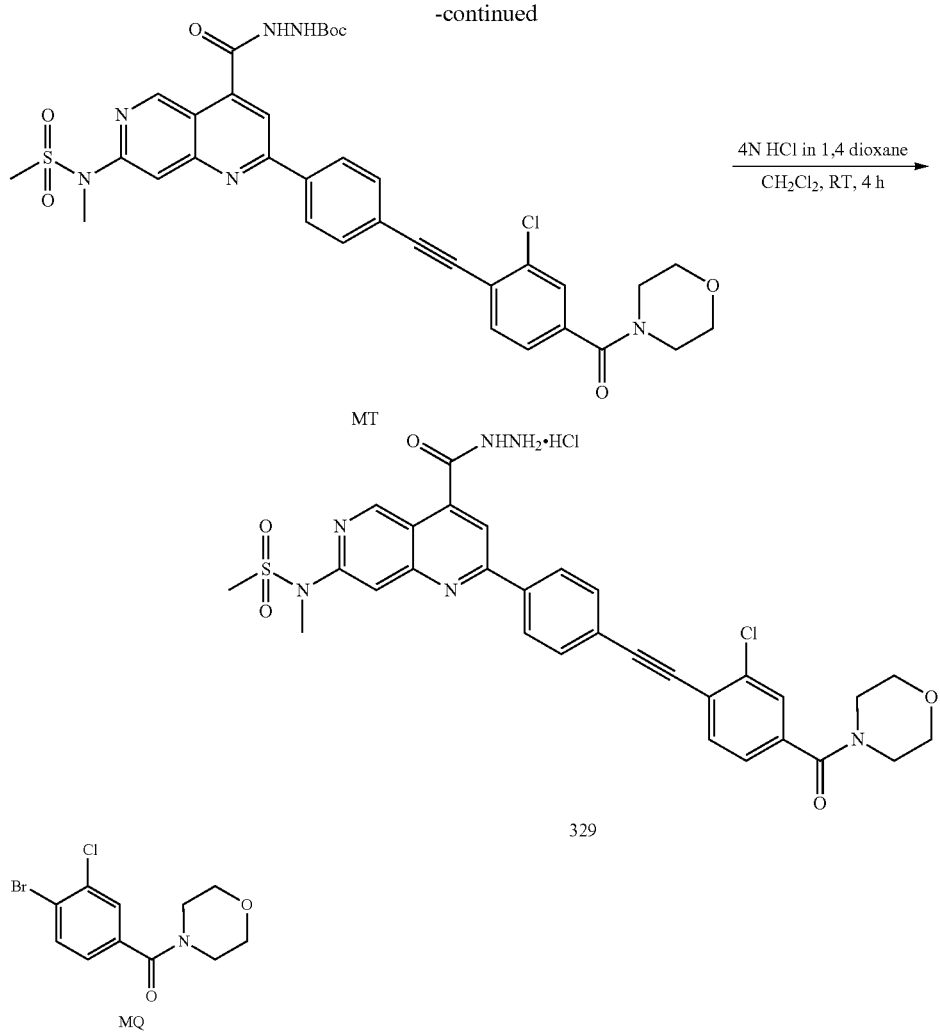

Example 329

Synthesis of N-(2-(4-((2-chloro-4-(morpholine-4-carbonyl)phenyl)ethynyl)phenyl)-4-(hydrazinecarbonyl)-1,6-naphthyridin-7-yl)-N-methylmethanesulfonamide hydrochloride (329)

MQ is synthesized from 4-bromo-3-chlorobenzoic acid and morpholine following a similar procedure as used to synthesize HJ.

To a stirred solution of compound KG (1 g, 2.4 mmol) in DMF (5 mL) under argon atmosphere were added compound MQ (1.2 g, 3.7 mmol) and TEA (3.6 mL, 24.8 mmol). The solution was purged with argon for 10 min followed by the addition of copper iodide (47 mg, 0.24 mmol) and Pd(PPh$_3$)$_2$Cl$_2$ (174 mg, 0.24 mmol). The reaction was heated to 70° C. and was stirred for 4 h. After complete consumption of the starting material (by TLC) the reaction mixture was diluted with ice cold water (20 mL) and was extracted with EtOAc (2×30 mL). The combined organic extracts were washed with water (2×20 mL), dried over sodium sulfate, filtered and concentrated under reduced pressure. The crude product was purified by silica gel column chromatography eluting with 2-5% MeOH/DCM to afford compound MR (500 mg, 33%) as a yellow solid. $^1$H-NMR (DMSO-d$_6$, 500 MHz): δ 10.49 (br s, 1H), 9.19 (br s, 2H), 8.34 (d, J=7.0 Hz, 2H), 7.81-7.68 (m, 5H), 7.46 (d, J=7.5 Hz, 2H), 6.82 (S, 1H), 6.51 (br s, 2H), 3.62-3.51 (m, 6H), 3.32-3.30 (m, 2H), 1.50 (s, 9H). MS (ESI): m/z 627.10 [M+1]$^+$ To a stirred solution of compound MR (200 mg, 0.31 mmol) in DCM (25 mL) under nitrogen atmosphere were added pyridine (0.05 ml, 0.63 mmol) and methanesulfonyl-chloride (0.03 mL, 0.38 mmol) at 0° C. The reaction was allowed to warm to RT and was stirred for 12 h. After complete consumption of the starting material (by TLC) the reaction mixture was diluted with ice cold water (10 mL) and the compound was extracted with DCM (2×10 mL). The combined organic extracts were washed with water (2×20 mL), brine (20 ml), dried over sodium sulfate, filtered and concentrated under reduced pressure. The crude product was purified by silica gel column chromatography eluting with 3% MeOH/DCM to afford compound MS (100 mg, 45%) as a yellow solid. $^1$H-NMR (DMSO-d$_6$, 400 MHz): δ 11.00 (br s, 1H), 10.63 (br s, 1H), 9.51 (br s, 1H), 9.28 (br s, 1H), 8.44 (d, J=8 Hz, 2H), 8.15 (s, 1H), 7.82-7.79 (m, 3H), 7.68 (s, 1H), 7.55 (s, 1H), 7.47-7.44 (m, 1H), 3.69-3.54 (br s, 6H), 3.40-3.37 (m, 5H), 1.49 (s, 9H). MS (ESI): m/z 705.18 [M+1]$^+$ To a stirred solution of compound MS (60 mg, 0.08 mmol) in DMF (10 mL) under nitrogen atmosphere were added DIPEA (21.95 mg, 0.17 mmol) and MeI (12 mg, 0.08 mmol) at 0° C. The reaction was allowed to warm to RT and was stirred for 12 h. After complete consumption of the starting material (by TLC), the reaction mixture was diluted with ice cold water (10 mL) and the compound was extracted with DCM (2×10 mL). The combined organic extracts were washed with water (2×20 mL), brine (20 ml), dried over sodium sulfate, filtered and concentrated under reduced pressure. The crude was purified by silica gel column chromatography eluting with 2% MeOH/DCM to afford compound MT (42 mg, 69%) as a yellow solid. $^1$H-NMR (DMSO-d$_6$, 400 MHz): δ 9.56 (s, 1H), 8.23 (d, J=8.4 Hz, 2H), 8.20-8.19 (m, 1H), 8.03 (s, 1H), 7.86 (s, 1H), 7.74 (d, J=8.4 Hz, 2H), 7.61 (d, J=7.6 Hz, 1H), 7.50 (s, 1H), 7.29 (s, 1H), 6.80 (br s, 1H), 3.90-3.71 (br s, 6H), 3.51 (s, 5H), 3.25 (s, 3H), 1.55 (s, 9H). MS (ESI): m/z 719.21 [M+1]$^+$ To a stirred solution of compound MT (20 mg, 0.027 mmol) in DCM (2 mL) under nitrogen atmosphere was added 4N HCl in 1,4-dioxane (0.5 mL) at 0° C. The reaction was allowed to warm to RT and was stirred for 4 h. After complete consumption of the starting material (by LC-MS), the volatiles were evaporated under reduced pressure. The crude product was triturated with CH$_3$CN (2 mL) to afford 329 (20 mg as an HCl salt) as a brown solid. $^1$H-NMR (DMSO-d$_6$, 400 MHz): δ 11.69 (m, 1H), 11.65 (br s, 1H), 9.54 (s, 1H), 8.48 (d, J=8.4 Hz, 2H), 8.40 (s, 1H), 7.95 (s, 1H), 7.86-7.79 (m, 3H), 7.68 (s, 1H), 7.46 (d, J=8.0 Hz, 1H), 3.73-3.63 (br s, 8H), 3.47 (s, 3H), 3.31 (s, 3H). MS (ESI): m/z 619.09 [M+1]$^+$. HPLC: 85.87%

Scheme 90

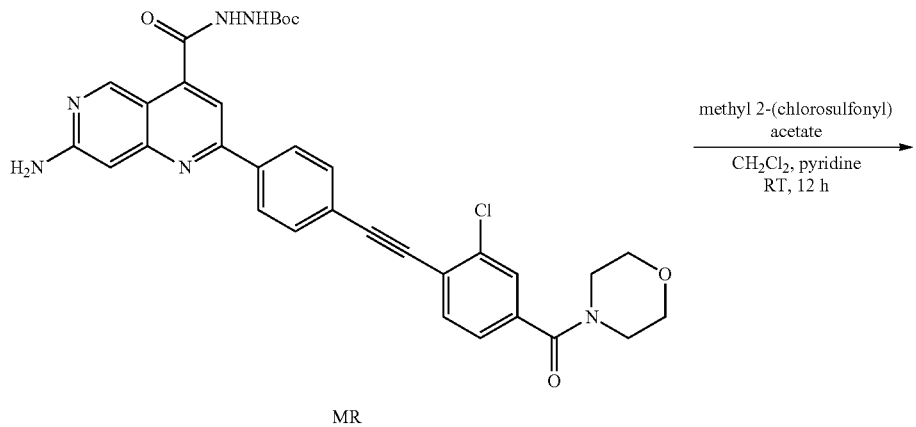

MR

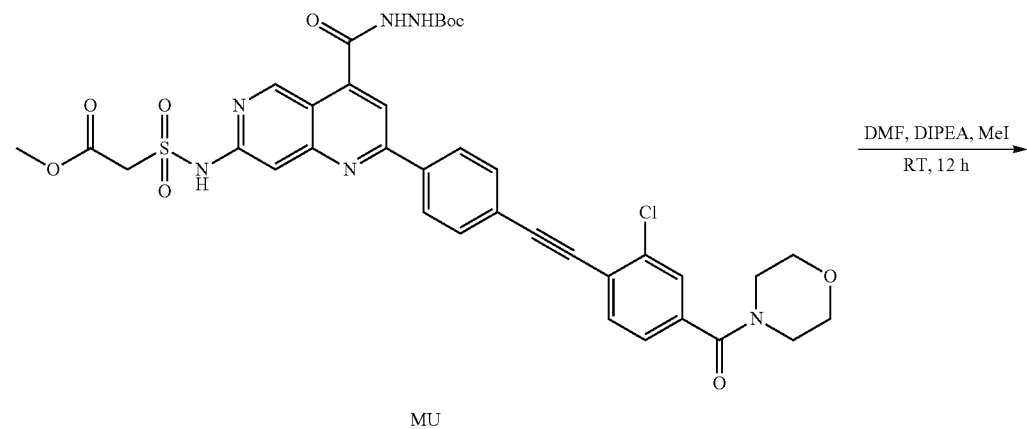

MU

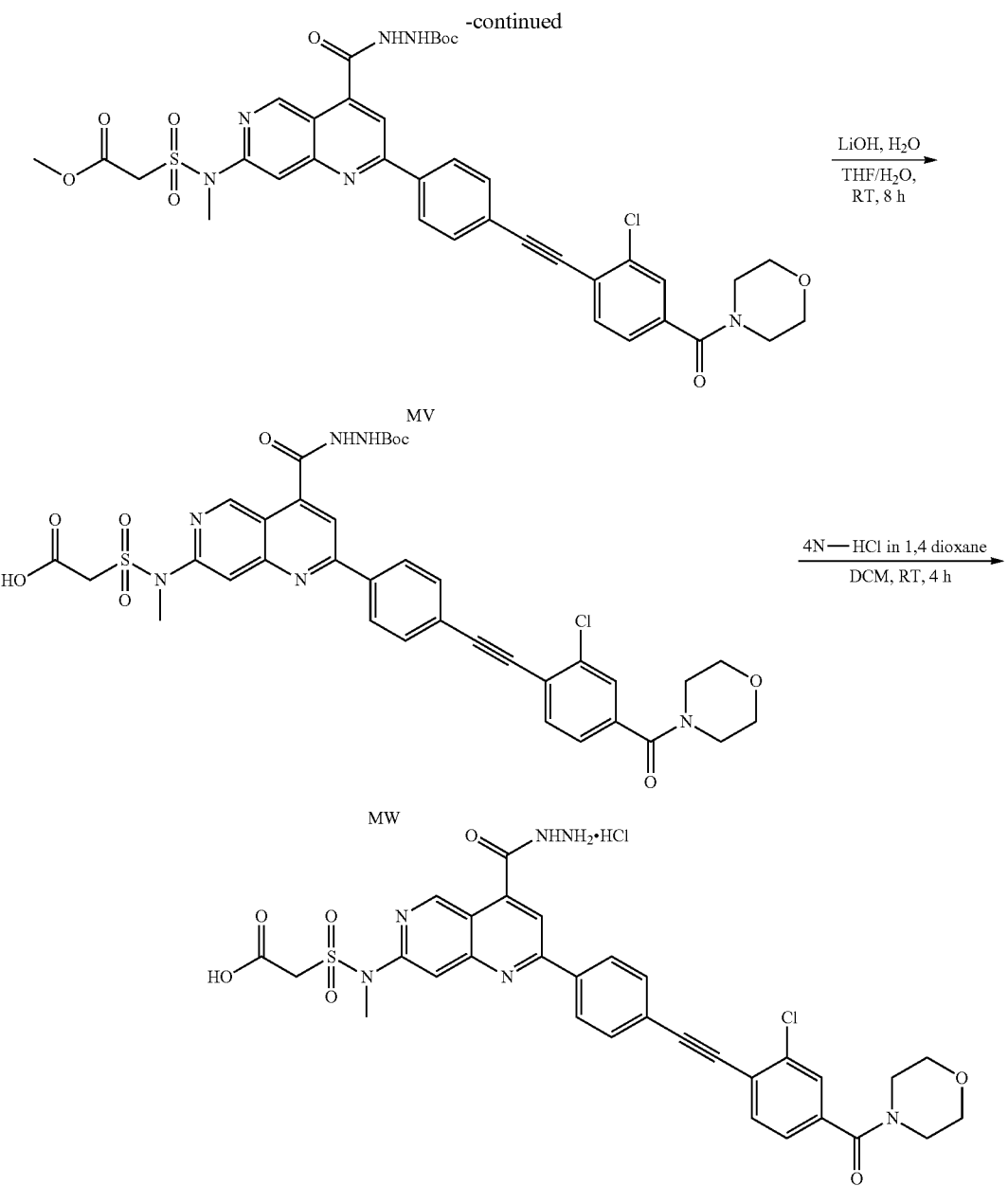

Example 330

Synthesis of 2-(N-(2-(4-((2-chloro-4-(morpholine-4-carbonyl)phenyl)ethynyl)phenyl)-4-(hydrazinecarbonyl)-1,6-naphthyridin-7-yl)-N-methylsulfamoyl) acetic acid hydrochloride (330)

To a stirred solution of compound MR (200 mg, 0.31 mmol) in DCM (25 mL) under nitrogen atmosphere were added pyridine (0.05 ml, 0.63 mmol) and methyl 2-(chlorosulfonyl)acetate (0.03 mL, 0.31 mmol) at 0° C. The reaction was allowed to warm to RT and was stirred for 12 h. After complete consumption of the starting material (by TLC), the reaction mixture was diluted with ice cold water (10 mL) and the compound was extracted with DCM (2×10 mL). The combined organic extracts were washed with water (2×20 mL), brine (20 ml), dried over sodium sulfate, filtered and concentrated under reduced pressure. The crude product was purified by silica gel column chromatography eluting with 2% MeOH/DCM to afford compound MU (100 mg, 41%) as a yellow solid. $^1$H-NMR (DMSO-$d_6$, 400 MHz): δ 11.45 (br s, 1H), 10.64 (br s, 1H), 9.51 (br s, 1H), 9.29 (s, 1H), 8.44 (d, J=8.0 Hz, 2H), 8.17 (s, 1H), 7.83-7.80 (m, 3H), 7.72-7.66 (m, 3H), 7.54 (s, 1H), 6.71 (s, 1H), 5.99 (s, 1H), 4.15-4.10 (m, 2H), 3.65 (s, 3H), 3.57 (br s, 8H), 1.49 (s, 9H). MS (ESI): m/z 763.22 [M+1]$^+$ To a stirred solution of compound MU (100 mg, 0.18 mmol) in DMF (10 mL) under nitrogen atmosphere were added DIPEA (0.07 ml, 0.37 mmol) and MeI (0.012 ml, 0.18 mmol) at 0° C. The reaction was allowed to warm to RT and was stirred for 12 h. After complete consumption of the starting material (by TLC), the reaction mixture was diluted with ice cold water (10 mL) and was extracted with DCM (2×10 mL). The combined organic extracts were washed with water (2×20 mL), brine (20 ml), dried over sodium sulfate, filtered and concentrated under reduced pressure. The crude product was purified by silica gel column chromatography eluting with 2% MeOH/DCM to afford compound MV (75 mg, 74%) as a yellow solid. $^1$H-NMR (DMSO-$d_6$, 400 MHz): δ 9.55 (s, 1H), 8.23 (d, J=8.4 Hz, 1H), 8.03 (s, 1H), 7.75-7.69 (m, 3H), 7.62 (d, J=8.4 Hz, 1H), 7.53-7.50 (m, 2H), 7.29 (s, 1H), 6.83 (br s, 1H), 4.69 (s, 2H), 4.23-4.20 (m, 1H), 3.77 (s, 9H), 3.72 (s, 3H), 3.57 (s, 2H), 1.57 (s, 9H). MS (ESI): m/z 777.25 [M+1]$^+$ To a stirred solution of compound MV (70 mg, 0.09 mmol) in THF:H$_2$O (5 mL:1 mL) was added lithium hydroxide monohydrate (7.6 mg, 0.18 mmol) at 0° C. The reaction was allowed to warm to RT and was stirred for 8 h. After complete consumption of the starting material (by TLC) the volatiles were evaporated under reduced pressure. The crude material was diluted with water and the pH was adjusted to pH~4 by using an acetic acid solution (0.1 mL). The precipitate was filtered and dried under reduced pressure to afford compound MW (51.5 mg, 75%) as a yellow solid. $^1$H-NMR (DMSO-$d_6$, 400 MHz): δ 10.66 (br s, 1H), 9.56 (br s, 1H), 9.29 (br s, 1H), 8.47 (d, J=8 Hz, 2H), 8.24 (br s, 1H), 7.92 (s, 1H), 7.83-7.79 (m, 3H), 7.71-7.68 (m, 2H), 7.46 (d, J=7.6 Hz, 1H), 4.52 (br s, 2H), 3.61 (br s, 8H), 3.51 (s, 3H), 1.49 (s, 9H). MS (ESI): m/z 763.22 [M+1]$^+$ To a stirred solution of compound MW (40 mg, 0.05 mmol) in DCM (2 mL) under nitrogen atmosphere was added 4N HCl in 1,4-dioxane (1.0 mL) at 0° C. The reaction was allowed to warm to RT and was stirred for 4 h. After complete consumption of the starting material (by LC-MS), the volatiles were evaporated under reduced pressure. The crude product was triturated with CH$_3$CN (2 mL) to afford 330 (20 mg as an HCl salt) as a brown solid. $^1$H-NMR (DMSO-$d_6$, 400 MHz): δ 11.62 (br s, 1H), 9.53 (s, 1H), 8.48 (d, J=8.0 Hz, 2H), 8.40 (s, 1H), 7.93 (s 1H), 7.86-7.79 (m, 3H), 7.68 (s, 1H), 7.46 (d, J=8.0 Hz, 1H), 4.70 (s, 2H), 3.61 (br s, 8H), 3.37 (s, 3H). MS (ESI): m/z 663.05 [M+1]$^+$. HPLC: 90.05%.

TABLE 1

Analytical Data

| Example # | HPLC Method | HPLC RT | MS(ESI) (M + H) | Chirality | Structure |
|---|---|---|---|---|---|
| 1 | A | 1.47 | 454.6 | Racemate | 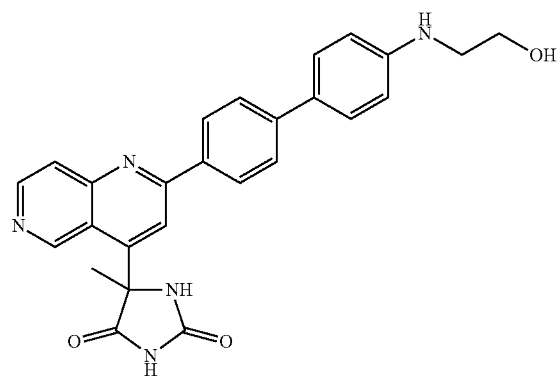 [SMILES: CC1(c2cc(-c3ccc(-c4ccc(NCCO)cc4)cc3)nc3ccncc23)NC(=O)NC1=O] |
| 2 | A | 1.38 | 416 | | 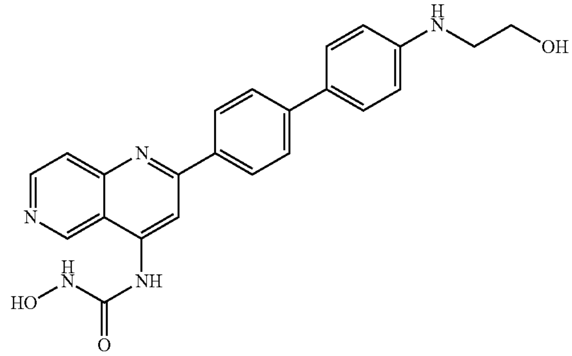 [SMILES: O=C(NO)Nc1cc(-c2ccc(-c3ccc(NCCO)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 3 | A | 1.45 | 386.2 | | 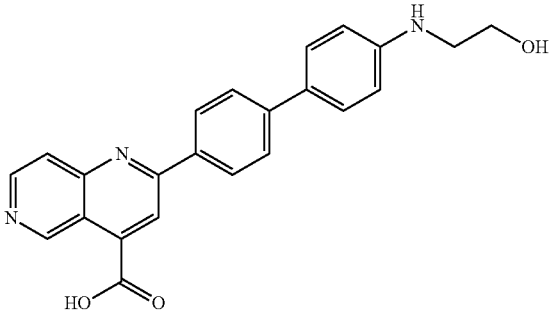 [SMILES: O=C(O)c1cc(-c2ccc(-c3ccc(NCCO)cc3)cc2)nc2ccncc12] |
| 4 | A | 1.41 | 400.2 | | 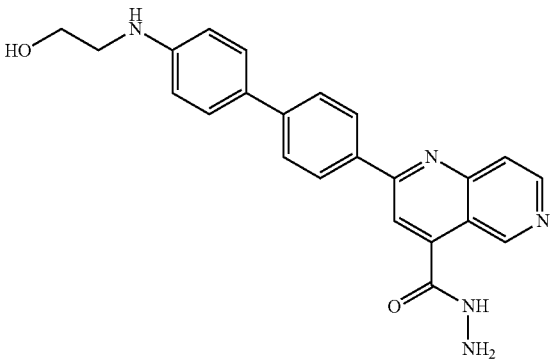 [SMILES: NNC(=O)c1cc(-c2ccc(-c3ccc(NCCO)cc3)cc2)nc2ccncc12] |
| 5 | A | 1.85 | 470 | | 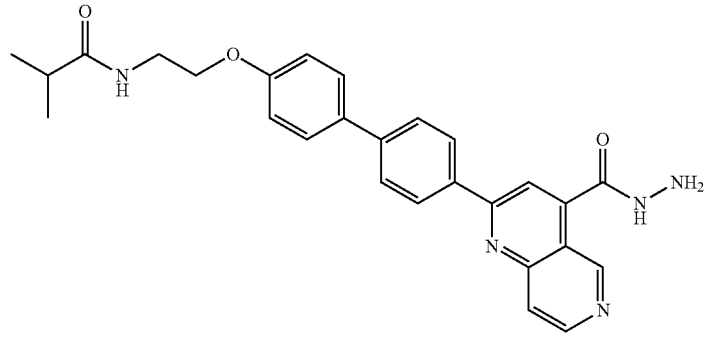 [SMILES: CC(C)C(=O)NCCOc1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 6 | A | 1.70 | 478 | | 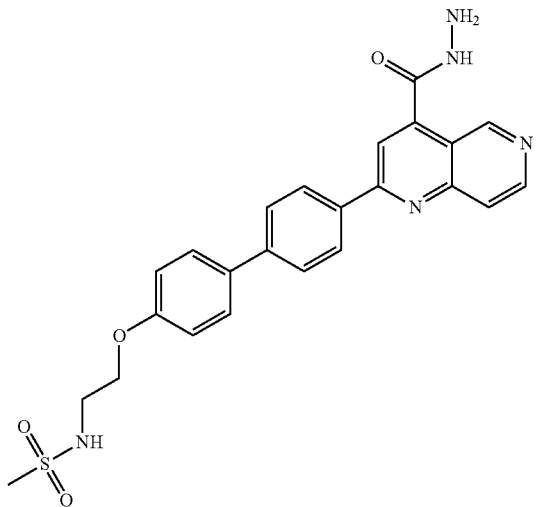 [SMILES: CS(=O)(=O)NCCOc1ccc(-c2ccc(-c3cc(C(=O)NN)c4cnccc4n3)cc2)cc1] |
| 7 | A | 1.61 | 437 | | 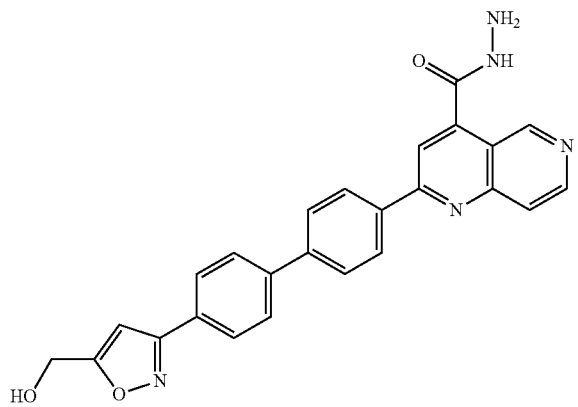 [SMILES: NNC(=O)c1cc(-c2ccc(-c3ccc(-c4cc(CO)on4)cc3)cc2)nc2ccncc12] |
| 8 | A | 2.63 | 552.8 | Racemate | 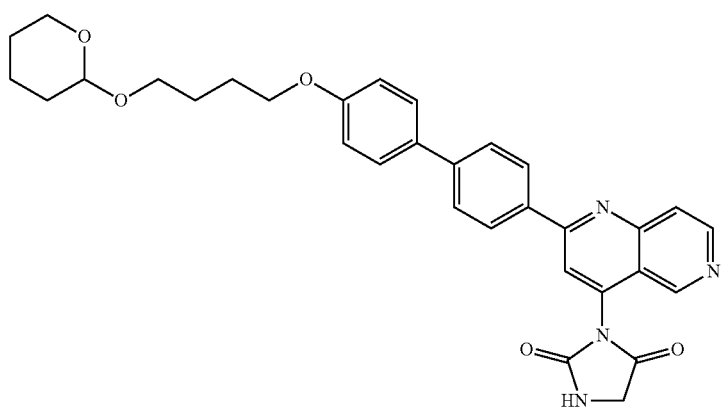 |

TABLE 1-continued
Analytical Data
| Example # | HPLC Method | HPLC RT | MS(ESI) (M + H) | Chirality | Structure |
|---|---|---|---|---|---|
| 9 | A | 1.90 | 469 | | 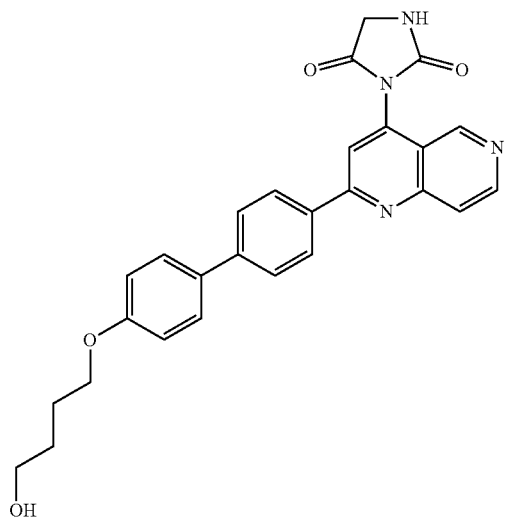 |
| 10 | A | 2.88 | 569.5 | Racemate | 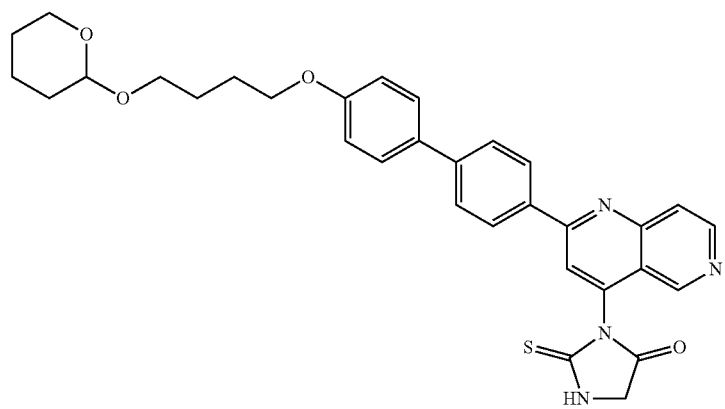 [SMILES: O=C1CNC(=O)N1c1cc(-c2ccc(-c3ccc(OCCCCOC4CCCCO4)cc3)cc2)nc2ccncc12] |
| 11 | A | 2.06 | 483.6 | | 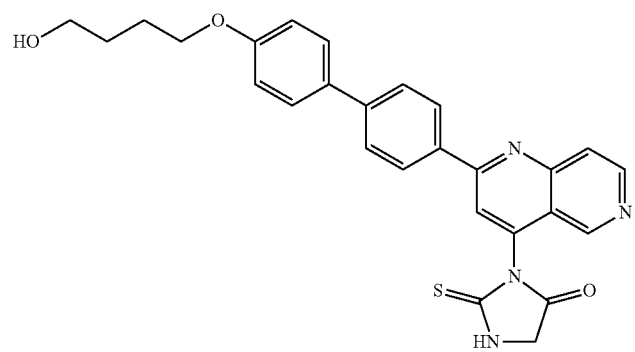 [SMILES: O=C1CNC(=S)N1c1cc(-c2ccc(-c3ccc(OCCCCO)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 12 | A | 2.20 | 468.6 | | 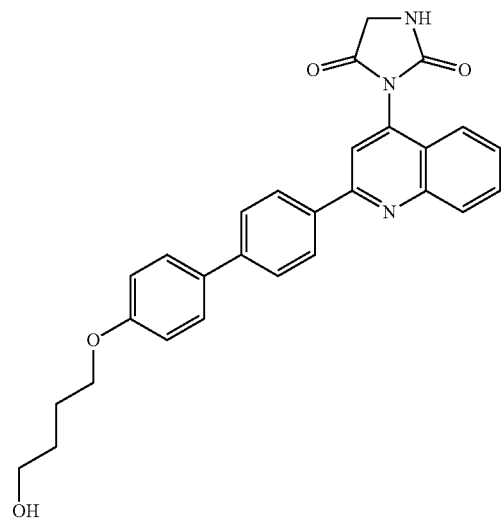 [SMILES: O=C1CNC(=O)N1c1cc(-c2ccc(-c3ccc(OCCCCO)cc3)cc2)nc2ccccc12] |
| 13 | A | 1.40 | 412 (M − 1) | | 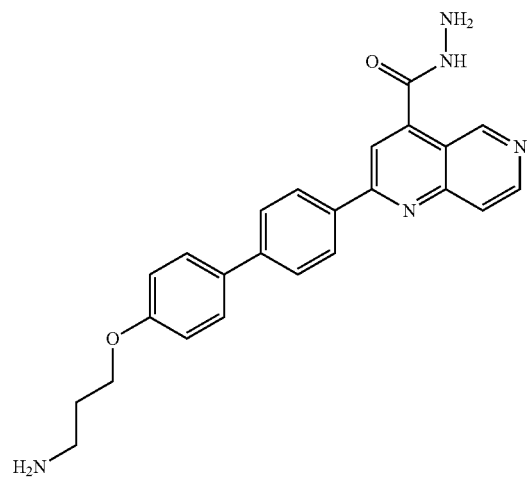 [SMILES: NCCCOc1ccc(-c2ccc(-c3cc(C(=O)NN)c4cnccc4n3)cc2)cc1] |

TABLE 1-continued

Analytical Data

| Example # | HPLC Method | HPLC RT | MS(ESI) (M + H) | Chirality | Structure |
|---|---|---|---|---|---|
| 14 | A | 1.79 | 492.7 | | 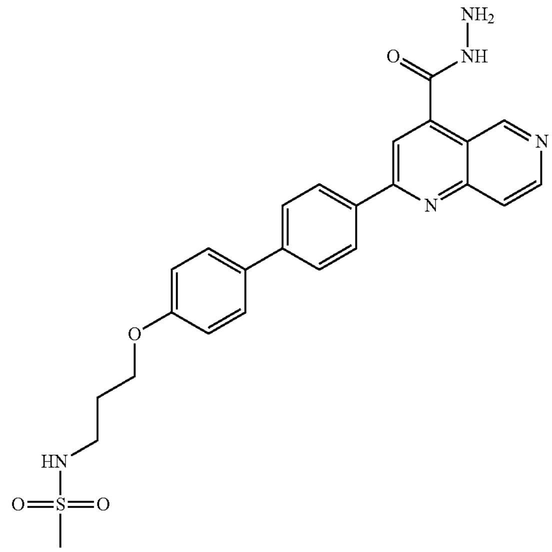 [SMILES: CS(=O)(=O)NCCCOc1ccc(-c2ccc(-c3cc(C(=O)NN)c4cnccc4n3)cc2)cc1] |
| 15 | A | 1.65 | 456.7 | | 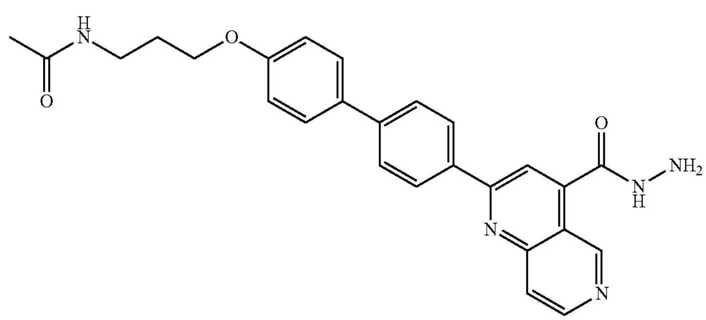 [SMILES: CC(=O)NCCCOc1ccc(-c2ccc(-c3cc(C(=O)NN)c4cnccc4n3)cc2)cc1] |
| 16 | A | 1.83 | 521 | | 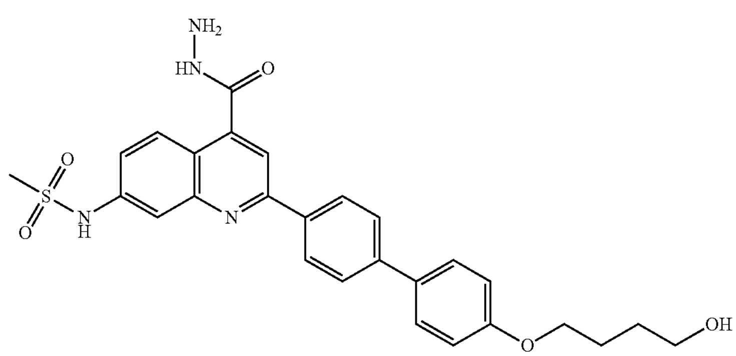 [SMILES: CS(=O)(=O)Nc1ccc2c(C(=O)NN)cc(-c3ccc(-c4ccc(OCCCCO)cc4)cc3)nc2c1] |

TABLE 1-continued
Analytical Data
| Example # | HPLC Method | HPLC RT | MS(ESI) (M + H) | Chirality | Structure |
|---|---|---|---|---|---|
| 17 | A | 1.53 | 477 | | 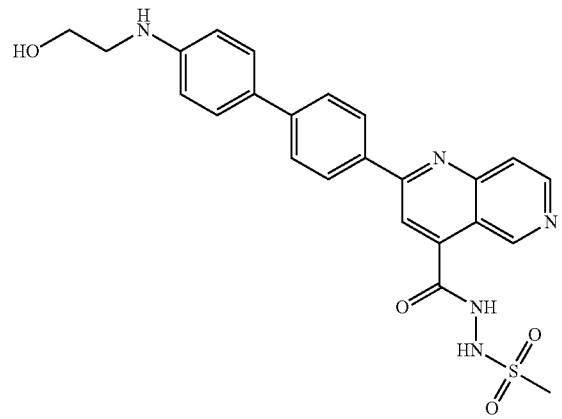 [SMILES: CS(=O)(=O)NNC(=O)c1cc(-c2ccc(-c3ccc(NCCO)cc3)cc2)nc2ccncc12] |
| 18 | A | 1.49 | 414 | | 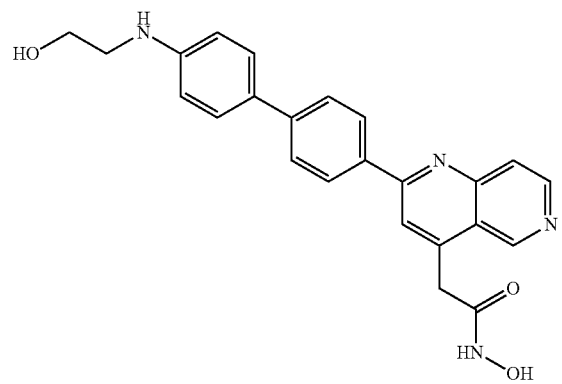 [SMILES: O=C(Cc1cc(-c2ccc(-c3ccc(NCCO)cc3)cc2)nc2ccncc12)NO] |
| 19 | A | 2.01 | 385.7 | | 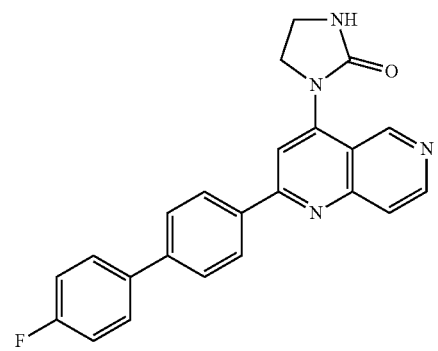 [SMILES: O=C1NCCN1c1cc(-c2ccc(-c3ccc(F)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 20 | A | 2.16 | 399.4 | | 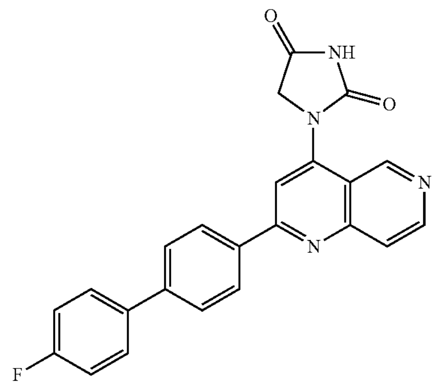 [SMILES: O=C1CN(c2cc(-c3ccc(-c4ccc(F)cc4)cc3)nc3ccncc23)C(=O)N1] |
| 21 | C | 10.64 | 384.4 | | 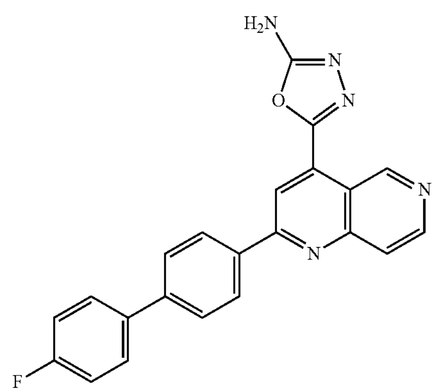 [SMILES: Nc1nnc(-c2cc(-c3ccc(-c4ccc(F)cc4)cc3)nc3ccncc23)o1] |
| 22 | A | 1.59 | 434 | | 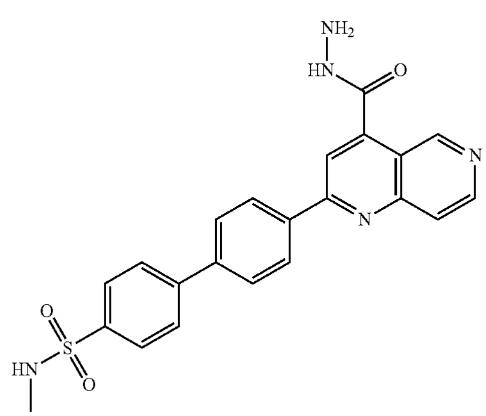 [SMILES: CNS(=O)(=O)c1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 23 | C | 8.07 | 432.5 (M − 1) | | 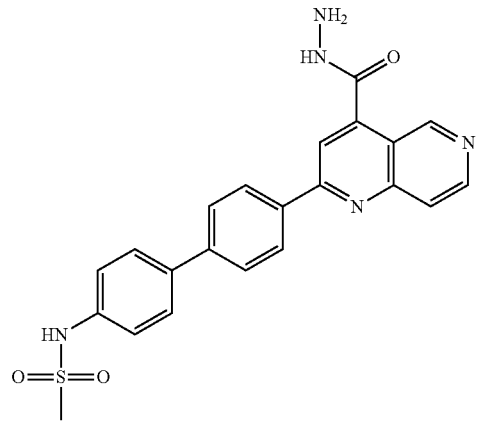 [SMILES: CS(=O)(=O)Nc1ccc(-c2ccc(-c3cc(C(=O)NN)c4cnccc4n3)cc2)cc1] |
| 24 | C | 7.83 | 398 | | 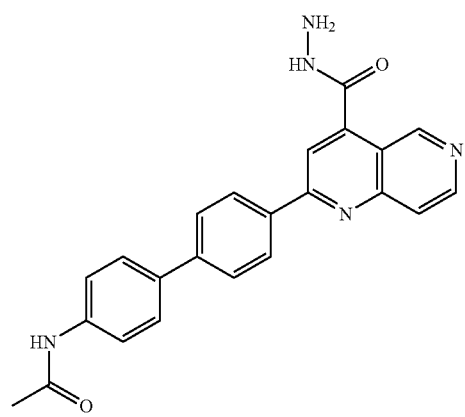 [SMILES: CC(=O)Nc1ccc(-c2ccc(-c3cc(C(=O)NN)c4cnccc4n3)cc2)cc1] |
| 25 | A | 1.47 | 398 | | 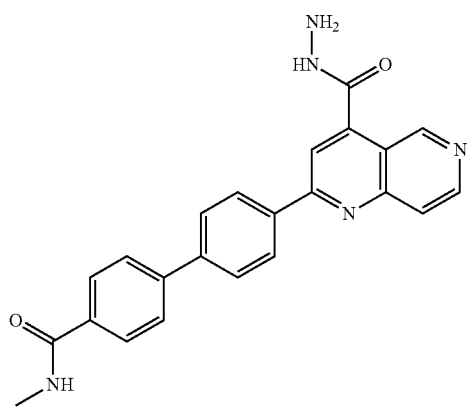 [SMILES: CNC(=O)c1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 26 | A | 1.76 | 454 | Racemate | 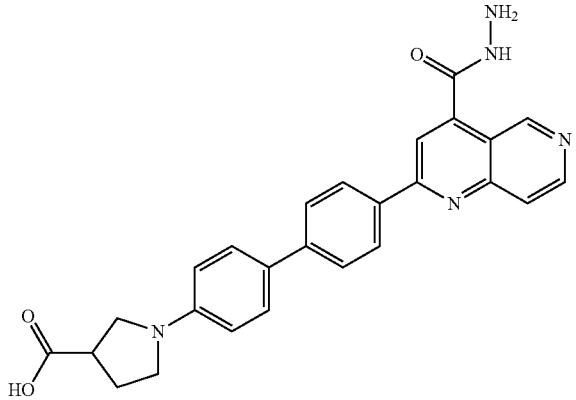 [SMILES: NNC(=O)c1cc(-c2ccc(-c3ccc(N4CCC(C(=O)O)C4)cc3)cc2)nc2ccncc12] |
| 27 | A | 1.61 | 468.3 | | 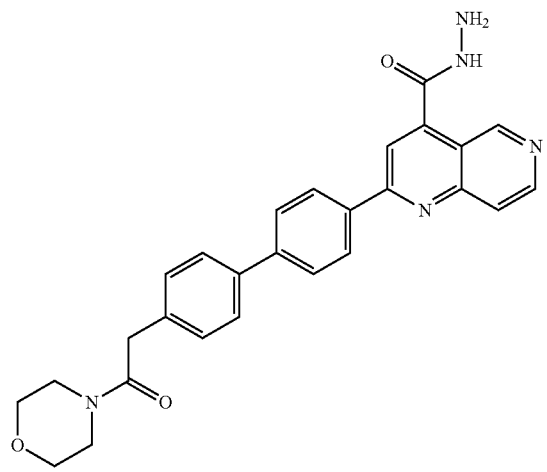 [SMILES: NNC(=O)c1cc(-c2ccc(-c3ccc(CC(=O)N4CCOCC4)cc3)cc2)nc2ccncc12] |
| 28 | A | 1.68 | 484 | | 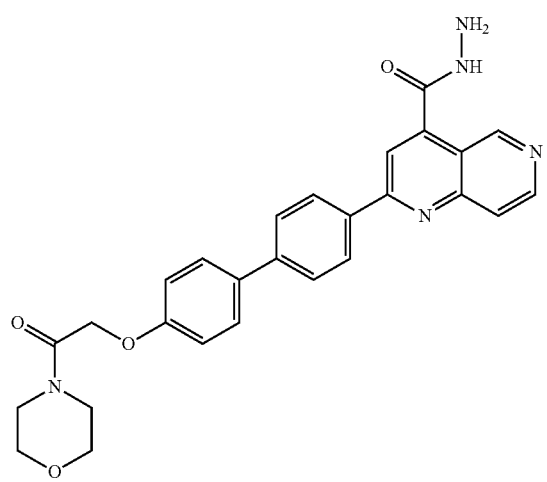 [SMILES: NNC(=O)c1cc(-c2ccc(-c3ccc(OCC(=O)N4CCOCC4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 29 | A | 2.10 | 504 | | 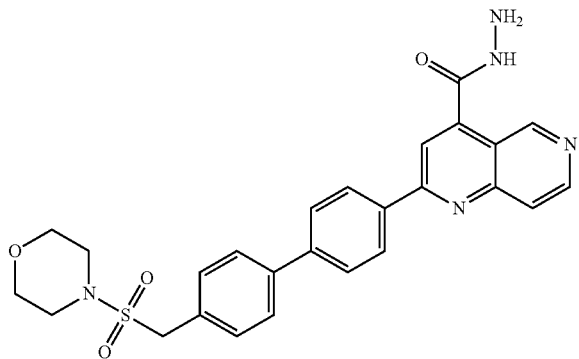 [SMILES: NNC(=O)c1cc(-c2ccc(-c3ccc(CS(=O)(=O)N4CCOCC4)cc3)cc2)nc2ccncc12] |
| 30 | | | 452.3 | | 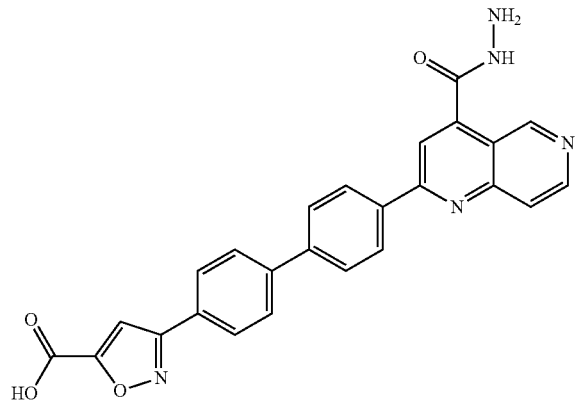 [SMILES: NNC(=O)c1cc(-c2ccc(-c3ccc(-c4cc(C(=O)O)on4)cc3)cc2)nc2ccncc12] |
| 31 | B | 8.02 | 549.3 | R | 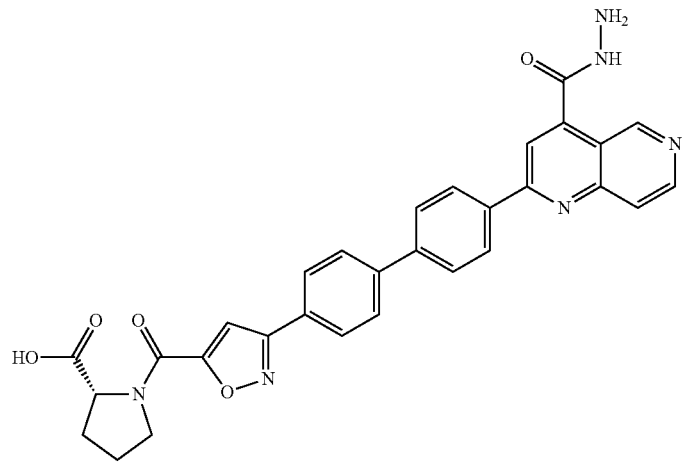 [SMILES: NNC(=O)c1cc(-c2ccc(-c3ccc(-c4cc(C(=O)N5CCC[C@@H]5C(=O)O)on4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 32 | A | 1.81 | 495.2 | | 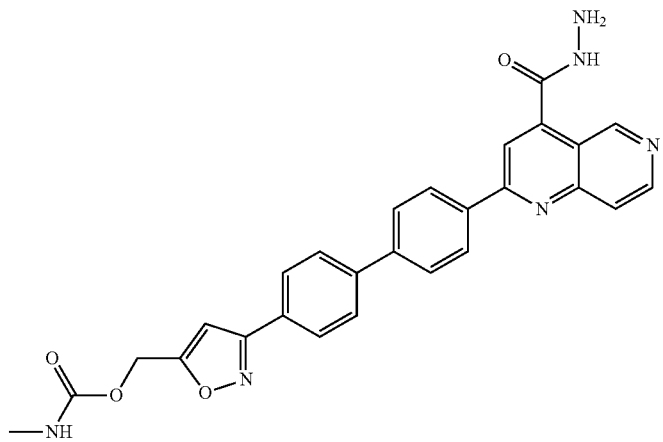 [SMILES: CNC(=O)OCc1cc(-c2ccc(-c3ccc(-c4cc(C(=O)NN)c5cnccc5n4)cc3)cc2)no1] |
| 33 | A | 1.60 | 494.3 | | 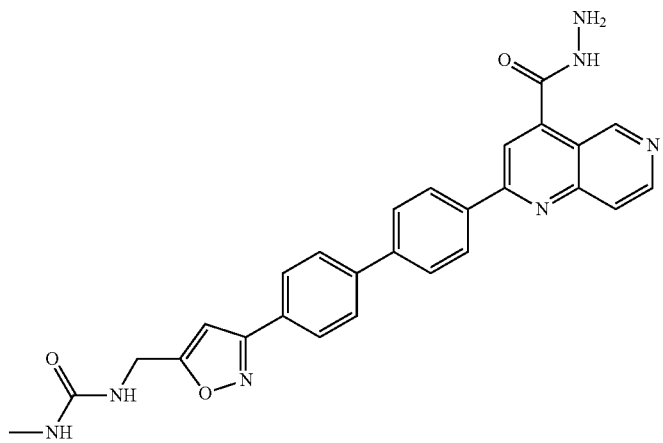 [SMILES: CNC(=O)NCc1cc(-c2ccc(-c3ccc(-c4cc(C(=O)NN)c5cnccc5n4)cc3)cc2)no1] |
| 34 | A | 1.60 | 479.3 | | 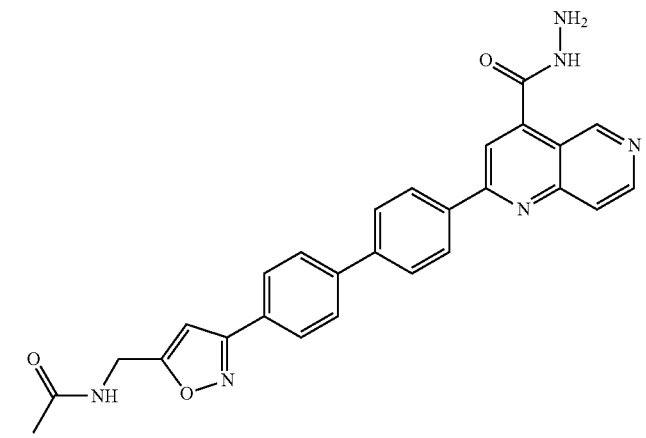 [SMILES: CC(=O)NCc1cc(-c2ccc(-c3ccc(-c4cc(C(=O)NN)c5cnccc5n4)cc3)cc2)no1] |

TABLE 1-continued
Analytical Data
| Example # | HPLC Method | HPLC RT | MS(ESI) (M + H) | Chirality | Structure |
|---|---|---|---|---|---|
| 35 | A | 1.70 | 515.4 | | 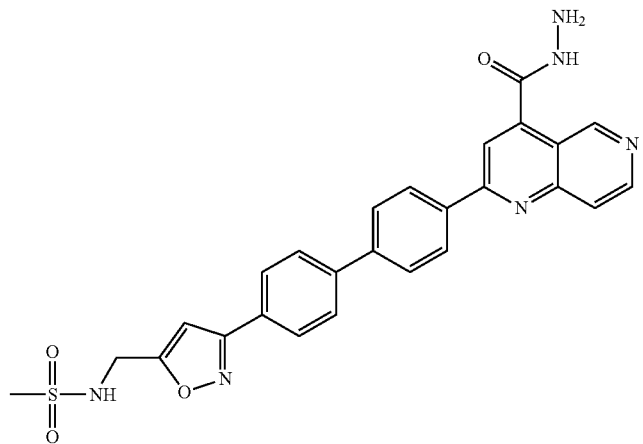 [SMILES: CS(=O)(=O)NCc1cc(-c2ccc(-c3ccc(-c4cc(C(=O)NN)c5cnccc5n4)cc3)cc2)no1] |
| 36 | A | 1.85 | 562.4 | R | 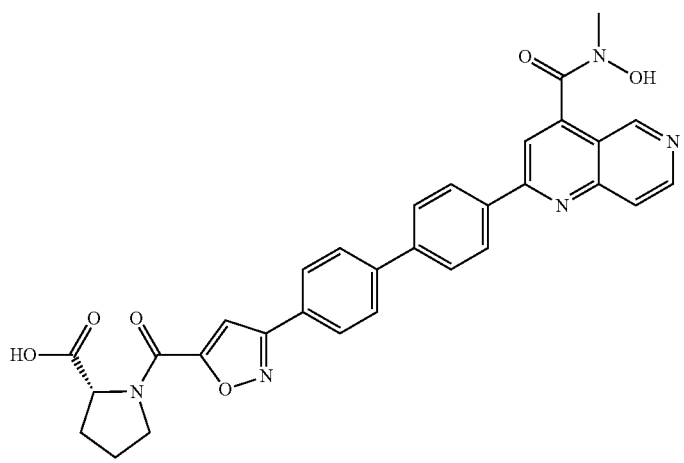 [SMILES: CN(O)C(=O)c1cc(-c2ccc(-c3ccc(-c4cc(C(=O)N5CCC[C@@H]5C(=O)O)on4)cc3)cc2)nc2ccncc12] |
| 37 | A | 1.97 | 521 | | 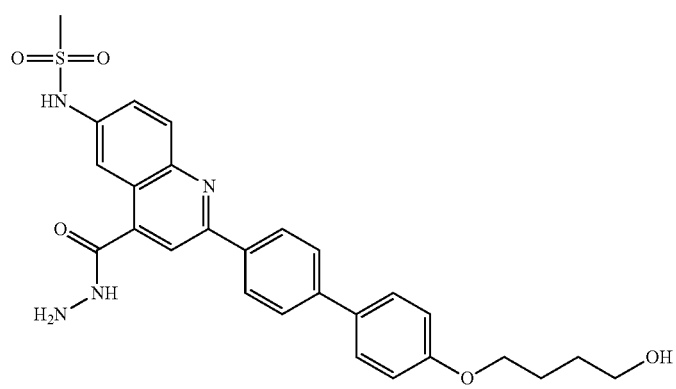 [SMILES: CS(=O)(=O)Nc1ccc2nc(-c3ccc(-c4ccc(OCCCCO)cc4)cc3)cc(C(=O)NN)c2c1] |

TABLE 1-continued
Analytical Data
| Example # | HPLC Method | HPLC RT | MS(ESI) (M + H) | Chirality | Structure |
|---|---|---|---|---|---|
| 38 | D | 9.83 | 365.0 | | 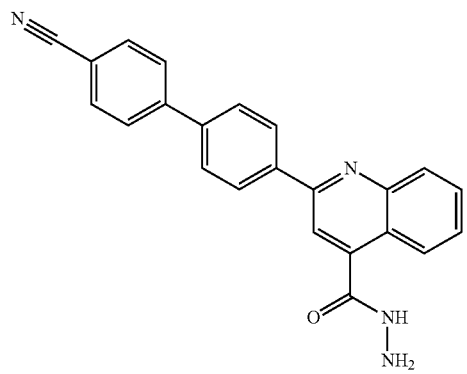 [SMILES: N#Cc1ccc(-c2ccc(-c3cc(C(=O)NN)c4ccccc4n3)cc2)cc1] |
| 39 | A | 1.37 | 414 | | 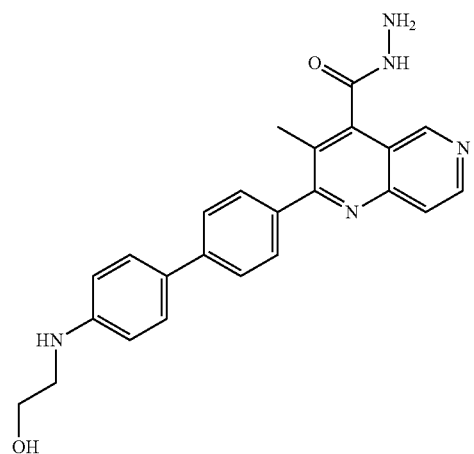 [SMILES: Cc1c(-c2ccc(-c3ccc(NCCO)cc3)cc2)nc2ccncc2c1C(=O)NN] |
| 40 | A | 1.45 | 492 | | 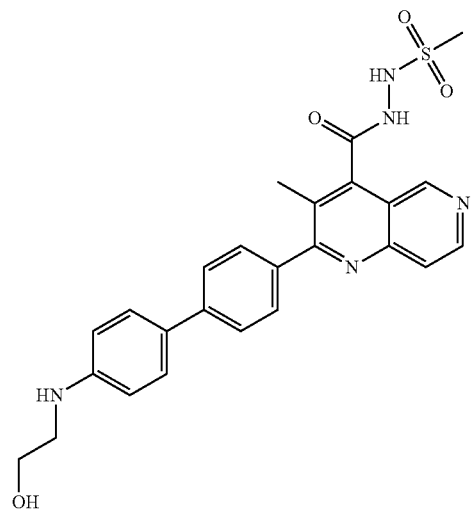 [SMILES: Cc1c(-c2ccc(-c3ccc(NCCO)cc3)cc2)nc2ccncc2c1C(=O)NNS(C)(=O)=O] |

TABLE 1-continued
Analytical Data
| Example # | HPLC Method | HPLC RT | MS(ESI) (M + H) | Chirality | Structure |
|---|---|---|---|---|---|
| 41 | C | 7.98 | 415 | | 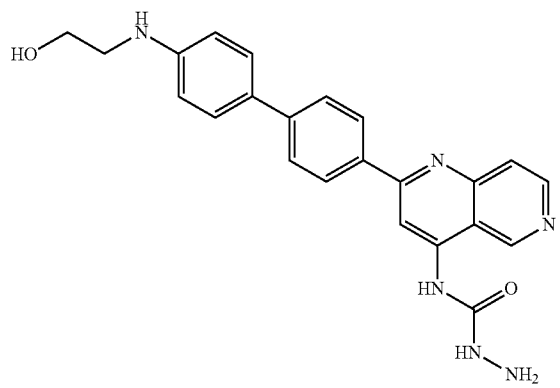 [SMILES: NNC(=O)Nc1cc(-c2ccc(-c3ccc(NCCO)cc3)cc2)nc2ccncc12] |
| 42 | A | 1.89 | 385 | | 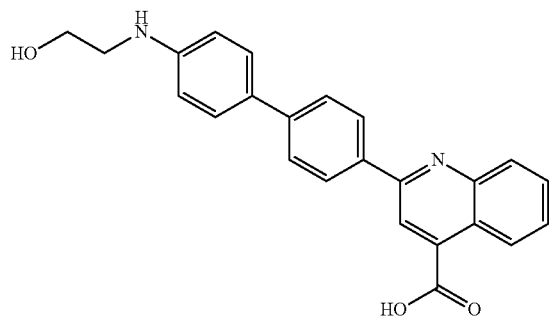 [SMILES: O=C(O)c1cc(-c2ccc(-c3ccc(NCCO)cc3)cc2)nc2ccccc12] |
| 43 | A | 1.66 | 399.1 | | 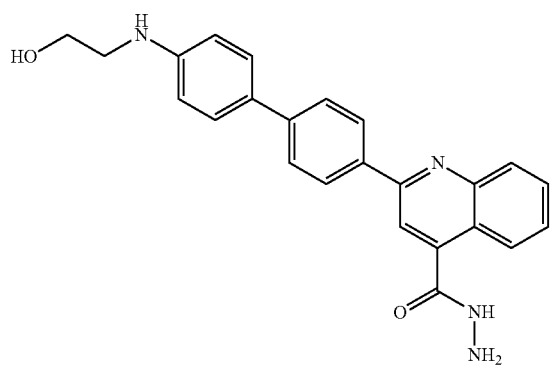 [SMILES: NNC(=O)c1cc(-c2ccc(-c3ccc(NCCO)cc3)cc2)nc2ccccc12] |

TABLE 1-continued
Analytical Data
| Example # | HPLC Method | HPLC RT | MS(ESI) (M + H) | Chirality | Structure |
|---|---|---|---|---|---|
| 44 | A | 1.32 | 430.1 | | 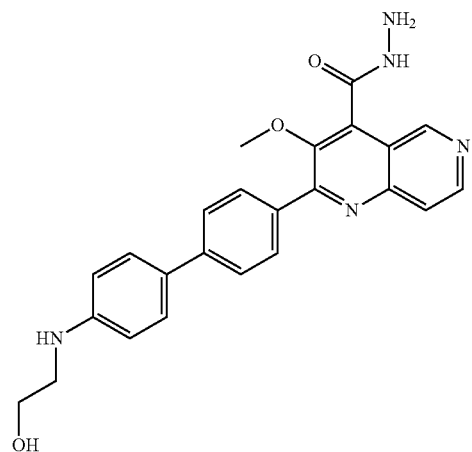 [SMILES: COc1c(-c2ccc(-c3ccc(NCCO)cc3)cc2)nc2ccncc2c1C(=O)NN] |
| 45 | A | 1.27 | 416 | | 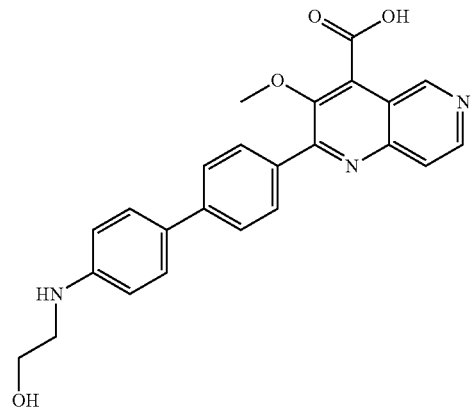 [SMILES: COc1c(-c2ccc(-c3ccc(NCCO)cc3)cc2)nc2ccncc2c1C(=O)O] |
| 46 | C | 7.07 | 400.2 | | 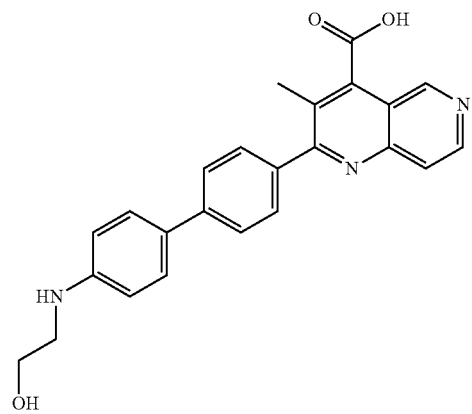 [SMILES: Cc1c(-c2ccc(-c3ccc(NCCO)cc3)cc2)nc2ccncc2c1C(=O)O] |

TABLE 1-continued
Analytical Data
| Example # | HPLC Method | HPLC RT | MS(ESI) (M + H) | Chirality | Structure |
|---|---|---|---|---|---|
| 47 | A | 2.67 | 351.1 | | 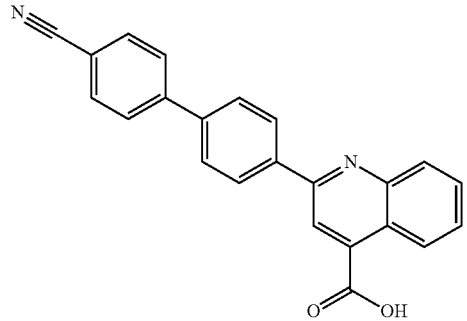 [SMILES: N#Cc1ccc(-c2ccc(-c3cc(C(=O)O)c4ccccc4n3)cc2)cc1] |
| 48 | A | 1.32 | 413 | | 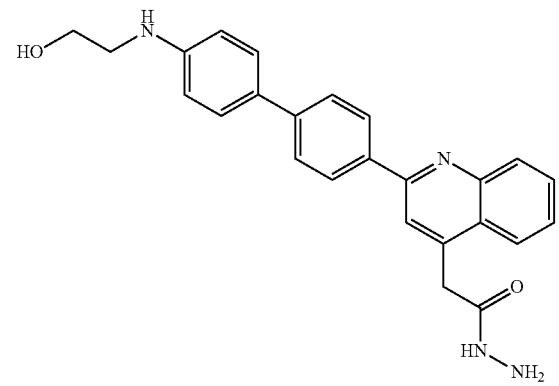 [SMILES: NNC(=O)Cc1cc(-c2ccc(-c3ccc(NCCO)cc3)cc2)nc2ccccc12] |
| 49 | A | 1.53 | 415 | | 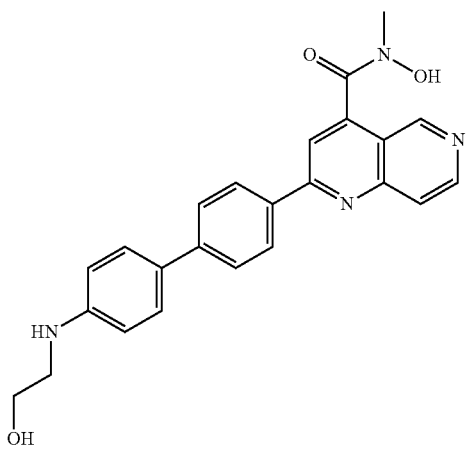 [SMILES: CN(O)C(=O)c1cc(-c2ccc(-c3ccc(NCCO)cc3)cc2)nc2ccncc12] |
| 50 | C | 8.71 | 375 | | 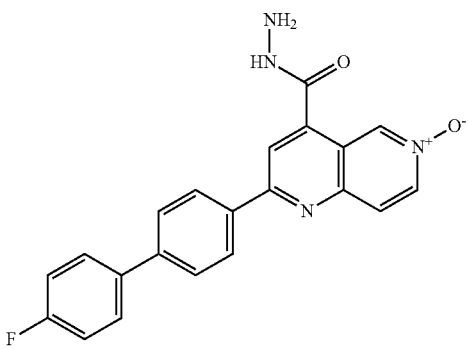 [SMILES: NNC(=O)c1cc(-c2ccc(-c3ccc(F)cc3)cc2)nc2cc[n+]([O-])cc12] |

TABLE 1-continued
Analytical Data
| Example # | HPLC Method | HPLC RT | MS(ESI) (M + H) | Chirality | Structure |
|---|---|---|---|---|---|
| 51 | A | 1.34 | 416 | | 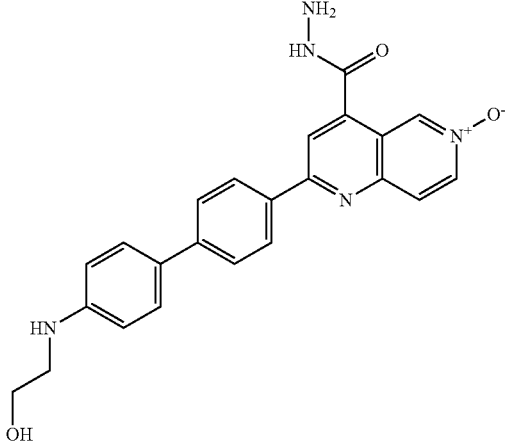 [SMILES: NNC(=O)c1cc(-c2ccc(-c3ccc(NCCO)cc3)cc2)nc2cc[n+]([O-])cc12] |
| 52 | A | 1.83 | 439 | | 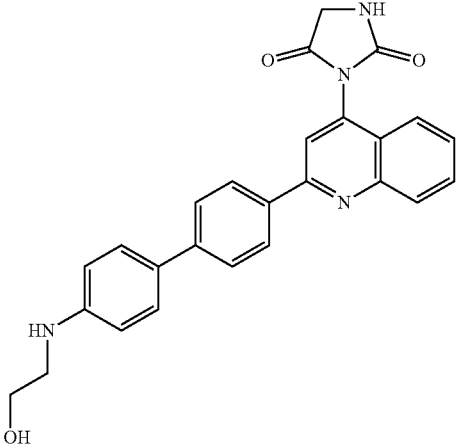 [SMILES: O=C1CNC(=O)N1c1cc(-c2ccc(-c3ccc(NCCO)cc3)cc2)nc2ccccc12] |
| 53 | A | 1.70 | 429.6 | | 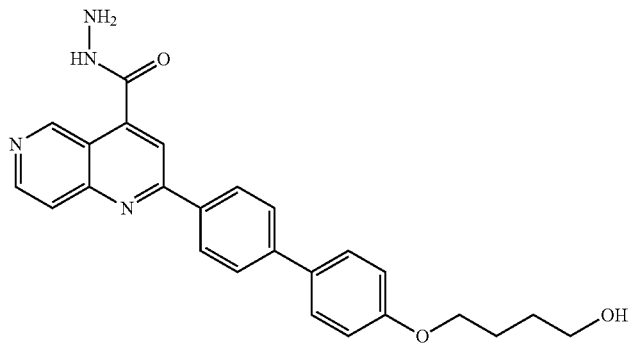 [SMILES: NNC(=O)c1cc(-c2ccc(-c3ccc(OCCCCO)cc3)cc2)nc2ccncc12] |

TABLE 1-continued
| Example # | HPLC Method | HPLC RT | MS(ESI) (M + H) | Chirality | Structure |
|---|---|---|---|---|---|
| 54 | C | 8.96 | 366.3 | | 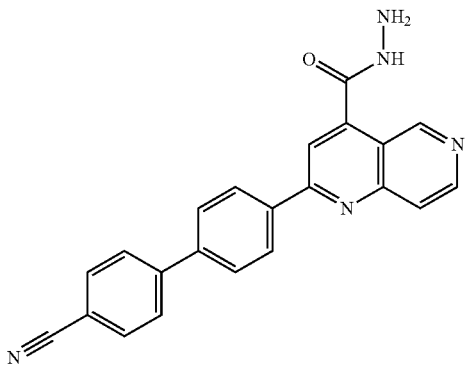 [SMILES: N#Cc1ccc(-c2ccc(-c3cc(C(=O)NN)c4cnccc4n3)cc2)cc1] |
| 55 | A | 1.36 | 401 | | 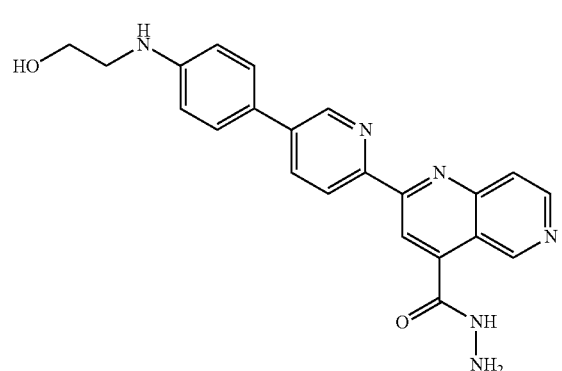 |
| 56 | C | 7.00 | 401 | | 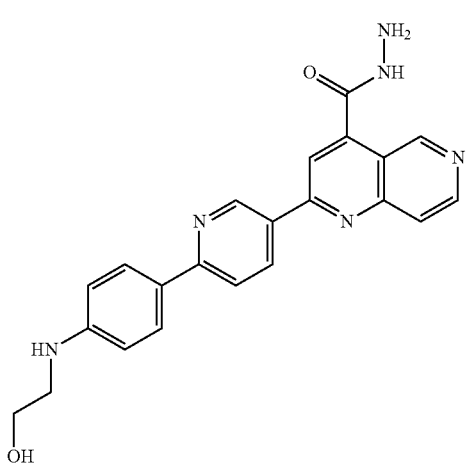 [SMILES: NNC(=O)c1cc(-c2ccc(-c3ccc(NCCO)cc3)nc2)nc2ccncc12] |

TABLE 1-continued

Analytical Data

| Example # | HPLC Method | HPLC RT | MS(ESI) (M + H) | Chirality | Structure |
|---|---|---|---|---|---|
| 57 | A | 3.03 | 342 | | 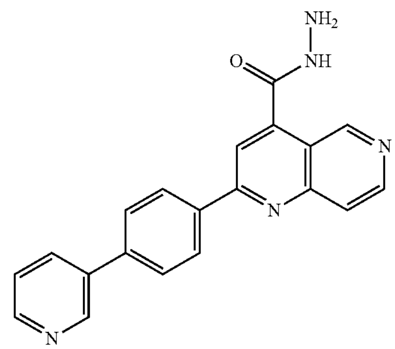 [SMILES: NNC(=O)c1cc(-c2ccc(-c3cccnc3)cc2)nc2ccncc12] |
| 58 | C | 7.87 | 342 | | 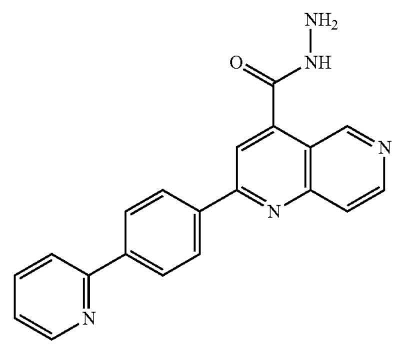 [SMILES: NNC(=O)c1cc(-c2ccc(-c3ccccn3)cc2)nc2ccncc12] |
| 59 | E | 10.52 | 342 | | 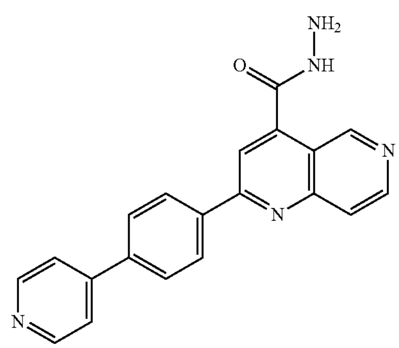 [SMILES: NNC(=O)c1cc(-c2ccc(-c3ccncc3)cc2)nc2ccncc12] |
| 60 | C | 7.89 | 331.4 | | 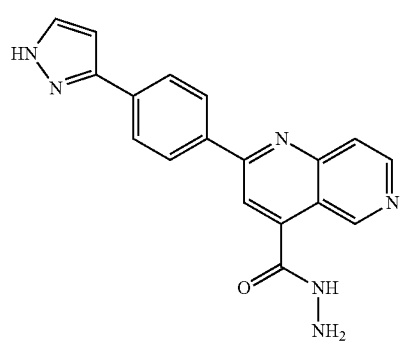 [SMILES: NNC(=O)c1cc(-c2ccc(-c3cc[nH]n3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 61 | A | 1.24 | 331 | | 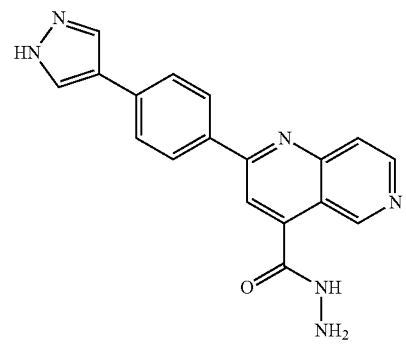 [SMILES: NNC(=O)c1cc(-c2ccc(-c3cn[nH]c3)cc2)nc2ccncc12] |
| 62 | A | 1.49 | 332 | | 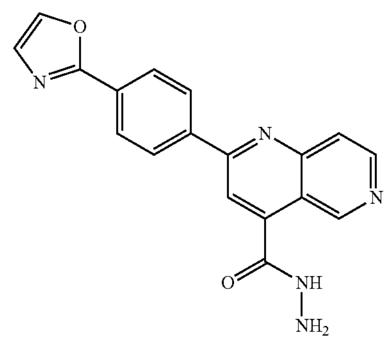 [SMILES: NNC(=O)c1cc(-c2ccc(-c3ncco3)cc2)nc2ccncc12] |
| 63 | A | 1.43 | 332 | | 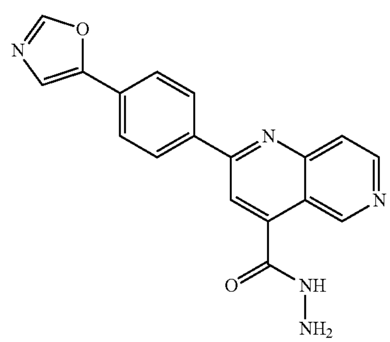 [SMILES: NNC(=O)c1cc(-c2ccc(-c3cnco3)cc2)nc2ccncc12] |
| 64 | A | 1.95 | 341 | | 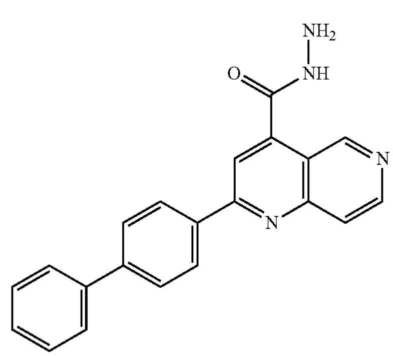 [SMILES: NNC(=O)c1cc(-c2ccc(-c3ccccc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 65 | A | 2.00 | 359 | | 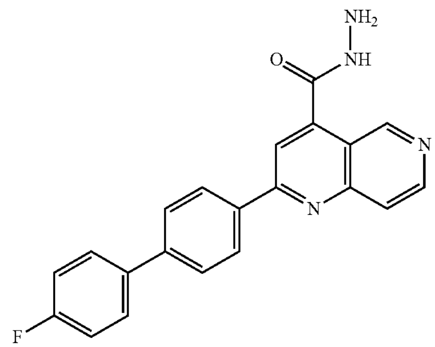 [SMILES: NNC(=O)c1cc(-c2ccc(-c3ccc(F)cc3)cc2)nc2ccncc12] |
| 66 | C | 8.73 | 440 | | 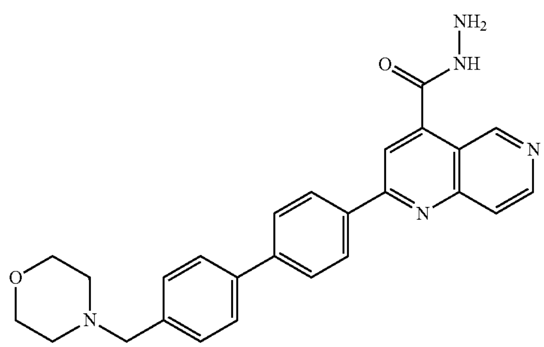 [SMILES: NNC(=O)c1cc(-c2ccc(-c3ccc(CN4CCOCC4)cc3)cc2)nc2ccncc12] |
| 67 | A | 1.44 | 430 | | 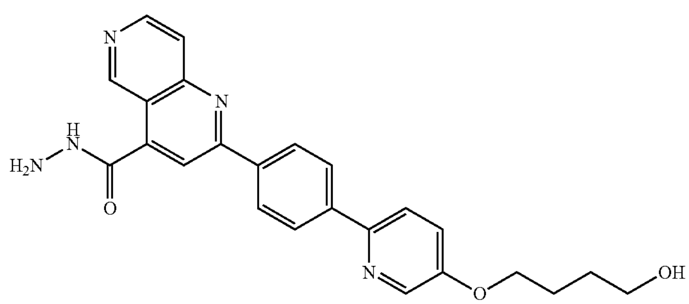 [SMILES: NNC(=O)c1cc(-c2ccc(-c3ccc(OCCCCO)cn3)cc2)nc2ccncc12] |
| 68 | C | 8.35 | 357 | | 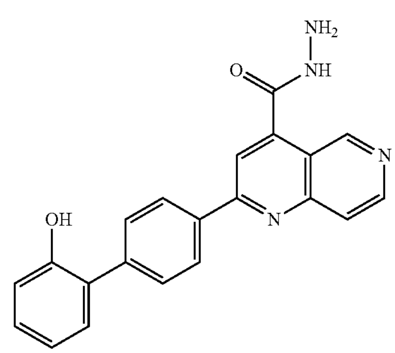 [SMILES: NNC(=O)c1cc(-c2ccc(-c3ccccc3O)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 69 | A | 1.48 | 348.5 | | 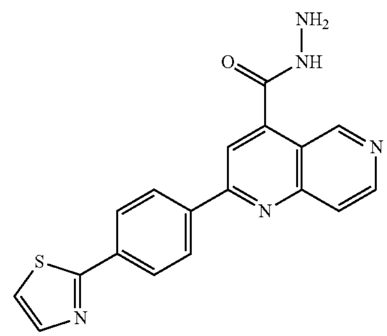 [SMILES: NNC(=O)c1cc(-c2ccc(-c3nccs3)cc2)nc2ccncc12] |
| 70 | A | 2.28 | 397.3 (M − 1) | | 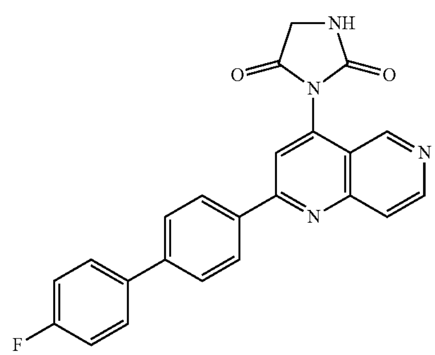 [SMILES: O=C1CNC(=O)N1c1cc(-c2ccc(-c3ccc(F)cc3)cc2)nc2ccncc12] |
| 71 | A | 2.49 | 415.6 | | 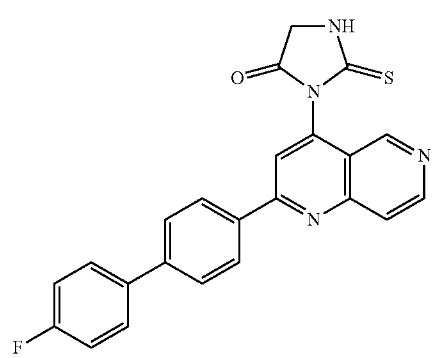 |
| 72 | A | 1.60 | 417.6 (M − 1) | | 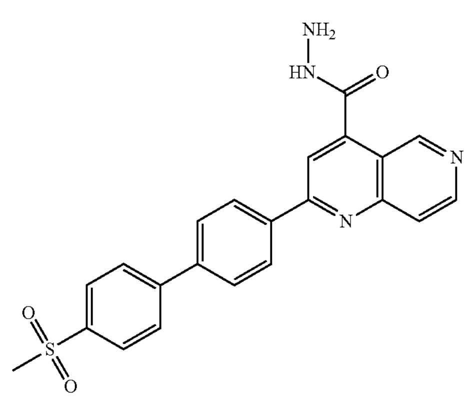 [SMILES: CS(=O)(=O)c1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 73 | C | 7.48 | 464 | | 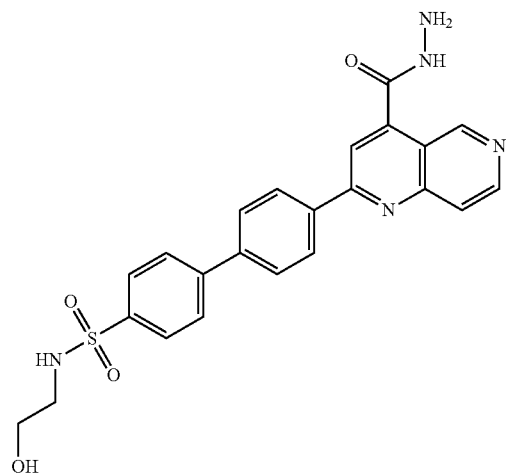 [SMILES: NNC(=O)c1cc(-c2ccc(-c3ccc(S(=O)(=O)NCCO)cc3)cc2)nc2ccncc12] |
| 74 | C | 8.81 | 478 | | 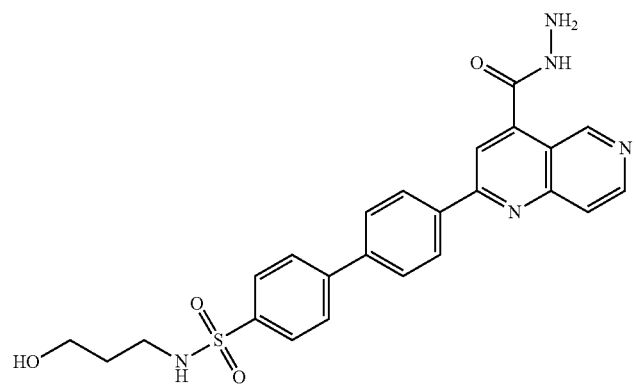 [SMILES: NNC(=O)c1cc(-c2ccc(-c3ccc(S(=O)(=O)NCCCO)cc3)cc2)nc2ccncc12] |
| 75 | A | 1.73 | 486.8 | | 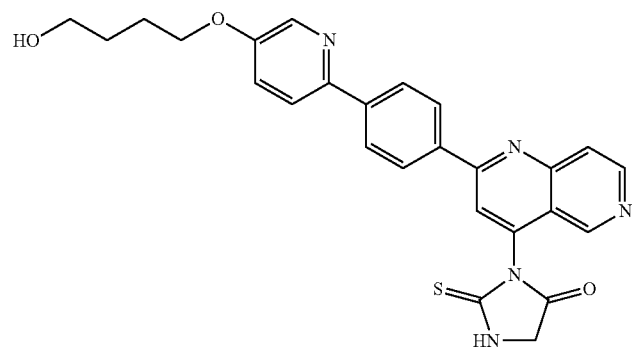 |

TABLE 1-continued

Analytical Data

| Example # | HPLC Method | HPLC RT | MS(ESI) (M + H) | Chirality | Structure |
|---|---|---|---|---|---|
| 76 | C | 6.9 | 443 | | 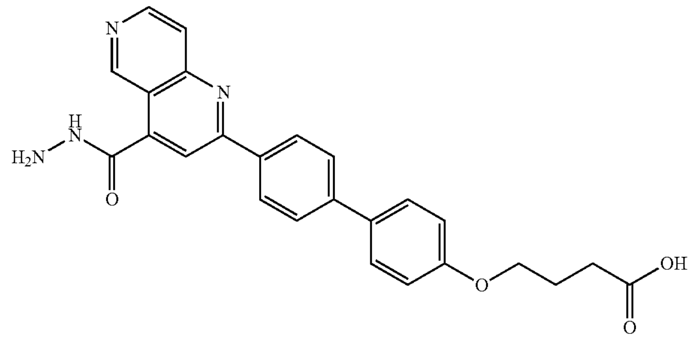 [SMILES: NNC(=O)c1cc(-c2ccc(-c3ccc(OCCCC(=O)O)cc3)cc2)nc2ccncc12] |
| 77 | C | 7.56 | 457 | | 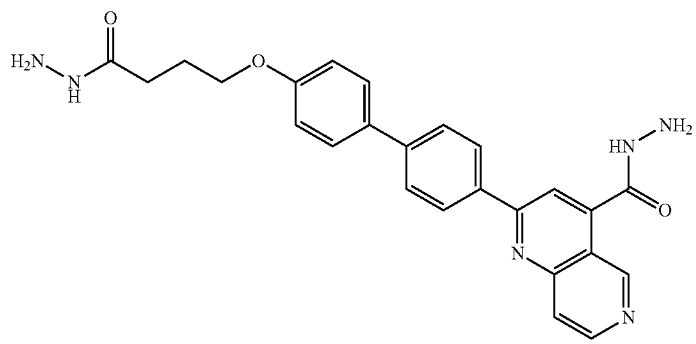 [SMILES: NNC(=O)CCCOc1ccc(-c2ccc(-c3cc(C(=O)NN)c4cnccc4n3)cc2)cc1] |
| 78 | A | 1.53 | 458 | | 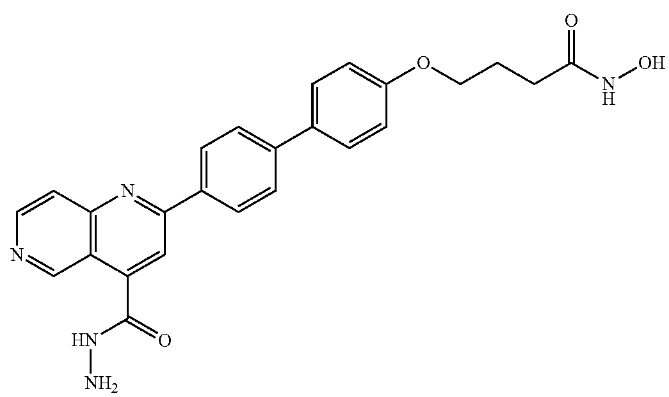 [SMILES: NNC(=O)c1cc(-c2ccc(-c3ccc(OCCCC(=O)NO)cc3)cc2)nc2ccncc12] |
| 79 | A | 1.69 | 496.2 | | 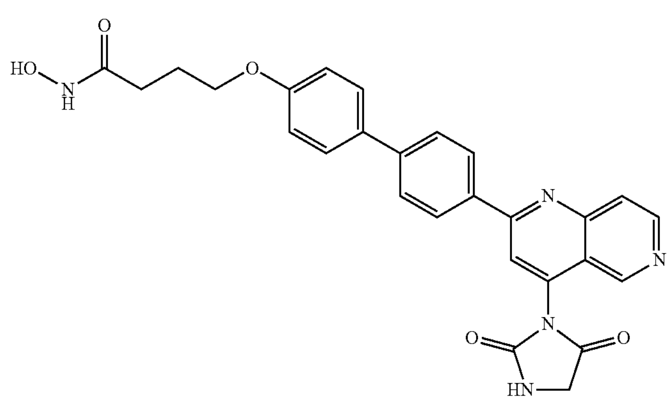 |

TABLE 1-continued
Analytical Data
| Example # | HPLC Method | HPLC RT | MS(ESI) (M + H) | Chirality | Structure |
|---|---|---|---|---|---|
| 80 | C | 7.47 | 483 | | 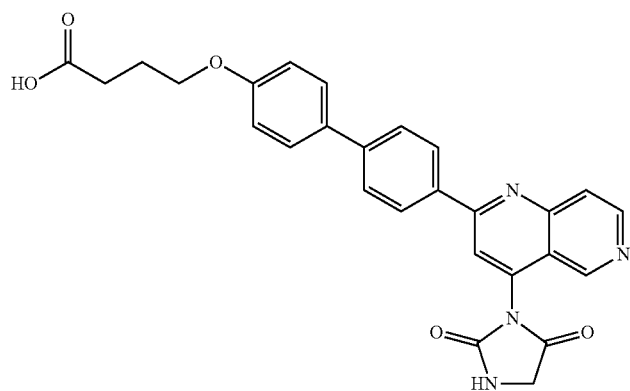 [SMILES: O=C(O)CCCOc1ccc(-c2ccc(-c3cc(N4C(=O)CNC4=O)c4cnccc4n3)cc2)cc1] |
| 81 | F | 4.07 | 512.0 | | 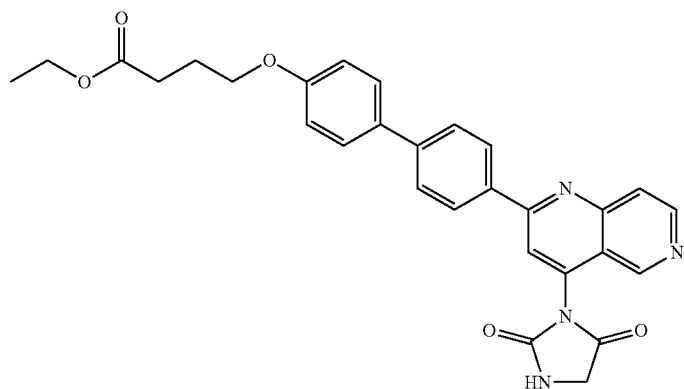 [SMILES: CCOC(=O)CCCOc1ccc(-c2ccc(-c3cc(N4C(=O)CNC4=O)c4cnccc4n3)cc2)cc1] |
| 82 | A | 1.81 | 514.2 | | 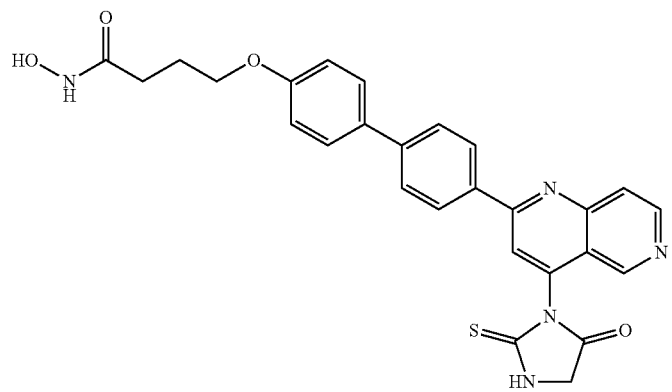 [SMILES: O=C(CCCOc1ccc(-c2ccc(-c3cc(N4C(=O)CNC4=S)c4cnccc4n3)cc2)cc1)NO] |

TABLE 1-continued
| Example # | HPLC Method | HPLC RT | MS(ESI) (M + H) | Chirality | Structure |
|---|---|---|---|---|---|
| 83 | A | 2.10 | 499 | | 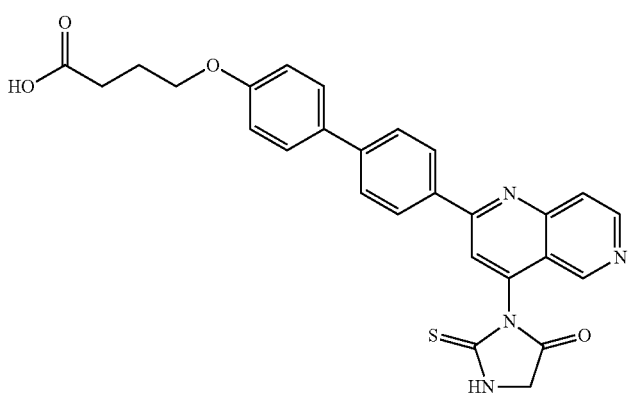 |
| 84 | A | 2.55 | 527 | | 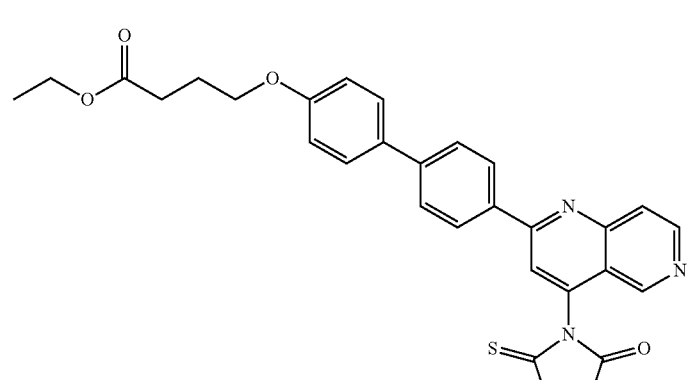 |
| 85 | A | 1.33 | 400 | | 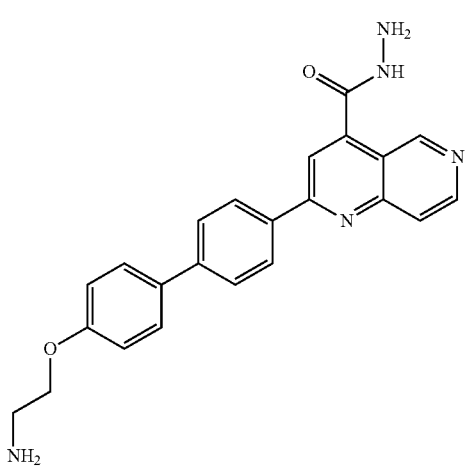 [SMILES: NCCOc1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 86 | A | 1.56 | 442 | | 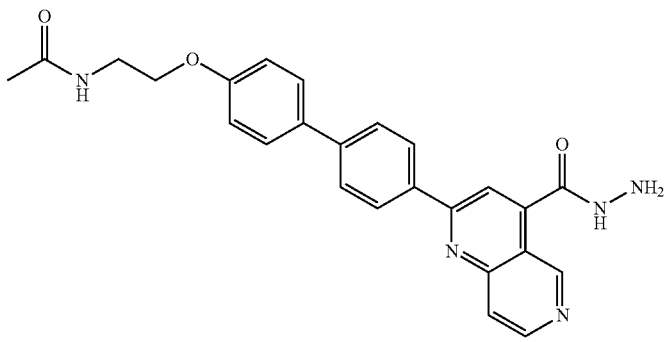 [SMILES: CC(=O)NCCOc1ccc(-c2ccc(-c3cc(C(=O)NN)c4cnccc4n3)cc2)cc1] |
| 87 | A | 1.89 | 454.3 | R | 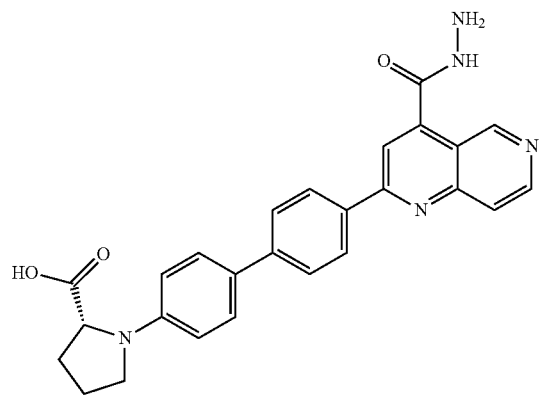 [SMILES: NNC(=O)c1cc(-c2ccc(-c3ccc(N4CCC[C@@H]4C(=O)O)cc3)cc2)nc2ccncc12] |
| 88 | A | 1.91 | 452.5 (M − 1) | S | 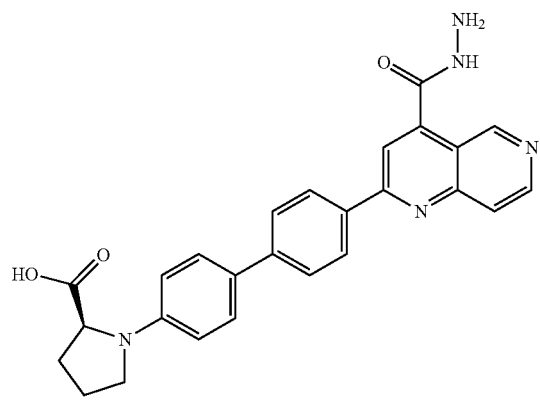 [SMILES: NNC(=O)c1cc(-c2ccc(-c3ccc(N4CCC[C@H]4C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 89 | A | 1.61 | 468 | Racemate | 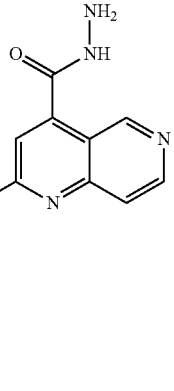 |
| 90 | A | 1.44 | 468.4 | | 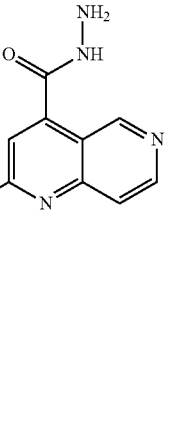 |
| 91 | A | 1.76 | 470.5 | | 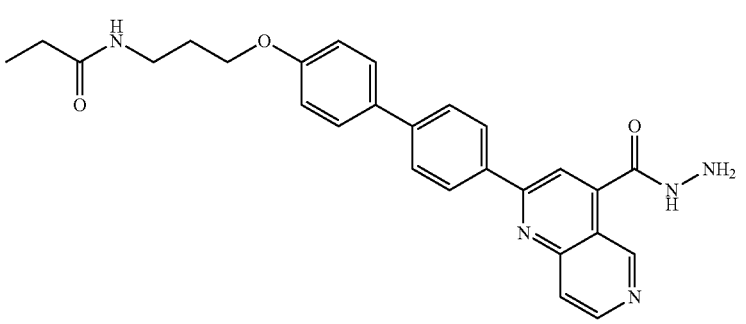 [SMILES: CCC(=O)NCCCOc1ccc(-c2ccc(-c3cc(C(=O)NN)c4cnccc4n3)cc2)cc1] |
| 92 | A | 1.84 | 484 | | 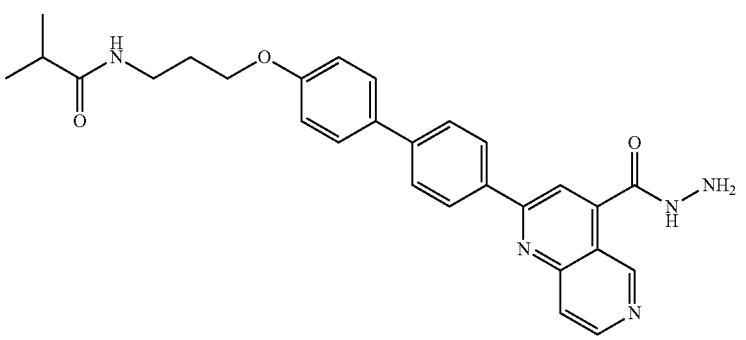 [SMILES: CC(C)C(=O)NCCCOc1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 93 | A | 1.40 | 510 | | 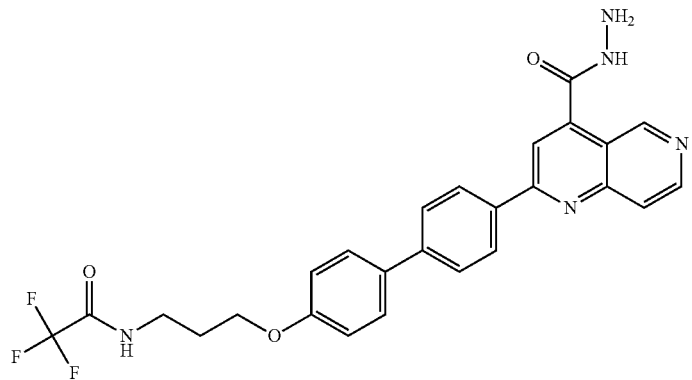 [SMILES: NNC(=O)c1cc(-c2ccc(-c3ccc(OCCCNC(=O)C(F)(F)F)cc3)cc2)nc2ccncc12] |
| 94 | A | 1.85 | 506.3 | | 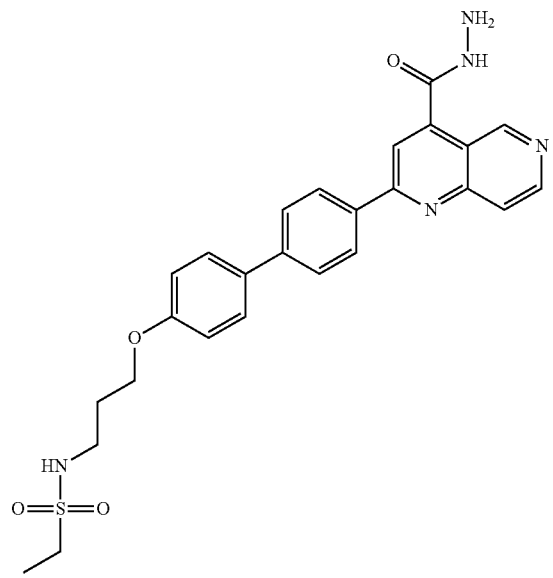 [SMILES: CCS(=O)(=O)NCCCOc1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 95 | A | 1.94 | 520.5 | | 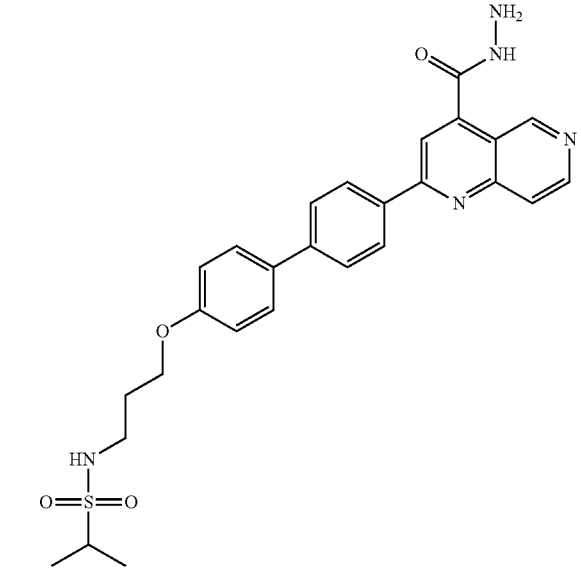 [SMILES: CC(C)S(=O)(=O)NCCCOc1ccc(-c2ccc(-c3cc(C(=O)NN)c4cnccc4n3)cc2)cc1] |
| 96 | A | 2.25 | 544 | | 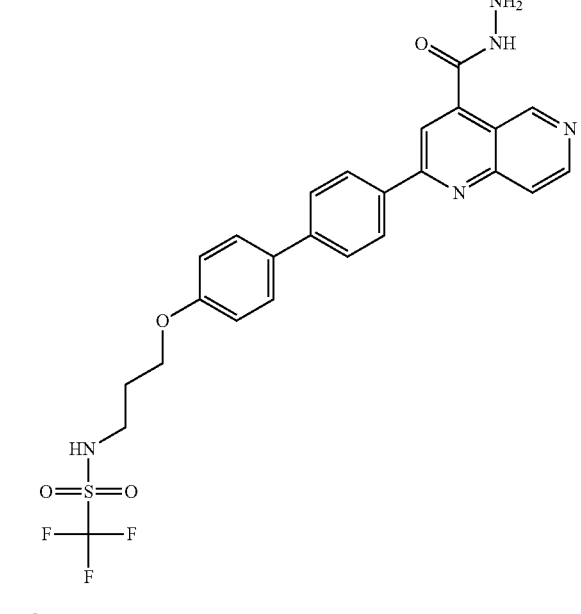 [SMILES: NNC(=O)c1cc(-c2ccc(-c3ccc(OCCCNS(=O)(=O)C(F)(F)F)cc3)cc2)nc2ccncc12] |
| 97 | A | 1.68 | 456.8 | | 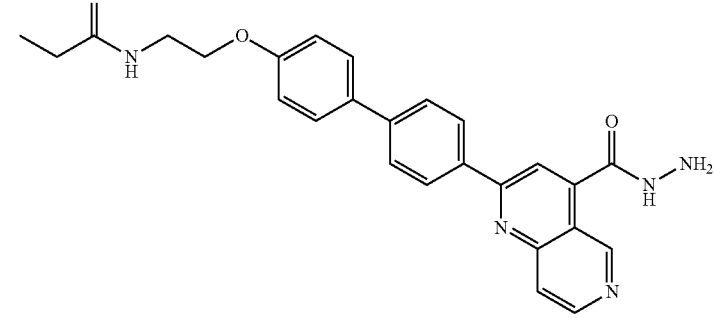 |

TABLE 1-continued
Analytical Data
| Example # | HPLC Method | HPLC RT | MS(ESI) (M + H) | Chirality | Structure |
|---|---|---|---|---|---|
| 98 | A | 1.32 | 496 | | 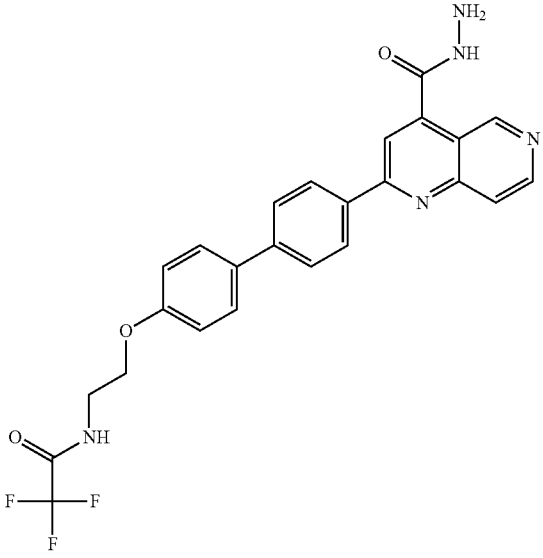 [SMILES: NNC(=O)c1cc(-c2ccc(-c3ccc(OCCNC(=O)C(F)(F)F)cc3)cc2)nc2ccncc12] |
| 99 | A | 1.78 | 492.2 | | 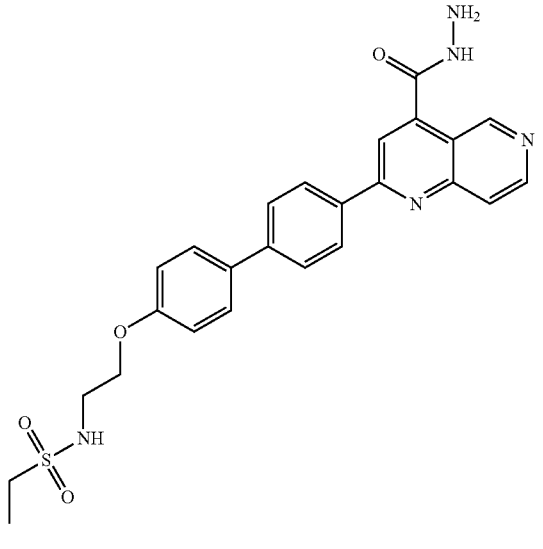 [SMILES: CCS(=O)(=O)NCCOc1ccc(-c2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 100 | A | 1.88 | 506.5 | | 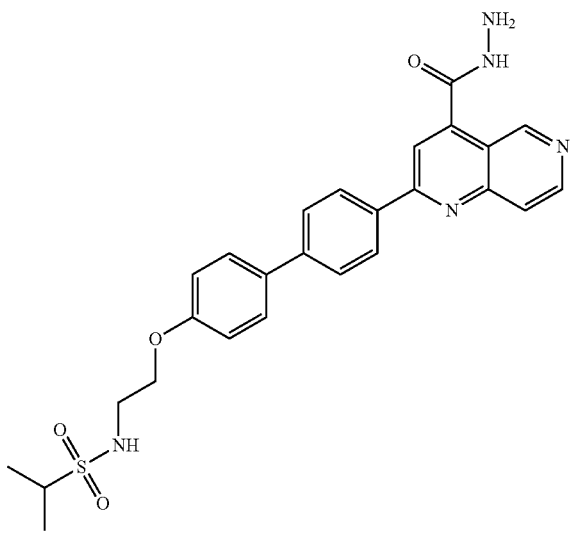 [SMILES: CC(C)S(=O)(=O)NCCOc1ccc(-c2ccc(-c3cc(C(=O)NN)c4cnccc4n3)cc2)cc1] |
| 101 | A | 2.18 | 530.4 (M − 1) | | 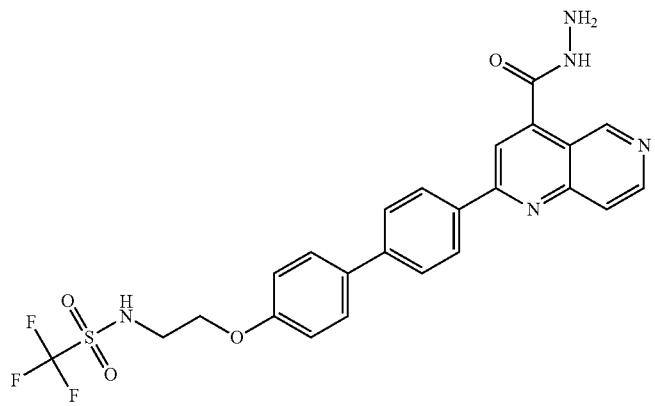 [SMILES: NNC(=O)c1cc(-c2ccc(-c3ccc(OCCNS(=O)(=O)C(F)(F)F)cc3)cc2)nc2ccncc12] |
| 102 | A | 1.48 | 371 (M − 1) | | 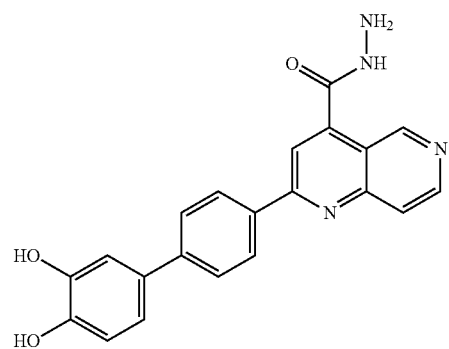 [SMILES: NNC(=O)c1cc(-c2ccc(-c3ccc(O)c(O)c3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 103 | A | 1.91 | 497.1 | R | 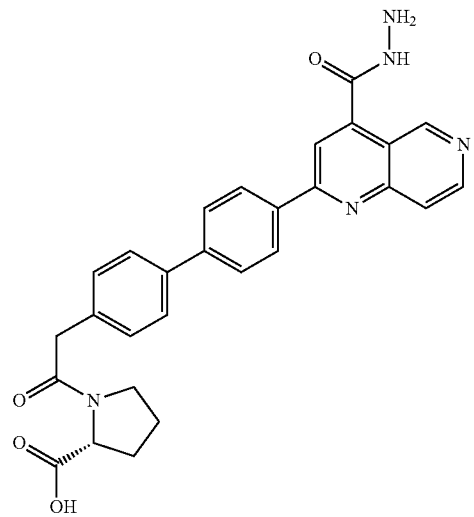 [SMILES: NNC(=O)c1cc(-c2ccc(-c3ccc(CC(=O)N4CCC[C@@H]4C(=O)O)cc3)cc2)nc2ccncc12] |
| 104 | A | 1.68 | 512 | R | 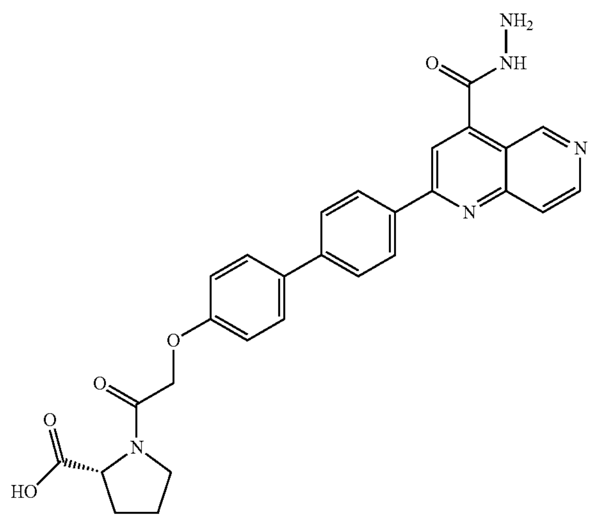 [SMILES: NNC(=O)c1cc(-c2ccc(-c3ccc(OCC(=O)N4CCC[C@@H]4C(=O)O)cc3)cc2)nc2ccncc12] |
| 105 | A | 1.66 | 532 | R | 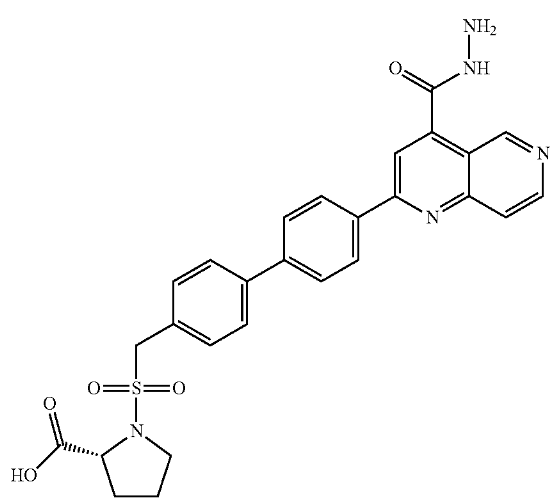 [SMILES: NNC(=O)c1cc(-c2ccc(-c3ccc(CS(=O)(=O)N4CCC[C@@H]4C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 106 | A | 1.54 | 454.4 | | 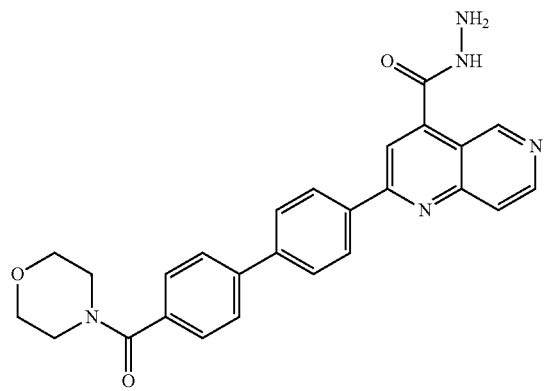 [SMILES: NNC(=O)c1cc(-c2ccc(-c3ccc(C(=O)N4CCOCC4)cc3)cc2)nc2ccncc12] |
| 107 | A | 1.53 | 482 | R | 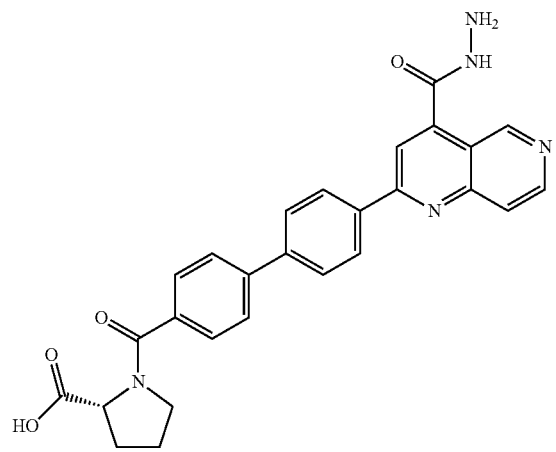 [SMILES: NNC(=O)c1cc(-c2ccc(-c3ccc(C(=O)N4CCC[C@@H]4C(=O)O)cc3)cc2)nc2ccncc12] |
| 108 | A | 1.56 | 496 | Racemate | 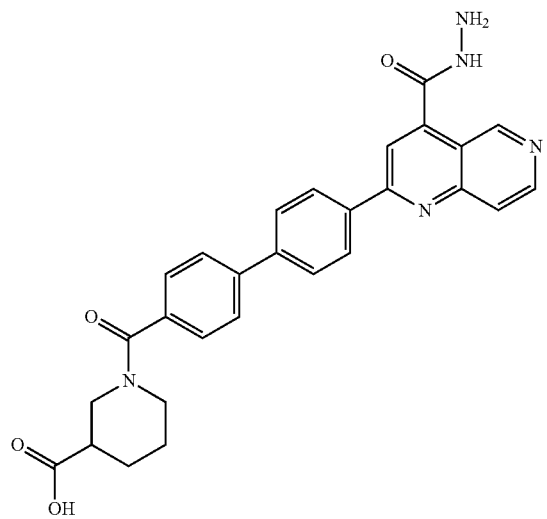 [SMILES: NNC(=O)c1cc(-c2ccc(-c3ccc(C(=O)N4CCCC(C(=O)O)C4)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 109 | A | 1.80 | 521.3 | | 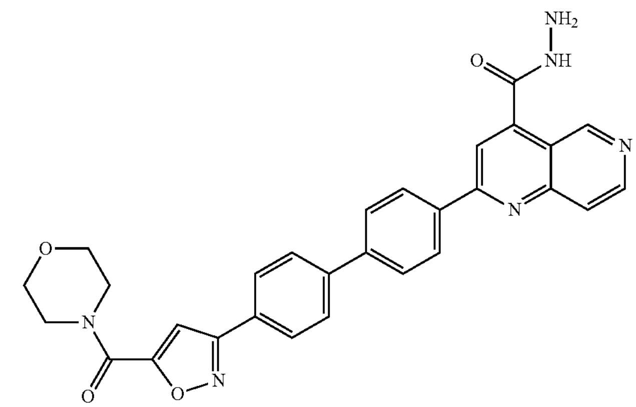 [SMILES: NNC(=O)c1cc(-c2ccc(-c3ccc(-c4cc(C(=O)N5CCOCC5)on4)cc3)cc2)nc2ccncc12] |
| 110 | A | 1.78 | 488.3 (M − 1) | | 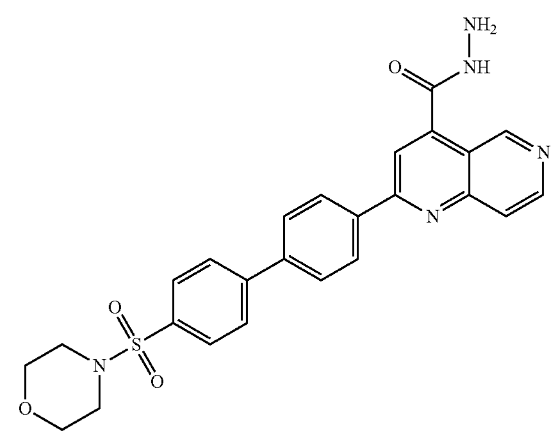 [SMILES: NNC(=O)c1cc(-c2ccc(-c3ccc(S(=O)(=O)N4CCOCC4)cc3)cc2)nc2ccncc12] |
| 111 | A | 1.62 | 518 | R | 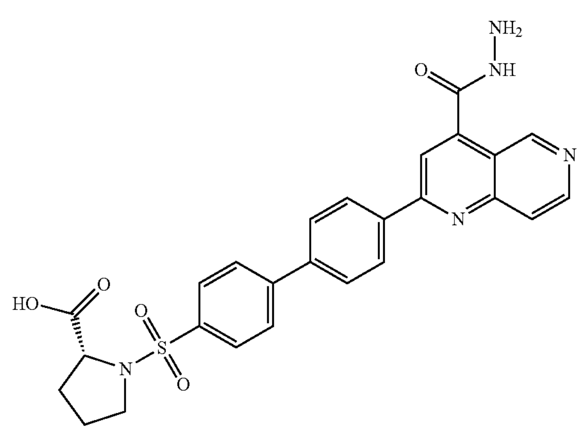 [SMILES: NNC(=O)c1cc(-c2ccc(-c3ccc(S(=O)(=O)N4CCC[C@@H]4C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 112 | A | 1.78 | 532 | Racemate | 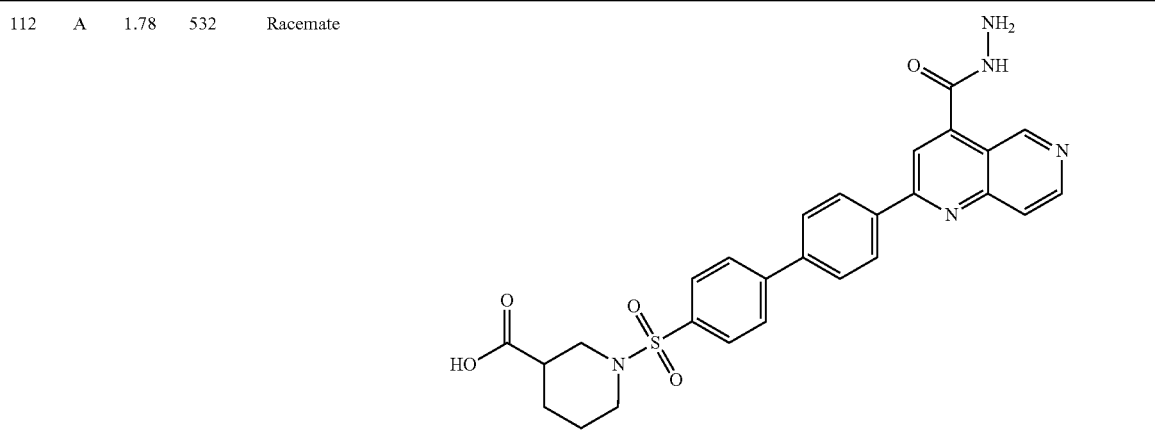 |
| 113 | A | 1.69 | 465.7 | | 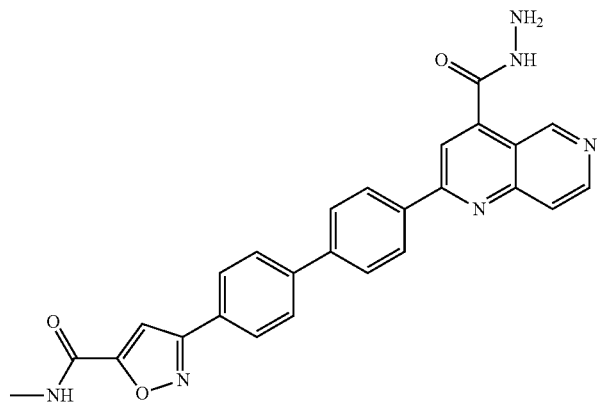 [SMILES: CNC(=O)c1cc(-c2ccc(-c3ccc(-c4cc(C(=O)NN)c5cnccc5n4)cc3)cc2)no1] |
| 114 | A | 1.81 | 563.3 | Racemate | 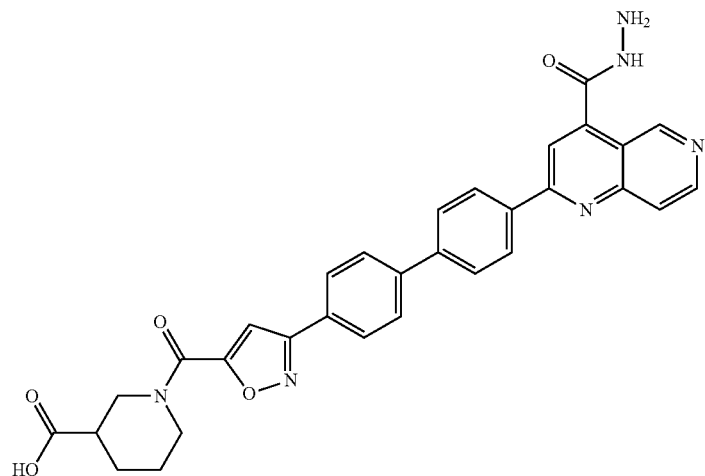 [SMILES: NNC(=O)c1cc(-c2ccc(-c3ccc(-c4cc(C(=O)N5CCCC(C(=O)O)C5)on4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 115 | A | 1.90 | 563.5 | Racemate | 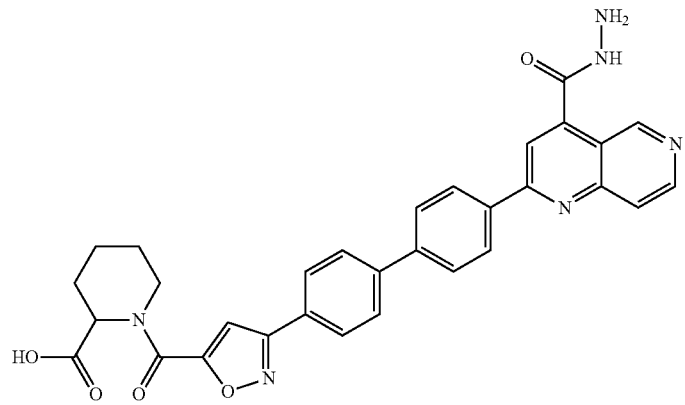 [SMILES: NNC(=O)c1cc(-c2ccc(-c3ccc(-c4cc(C(=O)N5CCCCC5C(=O)O)on4)cc3)cc2)nc2ccncc12] |
| 116 | A | 1.72 | 422 | | 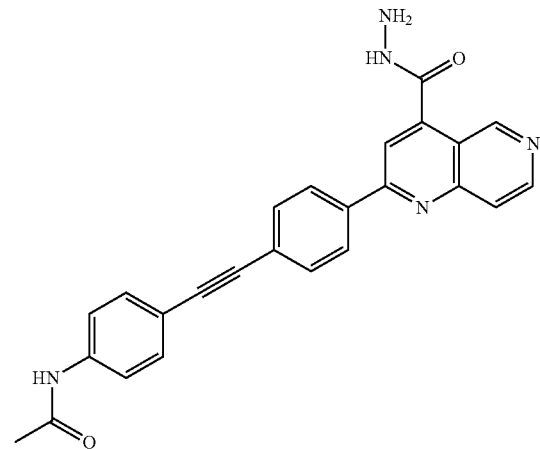 [SMILES: CC(=O)Nc1ccc(C#Cc2ccc(-c3cc(C(=O)NN)c4cnccc4n3)cc2)cc1] |
| 117 | A | 1.77 | 458 | | 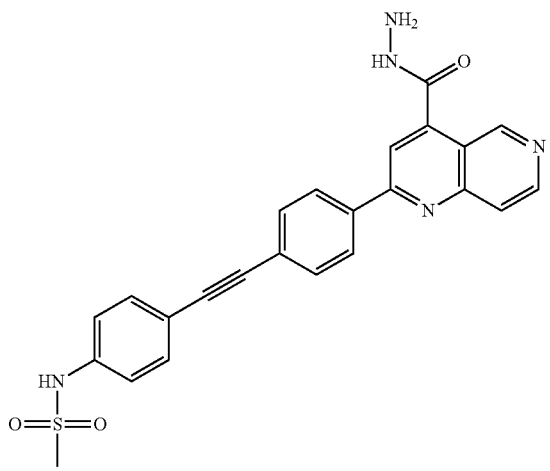 [SMILES: CS(=O)(=O)Nc1ccc(C#Cc2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 118 | A | 1.75 | 487 | | 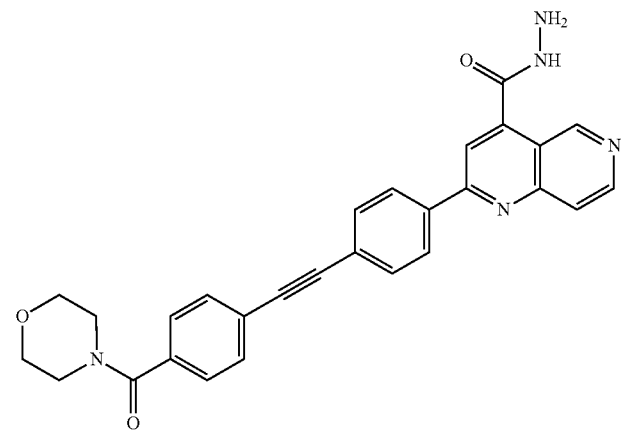 [SMILES: NNC(=O)c1cc(-c2ccc(C#Cc3ccc(C(=O)N4CCOCC4)cc3)cc2)nc2ccncc12] |
| 119 | A | 1.85 | 542 | R | 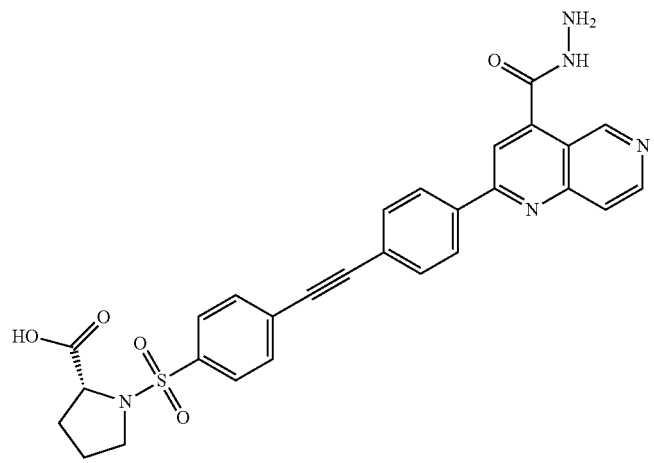 [SMILES: NNC(=O)c1cc(-c2ccc(C#Cc3ccc(S(=O)(=O)N4CCC[C@@H]4C(=O)O)cc3)cc2)nc2ccncc12] |
| 120 | A | 1.39 | 426 | | 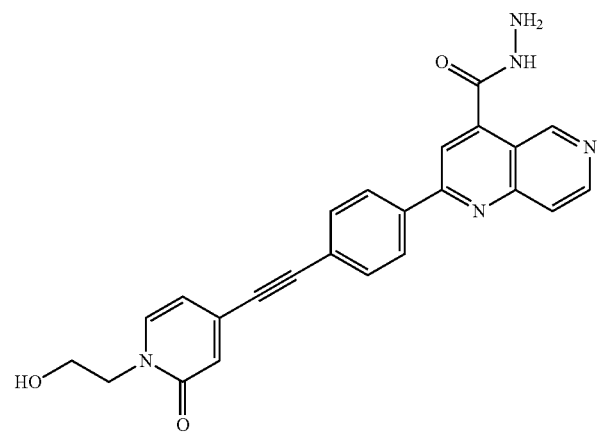 [SMILES: NNC(=O)c1cc(-c2ccc(C#Cc3ccn(CCO)c(=O)c3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 121 | A | 1.38 | 467.4 | | 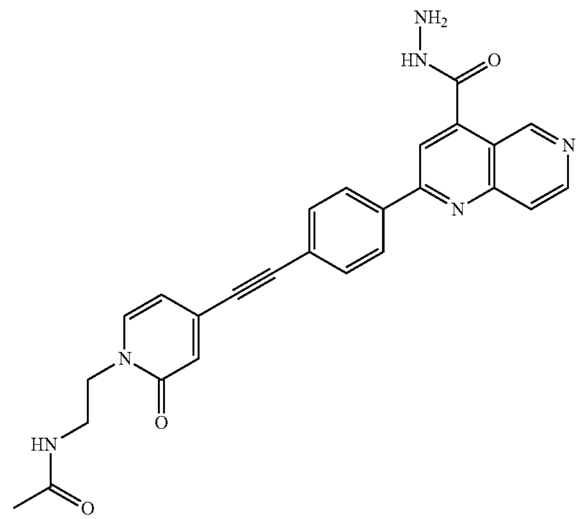 [SMILES: CC(=O)NCCn1ccc(C#Cc2ccc(-c3cc(C(=O)NN)c4cnccc4n3)cc2)cc1=O] |
| 122 | A | 1.87 | 538.4 | Racemate | 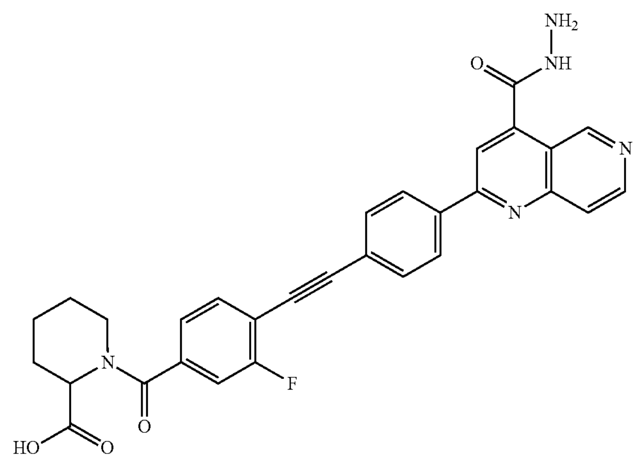 [SMILES: NNC(=O)c1cc(-c2ccc(C#Cc3ccc(C(=O)N4CCCCC4C(=O)O)cc3F)cc2)nc2ccncc12] |
| 123 | A | 1.89 | 538.8 | Racemate | 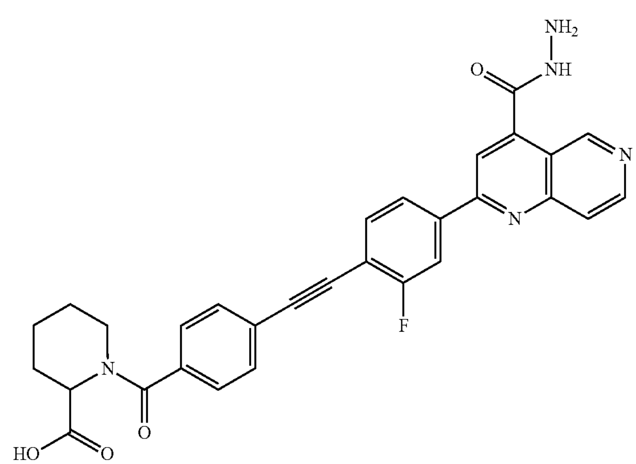 [SMILES: NNC(=O)c1cc(-c2ccc(C#Cc3ccc(C(=O)N4CCCCC4C(=O)O)cc3)c(F)c2)nc2ccncc12] |

TABLE 1-continued
Analytical Data
| Example # | HPLC Method | HPLC RT | MS(ESI) (M + H) | Chirality | Structure |
|---|---|---|---|---|---|
| 124 | A | 1.44 | 464.6 | | 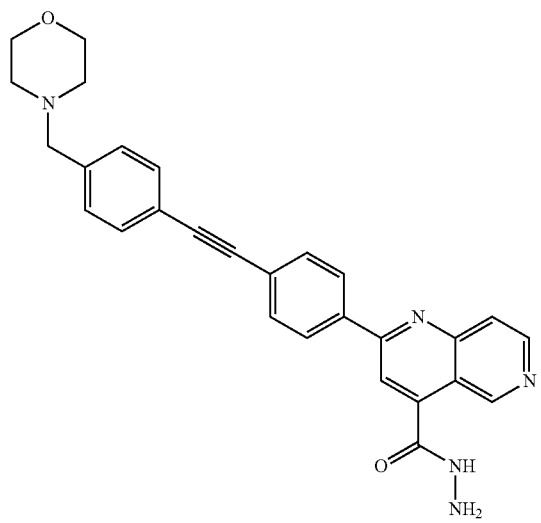 [SMILES: NNC(=O)c1cc(-c2ccc(C#Cc3ccc(CN4CCOCC4)cc3)cc2)nc2ccncc12] |
| 125 | A | 1.66 | 424 | | 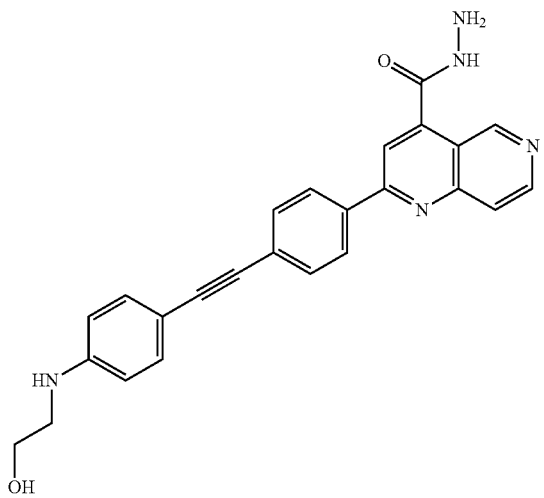 [SMILES: NNC(=O)c1cc(-c2ccc(C#Cc3ccc(NCCO)cc3)cc2)nc2ccncc12] |
| 126 | C | 8.48 | 366.4 | | 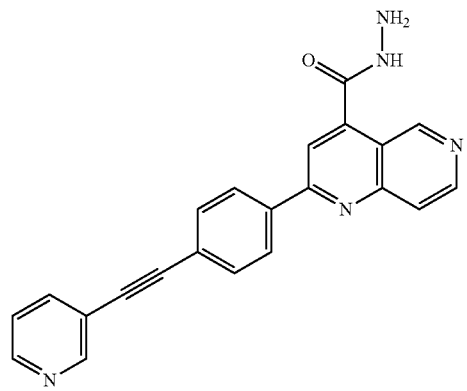 [SMILES: NNC(=O)c1cc(-c2ccc(C#Cc3cccnc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 127 | C | 11.21 | 520 | | 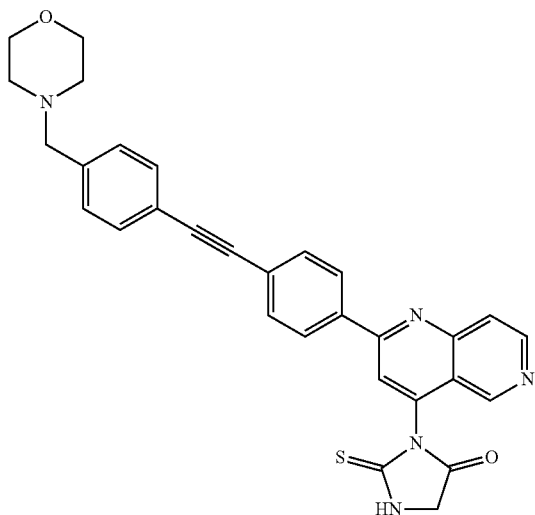 [SMILES: O=C1CNC(=S)N1c1cc(-c2ccc(C#Cc3ccc(CN4CCOCC4)cc3)cc2)nc2ccncc12] |
| 128 | A | 1.67 | 422 | | 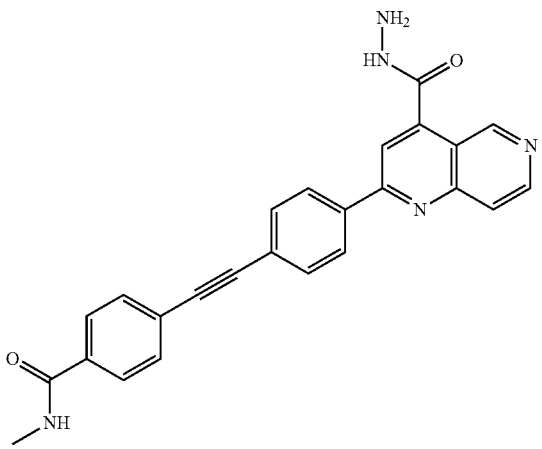 [SMILES: CNC(=O)c1ccc(C#Cc2ccc(-c3cc(C(=O)NN)c4cnccc4n3)cc2)cc1] |
| 129 | A | 1.84 | 458 | | 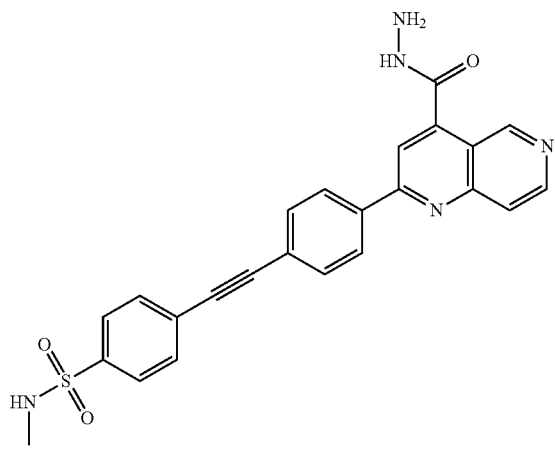 [SMILES: CNS(=O)(=O)c1ccc(C#Cc2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 130 | A | 1.77 | 506.4 | S | 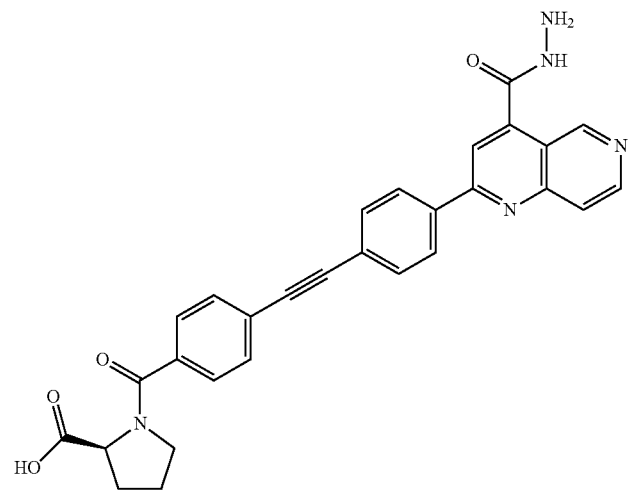 [SMILES: NNC(=O)c1cc(-c2ccc(C#Cc3ccc(C(=O)N4CCC[C@H]4C(=O)O)cc3)cc2)nc2ccncc12] |
| 131 | A | 1.74 | 506.4 | R | 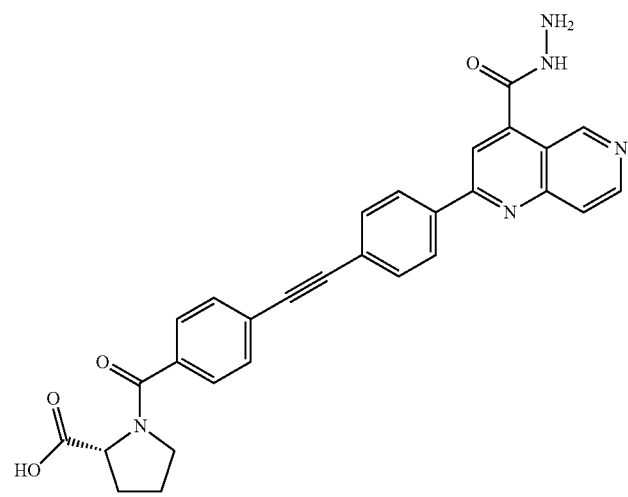 [SMILES: NNC(=O)c1cc(-c2ccc(C#Cc3ccc(C(=O)N4CCC[C@@H]4C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 132 | A | 1.82 | 520.5 | Racemate | 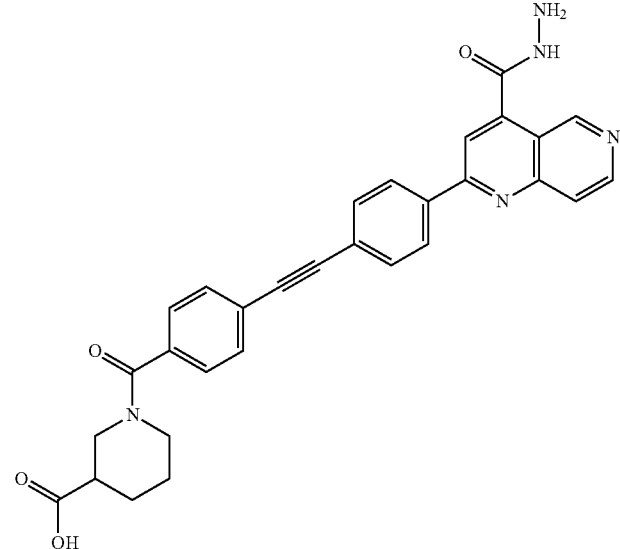 [SMILES: NNC(=O)c1cc(-c2ccc(C#Cc3ccc(C(=O)N4CCCC(C(=O)O)C4)cc3)cc2)nc2ccncc12] |
| 133 | A | 1.73 | 520.6 | (−) | 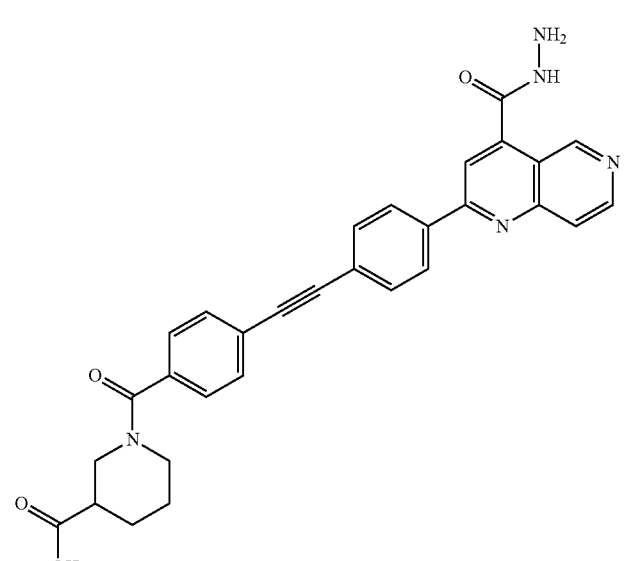 |

TABLE 1-continued

Analytical Data

| Example # | HPLC Method | HPLC RT | MS(ESI) (M + H) | Chirality | Structure |
|---|---|---|---|---|---|
| 134 | A | 1.72 | 520.5 | (+) | 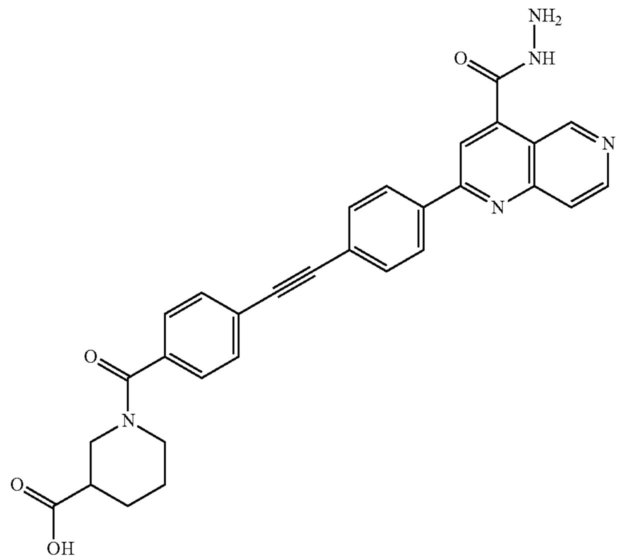 |
| 135 | A | 1.72 | 506 | Racemate | 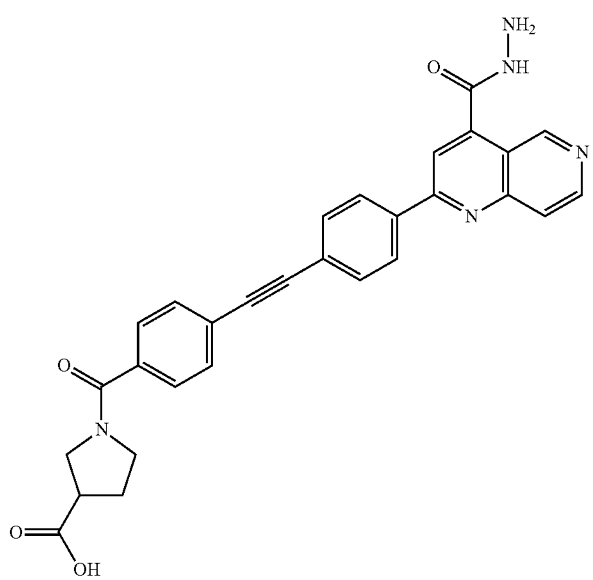 [SMILES: NNC(=O)c1cc(-c2ccc(C#Cc3ccc(C(=O)N4CCC(C(=O)O)C4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 136 | A | 1.84 | 520 | | 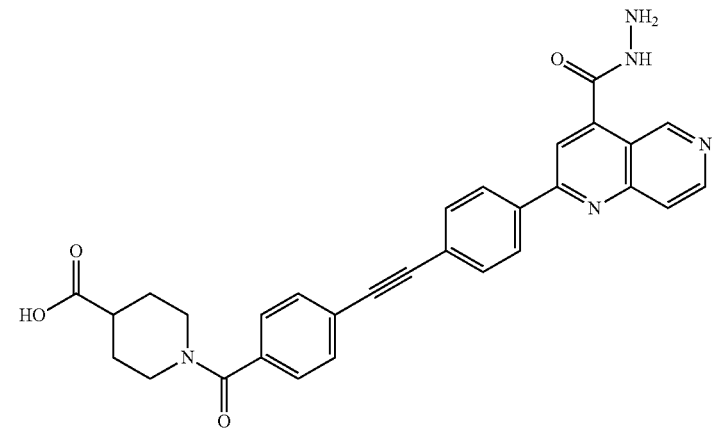 [SMILES: NNC(=O)c1cc(-c2ccc(C#Cc3ccc(C(=O)N4CCC(C(=O)O)CC4)cc3)cc2)nc2ccncc12] |
| 137 | A | 1.42 | 491 | | 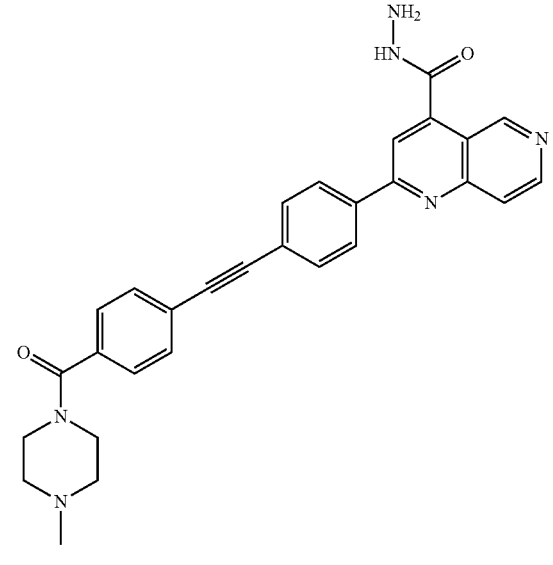 [SMILES: CN1CCN(C(=O)c2ccc(C#Cc3ccc(-c4cc(C(=O)NN)c5cnccc5n4)cc3)cc2)CC1] |
| 138 | A | 1.57 | 425 | | 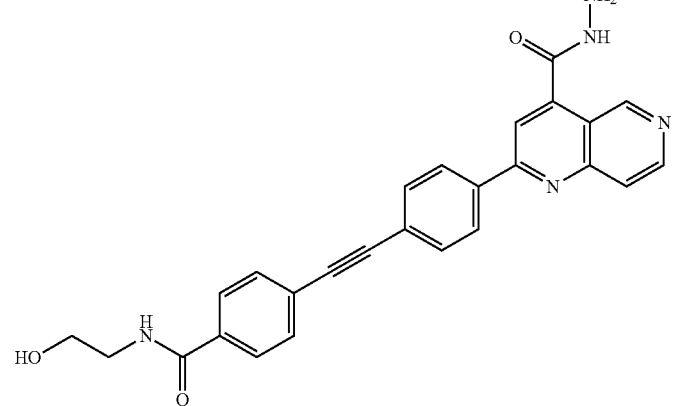 |

TABLE 1-continued
Analytical Data
| Example # | HPLC Method | HPLC RT | MS(ESI) (M + H) | Chirality | Structure |
|---|---|---|---|---|---|
| 139 | A | 1.61 | 466.4 | | 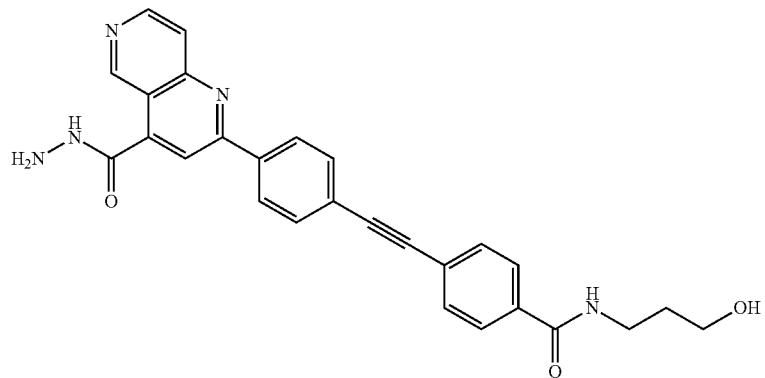 [SMILES: NNC(=O)c1cc(-c2ccc(C#Cc3ccc(C(=O)NCCCO)cc3)cc2)nc2ccncc12] |
| 140 | A | 1.67 | 466 | | 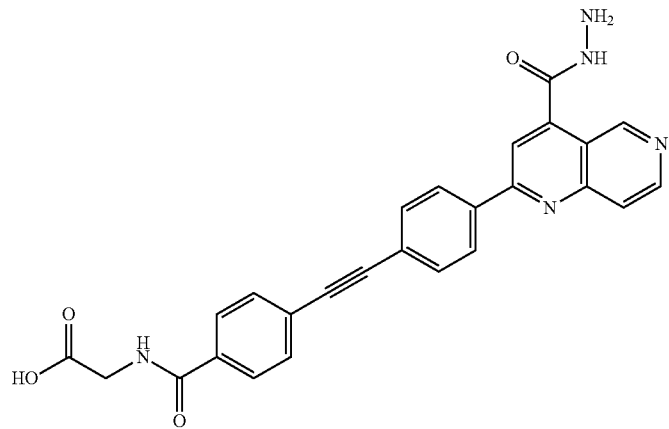 [SMILES: NNC(=O)c1cc(-c2ccc(C#Cc3ccc(C(=O)NCC(=O)O)cc3)cc2)nc2ccncc12] |
| 141 | A | 1.87 | 542 | S | 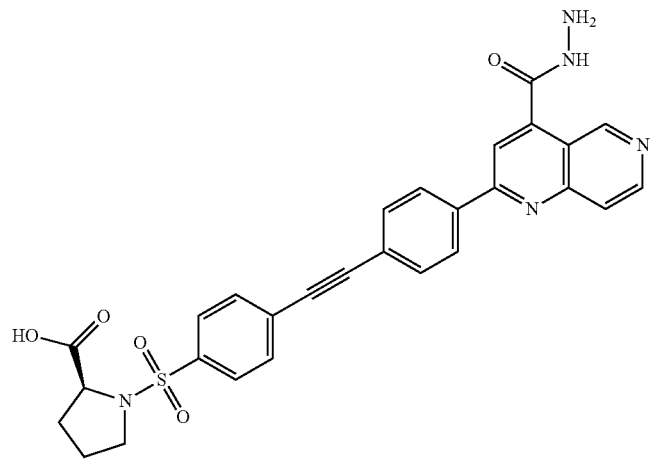 [SMILES: NNC(=O)c1cc(-c2ccc(C#Cc3ccc(S(=O)(=O)N4CCC[C@H]4C(=O)O)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 142 | A | 1.99 | 556 | Racemate | 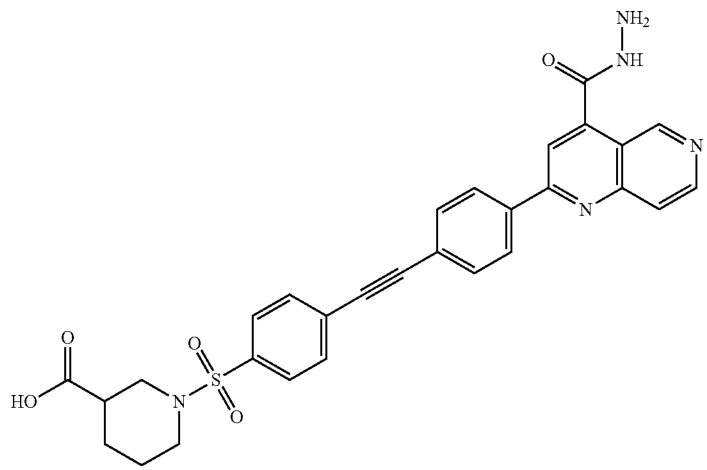 [SMILES: NNC(=O)c1cc(-c2ccc(C#Cc3ccc(S(=O)(=O)N4CCCC(C(=O)O)C4)cc3)cc2)nc2ccncc12] |
| 143 | A | 1.86 | 542.2 | Racemate | 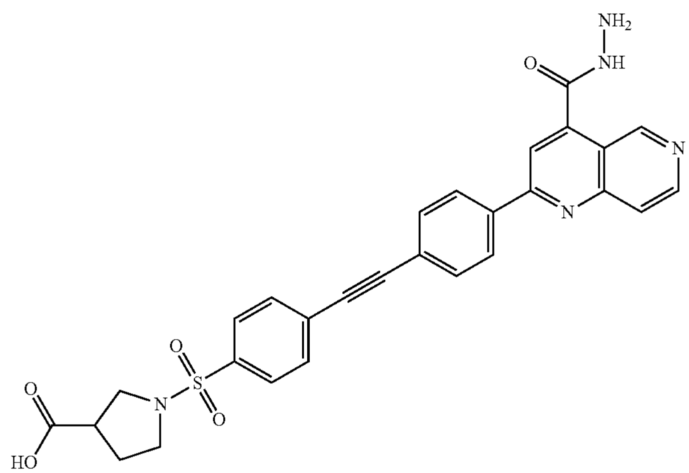 [SMILES: NNC(=O)c1cc(-c2ccc(C#Cc3ccc(S(=O)(=O)N4CCC(C(=O)O)C4)cc3)cc2)nc2ccncc12] |
| 144 | A | 2.06 | 556.6 | | 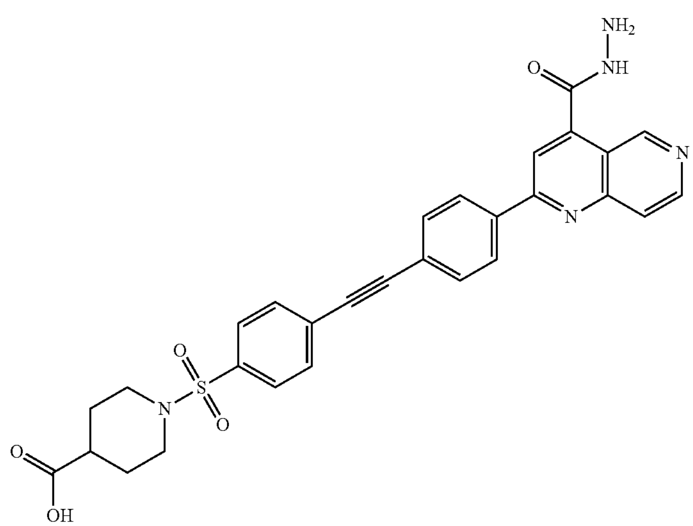 [SMILES: NNC(=O)c1cc(-c2ccc(C#Cc3ccc(S(=O)(=O)N4CCC(C(=O)O)CC4)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 145 | A | 2.02 | 514 | | 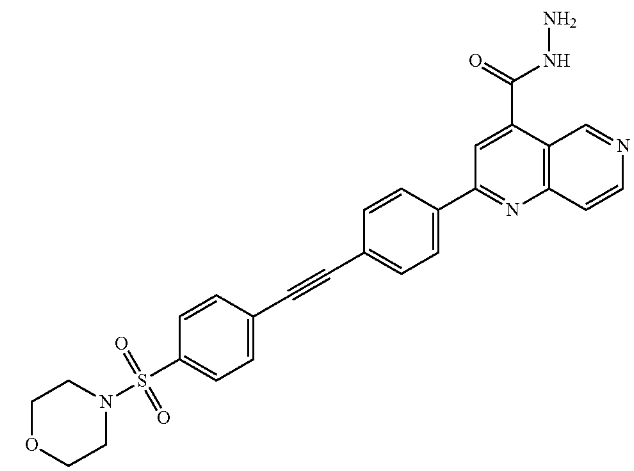 [SMILES: NNC(=O)c1cc(-c2ccc(C#Cc3ccc(S(=O)(=O)N4CCOCC4)cc3)cc2)nc2ccncc12] |
| 146 | A | 1.64 | 527.8 | | 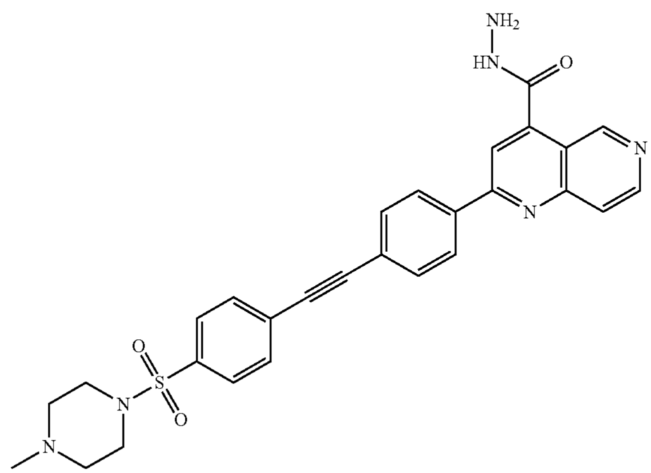 [SMILES: CN1CCN(S(=O)(=O)c2ccc(C#Cc3ccc(-c4cc(C(=O)NN)c5cnccc5n4)cc3)cc2)CC1] |
| 147 | A | 1.70 | 486.6 (M − 1) | | 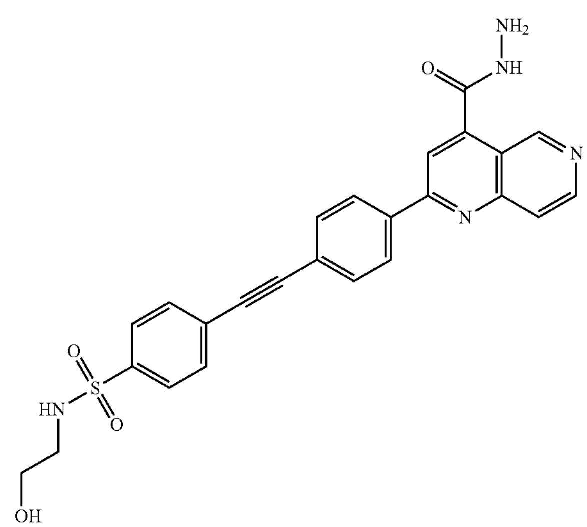 [SMILES: NNC(=O)c1cc(-c2ccc(C#Cc3ccc(S(=O)(=O)NCCO)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 148 | A | 1.75 | 500.5 (M − 1) | | 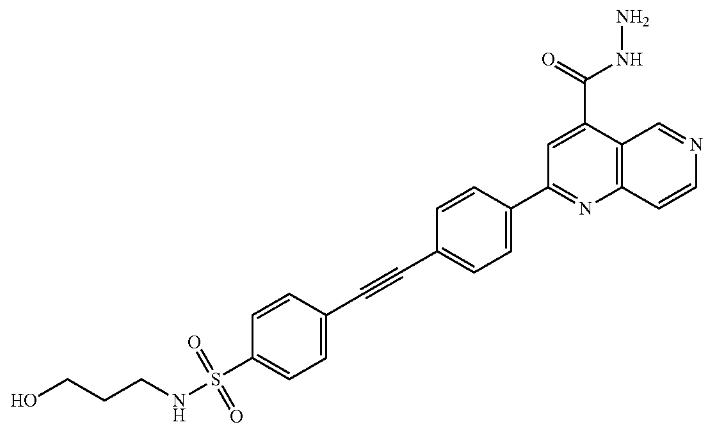 [SMILES: NNC(=O)c1cc(-c2ccc(C#Cc3ccc(S(=O)(=O)NCCCO)cc3)cc2)nc2ccncc12] |
| 149 | A | 1.65 | 500.3 | | 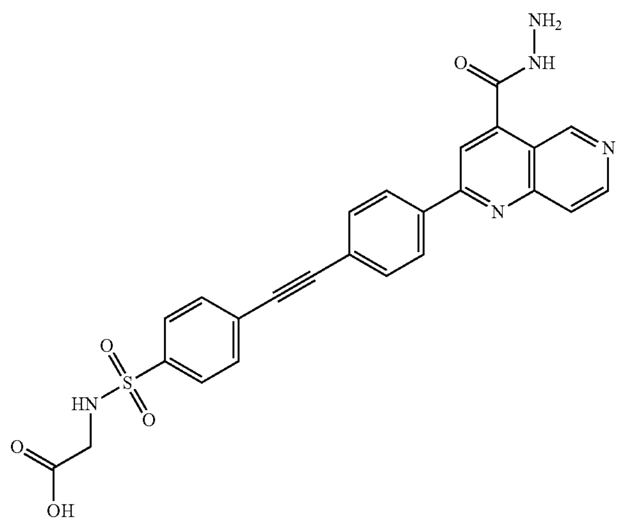 [SMILES: NNC(=O)c1cc(-c2ccc(C#Cc3ccc(S(=O)(=O)NCC(=O)O)cc3)cc2)nc2ccncc12] |
| 150 | A | 1.59 | 451.4 | | 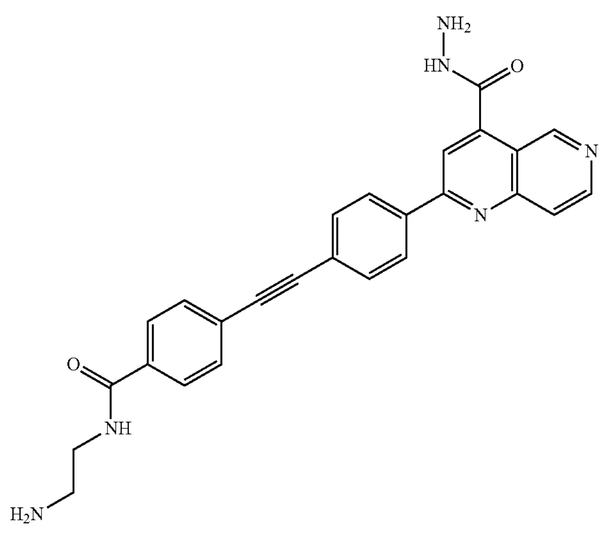 [SMILES: NCCNC(=O)c1ccc(C#Cc2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 151 | A | 1.55 | 487 | | 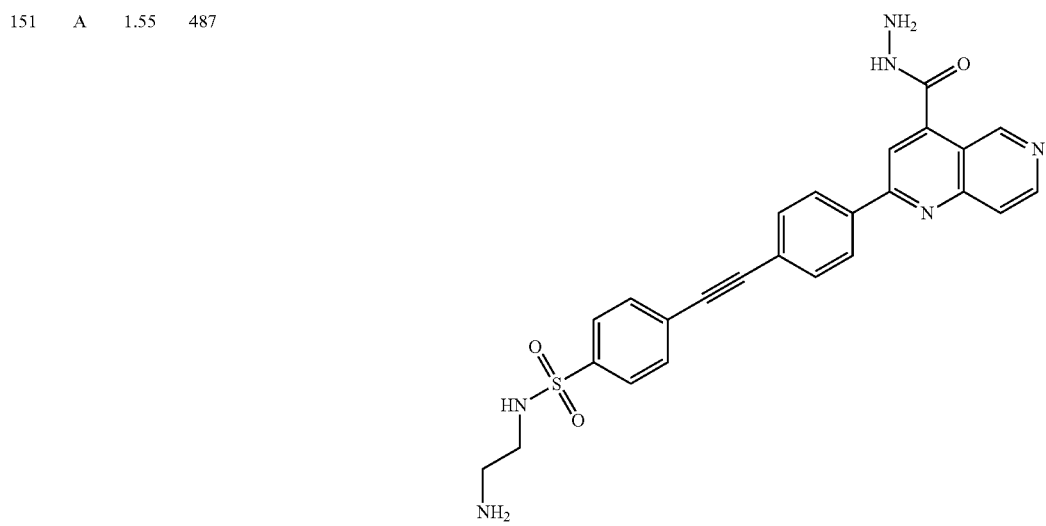 |
| 152 | A | 2.08 | 581 | R | 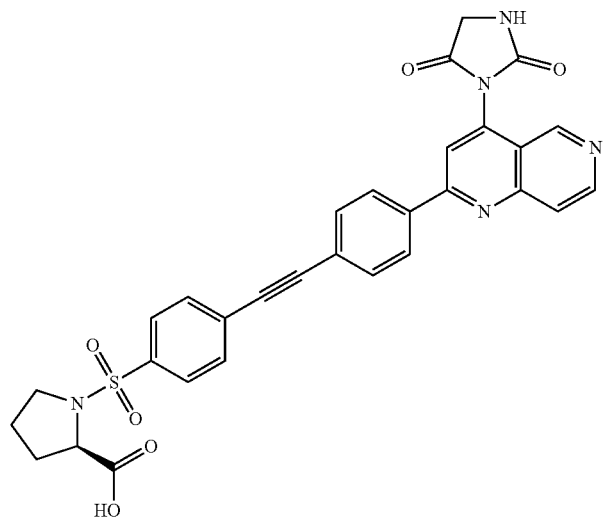 [SMILES: O=C(O)[C@H]1CCCN1S(=O)(=O)c1ccc(C#Cc2ccc(-c3cc(N4C(=O)CNC4=O)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 153 | A | 2.08 | 598.4 | R | 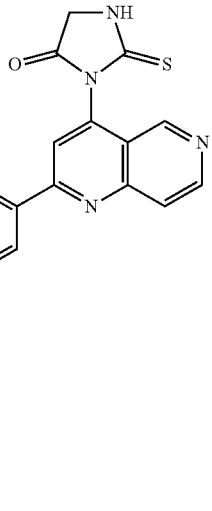 |
| 154 | A | 1.69 | 492.5 | Racemate | 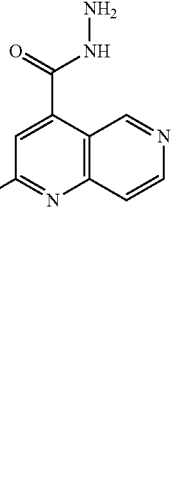 |
| 155 | A | 1.88 | 520.4 | Racemate | 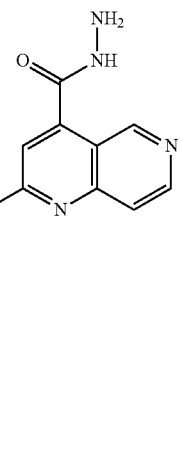 |

TABLE 1-continued

Analytical Data

| Example # | HPLC Method | HPLC RT | MS(ESI) (M + H) | Chirality | Structure |
|---|---|---|---|---|---|
| 156 | A | 1.84 | 520.4 | (−) | 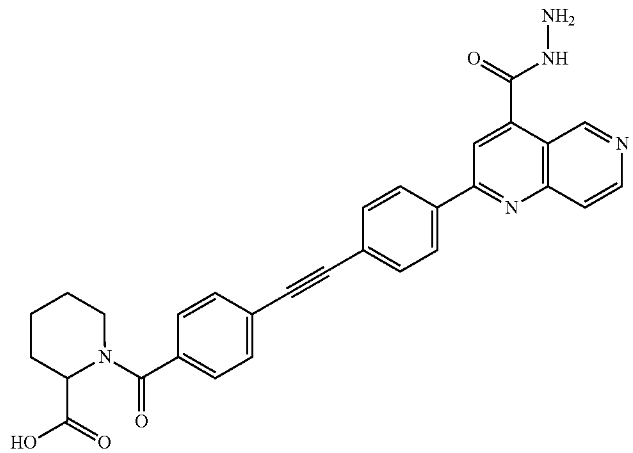 |
| 157 | A | 1.83 | 518.4 (M − 1) | (+) | 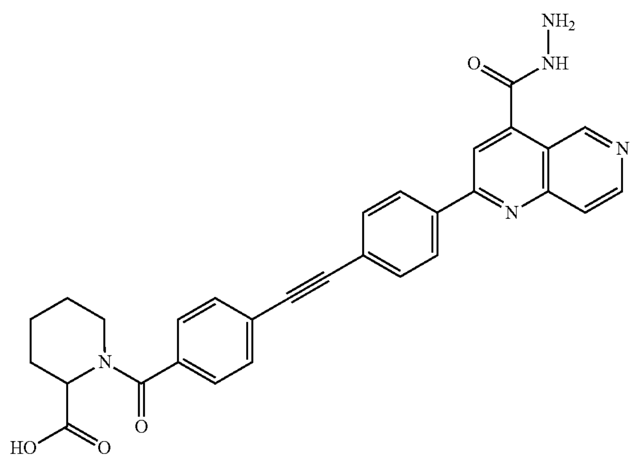 [SMILES: NNC(=O)c1cc(-c2ccc(C#Cc3ccc(C(=O)N4CCCCC4C(=O)O)cc3)cc2)nc2ccncc12] |
| 158 | A | 1.98 | 528.3 | Racemate | 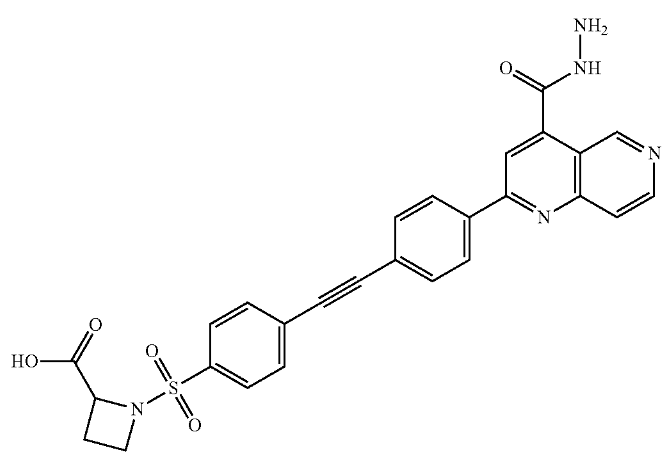 [SMILES: NNC(=O)c1cc(-c2ccc(C#Cc3ccc(S(=O)(=O)N4CCC4C(=O)O)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 159 | A | 2.10 | 556 | Racemate | 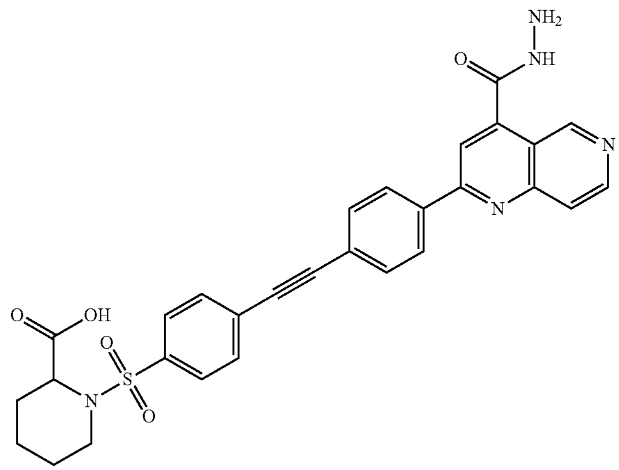 [SMILES: NNC(=O)c1cc(-c2ccc(C#Cc3ccc(S(=O)(=O)N4CCCCC4C(=O)O)cc3)cc2)nc2ccncc12] |
| 160 | A | 1.65 | 522.2 | Racemate | 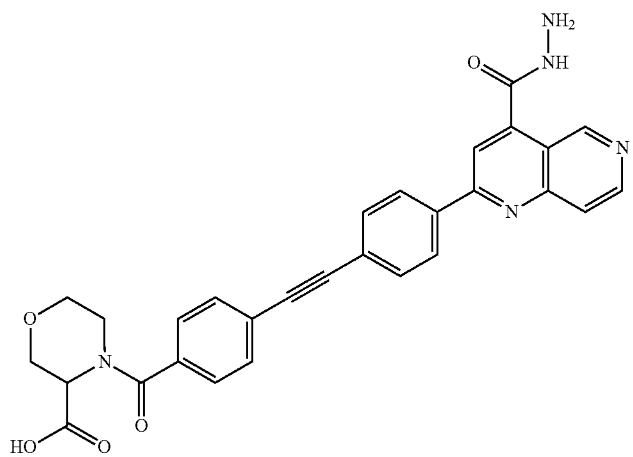 [SMILES: NNC(=O)c1cc(-c2ccc(C#Cc3ccc(C(=O)N4CCOCC4C(=O)O)cc3)cc2)nc2ccncc12] |
| 161 | G | 2.19 | 522 | Racemate | 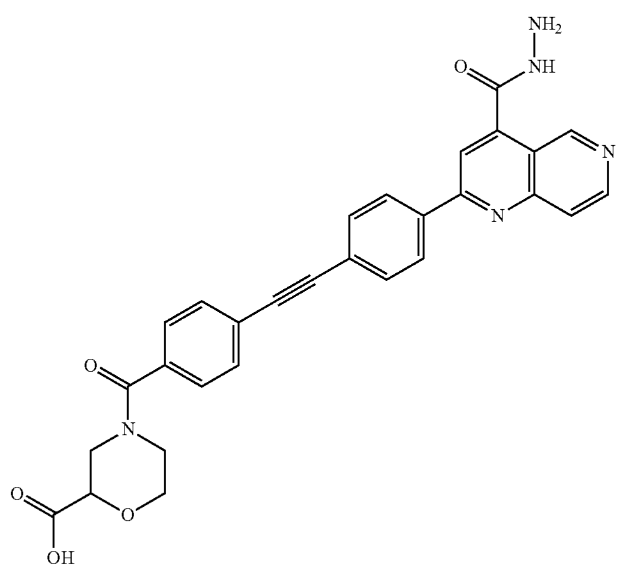 [SMILES: NNC(=O)c1cc(-c2ccc(C#Cc3ccc(C(=O)N4CCOC(C(=O)O)C4)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 162 | G | 2.54 | 440.3 | | 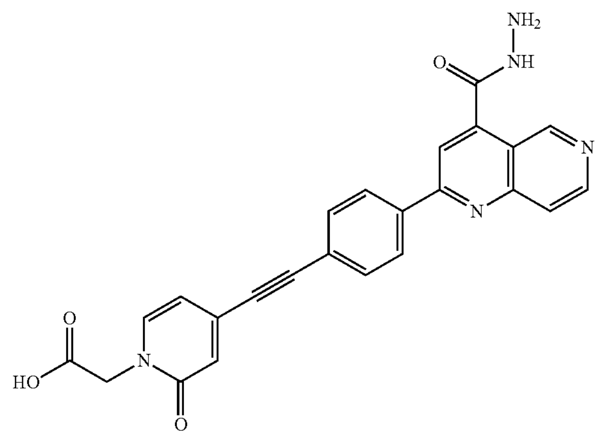 [SMILES: NNC(=O)c1cc(-c2ccc(C#Cc3ccn(CC(=O)O)c(=O)c3)cc2)nc2ccncc12] |
| 163 | A | 1.45 | 453.2 | | 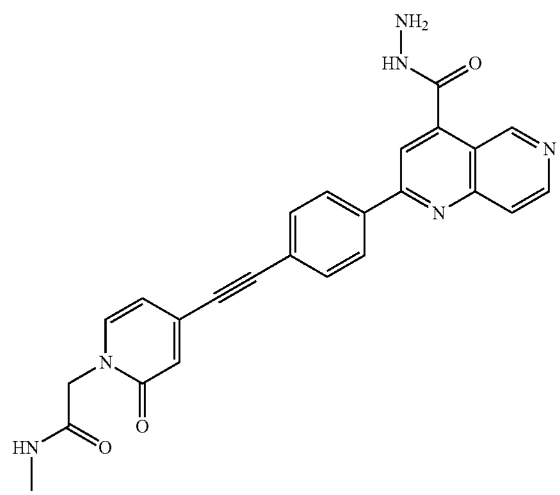 [SMILES: CNC(=O)Cn1ccc(C#Cc2ccc(-c3cc(C(=O)NN)c4cnccc4n3)cc2)cc1=O] |
| 164 | A | 1.76 | 526 | Racemate | 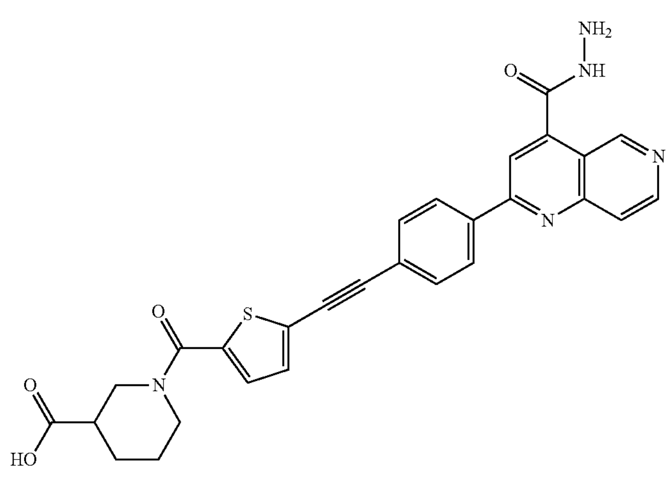 |

TABLE 1-continued
Analytical Data
| Example # | HPLC Method | HPLC RT | MS(ESI) (M + H) | Chirality | Structure |
|---|---|---|---|---|---|
| 165 | A | 1.86 | 526.3 | Racemate | 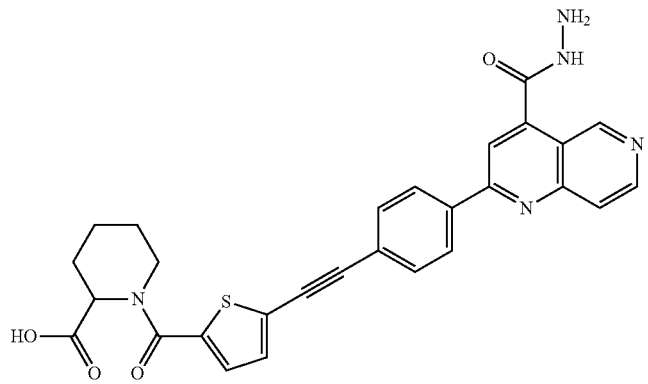 [SMILES: NNC(=O)c1cc(-c2ccc(C#Cc3ccc(C(=O)N4CCCCC4C(=O)O)s3)cc2)nc2ccncc12] |
| 166 | A | 1.81 | 510.5 | Racemate | 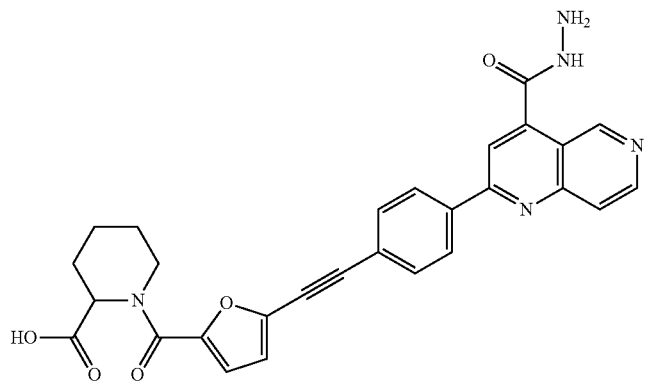 [SMILES: NNC(=O)c1cc(-c2ccc(C#Cc3ccc(C(=O)N4CCCCC4C(=O)O)o3)cc2)nc2ccncc12] |
| 167 | A | 1.70 | 510 | Racemate | 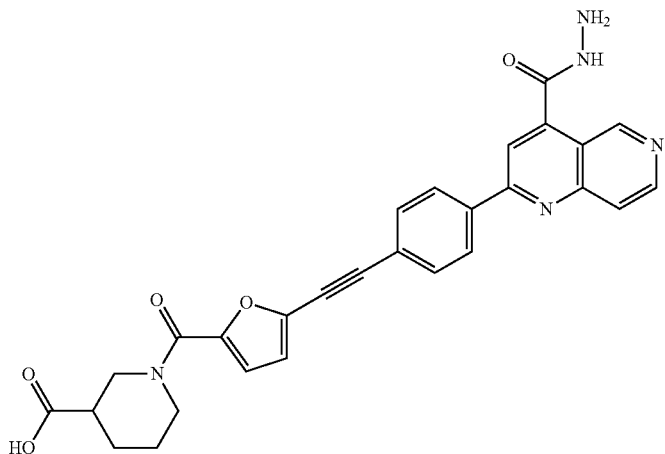 [SMILES: NNC(=O)c1cc(-c2ccc(C#Cc3ccc(C(=O)N4CCCC(C(=O)O)C4)o3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 168 | A | 1.70 | 521 | Racemate | 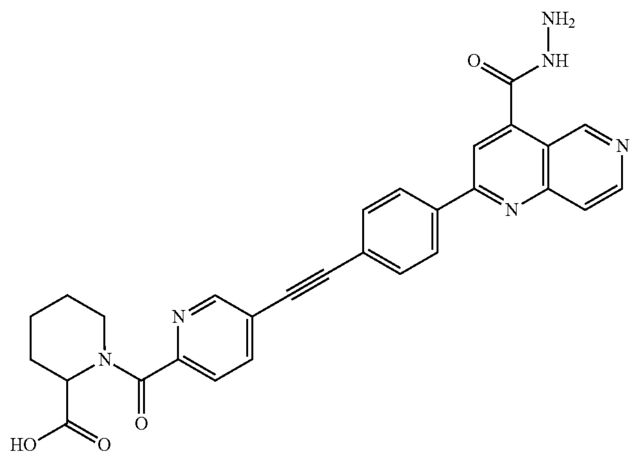 [SMILES: NNC(=O)c1cc(-c2ccc(C#Cc3ccc(C(=O)N4CCCCC4C(=O)O)nc3)cc2)nc2ccncc12] |
| 169 | A | 1.89 | 538.4 | Racemate | 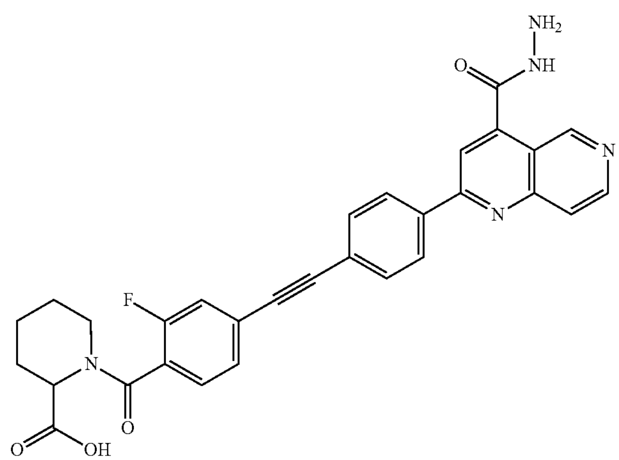 [SMILES: NNC(=O)c1cc(-c2ccc(C#Cc3ccc(C(=O)N4CCCCC4C(=O)O)c(F)c3)cc2)nc2ccncc12] |
| 170 | A | 1.65 | 480.3 | Racemate | 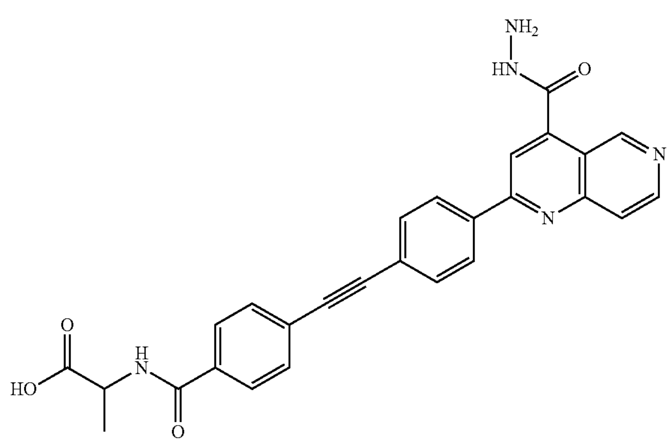 [SMILES: CC(NC(=O)c1ccc(C#Cc2ccc(-c3cc(C(=O)NN)c4cnccc4n3)cc2)cc1)C(=O)O] |

TABLE 1-continued
Analytical Data
| Example # | HPLC Method | HPLC RT | MS(ESI) (M + H) | Chirality | Structure |
|---|---|---|---|---|---|
| 171 | A | 1.87 | 506.4 | Racemate | 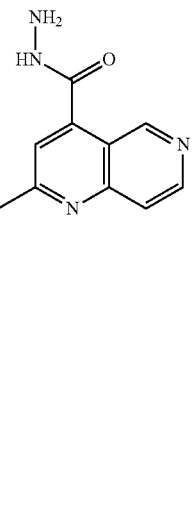 |
| 172 | A | 1.96 | 522.6 | Racemate | 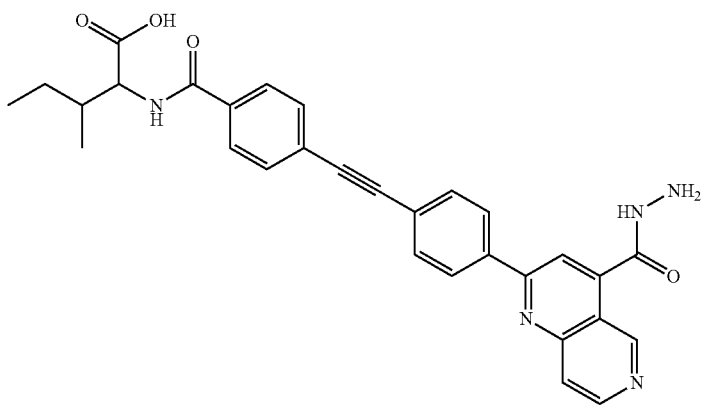 [SMILES: CCC(C)C(NC(=O)c1ccc(C#Cc2ccc(-c3cc(C(=O)NN)c4cnccc4n3)cc2)cc1)C(=O)O] |
| 173 | A | 2.00 | 522.4 | Racemate | 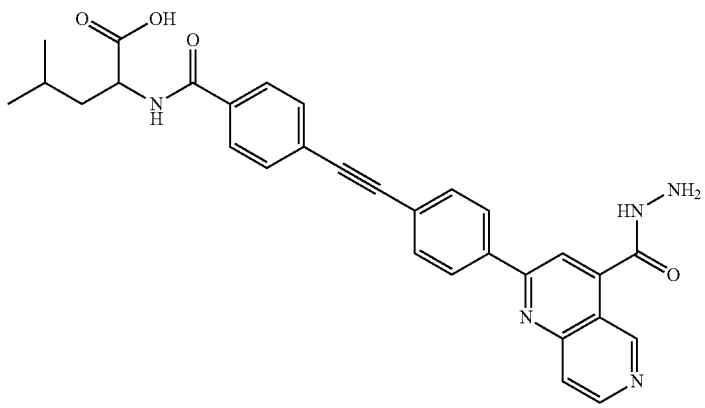 [SMILES: CC(C)CC(NC(=O)c1ccc(C#Cc2ccc(-c3cc(C(=O)NN)c4cnccc4n3)cc2)cc1)C(=O)O] |

TABLE 1-continued
Analytical Data
| Example # | HPLC Method | HPLC RT | MS(ESI) (M + H) | Chirality | Structure |
|---|---|---|---|---|---|
| 174 | A | 1.51 | 522.4 | Racemate | 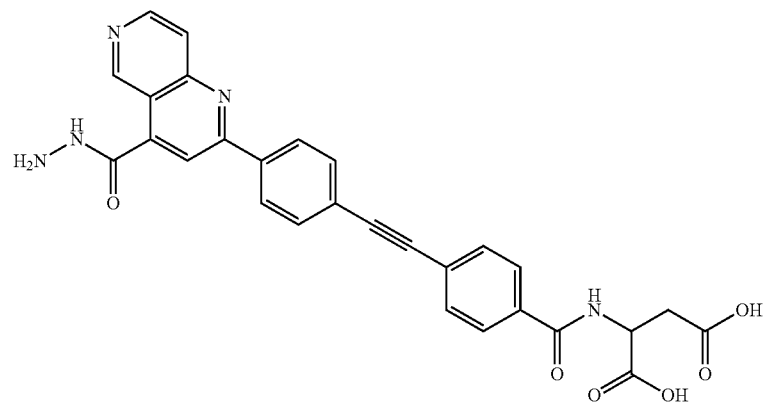 [SMILES: NNC(=O)c1cc(-c2ccc(C#Cc3ccc(C(=O)NC(CC(=O)O)C(=O)O)cc3)cc2)nc2ccncc12] |
| 175 | A | 1.52 | 538 | Racemate | 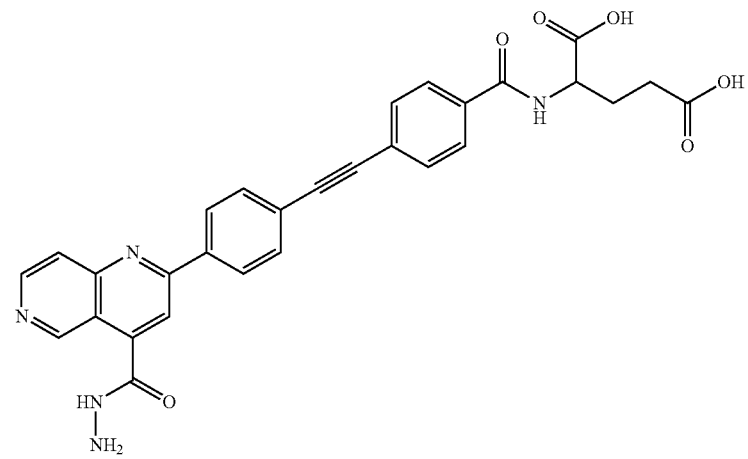 [SMILES: NNC(=O)c1cc(-c2ccc(C#Cc3ccc(C(=O)NC(CCC(=O)O)C(=O)O)cc3)cc2)nc2ccncc12] |
| 176 | A | 1.49 | 496.2 | Racemate | 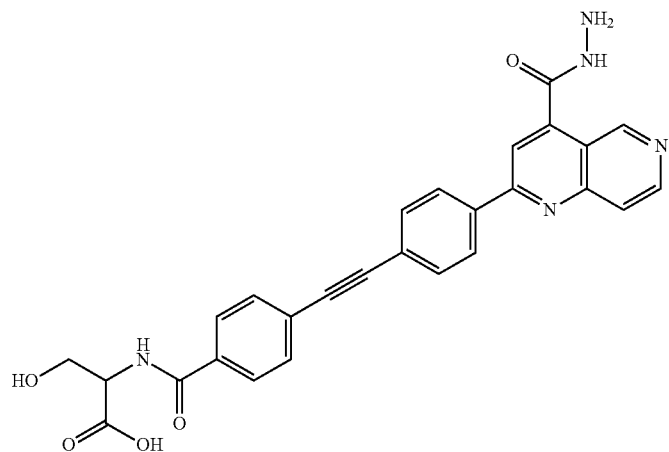 [SMILES: NNC(=O)c1cc(-c2ccc(C#Cc3ccc(C(=O)NC(CO)C(=O)O)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 177 | A | 1.57 | 508.4 | Racemate | 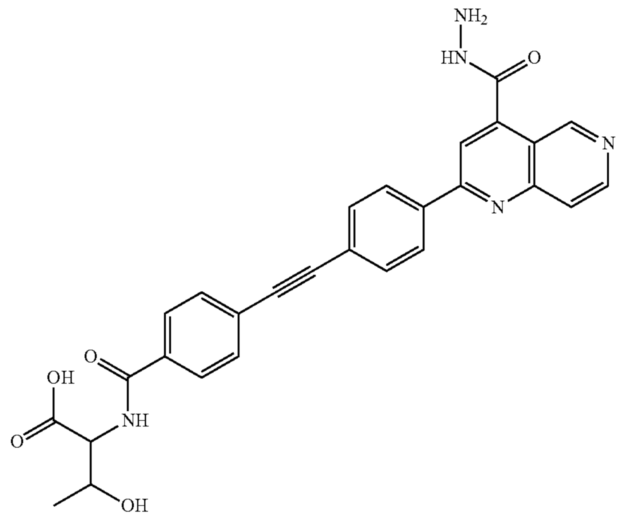 [SMILES: CC(O)C(NC(=O)c1ccc(C#Cc2ccc(-c3cc(C(=O)NN)c4cnccc4n3)cc2)cc1)C(=O)O] |
| 178 | A | 1.82 | 540 | Racemate | 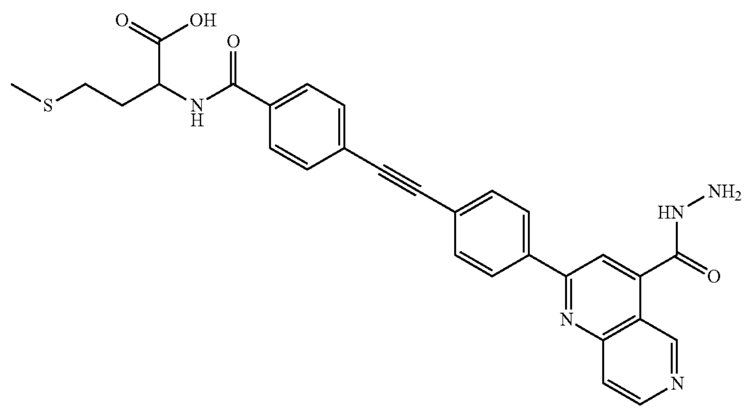 [SMILES: CSCCC(NC(=O)c1ccc(C#Cc2ccc(-c3cc(C(=O)NN)c4cnccc4n3)cc2)cc1)C(=O)O] |
| 179 | A | 1.96 | 556.6 | Racemate | 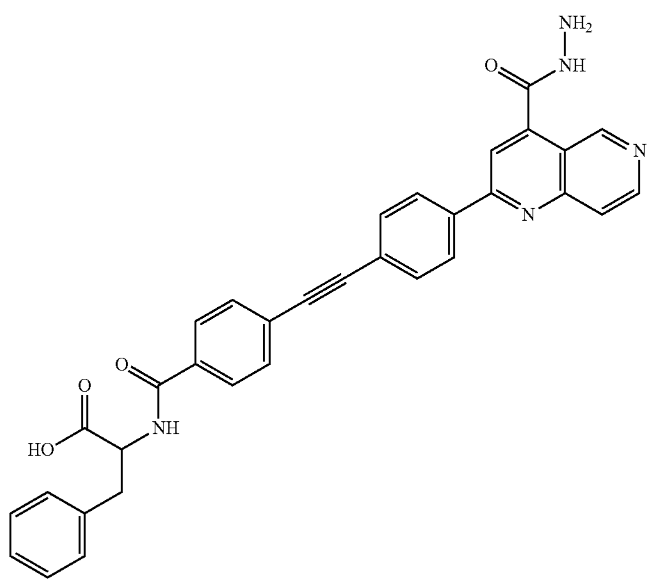 [SMILES: NNC(=O)c1cc(-c2ccc(C#Cc3ccc(C(=O)NC(Cc4ccccc4)C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 180 | A | 1.71 | 572 | Racemate | 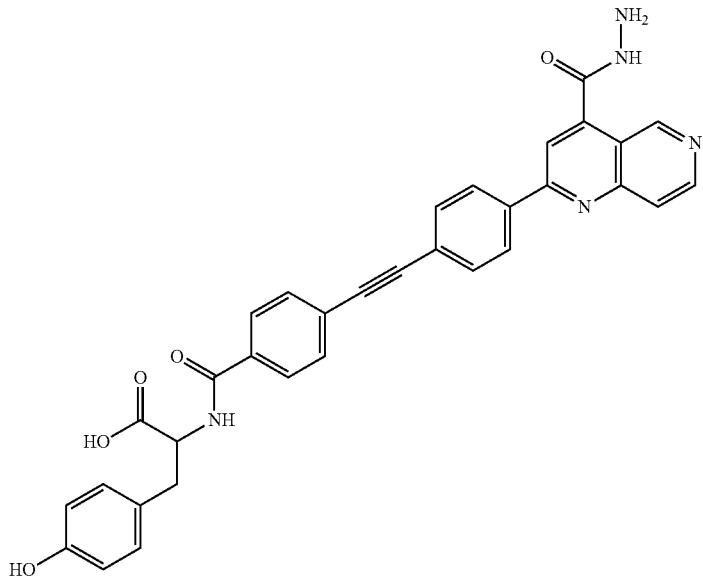 [SMILES: NNC(=O)c1cc(-c2ccc(C#Cc3ccc(C(=O)NC(Cc4ccc(O)cc4)C(=O)O)cc3)cc2)nc2ccncc12] |
| 181 | A | 1.80 | 538.4 | Racemate | 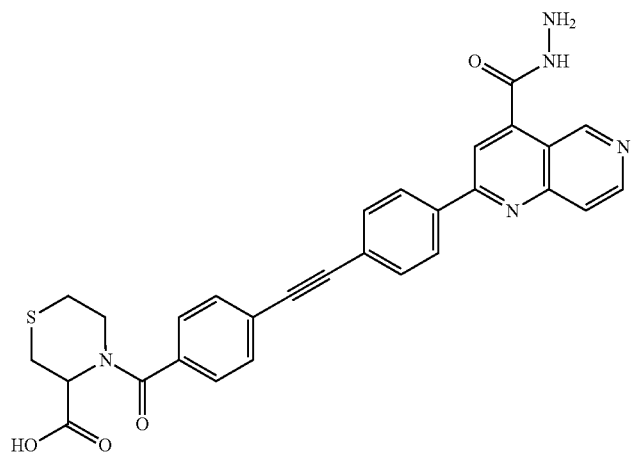 |

TABLE 1-continued
Analytical Data
| Example # | HPLC Method | HPLC RT | MS(ESI) (M + H) | Chirality | Structure |
|---|---|---|---|---|---|
| 182 | A | 1.74 | 492.4 | | 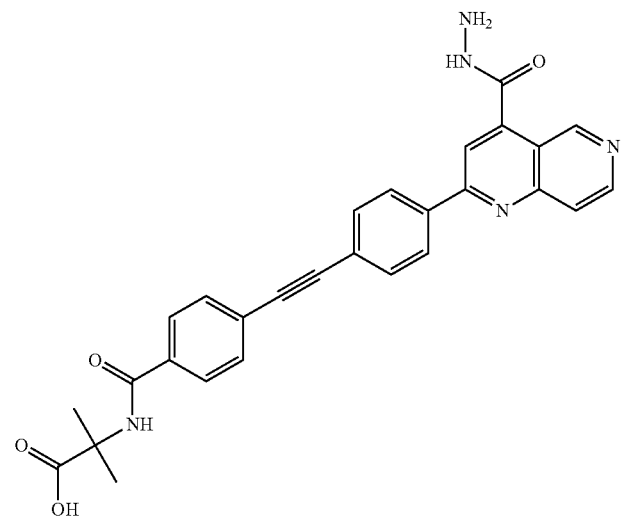 [SMILES: CC(C)(NC(=O)c1ccc(C#Cc2ccc(-c3cc(C(=O)NN)c4cnccc4n3)cc2)cc1)C(=O)O] |
| 183 | A | 1.84 | 470.4 (M − 1) | | 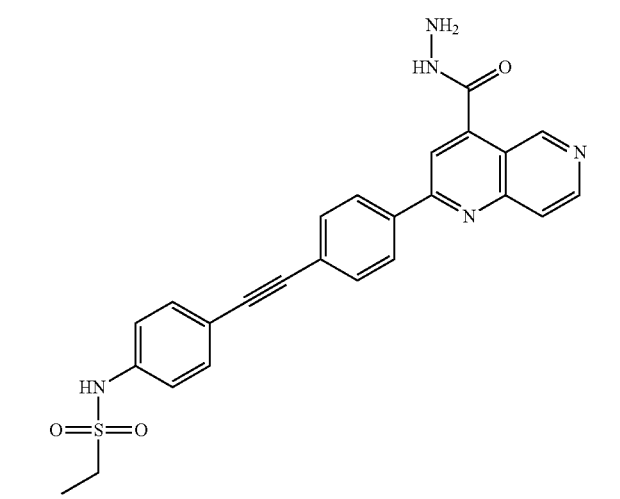 [SMILES: CCS(=O)(=O)Nc1ccc(C#Cc2ccc(-c3cc(C(=O)NN)c4cnccc4n3)cc2)cc1] |
| 184 | A | 1.95 | 486.3 | | 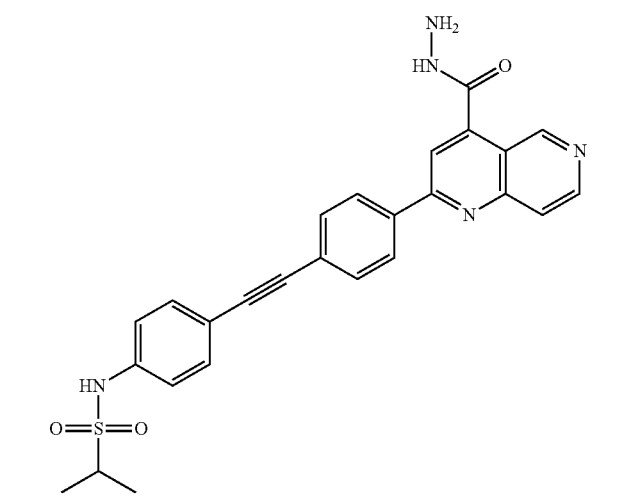 [SMILES: CC(C)S(=O)(=O)Nc1ccc(C#Cc2ccc(-c3cc(C(=O)NN)c4cnccc4n3)cc2)cc1] |

TABLE 1-continued

Analytical Data

| Example # | HPLC Method | HPLC RT | MS(ESI) (M + H) | Chirality | Structure |
|---|---|---|---|---|---|
| 185 | A | 2.18 | 512 | | 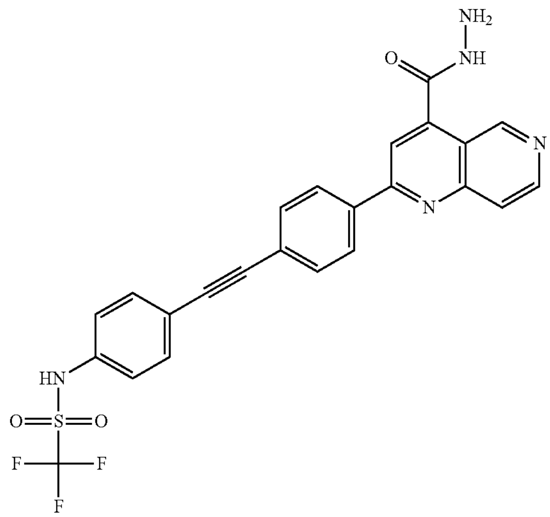 [SMILES: NNC(=O)c1cc(-c2ccc(C#Cc3ccc(NS(=O)(=O)C(F)(F)F)cc3)cc2)nc2ccncc12] |
| 186 | A | 1.68 | 502.8 | | 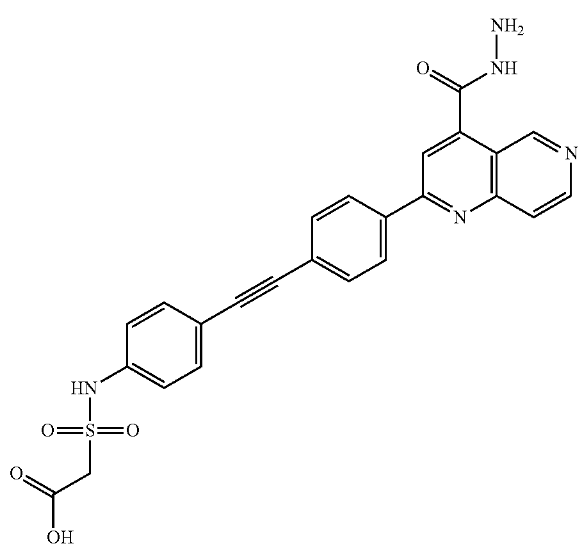 [SMILES: NNC(=O)c1cc(-c2ccc(C#Cc3ccc(NS(=O)(=O)CC(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 187 | A | 1.74 | 520.4 | Racemate | 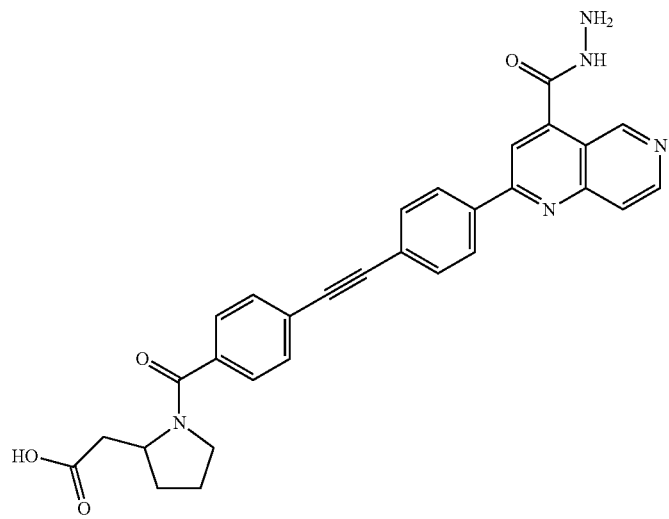 [SMILES: NNC(=O)c1cc(-c2ccc(C#Cc3ccc(C(=O)N4CCCC4CC(=O)O)cc3)cc2)nc2ccncc12] |
| 188 | A | 1.83 | 534.4 | Racemate | 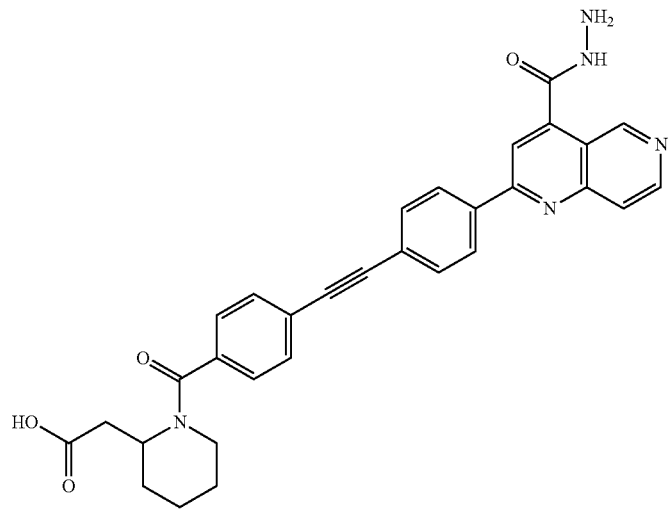 [SMILES: NNC(=O)c1cc(-c2ccc(C#Cc3ccc(C(=O)N4CCCCC4CC(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 189 | A | 1.61 | 480.4 | | 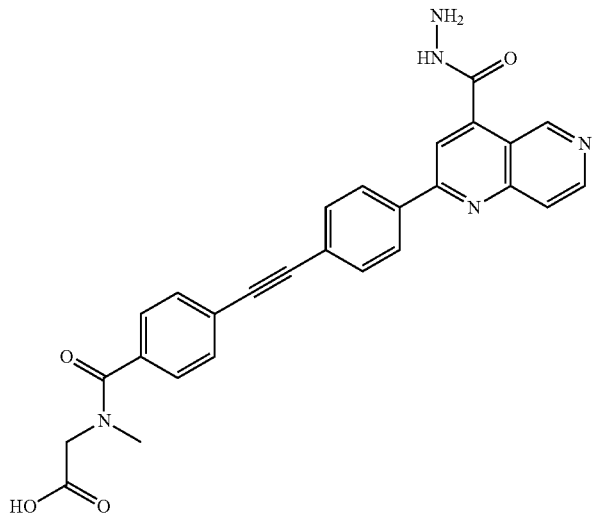 [SMILES: CN(CC(=O)O)C(=O)c1ccc(C#Cc2ccc(-c3cc(C(=O)NN)c4cnccc4n3)cc2)cc1] |
| 190 | A | 1.70 | 494.7 | Racemate | 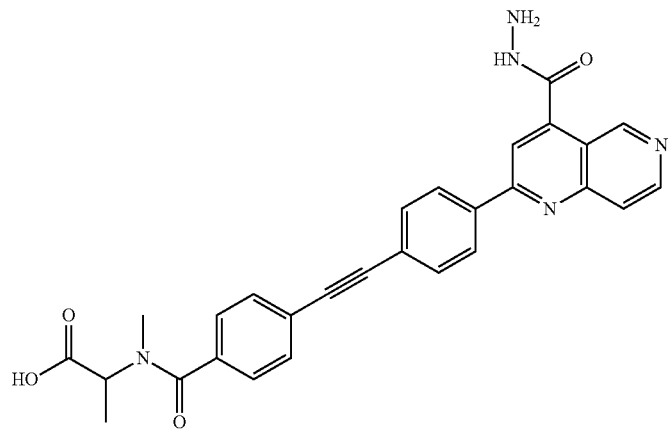 [SMILES: CC(C(=O)O)N(C)C(=O)c1ccc(C#Cc2ccc(-c3cc(C(=O)NN)c4cnccc4n3)cc2)cc1] |
| 191 | A | 1.59 | 480.4 | | 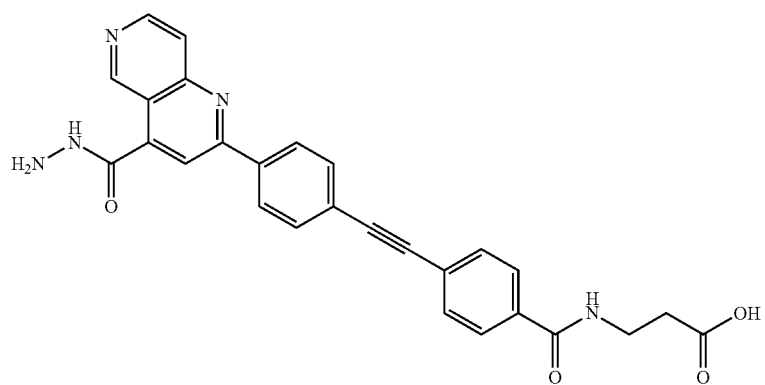 [SMILES: NNC(=O)c1cc(-c2ccc(C#Cc3ccc(C(=O)NCCC(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 192 | A | 1.60 | 494.6 | | 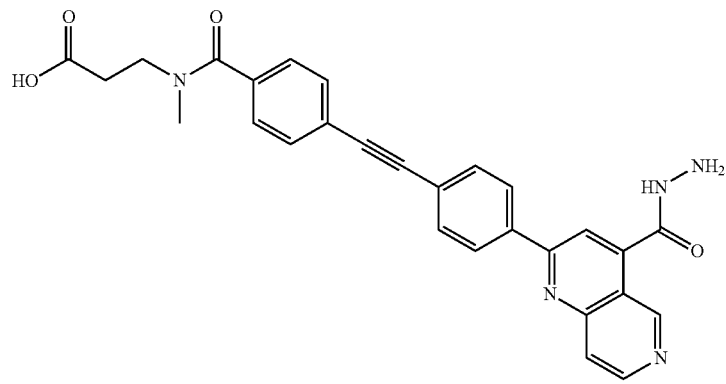 [SMILES: CN(CCC(=O)O)C(=O)c1ccc(C#Cc2ccc(-c3cc(C(=O)NN)c4cnccc4n3)cc2)cc1] |
| 193 | A | 1.67 | 494.4 | Racemate | 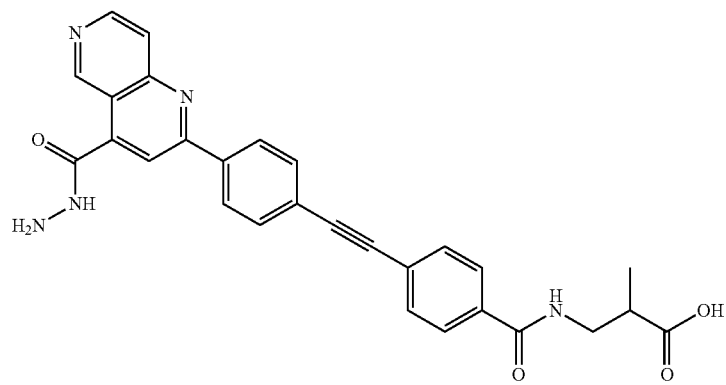 [SMILES: CC(CNC(=O)c1ccc(C#Cc2ccc(-c3cc(C(=O)NN)c4cnccc4n3)cc2)cc1)C(=O)O] |
| 194 | A | 1.65 | 494.4 | Racemate | 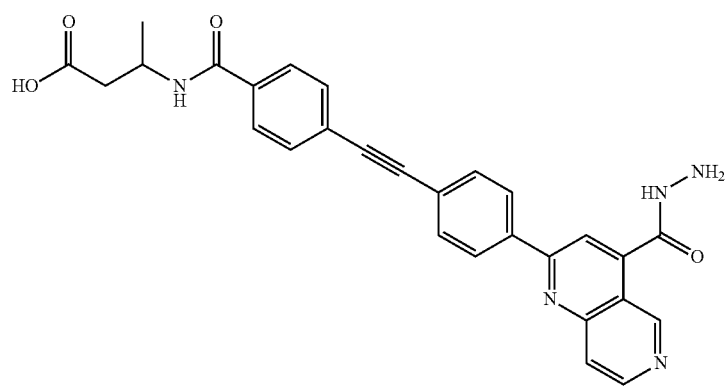 [SMILES: CC(CC(=O)O)NC(=O)c1ccc(C#Cc2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 195 | A | 1.69 | 508.4 | Racemate | 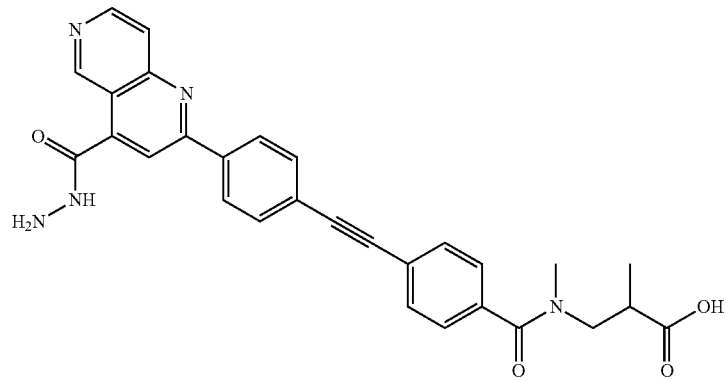 [SMILES: CC(CN(C)C(=O)c1ccc(C#Cc2ccc(-c3cc(C(=O)NN)c4cnccc4n3)cc2)cc1)C(=O)O] |
| 196 | A | 1.68 | 508.6 | Racemate | 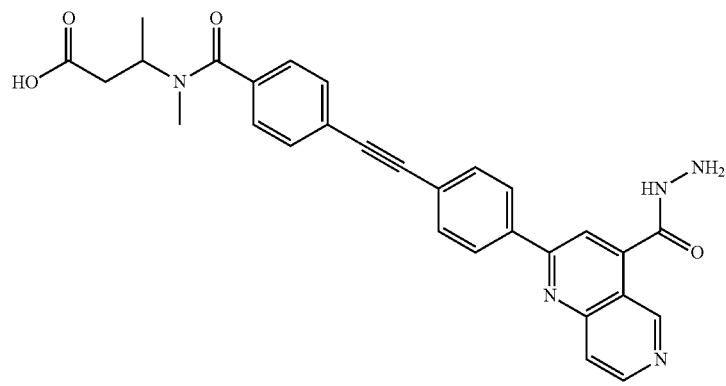 [SMILES: CC(CC(=O)O)N(C)C(=O)c1ccc(C#Cc2ccc(-c3cc(C(=O)NN)c4cnccc4n3)cc2)cc1] |
| 197 | A | 1.90 | 556.3 | Racemate | 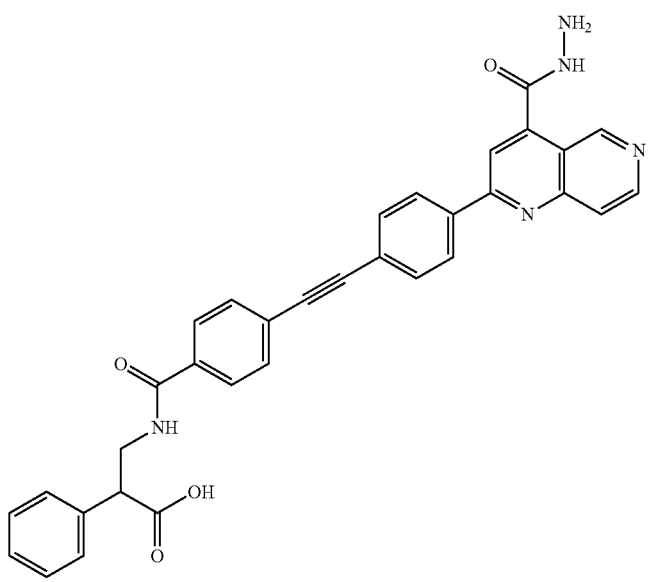 [SMILES: NNC(=O)c1cc(-c2ccc(C#Cc3ccc(C(=O)NCC(C(=O)O)c4ccccc4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 198 | A | 1.91 | 556.4 | Racemate | 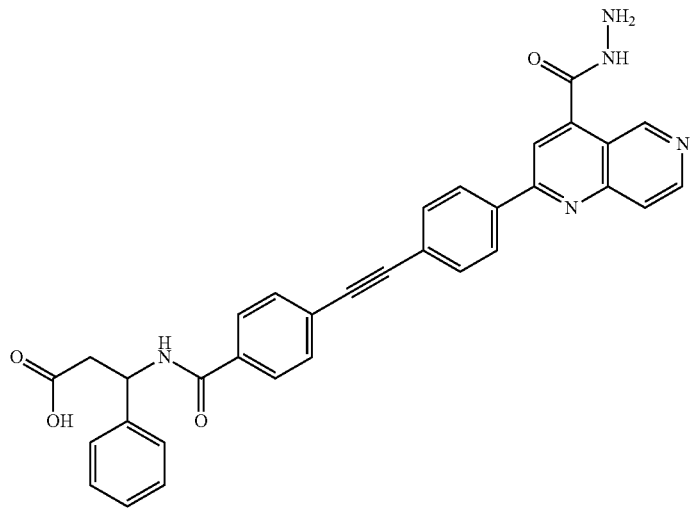 [SMILES: NNC(=O)c1cc(-c2ccc(C#Cc3ccc(C(=O)NC(CC(=O)O)c4ccccc4)cc3)cc2)nc2ccncc12] |
| 199 | G | 2.51 | 544.4 | | 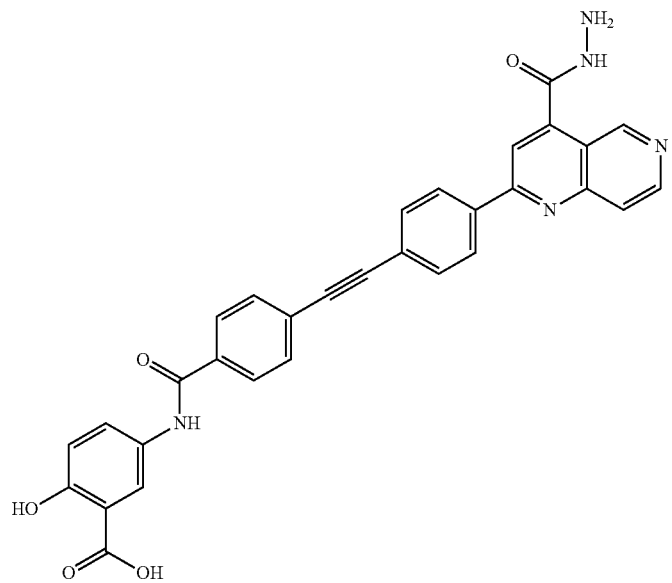 [SMILES: NNC(=O)c1cc(-c2ccc(C#Cc3ccc(C(=O)Nc4ccc(O)c(C(=O)O)c4)cc3)cc2)nc2ccncc12] |

TABLE 1-continued
| Example # | HPLC Method | HPLC RT | MS(ESI) (M + H) | Chirality | Structure |
|---|---|---|---|---|---|
| 200 | F | 2.88 | 528 | | 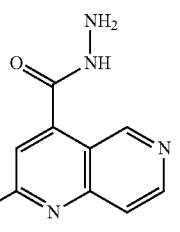 |
| 201 | NA | NA | 510 | | 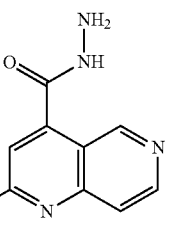 |

TABLE 1-continued
Analytical Data
| Example # | HPLC Method | HPLC RT | MS(ESI) (M + H) | Chirality | Structure |
|---|---|---|---|---|---|
| 202 | A | 1.93 | 554.5 | S | 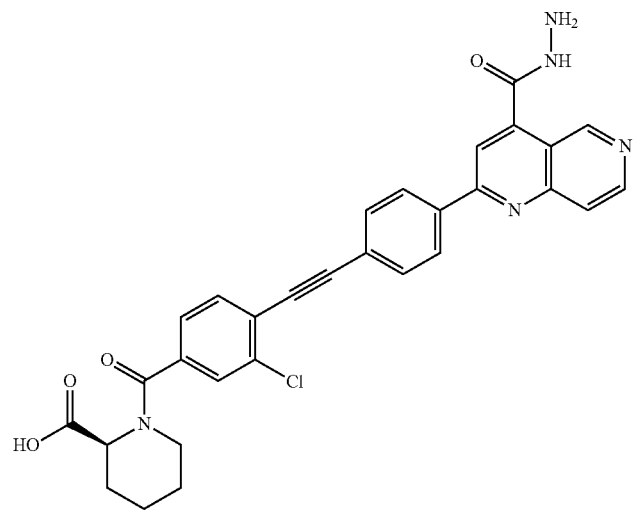 [SMILES: NNC(=O)c1cc(-c2ccc(C#Cc3ccc(C(=O)N4CCCC[C@H]4C(=O)O)cc3Cl)cc2)nc2ccncc12] |
| 203 | C | 7.52 | 528.5 | | 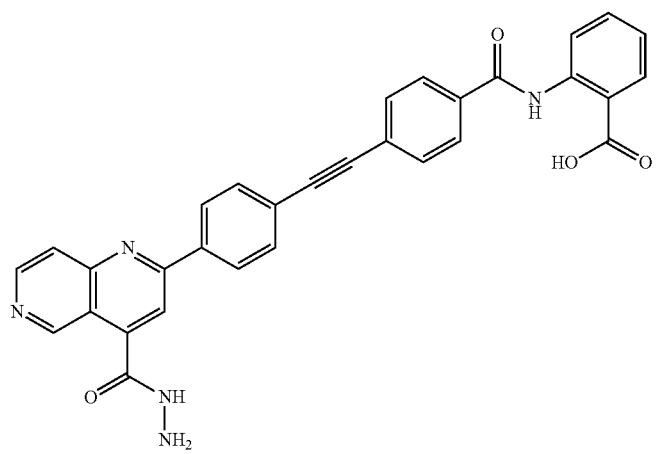 [SMILES: NNC(=O)c1cc(-c2ccc(C#Cc3ccc(C(=O)Nc4ccccc4C(=O)O)cc3)cc2)nc2ccncc12] |
| 204 | C | 6.91 | 548.4 | Racemate | 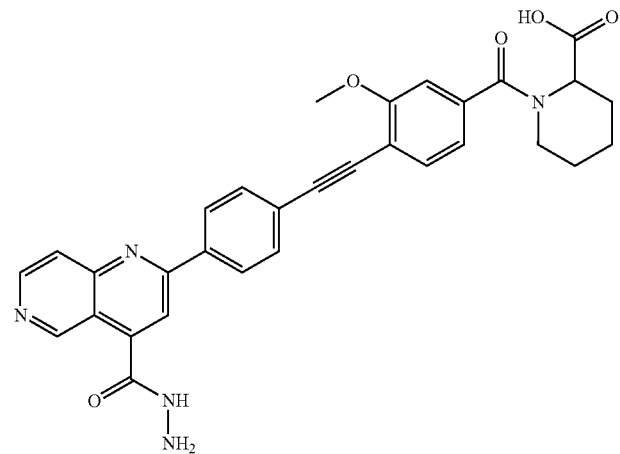 [SMILES: COc1cc(C(=O)N2CCCCC2C(=O)O)ccc1C#Cc1ccc(-c2cc(C(=O)NN)c3cnccc3n2)cc1] |

TABLE 1-continued
Analytical Data
| Example # | HPLC Method | HPLC RT | MS(ESI) (M + H) | Chirality | Structure |
|---|---|---|---|---|---|
| 205 | C | 6.85 | 536.4 | Racemate | 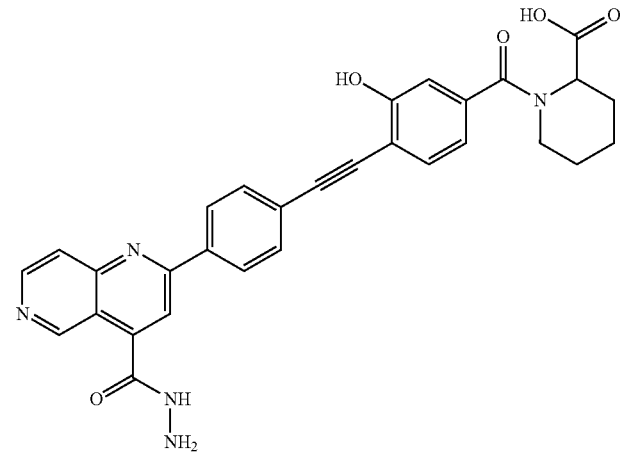 [SMILES: NNC(=O)c1cc(-c2ccc(C#Cc3ccc(C(=O)N4CCCCC4C(=O)O)cc3O)cc2)nc2ccncc12] |
| 206 | G | 2.65 | 588.8 | Racemate | 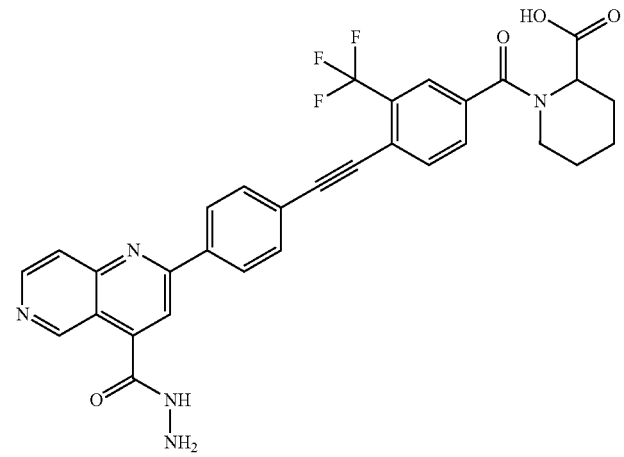 [SMILES: NNC(=O)c1cc(-c2ccc(C#Cc3ccc(C(=O)N4CCCCC4C(=O)O)cc3C(F)(F)F)cc2)nc2ccncc12] |
| 207 | A | 1.53 | 536.6 | Racemate | 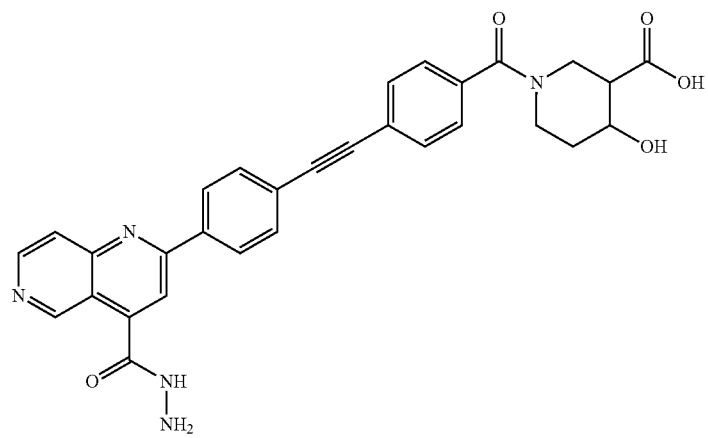 [SMILES: NNC(=O)c1cc(-c2ccc(C#Cc3ccc(C(=O)N4CCC(O)C(C(=O)O)C4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 208 | A | 1.86 | 538.8 | R | 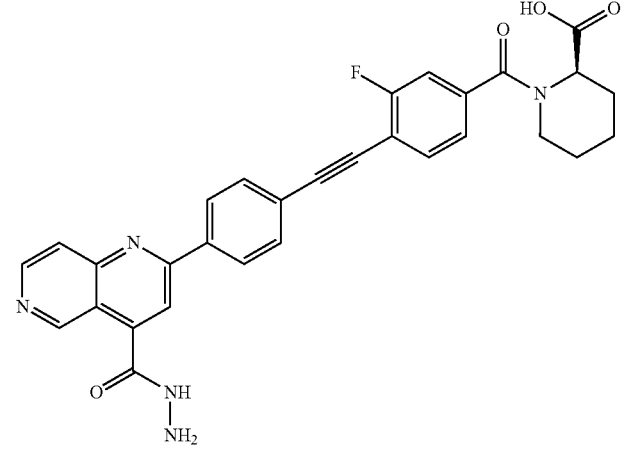 [SMILES: NNC(=O)c1cc(-c2ccc(C#Cc3ccc(C(=O)N4CCCC[C@@H]4C(=O)O)cc3F)cc2)nc2ccncc12] |
| 209 | A | 1.85 | 538 | S | 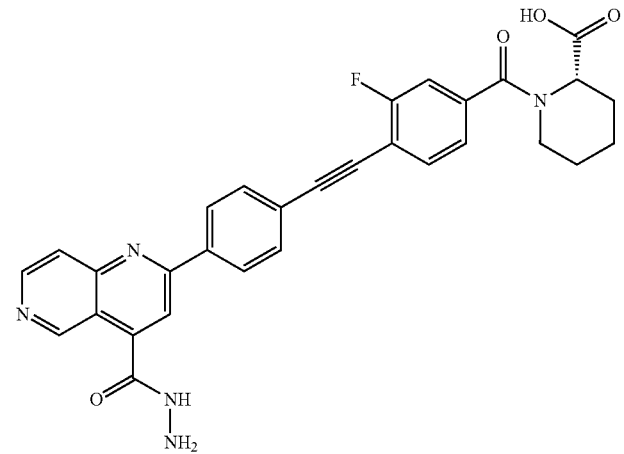 [SMILES: NNC(=O)c1cc(-c2ccc(C#Cc3ccc(C(=O)N4CCCC[C@H]4C(=O)O)cc3F)cc2)nc2ccncc12] |
| 210 | A | 1.9 | 556.7 | Racemate | 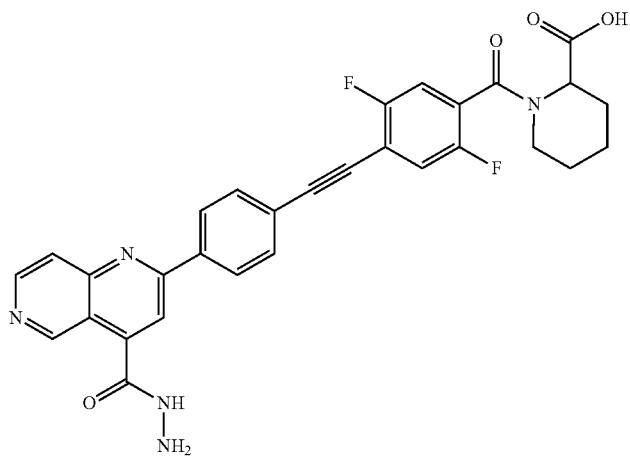 [SMILES: NNC(=O)c1cc(-c2ccc(C#Cc3cc(F)c(C(=O)N4CCCCC4C(=O)O)cc3F)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 211 | A | 1.67 | 450.5 | Racemate | 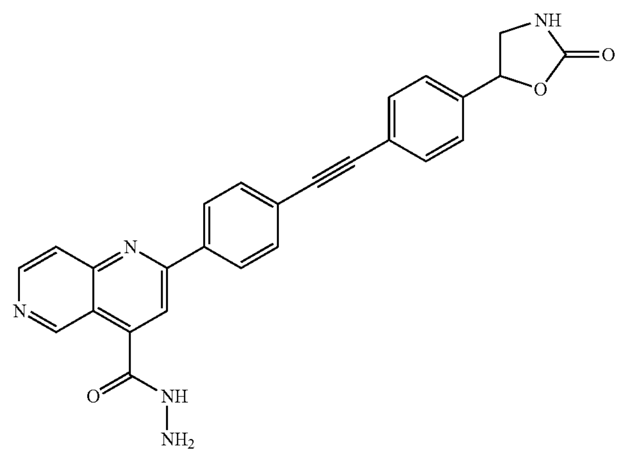 [SMILES: NNC(=O)c1cc(-c2ccc(C#Cc3ccc(C4CNC(=O)O4)cc3)cc2)nc2ccncc12] |
| 212 | C | 7.2 | 554.6 | Racemate | 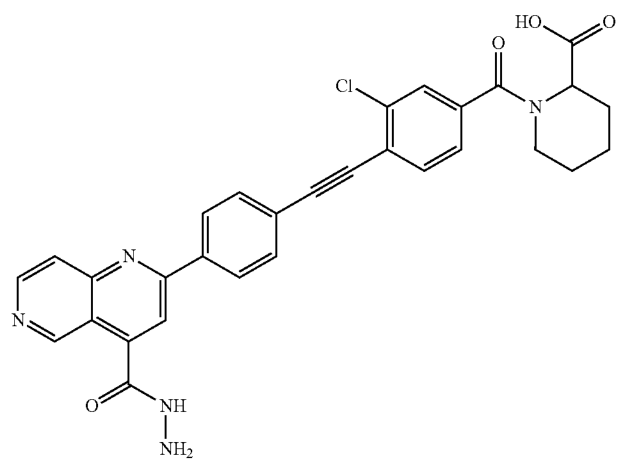 [SMILES: NNC(=O)c1cc(-c2ccc(C#Cc3ccc(C(=O)N4CCCCC4C(=O)O)cc3Cl)cc2)nc2ccncc12] |
| 213 | C | 7.36 | 570.6 | Racemate | 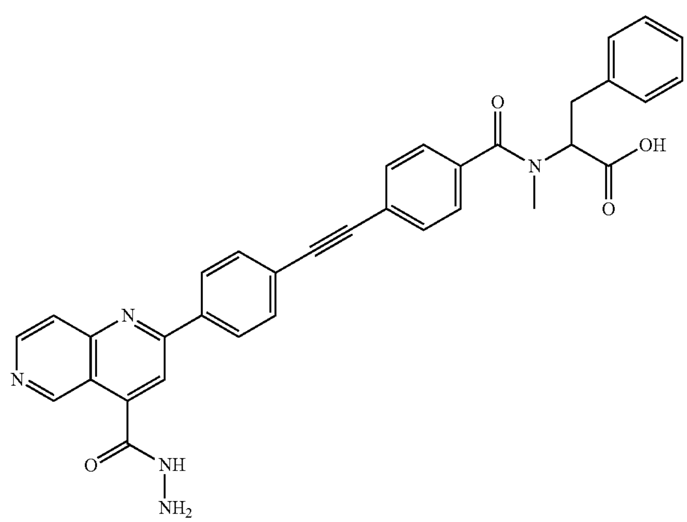 [SMILES: CN(C(=O)c1ccc(C#Cc2ccc(-c3cc(C(=O)NN)c4cnccc4n3)cc2)cc1)C(Cc1ccccc1)C(=O)O] |

TABLE 1-continued
Analytical Data
| Example # | HPLC Method | HPLC RT | MS(ESI) (M + H) | Chirality | Structure |
|---|---|---|---|---|---|
| 214 | C | 7.49 | 574.6 | Racemate | 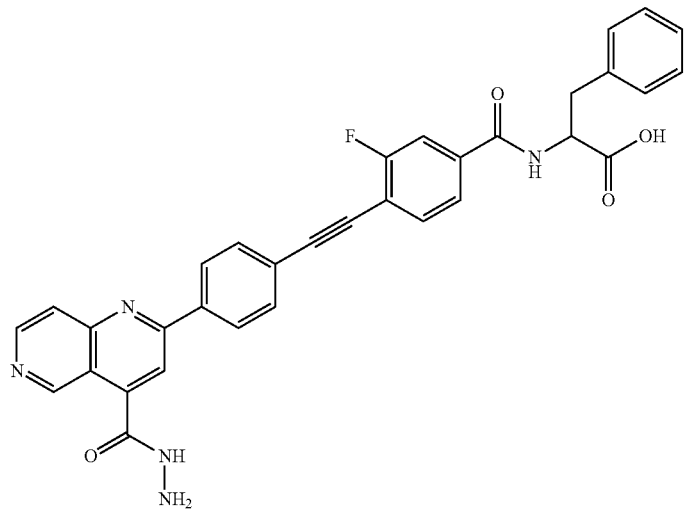 [SMILES: NNC(=O)c1cc(-c2ccc(C#Cc3ccc(C(=O)NC(Cc4ccccc4)C(=O)O)cc3F)cc2)nc2ccncc12] |
| 215 | C | 7.14 | 544 | | 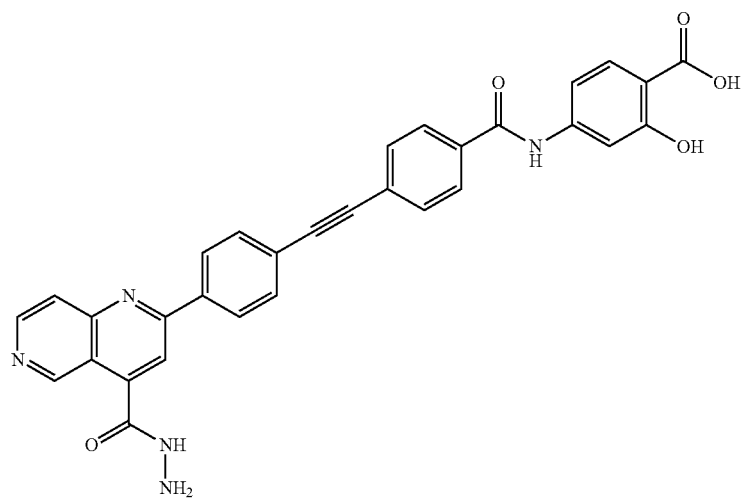 [SMILES: NNC(=O)c1cc(-c2ccc(C#Cc3ccc(C(=O)Nc4ccc(C(=O)O)c(O)c4)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 216 | A | 2.01 | 588.6 | Racemate | 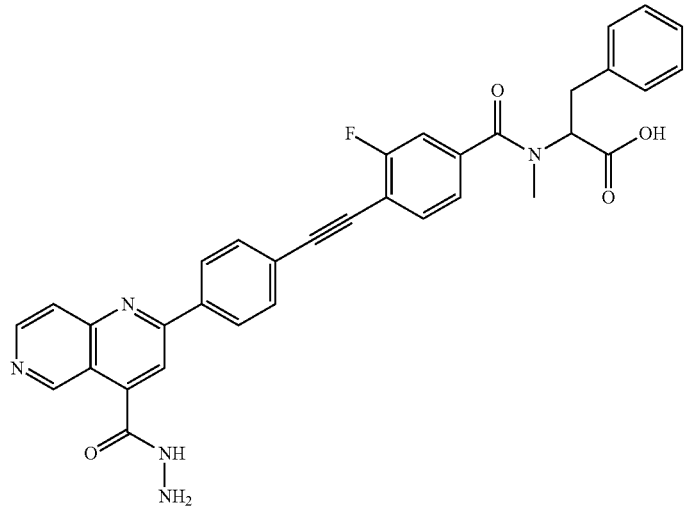 [SMILES: CN(C(=O)c1ccc(C#Cc2ccc(-c3cc(C(=O)NN)c4cnccc4n3)cc2)c(F)c1)C(Cc1ccccc1)C(=O)O] |
| 217 | A | 1.99 | 536.5 | Racemate | 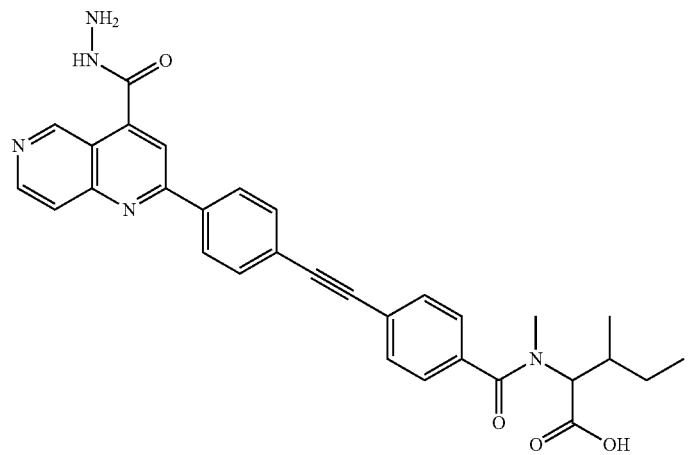 [SMILES: CCC(C)C(C(=O)O)N(C)C(=O)c1ccc(C#Cc2ccc(-c3cc(C(=O)NN)c4cnccc4n3)cc2)cc1] |
| 218 | A | 1.96 | 556.6 | Racemate | 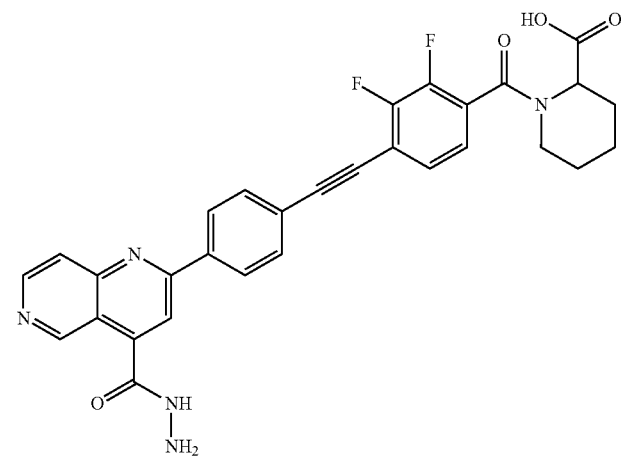 [SMILES: NNC(=O)c1cc(-c2ccc(C#Cc3ccc(C(=O)N4CCCCC4C(=O)O)c(F)c3F)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 219 | A | 1.98 | 536.6 | Racemate | 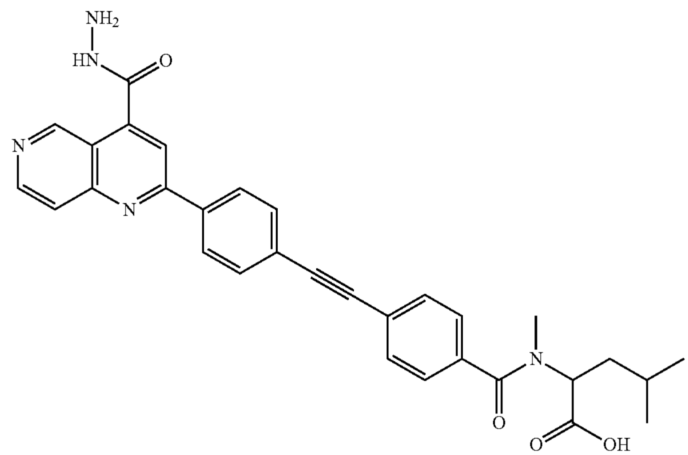 [SMILES: CC(C)CC(C(=O)O)N(C)C(=O)c1ccc(C#Cc2ccc(-c3cc(C(=O)NN)c4cnccc4n3)cc2)cc1] |
| 220 | A | 2.01 | 540.6 | Racemate | 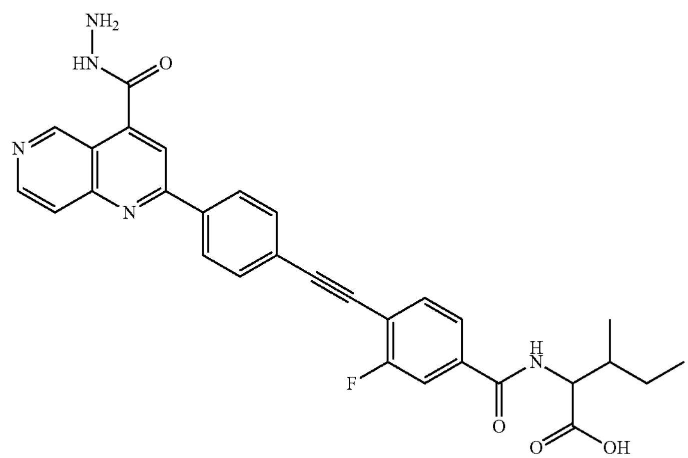 [SMILES: CCC(C)C(NC(=O)c1ccc(C#Cc2ccc(-c3cc(C(=O)NN)c4cnccc4n3)cc2)c(F)c1)C(=O)O] |
| 221 | A | 1.88 | 522.6 | Racemate | 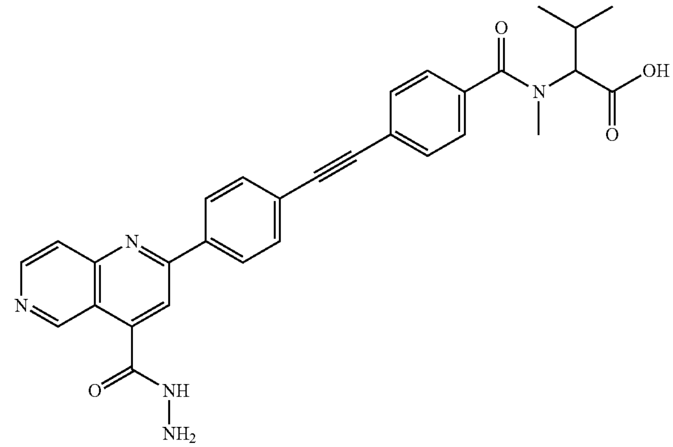 [SMILES: CC(C)C(C(=O)O)N(C)C(=O)c1ccc(C#Cc2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 222 | A | 1.53 | 552.6 | | 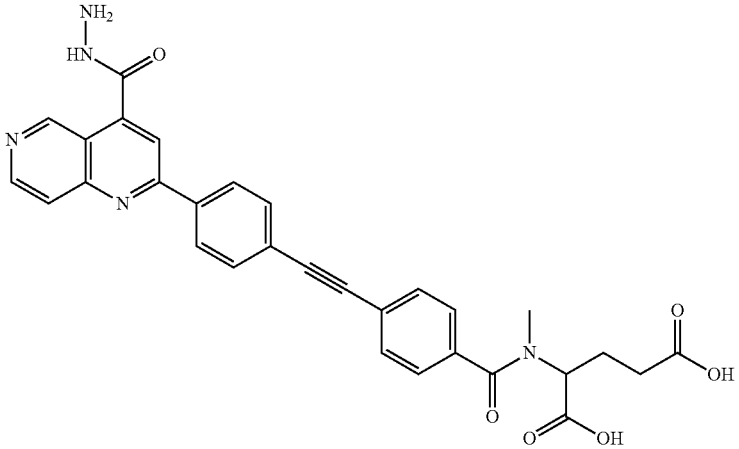 [SMILES: CN(C(=O)c1ccc(C#Cc2ccc(-c3cc(C(=O)NN)c4cnccc4n3)cc2)cc1)C(CCC(=O)O)C(=O)O] |
| 223 | A | 1.92 | 536.5 | | 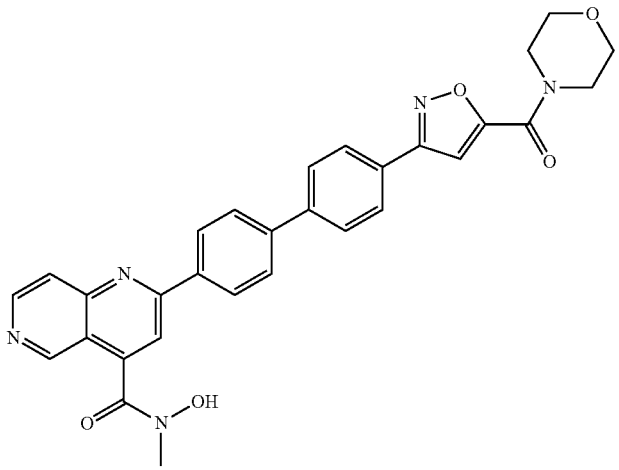 [SMILES: CN(O)C(=O)c1cc(-c2ccc(-c3ccc(-c4cc(C(=O)N5CCOCC5)on4)cc3)cc2)nc2ccncc12] |
| 224 | C | 7.49 | 552.3 [M − 1] | Racemate | 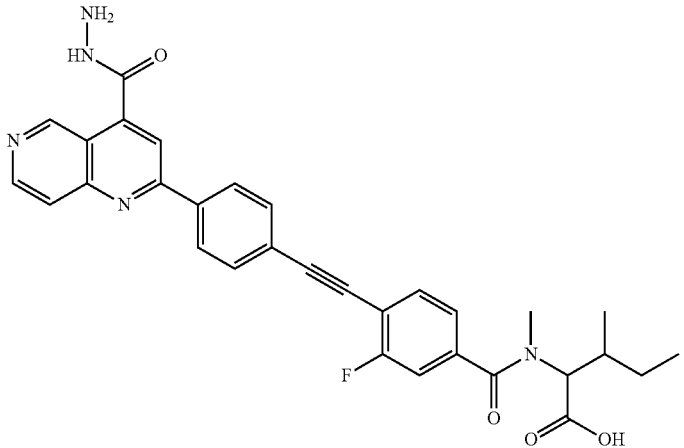 [SMILES: CCC(C)C(C(=O)O)N(C)C(=O)c1ccc(C#Cc2ccc(-c3cc(C(=O)NN)c4cnccc4n3)cc2)c(F)c1] |

TABLE 1-continued

Analytical Data

| Example # | HPLC Method | HPLC RT | MS(ESI) (M + H) | Chirality | Structure |
|---|---|---|---|---|---|
| 225 | A | 1.53 | 538.5 | Racemate | 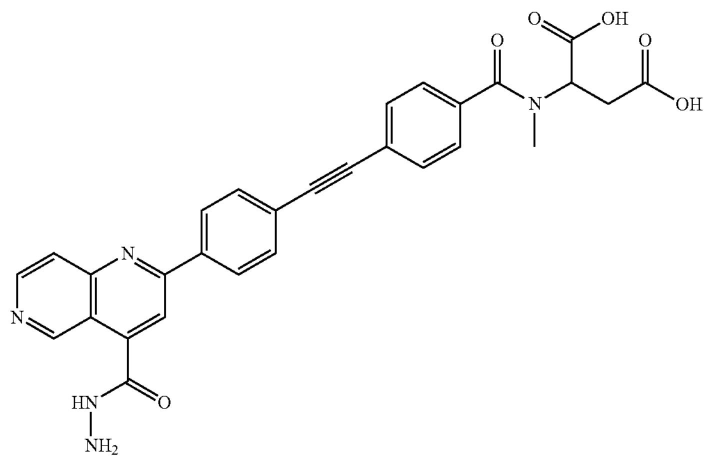 [SMILES: CN(C(=O)c1ccc(C#Cc2ccc(-c3cc(C(=O)NN)c4cnccc4n3)cc2)cc1)C(CC(=O)O)C(=O)O] |
| 226 | A | 1.79 | 550 | Racemate | 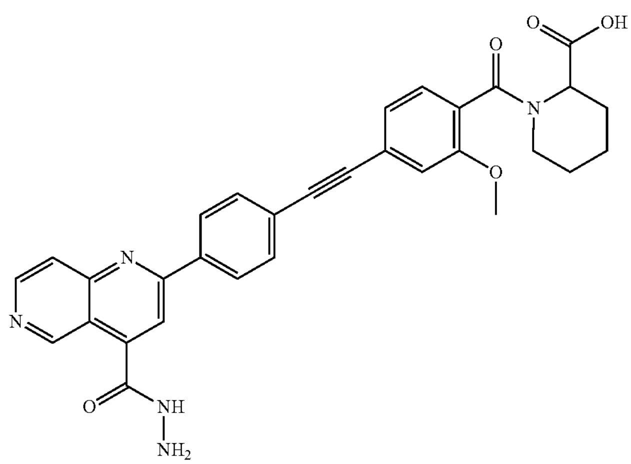 [SMILES: COc1cc(C#Cc2ccc(-c3cc(C(=O)NN)c4cnccc4n3)cc2)ccc1C(=O)N1CCCCC1C(=O)O] |
| 227 | A | 1.92 | 554.4 | Racemate | 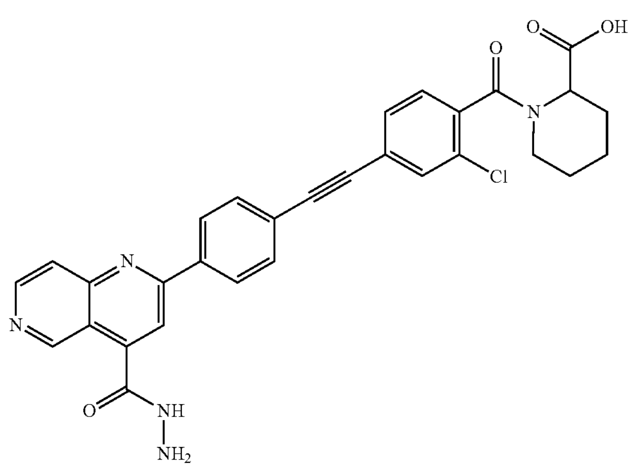 [SMILES: NNC(=O)c1cc(-c2ccc(C#Cc3ccc(C(=O)N4CCCCC4C(=O)O)c(Cl)c3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 228 | A | 2.02 | 588 | Racemate | 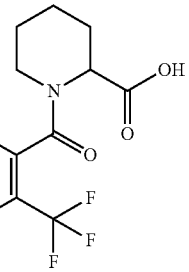 |
| 229 | A | 1.72 | 536.4 | Racemate | 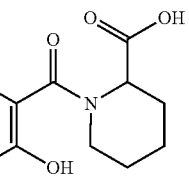 |
| 230 | A | 1.93 | 521.5 | Racemate | 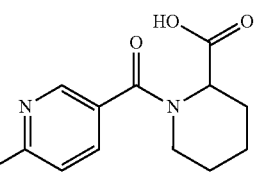 |

TABLE 1-continued
Analytical Data
| Example # | HPLC Method | HPLC RT | MS(ESI) (M + H) | Chirality | Structure |
|---|---|---|---|---|---|
| 231 | A | 1.82 | 530.5 | | 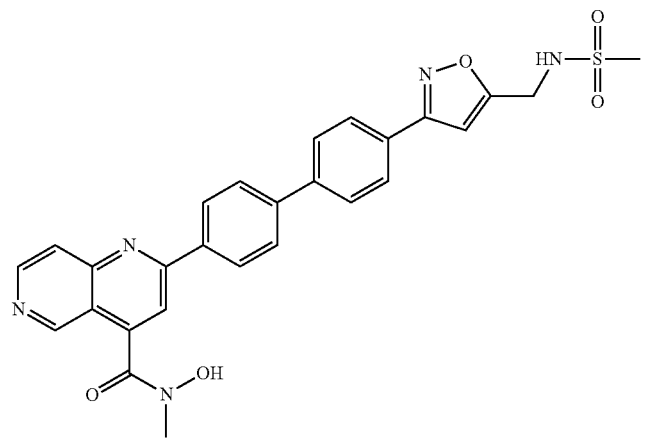 [SMILES: CN(O)C(=O)c1cc(-c2ccc(-c3ccc(-c4cc(CNS(C)(=O)=O)on4)cc3)cc2)nc2ccncc12] |
| 232 | A | 2.04 | 590 | Racemate | 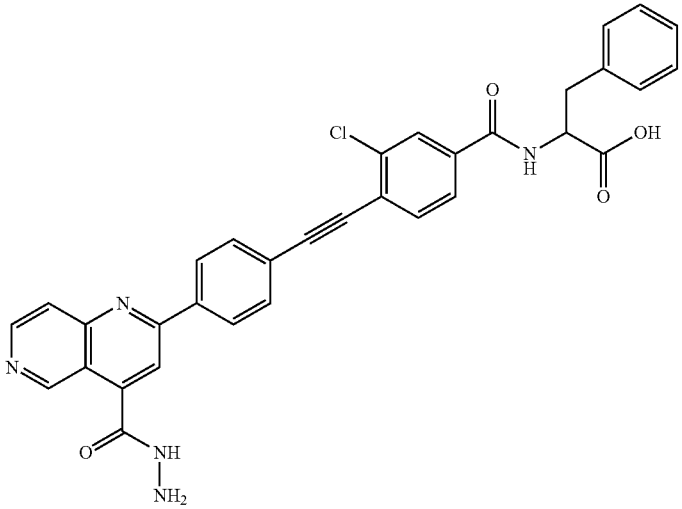 [SMILES: NNC(=O)c1cc(-c2ccc(C#Cc3ccc(C(=O)NC(Cc4ccccc4)C(=O)O)cc3Cl)cc2)nc2ccncc12] |
| 233 | A | 1.96 | 591 | Racemate | 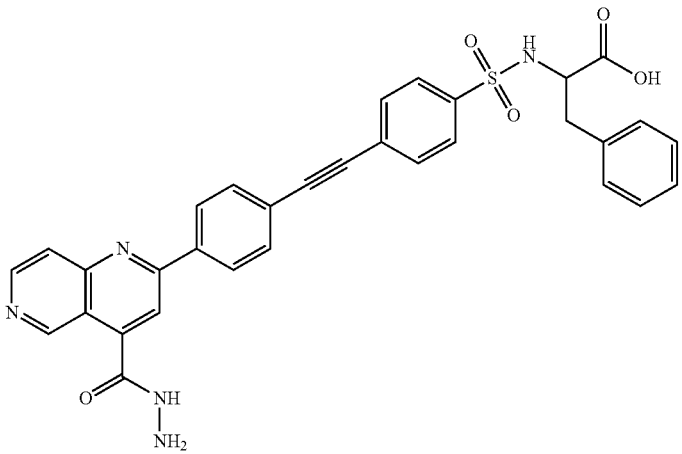 [SMILES: NNC(=O)c1cc(-c2ccc(C#Cc3ccc(S(=O)(=O)NC(Cc4ccccc4)C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 234 | A | 2.11 | 606 | Racemate | 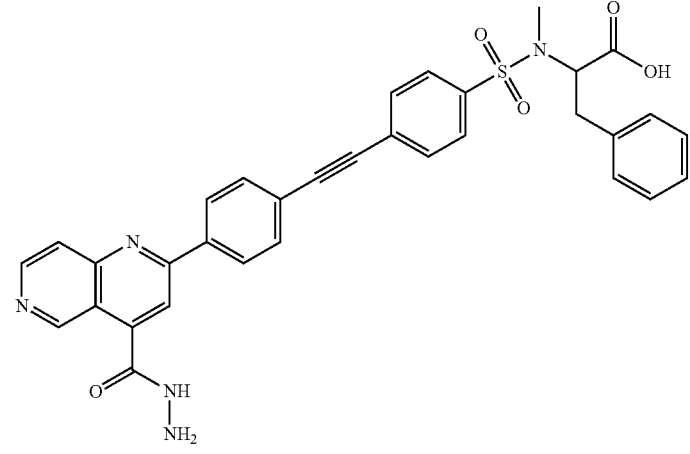 [SMILES: CN(C(Cc1ccccc1)C(=O)O)S(=O)(=O)c1ccc(C#Cc2ccc(-c3cc(C(=O)NN)c4cnccc4n3)cc2)cc1] |
| 235 | A | 1.87 | 556 | Racemate | 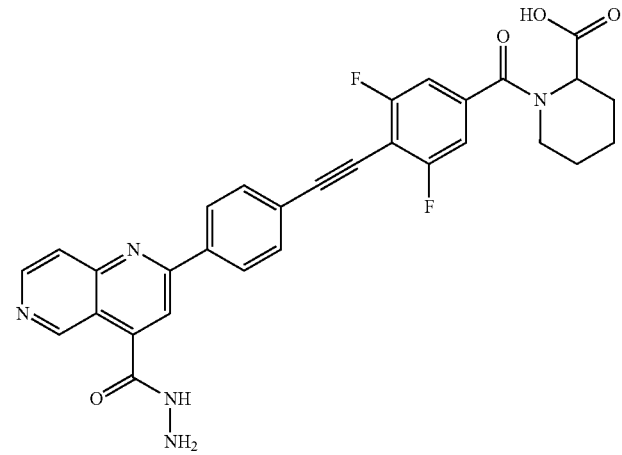 [SMILES: NNC(=O)c1cc(-c2ccc(C#Cc3c(F)cc(C(=O)N4CCCCC4C(=O)O)cc3F)cc2)nc2ccncc12] |
| 236 | C | 7.49 | 556.5 | Racemate | 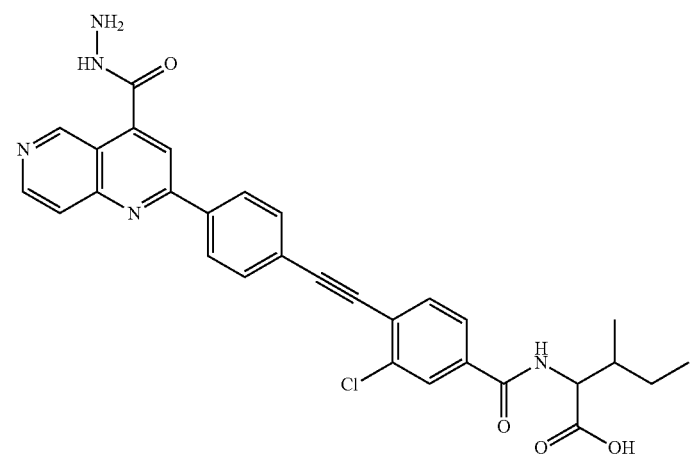 |

TABLE 1-continued

Analytical Data

| Example # | HPLC Method | HPLC RT | MS(ESI) (M + H) | Chirality | Structure |
|---|---|---|---|---|---|
| 237 | C | 6.85 | 494.3 | | 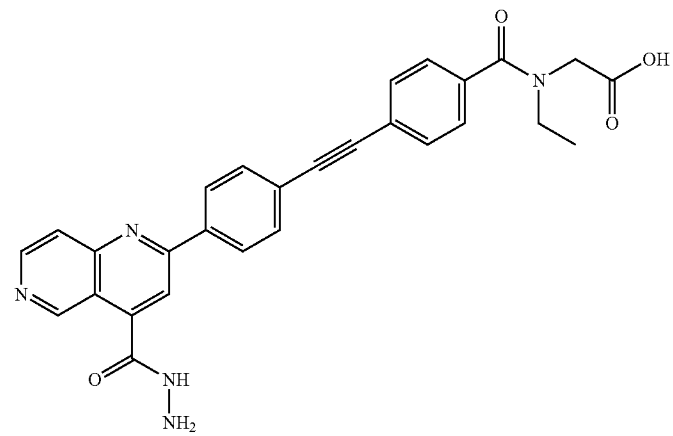 [SMILES: CCN(CC(=O)O)C(=O)c1ccc(C#Cc2ccc(-c3cc(C(=O)NN)c4cnccc4n3)cc2)cc1] |
| 238 | C | 6.98 | 508 | | 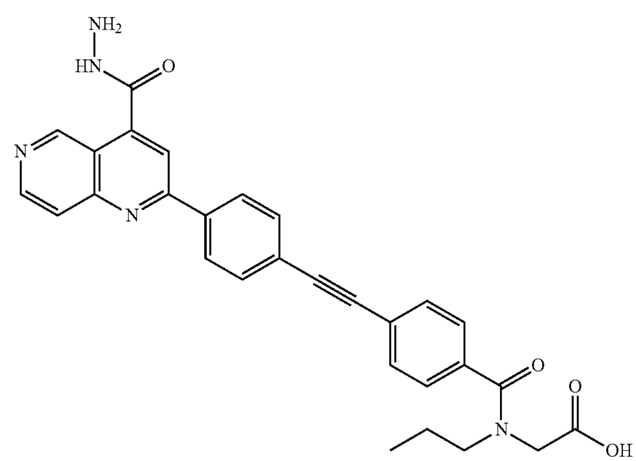 [SMILES: CCCN(CC(=O)O)C(=O)c1ccc(C#Cc2ccc(-c3cc(C(=O)NN)c4cnccc4n3)cc2)cc1] |
| 239 | C | 7.16 | 558.6 | Racemate | 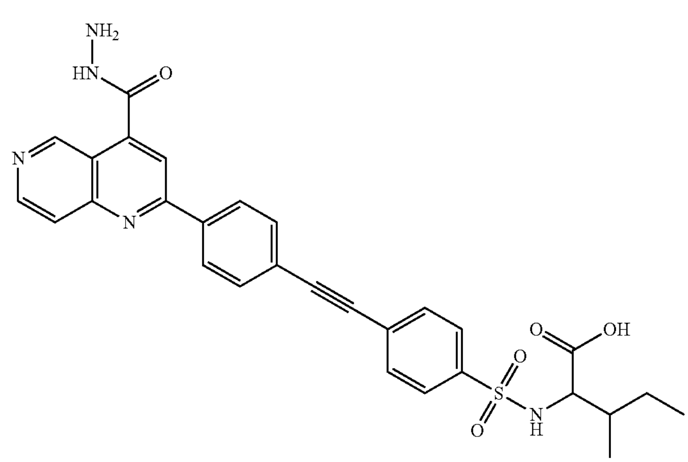 [SMILES: CCC(C)C(NS(=O)(=O)c1ccc(C#Cc2ccc(-c3cc(C(=O)NN)c4cnccc4n3)cc2)cc1)C(=O)O] |

TABLE 1-continued

Analytical Data

| Example # | HPLC Method | HPLC RT | MS(ESI) (M + H) | Chirality | Structure |
|---|---|---|---|---|---|
| 240 | A | 7.5 | 572.7 | Racemate | 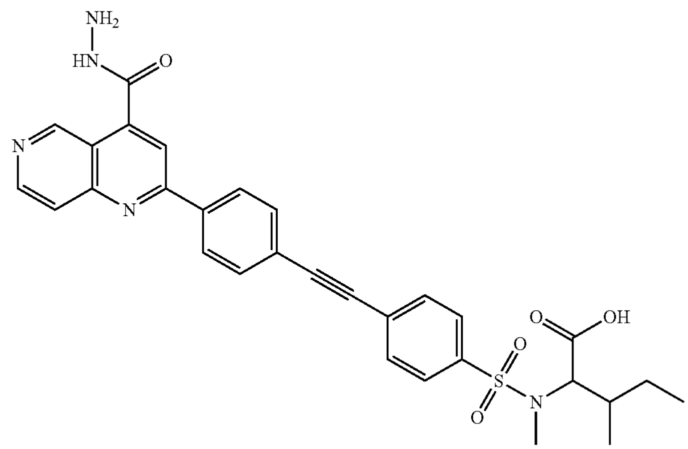 [SMILES: CCC(C)C(C(=O)O)N(C)S(=O)(=O)c1ccc(C#Cc2ccc(-c3cc(C(=O)NN)c4cnccc4n3)cc2)cc1] |
| 241 | C | 7.15 | 556.4 | | 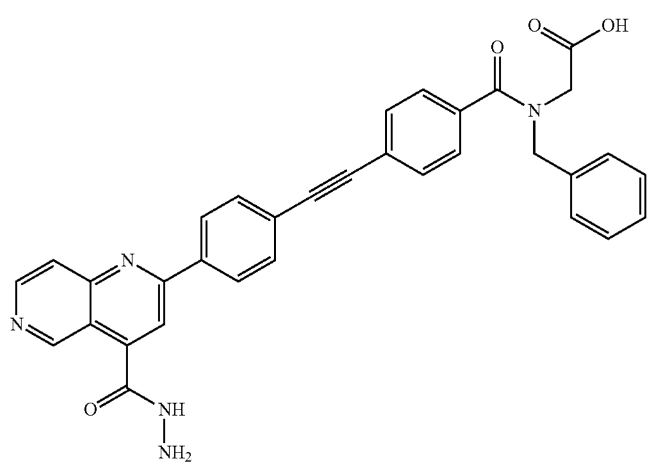 [SMILES: NNC(=O)c1cc(-c2ccc(C#Cc3ccc(C(=O)N(CC(=O)O)Cc4ccccc4)cc3)cc2)nc2ccncc12] |
| 242 | NA | NA | 528.4 | | 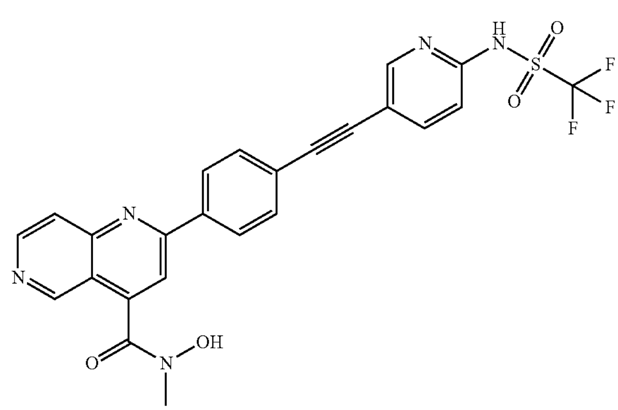 [SMILES: CN(O)C(=O)c1cc(-c2ccc(C#Cc3ccc(NS(=O)(=O)C(F)(F)F)nc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 243 | C | 6.97 | 508 | | 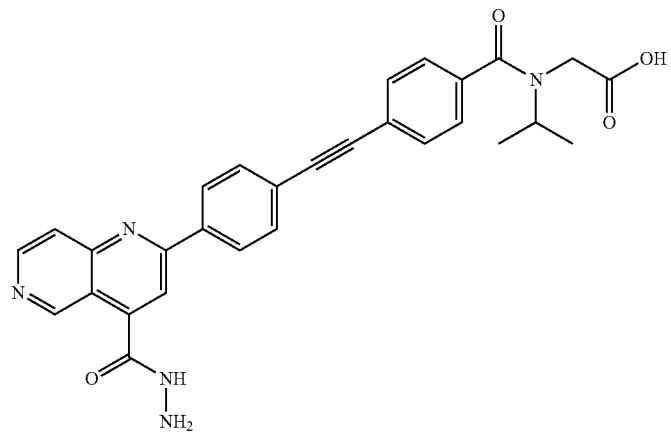 [SMILES: CC(C)N(CC(=O)O)C(=O)c1ccc(C#Cc2ccc(-c3cc(C(=O)NN)c4cnccc4n3)cc2)cc1] |
| 244 | C | 7.15 | 522.6 | | 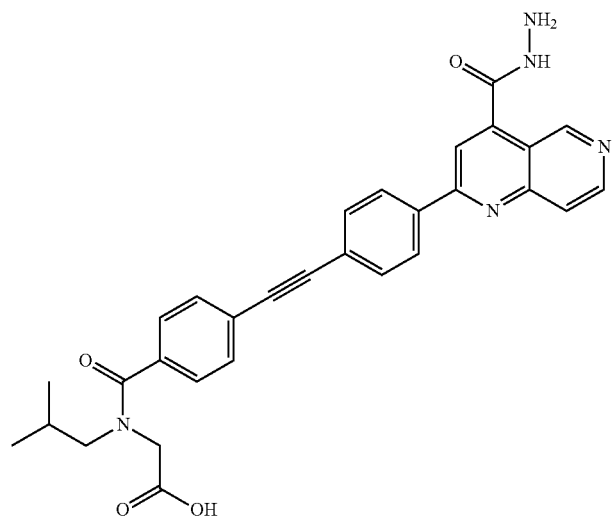 [SMILES: CC(C)CN(CC(=O)O)C(=O)c1ccc(C#Cc2ccc(-c3cc(C(=O)NN)c4cnccc4n3)cc2)cc1] |
| 245 | NA | NA | 527.4 | | 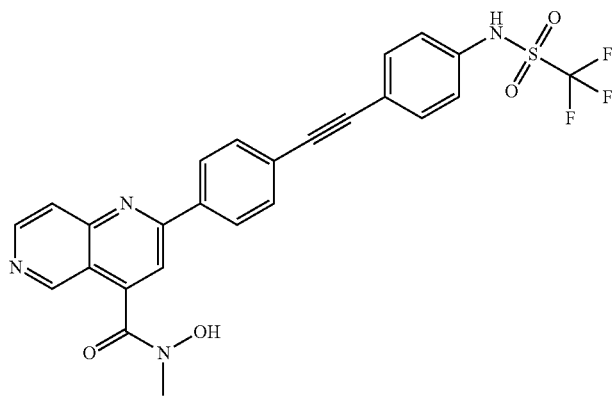 [SMILES: CN(O)C(=O)c1cc(-c2ccc(C#Cc3ccc(NS(=O)(=O)C(F)(F)F)cc3)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 246 | C | 7.37 | 576.5 | Racemate | 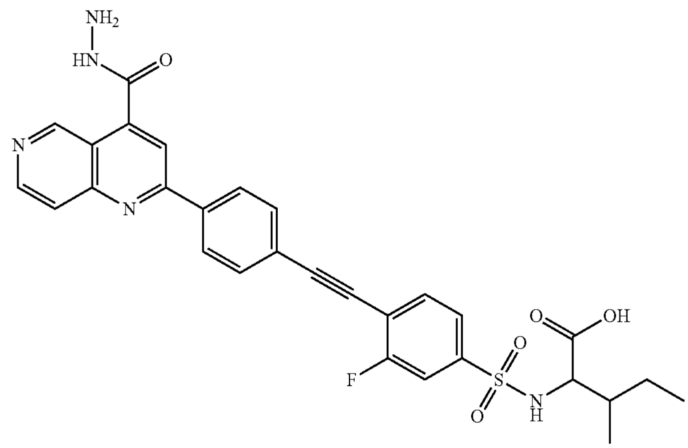 [SMILES: CCC(C)C(NS(=O)(=O)c1ccc(C#Cc2ccc(-c3cc(C(=O)NN)c4cnccc4n3)cc2)c(F)c1)C(=O)O] |
| 247 | C | 8.11 | 646.6 | Racemate | 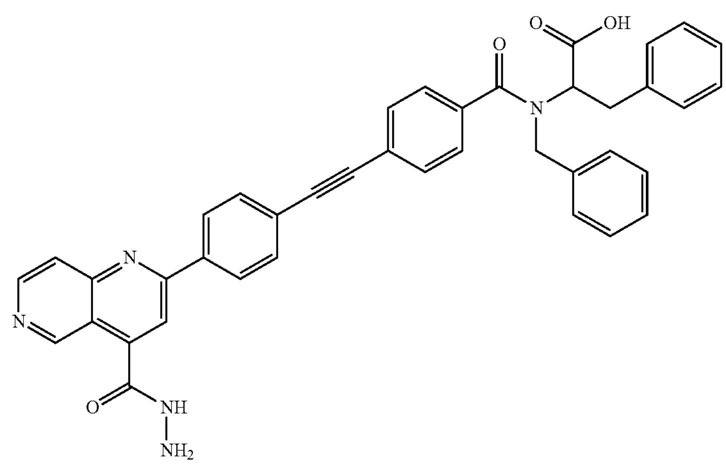 [SMILES: NNC(=O)c1cc(-c2ccc(C#Cc3ccc(C(=O)N(Cc4ccccc4)C(Cc4ccccc4)C(=O)O)cc3)cc2)nc2ccncc12] |
| 248 | C | 7.52 | 590.4 | Racemate | 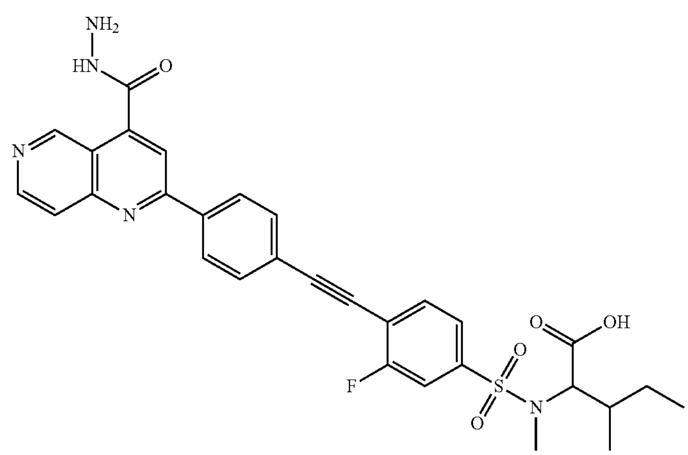 [SMILES: CCC(C)C(C(=O)O)N(C)S(=O)(=O)c1ccc(C#Cc2ccc(-c3cc(C(=O)NN)c4cnccc4n3)cc2)c(F)c1] |

TABLE 1-continued
Analytical Data
| Example # | HPLC Method | HPLC RT | MS(ESI) (M + H) | Chirality | Structure |
|---|---|---|---|---|---|
| 249 | C | 7.23 | 574.4 | R | 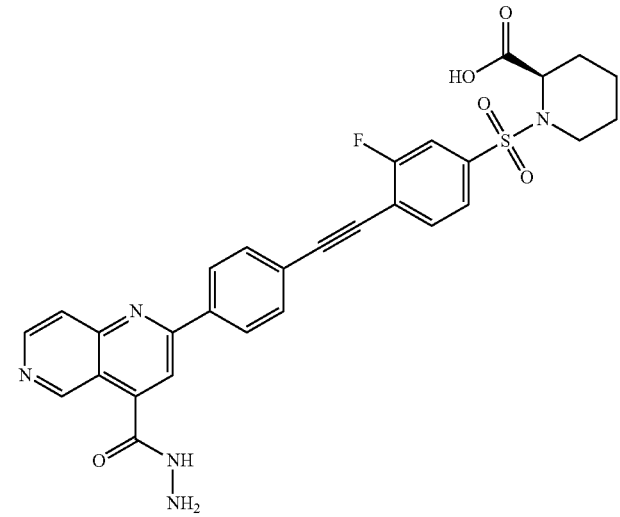 [SMILES: NNC(=O)c1cc(-c2ccc(C#Cc3ccc(S(=O)(=O)N4CCCC[C@@H]4C(=O)O)cc3F)cc2)nc2ccncc12] |
| 250 | C | 7.42 | 574.3 | S | 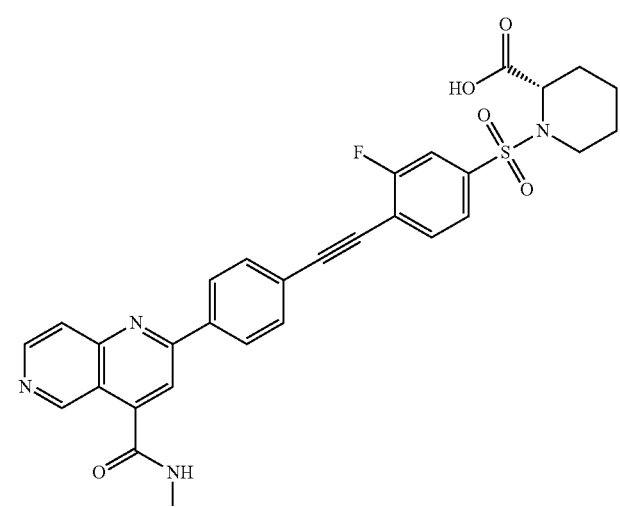 |
| 251 | A | 2 | 608.2 [M − 1] | Racemate | 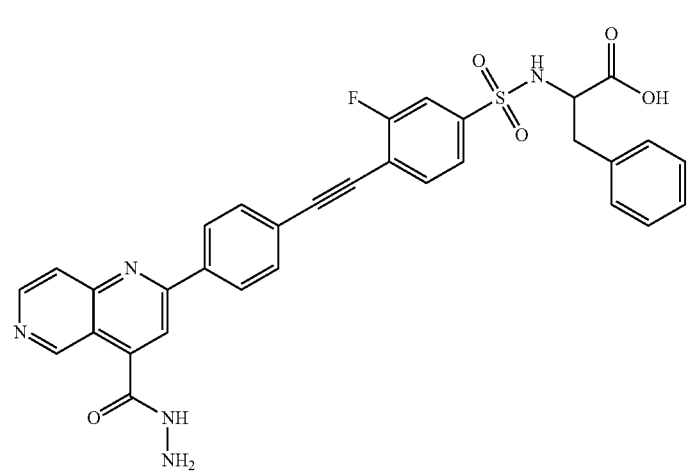 [SMILES: NNC(=O)c1cc(-c2ccc(C#Cc3ccc(S(=O)(=O)NC(Cc4ccccc4)C(=O)O)cc3F)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 252 | C | 7.55 | 624.8 | Racemate | 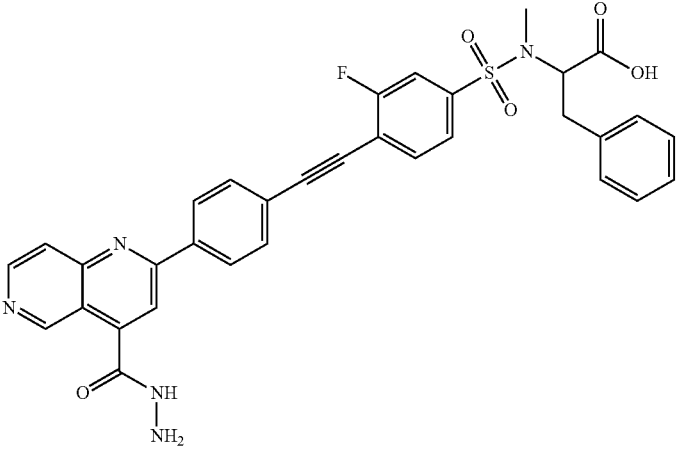 [SMILES: CN(C(Cc1ccccc1)C(=O)O)S(=O)(=O)c1ccc(C#Cc2ccc(-c3cc(C(=O)NN)c4cnccc4n3)cc2)c(F)c1] |
| 253 | A | 1.66 | 521.6 | Racemate | 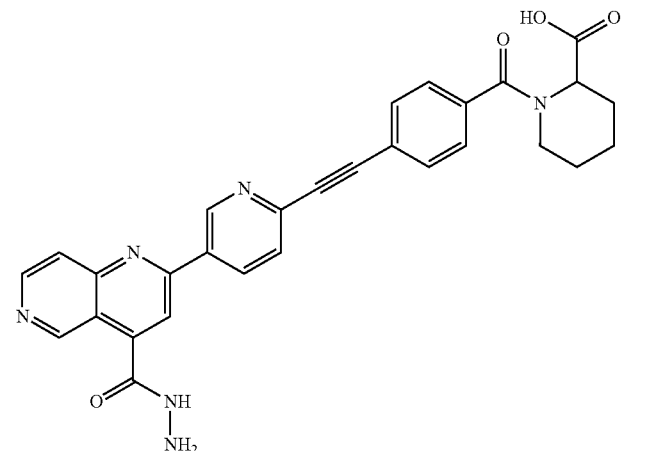 |
| 254 | A | 1.91 | 556.5 | Racemate | 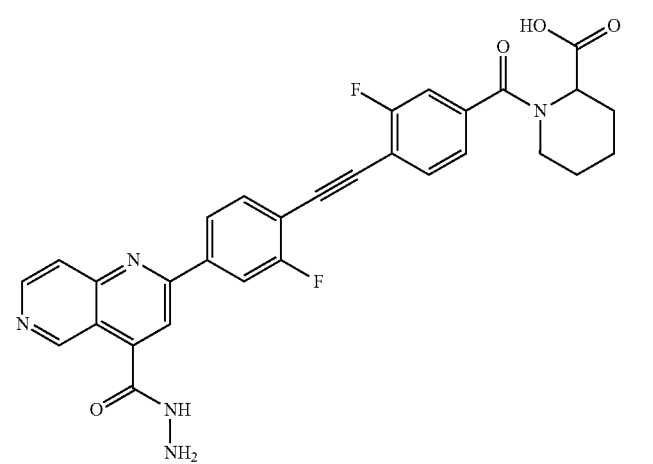 [SMILES: NNC(=O)c1cc(-c2ccc(C#Cc3ccc(C(=O)N4CCCCC4C(=O)O)cc3F)c(F)c2)nc2ccncc12] |

TABLE 1-continued
Analytical Data
| Example # | HPLC Method | HPLC RT | MS(ESI) (M + H) | Chirality | Structure |
|---|---|---|---|---|---|
| 255 | A | 2.09 | 584.6 | Racemate | 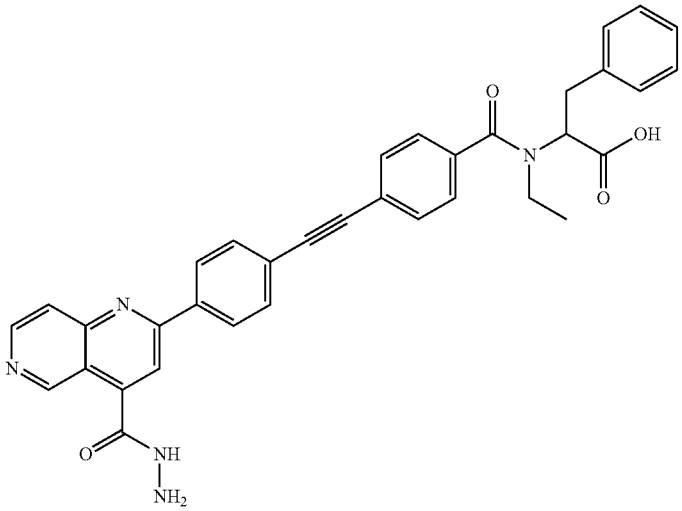 [SMILES: CCN(C(=O)c1ccc(C#Cc2ccc(-c3cc(C(=O)NN)c4cnccc4n3)cc2)cc1)C(Cc1ccccc1)C(=O)O] |
| 256 | C | 7.97 | 598.4 | Racemate | 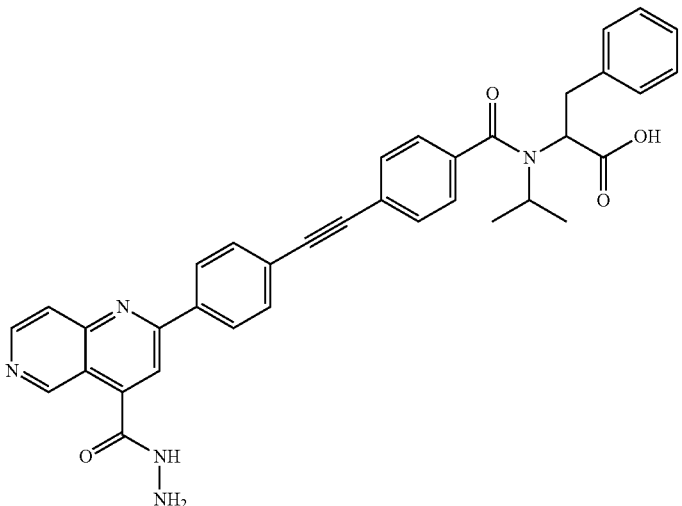 |
| 257 | A | 2.16 | 553.5 | Racemate | 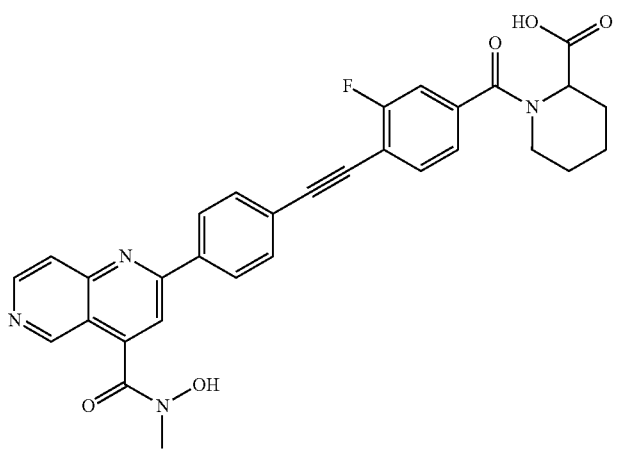 [SMILES: CN(O)C(=O)c1cc(-c2ccc(C#Cc3ccc(C(=O)N4CCCCC4C(=O)O)cc3F)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 258 | C | 6.93 | 549.6 | R | 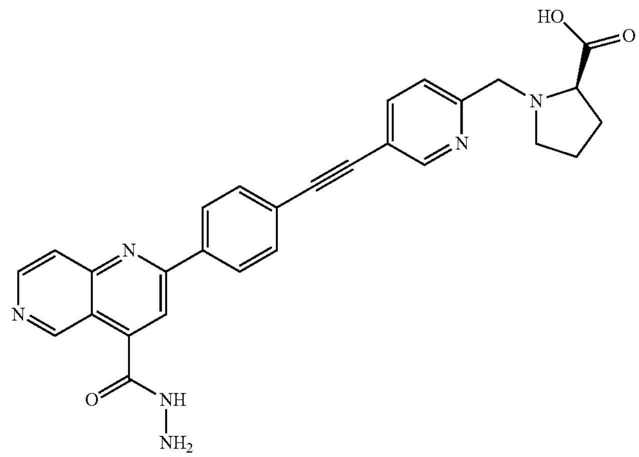 [SMILES: NNC(=O)c1cc(-c2ccc(C#Cc3ccc(CN4CCC[C@@H]4C(=O)O)nc3)cc2)nc2ccncc12] |
| 259 | A | 2.25 | 612.4 | Racemate | 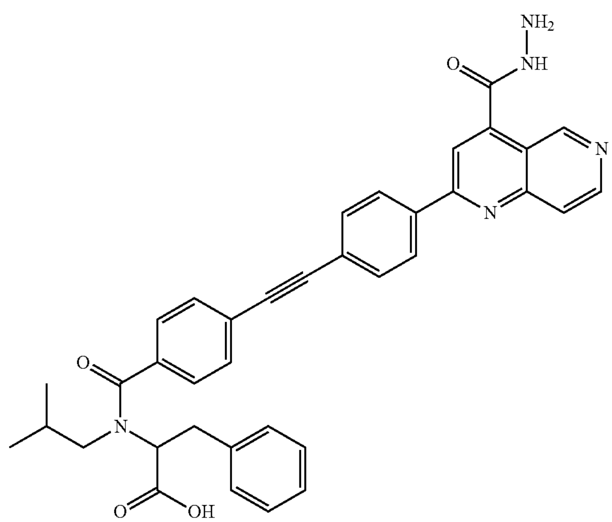 [SMILES: CC(C)CN(C(=O)c1ccc(C#Cc2ccc(-c3cc(C(=O)NN)c4cnccc4n3)cc2)cc1)C(Cc1ccccc1)C(=O)O] |
| 260 | C | 7.27 | 590.4 | R | 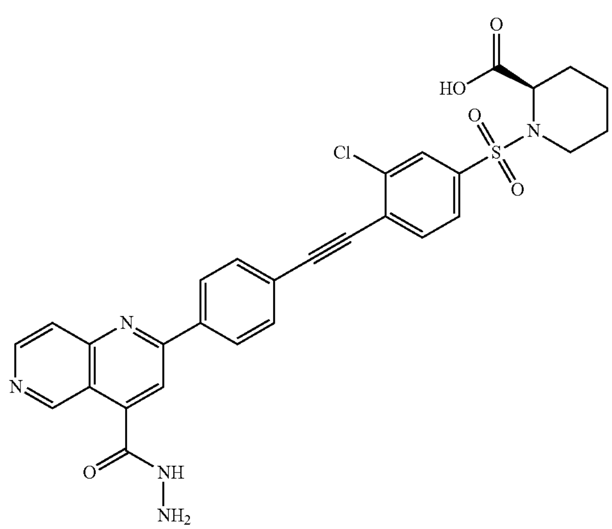 [SMILES: NNC(=O)c1cc(-c2ccc(C#Cc3ccc(S(=O)(=O)N4CCCC[C@@H]4C(=O)O)cc3Cl)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 261 | C | 7.26 | 590.5 | S | 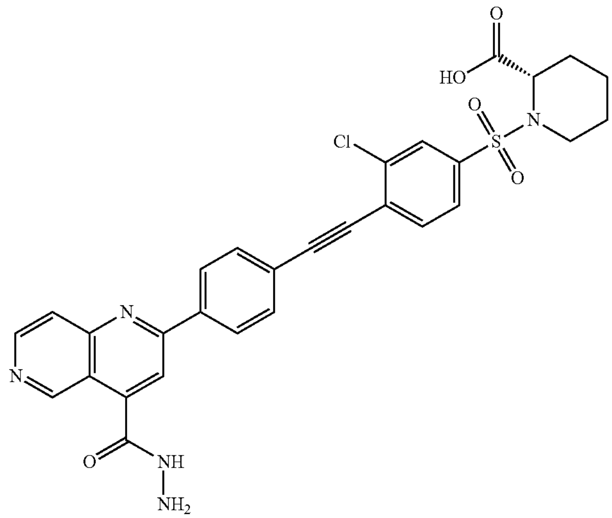 [SMILES: NNC(=O)c1cc(-c2ccc(C#Cc3ccc(S(=O)(=O)N4CCCC[C@H]4C(=O)O)cc3Cl)cc2)nc2ccncc12] |
| 262 | A | 1.42 | 529.4 | Racemate | 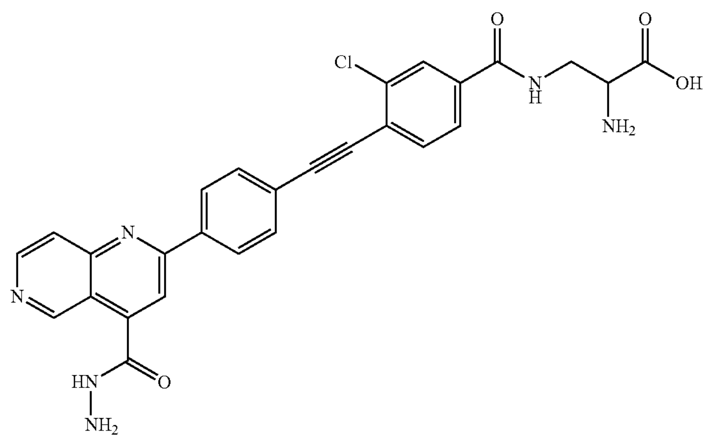 [SMILES: NNC(=O)c1cc(-c2ccc(C#Cc3ccc(C(=O)NCC(N)C(=O)O)cc3Cl)cc2)nc2ccncc12] |
| 263 | C | 7.79 | 598.7 | Racemate | 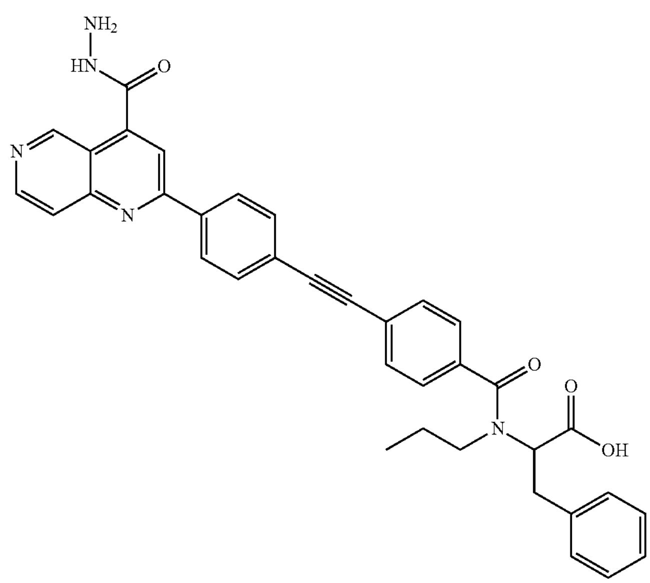 [SMILES: CCCN(C(=O)c1ccc(C#Cc2ccc(-c3cc(C(=O)NN)c4cnccc4n3)cc2)cc1)C(Cc1ccccc1)C(=O)O] |

TABLE 1-continued
Analytical Data
| Example # | HPLC Method | HPLC RT | MS(ESI) (M + H) | Chirality | Structure |
|---|---|---|---|---|---|
| 264 | C | 7.28 | 554.7 | Racemate | 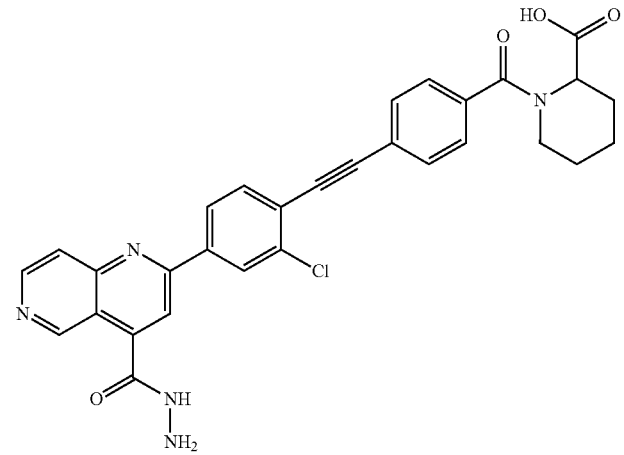 [SMILES: NNC(=O)c1cc(-c2ccc(C#Cc3ccc(C(=O)N4CCCCC4C(=O)O)cc3)c(Cl)c2)nc2ccncc12] |
| 265 | A | 1.7 | 538.1 | Racemate | 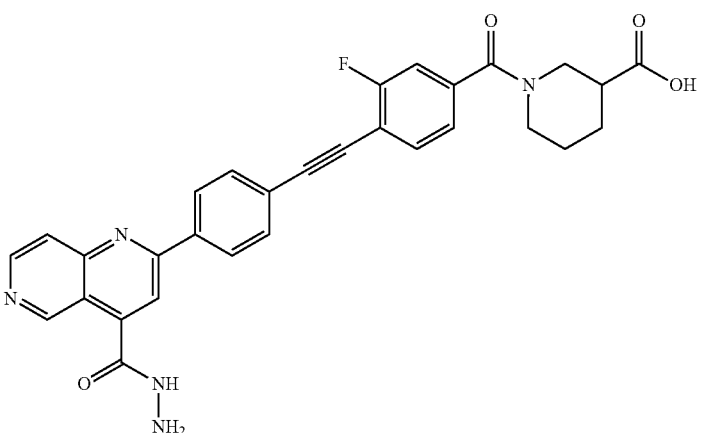 |
| 266 | A | 1.7 | 524.6 | R | 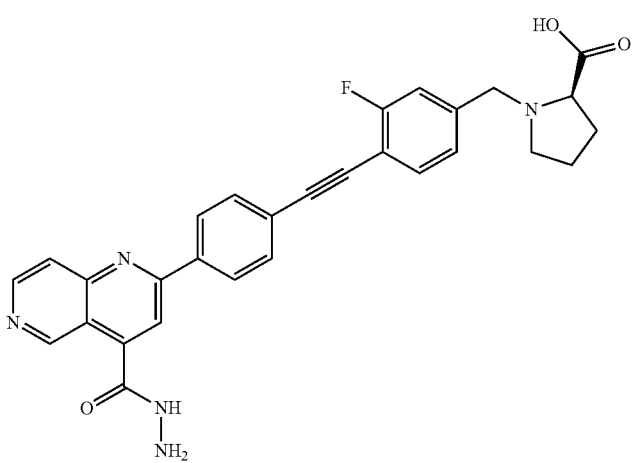 [SMILES: NNC(=O)c1cc(-c2ccc(C#Cc3ccc(CN4CCC[C@@H]4C(=O)O)cc3F)cc2)nc2ccncc12] |

TABLE 1-continued

Analytical Data

| Example # | HPLC Method | HPLC RT | MS(ESI) (M + H) | Chirality |
|---|---|---|---|---|
| 267 | C | 7.16 | 554.5 | Racemate |
| 268 | A | 6.94 | 540.5 | R |
| 269 | G | 2.76 | 574.6 | Racemate |

TABLE 1-continued
Analytical Data
| Example # | HPLC Method | HPLC RT | MS(ESI) (M + H) | Chirality | Structure |
|---|---|---|---|---|---|
| 270 | C | 7.01 | 560.5 | R | 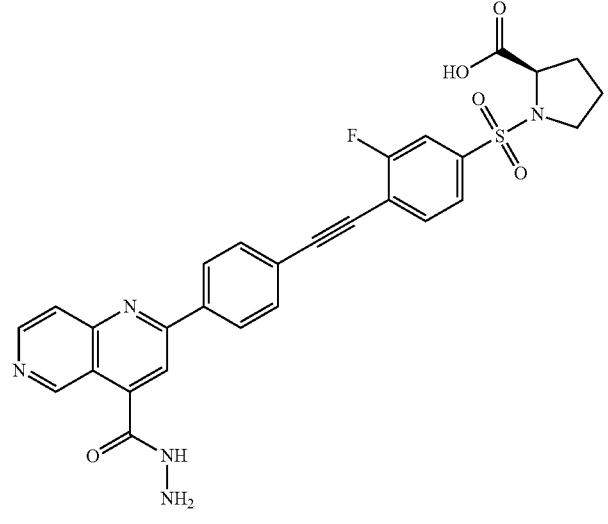 [SMILES: NNC(=O)c1cc(-c2ccc(C#Cc3ccc(S(=O)(=O)N4CCC[C@@H]4C(=O)O)cc3F)cc2)nc2ccncc12] |
| 271 | C | 7.21 | 556.5 | | 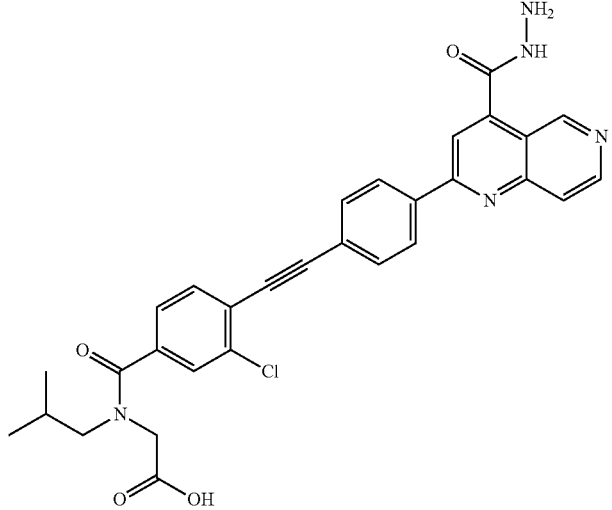 [SMILES: CC(C)CN(CC(=O)O)C(=O)c1ccc(C#Cc2ccc(-c3cc(C(=O)NN)c4cnccc4n3)cc2)c(F)c1] |

TABLE 1-continued
Analytical Data
| Example # | HPLC Method | HPLC RT | MS(ESI) (M + H) | Chirality | Structure |
|---|---|---|---|---|---|
| 272 | C | 7.09 | 540.6 | | 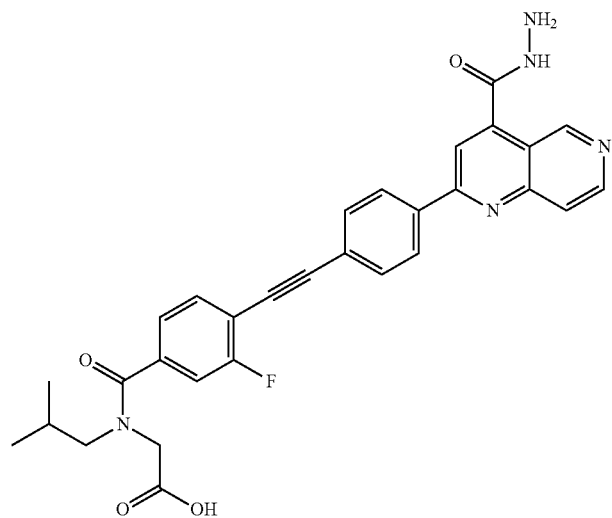 |
| 273 | A | 2.14 | 592.3 | | 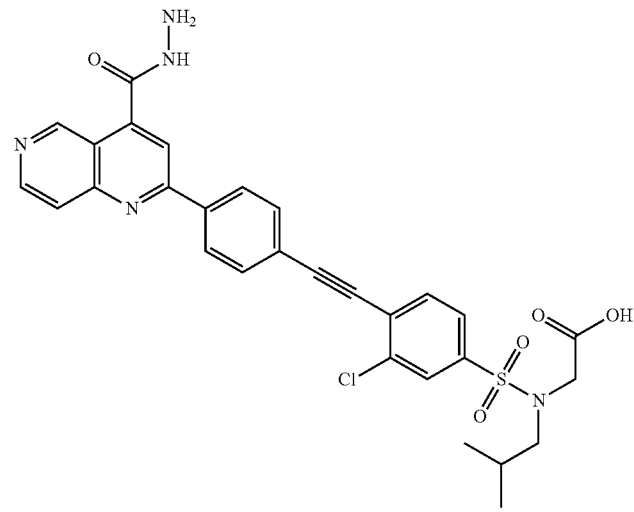 [SMILES: CC(C)CN(CC(=O)O)S(=O)(=O)c1ccc(C#Cc2ccc(-c3cc(C(=O)NN)c4cnccc4n3)cc2)c(Cl)c1] |

TABLE 1-continued

Analytical Data

| Example # | HPLC Method | HPLC RT | MS(ESI) (M + H) | Chirality |
|---|---|---|---|---|
| 274 | A | 2.08 | 576.3 | |
| 275 | A | 2.04 | 591.3 | Racemate |
| 276 | A | 1.87 | 576.6 | R |

TABLE 1-continued
Analytical Data
| Example # | HPLC Method | HPLC RT | MS(ESI) (M + H) | Chirality | Structure |
|---|---|---|---|---|---|
| 277 | A | 1.31 | 468.3 | Racemate | 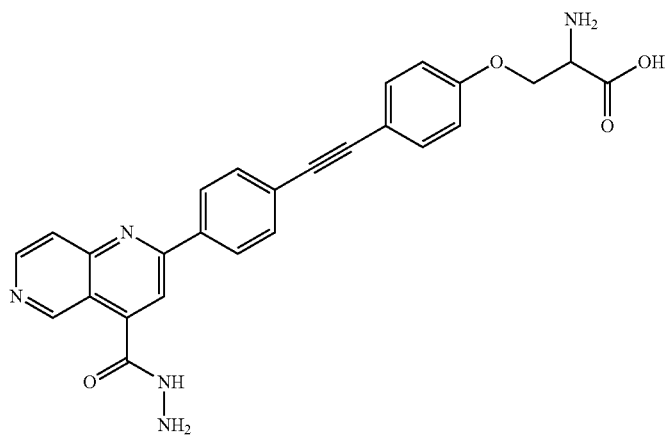 [SMILES: NNC(=O)c1cc(-c2ccc(C#Cc3ccc(OCC(N)C(=O)O)cc3)cc2)nc2ccncc12] |
| 278 | C | 6.86 | 550.5 | Racemate | 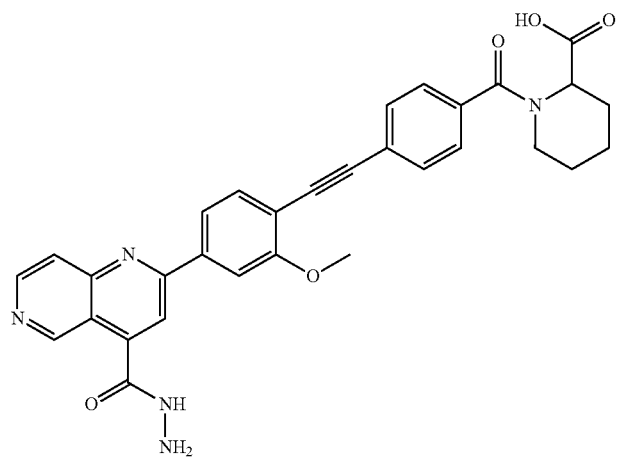 [SMILES: COc1cc(-c2cc(C(=O)NN)c3cnccc3n2)ccc1C#Cc1ccc(C(=O)N2CCCCC2C(=O)O)cc1] |
| 279 | A | 1.94 | 536.6 | Racemate | 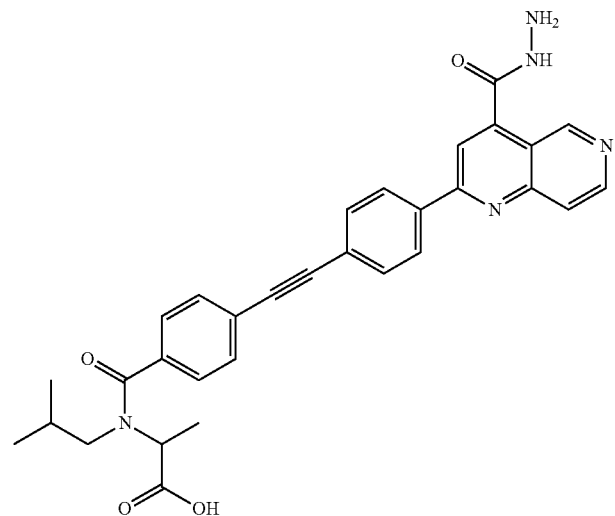 [SMILES: CC(C)CN(C(=O)c1ccc(C#Cc2ccc(-c3cc(C(=O)NN)c4cnccc4n3)cc2)cc1)C(C)C(=O)O] |

TABLE 1-continued
Analytical Data
| Example # | HPLC Method | HPLC RT | MS(ESI) (M + H) | Chirality | Structure |
|---|---|---|---|---|---|
| 280 | C | 6.64 | 536.6 | Racemate | 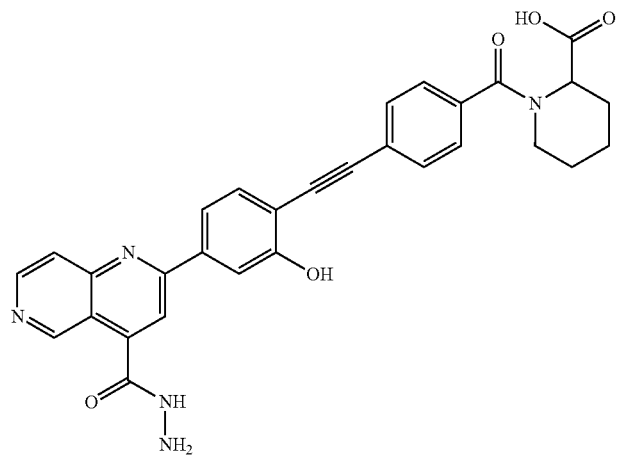 [SMILES: NNC(=O)c1cc(-c2ccc(C#Cc3ccc(C(=O)N4CCCCC4C(=O)O)cc3)c(O)c2)nc2ccncc12] |
| 281 | G | 2.34 | 540.6 | S | 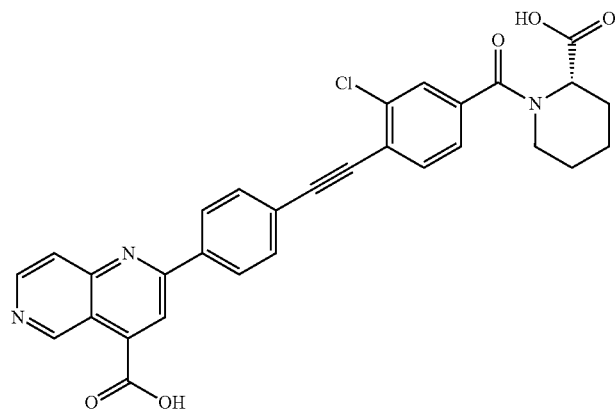 [SMILES: O=C(O)c1cc(-c2ccc(C#Cc3ccc(C(=O)N4CCCC[C@H]4C(=O)O)cc3Cl)cc2)nc2ccncc12] |
| 282 | A | 1.93 | 554.6 | Racemate | 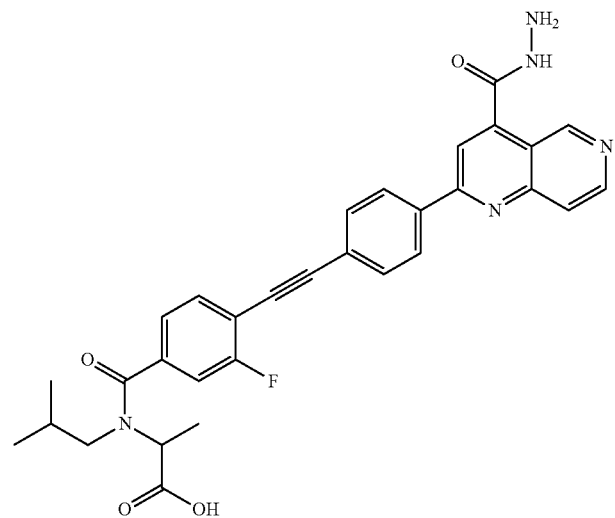 [SMILES: CC(C)CN(C(=O)c1ccc(C#Cc2ccc(-c3cc(C(=O)NN)c4cnccc4n3)cc2)c(F)c1)C(C)C(=O)O] |

TABLE 1-continued
Analytical Data
| Example # | HPLC Method | HPLC RT | MS(ESI) (M + H) | Chirality | Structure |
|---|---|---|---|---|---|
| 283 | C | 7.47 | 543.6 | Racemate | 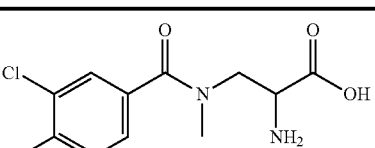 |
| 284 | A | 1.99 | 570.6 | Racemate | 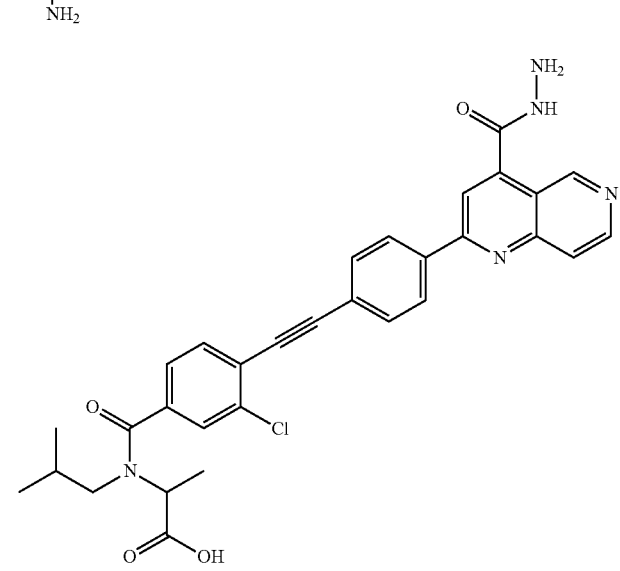 |
| 285 | A | 1.68 | 552.5 | Racemate | 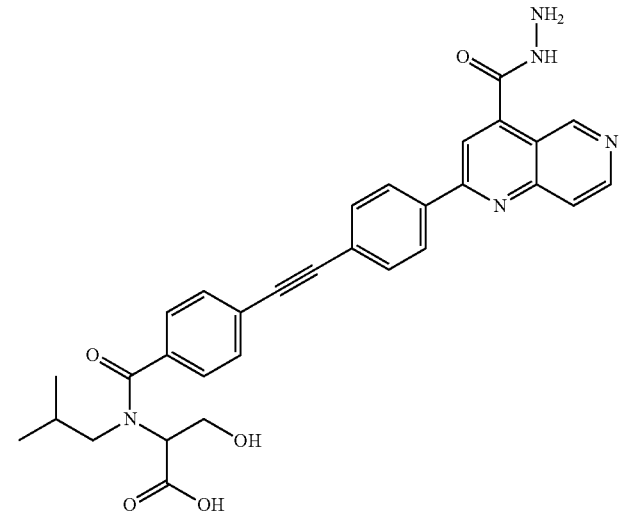 [SMILES: CC(C)CN(C(=O)c1ccc(C#Cc2ccc(-c3cc(C(=O)NN)c4cnccc4n3)cc2)cc1)C(CO)C(=O)O] |

TABLE 1-continued
Analytical Data
| Example # | HPLC Method | HPLC RT | MS(ESI) (M + H) | Chirality | Structure |
|---|---|---|---|---|---|
| 286 | A | 1.59 | 568.6 | S | 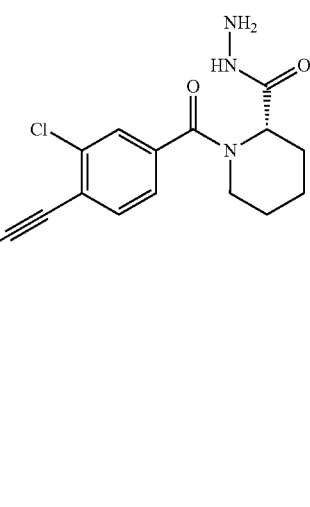 |
| 287 | A | 1.69 | 554.6 | S | 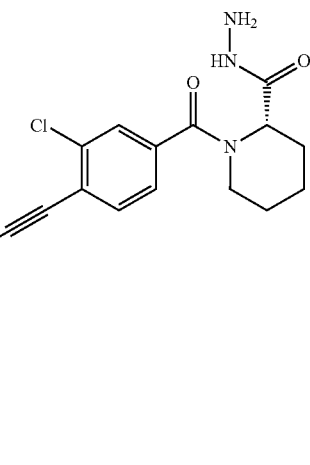 |
| 288 | G | 3.59 | 569.5 | S | 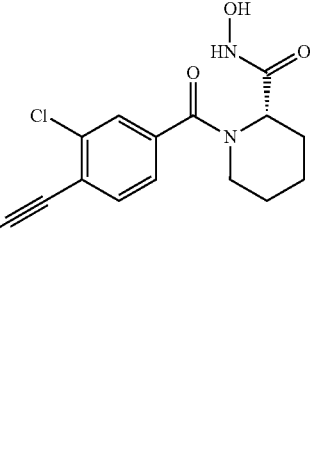 |

TABLE 1-continued

Analytical Data

| Example # | HPLC Method | HPLC RT | MS(ESI) (M + H) | Chirality | Structure |
|---|---|---|---|---|---|
| 289 | A | 1.35 | 546.3 | Racemate | 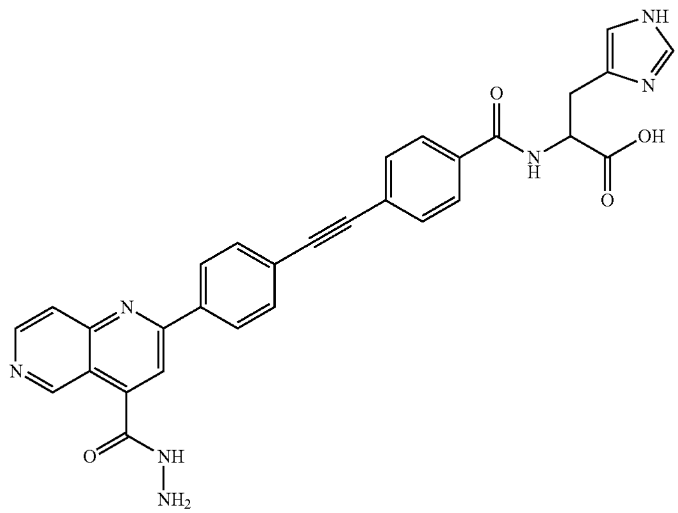 [SMILES: NNC(=O)c1cc(-c2ccc(C#Cc3ccc(C(=O)NC(Cc4c[nH]cn4)C(=O)O)cc3)cc2)nc2ccncc12] |
| 290 | C | 12.95 | 642.6 | Racemate | 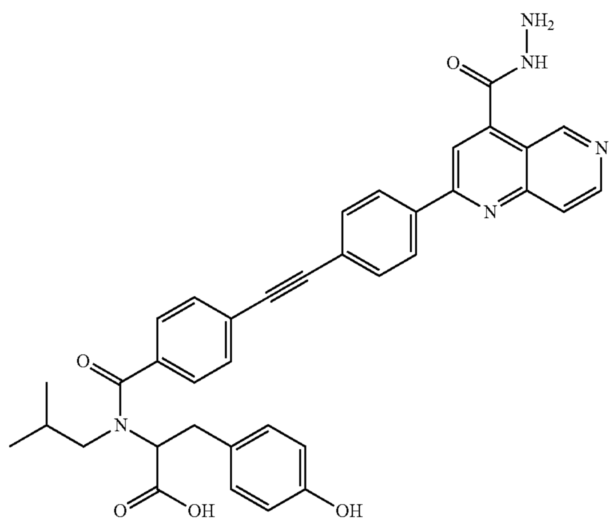 [SMILES: CC(C)CN(C(=O)c1ccc(C#Cc2ccc(-c3cc(C(=O)NN)c4cnccc4n3)cc2)cc1)C(Cc1ccc(O)cc1)C(=O)O] |
| 291 | A | 1.47 | 560.5 | Racemate | 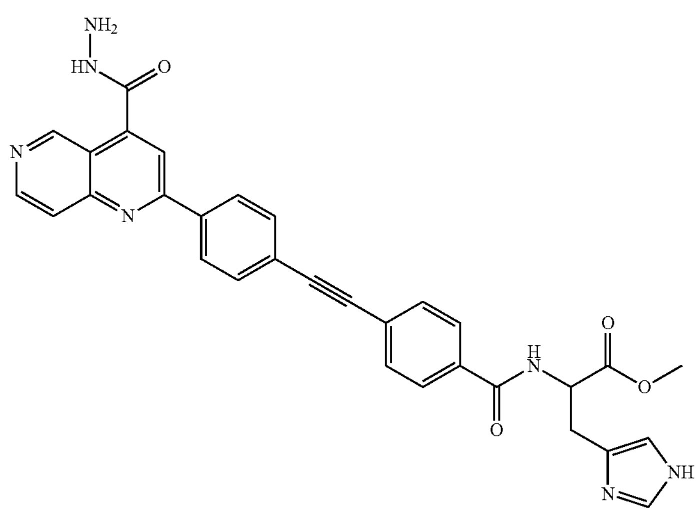 [SMILES: COC(=O)C(Cc1c[nH]cn1)NC(=O)c1ccc(C#Cc2ccc(-c3cc(C(=O)NN)c4cnccc4n3)cc2)cc1] |

TABLE 1-continued
Analytical Data
| Example # | HPLC Method | HPLC RT | MS(ESI) (M + H) | Chirality | Structure |
|---|---|---|---|---|---|
| 292 | A | 1.74 | 570.6 | Racemate | 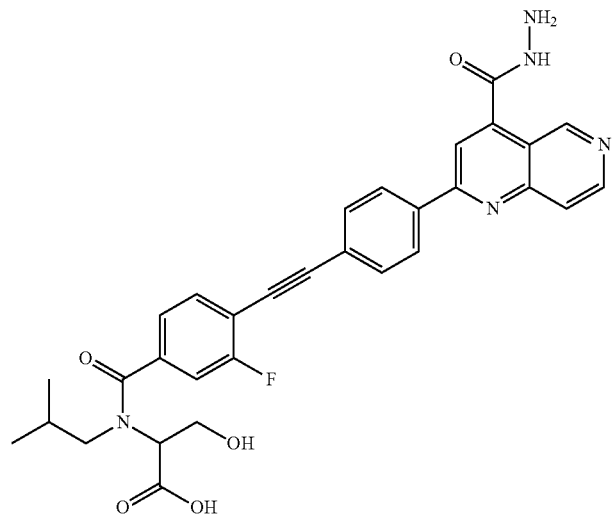 [SMILES: CC(C)CN(C(=O)c1ccc(C#Cc2ccc(-c3cc(C(=O)NN)c4cnccc4n3)cc2)c(F)c1)C(CO)C(=O)O] |
| 293 | A | 1.45 | 580.6 | Racemate | 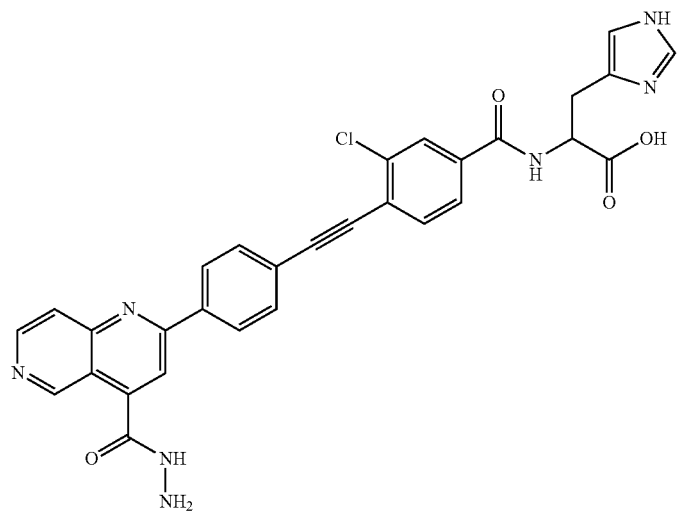 [SMILES: NNC(=O)c1cc(-c2ccc(C#Cc3ccc(C(=O)NC(Cc4c[nH]cn4)C(=O)O)cc3Cl)cc2)nc2ccncc12] |

TABLE 1-continued

Analytical Data

| Example # | HPLC Method | HPLC RT | MS(ESI) (M + H) | Chirality | Structure |
|---|---|---|---|---|---|
| 294 | A | 1.4 | 564.5 | Racemate | 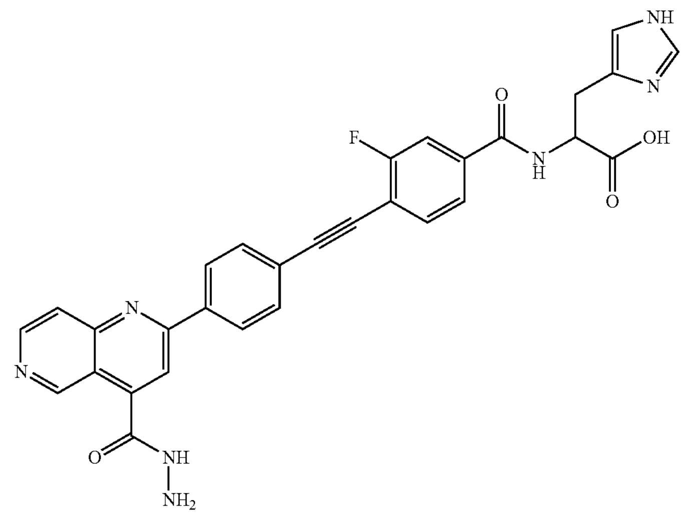 [SMILES: NNC(=O)c1cc(-c2ccc(C#Cc3ccc(C(=O)NC(Cc4c[nH]cn4)C(=O)O)cc3F)cc2)nc2ccncc12] |
| 295 | A | 1.45 | 594.6 | Racemate | 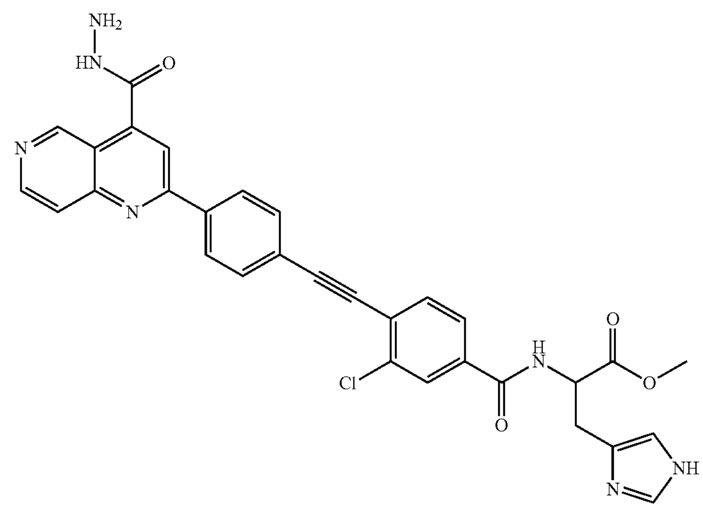 |
| 296 | A | 1.51 | 578.6 | Racemate | 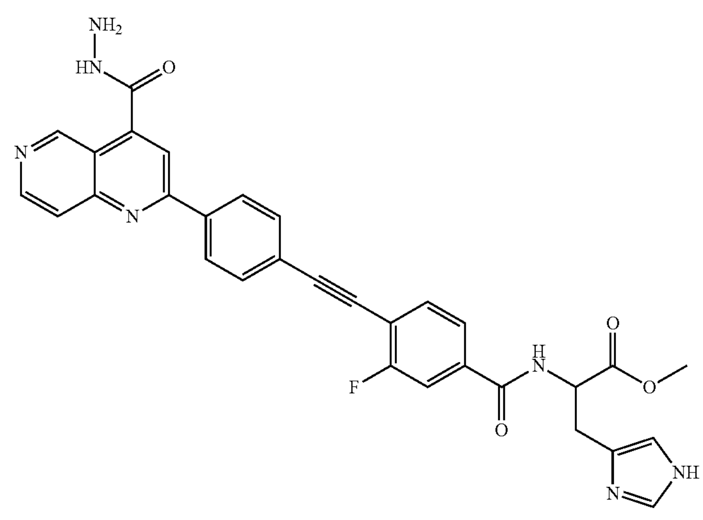 [SMILES: COC(=O)C(Cc1c[nH]cn1)NC(=O)c1ccc(C#Cc2ccc(-c3cc(C(=O)NN)c4cnccc4n3)cc2)c(Cl)c1] |

TABLE 1-continued
Analytical Data
| Example # | HPLC Method | HPLC RT | MS(ESI) (M + H) | Chirality | Structure |
|---|---|---|---|---|---|
| 297 | A | 1.41 | 495.4 | Racemate | 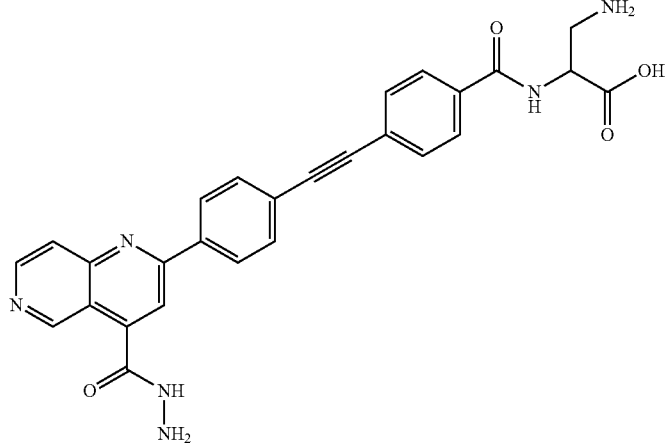 [SMILES: NCC(NC(=O)c1ccc(C#Cc2ccc(-c3cc(C(=O)NN)c4cnccc4n3)cc2)cc1)C(=O)O] |
| 298 | C | 7.27 | 529.7 | Racemate | 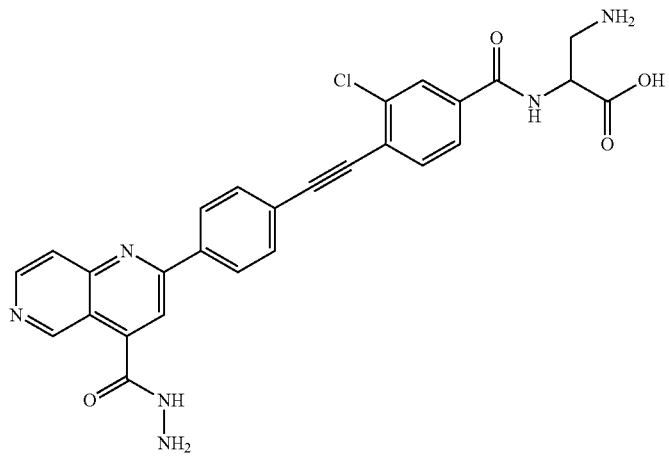 [SMILES: NCC(NC(=O)c1ccc(C#Cc2ccc(-c3cc(C(=O)NN)c4cnccc4n3)cc2)c(Cl)c1)C(=O)O] |
| 299 | C | 7.11 |  | Racemate | 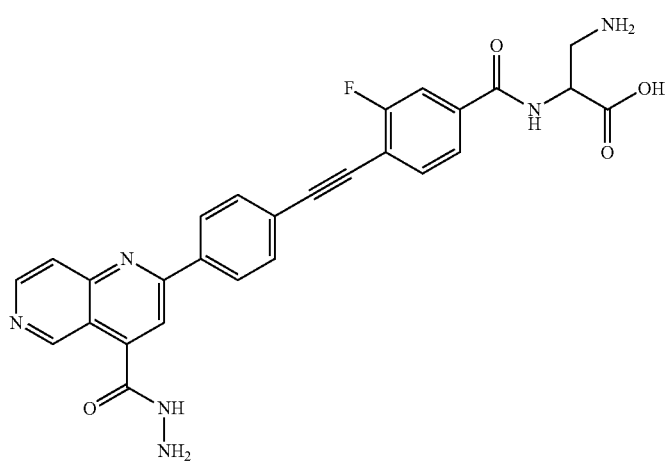 [SMILES: NCC(NC(=O)c1ccc(C#Cc2ccc(-c3cc(C(=O)NN)c4cnccc4n3)cc2)c(F)c1)C(=O)O] |

TABLE 1-continued

Analytical Data

| Example # | HPLC Method | HPLC RT | MS(ESI) (M + H) | Chirality | Structure |
|---|---|---|---|---|---|
| 300 | A | 2.38 | 589.4 | S | 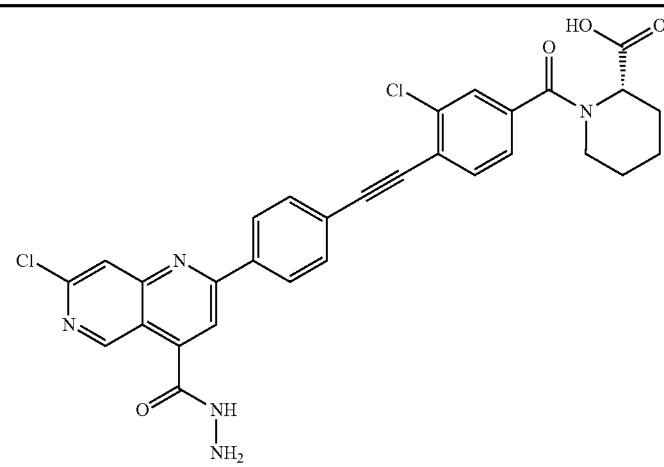 |
| 301 | A | 1.53 | 551.8 | Racemate | 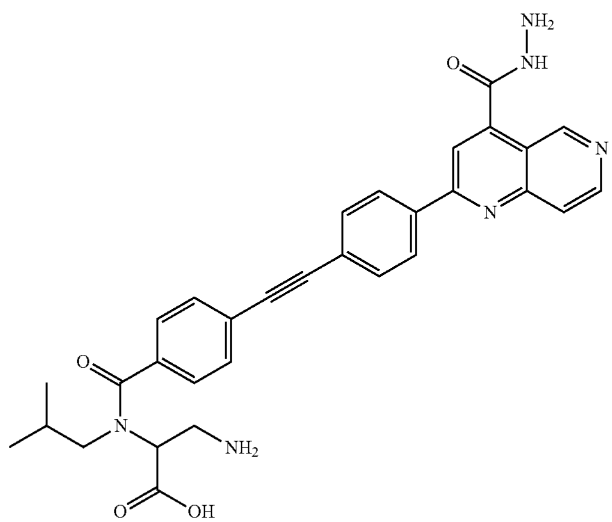 |
| 302 | G | 2.7 | 585.6 | Racemate | 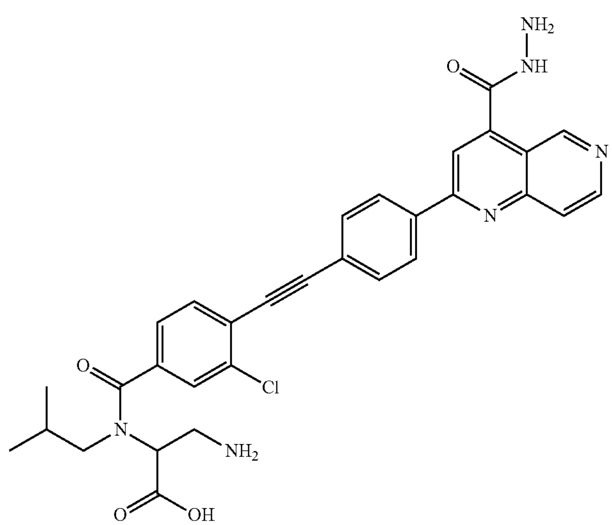 [SMILES: CC(C)CN(C(=O)c1ccc(C#Cc2ccc(-c3cc(C(=O)NN)c4cnccc4n3)cc2)c(Cl)c1)C(CN)C(=O)O] |

TABLE 1-continued
Analytical Data
| Example # | HPLC Method | HPLC RT | MS(ESI) (M + H) | Chirality | Structure |
|---|---|---|---|---|---|
| 303 | A | 1.55 | 569.8 | Racemate | 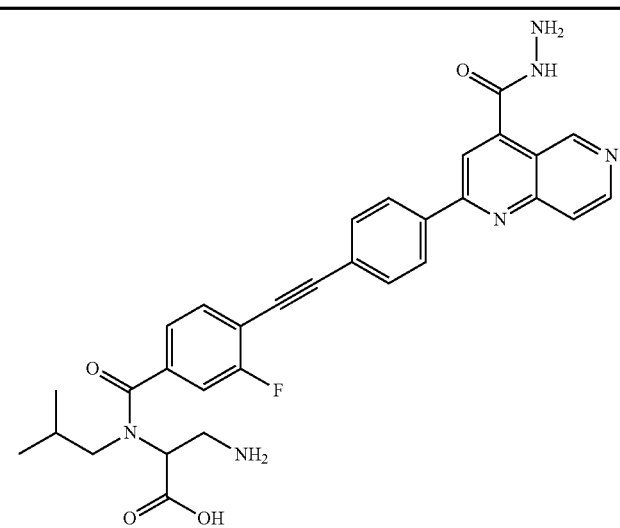 |
| 304 | A | 1.89 | 517.5 | Racemate | 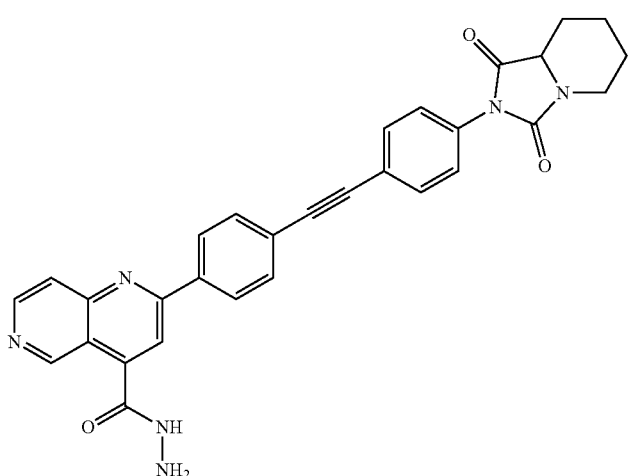 [SMILES: NNC(=O)c1cc(-c2ccc(C#Cc3ccc(N4C(=O)C5CCCCN5C4=O)cc3)cc2)nc2ccncc12] |
| 305 | G | 2.51 | 509.6 | Racemate | 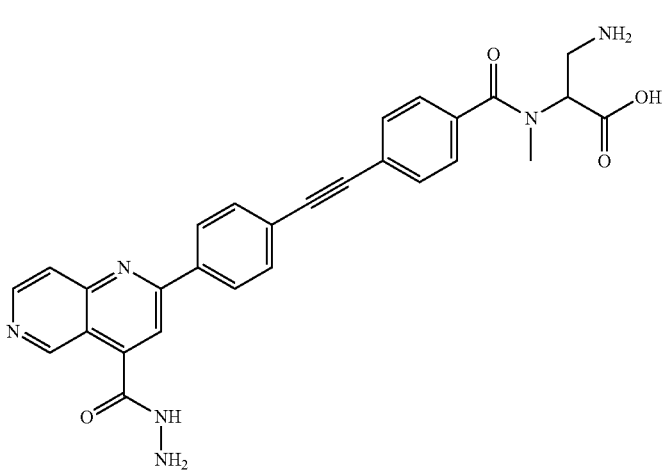 [SMILES: CN(C(=O)c1ccc(C#Cc2ccc(-c3cc(C(=O)NN)c4cnccc4n3)cc2)cc1)C(CN)C(=O)O] |

TABLE 1-continued
Analytical Data
| Example # | HPLC Method | HPLC RT | MS(ESI) (M + H) | Chirality | Structure |
|---|---|---|---|---|---|
| 306 | A | 1.79 | 569.6 | S | 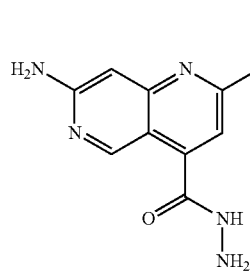 |
| 307 | A | 1.35 | 572.4 | Racemate | 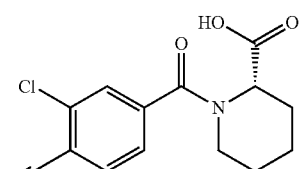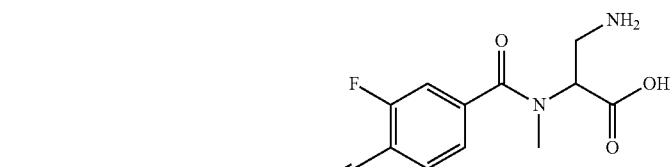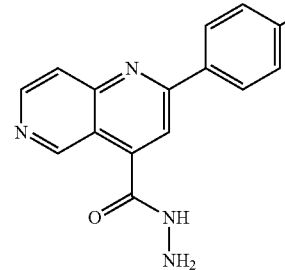 |
| 308 | G | 2.37 | 526.4 | Racemate | 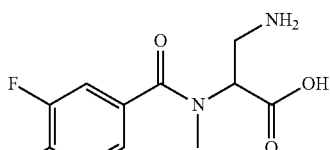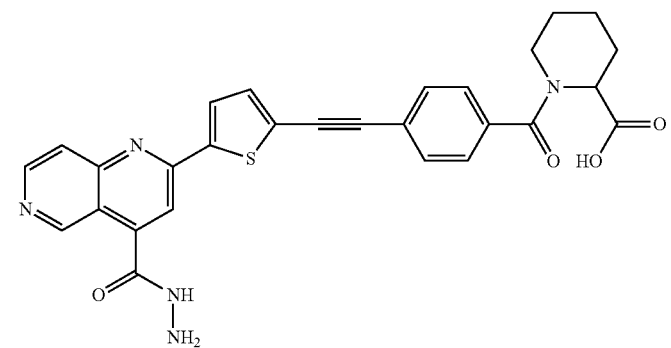 [SMILES: NNC(=O)c1cc(-c2ccc(C#Cc3ccc(C(=O)N4CCCCC4C(=O)O)cc3)s2)nc2ccncc12] |

TABLE 1-continued
Analytical Data
| Example # | HPLC Method | HPLC RT | MS(ESI) (M + H) | Chirality | Structure |
|---|---|---|---|---|---|
| 309 | A | 1.99 | 647.7 | S | 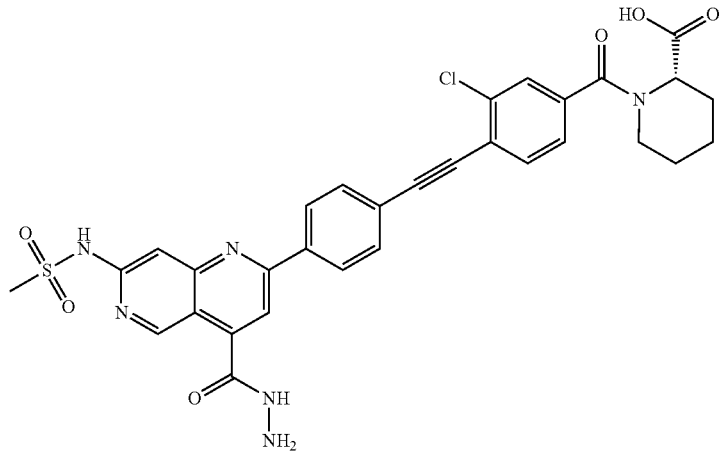 [SMILES: CS(=O)(=O)Nc1cc2nc(-c3ccc(C#Cc4ccc(C(=O)N5CCCC[C@H]5C(=O)O)cc4Cl)cc3)cc(C(=O)NN)c2cn1] |
| 310 | C | 7.35 | 584.8 | S | 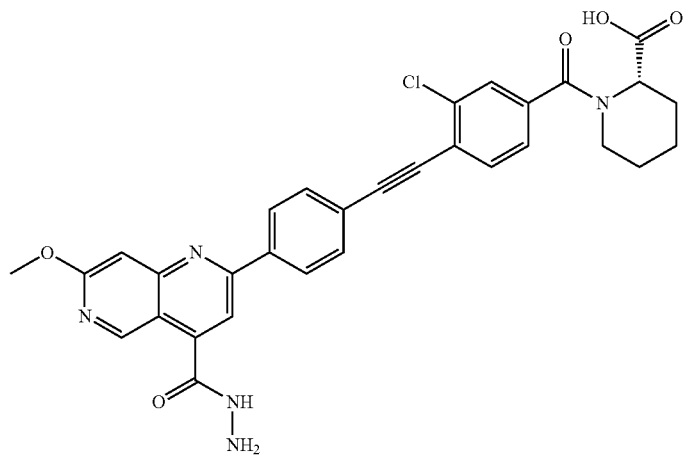 [SMILES: COc1cc2nc(-c3ccc(C#Cc4ccc(C(=O)N5CCCC[C@H]5C(=O)O)cc4Cl)cc3)cc(C(=O)NN)c2cn1] |
| 311 | A | 1.73 | 397.4 | Racemate | 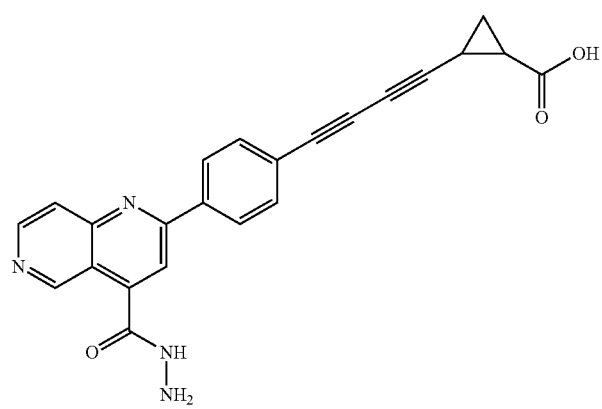 [SMILES: NNC(=O)c1cc(-c2ccc(C#CC#CC3CC3C(=O)O)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 312 | A | 1.99 | 613.5 | S | 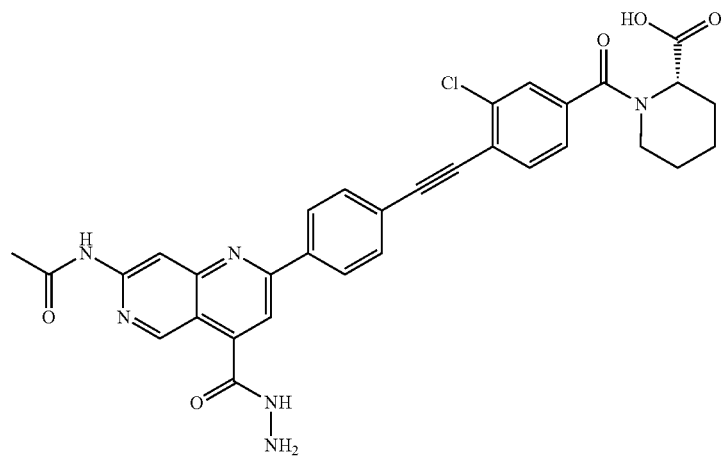 [SMILES: CC(=O)Nc1cc2nc(-c3ccc(C#Cc4ccc(C(=O)N5CCCC[C@H]5C(=O)O)cc4Cl)cc3)cc(C(=O)NN)c2cn1] |
| 313 | F | 3.31 | 639.7 | S | 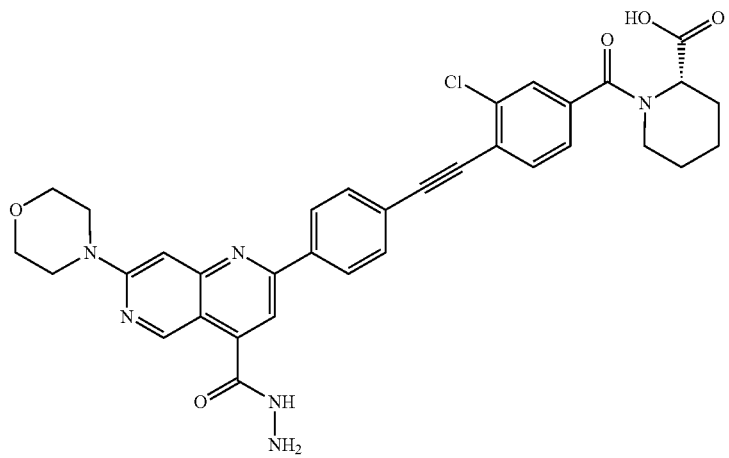 [SMILES: NNC(=O)c1cc(-c2ccc(C#Cc3ccc(C(=O)N4CCCC[C@H]4C(=O)O)cc3Cl)cc2)nc2cc(N3CCOCC3)ncc12] |
| 314 | H | 2.88 | 508.9 | Racemate | 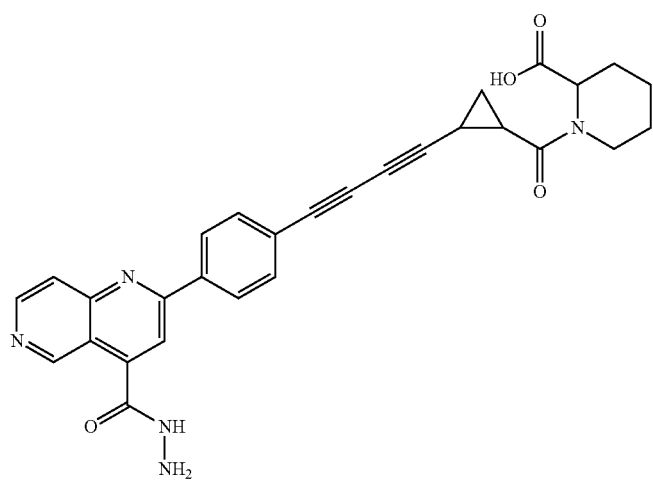 [SMILES: NNC(=O)c1cc(-c2ccc(C#CC#CC3CC3C(=O)N3CCCCC3C(=O)O)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 315 | H | 3.4 | 655.5 | S | 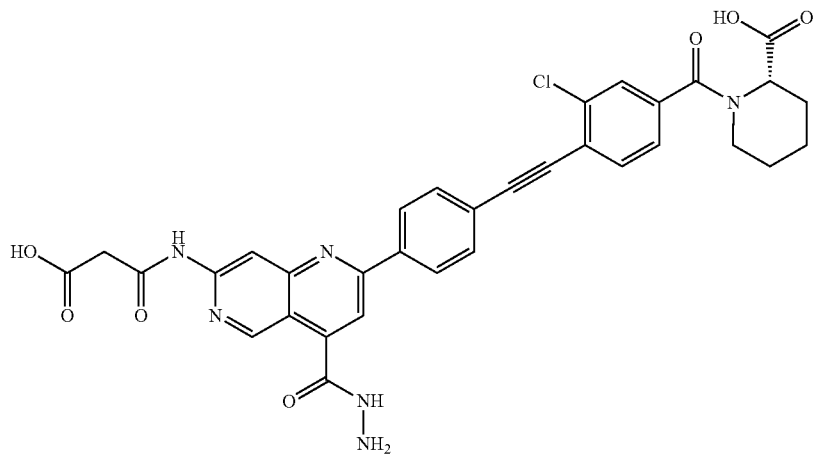 [SMILES: NNC(=O)c1cc(-c2ccc(C#Cc3ccc(C(=O)N4CCCC[C@H]4C(=O)O)cc3Cl)cc2)nc2cc(NC(=O)CC(=O)O)ncc12] |
| 316 | I | 8.31 | 691.5 | S | 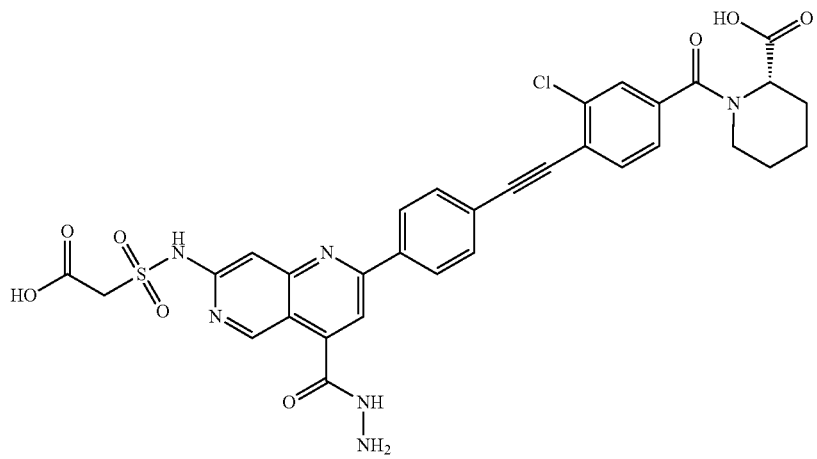 [SMILES: NNC(=O)c1cc(-c2ccc(C#Cc3ccc(C(=O)N4CCCC[C@H]4C(=O)O)cc3Cl)cc2)nc2cc(NS(=O)(=O)CC(=O)O)ncc12] |
| 317 | A | 1.93 | NA | Racemate | 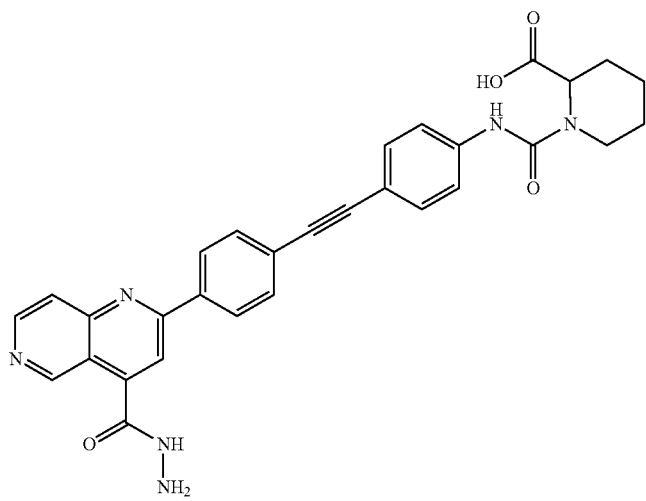 [SMILES: NNC(=O)c1cc(-c2ccc(C#Cc3ccc(NC(=O)N4CCCCC4C(=O)O)cc3)cc2)nc2ccncc12] |

TABLE 1-continued
Analytical Data
| Example # | HPLC Method | HPLC RT | MS(ESI) (M + H) | Chirality | Structure |
|---|---|---|---|---|---|
| 318 | C | 7.19 | 653.7 | S | 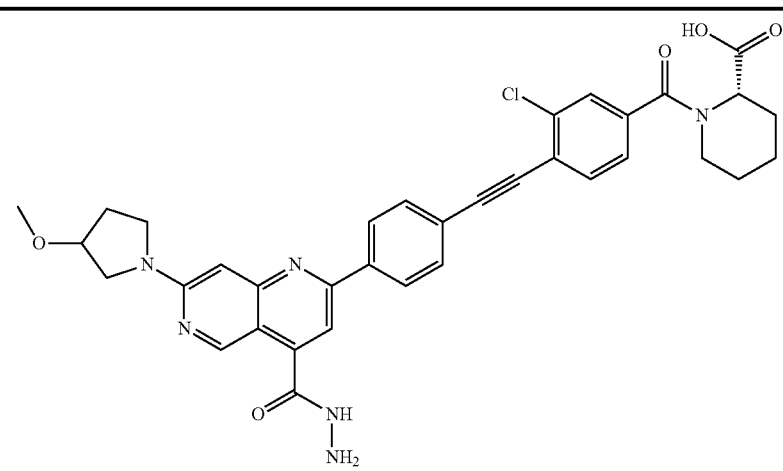 |
| 319 | J | 3.23 | 473.4 | | 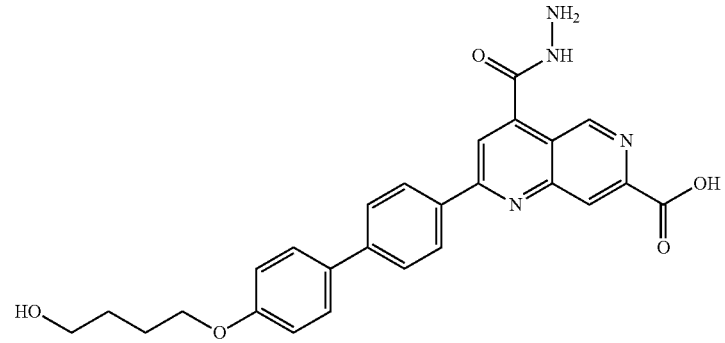 [SMILES: NNC(=O)c1cc(-c2ccc(-c3ccc(OCCCCO)cc3)cc2)nc2cc(C(=O)O)ncc12] |
| 320 | C | 8.3 | 605.3 | | 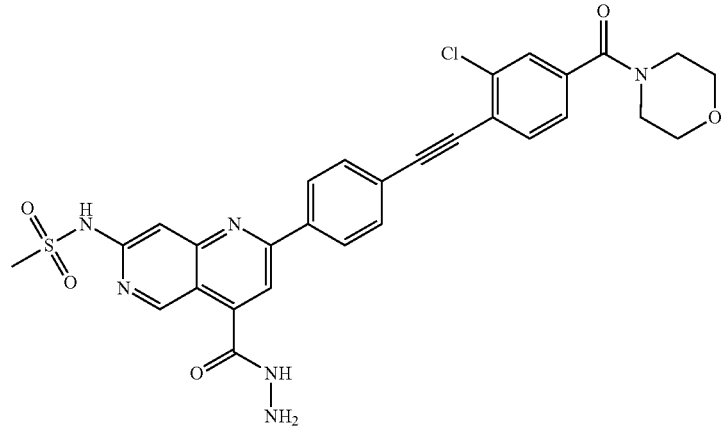 [SMILES: CS(=O)(=O)Nc1cc2nc(-c3ccc(C#Cc4ccc(C(=O)N5CCOCC5)cc4Cl)cc3)cc(C(=O)NN)c2cn1] |

TABLE 1-continued
Analytical Data
| Example # | HPLC Method | HPLC RT | MS(ESI) (M + H) | Chirality | Structure |
|---|---|---|---|---|---|
| 321 | H | 0.44 | 626.6 | S | 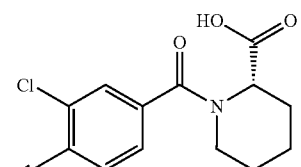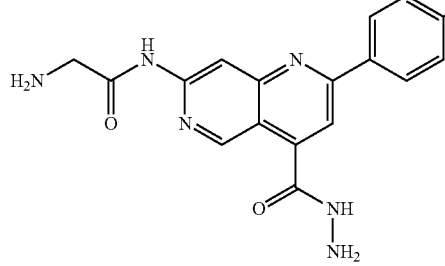 |
| 322 | I | 8.19 | 649.4 | | 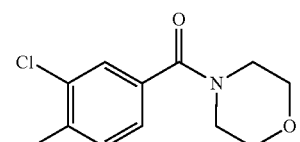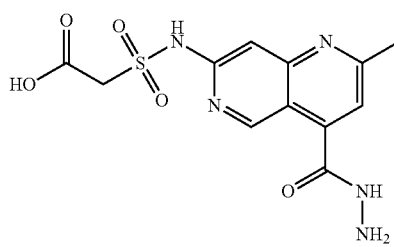 |
| 323 | J | 2.95 | 570.5 | R | 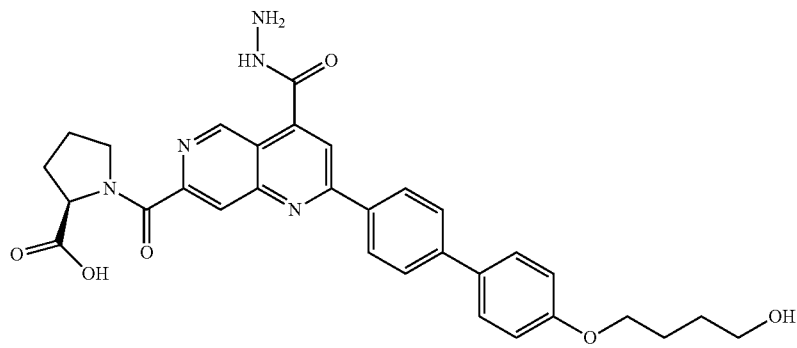 [SMILES: NNC(=O)c1cc(-c2ccc(-c3ccc(OCCCCO)cc3)cc2)nc2cc(C(=O)N3CCC[C@@H]3C(=O)O)ncc12] |

TABLE 1-continued
Analytical Data
| Example # | HPLC Method | HPLC RT | MS(ESI) (M + H) | Chirality | Structure |
|---|---|---|---|---|---|
| 324 | NA | NA | 568.4 [M − 1] | S | 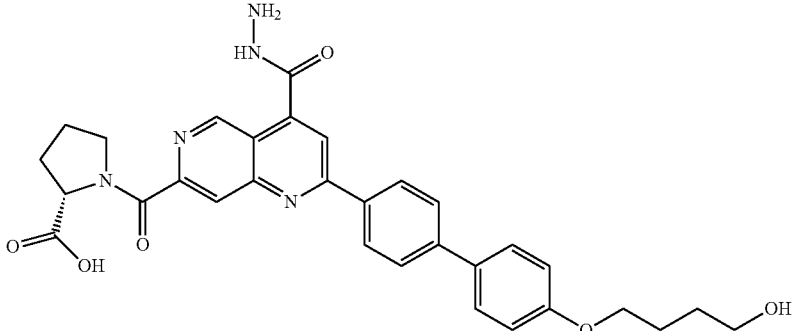 |
| 325 | C | 7.98 | 520.2 [M − 1] | | 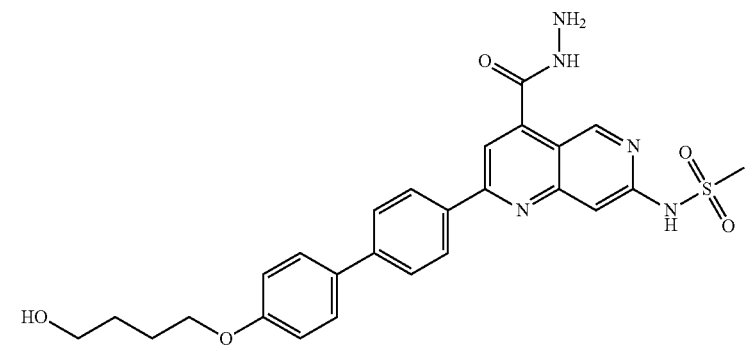 [SMILES: CS(=O)(=O)Nc1cc2nc(-c3ccc(-c4ccc(OCCCCO)cc4)cc3)cc(C(=O)NN)c2cn1] |
| 326 | I | 7.9 | 566.7 | | 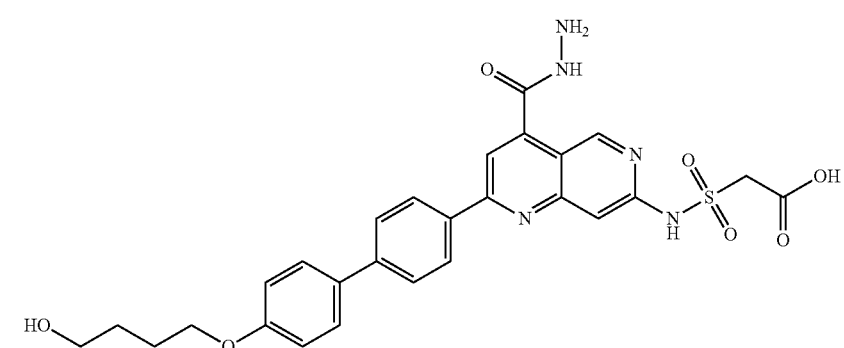 |
| 327 | NA | NA | 529.2 [M − 1] | | 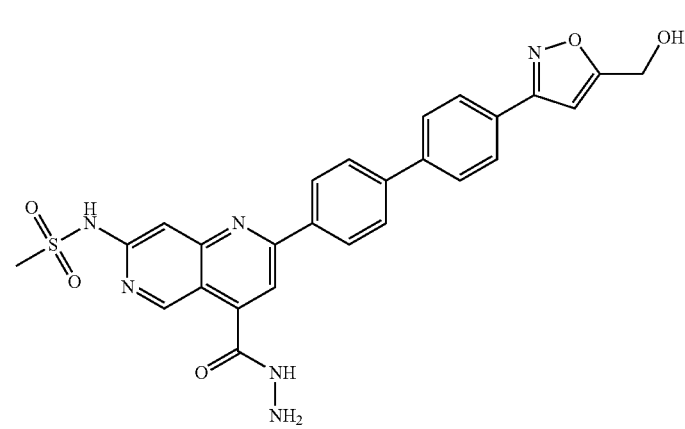 [SMILES: CS(=O)(=O)Nc1cc2nc(-c3ccc(-c4ccc(-c5cc(CO)on5)cc4)cc3)cc(C(=O)NN)c2cn1] |

TABLE 1-continued

Analytical Data

| Example # | HPLC Method | HPLC RT | MS(ESI) (M + H) | Chirality | Structure |
|---|---|---|---|---|---|
| 328 | J | 3.01 | 575.5 | | 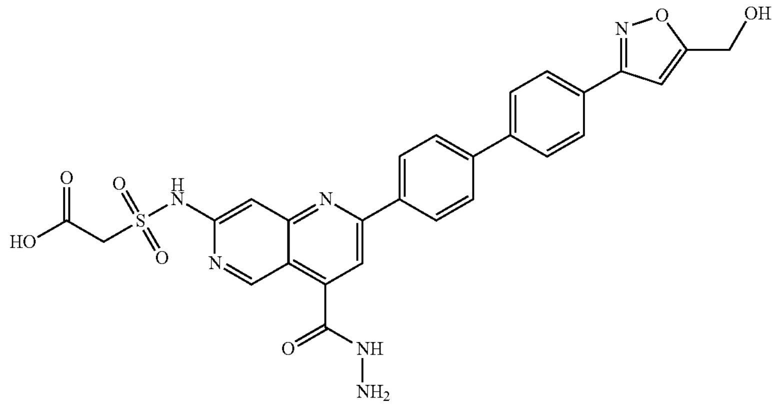 [SMILES: NNC(=O)c1cc(-c2ccc(-c3ccc(-c4cc(CO)on4)cc3)cc2)nc2cc(NS(=O)(=O)CC(=O)O)ncc12] |
| 329 | A | 2.02 | 620.4 | | 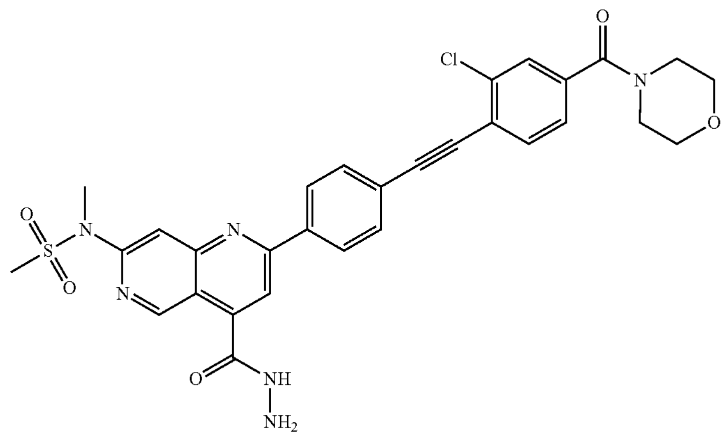 [SMILES: CN(c1cc2nc(-c3ccc(C#Cc4ccc(C(=O)N5CCOCC5)cc4Cl)cc3)cc(C(=O)NN)c2cn1)S(C)(=O)=O] |
| 330 | A | 1.9 | 663.5 | | 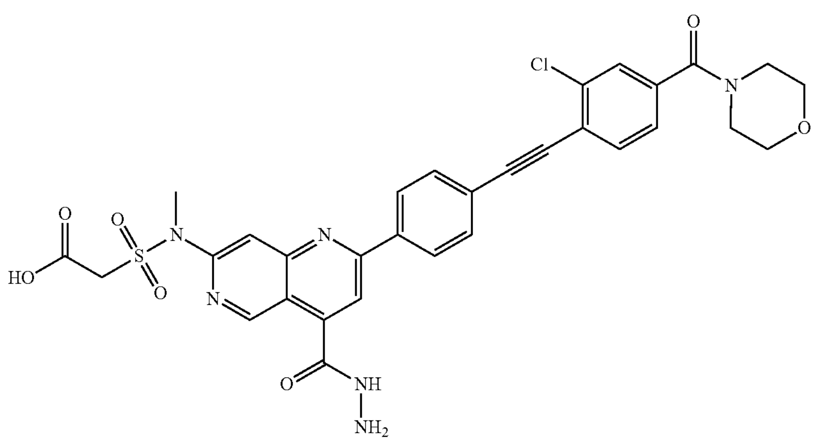 [SMILES: CN(c1cc2nc(-c3ccc(C#Cc4ccc(C(=O)N5CCOCC5)cc4Cl)cc3)cc(C(=O)NN)c2cn1)S(=O)(=O)CC(=O)O] |

Example 331

Analytical Methods

Method A Specifications
Column: Aquity BEH C-18 (50×2.1 mm, 1.7μ)
Mobile Phase: A) CH$_3$CN; B) 0.025% aq TFA
Flow Rate: 0.50 mL/min
Time (min)/% B: 0.01/90, 0.5/90, 3/10, 6/10
Method B Specifications:
Column: Eclipse XDB C-18 (150×4.6 mm, 5.0μ)
Mobile Phase: A) CH$_3$CN; B) 5 millimolar (mM) acetic acid
Flow Rate: 1.0 mL/min
Time (min)/% B: 0.01/80, 2/80, 15/10, 15.01/stop
Method C Specifications:

Column: Eclipse XDB C-18 (150×4.6 mm, 5.0µ)
Mobile Phase: A) CH$_3$CN; B) 5 mM ammonium acetate (NH$_4$OAc)
Flow Rate: 1.0 mL/min
Time (min)/% B: 0.01/80, 3/80, 10/10, 20/10
Method D Specifications:
Column: Eclipse XDB C-18 (150×4.6 mm, 5.0µ)
Mobile Phase: A) CH$_3$CN; B) 5 mM ammonium formate
Flow Rate: 1.0 mL/min
Time (min)/% B: 0.01/80, 3/80, 10/10, 20/10
Method E Specifications:
Column: Zorbax SB C-18 (250×4.6 mm, 5µ)
Mobile Phase: A) CH$_3$CN; B) 0.1% aq HClO4
Flow Rate: 1.00 mL/min
Time (min)/% B: 0.01/90, 5/90, 15/10, 25/10
Method F Specifications:
Column: XBridge C-18 (50×3.0 mm, 3.5µ)
Mobile Phase: A) 0.1% aq TFA; B) CH$_3$CN
Flow Rate: 0.8 mL/min
Time (min)/% B: 0.01/10, 0.5/10, 4/90, 8/90
Method G Specifications:
Column: XBridge C-18 (50×3.0 mm, 3.5µ)
Mobile Phase: A) 5.0 mM NH4OAc; B) CH$_3$CN
Flow Rate: 0.8 mL/min
Time (min)/% B: 0.01/10, 0.5/10, 4/90, 8/90
Method H Specifications:
Column: XSelect C-18 (50×3.0 mm, 3.5µ)
Mobile Phase: A) 5.0 mM NH4OAc; B) CH$_3$CN
Flow Rate: 0.8 mL/min
Time (min)/% B: 0.01/10, 0.5/10, 4/90, 8/90
Method I Specifications:
Column: Eclipse XDB C-18 (150×4.6 mm, 5.0µ)
Mobile Phase: A) CH$_3$CN; B) 0.05% aq TFA
Flow Rate: 1.0 mL/min
Time (min)/% B: 0.01/80, 3/80, 10/10, 20/10
Method J Specifications:
Column: XSelect CSH C-18 (50×3.0 mm, 3.5µ)
Mobile Phase: A) 5.0 mM NH4OAc; B) CH$_3$CN
Flow Rate: 0.8 mL/min
Time (min)/% B: 0.01/10, 0.5/10, 4/90, 8/90

Example 332

Antibacterial Activity

A. Minimum Inhibitory Concentration (MIC)

Minimum Inhibitory Concentrations (MICS) were determined for *Escherichia coli* (American Type Culture Collection (ATCC) 25922) and *Pseudomonas aeruginosa* (ATCC 27853) in accordance with the Clinical and Laboratory Standards Institute (CLSI). Serial, one-half dilutions of compounds were prepared in 96-well dilution blocks in cation-adjusted Mueller-Hinton Broth (MBH)+2% DMSO and transferred to 96-well assay plates in duplicate. Cell suspensions of *E. coli* and *P. aeruginosa* were prepared in MHB and added to each well at concentrations of approximately 1.2×10$^6$ and 3.3×10$^6$ colony-forming-units per milliliter (cfu/mL), respectively. The inoculated plates were incubated at 35±1° C. for 18±2 h. At the completion of incubation the wells of each plate were evaluated visually for the presence of growth. The MIC was the concentration which completely inhibited growth (per CLSI, M2-A7). In addition to visual evaluation, optical densities were determined using a Tecan Infinite M200 microplate reader measuring absorbance at 600 nm. Example 202 exhibited an MIC of 128 µg/mL for *Pseudomonas aeruginosa* (ATCC 27853).

Example 333

Metalloenzyme Activity

A. Inhibition of LpxC Enzyme

Test compounds were dissolved in 100% DMSO @ 10 mM. Then a series of dilutions were done with 100% DMSO, these were the first intermediate dilutions. Individual 100% DMSO dilutions were diluted independently to another intermediate dilution using assay buffer (bringing the DMSO concentration to 5%). Finally, 10 µl of all these 5% intermediate dilutions were used directly in the 50 µl reaction, making the final DMSO testing concentration at 1%. The enzymatic reactions were conducted in duplicate at room temperature for 1 hour in a 50 µL mixture containing MMP-2 assay buffer, 1 µM Mca-PLGLDpaAR, 10 uL MPP-2 enzyme (1.8 ng) and 10 µL of a test compound. All the reactions were conducted using 10 µl MMP-2 assay buffer in place of enzyme, to detect just the background fluorescence from the compound. After enzymatic reactions, fluorescence intensity was measured at an excitation of 328 nm and an emission of 393 nm using a Tecan Infinite M1000™ microplate reader.

Results

| Example | LpxC IC50* |
|---|---|
| 31 | 0.004 |
| 35 | 0.002 |
| 83 | 0.004 |
| 101 | 0.006 |
| 115 | 0.008 |
| 172 | 0.018 |
| 185 | 0.005 |
| 202 | 0.002 |
| 309 | 0.002 |
| 327 | 0.005 |
| 328 | 0.002 |
| BB-78485 | 0.020 |

*IC50s are in uM; LpxC enzyme is pseudomonas construct.

Select compounds of the invention exhibit growth arrest of *P. aeruginosa* and/or *E. coli*.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A compound of formula (I), (II), (III), (IV), or salt thereof, wherein:

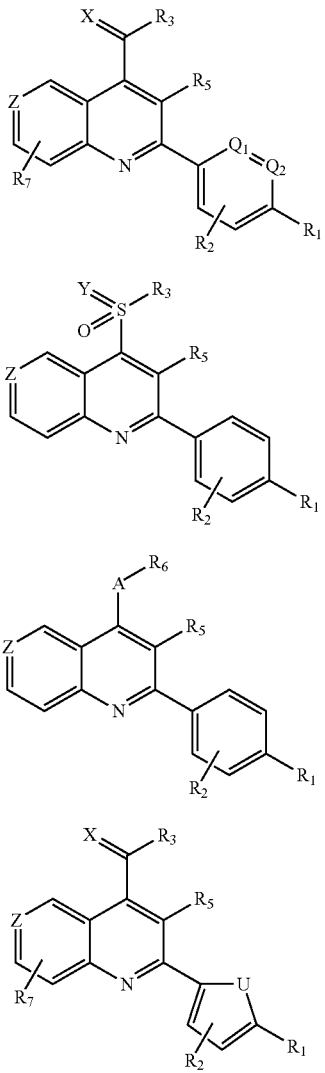

U is O or S;
each X is independently O; S; NR$_4$; or H and R$_4$;
each R$_1$ is independently selected from:
a)

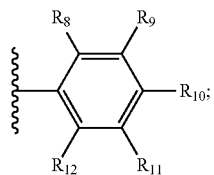

b) heteroaryl optionally substituted with alkoxy wherein alkoxy is optionally substituted with 1, 2, or 3 OR$_4$; c) C≡C—R$_{13}$; d) C(=O)NR$_4$R$_7$; e) N(R$_7$)C(=O)R$_4$; f) SO$_2$NR$_4$R$_7$; g) N(R$_7$)SO$_2$R$_4$; h) hydrogen; i) hydroxy; j) optionally substituted alkoxy; k) SO$_2$NHR$_4$;

l) optionally substituted alkenyl; or m) optionally substituted arylalkyl;
each R$_8$, R$_9$, R$_{10}$, R$_{11}$, and R$_{12}$ is independently selected from:
a) H; b) hydroxyalkylamino; c) alkoxy optionally substituted with 1, 2, or 3 independent heterocycloalkoxy, heterocycloalkylcarbonyl, hydroxy, amino, NHSO$_2$R$_4$, NHC(=O)R$_4$, C(=O)OR$_4$, C(=O)NHNHR$_4$, or C(=O)NR$_4$OH; d) halogen; e) SO$_2$NHR$_{18}$; f) NHSO$_2$R$_4$; g) NHC(=O)R$_4$; h) C(=O)NHR$_4$; i) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; j) heteroaryl containing 5 to 6 ring atoms optionally substituted with 1, 2, or 3 independent:
(1) C(=O)OR$_{17}$;
(2) heterocycloalkylcarbonyl optionally substituted with 1, 2, or 3 independent C(=O)OR$_{17}$, C(=O)NR$_4$R$_7$, or SO$_2$NR$_4$R$_7$;
(3) alkyl optionally substituted with 1, 2, or 3 independent OC(=O)NHR$_4$, NHC(=O)NHR$_4$, NHSO$_2$R$_4$, hydroxy, or C(=O)NHR$_4$; or
(4) C(=O)NHR$_4$;
k) cyano; l) hydroxy; m) SO$_2$R$_4$; n) heterocycloalkylcarbonyl optionally substituted with 1, 2, or 3 independent C(=O)OR$_4$, C(=O)NR$_4$R$_7$, or SO$_2$NR$_4$R$_7$; o) heterocycloalkylsulfonyl optionally substituted with 1, 2, or, 3 independent C(=O)OR$_4$, C(=O)NR$_4$R$_7$, or SO$_2$NR$_4$R$_7$; p)

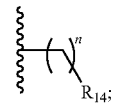

q) mercapto; r) thioalkoxy; s) alkylamino; t) alkyl optionally substituted with 1, 2, or 3 independent heterocycloalkylcarbonyl, heterocycloalkyl, or heterocycloalkylsulfonyl, each optionally substituted with independent C(=O)OR$_4$, C(=O)NR$_4$R$_7$, or SO$_2$NR$_4$R$_7$; u) dialkylamino; or v) —O—CH$_2$)$_n$—C(=O)-heterocycloalkyl optionally substituted with 1, 2, or 3 independent C(=O)OR$_4$, C(=O)NR$_4$R$_7$, or SO$_2$NR$_4$R$_7$;
R$_2$ is H, alkyl, fluoroalkyl, alkoxy, fluoroalkoxy, halogen, aryl, or heteroaryl;
R$_3$ is CH(R$_4$)NHR$_4$, CH(R$_4$)NHSO$_2$R$_4$, CH(R$_4$)SH, CH(R$_4$)OH, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NHNHR$_4$, C(=S)NHR$_4$, C(=S)NHNHR$_4$, C≡N, C(=NH)NH$_2$, NHC(=NH)NH$_2$, N(R$_4$)OH, N(OH)C(=O)R$_4$, NHR$_4$, NHNHR$_4$, NHC(=O)R$_4$, N(R$_4$)NHC(=O)R$_4$, NHC(=O)NHR$_4$, NHC(=S)NHR$_4$, NHSO$_2$R$_4$, NHSO$_2$NHR$_4$; NHNHSO$_2$R$_4$, NO$_2$, SO$_2$NHR$_4$ (only in the case of formula I), SO$_2$NHOH (only in the case of formula I), SO$_3$H (only in the case of formula I), OR$_4$, OSO$_2$R$_4$, OSO$_2$NHR$_4$, SR$_4$, B(OR$_4$)$_2$, CH$_2$B(OR$_4$)$_2$, P(=O)OH, P(=O)$_2$OH, Se(=O)OH, Se(=O)$_2$OH, a heterocycle that is preferably a 5-membered ring with 1-4 heteroatoms, or a 5-membered heterocycle that is connected through a CH$_2$;
Y is O or null;
Z is N;
each R$_4$ is independently a) H; b) alkyl optionally substituted with 1, 2, or 3 independent hydroxy, halogen, C(=O)OR$_{27}$, amino, alkylthio, or optionally substituted aryl; c) fluoroalkyl; d) optionally substituted aryl; e) optionally substituted heteroaryl; or f) heterocycloalkyl optionally substituted with 1, 2, or 3 independent C(=O)OR$_{27}$, C(=O)NR$_{27}$R$_{27}$, or SO$_2$NR$_{27}$R$_{27}$;

each R$_5$ is independently H, alkyl, fluoroalkyl, halogen, alkoxy, fluoroalkoxy, substituted amino, aryl, or heteroaryl;

A is O, S, CH$_2$ or N(R$_4$);

A may also be the following when R$_6$ is null: an optionally substituted heterocycle that is preferably a 5-membered ring with 1-4 heteroatoms, B(OR$_4$)$_2$, P(=O)OH, P(=O)$_2$OH, Se(=O)OH, Se(=O)$_2$OH;

R$_6$ is null, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NR$_4$OH, C(=O)NHNHR$_4$, C(=S)NHR$_4$, C(=S)NR$_4$OH, C(=S)NHNHR$_4$, C≡N, C(=NH)NH$_2$, SO$_2$NHR$_4$ (with the proviso that A cannot be S), SO$_2$NHR$_4$ (with the proviso that A cannot be S), SO$_2$NHOH (with the proviso that A cannot be S); a heterocycle that is preferably a 5-membered ring with 1-4 heteroatoms, or a (preferably 5-membered) heterocycle that is connected through a CH$_2$; and each R$_7$ is independently H; alkyl; alkoxy; hydroxy; C(=O)OR$_4$; NHSO$_2$R$_4$; N(alkyl)SO$_2$R$_4$; NHR$_4$; NHC(=O)R$_4$; N(alkyl)C(=O)R$_4$; C(=O)NR$_{27}$R$_4$; SO$_2$NR$_{27}$R$_4$; C(=O)NR$_{27}$NHR$_4$; C(=O)NR$_{27}$OR$_4$; halogen; optionally substituted aryl; optionally substituted heteroaryl; heterocycloalkyl optionally substituted with 1, 2, or 3 independent OR$_4$, C(=O)OR$_4$, or NHSO$_2$R$_4$; or heterocycloalkylcarbonyl optionally substituted with 1, 2, or 3 independent OR$_4$, C(=O)OR$_4$, or NHSO$_2$R$_4$;

each R$_{13}$ is independently selected from:
a)

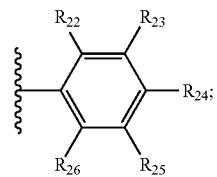

b) heterocycloalkyl optionally substituted with 1, 2, or 3 independent alkyl wherein alkyl is optionally substituted with independent:
  i) OR$_4$;
  ii) NHC(=O)R$_4$;
  iii) C(=O)OR$_4$; or
  iv) C(=O)NHR$_4$;
c) heteroaryl optionally substituted with 1, 2, or 3 independent 1) heterocycloalkylcarbonyl, 2) NR$_{27}$SO$_2$R$_4$, 3) alkylaminocarbonyl, each optionally substituted with 1, 2, or 3 independent C(=O)OR$_4$, C(=O)NR$_4$R$_7$, or SO$_2$NR$_4$R$_7$, 4) (heterocycloalkyl)alkyl; or 5) NR$_{27}$C(=O)R$_4$; or
d) cycloalkyl optionally substituted with 1, 2, or 3 independent C(=O)OR$_4$, C(=O)NR$_4$R$_7$, hydroxyalkyl, or SO$_2$NR$_4$R$_7$;

each R$_{14}$ is independently selected from heterocycloalkylcarbonyl, heterocycloalkylsulfonyl, or heterocycloalkyl, each optionally substituted with 1, 2, or 3 independent C(=O)OR$_4$, C(=O)NR$_4$R$_7$, or SO$_2$NR$_4$R$_7$;

each R$_{15}$ is independently H; alkyl; fluoroalkyl; aryl; arylalkyl; or heteroaryl;

each R$_{16}$ is independently hydrogen; alkyl; alkoxy; hydroxy; NHR$_4$; NHC(=O)R$_4$; halogen; optionally substituted aryl; optionally substituted heteroaryl; heterocycloalkyl optionally substituted with 1, 2, or 3 independent C(=O)OR$_4$, C(=O)NR$_4$R$_7$, or SO$_2$NR$_4$R$_7$; or NHSO$_2$R$_4$;

each R$_{17}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{18}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{19}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{20}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, optionally substituted heteroaryl, or optionally substituted aryl; c) fluoroalkyl; d) aryl optionally substituted with 1, 2, or 3 independent C(=O)OR$_4$ or OR$_4$; or e) heteroaryl;

each R$_{21}$ is independently a) H; b) alkyl optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; c) fluoroalkyl; d) aryl; or e) heteroaryl;

each R$_{22}$, R$_{23}$, R$_{24}$, R$_{25}$, and R$_{26}$ is independently selected from
  i) hydrogen; ii) NHC(=O)R$_4$; iii) NHSO$_2$R$_4$; iv) heterocycloalkylcarbonyl optionally substituted with 1, 2, or 3 independent alkyl, CH$_2$C(=O)OR$_{19}$, CH$_2$C(=O)NR$_4$R$_7$, OR$_4$, CH$_2$SO$_2$NR$_4$R$_7$, C(=O)OR$_{19}$, C(=O)NR$_4$R$_7$, or SO$_2$NR$_4$R$_7$; v) heterocycloalkylsulfonyl optionally substituted with 1, 2, or 3 independent C(=O)OR$_4$, C(=O)NR$_4$R$_7$, or SO$_2$NR$_4$R$_7$, or alkyl; vi) halogen; vii) alkyl optionally substituted with heterocycloalkyl wherein heterocycloalkyl is optionally substituted with 1, 2, or 3 independent C(=O)OR$_4$, C(=O)NR$_4$R$_7$, or SO$_2$NR$_4$R$_7$; viii) hydroxyalkylamino; ix) C(=O)NR$_{15}$R$_{20}$; x) alkoxy optionally substituted with 1, 2, or 3 independent hydroxy, halogen, C(=O)OR$_4$, C(=O)NR$_4$R$_7$, SO$_2$NR$_4$R$_7$, amino, alkylthio, or optionally substituted aryl; xi) haloalkoxy; xii) haloalkyl; xiii) hydroxy; xiv) SO$_2$NR$_4$R$_{21}$; or xv) heterocycloalkyl optionally substituted with 1, 2, or 3 independent C(=O)OR$_4$, C(=O)NR$_4$R$_7$, SO$_2$NR$_4$R$_7$, or CH$_2$C(=O)OR$_4$;

each R$_{27}$ is independently a) H; b) alkyl optionally substituted with 1, 2, or 3 independent hydroxy, halogen, amino, alkylthio, or optionally substituted aryl; c) fluoroalkyl; d) optionally substituted aryl; or e) optionally substituted heteroaryl;

each n is independently 0, 1, 2, 3, or 4; and $Q_1$ and $Q_2$ are each independently CH or N.

2. The compound of claim 1, wherein $R_1$ is

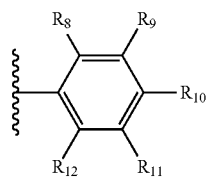

and each $R_8$, $R_9$, $R_{10}$, $R_{11}$, and $R_{12}$ is independently selected from:

a) hydrogen; b) hydroxyalkylamino; c) alkoxy optionally substituted with 1, 2, or 3 independent hydroxy, C(=O)OR$_4$, C(=O)NHNHR$_4$, or C(=O)NR$_4$OH; d) halogen; e) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; f) heteroaryl optionally substituted with 1, 2, or 3 independent:

i) C(=O)OR$_{17}$; or ii) heterocycloalkylcarbonyl optionally substituted with 1, 2, or 3 independent C(=O)OR$_{17}$, C(=O)NR$_4$R$_7$, or SO$_2$NR$_4$R$_7$; or iii) alkyl optionally substituted with 1, 2, or 3 independent OC(=O)NHR$_4$, NHC(=O)NHR$_4$, NHSO$_2$R$_4$, hydroxy, or C(=O)NHR$_4$;

g) alkyl optionally substituted with 1, 2, or 3 heterocycloalkylcarbonyl substituted with C(=O)OR$_4$, C(=O)NR$_4$R$_7$, or SO$_2$NR$_4$R$_7$; h) heterocycloalkylcarbonyl optionally substituted with 1, 2, or 3 independent C(=O)OR$_4$, C(=O)NR$_4$R$_7$, or SO$_2$NR$_4$R$_7$; or i) heterocycloalkylsulfonyl optionally substituted with 1, 2, or 3 independent C(=O)OR$_4$, C(=O)NR$_4$R$_7$, or SO$_2$NR$_4$R$_7$.

3. The compound of claim 2 wherein each $R_8$, $R_9$, $R_{10}$, $R_{11}$, and $R_{12}$ is independently selected from halogen, hydrogen,

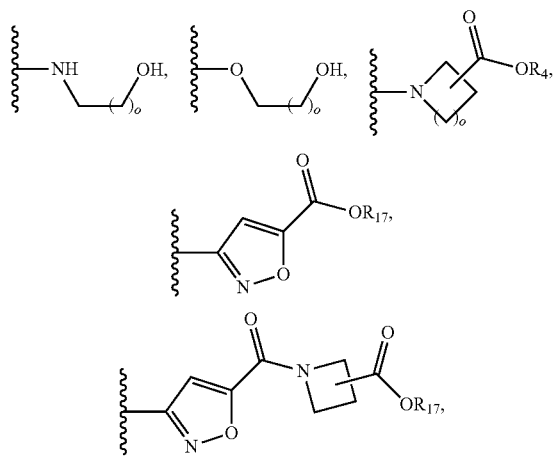

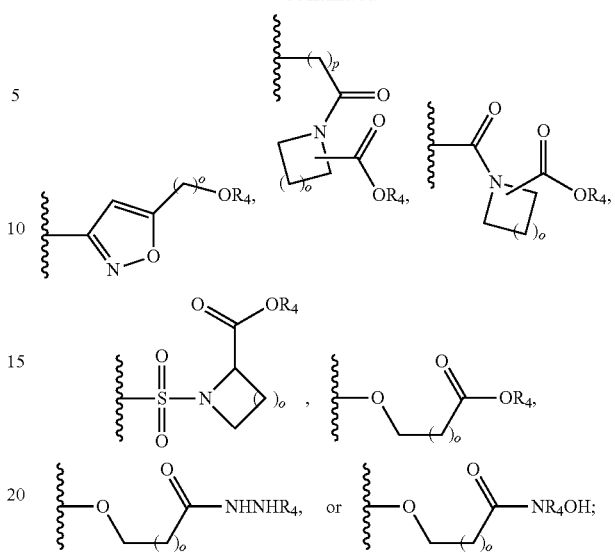

each o is independently 1, 2, 3, or 4; and each p is independently 1, 2, 3, or 4.

4. The compound of claim 3, wherein each $R_8$, $R_9$, $R_{10}$, $R_{11}$, and $R_{12}$ is independently selected from hydrogen,

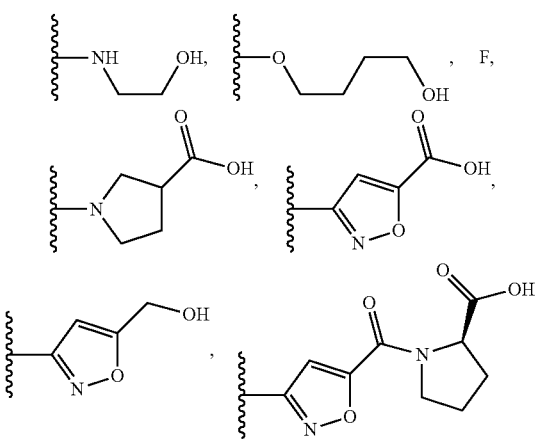

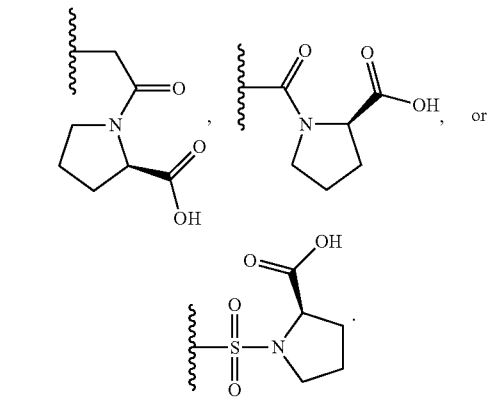

5. The compound of formulae (I) or (IV) in claim 1, wherein X is O and $R_3$ is selected from NHNHR$_4$, NHNHSO$_2$R$_4$, C(=O)NR$_4$OH, or C(=O)OR$_4$.

6. The compound of claim 5, wherein $R_3$ is $NHNH_2$.

7. The compound of claim 6, wherein $R_3$ is $NHNH_2$, $R_1$ is

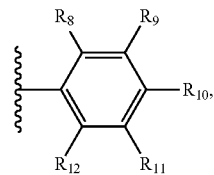

$R_{10}$ is selected from

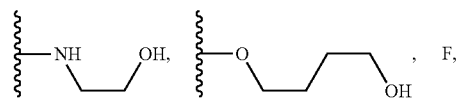

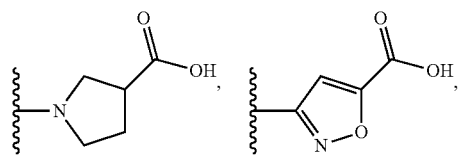

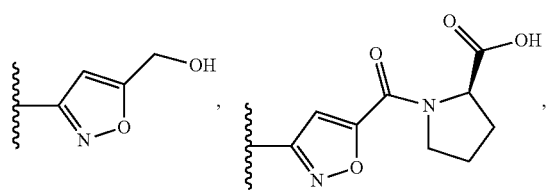

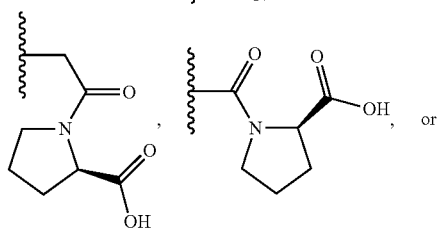

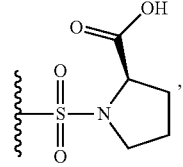

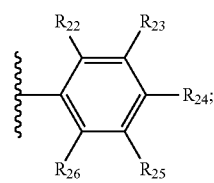

and $R_8$, $R_9$, $R_{11}$, and $R_{12}$ are each H.

8. The compound of claim 1, wherein $R_1$ is $C{\equiv}C{-}R_{13}$ and
  $R_{13}$ is independently selected from:
  a)

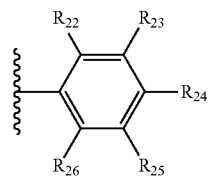

b) heterocycloalkyl optionally substituted with 1, 2, or 3 independent alkyl wherein alkyl is optionally substituted with independent:
  i) $OR_4$;
  ii) $NHC({=}O)R_4$;
  iii) $C({=}O)OR_4$; or
  iv) $C({=}O)NHR_4$;
  c) heteroaryl optionally substituted with 1, 2, or 3 independent 1) heterocycloalkylcarbonyl, 2) $NH_2SO_4$, 3) alkylaminocarbonyl, each optionally substituted with 1, 2, or 3 independent $C({=}O)OR_4$, $C({=}O)NR_4R_7$, or $SO_2NR_4R_7$, or 4) (heterocycloalkyl)alkyl; or
  d) cycloalkyl optionally substituted with 1, 2, or 3 independent $C({=}O)OR_4$, $C({=}O)NR_4R_7$, or $SO_2NR_4R_7$.

9. The compound of claim 8, wherein $R_{13}$ is

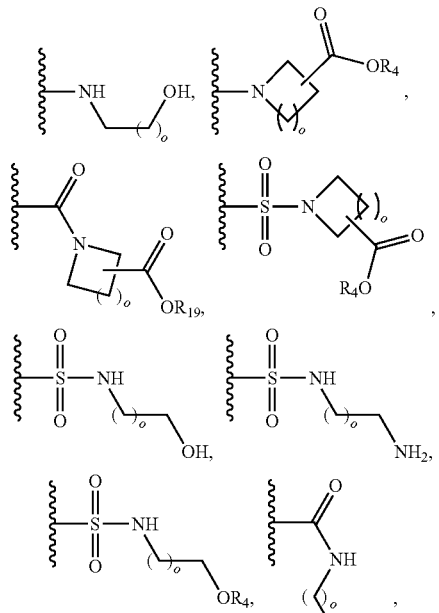

and each $R_{22}$, $R_{23}$, $R_{24}$, $R_{25}$, and $R_{26}$ is independently selected from halogen, hydrogen,

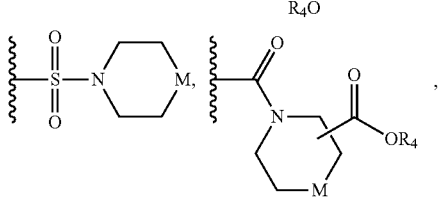

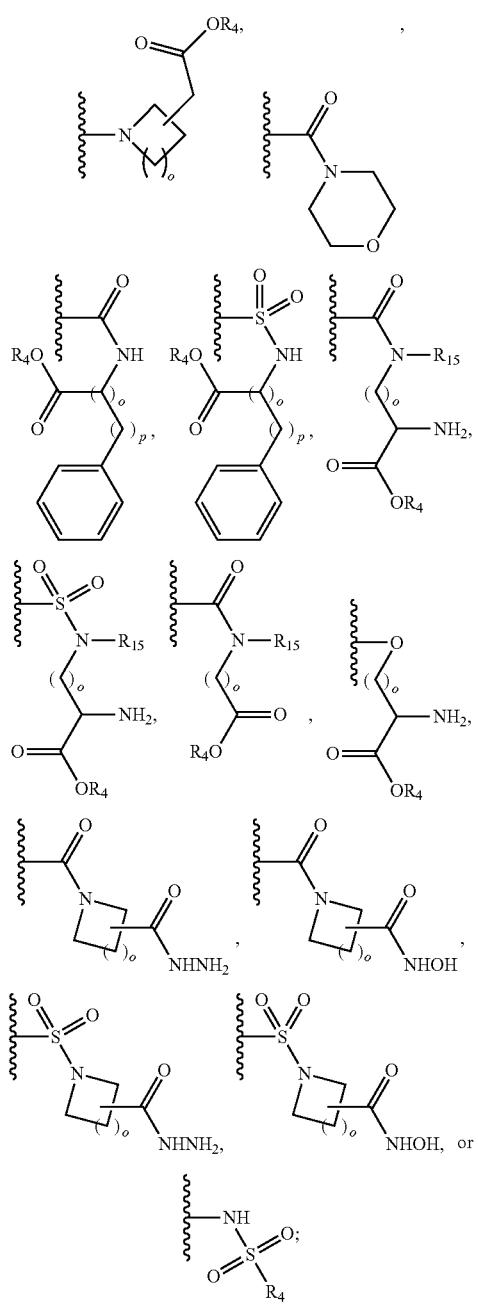
each M is independently O, CH$_2$, or S;
each o is independently 1, 2, 3, or 4; and
each p is independently 1, 2, 3, or 4.
10. The compound of claim 9, wherein each R$_{22}$, R$_{23}$, R$_{24}$, R$_{25}$, and R$_{26}$ is independently selected from hydrogen,
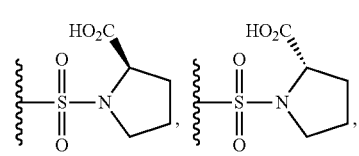
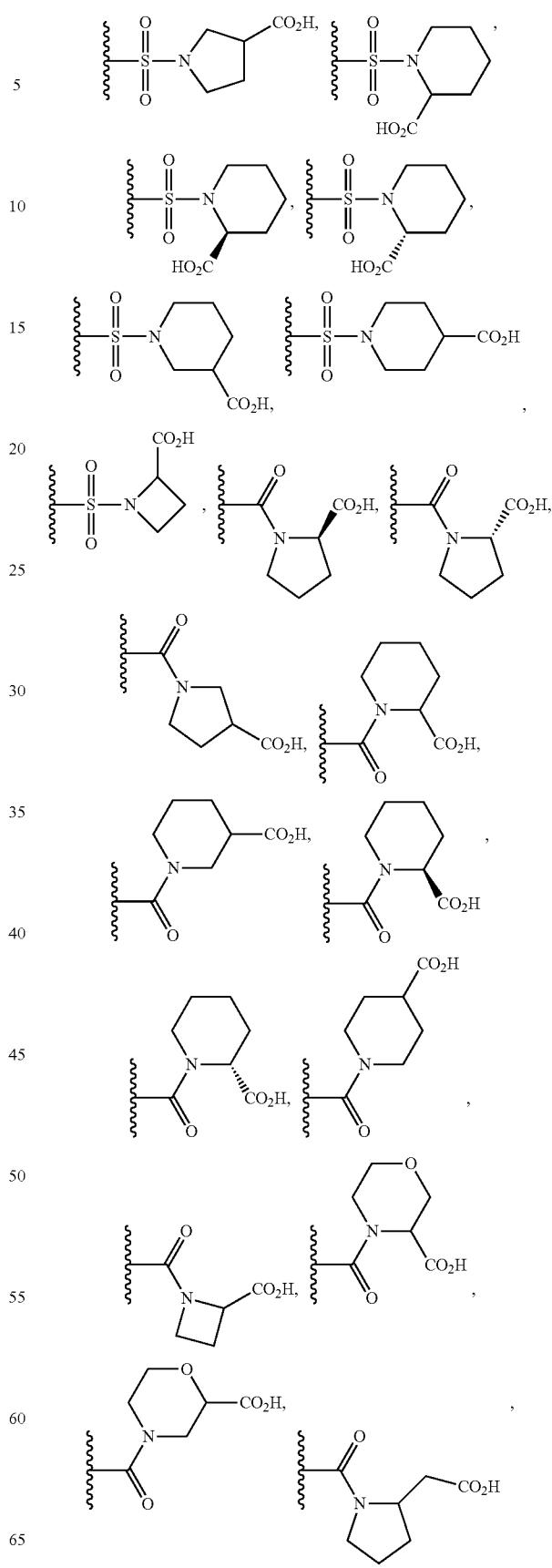

-continued
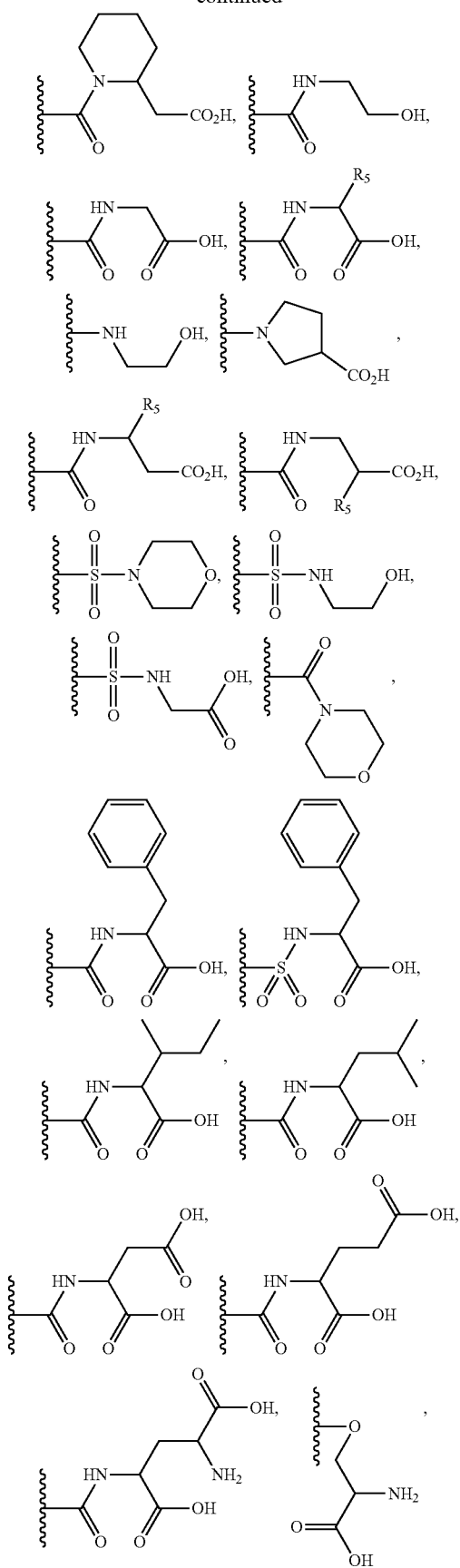
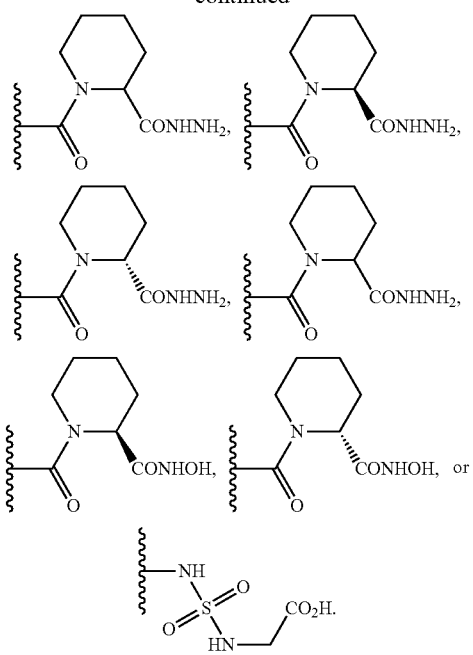
11. The compound of claim 6, wherein $R_3$ is $NHNH_2$, $R_1$ is $C≡C—R_{13}$, $R_{13}$ is
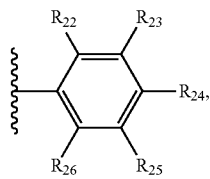
$R_{24}$ is independently selected from hydrogen,
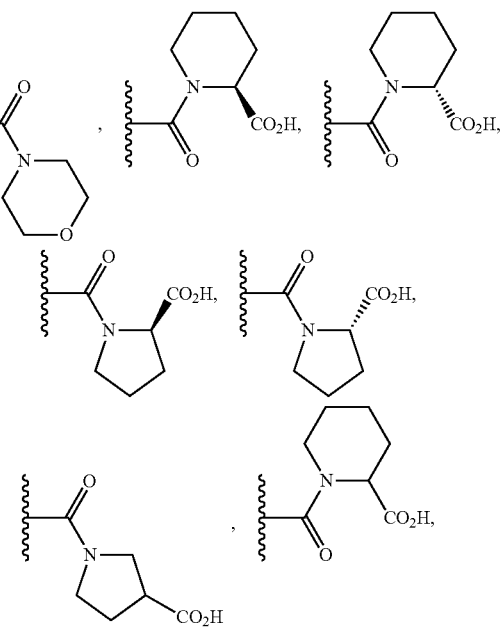

-continued

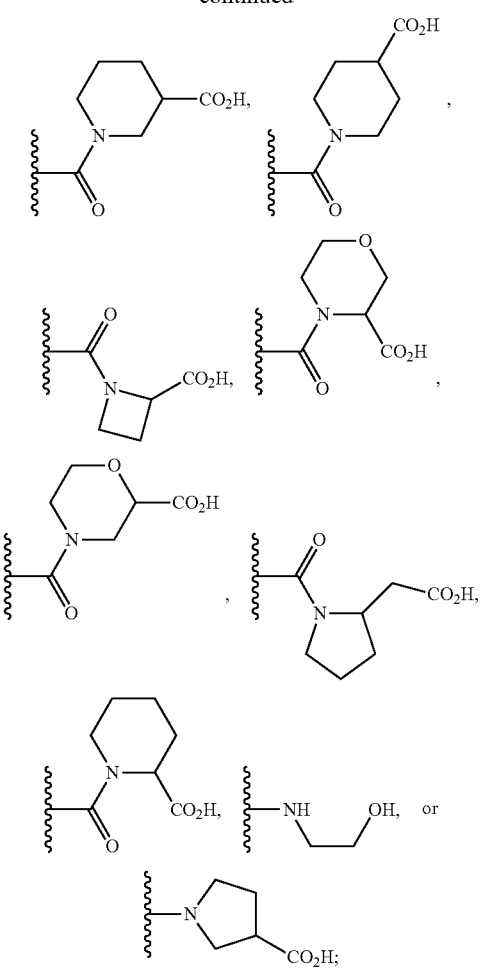

and

R$_{22}$, R$_{23}$, R$_{25}$, and R$_{26}$ are each independently hydrogen or halogen.

12. The compound of formula (I) in claim 1, wherein each R$_7$ is independently C(=O)OR$_4$; NHSO$_2$R$_4$; N(alkyl)SO$_2$R$_4$; NHC(=O)R$_4$; N(alkyl)C(=O)R$_4$; C(=O)NR$_{27}$R$_4$; SO$_2$NR$_{27}$R$_4$; C(=O)NR$_{27}$NHR$_4$; C(=O)NR$_{27}$OR$_4$; or heterocycloalkylcarbonyl optionally substituted with 1, 2, or 3 independent OR$_4$, C(=O)OR$_4$, or NHSO$_2$R$_4$.

13. The compound of claim 12, wherein each R$_7$ is independently

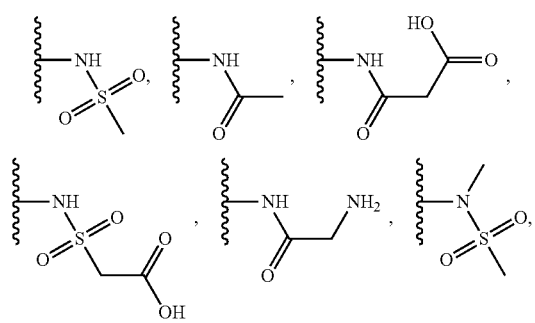

-continued

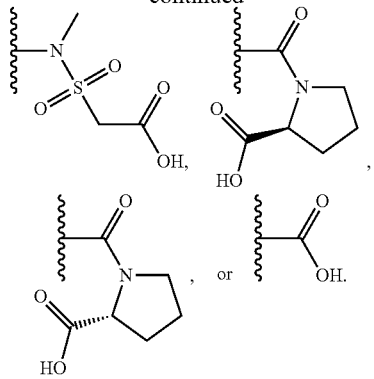

14. The compound of claim 12, wherein R$_1$ is

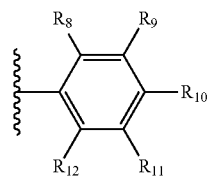

and each R$_8$, R$_9$, R$_{10}$, R$_{11}$, and R$_{12}$ is independently selected from:
a) hydrogen; b) hydroxyalkylamino; c) alkoxy optionally substituted with 1, 2, or 3 independent hydroxy, C(=O)OR$_4$, C(=O)NHNHR$_4$, or C(=O)NR$_4$OH; d) halogen; e) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; f) heteroaryl optionally substituted with 1, 2, or 3 independent:
  i) C(=O)OR$_{17}$; or
  ii) heterocycloalkylcarbonyl optionally substituted with 1, 2, or 3 independent C(=O)OR$_{17}$, C(=O)NR$_4$R$_7$, or SO$_2$NR$_4$R$_7$;
  iii) alkyl optionally substituted with 1, 2, or 3 independent OC(=O)NHR$_4$, NHC(=O)NHR$_4$, NHSO$_2$R$_4$, hydroxy, or C(=O)NHR$_4$;
g) alkyl optionally substituted with 1, 2, or 3 heterocycloalkylcarbonyl substituted with C(=O)OR$_4$, C(=O)NR$_4$R$_7$, or SO$_2$NR$_4$R$_7$; h) heterocycloalkylcarbonyl optionally substituted with 1, 2, or 3 independent C(=O)OR$_4$, C(=O)NR$_4$R$_7$, or SO$_2$NR$_4$R$_7$; or i) heterocycloalkylsulfonyl optionally substituted with 1, 2, or 3 independent C(=O)OR$_4$, C(=O)NR$_4$R$_7$, or SO$_2$NR$_4$R$_7$.

15. The compound of claim 12, wherein R$_1$ is C≡C—R$_{13}$ and
R$_{13}$ is independently selected from:
a)

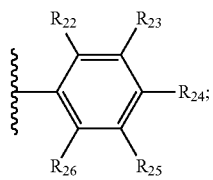

b) heterocycloalkyl optionally substituted with 1, 2, or 3 independent alkyl wherein alkyl is optionally substituted with independent:
  i) $OR_4$;
  ii) $NHC(=O)R_4$;
  iii) $C(=O)OR_4$; or
  iv) $C(=O)NHR_4$;
c) heteroaryl optionally substituted with 1, 2, or 3 independent 1) heterocycloalkylcarbonyl, 2) $NH_2SO_4$, 3) alkylaminocarbonyl, each optionally substituted with 1, 2, or 3 independent $C(=O)OR_4$, $C(=O)NR_4R_7$, or $SO_2NR_4R_7$, or 4) (heterocycloalkyl)alkyl; or
d) cycloalkyl optionally substituted with 1, 2, or 3 independent $C(=O)OR_4$, $C(=O)NR_4R_7$, or $SO_2NR_4R_7$.

16. The compound of formula (III) in claim 1, wherein A is an optionally substituted heterocycle that is preferably a 5-membered ring with 1-4 heteroatoms and $R_6$ is null.

17. A compound which is:
5-(2-(4'-((2-hydroxyethyl)amino)-[1,1'-biphenyl]-4-yl)-1,6-naphthyridin-4-yl)-5-methylimidazolidine-2,4-dione (1);
1-hydroxy-3-(2-(4'-((2-hydroxyethyl)amino)-[1,1'-biphenyl]-4-yl)-1,6-naphthyridin-4-yl)urea (2);
2-(4'4(2-hydroxyethyl)amino)-[1,1'-biphenyl]-4-yl)-1,6-naphthyridine-4-carboxylic acid (3);
2-(4'4(2-hydroxyethyl)amino)-[1,1'-biphenyl]-4-yl)-1,6-naphthyridine-4-carbohydrazide (4);
N-(2-((4'-(4-(hydrazinecarbonyl)-1,6-naphthyridin-2-yl)-[1,1'-biphenyl]-4-yl)oxy)ethyl)isobutyramide (5);
N-(2-((4'-(4-(hydrazinecarbonyl)-1,6-naphthyridin-2-yl)-[1,1'-biphenyl]-4-yl)oxy)ethyl)methanesulfonamide (6);
2-(4'-(5-(hydroxymethyl)isoxazol-3-yl)-[1,1'-biphenyl]-4-yl)-1,6-naphthyridine-4-carbohydrazide (7);
3-(2-(4'-(4-((tetrahydro-2H-pyran-2-yl)oxy)butoxy)-[1,1'-biphenyl]-4-yl)-1,6-naphthyridin-4-yl)imidazolidine-2,4-dione (8);
3-(2-(4'-(4-hydroxybutoxy)-[1,1'-biphenyl]-4-yl)-1,6-naphthyridin-4-yl)imidazolidine-2,4-dione (9);
3-(2-(4'-(4-((tetrahydro-2H-pyran-2-yl)oxy)butoxy)-[1,1'-biphenyl]-4-yl)-1,6-naphthyridin-4-yl)-2-thioxoimidazolidin-4-one (10);
3-(2-(4'-(4-hydroxybutoxy)-[1,1'-biphenyl]-4-yl)-1,6-naphthyridin-4-yl)-2-thioxoimidazolidin-4-one (11);
2-(4'-(3-aminopropoxy)-[1,1'-biphenyl]-4-yl)-1,6-naphthyridine-4-carbohydrazide (13);
N-(3-((4'-(4-(hydrazinecarbonyl)-1,6-naphthyridin-2-yl)-[1,1'-biphenyl]-4-yl)oxy)propyl)methanesulfonamide (14);
N-(3-((4'-(4-(hydrazinecarbonyl)-1,6-naphthyridin-2-yl)-[1,1'-biphenyl]-4-yl)oxy)propyl)acetamide (15);
N'-(2-(4'-((2-hydroxyethyl)amino)-[1,1'-biphenyl]-4-yl)-1,6-naphthyridine-4-carbonyl)methanesulfonohydrazide (17);
1-(2-(4'-fluoro-[1,1'-biphenyl]-4-yl)-1,6-naphthyridin-4-yl)imidazolidin-2-one (19);
1-(2-(4'-fluoro-[1,1'-biphenyl]-4-yl)-1,6-naphthyridin-4-yl)imidazolidine-2,4-dione (20);
5-(2-(4'-fluoro-[1,1'-biphenyl]-4-yl)-1,6-naphthyridin-4-yl)-1,3,4-oxadiazol-2-amine (21);
4'-(4-(hydrazinecarbonyl)-1,6-naphthyridin-2-yl)-N-methyl-[1,1'-biphenyl]-4-sulfonamide (22);
N-(4'-(4-(hydrazinecarbonyl)-1,6-naphthyridin-2-yl)-[1,1'-biphenyl]-4-yl)methanesulfonamide (23);
N-(4'-(4-(hydrazinecarbonyl)-1,6-naphthyridin-2-yl)-[1,1'-biphenyl]-4-yl)acetamide (24);
4'-(4-(hydrazinecarbonyl)-1,6-naphthyridin-2-yl)-N-methyl-[1,1'-biphenyl]-4-carboxamide (25);
1-(4'-(4-(hydrazinecarbonyl)-1,6-naphthyridin-2-yl)-[1,1'-biphenyl]-4-yl)pyrrolidine-3-carboxylic acid (26);
2-(4'-(2-morpholino-2-oxoethyl)-[1,1'-biphenyl]-4-yl)-1,6-naphthyridine-4-carbohydrazide (27);
2-(4'-(2-morpholino-2-oxoethoxy)-[1,1'-biphenyl]-4-yl)-1,6-naphthyridine-4-carbohydrazide (28);
2-(4'-((morpholino sulfonyl)methyl)-[1,1'-biphenyl]-4-yl)-1,6-naphthyridine-4-carbohydrazide (29);
3-(4'-(4-(hydrazinecarbonyl)-1,6-naphthyridin-2-yl)-[1,1'-biphenyl]-4-yl)isoxazole-5-carboxylic acid (30);
(R)-1-(3-(4'-(4-(hydrazinecarbonyl)-1,6-naphthyridin-2-yl)-[1,1'-biphenyl]-4-yl)isoxazole-5-carbonyl)pyrrolidine-2-carboxylic acid (31);
(3-(4'-(4-(hydrazinecarbonyl)-1,6-naphthyridin-2-yl)-[1,1'-biphenyl]-4-yl)isoxazol-5-yl)methyl methylcarbamate (32);
1-((3-(4'-(4-(hydrazinecarbonyl)-1,6-naphthyridin-2-yl)-[1,1'-biphenyl]-4-yl)isoxazol-5-yl)methyl)-3-methylurea (33);
N-((3-(4'-(4-(hydrazinecarbonyl)-1,6-naphthyridin-2-yl)-[1,1'-biphenyl]-4-yl)isoxazol-5-yl)methyl)acetamide (34);
N-((3-(4'-(4-(hydrazinecarbonyl)-1,6-naphthyridin-2-yl)-[1,1'-biphenyl]-4-yl)isoxazol-5-yl)methyl)methanesulfonamide (35);
(R)-1-(3-(4'-(4-(hydroxy(methyl)carbamoyl)-1,6-naphthyridin-2-yl)-[1,1'-biphenyl]-4-yl)isoxazole-5-carbonyl)pyrrolidine-2-carboxylic acid (36);
2-(4'-((2-hydroxyethyl)amino)-[1,1'-biphenyl]-4-yl)-3-methyl-1,6-naphthyridine-4-carbohydrazide (39);
N'-(2-(4'-((2-hydroxyethyl)amino)-[1,1'-biphenyl]-4-yl)-3-methyl-1,6-naphthyridine-4-carbonyl)methanesulfonohydrazide (40);
N-(2-(4'4(2-hydroxyethyl)amino)-[1,1'-biphenyl]-4-yl)-1,6-naphthyridin-4-yl)hydrazinecarboxamide (41);
2-(4'4(2-hydroxyethyl)amino)-[1,1'-biphenyl]-4-yl)-3-methoxy-1,6-naphthyridine-4-carbohydrazide (44);
2-(4'4(2-hydroxyethyl)amino)-[1,1'-biphenyl]-4-yl)-3-methoxy-1,6-naphthyridine-4-carboxylic acid (45);
2-(4'-((2-hydroxyethyl)amino)-[1,1'-biphenyl]-4-yl)-3-methyl-1,6-naphthyridine-4-carboxylic acid (46);
N-hydroxy-2-(4'-((2-hydroxyethyl)amino)-[1,1'-biphenyl]-4-yl)-N-methyl-1,6-naphthyridine-4-carboxamide (49);
2-(4'-fluoro-[1,1'-biphenyl]-4-yl)-4-(hydrazinecarbonyl)-1,6-naphthyridine 6-oxide (50);
4-(hydrazinecarbonyl)-2-(4'-((2-hydroxyethyl)amino)-[1,1'-biphenyl]-4-yl)-1,6-naphthyridine 6-oxide (51);
2-(4'-(4-hydroxybutoxy)-[1,1'-biphenyl]-4-yl)-1,6-naphthyridine-4-carbohydrazide (53);
2-(4'-cyano-[1,1'-biphenyl]-4-yl)-1,6-naphthyridine-4-carbohydrazide (54);
2-(5-(4-((2-hydroxyethyl)amino)phenyl)pyridin-2-yl)-1,6-naphthyridine-4-carbohydrazide (55);
2-(6-(4-((2-hydroxyethyl)amino)phenyl)pyridin-3-yl)-1,6-naphthyridine-4-carbohydrazide (56);
2-(4-(pyridin-3-yl)phenyl)-1,6-naphthyridine-4-carbohydrazide (57);
2-(4-(pyridin-2-yl)phenyl)-1,6-naphthyridine-4-carbohydrazide (58);
2-(4-(pyridin-4-yl)phenyl)-1,6-naphthyridine-4-carbohydrazide (59);

2-(4-(1H-pyrazol-3-yl)phenyl)-1,6-naphthyridine-4-carbohydrazide (60);
2-(4-(1H-pyrazol-4-yl)phenyl)-1,6-naphthyridine-4-carbohydrazide (61);
2-(4-(oxazol-2-yl)phenyl)-1,6-naphthyridine-4-carbohydrazide (62);
2-(4-(oxazol-5-yl)phenyl)-1,6-naphthyridine-4-carbohydrazide (63);
2-([1,1'-biphenyl]-4-yl)-1,6-naphthyridine-4-carbohydrazide (64);
2-(4'-fluoro-[1,1'-biphenyl]-4-yl)-1,6-naphthyridine-4-carbohydrazide (65);
2-(4'-(morpholinomethyl)-[1,1'-biphenyl]-4-yl)-1,6-naphthyridine-4-carbohydrazide (66);
2-(4-(5-(4-hydroxybutoxy)pyridin-2-yl)phenyl)-1,6-naphthyridine-4-carbohydrazide (67);
2-(2'-hydroxy-[1,1'-biphenyl]-4-yl)-1,6-naphthyridine-4-carbohydrazide (68);
2-(4-(thiazol-2-yl)phenyl)-1,6-naphthyridine-4-carbohydrazide (69);
3-(2-(4'-fluoro-[1,1'-biphenyl]-4-yl)-1,6-naphthyridin-4-yl)imidazolidine-2,4-dione (70);
3-(2-(4'-fluoro-[1,1'-biphenyl]-4-yl)-1,6-naphthyridin-4-yl)-2-thioxoimidazolidin-4-one (71);
2-(4'-(methylsulfonyl)-[1,1'-biphenyl]-4-yl)-1,6-naphthyridine-4-carbohydrazide (72);
4'-(4-(hydrazinecarbonyl)-1,6-naphthyridin-2-yl)-N-(2-hydroxyethyl)-[1,1'-biphenyl]-4-sulfonamide (73);
4'-(4-(hydrazinecarbonyl)-1,6-naphthyridin-2-yl)-N-(3-hydroxypropyl)-[1,1'-biphenyl]-4-sulfonamide (74);
3-(2-(4-(5-(4-hydroxybutoxy)pyridin-2-yl)phenyl)-1,6-naphthyridin-4-yl)-2-thioxoimidazolidin-4-one (75);
4-((4'-(4-(hydrazinecarbonyl)-1,6-naphthyridin-2-yl)-[1,1'-biphenyl]-4-yl)oxy)butanoic acid (76);
2-(4'-(4-hydrazinyl-4-oxobutoxy)-[1,1'-biphenyl]-4-yl)-1,6-naphthyridine-4-carbohydrazide (77);
4-((4'-(4-(hydrazinecarbonyl)-1,6-naphthyridin-2-yl)-[1,1'-biphenyl]-4-yl)oxy)-N-hydroxybutanamide (78);
4-((4'-(4-(2,5-dioxoimidazolidin-1-yl)-1,6-naphthyridin-2-yl)-[1,1'-biphenyl]-4-yl)oxy)-N-hydroxybutanamide (79);
4-((4'-(4-(2,5-dioxoimidazolidin-1-yl)-1,6-naphthyridin-2-yl)-[1,1'-biphenyl]-4-yl)oxy)butanoic acid (80);
ethyl 4-((4'-(4-(2,5-dioxoimidazolidin-1-yl)-1,6-naphthyridin-2-yl)-[1,1'-biphenyl]-4-yl)oxy)butanoate (81);
N-hydroxy-4-((4'-(4-(5-oxo-2-thioxoimidazolidin-1-yl)-1,6-naphthyridin-2-yl)-[1,1'-biphenyl]-4-yl)oxy)butanamide (82);
4-((4'-(4-(5-oxo-2-thioxoimidazolidin-1-yl)-1,6-naphthyridin-2-yl)-[1,1'-biphenyl]-4-yl)oxy)butanoic acid (83);
ethyl 4-((4'-(4-(5-oxo-2-thioxoimidazolidin-1-yl)-1,6-naphthyridin-2-yl)-[1,1'-biphenyl]-4-yl)oxy)butanoate (84);
2-(4'-(2-aminoethoxy)-[1,1'-biphenyl]-4-yl)-1,6-naphthyridine-4-carbohydrazide (85);
N-(2-((4'-(4-(hydrazinecarbonyl)-1,6-naphthyridin-2-yl)-[1,1'-biphenyl]-4-yl)oxy)ethyl)acetamide (86);
(R)-1-(4'-(4-(hydrazinecarbonyl)-1,6-naphthyridin-2-yl)-[1,1'-biphenyl]-4-yl)pyrrolidine-2-carboxylic acid (87);
(S)-1-(4'-(4-(hydrazinecarbonyl)-1,6-naphthyridin-2-yl)-[1,1'-biphenyl]-4-yl)pyrrolidine-2-carboxylic acid (88);
1-(4'-(4-(hydrazinecarbonyl)-1,6-naphthyridin-2-yl)-[1,1'-biphenyl]-4-yl)piperidine-3-carboxylic acid (89);
1-(4'-(4-(hydrazinecarbonyl)-1,6-naphthyridin-2-yl)-[1,1'-biphenyl]-4-yl)piperidine-4-carboxylic acid (90);
N-(3-((4'-(4-(hydrazinecarbonyl)-1,6-naphthyridin-2-yl)-[1,1'-biphenyl]-4-yl)oxy)propyl)propionamide (91);
N-(3-((4'-(4-(hydrazinecarbonyl)-1,6-naphthyridin-2-yl)-[1,1'-biphenyl]-4-yl)oxy)propyl)isobutyramide (92);
2,2,2-trifluoro-N-(3-((4'-(4-(hydrazinecarbonyl)-1,6-naphthyridin-2-yl)-[1,1'-biphenyl]-4-yl)oxy)propyl)acetamide (93);
N-(3-((4'-(4-(hydrazinecarbonyl)-1,6-naphthyridin-2-yl)-[1,1'-biphenyl]-4-yl)oxy)propyl)ethanesulfonamide (94);
N-(3-((4'-(4-(hydrazinecarbonyl)-1,6-naphthyridin-2-yl)-[1,1'-biphenyl]-4-yl)oxy)propyl)propane-2-sulfonamide (95);
1,1,1-trifluoro-N-(3-((4'-(4-(hydrazinecarbonyl)-1,6-naphthyridin-2-yl)-[1,1'-biphenyl]-4-yl)oxy)propyl)methanesulfonamide (96);
N-(2-((4'-(4-(hydrazinecarbonyl)-1,6-naphthyridin-2-yl)-[1,1'-biphenyl]-4-yl)oxy)ethyl)propionamide (97);
2,2,2-trifluoro-N-(2-((4'-(4-(hydrazinecarbonyl)-1,6-naphthyridin-2-yl)-[1,1'-biphenyl]-4-yl)oxy)ethyl)acetamide (98);
N-(2-((4'-(4-(hydrazinecarbonyl)-1,6-naphthyridin-2-yl)-[1,1'-biphenyl]-4-yl)oxy)ethyl)ethanesulfonamide (99);
N-(2-((4'-(4-(hydrazinecarbonyl)-1,6-naphthyridin-2-yl)-[1,1'-biphenyl]-4-yl)oxy)ethyl)propane-2-sulfonamide (100);
1,1,1-trifluoro-N-(2-((4'-(4-(hydrazinecarbonyl)-1,6-naphthyridin-2-yl)-[1,1'-biphenyl]-4-yl)oxy)ethyl)methanesulfonamide (101);
2-(3',4'-dihydroxy-[1,1'-biphenyl]-4-yl)-1,6-naphthyridine-4-carbohydrazide (102);
(R)-1-(2-(4'-(4-(hydrazinecarbonyl)-1,6-naphthyridin-2-yl)-[1,1'-biphenyl]-4-yl)acetyl)pyrrolidine-2-carboxylic acid (103);
(R)-1-(2-((4'-(4-(hydrazinecarbonyl)-1,6-naphthyridin-2-yl)-[1,1'-biphenyl]-4-yl)oxy)acetyl)pyrrolidine-2-carboxylic acid (104);
(R)-1-(((4'-(4-(hydrazinecarbonyl)-1,6-naphthyridin-2-yl)-[1,1'-biphenyl]-4-yl)methyl)sulfonyl)pyrrolidine-2-carboxylic acid (105);
2-(4'-(morpholine-4-carbonyl)-[1,1'-biphenyl]-4-yl)-1,6-naphthyridine-4-carbohydrazide (106);
(R)-1-(4'-(4-(hydrazinecarbonyl)-1,6-naphthyridin-2-yl)-[1,1'-biphenyl]-4-carbonyl)pyrrolidine-2-carboxylic acid (107);
1-(4'-(4-(hydrazinecarbonyl)-1,6-naphthyridin-2-yl)-[1,1'-biphenyl]-4-carbonyl)piperidine-3-carboxylic acid (108);
2-(4'-(5-(morpholine-4-carbonyl)isoxazol-3-yl)-[1,1'-biphenyl]-4-yl)-1,6-naphthyridine-4-carbohydrazide (109);
2-(4'-(morpholinosulfonyl)-[1,1'-biphenyl]-4-yl)-1,6-naphthyridine-4-carbohydrazide (110);
(R)-1-((4'-(4-(hydrazinecarbonyl)-1,6-naphthyridin-2-yl)-[1,1'-biphenyl]-4-yl)sulfonyl)pyrrolidine-2-carboxylic acid (111);
1-((4'-(4-(hydrazinecarbonyl)-1,6-naphthyridin-2-yl)-[1,1'-biphenyl]-4-yl)sulfonyl)piperidine-3-carboxylic acid (112);
3-(4'-(4-(hydrazinecarbonyl)-1,6-naphthyridin-2-yl)-[1,1'-biphenyl]-4-yl)-N-methylisoxazole-5-carboxamide (113);
1-(3-(4'-(4-(hydrazinecarbonyl)-1,6-naphthyridin-2-yl)-[1,1'-biphenyl]-4-yl)isoxazole-5-carbonyl)piperidine-3-carboxylic acid (114);

1-(3-(4'-(4-(hydrazinecarbonyl)-1,6-naphthyridin-2-yl)-[1,1'-biphenyl]-4-yl)isoxazole-5-carbonyl)piperidine-2-carboxylic acid (115);

N-(4-((4-(4-(hydrazinecarbonyl)-1,6-naphthyridin-2-yl)phenyl)ethynyl)phenyl)acetamide (116);

N-(4-((4-(4-(hydrazinecarbonyl)-1,6-naphthyridin-2-yl)phenyl)ethynyl)phenyl)methanesulfonamide (117);

2-(4-((4-(morpholine-4-carbonyl)phenyl)ethynyl)phenyl)-1,6-naphthyridine-4-carbohydrazide (118);

(R)-1-((4-((4-(4-(hydrazinecarbonyl)-1,6-naphthyridin-2-yl)phenyl)ethynyl)phenyl)sulfonyl)pyrrolidine-2-carboxylic acid (119);

2-(4-((1-(2-hydroxyethyl)-2-oxo-1,2-dihydropyridin-4-yl)ethynyl)phenyl)-1,6-naphthyridine-4-carbohydrazide (120);

N-(2-(4-((4-(4-(hydrazinecarbonyl)-1,6-naphthyridin-2-yl)phenyl)ethynyl)-2-oxopyridin-1(2H)-yl)ethyl)acetamide (121);

1-(3-fluoro-4-((4-(4-(hydrazinecarbonyl)-1,6-naphthyridin-2-yl)phenyl)ethynyl)benzoyl)piperidine-2-carboxylic acid (122);

1-(4-((2-fluoro-4-(4-(hydrazinecarbonyl)-1,6-naphthyridin-2-yl)phenyl)ethynyl)benzoyl)piperidine-2-carboxylic acid (123);

2-(4-((4-(morpholinomethyl)phenyl)ethynyl)phenyl)-1,6-naphthyridine-4-carbohydrazide (124);

2-(4-((4-((2-hydroxyethyl)amino)phenyl)ethynyl)phenyl)-1,6-naphthyridine-4-carbohydrazide (125);

2-(4-(pyridin-3-ylethynyl)phenyl)-1,6-naphthyridine-4-carbohydrazide (126);

3-(2-(4-((4-(morpholinomethyl)phenyl)ethynyl)phenyl)-1,6-naphthyridin-4-yl)-2-thioxoimidazolidin-4-one (127);

4-((4-(4-(hydrazinecarbonyl)-1,6-naphthyridin-2-yl)phenyl)ethynyl)-N-methylbenzamide (128);

4-((4-(4-(hydrazinecarbonyl)-1,6-naphthyridin-2-yl)phenyl)ethynyl)-N-methylbenzenesulfonamide (129);

(S)-1-(4-((4-(4-(hydrazinecarbonyl)-1,6-naphthyridin-2-yl)phenyl)ethynyl)benzoyl)pyrrolidine-2-carboxylic acid (130);

(R)-1-(4-((4-(4-(hydrazinecarbonyl)-1,6-naphthyridin-2-yl)phenyl)ethynyl)benzoyl)pyrrolidine-2-carboxylic acid (131);

1-(4-((4-(4-(hydrazinecarbonyl)-1,6-naphthyridin-2-yl)phenyl)ethynyl)benzoyl)piperidine-3-carboxylic acid (132);

(−)-1-(4-((4-(4-(hydrazinecarbonyl)-1,6-naphthyridin-2-yl)phenyl)ethynyl)benzoyl)piperidine-3-carboxylic acid (133);

(+)-1-(4-((4-(4-(hydrazinecarbonyl)-1,6-naphthyridin-2-yl)phenyl)ethynyl)benzoyl)piperidine-3-carboxylic acid (134);

1-(4-((4-(4-(hydrazinecarbonyl)-1,6-naphthyridin-2-yl)phenyl)ethynyl)benzoyl)pyrrolidine-3-carboxylic acid (135);

1-(4-((4-(4-(hydrazinecarbonyl)-1,6-naphthyridin-2-yl)phenyl)ethynyl)benzoyl)piperidine-4-carboxylic acid (136);

2-(4-((4-(4-methylpiperazine-1-carbonyl)phenyl)ethynyl)phenyl)-1,6-naphthyridine-4-carbohydrazide (137);

4-((4-(4-(hydrazinecarbonyl)-1,6-naphthyridin-2-yl)phenyl)ethynyl)-N-(2-hydroxyethyl)benzamide (138);

4-((4-(4-(hydrazinecarbonyl)-1,6-naphthyridin-2-yl)phenyl)ethynyl)-N-(3-hydroxypropyl)benzamide (139);

2-(4-((4-(4-(hydrazinecarbonyl)-1,6-naphthyridin-2-yl)phenyl)ethynyl)benzamido)acetic acid (140);

(S)-1-((4-((4-(4-(hydrazinecarbonyl)-1,6-naphthyridin-2-yl)phenyl)ethynyl)phenyl)sulfonyl)pyrrolidine-2-carboxylic acid (141);

1-((4-((4-(4-(hydrazinecarbonyl)-1,6-naphthyridin-2-yl)phenyl)ethynyl)phenyl)sulfonyl)piperidine-3-carboxylic acid (142);

1-((4-((4-(4-(hydrazinecarbonyl)-1,6-naphthyridin-2-yl)phenyl)ethynyl)phenyl)sulfonyl)pyrrolidine-3-carboxylic acid (143);

1-((4-((4-(4-(hydrazinecarbonyl)-1,6-naphthyridin-2-yl)phenyl)ethynyl)phenyl)sulfonyl)piperidine-4-carboxylic acid (144);

2-(4-((4-(morpholinosulfonyl)phenyl)ethynyl)phenyl)-1,6-naphthyridine-4-carbohydrazide (145);

2-(4-((4-((4-methylpiperazin-1-yl) sulfonyl)phenyl)ethynyl)phenyl)-1,6-naphthyridine-4-carbohydrazide (146);

4-((4-(4-(hydrazinecarbonyl)-1,6-naphthyridin-2-yl)phenyl)ethynyl)-N-(2-hydroxyethyl)benzenesulfonamide (147);

4-((4-(4-(hydrazinecarbonyl)-1,6-naphthyridin-2-yl)phenyl)ethynyl)-N-(3-hydroxypropyl)benzenesulfonamide (148);

2-(4-((4-(4-(hydrazinecarbonyl)-1,6-naphthyridin-2-yl)phenyl)ethynyl)phenylsulfonamido)acetic acid (149);

N-(2-aminoethyl)-4-((4-(4-(hydrazinecarbonyl)-1,6-naphthyridin-2-yl)phenyl)ethynyl)benzamide (150);

N-(2-aminoethyl)-4-((4-(4-(hydrazinecarbonyl)-1,6-naphthyridin-2-yl)phenyl)ethynyl)benzenesulfonamide (151);

(R)-1-((4-((4-(4-(5-oxo-2-thioxoimidazolidin-1-yl)-1,6-naphthyridin-2-yl)phenyl)ethynyl)phenyl)sulfonyl)pyrrolidine-2-carboxylic acid (152);

(R)-1-((4-((4-(4-(2,5-dioxoimidazolidin-1-yl)-1,6-naphthyridin-2-yl)phenyl)ethynyl)phenyl)sulfonyl)pyrrolidine-2-carboxylic acid (153);

1-(4-((4-(4-(hydrazinecarbonyl)-1,6-naphthyridin-2-l)phenyl)ethynyl)benzoyl)azetidine-2-carboxylic acid (154);

1-(4-((4-(4-(hydrazinecarbonyl)-1,6-naphthyridin-2-yl)phenyl)ethynyl)benzoyl)piperidine-2-carboxylic acid (155);

(−)-1-(4-((4-(4-(hydrazinecarbonyl)-1,6-naphthyridin-2-yl)phenyl)ethynyl)benzoyl)piperidine-2-carboxylic acid (156);

(+)-1-(4-((4-(4-(hydrazinecarbonyl)-1,6-naphthyridin-2-yl)phenyl)ethynyl)benzoyl)piperidine-2-carboxylic acid (157);

1-((4-((4-(4-(hydrazinecarbonyl)-1,6-naphthyridin-2-yl)phenyl)ethynyl)phenyl)sulfonyl)azetidine-2-carboxylic acid (158);

1-((4-((4-(4-(hydrazinecarbonyl)-1,6-naphthyridin-2-yl)phenyl)ethynyl)phenyl)sulfonyl)piperidine-2-carboxylic acid (159);

4-(4-((4-(4-(hydrazinecarbonyl)-1,6-naphthyridin-2-yl)phenyl)ethynyl)benzoyl)morpholine-3-carboxylic acid (160);

4-(4-((4-(4-(hydrazinecarbonyl)-1,6-naphthyridin-2-yl)phenyl)ethynyl)benzoyl)morpholine-2-carboxylic acid (161);

2-(4-((4-(4-(hydrazinecarbonyl)-1,6-naphthyridin-2-yl)phenyl)ethynyl)-2-oxopyridin-1(2H)-yl)acetic acid (162);

2-(4-((4-(4-(hydrazinecarbonyl)-1,6-naphthyridin-2-yl)phenyl)ethynyl)-2-oxopyridin-1(2H)-yl)-N-methylacetamide (163);

1-(5-((4-(4-(hydrazinecarbonyl)-1,6-naphthyridin-2-yl)phenyl)ethynyl)thiophene-2-carbonyl)piperidine-3-carboxylic acid (164);

1-(5-((4-(4-(hydrazinecarbonyl)-1,6-naphthyridin-2-yl)phenyl)ethynyl)thiophene-2-carbonyl)piperidine-2-carboxylic acid (165);

1-(5-((4-(4-(hydrazinecarbonyl)-1,6-naphthyridin-2-yl)phenyl)ethynyl)furan-2-carbonyl)piperidine-2-carboxylic acid (166);

1-(5-((4-(4-(hydrazinecarbonyl)-1,6-naphthyridin-2-yl)phenyl)ethynyl)furan-2-carbonyl)piperidine-3-carboxylic acid (167);

1-(5-((4-(4-(hydrazinecarbonyl)-1,6-naphthyridin-2-yl)phenyl)ethynyl)picolinoyl)piperidine -2-carboxylic acid (168);

1-(2-fluoro -4-((4-(4-(hydrazinecarbonyl)-1,6-naphthyridin-2-yl)phenyl)ethynyl)benzoyl)piperidine-2-carboxylic acid (169);

2-(4-((4-(4-(hydrazinecarbonyl)-1,6-naphthyridin-2-yl)phenyl)ethynyl)benzamido)propanoic acid (170);

2-(4-((4-(4-(hydrazinecarbonyl)-1,6-naphthyridin-2-yl)phenyl)ethynyl)benzamido)-3-methylbutanoic acid (171);

2-(4-((4-(4-(hydrazinecarbonyl)-1,6-naphthyridin-2-yl)phenyl)ethynyl)benzamido)-3-methylpentanoic acid (172);

2-(4-((4-(4-(hydrazinecarbonyl)-1,6-naphthyridin-2-yl)phenyl)ethynyl)benzamido)-4-methylpentanoic acid (173);

2-(4-((4-(4-(hydrazinecarbonyl)-1,6-naphthyridin-2-yl)phenyl)ethynyl)benzamido)succinic acid (174);

2-(4-((4-(4-(hydrazinecarbonyl)-1,6-naphthyridin-2-yl)phenyl)ethynyl)benzamido)pentanedioic acid (175);

2-(4-((4-(4-(hydrazinecarbonyl)-1,6-naphthyridin-2-yl)phenyl)ethynyl)benzamido)-3-hydroxypropanoic acid (176);

2-(4-((4-(4-(hydrazinecarbonyl)-1,6-naphthyridin-2-yl)phenyl)ethynyl)benzamido)-3-hydroxybutanoic acid (177);

2-(4-((4-(4-(hydrazinecarbonyl)-1,6-naphthyridin-2-yl)phenyl)ethynyl)benzamido)-4-(methylthio)butanoic acid (178);

2-(4-((4-(4-(hydrazinecarbonyl)-1,6-naphthyridin-2-yl)phenyl)ethynyl)benzamido)-3-phenylpropanoic acid (179);

2-(4-((4-(4-(hydrazinecarbonyl)-1,6-naphthyridin-2-yl)phenyl)ethynyl)benzamido)-3-(4-hydroxyphenyl)propanoic acid (180);

4-(4-((4-(4-(hydrazinecarbonyl)-1,6-naphthyridin-2-yl)phenyl)ethynyl)benzoyl)thiomorpholine-3-carboxylic acid (181);

2-(4-((4-(4-(hydrazinecarbonyl)-1,6-naphthyridin-2-yl)phenyl)ethynyl)benzamido)-2-methylpropanoic acid (182);

N-(4-((4-(4-(hydrazinecarbonyl)-1,6-naphthyridin-2-yl)phenyl)ethynyl)phenyl)ethanesulfonamide (183);

N-(4-((4-(4-(hydrazinecarbonyl)-1,6-naphthyridin-2-yl)phenyl)ethynyl)phenyl)propane-2-sulfonamide (184);

1,1,1-trifluoro-N-(4-((4-(4-(hydrazinecarbonyl)-1,6-naphthyridin-2-yl)phenyl)ethynyl)phenyl)methanesulfonamide (185);

2-(N-(4-((4-(4-(hydrazinecarbonyl)-1,6-naphthyridin-2-yl)phenyl)ethynyl)phenyl)sulfamoyl)acetic acid (186);

2-(1-(4-((4-(4-(hydrazinecarbonyl)-1,6-naphthyridin-2-yl)phenyl)ethynyl)benzoyl)pyrrolidin-2-yl)acetic acid (187);

2-(1-(4-((4-(4-(hydrazinecarbonyl)-1,6-naphthyridin-2-yl)phenyl)ethynyl)benzoyl)piperidin-2-yl)acetic acid (188);

2-(4-((4-(4-(hydrazinecarbonyl)-1,6-naphthyridin-2-yl)phenyl)ethynyl)-N-methylbenzamido)acetic acid (189);

2-(4-((4-(4-(hydrazinecarbonyl)-1,6-naphthyridin-2-yl)phenyl)ethynyl)-N-methylbenzamido)propanoic acid (190);

3-(4-((4-(4-(hydrazinecarbonyl)-1,6-naphthyridin-2-yl)phenyl)ethynyl)benzamido)propanoic acid (191);

3-(4-((4-(4-(hydrazinecarbonyl)-1,6-naphthyridin-2-yl)phenyl)ethynyl)-N-methylbenzamido)propanoic acid (192);

3-(4-((4-(4-(hydrazinecarbonyl)-1,6-naphthyridin-2-yl)phenyl)ethynyl)benzamido)-2-methylpropanoic acid (193);

3-(4-((4-(4-(hydrazinecarbonyl)-1,6-naphthyridin-2-yl)phenyl)ethynyl)benzamido)butanoic acid (194);

3-(4-((4-(4-(hydrazinecarbonyl)-1,6-naphthyridin-2-yl)phenyl)ethynyl)-N-methylbenzamido)-2-methylpropanoic acid (195);

3-(4-((4-(4-(hydrazinecarbonyl)-1,6-naphthyridin-2-yl)phenyl)ethynyl)-N -methylbenzamido)butanoic acid (196);

3-(4-((4-(4-(hydrazinecarbonyl)-1,6-naphthyridin-2-yl)phenyl)ethynyl)benzamido)-2-phenylpropanoic acid (197);

3-(4-((4-(4-(hydrazinecarbonyl)-1,6-naphthyridin-2-yl)phenyl)ethynyl)benzamido)-3-phenylpropanoic acid (198);

5-(4-((4-(4-(hydrazinecarbonyl)-1,6-naphthyridin-2-yl)phenyl)ethynyl)benzamido)-2-hydroxybenzoic acid (199);

3-(4-((4-(4-(hydrazinecarbonyl)-1,6-naphthyridin-2-yl)phenyl)ethynyl)benzamido)benzoic acid (200);

2-(4-((4-(4-(hydrazinecarbonyl)-1,6-naphthyridin-2-yl)phenyl)ethynyl)benzamido)malonic acid (201); or (S)-1-(3-chloro-4-((4-(4-(hydrazinecarbonyl)-1,6-naphthyridin-2-yl)phenyl)ethynyl)benzoyl)piperidine-2-carboxylic acid (202);

2-[4-(2-{4-[4-(hydrazinecarbonyl)-1,6-naphthyridin-2-yl]phenyl}ethynyl)benzamido]benzoic acid (203);

1-[4-(2-{4-[4-(hydrazinecarbonyl)-1,6-naphthyridin-2-yl]phenyl}ethynyl)-3-methoxybenzoyl]piperidine-2-carboxylic acid (204);

1-[4-(2-{4-[4-(hydrazinecarbonyl)-1,6-naphthyridin-2-yl]phenyl}ethynyl)-3-hydroxybenzoyl]piperidine-2-carboxylic acid (205);

1-[4-(2-{4-[4-(hydrazinecarbonyl)-1,6-naphthyridin-2-yl]phenyl}ethynyl)-3-(trifluoromethyl)benzoyl]piperidine-2-carboxylic acid (206);

1-[4-(2-{4-[4-(hydrazinecarbonyl)-1,6-naphthyridin-2-yl]phenyl}ethynyl)benzoyl]-4-hydroxypiperidine-3-carboxylic acid (207);

(2R)-1-[3-fluoro-4-(2-{4-[4-(hydrazinecarbonyl)-1,6-naphthyridin-2-yl]phenyl}ethynyl)benzoyl]piperidine-2-carboxylic acid (208);

(2S)-1-[3-fluoro-4-(2-{4-[4-(hydrazinecarbonyl)-1,6-naphthyridin-2-yl]phenyl}ethynyl)benzoyl]piperidine-2-carboxylic acid (209);

1-[2,5-difluoro-4-(2-{4-[4-(hydrazinecarbonyl)-1,6-naphthyridin-2-yl]phenyl}ethynyl)benzoyl]piperidine-2-carboxylic acid (210);

2-(4-{2-[4-(2-oxo-1,3-oxazolidin-5-yl)phenyl]ethynyl}phenyl)-1,6-naphthyridine-4-carbohydrazide (211);

1-[3-chloro-4-(2-{4-[4-(hydrazinecarbonyl)-1,6-naphthyridin-2-yl]phenyl}ethynyl)benzoyl]piperidine-2-carboxylic acid (212);

2-{1-[4-(2-{4-[4-(hydrazinecarbonyl)-1,6-naphthyridin-2-yl]phenyl}ethynyl)phenyl]-N-methylformamido}-3-phenylprop anoic acid (213);

2-{[3-fluoro-4-(2-{4-[4-(hydrazinecarbonyl)-1,6-naphthyridin-2-yl]phenyl}ethynyl)phenyl]formamido}-3-phenylpropanoic acid (214);

4-[4-(2-{4-[4-(hydrazinecarbonyl)-1,6-naphthyridin-2-yl]phenyl}ethynyl)benzamido]-2-hydroxybenzoic acid (215);

2-{1-[3-fluoro-4-(2-{4-[4-(hydrazinecarbonyl)-1,6-naphthyridin-2-yl]phenyl}ethynyl)phenyl]-N-methylformamido}-3-phenylpropanoic acid (216);

2-{1-[4-(2-{4-[4-(hydrazinecarbonyl)-1,6-naphthyridin-2-yl]phenyl}ethynyl)phenyl]-N-methylformamido}-3-methylpentanoic acid (217);

1-[2,3-difluoro-4-(2-{4-[4-(hydrazinecarbonyl)-1,6-naphthyridin-2-yl]phenyl}ethynyl)benzoyl]piperidine-2-carboxylic acid (218);

2-{1-[4-(2-{4-[4-(hydrazinecarbonyl)-1,6-naphthyridin-2-yl]phenyl}ethynyl)phenyl]-N-methylformamido}-4-methylpentanoic acid (219);

2-{1-[3-fluoro-4-(2-{4-[4-(hydrazinecarbonyl)-1,6-naphthyridin-2-yl]phenyl}ethynyl)phenyl]formamido}-3-methylpentanoic acid (220);

2-{1-[4-(2-{4-[4-(hydrazinecarbonyl)-1,6-naphthyridin-2-yl]phenyl}ethynyl)phenyl]-N-methylformamido}-3-methylbutanoic acid (221);

2-{1-[4-(2-{4-[4-(hydrazinecarbonyl)-1,6-naphthyridin-2-yl]phenyl}ethynyl)phenyl]-N-methylformamido}pentanedioic acid (222);

N-hydroxy-N-methyl-2-(4-{4-[5-(morpholine-4-carbonyl)-1,2-oxazol-3-yl]phenyl}phenyl)-1,6-naphthyridine-4-carboxamide (223);

2-{1-[3-fluoro-4-(2-{4-[4-(hydrazinecarbonyl)-1,6-naphthyridin-2-yl]phenyl}ethynyl)phenyl]-N-methylformamido}-3-methylpentanoic acid (224);

2-{1-[4-(2-{4-[4-(hydrazinecarbonyl)-1,6-naphthyridin-2-yl]phenyl}ethynyl)phenyl]-N-methylformamido}butanedioic acid (225);

1-[4-(2-{4-[4-(hydrazinecarbonyl)-1,6-naphthyridin-2-yl]phenyl}ethynyl)-2-methoxybenzoyl]piperidine-2-carboxylic acid (226);

1-[2-chloro-4-(2-{4-[4-(hydrazinecarbonyl)-1,6-naphthyridin-2-yl]phenyl}ethynyl)benzoyl]piperidine-2-carboxylic acid (227);

1-[4-(2-{4-[4-(hydrazinecarbonyl)-1,6-naphthyridin-2-yl]phenyl}ethynyl)-2-(trifluoromethyl)benzoyl]piperidine-2-carboxylic acid (228);

1-[4-(2-{4-[4-(hydrazinecarbonyl)-1,6-naphthyridin-2-yl]phenyl}ethynyl)-2-hydroxybenzoyl]piperidine-2-carboxylic acid (229);

1-[6-(2-{4-[4-(hydrazinecarbonyl)-1,6-naphthyridin-2-yl]phenyl}ethynyl)pyridine-3-carbonyl]piperidine-2-carboxylic acid (230);

N-hydroxy-2-(4-{4-[5-(methanesulfonamidomethyl)-1,2-oxazol-3-yl]phenyl}phenyl)-N-methyl-1,6-naphthyridine-4-carboxamide (231);

2-{1-[3-chloro-4-(2-{4-[4-(hydrazinecarbonyl)-1,6-naphthyridin-2-yl]phenyl}ethynyl)phenyl]formamido}-3-phenylpropanoic acid (232);

2-[4-(2-{4-[4-(hydrazinecarbonyl)-1,6-naphthyridin-2-yl]phenyl}ethynyl)benzenesulfonamido]-3-phenylpropanoic acid (233);

2-[N-methyl4-(2-{4-[4-(hydrazinecarbonyl)-1,6-naphthyridin-2-yl]phenyl}ethynyl)benzenesulfonamido]-3-phenylpropanoic acid (234);

1-[3 ,5-difluoro-4-(2-{4-[4-(hydrazinecarbonyl)-1,6-naphthyridin-2-yl]phenyl}ethynyl)benzoyl]piperidine-2-carboxylic acid (235);

2-{1-[3-chloro-4-(2-{4-[4-(hydrazinecarbonyl)-1,6-naphthyridin-2-yl]phenyl}ethynyl)phenyl]formamido}-3-methylpentanoic acid (236);

2-{N-ethyl-1-[4-(2-{4-[4-(hydrazinecarbonyl)-1,6-naphthyridin-2-yl]phenyl}ethynyl)phenyl]formamido}acetic acid (237);

2-{1-[4-(2-{4-[4-(hydrazinecarbonyl)-1,6-naphthyridin-2-yl]phenyl}ethynyl)phenyl]-N-propylformamido}acetic acid (238);

2-[4-(2-{4-[4-(hydrazinecarbonyl)-1,6-naphthyridin-2-yl]phenyl}ethynyl)benzenesulfonamido]-3-methylpentanoic acid (239);

3-methyl-2-[N-methyl4-(2-{4-[4-(hydrazinecarbonyl)-1,6-naphthyridin-2-yl]phenyl}ethynyl)benzenesulfonamido]pentanoic acid (240);

2-{N-benzyl-1-[4-(2-{4-[4-(hydrazinecarbonyl)-1,6-naphthyridin-2-yl]phenyl}ethynyl)phenyl]formamido}acetic acid (241);

N-hydroxy-N-methyl-2-{4-[2-(6-trifluoromethanesulfonamidopyridin-3-yl)ethynyl]phenyl}-1,6-naphthyridine-4-carboxamide (242);

2-{1-[4-(2-{4-[4-(hydrazinecarbonyl)-1,6-naphthyridin-2-yl]phenyl}ethynyl)phenyl]-N-(propan-2-yl)formamido}acetic acid (243);

2-{1-[4-(2-{4-[4-(hydrazinecarbonyl)-1,6-naphthyridin-2-yl]phenyl}ethynyl)phenyl]-N-(2-methylpropyl)formamido}acetic acid (244);

N-hydroxy-N-methyl-2-{4-[2-(4-trifluoromethanesulfonamidophenyl)ethynyl]phenyl}-1,6-naphthyridine-4-carboxamide (245);

2-[3-fluoro-4-(2-{4-[4-(hydrazinecarbonyl)-1,6-naphthyridin-2-yl]phenyl}ethynyl)benzenesulfonamido]-3-methylpentanoic acid (246);

2-{N-benzyl-1-[4-(2-{4-[4-(hydrazinecarbonyl)-1,6-naphthyridin-2-yl]phenyl}ethynyl)phenyl]formamido}-3-phenylpropanoic acid (247);

3-methyl-2-[N-methyl3-fluoro-4-(2-{4-[4-(hydrazinecarbonyl)-1,6-naphthyridin-2-yl]phenyl}ethynyl)benzenesulfonamido]pentanoic acid (248);

(2R)-1-[3-fluoro-4-(2-{4-[4-(hydrazinecarbonyl)-1,6-naphthyridin-2-yl]phenyl}ethynyl)benzenesulfonyl]piperidine-2-carboxylic acid (249);

(2S)-1-[3-fluoro-4-(2-{4-[4-(hydrazinecarbonyl)-1,6-naphthyridin-2-yl]phenyl}ethynyl)benzenesulfonyl]piperidine-2-carboxylic acid (250);

2-[3-fluoro-4-(2-{4-[4-(hydrazinecarbonyl)-1,6-naphthyridin-2-yl]phenyl}ethynyl)benzenesulfonamido]-3-phenylpropanoic acid (251);

2-[N-methyl3-fluoro-4-(2-{4-[4-(hydrazinecarbonyl)-1,6-naphthyridin-2-yl]phenyl}ethynyl)benzenesulfonamido]-3-phenylpropanoic acid (252);

1-[4-(2-{5-[4-(hydrazinecarbonyl)-1,6-naphthyridin-2-yl]pyridin-2-yl}ethynyl)benzoyl]piperidine-2-carboxylic acid (253);

1-[3-fluoro-4-(2-{2-fluoro-4-[4-(hydrazinecarbonyl)-1,6-naphthyridin-2-yl]phenyl}ethynyl)benzoyl]piperidine-2-carboxylic acid (254);

2-{N-ethyl-1-[4-(2-{4-[4-(hydrazinecarbonyl)-1,6-naphthyridin-2-yl]phenyl}ethynyl)phenyl]formamido}-3-phenylpropanoic acid (255);

2-{1-[4-(2-{4-[4-(hydrazinecarbonyl)-1,6-naphthyridin-2-yl]phenyl}ethynyl)phenyl]-N-(propan-2-yl)formamido}-3-phenylpropanoic acid (256);

1-{3-fluoro-4-[2-(4-{4-[hydroxy(methyl)carbamoyl]-1,6-naphthyridin-2-yl}phenyl)ethynyl]benzoyl}piperidine-2-carboxylic acid (257);

(2R)-1-{[5-(2-{4-[4-(hydrazinecarbonyl)-1,6-naphthyridin-2-yl]phenyl}ethynyl)pyridin-2-yl]methyl}pyrrolidine-2-carboxylic acid (258);

2-{1-[4-(2-{4-[4-(hydrazinecarbonyl)-1,6-naphthyridin-2-yl]phenyl}ethynyl)phenyl]-N-(2-methylpropyl)formamido}-3-phenylpropanoic acid (259);

(2R)-1-[3-chloro-4-(2-{4-[4-(hydrazinecarbonyl)-1,6-naphthyridin-2-yl]phenyl}ethynyl)benzenesulfonyl]piperidine-2-carboxylic acid (260);

(2S)-1-[3-chloro-4-(2-{4-[4-(hydrazinecarbonyl)-1,6-naphthyridin-2-yl]phenyl}ethynyl)benzenesulfonyl]piperidine-2-carboxylic acid (261);

2-amino-3-{1-[3-chloro-4-(2-{4-[4-(hydrazinecarbonyl)-1,6-naphthyridin-2-yl]phenyl}ethynyl)phenyl]formamido}propanoic acid (262);

2-{1-[4-(2-{4-[4-(hydrazinecarbonyl)-1,6-naphthyridin-2-yl]phenyl}ethynyl)phenyl]-N-propylformamido}-3-phenylpropanoic acid (263);

1-[4-(2-{2-chloro-4-(hydrazinecarbonyl)-1,6-naphthyridin-2-yl]phenyl}ethynyl)benzoyl]piperidine-2-carboxylic acid (264);

1-[3-fluoro-4-(2-{4-[4-(hydrazinecarbonyl)-1,6-naphthyridin-2-yl]phenyl}ethynyl)benzoyl]piperidine-3-carboxylic acid (265);

(2R)-1-[3-fluoro-4-(2-{4-[4-(hydrazinecarbonyl)-1,6-naphthyridin-2-yl]phenyl}ethynyl)benzoyl]pyrrolidine-2-carboxylic acid (266);

1-[3-chloro-4-(2-{4-[4-(hydrazinecarbonyl)-1,6-naphthyridin-2-yl]phenyl}ethynyl)benzoyl]piperidine-3-carboxylic acid (267);

(2R)-1-[3-chloro-4-(2-{4-[4-(hydrazinecarbonyl)-1,6-naphthyridin-2-yl]phenyl}ethynyl)benzoyl]pyrrolidine-2-carboxylic acid (268);

1-[3-fluoro-4-(2-{4-[4-(hydrazinecarbonyl)-1,6-naphthyridin-2-yl]phenyl}ethynyl)benzenesulfonyl]piperidine-3-carboxylic acid (269);

(2R)-1-[3-fluoro-4-(2-{4-[4-(hydrazinecarbonyl)-1,6-naphthyridin-2-yl]phenyl}ethynyl)benzenesulfonyl]pyrrolidine-2-carboxylic acid (270);

2-{1-[3-chloro-4-(2-{4-[4-(hydrazinecarbonyl)-1,6-naphthyridin-2-yl]phenyl}ethynyl)phenyl]-N-(2-methylpropyl)formamido}acetic acid (271);

2-{1-[3-fluoro-4-(2-{4-[4-(hydrazinecarbonyl)-1,6-naphthyridin-2-yl]phenyl}ethynyl)phenyl]-N-(2-methylpropyl)formamido}acetic acid (272);

2-[N-(2-methylpropyl)3-chloro-4-(2-{4-[4-(hydrazinecarbonyl)-1,6-naphthyridin-2-yl]phenyl}ethynyl)benzenesulfonamido]acetic acid (273);

2-[N-(2-methylpropyl)3-fluoro-4-(2-{4-[4-(hydrazinecarbonyl)-1,6-naphthyridin-2-yl]phenyl}ethynyl)benzenesulfonamido]acetic acid (274);

1-[3-chloro-4-(2-{4-[4-(hydrazinecarbonyl)-1,6-naphthyridin-2-yl]phenyl}ethynyl)benzenesulfonyl]piperidine-3-carboxylic acid (275);

(2R)-1-[3-chloro-4-(2-{4-[4-(hydrazinecarbonyl)-1,6-naphthyridin-2-yl]phenyl}ethynyl)benzenesulfonyl]pyrrolidine-2-carboxylic acid (276);

2-amino-3-[4-(2-{4-[4-(hydrazinecarbonyl)-1,6-naphthyridin-2-yl]phenyl}ethynyl)phenoxy]propanoic acid (277);

1-[4-(2-{4-[4-(hydrazinecarbonyl)-1,6-naphthyridin-2-yl]-2-methoxyphenyl}ethynyl)benzoyl]piperidine-2-carboxylic acid (278);

2-{1-[4-(2-{4-[4-(hydrazinecarbonyl)-1,6-naphthyridin-2-yl]phenyl}ethynyl)phenyl]-N-(2-methylpropyl)formamido}propanoic acid (279);

1-[4-(2-{4-[4-(hydrazinecarbonyl)-1,6-naphthyridin-2-yl]-2-hydroxyphenyl}ethynyl)benzoyl]piperidine-2-carboxylic acid (280);

2-[4-(2-{4-[(2S)-2-carboxypiperidine-1-carbonyl]-2-chlorophenyl}ethynyl)phenyl]-1,6-naphthyridine-4-carboxylic acid (281);

2-{1-[3-fluoro-4-(2-{4-[4-(hydrazinecarbonyl)-1,6-naphthyridin-2-yl]phenyl}ethynyl)phenyl]-N-(2-methylpropyl)formamido}propanoic acid (282);

2-amino-3-{1-[3-chloro-4-(2-{4-[4-(hydrazinecarbonyl)-1,6-naphthyridin-2-yl]phenyl}ethynyl)phenyl]-N-methylformamido}propanoic acid (283);

2-{1-[3-chloro-4-(2-{4-[4-(hydrazinecarbonyl)-1,6-naphthyridin-2-yl]phenyl}ethynyl)phenyl]-N-(2-methylpropyl)formamido}propanoic acid (284);

2-{1-[4-(2-{4-[4-(hydrazinecarbonyl)-1,6-naphthyridin-2-yl]phenyl}ethynyl)phenyl]-N-(2-methylpropyl)formamido}-3-hydroxyprop anoic acid (285);

2-[4-(2-{2-chloro-4-[(2S)-2-(hydrazinecarbonyl)piperidine-1-carbonyl]phenyl}ethynyl)phenyl]-1,6-naphthyridine-4-carbohydrazide (286);

2-[4-(2-{2-chloro-4-[(2S)-2-(hydrazinecarbonyl)piperidine-1-carbonyl]phenyl}ethynyl)phenyl]-1,6-naphthyridine-4-carboxylic acid (287);

(2S)-1-[3-chloro-4-(2-{4-[4-(hydrazinecarbonyl)-1,6-naphthyridin-2-yl]phenyl}ethynyl)benzoyl]-N-hydroxypiperidine-2-carboxamide (288);

2-{1-[4-(2-{4-[4-(hydrazinecarbonyl)-1,6-naphthyridin-2-yl]phenyl}ethynyl)phenyl]formamido}-3-(1H-imidazol-4-yl)propanoic acid (289);

2-{1-[4-(2-{4-[4-(hydrazinecarbonyl)-1,6-naphthyridin-2-yl]phenyl}ethynyl)phenyl]-N-(2-methylpropyl)formamido}-3-(4-hydroxyphenyl)propanoic acid (290);

methyl 2-{1-[4-(2-{4-[4-(hydrazinecarbonyl)-1,6-naphthyridin-2-yl]phenyl}ethynyl)phenyl]formamido}-3-(1H-imidazol-4-yl)propanoate (291);

2-{1-[3-fluoro-4-(2-{4-[4-(hydrazinecarbonyl)-1,6-naphthyridin-2-yl]phenyl}ethynyl)phenyl]-N-(2-methylpropyl)formamido}-3-hydroxypropanoic acid (292);

2-{1-[3-fluoro-4-(2-{4-[4-(hydrazinecarbonyl)-1,6-naphthyridin-2-yl]phenyl}ethynyl)phenyl]-N-(2-methylpropyl)formamido}-3-hydroxypropanoic acid (293);

2-{1-[3-fluoro-4-(2-{4-[4-(hydrazinecarbonyl)-1,6-naphthyridin-2-yl]phenyl}ethynyl)phenyl]-N-(2-methylpropyl)formamido}-3-hydroxypropanoic acid (294);

methyl 2-{1-[3-chloro-4-(2-{4-[4-(hydrazinecarbonyl)-1,6-naphthyridin-2-yl]phenyl}ethynyl)phenyl]formamido}-3-(1H-imidazol-4-yl)propanoate (295);

methyl 2-{1-[3-fluoro-4-(2-{4-[4-(hydrazinecarbonyl)-1,6-naphthyridin-2-yl]phenyl}ethynyl)phenyl]formamido}-3-(1H-imidazol-4-yl)propanoate (296);

3-amino-2-{1-[4-(2-{4-[4-(hydrazinecarbonyl)-1,6-naphthyridin-2-yl]phenyl}ethynyl)phenyl]formamido}propanoic acid (297);

3-amino-2-{1-[3-chloro-4-(2-{4-[4-(hydrazinecarbonyl)-1,6-naphthyridin-2-yl]phenyl}ethynyl)phenyl]formamido}propanoic acid (298);

3-amino-2-{1-[3-fluoro-4-(2-{4-[4-(hydrazinecarbonyl)-1,6-naphthyridin-2-yl]phenyl}ethynyl)phenyl]formamido}propanoic acid (299);

(2S)-1-[3-chloro-4-(2-{4-[7-chloro-4-(hydrazinecarbonyl)-1,6-naphthyridin-2-yl]phenyl}ethynyl)benzoyl]piperidine-2-carboxylic acid (300);

3-amino-2-{1-[4-(2-{4-[4-(hydrazinecarbonyl)-1,6-naphthyridin-2-yl]phenyl}ethynyl)phenyl]-N-(2-methylpropyl)formamido}propanoic acid (301);

3-amino-2-{1-[3-chloro-4-(2-{4-[4-(hydrazinecarbonyl)-1,6-naphthyridin-2-yl]phenyl}ethynyl)phenyl]-N-(2-methylpropyl)formamido}propanoic acid (302);

3-amino-2-{1-[3-fluoro-4-(2-{4-[4-(hydrazinecarbonyl)-1,6-naphthyridin-2-yl]phenyl}ethynyl)phenyl]-N-(2-methylpropyl)formamido}propanoic acid (303);

2-{4-[2-(4-{1,3-dioxo-octahydroimidazolidino[1,5-a]pyridin-2-yl}phenyl)ethynyl]phenyl}-1,6-naphthyridine-4-carbohydrazide (304);

3-amino-2-{1-[4-(2-{4-[4-(hydrazinecarbonyl)-1,6-naphthyridin-2-yl]phenyl}ethynyl)phenyl]-N-methylformamido}propanoic acid (305);

(2S)-1-[4-(2-{4-[7-amino-4-(hydrazinecarbonyl)-1,6-naphthyridin-2-yl]phenyl}ethynyl)-3-chlorobenzoyl]piperidine-2-carboxylic acid (306);

3-amino-2-{1-[3-fluoro-4-(2-{4-[4-(hydrazinecarbonyl)-1,6-naphthyridin-2-yl]phenyl}ethynyl)phenyl]-N-methylformamido}propanoic acid (307);

1-[4-(2-{5-[4-(hydrazinecarbonyl)-1,6-naphthyridin-2-yl]thiophen-2-yl}ethynyl)benzoyl]piperidine-2-carboxylic acid (308);

(2S)-1-[3-chloro-4-(2-{4-[4-(hydrazinecarbonyl)-7-methanesulfonamido-1,6-naphthyridin-2-yl]phenyl}ethynyl)benzoyl]piperidine-2-carboxylic acid (309);

(2S)-1-[3-chloro-4-(2-{4-[4-(hydrazinecarbonyl)-7-methoxy-1,6-naphthyridin-2-yl]phenyl}ethynyl)benzoyl]piperidine-2-carboxylic acid (310);

2-(4-{4-[4-(hydrazinecarbonyl)-1,6-naphthyridin-2-yl]phenyl}buta-1,3-diyn-1-yl)cyclopropane-1-carboxylic acid (311);

(2S)-1-[3-chloro-4-(2-{4-[7-acetamido-4-(hydrazinecarbonyl)-1,6-naphthyridin-2-yl]phenyl}ethynyl)benzoyl]piperidine-2-carboxylic acid (312);

(2S)-1-[3-chloro-4-(2-{4-[4-(hydrazinecarbonyl)-7-(morpholin-4-yl)-1,6-naphthyridin-2-yl]phenyl}ethynyl)benzoyl]piperidine-2-carboxylic acid (313);

1-[2-(4-{4-[4-(hydrazinecarbonyl)-1,6-naphthyridin-2-yl]phenyl}buta-1,3-diyn-1-yl)cyclopropanecarbonyl]piperidine-2-carboxylic acid (314);

(2S)-1-[4-(2-{4-[7-(2-carboxyacetamido)-4-(hydrazinecarbonyl)-1,6-naphthyridin-2-yl]phenyl}ethynyl)-3-chlorobenzoyl]piperidine-2-carboxylic acid (315);

(2S)-1-[4-(2-{4-[7-carboxymethanesulfonamido-4-(hydrazinecarbonyl)-1,6-naphthyridin-2-yl]phenyl}ethynyl)-3-chlorobenzoyl]piperidine-2-carboxylic acid (316);

1-{[4-(2-{4-[4-(hydrazinecarbonyl)-1,6-naphthyridin-2-yl]phenyl}ethynyl)phenyl]carbamoyl}piperidine-2-carboxylic acid (317);

(2S)-1-[3-chloro-4-(2-{4-[4-(hydrazinecarbonyl)-7-(3-methoxypyrrolidin-1-yl)-1,6-naphthyridin-2-yl]phenyl}ethynyl)benzoyl]piperidine-2-carboxylic acid (318);

4-(hydrazinecarbonyl)-2-{4-[4-(4-hydroxybutoxy)phenyl]phenyl}-1,6-naphthyridine-7-carboxylic acid (319);

N-[2-(4-{2-[2-chloro-4-(morpholine-4-carbonyl)phenyl]ethynyl}phenyl)-4-(hydrazinecarbonyl)-1,6-naphthyridin-7-yl]methanesulfonamide (320);

(2S)-1-[4-(2-{4-[7-(2-aminoacetamido)-4-(hydrazinecarbonyl)-1,6-naphthyridin-2-yl]phenyl}ethynyl)-3-chlorobenzoyl]piperidine-2-carboxylic acid (321);

2-{[2-(4-{2-[2-chloro-4-(morpholine-4-carbonyl)phenyl]ethynyl}phenyl)-4-(hydrazinecarbonyl)-1,6-naphthyridin-7-yl]sulfamoyl}acetic acid (322);

(2R)-1-[4-(hydrazinecarbonyl)-2-{4-[4-(4-hydroxybutoxy)phenyl]phenyl}-1,6-naphthyridine-7-carbonyl]pyrrolidine-2-carboxylic acid (323);

(2S)-1-[4-(hydrazinecarbonyl)-2-{4-[4-(4-hydroxybutoxy)phenyl]phenyl}-1,6-naphthyridine-7-carbonyl]pyrrolidine-2-carboxylic acid (324);

N-[4-(hydrazinecarbonyl)-2-{4-[4-(4-hydroxybutoxy)phenyl]phenyl}-1,6-naphthyridin-7-yl]methanesulfonamide (325);

2-{[4-(hydrazinecarbonyl)-2-{4-[4-(4-hydroxybutoxy)phenyl]phenyl}-1,6-naphthyridin-7-yl]sulfamoyl}acetic acid (326);

N-[4-(hydrazinecarbonyl)-2-(4-{4-[5-(hydroxymethyl)-1,2-oxazol-3-yl]phenyl}phenyl)-1,6-naphthyridin-7-yl]methanesulfonamide (327);

2-{1-[4-(hydrazinecarbonyl)-2-(4-{4-[5-(hydroxymethyl)-1,2-oxazol-3-yl]phenyl}phenyl)-1,6-naphthyridin-7-yl]sulfamoyl}acetic acid (328);

N-[2-(4-{2-[2-chloro-4-(morpholine-4-carbonyl)phenyl]ethynyl}phenyl)-4-(hydrazinecarbonyl)-1,6-naphthyridin-7-yl]-N-methylmethanesulfonamide (329); or 2-{[2-(4-{2-[2-chloro-4-(morpholine-4-carbonyl)phenyl]ethynyl}phenyl)-4-(hydrazinecarbonyl)-1,6-naphthyridin-7-yl](methyl)sulfamoyl}acetic acid (330);

or salt thereof.

18. A method of treating a subject suffering from or susceptible to a disorder or disease, comprising administering to the subject an effective amount of a compound of claim 1, wherein the disease or disorder is bacterial infection.

19. A composition comprising a compound of claim 1 and a pharmaceutically acceptable carrier.

20. The composition of claim 19 further comprising an additional therapeutic agent.

21. The method of claim 18, wherein the bacterial infection is gram-negative bacterial infection.

22. A compound of formula (I), (II), (III), (IV), or salt thereof, wherein:

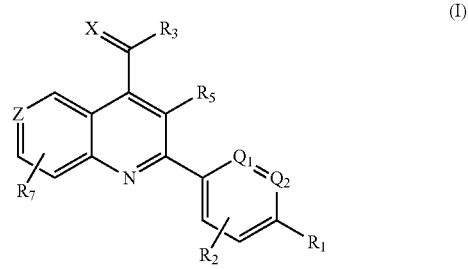

(I)

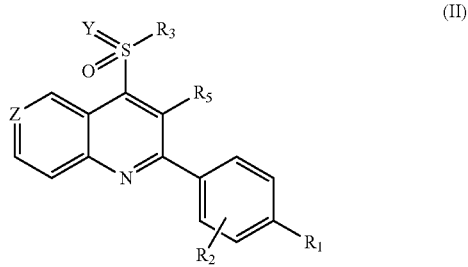

(II)

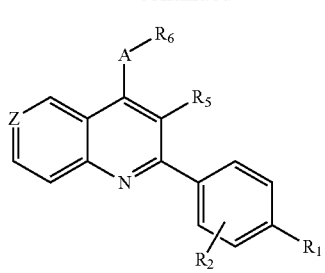

(III)

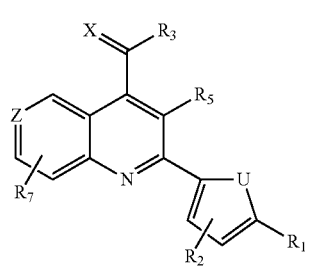

(IV)

U is O or S;

each X is independently O; S; NR$_4$; or H and R$_4$;

each R$_1$ is independently selected from:

a)

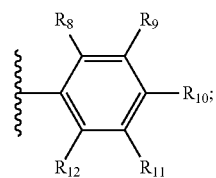

b) heteroaryl optionally substituted with alkoxy wherein alkoxy is optionally substituted with 1, 2, or 3 OR$_4$; c) C≡C—R$_{13}$; d) C(=O)NR$_4$R$_7$; e) N(R$_7$)C(=O)R$_4$; f) SO$_2$NR$_4$R$_7$; g) N(R$_7$)SO$_2$R$_4$; h) hydrogen; i) hydroxy; j) optionally substituted alkoxy; k) SO$_2$NHR$_4$; l) optionally substituted alkenyl; m) optionally substituted arylalkyl; or n) C≡C—C≡C—R$_{13}$;

each R$_8$, R$_9$, R$_{10}$, R$_{11}$, and R$_{12}$ is independently selected from:

a) H; b) hydroxyalkylamino; c) alkoxy optionally substituted with 1, 2, or 3 independent heterocycloalkoxy, heterocycloalkylcarbonyl, hydroxy, amino, NHSO$_2$R$_4$, NHC(=O)R$_4$, C(=O)OR$_4$, C(=O)NHNHR$_4$, or C(=O)NR$_4$OH; d) halogen; e) SO$_2$NHR$_{18}$; f) NHSO$_2$R$_4$; g) NHC(=O)R$_4$; h) C(=O)NHR$_4$; i) heterocycloalkyl containing 5 to 6 ring atoms, optionally substituted with 1, 2, or 3 independent C(=O)OR$_4$, C(=O)NR$_4$R$_7$, or SO$_2$NR$_4$R$_7$; j) heteroaryl containing 5 to 6 ring atoms optionally substituted with 1, 2, or 3 independent:

(1) C(=O)OR$_{17}$;

(2) heterocycloalkylcarbonyl optionally substituted with 1, 2, or 3 independent C(=O)OR$_{17}$,C(=O)NR$_4$R$_7$, or SO$_2$NR$_4$R$_7$;

(3) alkyl optionally substituted with 1, 2, or 3 independent OC(=O)NHR$_4$, NHC(=O)NHR$_4$, NHSO$_2$R$_4$, hydroxy, or C(=O)NHR$_4$; or (4) C(=O)NHR$_4$;

k) cyano; l) hydroxy; m) SO$_2$R$_4$; n) heterocycloalkylcarbonyl optionally substituted with 1, 2, or 3 independent C(=O)OR$_4$, C(=O)NR$_4$R$_7$, or SO$_2$NR$_4$R$_7$; o) heterocycloalkylsulfonyl optionally substituted with 1, 2, or, 3 independent C(=O)OR$_4$, C(=O)NR$_4$R$_7$, or SO$_2$NR$_4$R$_7$; p)

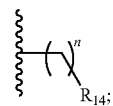

q) mercapto; r) thioalkoxy; s) alkylamino; t) alkyl optionally substituted with 1, 2, or 3 independent heterocycloalkylcarbonyl, heterocycloalkyl, or heterocycloalkylsulfonyl, each optionally substituted with independent C(=O)OR$_4$, C(=O)NR$_4$R$_7$, or SO$_2$NR$_4$R$_7$; u) dialkylamino; or v) —O—(CH$_2$)$_n$—C(=O)-heterocycloalkyl optionally substituted with 1, 2, or 3 independent C(=O)OR$_4$, C(=O)NR$_4$R$_7$, or SO$_2$NR$_4$R$_7$;

R$_2$ is H, alkyl, fluoroalkyl, alkoxy, fluoroalkoxy, halogen, aryl, or heteroaryl;

R$_3$ is CH(R$_4$)NHR$_4$, CH(R$_4$)NHSO$_2$R$_4$, CH(R$_4$)SH, CH(R$_4$)OH, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NHNHR$_4$, C(=S)NHR$_4$, C(=S)NHNHR$_4$, C≡N, C(=NH)NH$_2$, NHC(=NH)NH$_2$, N(OH)C(=O)R$_4$, NHR$_4$, NHNHR$_4$, NHC(=O)R$_4$, N(R$_4$)NHC(=O)R$_4$, NHC(=O)NHR$_4$, NHC(=S)NHR$_4$, NHSO$_2$R$_4$, NHSO$_2$NHR$_4$; NHNHSO$_2$R$_4$, NO$_2$, SO$_2$NHR$_4$ (only in the case of formula I), SO$_2$NHOH (only in the case of formula I), SO$_3$H (only in the case of formula I), OR$_4$, OSO$_2$R$_4$, OSO$_2$NHR$_4$, SR$_4$, B(OR$_4$)$_2$, CH$_2$B(OR$_4$)$_2$, P(=O)OH, P(=O)$_2$OH, Se(=O)OH, Se(=O)$_2$OH, a heterocycle that is preferably a 5-membered ring with 1-4 heteroatoms, or a 5-membered heterocycle that is connected through a CH$_2$;

Y is O or null;

Z is N;

each R$_4$ is independently a) H; b) alkyl optionally substituted with 1, 2, or 3 independent hydroxy, halogen, C(=O)OR$_{27}$, amino, alkylthio, or optionally substituted aryl; c) fluoroalkyl; d) optionally substituted aryl; e) optionally substituted heteroaryl; or f) heterocycloalkyl optionally substituted with 1, 2, or 3 independent C(=O)OR$_{27}$, C(=O)NR$_{27}$R$_{27}$, or SO$_2$NR$_{27}$R$_{27}$;

each R$_5$ is independently H, alkyl, fluoroalkyl, halogen, alkoxy, fluoroalkoxy, substituted amino, aryl, or heteroaryl;

A is O, S, CH$_2$ or N(R$_4$);

A may also be the following when R$_6$ is null: an optionally substituted heterocycle that is preferably a 5-membered ring with 1-4 heteroatoms, B(OR$_4$)$_2$, P(=O)$_2$OH, Se(=O)OH, Se(=O)$_2$OH;

R$_6$ is null, CH(R$_4$)CO$_2$R$_4$, CH(R$_4$)CONHR$_4$; CH(R$_4$)CONHOH; CH(R$_4$)CONHNHR$_4$; C(=O)R$_4$, CO$_2$R$_4$, C(=O)NHR$_4$, C(=O)NR$_4$OH, C(=O)NHNHR$_4$, C(=S)NHR$_4$, C(=S)NR$_4$OH, C(=S)NHNHR$_4$, C≡N, C(=NH)NH$_2$, SO$_2$NHNR$_4$ (with the proviso that A cannot be S), SO$_2$NHR$_4$ (with the proviso that A cannot be S), SO$_2$NHOH (with the proviso that A cannot be S); a heterocycle that is preferably a 5-membered ring with 1-4 heteroatoms, or a (preferably 5-membered) heterocycle that is connected through a $CH_2$; and each $R_7$ is independently H; alkyl; alkoxy; hydroxy; $C(=O)OR_4$; $NHSO_2R_4$; $N(alkyl)SO_2R_4$; $NHR_4$; $NHC(=O)R_4$; $N(alkyl)C(=O)R_4$; $C(=O)NR_{27}R_4$; $SO_2NR_{27}R_4$; $C(=O)NR_{27}NHR_4$; $C(=O)NR_{27}OR_4$; halogen; optionally substituted aryl; optionally substituted heteroaryl; heterocycloalkyl optionally substituted with 1, 2, or 3 independent $OR_4$, $C(=O)OR_4$, or $NHSO_2R_4$; or heterocycloalkylcarbonyl optionally substituted with 1, 2, or 3 independent $OR_4$, $C(=O)OR_4$, or $NHSO_2R_4$;

each $R_{13}$ is independently selected from:
a)

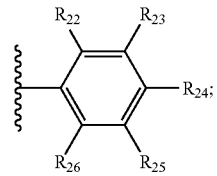

b) heterocycloalkyl optionally substituted with 1, 2, or 3 independent alkyl wherein alkyl is optionally substituted with independent:
  i) $OR_4$;
  ii) $NHC(=O)R_4$;
  iii) $C(=O)OR_4$; or
  iv) $C(=O)NHR_4$;
c) heteroaryl optionally substituted with 1, 2, or 3 independent 1) heterocycloalkylcarbonyl, 2) $NR_{27}SO_2R_4$, 3) alkylaminocarbonyl, each optionally substituted with 1, 2, or 3 independent $C(=O)OR_4$, $C(=O)NR_4R_7$, or $SO_2NR_4R_7$, 4) (heterocycloalkyl)alkyl; or 5) $NR_{27}C(=O)R_4$; or
d) cycloalkyl optionally substituted with 1, 2, or 3 independent $C(=O)OR_4$, $C(=O)NR_4R_7$, hydroxyalkyl, or $SO_2NR_4R_7$;

each $R_{14}$ is independently selected from heterocycloalkylcarbonyl, heterocycloalkylsulfonyl, or heterocycloalkyl, each optionally substituted with 1, 2, or 3 independent $C(=O)OR_4$, $C(=O)NR_4R_7$, or $SO_2NR_4R_7$;

each $R_{15}$ is independently H; alkyl; fluoroalkyl; aryl; arylalkyl; or heteroaryl;

each $R_{16}$ is independently hydrogen; alkyl; alkoxy; hydroxy; $NHR_4$; $NHC(=O)R_4$; halogen; optionally substituted aryl; optionally substituted heteroaryl; heterocycloalkyl optionally substituted with 1, 2, or 3 independent $C(=O)OR_4$, $C(=O)NR_4R_7$, or $SO_2NR_4R_7$; or $NHSO_2R_4$;

each $R_{17}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{18}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{19}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{20}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, optionally substituted heteroaryl, or optionally substituted aryl; c) fluoroalkyl; d) aryl optionally substituted with 1, 2, or 3 independent $C(=O)OR_4$ or $OR_4$; or e) heteroaryl;

each $R_{21}$ is independently a) H; b) alkyl optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; c) fluoroalkyl; d) aryl; or e) heteroaryl;

each $R_{22}$, $R_{23}$, $R_{24}$, $R_{25}$, and $R_{26}$ is independently selected from
  i) hydrogen; ii) $NHC(=O)R_4$; iii) $NHSO_2R_4$; iv) heterocycloalkylcarbonyl optionally substituted with 1, 2, or 3 independent alkyl, $CH_2C(=O)OR_{19}$, $CH_2C(=O)NR_4R_7$, $OR_4$, $CH_2SO_2NR_4R_7$, $C(=O)OR_{19}$, $C(=O)NR_4R_7$, or $SO_2NR_4R_7$; v) heterocycloalkylsulfonyl optionally substituted with 1, 2, or 3 independent $C(=O)OR_4$, $C(=O)NR_4R_7$, or $SO_2NR_4R_7$, or alkyl; vi) halogen; vii) alkyl optionally substituted with heterocycloalkyl wherein heterocycloalkyl is optionally substituted with 1, 2, or 3 independent $C(=O)OR_4$, $C(=O)NR_4R_7$, or $SO_2NR_4R_7$; viii) hydroxyalkylamino; ix) $C(=O)NR_{15}R_{20}$; x) alkoxy optionally substituted with 1, 2, or 3 independent hydroxy, halogen, $C(=O)OR_4$, $C(=O)NR_4R_7$, $SO_2NR_4R_7$, amino, alkylthio, or optionally substituted aryl; xi) haloalkoxy; xii) haloalkyl; xiii) hydroxy; xiv) $SO_2NR_4R_{21}$; or xv) heterocycloalkyl optionally substituted with 1, 2, or 3 independent $C(=O)OR_4$, $C(=O)NR_4R_7$, $SO_2NR_4R_7$, or $CH_2C(=O)OR_4$;

each $R_{27}$ is independently a) H; b) alkyl optionally substituted with 1, 2, or 3 independent hydroxy, halogen, amino, alkylthio, or optionally substituted aryl; c) fluoroalkyl; d) optionally substituted aryl; or e) optionally substituted heteroaryl;

each n is independently 0, 1, 2, 3, or 4; and
$Q_1$ and $Q_2$ are each independently CH or N.

* * * * *